US010238645B2

(12) United States Patent
Nordsiek et al.

(10) Patent No.: US 10,238,645 B2
(45) Date of Patent: *Mar. 26, 2019

(54) LOWER DOSAGE STRENGTH IMIQUIMOD FORMULATIONS AND SHORT DOSING REGIMENS FOR TREATING GENITAL AND PERIANAL WARTS

(71) Applicant: Medicis Pharmaceutical Corporation, Bridgewater, NJ (US)

(72) Inventors: Michael T. Nordsiek, Wayne, PA (US); Jefferson J. Gregory, Bristol, TN (US)

(73) Assignee: Medicis Pharmaceutical Corporation, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/990,590

(22) Filed: May 26, 2018

(65) Prior Publication Data

US 2018/0271854 A1 Sep. 27, 2018

Related U.S. Application Data

(63) Continuation of application No. 14/796,296, filed on Jul. 10, 2015, now Pat. No. 9,980,955, which is a continuation of application No. 14/091,965, filed on Nov. 27, 2013, now Pat. No. 9,078,889, which is a continuation of application No. 13/559,473, filed on Jul. 26, 2012, now Pat. No. 8,642,616, which is a continuation of application No. 12/771,076, filed on Apr. 30, 2010, now abandoned.

(60) Provisional application No. 61/341,721, filed on Apr. 1, 2010, provisional application No. 61/341,476, filed on Mar. 30, 2010, provisional application No. 61/225,202, filed on Jul. 13, 2009.

(51) Int. Cl.

| | |
|---|---|
| ***A61K 9/00*** | (2006.01) |
| ***A61K 9/06*** | (2006.01) |
| ***A61K 31/44*** | (2006.01) |
| ***A61K 47/10*** | (2017.01) |
| ***A61K 47/12*** | (2006.01) |
| ***A61K 31/4745*** | (2006.01) |

(52) U.S. Cl.

CPC ........ *A61K 31/4745* (2013.01); *A61K 9/0014* (2013.01); *A61K 31/44* (2013.01); *A61K 47/10* (2013.01); *A61K 47/12* (2013.01); *A61K 9/06* (2013.01)

(58) Field of Classification Search

CPC ............................ A61K 31/44; A61K 31/4745

See application file for complete search history.

(56) References Cited

U.S. PATENT DOCUMENTS

| | | | |
|---|---|---|---|
| 4,411,893 | A | 10/1983 | Johnson et al. |
| 4,689,338 | A | 8/1987 | Gerster |
| 4,722,941 | A | 2/1988 | Eckert et al. |
| 4,746,515 | A | 5/1988 | Cheng et al. |
| 4,751,087 | A | 6/1988 | Wick |
| 4,929,624 | A | 5/1990 | Gerster et al. |
| 5,238,944 | A | 8/1993 | Wick et al. |
| 5,346,905 | A | 9/1994 | Gerster |
| 5,736,553 | A | 4/1998 | Wick et al. |
| 6,245,776 | B1 | 6/2001 | Skwierczynski et al. |
| 6,335,030 | B1 | 1/2002 | Hoeck et al. |
| 6,486,168 | B1 | 11/2002 | Skwierczynski et al. |
| 6,693,113 | B2 | 2/2004 | Lindstrom |
| 6,706,728 | B2 | 3/2004 | Hedenstrom et al. |
| 6,894,060 | B2 | 5/2005 | Slade |
| 7,038,051 | B2 | 5/2006 | Gerster et al. |
| 7,179,253 | B2 | 2/2007 | Graham et al. |
| 7,507,703 | B2 | 3/2009 | Woodward |
| 7,521,459 | B2 | 4/2009 | Baumann et al. |
| 7,655,672 | B2 | 2/2010 | Statham et al. |
| 7,696,159 | B2 | 4/2010 | Owens et al. |
| 7,699,057 | B2 | 4/2010 | Miller et al. |
| 7,893,083 | B2 | 2/2011 | Mandrea |
| 7,902,210 | B2 | 3/2011 | Statham et al. |

(Continued)

FOREIGN PATENT DOCUMENTS

| | | | |
|---|---|---|---|
| CA | 2679067 | A1 | 2/2008 |
| CN | 1583175 | A | 2/2005 |

(Continued)

OTHER PUBLICATIONS

Aldara Product Insert, Mar. 2004.

Aldara Package Insert, obtained Sep. 3, 2002 online at http://www.accessdata.fda.gov/drugsaUda docs/label/2002/20723s11 s121bl.pdf.

Alomar, A. et al., "Vehicle-controlled, randomized, double-blind study to assess safety and efficacy of imiquimod 5% cream applied once daily 3 days per week in one or two courses of treatment of actinic keratoses on the head," Br. J. Dermatol., 157(1):133-41, 2007.

(Continued)

*Primary Examiner* — Jean P Cornet

(74) *Attorney, Agent, or Firm* — Kilpatrick Townsend & Stockton LLP

(57) ABSTRACT

Pharmaceutical formulations and methods for the topical or transdermal delivery of 1isobutyl-1H-imidazo[4,5-c]-quinolin-4-amine or 1-(2-methylpropyl)-1H-imidazo[4,5 c]quinolin-4-amine, i.e., imiquimod, to treat genital/perianal warts with shorter durations of therapy than currently prescribed for the commercially available for Aldara® 5% imiquimod cream, as now approved by the U.S. Food & Drug Administration ("FDA"), are disclosed and described. More specifically, lower dosage strength imiquimod formulations to deliver an efficacious dose of imiquimod for treating genital/perianal warts with an acceptable safety profile and dosing regimens that are shorter and more convenient for patient use than the dosing regimen currently approved by the U.S. Food & Drug Administration ("FDA") for Aldara® 5% imiquimod cream to treat genital/perianal warts are also disclosed and described.

16 Claims, 41 Drawing Sheets

(56) References Cited

U.S. PATENT DOCUMENTS

| | | | |
|---|---|---|---|
| 7,902,211 | B2 | 3/2011 | Statham et al. |
| 7,902,212 | B2 | 3/2011 | Statham et al. |
| 7,902,213 | B2 | 3/2011 | Statham et al. |
| 7,902,214 | B2 | 3/2011 | Statham et al. |
| 7,902,215 | B2 | 3/2011 | Statham et al. |
| 7,902,216 | B2 | 3/2011 | Statham et al. |
| 7,906,524 | B2 | 3/2011 | Statham et al. |
| 7,906,525 | B2 | 3/2011 | Statham et al. |
| 7,906,526 | B2 | 3/2011 | Statham et al. |
| 7,906,527 | B2 | 3/2011 | Statham et al. |
| 7,915,277 | B2 | 3/2011 | Statham et al. |
| 7,923,429 | B2 | 4/2011 | Miller et al. |
| 7,928,116 | B2 | 4/2011 | Statham et al. |
| 7,928,117 | B2 | 4/2011 | Statham et al. |
| 7,928,118 | B2 | 4/2011 | Statham et al. |
| 7,932,429 | B2 | 4/2011 | Ragaru et al. |
| 8,642,616 | B2 | 2/2014 | Nordsiek et al. |
| 9,078,889 | B2 | 7/2015 | Nordsiek et al. |
| 2002/0147210 | A1 | 10/2002 | Smith |
| 2003/0007939 | A1 | 1/2003 | Murad |
| 2003/0072814 | A1 | 4/2003 | Maibach et al. |
| 2003/0199538 | A1 | 10/2003 | Skwierczynski et al. |
| 2004/0087614 | A1 | 5/2004 | Baumann et al. |
| 2004/0180919 | A1 | 9/2004 | Miller et al. |
| 2004/0181130 | A1 | 9/2004 | Miller et al. |
| 2004/0192585 | A1 | 9/2004 | Owens et al. |
| 2004/0265351 | A1 | 12/2004 | Miller et al. |
| 2005/0048072 | A1 | 3/2005 | Kedl et al. |
| 2005/0165043 | A1 | 7/2005 | Miller et al. |
| 2005/0232869 | A1 | 10/2005 | Tamarkin et al. |
| 2006/0105028 | A1 | 5/2006 | Zhang et al. |
| 2006/0105029 | A1 | 5/2006 | Zhang et al. |
| 2006/0195067 | A1 | 8/2006 | Wolter et al. |
| 2006/0216333 | A1 | 9/2006 | Miller et al. |
| 2007/0049518 | A1 | 3/2007 | Chandler et al. |
| 2007/0081962 | A1 | 4/2007 | Munshi |
| 2007/0123558 | A1 | 5/2007 | Statham et al. |
| 2007/0123559 | A1 | 5/2007 | Statham et al. |
| 2007/0134273 | A1 | 6/2007 | Romagne et al. |
| 2007/0166384 | A1 | 7/2007 | Zarraga |
| 2007/0190124 | A1 | 8/2007 | Zhang et al. |
| 2007/0196293 | A1 | 8/2007 | Zhang et al. |
| 2007/0196323 | A1 | 8/2007 | Zhang et al. |
| 2007/0196452 | A1 | 8/2007 | Zhang et al. |
| 2007/0196453 | A1 | 8/2007 | Zhang et al. |
| 2007/0196457 | A1 | 8/2007 | Zhang et al. |
| 2007/0264317 | A1 | 11/2007 | Yosha et al. |
| 2007/0280972 | A1 | 12/2007 | Zhang et al. |
| 2008/0015271 | A1 | 1/2008 | Abram et al. |
| 2008/0025929 | A1 | 1/2008 | Burton et al. |
| 2008/0125375 | A1 | 5/2008 | Yang et al. |
| 2008/0125485 | A1 | 5/2008 | Cuevas Sanchez et al. |
| 2008/0145375 | A1 | 6/2008 | Bembridge et al. |
| 2008/0161328 | A1 | 7/2008 | Muller et al. |
| 2008/0187511 | A1 | 8/2008 | Shurin et al. |
| 2008/0193487 | A1 | 8/2008 | Schild et al. |
| 2008/0214615 | A1 | 9/2008 | Muller et al. |
| 2008/0275077 | A1 | 11/2008 | Skwierczynski et al. |
| 2008/0280943 | A1 | 11/2008 | Slade et al. |
| 2009/0018155 | A1 | 1/2009 | Gregory |
| 2009/0041680 | A1 | 2/2009 | Tamarkin et al. |
| 2009/0093514 | A1 | 4/2009 | Statham et al. |
| 2009/0130029 | A1 | 5/2009 | Tamarkin et al. |
| 2009/0163532 | A1 | 6/2009 | Perman et al. |
| 2009/0182004 | A1 | 7/2009 | Winckle et al. |
| 2009/0202443 | A1 | 8/2009 | Miller et al. |
| 2009/0232755 | A1 | 9/2009 | Bauman |
| 2009/0246156 | A1 | 10/2009 | Kunin |
| 2009/0281047 | A1 | 11/2009 | Brown |
| 2009/0304812 | A1 | 12/2009 | Staniforth et al. |
| 2010/0021394 | A1 | 1/2010 | Yu |
| 2010/0056557 | A1 | 3/2010 | Benninghoff et al. |
| 2010/0092401 | A1 | 4/2010 | Vallejo et al. |
| 2010/0096287 | A1 | 4/2010 | Stoesz et al. |
| 2010/0129439 | A1 | 5/2010 | Alexis et al. |
| 2010/0150869 | A1 | 6/2010 | Sredni et al. |
| 2010/0160368 | A1 | 6/2010 | Gregory |
| 2010/0180902 | A1 | 7/2010 | Miller et al. |
| 2010/0197722 | A1 | 8/2010 | Owens et al. |
| 2010/0267678 | A1 | 10/2010 | Zhang et al. |
| 2011/0021555 | A1 | 1/2011 | Nordsiek et al. |
| 2011/0038900 | A1 | 2/2011 | Chakrapani et al. |
| 2011/0045037 | A1 | 2/2011 | Tamarkin et al. |
| 2011/0135604 | A1 | 6/2011 | Casarez et al. |
| 2011/0207766 | A1 | 8/2011 | Nordsiek et al. |
| 2011/0257216 | A1 | 10/2011 | Nordsiek et al. |
| 2011/0257217 | A1 | 10/2011 | Nordsiek et al. |
| 2011/0257218 | A1 | 10/2011 | Nordsiek et al. |
| 2011/0263633 | A1 | 10/2011 | Nordsiek et al. |
| 2011/0263634 | A1 | 10/2011 | Nordsiek et al. |
| 2011/0263635 | A1 | 10/2011 | Nordsiek et al. |
| 2011/0263636 | A1 | 10/2011 | Nordsiek et al. |
| 2011/0263637 | A1 | 10/2011 | Nordsiek et al. |

FOREIGN PATENT DOCUMENTS

| | | | |
|---|---|---|---|
| EP | 1889609 | A2 | 2/2008 |
| EP | 1891953 | | 2/2008 |
| IN | 1581/MUM/2005 | | 8/2007 |
| UA | 93496 | | 2/2011 |
| UA | 96124 | | 10/2011 |
| WO | WO 00/40228 | A1 | 7/2000 |
| WO | WO 02/102377 | A1 | 12/2002 |
| WO | WO 03/045391 | A1 | 6/2003 |
| WO | WO 2007/007208 | A2 | 1/2007 |
| WO | WO 2007/044639 | A2 | 4/2007 |
| WO | WO 2007/070643 | A2 | 6/2007 |
| WO | WO 2007/070694 | A2 | 6/2007 |
| WO | WO 2007/070695 | A2 | 6/2007 |
| WO | WO 2008/010963 | A2 | 1/2008 |
| WO | WO 2008/016475 | A2 | 2/2008 |
| WO | WO 2008/098232 | A1 | 8/2008 |
| WO | WO 2008/118762 | A1 | 10/2008 |
| WO | WO 2008/118763 | A1 | 10/2008 |
| WO | WO 2008/118765 | A1 | 10/2008 |
| WO | WO 2008/140713 | A1 | 11/2008 |
| WO | WO 2009/019473 | A1 | 2/2009 |
| WO | WO 2009/091541 | A1 | 7/2009 |
| WO | WO 2009/095226 | A2 | 8/2009 |
| WO | WO 2009/155070 | A2 | 12/2009 |
| WO | WO 2009/158687 | A1 | 12/2009 |
| WO | WO 2010/050889 | A1 | 5/2010 |
| WO | WO 2010/088924 | A1 | 8/2010 |

OTHER PUBLICATIONS

Arican et al., "Topical Imiquimod 5% Cream in External Anogential Warts: A Randomized, Double-Blind, Placebo-Controlled Study," The Journal of Dermatology, 2004, vol. 31: 627-631.

Aschenbrenner et al., Drug Therapy in Nursing, Third Edition, 2009, by Wolters Kluwer Health, Lippincott Williams & Wilkins, Philadelphia, PA, p. 51.

Ben M'Barek, L. et al., "5% topical imiquimod tolerance in transplant recipients," Dermatol., 215(2):130-3, 2007.

Berman, B. "Imiquimod: a new immune response modifier for the treatment of external genital warts and other diseases in dermatology," Int. J. Dermatol., 41(Suppl S1):7-11, 2002.

Berman, B. et al., "Determination of the area of skin capable of being covered by the application of 250 mg of 5% imiquimod cream," Dermatologic surgery: Official Publication for American Society for Dermatologic Surgery, 30(5):784-786, 2004.

Berman, B. et al., "Novel dermatologic uses of the immune response modifier imiquimod 5% cream," Skin Therapy Lett., 7(9):1-6, 2002.

Berman, B. et al., "Pharmacotherapy of actinic keratosis," Expert Opin. Pharmacother., 10(18):3015-31, 2009.

Berman, Brian et al., "The Role of Imiquimod 3.75% Cream in the Treatment of External Genital Warts," http://www.skintherapyletter.com/2012/17.4/2.html , 6 pages.

Beutner, K. et al., "Imiquimod, a patient-applied immune-response modifier for treatment of external genital warts," Antimicrobial Agents and Therapy, 42:789-794, 1998.

(56) References Cited

OTHER PUBLICATIONS

Beutner, K. et al., "Treatment of genital warts with an immune-response modifier (imiquimod)," J. Am. Acad. Dermatol., 1998, 38(2 Pt 1):230-9.
Bianchi, L. et al., "Actinic keratosis treated with an immune response modifier: a case report of six patients," Clin. Exp. Dermatol., 28(Suppl 1):39-41, 2003.
Bukhardt Pérez, M. et al., "Basal cell carcinoma: treatment with imiquimod," Int. J. Derm., 46:539-542, 2007.
Burns, C., "Imiquimod for the treatment of skin cancer," Dermatol. Clin., 23(1):151-64, 2005.
Chen, J. et al., "Short-course therapy with imiquimod 5% cream for solar keratoses: A randomizedcontrolled trial," Australasian J. Dermatol., 44:250-255, 2003.
Chollet, J. et al., "Development of a topically active imiquimod formulation," Pharm. Devel. Tech., 4(1):35-43, 1999.
CL2183-2009 Andromaco Opposition—Chilean counterpart.
CL2183-2009 Asilfa Opposition—Chilean counterpart.
CL2183-2009 Recalcine Opposition—Chilean counterpart.
Croda Oleochemicals, "Priolene TM 5936 High Purity Oleic Acid," 2008, 2 pages.
Del Rosso, J. et al., "Safety and efficacy of multiple 16-week courses of topical imiquimod for the treatment of large areas of skin involved with actinic keratoses," J. Clin. Aesth. Dermatol., 2(4):20-8, 2009.
Del Rosso, J., "New and emerging topical approaches for actinic keratoses," Cutis., 72(4):273-6, 279, 2003.
Del Rosso, J., "The use of topical imiquimod for the treatment of actinic keratosis: a status report," Cutis, 76(4):241-8, 2005.
Dockrell et al., "imiquimod and resiquimod as novel immunomodulators," Journal of Antimicrobial Chemotherapy, 2001, vol. 48, pp. 751-755.
Edwards et al., "Self-administered topical 5% imiquimod cream for external anogenital warts," Arch. Dermatol., 134:25-30, 1998.
Edwards et al., "Effect of intralesional alpha-2 interferon on actinic keratosis," Arch. Dermatol., 122:779-782, 1986.
Edwards, L. et al., "Imiquimod in clinical practice," Arch. Derm., 42:789-94, 1998. (Also reported in Aus. J. Derm., 39:S14-S16, 1998.).
Ezughah, F. et al., "Confirmation of histological clearance of superficial basal cell carcinoma with multiple serial sectioning and Mohs' micrographic surgery following treatment with imiquimod 5% cream," J. Derm. Treat., 19:111-117, 2008.
Fife, K. et al., "Treatment of External Genital Warts in Men Using 5% Imiquimod Cream Applied Three Times a Week, Once Daily, Twice Daily, or Three Times a Day," Sexually Transmitted Diseases, 2001 28(4):226-31.
Final Office Action dated Jan. 19, 2011 in U.S. Appl. No. 12/028,771.
Garland, S., "An open-label phase II pilot study investigating the optimal duration of imiquimod 5% cream for the treatment of external genital warts in women," Int. J. STD & AIDS, 2006,17(7):448-52.
Garland, S., "Imiquimod," Curr. Opin. Infect. Dis., 16(2):85-9, 2003.
Gaspari, A et al., "Beyond a decade of 5% Imiquimod topical therapy," J Drugs Dermatol, 2009; 8:467-674.
Gebauer, K. et al., "Effect of dosing frequency on the safety and efficacy of imiquimod 5% cream for treatment of actinic keratosis on the forearms and hands: a phase II, randomized placebo-controlled trial," Br. J. Dermatol., 161(4):897-903, 2009.
Gollnick, H. et al., "Safety and efficacy of imiquimod 5% cream in the treatment of penile genital warts in uncircumcised men when applied three times weekly or once per day," Int. J. STD & AIDS, 2001, 12(1):22-8.
Gotovtseva, E. et al., "Optimal frequency of imiquimod (Aldara) 5% cream for the treatment of external genital warts in immunocompetent adults: a meta-analysis," Sexually Transmitted Diseases, 35(4):346-351, 2008.
Gupta, A. et al., "Imiquimod: a review," J. Cutan. Med. Surg., 6(6):554-60, 2002.
Gupta, A. et al., "Viral and nonviral uses of imiquimod: a review," J. Cutaneous Med. Surg., 8(5):338-52, 2004.
Gupta, A. et al., "Evaluation of the effectiveness of imiquimod and 5-fluorouracil for the treatment of actinic keratosis: Critical review and meta-analysis of efficacy studies," J. Cutan. Med. Surg., 9(5):209-14, 2005.
Hadley, G. et al., "Imiquimod for actinic keratosis: systematic review and meta-analysis," J. Invest. Dermatol., 126(6):1251-5, 2006.
Harrison, L. et al., "Pharmacokinetics and safety of imiquimod 5% cream in the treatment of actinic kertoses of the face, scalp, or hands and arms," Arch. Dermatol. Res., 296:6-11, 2004.
Harrison, L. et al., "A pharmaceutical comparison of different commercially available imiquimod 5% cream poducts," J. Dermatol. Treat., 20(3):160-164, 2009.
He, Q., "Preparation of imiquimod cream and its clinical application in the treatment of condyloma acuminatum," Herald of Medicine, Yiyao Daobao, 23(10):758-760, 2004. (English abstract).
Imiquimod (topical) Package Insert, 1999, 7 pages.
International Search Report and Written Opinion dated Jun. 27, 2008 in PCT/US0853522.
Jorizzo, J. et al., "Vehicle-controlled, double-blind, randomized study of imiquimod 5% cream applied 3 days per week in one or two courses of treatment for actinic keratoses on the head," J. Am. Acad. Dermatol., 57(2):265-8, 2007.
Kim, Se-Jeong et al., "Analysis of cellular and behavioral responses to imiquimod reveals a unique itch pathway in transient receptor potential vanilloid 1 (TRPV1)-expressing neurons," PNAS, Feb. 22, 2011, vol. 108, No. 8, pp. 3371-3376.
Korman, N. et al., "Dosing with 5% imiquimod cream 3 times per week for the treatment of actinic keratosis: results of two phase 3, randomized, double-blind, parallel-group, vehicle-controlled trials," Arch. Dermatol. Res., 141(4):467-73, 2005.
Kose, O. et al., "Comparison of the efficacy and tolerability of 3% diclofenac sodium gel and 5% imiquimod cream in the treatment of actinic keratosis," J. Dermatol. Treat., 19(3):159-63, 2008.
Krawtchenko, N., "A randomised study of topical 5% imiquimod vs. topical5-fluorouracil vs. cryosurgery in immunocompetent atients with actinic keratoses: a comparison of clinical and histological outcomes including 1-year follow-up," Br. J. Dermatol., 157(Suppl. 2):34-40, 2007.
Lebwohl, M. et al., "Imiquimod 5% cream for the treatment of actinic keratosis: results from two phase III, randomized, double-blind, parallel group, vehicle-controlled trials," J. Am. Acad. Dermatol., 50(5):714-21, 2004.
Love, W. et al., "Topical Imiquimod or Fluorouracil Therapy for Basal and Squamous Cell Carcinoma," Arch. Derm., 145:1431-1438, 2009.
Majewski, S. et al., "Imiquimod is a strong inhibitor of tumor cell-induced angiogenesis," Int. J. Dermatol., 44(1):14-19, 2005.
Miller, R. et al., "Review article imiquimod applied topically: a novel immune response modifier and new class of drug," Int. J. of Immunopharm., 21(1):1-14, 1999.
Monograph of Aldara Product (Feb. 3, 2004).
Muzio, G. et al., "Treatment of non-genital warts with topical imiquimod 5% Cream," Eur. J. Derm., 12:347-349, 2002.
Office Action dated Jun. 27, 2012 for Canadian Application No. 2,697,978; Filing Date: Mar. 30, 2010; Owner: Medicis Pharmaceutical Corporation.
Office Action dated May 4, 2010 in U.S. Appl. No. 12/028,771.
Office Action dated Oct. 5, 2012 for U.S. Appl. No. 13/533,913, filed Jun. 26, 2012; First Named Inventor: Michael T. Nordsiek; Confirmation No. 8623.
Office Action dated Oct. 3, 2012 for U.S. Appl. No. 13/559,444, filed Jul. 26, 2012; First Named Inventor: Michael T. Nordsiek; Confirmation No. 8307.
Office Action dated Oct. 3, 2012 for U.S. Appl. No. 13/559,456, filed Jul. 26, 2012; First Named Inventor: Michael T. Nordsiek; Confirmation No. 2923.
Office Action dated Sep. 14, 2012 for U.S. Appl. No. 13/559,473, filed Jul. 26, 2012; First Named Inventor: Michael T. Nordsiek; Confirmation No. 5746.

(56) References Cited

OTHER PUBLICATIONS

Office Action dated Aug. 17, 2012 for U.S. Appl. No. 12/543,434, filed Aug. 18, 2009; First Named Inventor: Jefferson J. Gregory; Confirmation No. 7329.
Office Action dated Aug. 17, 2012 for U.S. Appl. No. 13/533,801, filed Jun. 26, 2012; First Named Inventor: Jefferson J. Gregory; Confirmation No. 9802.
Office Action dated Aug. 30, 2012 for U.S. Appl. No. 13/552,535, filed Jul. 18, 2012; First Named Inventor: Jefferson J. Gregory; Confirmation No. 2736.
Office Action dated Sep. 18, 2012 for U.S. Appl. No. 13/552,543, filed Jul. 18, 2012; First Named Inventor: Jefferson J. Gregory; Confirmation No. 7820.
Office Action dated Feb. 26, 2013 for U.S. Appl. No. 13/559,473, filed Jul. 26, 2012; First Named Inventor: Michael T. Nordsiek: Confirmation No. 5746; 25 pages.
Ooi, T. et al., "Imiquimod-induced regression of actinic keratosis is associated with infiltration by Tlymphocytes and dendritic cells: a randomized controlled trial," Br. J. Dermatol., 154(1):72-8, 2006.
Panama—Report on State of Art—foreign counterpart application No. 88551.
Papadavid, E. et al., "Imiquimod: an immune response modifier in the treatment of precancerous skin lesions and skin cancer," Expert Opin. Pharmacother., 8(11):1743-55, 2007.
Partial translation of Panama Report—foreign counterpart application No. 88551.
Perras, C., "Imiquimod 5% cream for actinic keratosis," Issues Emerg. Health Technol., 61:1-4, 2004.
Persaud, A. et al., "Clinical effect of imiquimod 5% cream in the treatment of actinic keratosis," J. Am. Acad. Dermatol., 47(4):553-6, 2002.
Persaud, A. et al., "Imiquimod cream in the treatment of actinic keratoses," J. Am. Acad. Dermatol., 47(4 Suppl): S236-9, 2002.
Peters-Kennedy, J. et al., "Apparent clinical resolution of pinnal actinic keratoses and squamous cell carcinoma in a cat using topical imiquimod 5% cream," J Feline Med. Surg., 10(6):593-9, 2008.
Quirk, C. et al., "Two-year interim results from a 5-year study evaluating clinical recurrence of superficial basal cell carcinoma after treatment with imiquimod 5% cream daily for 6 weeks," Aus. J. Derm., 47:258-265, 2006.
Ramoni, S. et al., "Penile intraepithelial carcinoma treated with imiquimod 1% in an HIV-positive patient," J. Derm. Treatment, 20: 177-178, 2009.
Rivers, J. et al., "Open-label study to assess the safety and efficacy of imiquimod 5% cream applied once daily three times per week in cycles for treatment of actinic keratoses on the head," J. Cutaneous Med. Surgery, 12(3):97-101, 2008.
Salasche, S. et al., "Cycle therapy of actinic keratoses of the face and scalp with 5% topical imiquimod cream: An open-label trial," J. Am. Acad. Dermatol., 47(4):571-7, 2002.
Schulze, H. et al., "Imiquimod 5% cream for the treatment of superficial basal cell carcinoma: results from a randomized vehicle-controlled phase III study in Europe," British J. Derm., 152:939-947, 2005.
Shaffelburg, M., "Treatment of actinic keratoses with sequential use of photodynamic therapy; and imiquimod 5% cream," J. Drugs Dermatol., 8(1):35-39, 2009.
Skinner, R., "Role of topical therapies in the management of cutaneous disease," J. Cutan. Med. Surg., 8(Suppl 3):22-31, 2004.
Somani, N. et al., "Imiquimod 5% cream for the treatment of actinic keratoses," Skin Ther. Lett., 10(2):1-6, 2005.
Sotiriou, E. et al., "Intraindividual, right-left comparison of topical 5-aminolevulinic acid photodynamic therapy vs. 5% imiquimod cream for actinic keratoses on the upper extremities," J. Eur. Acad. Dermatol. Venereol., 23(9):1061-5, 2009.
Stockfleth, E. et al., "A randomized, double-blind, vehicle-controlled study to assess 5% imiquimod cream for the treatment of multiple actinic keratoses," Arch. Dermatol., 138(11):1498-502, 2002.
Stockfleth, E. et al., "Multicentre, open-label study using imiquimod 5% cream in one or two 4-week courses of treatment for multiple actinic keratoses on the head," Br. J. Dermatol., 157(Suppl 2):41-6, 2007.
Stockfleth, E. et al., "Treatment of multiple, multiform actinic keratoses on the head with imiquimod 5% cream," Eur. J. Dermatol., 19(4):355-9, 2009.
Stockfleth, E. et al., "Successful treatment of actinic keratosis with imiquimod cream 5%: a report of six cases," Br. J. Dermatol., 144(5):1050-3, 2001.
Stockfleth, E., "Topical management of actinic keratosis and field cancerisation," G. Ital. Dermatol. Venereol., 144(4):459-62, 2009.
Swanson, N. et al., "Optimizing imiquimod for actinic keratoses on face or scalp: imiquimod 2.5% and 3.75% daily for two 2-week or 3-week cycles," The 12th World Congress on Cancers of the Skin, Presentation Date: May 4, 2009.
Syed et al., "Treatment of genital herpes in males with imiquimod 1% cream a randomised, double-blind, placebo-controlled study," Clin. Drug Invest., 16:187-191, 1998.
Syed, T. et al., "Management of female genital warts with an analog of imiquimod 2% in cream: a randomized, double-blind, placebo-controlled study," J. Dermatol., 25:429-33, 1998.
Syed, T. et al., "Treatment of external genital warts in men with imiquimod 2% in cream. A placebo-controlled, double-blind study," J. Infection, 41:148-151, 2000.
Szeimies, R. et al., "Imiquimod 5% cream for the treatment of actinic keratosis: results from a phase III, randomized, double-blind, vehicle-controlled, clinical trial with histology," J. Am. Acad. Dermatol., 51(4):547-55, 2004.
Tan, J. et al., "Efficacy of imiquimod as an adjunct to cryotherapy for actinic keratoses," J. Cutan. Med. Surg., 11(6):195-201, 2007.
Tanghetti, E. et al., "Comparison of 5% 5-fluorouracil cream and 5% imiquimod cream in the management of actinic keratoses on the face and scalp," J. Drugs Dermatol., 6(2):144-7, 2007.
Torres, A. et al., "Immune-mediated changes in actinic keratosis following topical treatment with imiquimod 5% cream," J. Transl. Med., 5(7):1-18, 2007.
Travis, L. et al., "Successful treatment of vulvar intraepitheilial neoplasia with topical imiquimod 5% cream in a lung transplanted patient," Acta Derm. Venereol., 82:475-6, 2002.
Trofatter, K. et al., "Increased frequency of dosing of imiquimod 5% cream in the treatment of external genital warts in women," Int. J. Gynecol. Obstet., 2002, 76(2):191-3.
Tyring, S. et al., "A randomized, controlled, molecular study of condylomata acuminata clearance during treatment with imiquimod," J. Infect. Dis., 1998, 178(2):551-5.
Tyring, S., "Imiquimod applied topically: A novel immune response modifier," Skin Therapy Lett., 6(6)1-4, 2001.
Ulrich, C. et al., "Topical immunomodulation under systemic immunosuppression: results of a multicentre, randomized, placebo-controlled safety and efficacy study of imiquimod 5% cream for the treatment of actinic keratoses in kidney, heart, and liver transplant patients," Br. J. Dermatol., 157(Suppl 2):25-31, 2007.
Vidal, D., "Topical imiquimod: mechanism of action and clinical applications," Mini Rev. Med. Chem., 6(5):499-503, 2006.
Wagman, F. et al., "Self-Administered Topical 5% Imiquimod Cream for External Anogenital Warts in Adolescent Girls," Obset. Gynecol., 2001, 97:S14.
Wagstaff, A. et al., "Topical imiquimod: a review of its use in the management of anogenital warts, actinic keratoses, basal cell carcinoma and other skin lesions," Drugs, 67(15):2187-210, 2007.
Walker, J. et al., "Is imiquimod effective and safe for actinic keratosis?," J. Fam. Pract., 52(3):84-5, 2003.
Wu, J. et al., "Treatment of Bowen's disease and basal cell carcinoma of the nose with imiquimod 5% cream," Australasian J. Dermatol., 44(2):123-125, 2003.
Zeichner, J. et al., "Placebo-controlled, double-blind, randomized pilot study of imiquimod 5% cream applied once per week for 6 months for the treatment of actinic keratoses," J. Am. Acad. Dermatol., 60(1):59-62, 2009.

Note: Points marked with ** show statistically significant difference from placebo. Subjects received treatment for 8 weeks or until complete clearance, whichever was sooner.

Complete Clearance Rates vs Analysis Week during the Evaluation Period – PP Population (Observed Cases)

B—B—B 3.75%  A···A···A 2.5%  C—C—C Placebo

Note: Points marked with ** show statistically significant difference from placebo. Subjects received treatment for 8 weeks or until complete clearance, whichever was sooner.

Rates of Partial (>75%) Clearance at End of Study -- ITT Populatoin (LOCF)

Rates of Partial (≥75%) Clearance at End of Study – PP Population (Observed Cases)

Bars marked with ** show statistically significant from placebo. The vertical lines represent 95% confidence intervals.

Note : Each bar is marked with the number of subjects included in the mean.

Complete Clearance Rates at End of Study -- ITT Population (LOCF)

Bars marked with ** show statistically significant difference from placebo. The vertical lines represent 95% confidence intervals.

Complete Clearance Rates at End of Study -- PP Population
(Observed Cases)

Bars marked with ** show statistically significant defference from placebo. The vertical lines represent 95% confidence intervals.

Complete Clearance Rates vs Analysis Week during the Evaluation Period -- ITT Population (LOCF)

Rates of Partial (>75%) Clearance at End of Study -- ITT Population (LOCF)

Rates of >50% Clearance at End of Study -- ITT Population (LOCF)

Note: The above graphs include mean serum concentrations that are <LLOQ (0.050 ng/mL). R-837=imiquimod Mean (±1.96*SE) Serum Concentrations of Imiquimod (R-837) and its Metabolites
(S-26704 and S-27700 Combined) on Day 21 (Linear and Semi-Log Scale)

Linear Scale

Note: The above graphs include mean serum concentrations that are <LLOQ (0.050 ng/mL).

LOWER DOSAGE STRENGTH IMIQUIMOD FORMULATIONS AND SHORT DOSING REGIMENS FOR TREATING GENITAL AND PERIANAL WARTS

CROSS-REFERENCE TO RELATED APPLICATIONS

This application is a continuation of U.S. patent application Ser. No. 14/796,296 filed Jul. 10, 2015, which is a continuation of U.S. patent application Ser. No. 14/091,965 filed Nov. 27, 2013, which is a continuation of U.S. patent application Ser. No. 13/559,473 filed Jul. 26, 2012, which is a continuation of U.S. patent application Ser. No. 12/771,076 filed Apr. 3, 2010; and which claims priority to U.S. Provisional Patent Application No. 61/341,721 filed Apr. 1, 2010, U.S. Provisional Patent Application No. 61/341,476 filed Mar. 30, 2010, and U.S. Provisional Patent Application No. 61/225,202 filed Jul. 13, 2009, the teachings of which are hereby incorporated by reference in their entireties for all purposes.

FIELD OF THE INVENTION

The present invention relates to pharmaceutical formulations and methods for the topical or transdermal delivery of 1-isobutyl-1H-imidazo[4,5-c]-quinolin-4-amine, also known as (a.k.a.) 1-(2-methylpropyl)-1H-imidazo[4,5-c]quinolin-4-amine, a.k.a. imiquimod, to treat genital and perianal warts with shorter durations of therapy, than currently prescribed for the commercially available Aldara® 5% imiquimod cream, as now approved by the U.S. Food & Drug Administration ("FDA"). More specifically, the present invention is directed to lower dosage strength imiquimod formulations to deliver an efficacious dose for treating genital and perianal warts with an acceptable safety profile, but with a dosing regimen that is shorter and more convenient for patient use than the dosing regimen currently approved by the FDA for Aldara® 5% imiquimod cream.

BACKGROUND OF THE INVENTION

External Genital Warts (EGW), or condylomata acuminate, are caused by infection with human papilloma virus (HPV), the most common sexually transmitted virus in the Western world (Lyttle 1994, Mayeaux 1995, Shah 1990). Approximately 1% of the sexually active population between 15 and 49 years of age in the US is estimated to have EGW (Koutsky 1988, Koutsky 1997). Most EGWs are associated with HPV types 6 and 11 (Phelps 1995).

In 1997, imiquimod 5% cream (Aldara®) was approved for the treatment of EGW and perianal warts. Imiquimod, an immune response modifier that stimulates the innate and adaptive immune response, has been demonstrated to be an effective and safe treatment for EGWs. Stimulation of the immune response has been shown to decrease HPV viral load (Kreuter 2006) and may decrease the recurrence rate of visible warts, although observed rates after treatments do vary.

Imiquimod, however, has no direct antiviral activity in cell culture. A study in 22 patients with genital/perianal warts comparing Aldara® 5% imiquimod cream and vehicle shows that Aldara® 5% imiquimod cream induces mRNA encoding cytokines including interferon-α at the treatment site. In addition, HPVL1 mRNA and HPV DNA are significantly decreased following treatment. However, the clinical relevance of these findings is unknown.

Specific antiviral therapy for the treatment of EGW is lacking, but drug and other therapies have been used. Ablative treatment modalities include procedures such as surgical excision, laser therapy, and cryotherapy. Other approaches include topical treatments, such as acetic acid, podophylline, podophyllotoxin, and 5-fluorouracil, which are cytodestructive, and sinecatechins, whose mechanism of action is unknown. Each of these therapies has disadvantages such as inconvenient regimens, pain or burning associated with the therapy, scarring, itching, or high recurrence rates.

Aldara® 5% imiquimod cream is approved for the treatment of external genital and perianal warts (condylomata acuminata) in individuals 12 years old and above (Aldara® Package Insert). The approved dosing regimen is 3 times per week, for up to 16 weeks of treatment.

The compound characterized as 1-isobutyl-1H-imidazo[4,5-c]-quinolin-4-amine or 1-(2-methylpropyl)-1H-imidazo[4,5-c]quinolin-4-amine, and known as imiquimod, is disclosed in U.S. Pat. No. 4,689,338 and described therein as an antiviral agent and as an interferon inducer. A variety of formulations for topical administration of imiquimod are also described therein. This U.S. Pat. No. 4,689,338 is incorporated herein by reference in its entirety.

U.S. Pat. No. 4,751,087 discloses the use of a combination of ethyl oleate and glyceryl monolaurate as a skin penetration enhancer for nitroglycerin, with all three components being contained in the adhesive layer of a transdermal patch; this U.S. patent is incorporated herein by reference in its entirety.

U.S. Pat. No. 4,411,893 discloses the use of N,N-dimethyldodecylamine-N-oxide as a skin penetration enhancer in aqueous systems; this U.S. patent is incorporated herein by reference in its entirety.

U.S. Pat. No. 4,722,941 discloses readily absorbable pharmaceutical compositions that comprise a pharmacologically active agent distributed in a vehicle comprising an absorption-enhancing amount of at least one fatty acid containing 6 to 12 carbon atoms and optionally a fatty acid monoglyceride. Such compositions are said to be particularly useful for increasing the absorption of pharmacologically active bases; this U.S. patent is incorporated herein by reference in its entirety.

U.S. Pat. No. 4,746,515 discloses a method of using glyceryl monolaurate to enhance the transdermal flux of a transdermally deliverable drug through intact skin; this U.S. patent is incorporated herein by reference in its entirety.

U.S. Pat. Nos. 5,238,944, 7,038,051, 6,693,113, 6,894,060, 7,655,672, U.S. Patent Publication No. 2009/0093514 A1, U.S. Patent Publication No. 2007/0123558, U.S. Patent Publication No. 2004/087614, U.S. Patent Publication No. 2002/147210, PCT Publication No. WO2008082381 and PCT Publication No. WO2008US53522 disclose topical formulations and/or topical and transdermal delivery systems containing 1-isobutyl-1H-imidazo[4,5-c]-quinolin-4-amine or 1-(2-methylpropyl)-1H-imidazo[4,5-c]quinolin-4-amine; each of these patents and patent publications are incorporated herein by reference in their entireties.

Currently, the FDA has approved a 5% imiquimod cream, commercially available under the brand name Aldara®, to treat certain dermal and mucosal associated conditions, such as (1) the topical treatment of clinically typical, nonhyperkeratotic actinic keratosis (AK) on the face or scalp in immunocompetent adults, (2) topical treatment of biopsy-confirmed, primary superficial basal cell carcinoma (sBCC) in immunocompetent adults, and (3) the topical treatment of external genital and perianal warts/condyloma acuminate (hereinafter, individually or jointly "EGWs") in patients 12 years or older.

Aldara® is the brand name for an FDA-approved 5% imiquimod cream, which is an immune response modifier. Each gram of the Aldara® 5% imiquimod cream contains 50 mg of imiquimod in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben. The Aldara® 5% imiquimod cream is packaged in single-use packets or sachets, each containing 250 mg of cream, equivalent to 12.5 mg of imiquimod.

Chemically, imiquimod, as indicated above, is known as 1-(2-methylpropyl)-1H-imidazo[4,5-c]quinolin-4-amine or 1-isobutyl-1H-imidazo[4,5-c]-quinolin-4-amine. Imiquimod has a molecular formula of $C_{14}H_{16}N_4$ and a molecular weight of 240.3. The chemical structural formula for imiquimod is as follows:

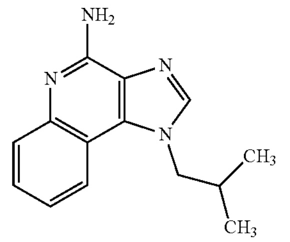 [SMILES: CC(C)Cn1cnc2c(N)nc3ccccc3c21]

Notwithstanding FDA approval, Aldara® 5% imiquimod cream treatment for EGWs is not without limitation, including an unsimplified and lengthy dosing regimen (administration three times per week until total clearance of EGWs is achieved, or up to 16 weeks). According to the LDA-approved label for Aldara® 5% imiquimod cream, the median time to complete wart clearance is 10 weeks. The eccentric dosing schedule is not easy to remember, which could lead to reduced compliance with resulting reduced efficacy. If applied too thickly or generously, Aldara® 5% imiquimod cream can cause site or local skin reactions, such as erosions or ulcerations, causing pain or dysfunction (e.g., of the foreskin or urethra). In addition, efficacy of treatment with Aldara® 5% imiquimod cream may be limited, especially in men, in patients with longstanding or recurrent disease, or for treatment of keratinized areas (e.g., inguinal). In some cases, a rest period from scheduled dosing with Aldara® 5% imiquimod cream may be needed, and consultation or reevaluation by healthcare provider may also be required. Other symptoms, such as perianal itching or systemic effects such as flu-like symptoms, may also occur in some cases after treatment with Aldara® 5% imiquimod cream.

In view of the above, there is a need for improved EGW topical treatment that overcomes the current limitations associated with the current FDA-approved topical treatment regimen for EGWs, i.e., administration until there is total clearance of the EGWs, for up to 16 weeks, three days per week, with FDA-approved Aldara® 5% imiquimod cream.

SUMMARY OF THE INVENTION

The present invention addresses the above-mentioned limitations associated with the treatment of EGWs with FDA-approved Aldara® 5% imiquimod cream through the discovery of novel and improved imiquimod treatment regimens of short duration, lower dosage strength imiquimod pharmaceutical formulations, and simplified dosing regimens to treat EGWs.

Generally speaking, the present invention provides for new and improved substantially less-irritating lower dosage strength imiquimod pharmaceutical formulations, which are suitable for daily application in connection with substantially condensed treatment regimens, for topical and/or transdermal administration of an effective amount of imiquimod to treat subjects who are diagnosed with external genital and perianal warts/condyloma acuminate (EGWs). In addition, the present invention provides for new and improved EGW treatments, wherein: (1) treatment periods of the present invention are substantially shorter in duration, i.e., up to eight weeks and preferably up to six weeks or four weeks, than the current FDA-approved up-to-16-week treatment regimen for EGWs treatment; (2) dosing regimens of the present invention are substantially simpler, i.e., one application daily each day for up to eight weeks and preferably up to six weeks or four weeks, than the current dosing regimen, as compared to the once-a-day but only three times per week for up to 16 weeks regimen for the current FDA-approved Aldara® 5% imiquimod cream for EGWs treatment; (3) less-irritating imiquimod pharmaceutical formulations of the present invention are formulated with a lower dosage strength, i.e., between about 1% and about 4.25% imiquimod, than the current FDA-approved Aldara® 5% imiquimod cream for EGWs treatment; and (4) lower subject incidence of application site reactions is experienced in accordance with the present invention, as compared with higher subject incidence of application site reactions experienced with the current FDA-approved Aldara® 5% imiquimod cream and treatment regimen for EGWs treatment.

In other words, the present invention provides for new and improved EGWs treatments that have short durations of therapies, use lower imiquimod dosage strengths, have simplified daily dosing regimens, and have a lower incidence of application site reactions, as compared to treatment of EGWs with Aldara® 5% imiquimod cream, as currently approved by the FDA.

The present invention thus provides numerous surprising advantages over current FDA-approved Aldara® 5% imiquimod cream therapy for EGWs treatment. For example, the present invention provides for (1) a shortened treatment regimen, i.e., up to about 8 weeks, or preferably up to about 6 weeks and preferably up to about 4 weeks, (2) a simplified dosing regimen, i.e., once daily on each day of the treatment period, (3) low systemic imiquimod blood levels even though the dosing frequency is increased, and (4) a lower subject incidence of application site reactions during the topical treatment regimen of EGWs, than currently associated with FDA-approved Aldara® 5% imiquimod cream therapy.

Thus, the present invention overcomes certain of the limitations associated with the treatment of EGWs with FDA-approved Aldara® 5% imiquimod cream and addresses current medical needs for (1) a shorter treatment period, (2) a more intuitive dosing regimen (daily dosing vs. thrice weekly dosing for Aldara® 5% imiquimod cream) and (3) less or a lower incidence of application site reactions.

The less-irritating lower dosage strength imiquimod pharmaceutical formulations of the present invention may comprise:

1. a lower dosage strength of 1-isobutyl-1H-imidazo[4,5-c]-quinolin-4-amine or 1-(2-methylpropyl)-1H-imidazo[4, 5-c]quinolin-4-amine (imiquimod) for delivering an effective amount of imiquimod; and 2. a pharmaceutically acceptable vehicle for imiquimod, which vehicle comprises a fatty acid, such as isostearic acid, palmitic acid, stearic acid, linoleic acid, unrefined oleic acid, refined oleic acid, such as Super Refined® oleic acid NF (e.g., a highly purified oleic acid, i.e., an oleic acid which has low polar purities, such as peroxides, a low peroxide value and is marketed by CRODA; see e.g., www.crodausa.com) and a combination thereof, in a total amount of about 3 percent to about 45 percent by weight based on the total weight of the formulation.

The lower dosage strength imiquimod formulations of the present invention, especially those wherein the vehicle comprises an isostearic acid as the fatty acid, are uniquely designed to have physical and chemical stability, solubility, emollient properties and dose proportionate delivery similar to or better than Aldara® 5% imiquimod cream. More specifically, the lower dosage strength imiquimod formulations of the present invention, especially those wherein the vehicle comprises an isostearic acid as the fatty acid, are believed to generally have similar or improved skin emolliency at the application site and dose proportionate release rates as to both the release rates of the imiquimod and the total amount of imiquimod released, relative to the Aldara® 5% imiquimod cream. In other words, the lower dosage strength imiquimod formulations of the present invention are concentration influenced and have similar release rates to the Aldara® 5% imiquimod cream. Additionally, the greater the amount of imiquimod in the formulation, the faster and the greater the total amount of imiquimod is released, evidencing that the amount in and the rate of release from the formulations are imiquimod concentration dependent. Thus, while the lower dose strength imiquimod formulations of the present invention deliver different cumulative amounts to the stratum corneum and epidermis, i.e., local skin delivery, than the Aldara® 5% imiquimod cream, such lower dosage strength imiquimod formulations are believed to have a proportional and linear relationship that is similar with the Aldara® 5% imiquimod cream as to both the rate of imiquimod release and the total amount of imiquimod released and delivered locally to the skin over time, so that the imiquimod concentrations in the formulations of the present invention, the imiquimod release rates and the amount of imiquimod unabsorbed and delivered to the stratum corneum and epidermis, which has been released from the formulations, are generally proportional and linear to the Aldara® 5% imiquimod cream.

In addition, the lower dosage strength imiquimod formulations of the present invention, especially those wherein the vehicle comprises an isostearic acid as the fatty acid, are uniquely designed to be stable and fall within the range of the specifications for the commercially available Aldara® 5% imiquimod cream, such as to viscosity, pH, and stability, including microscopic and macroscopic stability. More specifically, the imiquimod present in the lower dosage strength imiquimod formulations of the present invention, especially those wherein the vehicle comprises an isostearic acid as the fatty acid, (monograph range: 90 to 110%) and benzyl alcohol (monograph range: 50 to 105%) remain within limits at both about 25° C. and about 40° C. over about a one month period and within limits at both about 25° C. and about 40° C. over about a six month period. Furthermore, the lower dosage strength imiquimod formulations of the present invention, especially those wherein the vehicle comprises an isostearic acid as the fatty acid, remain stabile for about six months at about 25° C. and about 40° C., and also remain stable with respect to macroscopic and microscopic appearance, viscosity (monograph range: 2,000 to 35000 cPs) and pH (monograph range 4.0 to 5.5). In addition, the lower dosage strength imiquimod formulations of the present invention are uniquely designed to meet the requirements specified in both United States Pharmacopeia ("USP") and the European Pharmacopeia ("EP") as to preservative efficacy and remain free of degradation products when stored at about 25° C./60% RH, about 30° C./65% RH and about 40° C./75% RH over about one, about two, about three and about six months and analyzed at about 318 nm wavelength.

The present invention also contemplates lower dosage strength imiquimod formulations that have unique pharmacokinetic profiles when used, for example, in connection with the short durations of therapy to treat EGWs in accordance with the present invention. By way of example, a 3.75% imiquimod lower dosage strength formulation of the present invention, when approximately 250 mg of such a formulation (about 9.375 mg imiquimod) or less is applied daily for 21 days to EGWs in the genital/perianal area with a total wart area of greater than or equal to 100 $mm^2$, achieves steady state by about Day 7, and provides an in-vivo serum profile selected from one or more of the following:

(a) a Day 21 mean $T_{max}$ of about 9.7 hours with a standard deviation ("SD") of about 4.0, a median $T_{max}$ of about 12 hours and a geometric mean $T_{max}$ of about 8.3 hours and a coefficient of variation ("CV") of about 41%;

(b) a Day 21 mean $C_{max}$ of about 0.488 ng/ml with a standard deviation of about 0.368, a median $C_{max}$ of about 0.45 and a geometric mean $C_{max}$ of about 0.39 ng/mL and a coefficient of variation of about 75%;

(c) a Day 21 $T_{1/2}$ of from about 6.8 to about 54 hours and preferably a mean $T_{1/2}$, of about 24.1 hours with a standard deviation of about 12, a median $T_{1/2}$ of about 22.8 hours and a geometric mean $T_{1/2}$ of about 21 hours and a coefficient of variation of about 51%;

(d) a Day 21 $AUC_{0-24}$ of from about 1.9 to about 14 ng-hr/mL and preferably a mean $AUC_{0-24}$ of about 6.8 ng·hr/mL, with a standard deviation of about 3.6, a median $AUC_{0-24}$ of about 6.6 ng·hr/mL and a geometric mean $AUC_{0-24}$ of about 5.8 ng-hr/mL and a coefficient of variation of about 53%;

(e) a Day 21 λz of from about 0.013 $hr^{-1}$ to about 0.102 $hr^{-1}$ and preferably a mean λz of about 0.037 $hr^{-1}$ with a standard deviation of about 0.02, a median λz of about 0.03 $hr^{-1}$ and a geometric mean λz of about 0.03 $hr^{-1}$ and a coefficient of variation of about 60%;

(f) a Day 21 $C_{min}$ of from about 0.025 to about 0.47 and preferably a mean $C_{min}$ of about 0.158 with an SD of about 0.121, a median $C_{min}$ of about 0.14 and a geometric mean $C_{min}$ of about 0.11 and a coefficient of variation of about 77%;

(g) at Day 14/7 (a ratio of the trough concentration at Day 14 over the trough concentration at Day 7), a trough concentration geometric mean ratio of about 1.13 with a 90% confidence interval ("CI") within a range of between about 0.7 and about 1.7;

(h) at Day 21/14 (a ratio of the trough concentration at Day 21 over the trough concentration at Day 14), a trough concentration geometric mean ratio of about 0.84 with a 90% confidence interval ("CI") within a range of between about 0.5 and about 1.3;

(i) at Day 22/21 (a ratio of the trough concentration at Day 22 over the trough concentration at Day 21) a trough concentration geometric mean ratio of about 1.12 with a 90% confidence interval ("CI") within a range of between about 0.7 and about 1.6;

(j) a mean peak imiquimod serum concentration of about 0.488 ng/mL at Day 21;

(k) a Day 21 RAUC of from about 0.6 to about 7 and preferably a mean RAUC of about 2.2 with a standard deviation of about 1.8, a median RAUC of about 1.8 and a geometric mean RAUC of about 1.7 and a coefficient of variation of about 81%;

(l) a Day 21 $RC_{max}$ of from about 0.5 to about 5 and preferably a mean $RC_{max}$ of about 2.3 with a standard deviation of about 1.6, a median $RC_{max}$ of about 1.7 and a geometric mean $RC_{max}$, of about 1.8 and a coefficient of variation of about 70%;

(m) a Day 21 L $\lambda z_{eff}$ of from about 0.006 $hr^{-1}$ to about 0.09 $hr^{-1}$ and preferably a mean L $\lambda z_{eff}$ of about 0.04 hr-1 with a standard deviation of about 0.03, a median L $\lambda z_{eff}$ of about 0.03 $hr^{-1}$ and a geometric mean L $\lambda z_{eff}$ of about 0.03 $hr^{-1}$ and a coefficient of variation of about 69%;

(n) a Day 21 $T^{1/2\ eff}$ of from about 8 hr to about 111 hr and preferably a mean $T^{1/2}{}_{eff}$ of about 31 hr with a standard deviation of about 30, a median $T^{1/2}{}_{eff}$ of about 22 hr and a geometric mean $T^{1/2}{}_{eff}$ of about 23 $hr^{-1}$ and a coefficient of variation of about 97%;

(o) a Day 21 $C_{max}$ in female patients about 61% higher in female subjects than in male subjects (0.676 versus 0.420 ng/mL) and total systemic exposure AUC 0-24 8% higher in female subjects than in male subjects (7.192 versus 6.651 ng-hr/mL) when data is not dose normalized:

(p) a Day 21 $C_{max}$ in female patients about 35% higher than in male subjects (0.583 versus 0.431 ng/mL) and AUC 0-24 about 6% lower in female subjects than in male subjects (6.428 versus 6.858 ng-hr/mL) when using dose normalization to adjust for differences in dosage and reported without subjects who missed an application of study drug during the last week of dosing; and/or (q) a median $T_{max}$ occurring approximately twice as quickly in female subjects (about 6.50 hours) as in male subjects (about 12.0 hours).

In accordance with the present invention, a mean peak serum concentration is achieved with a 3.75% lower dosage strength imiquimod formulation of Examples 23-26. More specifically, a mean peak serum concentration of about 0.488 ng/mL is achieved with a 3.75% lower dosage strength imiquimod formulation of Examples 23-26 after about 9.4 mg of imiquimod is applied to the affected treatment area each day for up to 8 weeks.

Furthermore, this invention provides the following evidence of clinical efficacy: The wart area decreased by 45% from a mean of 108.3 $mm^2$ at baseline to 43.2 $mm^2$ at Day 21, e.g., see Table 145. The P value of <0.0001 for this change from baseline indicated a statistically significant ≤0.050) decrease in wart area after 3 weeks of treatment.

In accordance with the present invention, a mean peak serum concentration is achieved with a 3.75% lower dosage strength imiquimod formulation of Examples 23-26. More specifically, a mean peak serum concentration of about 0.488 ng/ml is achieved with a 3.75% lower dosage strength imiquimod formulation of Examples 23-26 after about 9.4 mg of imiquimod is applied to the affected treatment area, i.e., the external genital/perianal warts, each day until completely cleared or for up to eight weeks.

In addition, the present invention contemplates lower dosage strength formulations that are pharmaceutically equivalent, therapeutically equivalent, bioequivalent and/or interchangeable, regardless of the method selected to demonstrate equivalents or bioequivalence, such as dermatopharmacokinetic and pharmacokinetic methodologies, microdialysis, in vitro and in vivo methods and/or clinical endpoints. Thus, the present invention contemplates lower dosage strength imiquimod formulations that are bioequivalent, pharmaceutically equivalent and/or therapeutic equivalent, especially, 2.5% and 3.75% lower dosage strength imiquimod formulations that are bioequivalent, pharmaceutically equivalent and/or therapeutically equivalent, when used daily in accordance with the short durations of therapy of the present invention to treat EGWs, e.g., used on treatment areas, on a daily basis until complete wart clearance or for up to about eight weeks, six weeks, or up to about 4 weeks, optionally including a rest (no drug application) period.

Thus, the present invention contemplates: (a) pharmaceutically equivalent lower dosage strength imiquimod formulations which contain the same amount of imiquimod in the same dosage form; (b) bioequivalent lower dosage strength imiquimod formulations which are chemically equivalent and which, when administered to the same individuals in the same dosage regimens, result in comparable bioavailabilities; (c) therapeutic equivalent lower dosage strength imiquimod formulations which, when administered to the same individuals in the same dosage regimens, provide essentially the same efficacy and/or toxicity; and (d) interchangeable lower dosage strength imiquimod formulations of the present invention which are pharmaceutically equivalent, bioequivalent and therapeutically equivalent.

By the term "lower dosage strength(s)", as used herein, it refers to a pharmaceutical formulation containing imiquimod in an amount of between about 1.0 percent and about 4.25 percent by weight based on the total weight of the formulation and preferably a pharmaceutical formulation containing imiquimod in an amount of about 2.5% or about 3.75%.

By the term "short duration(s)" of therapy, as used herein, it refers to the daily topical application of an effective amount of imiquimod to a defined treatment area diagnosed with EGWs for a total on-treatment period of up to about 8 weeks, 6 weeks, or 4 weeks, depending upon which lower dosage strength imiquimod formulation of the present invention is selected for daily application, and more preferably a total on-treatment period of up to about 8, 6, or 4 weeks to treat EGWs. In addition, the "short durations" of therapy may also include an 8 week examination period (no further treatment) following the treatment period.

As indicated above, when the short durations of therapy are used in combination with the lower dosage strength imiquimod formulations of the present invention, it is surprisingly found that (1) simplified daily dosing regimens can be used, (2) the therapy is better tolerated than standard therapy with 5% imiquimod (Aldara®), resulting in effective treatment with lower dosage strength imiquimod formulations without inducing significant local skin reactions or irritation in the treatment area or treatment limiting adverse events which could result in premature therapy termination or significant voluntary rest periods of several days that are generally associated with higher concentrations of imiquimod therapy. It is also surprisingly found that as much as between about 250 mg of a low dosage strength imiquimod formulation may be used per application in accordance with the present invention, especially when the short durations of therapy are used in combination with the low dosage strength imiquimod formulations of the present invention.

Also quite surprisingly, the efficacy achieved by the lower dosage strength imiquimod formulations when used in either of the short durations of therapy, e.g., an up to 8-week treatment regimen, of the present invention for treatment of EGWs as to total clearance, partial clearance and a reduction in the number of warts is statistically significant over placebo, e.g., when a 3.75% imiquimod cream is used.

It should be noted that the efficacy P value that is achieved for a percent reduction in the number of warts for a 3.75% lower dosage strength imiquimod formulation versus a 2.5% lower dosage strength imiquimod formulation that is utilized in accordance with a treatment regimen of the present invention is not always statistically significant.

It should be understood that the short durations of therapy and lower dosage strength imiquimod formulations of the present invention are believed to be optimized to treat EGWs. By "optimized", it is meant herein that the short durations of therapy and lower dosage strength imiquimod formulations of the present invention are designed to achieve efficacy, stability and release rates profiles that are at least essentially equivalent to and linear with Aldara® 5% imiquimod cream, respectively, but with an improved acceptable safety profile. In this context, it should be appreciated that the primary efficacy variable used in the studies of the short durations of therapy and lower dosage strength imiquimod formulations of the present invention (complete clearance of all warts, both Baseline and newly emerged, in all assessed anatomic areas) was very conservative (see, e.g., Example 24), when compared to reported studies of Aldara® 5% imiquimod cream.

By the term "acceptable safety profile", it is meant herein to mean that treatment of EGWs with a short duration of therapy and a lower dosage strength imiquimod formulation in accordance with the present invention, does not cause treatment limiting side effects or rest periods in an appreciable number of subjects undergoing therapy for EGWs to a level that causes premature termination of treatment. The term "acceptable safety profile" also refers to treatment of EGWs with a short duration of therapy and a lower dosage strength imiquimod formulation of the present invention with a lower subject incidence of application site reactions as compared with treatment of EGWs with Aldara® 5% imiquimod cream.

The salient elements of a pharmaceutical formulation according to the present invention are (a) imiquimod and (b) a fatty acid, e.g., isostearic, palmitic, stearic, linoleic, unrefined oleic acid or refined oleic acid, such as Super Refined® oleic acid NF (e.g., a highly purified oleic acid, i.e., an oleic acid which has low polar impurities, such as peroxides, a low peroxide value and is marketed by CRODA; see e.g., www.crodausa.com) and mixtures thereof A pharmaceutical formulation of the invention can be in any form known to the art, including semi-solid dosage forms, such as a cream, an ointment, a foam, a gel, a lotion or a pressure-sensitive adhesive composition, each form containing the necessary elements in particular amounts and further containing various additional elements.

A cream of the invention contains an effective amount of imiquimod, such as between about greater than 1 percent and about 4.25 percent by weight of imiquimod, based on the total weight of the cream; about 5 percent to about 30 percent by weight of fatty acid, based on the total weight of the cream; and optional ingredients such as emollients, emulsifiers, thickeners, and/or preservatives.

An ointment of the invention contains an ointment base in addition to imiquimod and fatty acid. An ointment of the invention contains an effective amount of imiquimod, such as between about greater than 1 percent and about 4.25 percent by weight of imiquimod; about 3 percent to about 45 percent, more preferably about 3 percent to about 30 percent by weight fatty acid; and about 40 percent to about 95 percent by weight ointment base, all weights being based on the total weight of the ointment. Optionally, an ointment of the invention can also contain emulsifiers, emollients and thickeners.

A pressure-sensitive adhesive composition of the invention contains imiquimod, fatty acid, and an adhesive. The adhesives utilized in a pressure sensitive adhesive composition of the invention are preferably substantially chemically inert to imiquimod. A pressure sensitive adhesive composition of the invention preferably contains an effective amount of imiquimod, such as between about greater than 1 percent and about 4.25 percent by weight of imiquimod; about 10 percent to about 40 percent by weight, more preferably of about 15 percent to about 30 percent by weight, and most preferably about 20 percent to about 30 percent by weight of fatty acid; all weights being based on the total weight of the pressure sensitive adhesive composition.

Optionally, pressure sensitive adhesive compositions of the invention can also contain one or more skin penetration enhancers. The total amount of skin penetration enhancer(s) present in a pressure sensitive adhesive composition of the invention is preferably about 3 percent to about 25 percent by weight, and more preferably about 3 percent to about 10 percent by weight based on the total weight of the pressure sensitive adhesive composition.

A pressure-sensitive adhesive coated sheet material of the invention can be made from a pressure-sensitive adhesive composition of the invention in the form of an article such as a tape, a patch, a sheet, or a dressing.

A lower dosage strength formulation of the present invention may be used to topically and/or transdermally administer an effective amount of imiquimod to effectively treat EGWs with short durations of therapy and with an acceptable safety profile. Thus, lower dosage strength formulations according to the present invention can be applied to any suitable location, for example, topically to dermal, lip and/or mucosal surfaces. In the case of dermal application, for example, depending on the concentration, formulation composition, and dermal surface, the therapeutic effect of imiquimod may extend only to the superficial layers of the dermal surface or to tissues below the dermal surface.

It should be understood that while lower dosage strength formulations of the present invention containing, by weight based on the total weight of the formulation, between about 1% and about 4.25% imiquimod are contemplated, preferably between about 1.5%, 1.75%, 2.0%, 2.25%, 2.5%, 2.75%, 3.0%, 3.25%, 3.5%, 3.75%, 4.0% and 4.25% (between about 1.5% and about 4.25%), and even more preferably between about 2.0%, 2.25%, 2.5%, 2.75%, 3.0%, 3.25%, 3.5%, 3.75% and 4.0% (between about 2.0% and about 4.0%), and still even more preferably between about 2.5%, 2.75%, 3.0%, 3.25%, 3.5% and 3.75% (between about 2.5% and about 3.75%) are contemplated. Lower dosage strength formulations of the present invention that contain about 2.5% imiquimod or about 3.75% imiquimod by weight based on the total weight of the formulation are most preferred. It should also be understood that lower dosage strength imiquimod formulations of the present invention, which have dose proportionate release rates as to both the release rates of the imiquimod and the total amount of imiquimod released, relative to the Aldara® 5% imiquimod cream, are also preferred.

Thus, it should be understood by those versed in this art that an amount of imiquimod present in a formulation of the present invention will be an effective amount when a formulation of the present invention is applied daily in accordance with a short duration of therapy as described herein to a targeted area diagnosed with EGWs and permitted following each individual application to remain in contact with the targeted area for a sufficient time to allow an effective amount of imiquimod to clear such a disease or warts of the disease, to partially clear the number of warts of such a disease, to reduce the number of warts, to prevent the recurrence of such a disease without inducing treatment limiting local skin reactions or adverse events, including unscheduled rest periods caused by such treatment limiting local skin reactions or adverse events, in an appreciable number of people undergoing treatment. For example, when treating EGWs in accordance with the present invention, an effective amount will achieve a partial clearance in warts as a targeted endpoint, e.g., at least about 40% and preferably at least about 50% and more preferably at least about 60% and still more preferably at least about 70% and most preferably at least about a 75% reduction in the number of warts in the treatment area compared with baseline, or at least about 60% and preferably at least about 70% and even more preferably at least about 80% and most preferably at least about 90% median reduction in the number of warts in the treatment area compared with baseline as a secondary endpoint, or at least about 25% complete clearance and preferably at least about 30% complete clearance and even more preferably at least about 35% complete clearance and most preferably at least about 45% complete clearance of the warts as a primary endpoint. See, e.g., FIGS. 15-36. By "complete clearance", as used herein, the term means the absence of clinically visible warts in the treatment area.

Results from use of the lower dosage strength imiquimod formulations in accordance with the short durations of therapy of the present invention demonstrate that lower dosage strength imiquimod formulations dosed once daily until complete wart clearance or for up to an eight week treatment period is effective and well-tolerated treatments for EGWs. The condensed dosing regimens of the present invention allows for short treatment periods, minimizing exposure to imiquimod and further supporting an improved benefit-risk profile, as compared with EDA-approved Aldara® 5% imiquimod cream 16 week, thrice-weekly therapy.

Benefits of treatment with the lower dosage strength imiquimod formulations in accordance with the short durations of therapy of the present invention include complete clearance or partial clearance (≥30%, preferably ≥40%, preferably ≥50%, preferably ≥60%, even more preferably ≥70% even more preferably ≥80% and even more preferably ≥95%) of EGWs for a majority of the subjects that are treated. See Example 24.

While the present invention has identified what it believes to be preferred concentrations of imiquimod formulations, numbers of applications per week and durations of therapy, it should be understood by those versed in this art that any effective concentration of imiquimod in a formulation that delivers an effective amount of imiquimod and any numbers of application per week during a short duration of therapy, as described herein, that can effectively treat EGWs, without causing treatment limiting local skin reactions or related adverse events, including too many rest periods, is contemplated by the present invention.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The foregoing and other objects, advantages and features of the present invention, and the manner in which the same are accomplished, will become more readily apparent upon consideration of the following detailed description of the invention taken in conjunction with the accompanying figure and examples, which illustrate an embodiment, wherein.

DETAILED DESCRIPTION OF THE INVENTION

Figure 1:
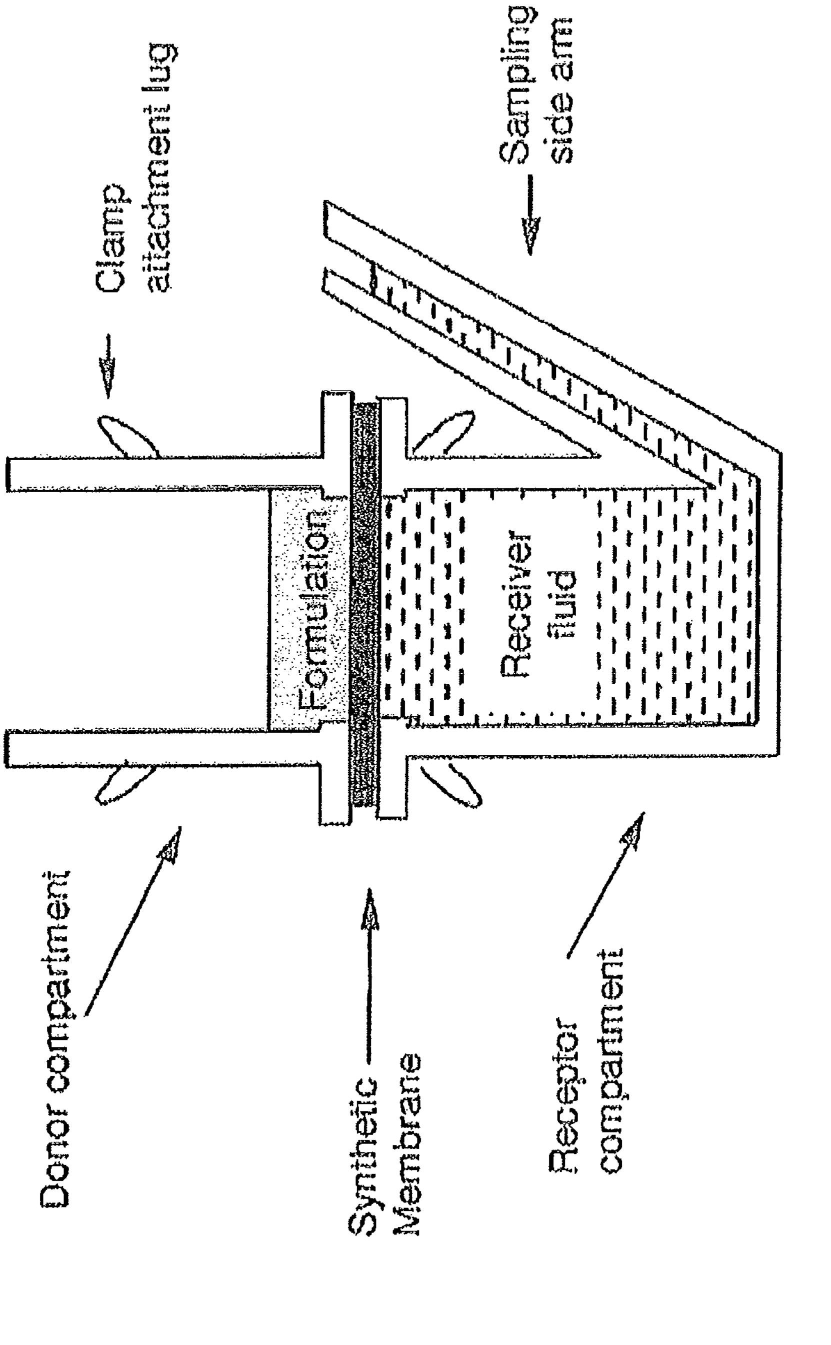
FIG. 1 shows a schematic representation of a Franz cell.

By way of illustrating and providing a more complete appreciation of the present invention and many of the attendant advantages thereof, the following detailed description and examples are given concerning the novel methods and compositions.

In one aspect, the present invention relates to a pharmaceutical composition comprising imiquimod and a pharmaceutically acceptable vehicle for imiquimod, which vehicle comprises a fatty acid. While the present invention may be embodied in many different focus, several specific embodiments are discussed herein with the understanding that the present disclosure is to be considered only as an exemplification of the principles of the invention, and it is not intended to limit the invention to the embodiments described or illustrated.

As used in the specification and claims, the phrase "substantially less-irritating" designates formulations that do not cause unacceptable skin irritation in conventional repeat skin irritation tests in albino rabbits such as that described in Draize et al., "Appraisal of the Safety of Chemicals in Food, Drugs and Cosmetics", prepared by the Division of Pharmacology of the Food and Drug Administration, published originally in 1959 by the Association of Food and Drug Officials of the United States; Topeka, Kans. (2nd priming 1965), incorporated herein by reference.

Unless otherwise indicated, all numbers expressing quantities, ratios, and numerical properties of ingredients, reaction conditions, and so forth used in the specification and claims are to be understood as being modified in all instances by the term "about".

All parts, percentages, ratios, etc. herein are by weight unless indicated otherwise. As used herein, the singular forms "a" or "an" "the" are used interchangeably and intended to include the plural forms as well and fall within each meaning, unless expressly stated otherwise. Also as used herein, "at least one" is intended to mean "one or more" of the listed element. Singular word forms are intended to include plural word forms and are likewise used herein interchangeably where appropriate and fall within each meaning, unless expressly stated otherwise. Except where noted otherwise, capitalized and non-capitalized forms of all terms fall within each meaning.

By the term "bioequivalence or bioequivalent", as used herein, it refers to lower dosage strength formulations in which they are pharmaceutically equivalent and their bioavailability (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which imiquimod becomes available from such formulations at the site of imiquimod action when administered at the same molar dose under similar conditions, e.g., the rate at which imiquimod can leave such a formulation and the rate at which imiquimod can either cross the stratum corneum and/or become available at the site of action to treat external genital or perineal warts (EGWs). In other words, there is a high degree of similarity in the bioavailabilities of two imiquimod pharmaceutical products (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, and/or (c) Health Canada.

By the term "bioavailability or bioavailable", as used herein, it means generally the rate and extent of absorption of imiquimod into the systemic circulation and, more specifically, the rate or measurements intended to reflect the rate and extent to which imiquimod becomes available at the site of action or is absorbed from a drug product and becomes available at the site of action. In other words, and by way of example, the extent and rate of imiquimod absorption from a lower dosage strength formulation of the present invention as reflected by a time-concentration curve of imiquimod in systemic circulation.

By "pharmaceutical equivalence or pharmaceutically equivalent", as used herein, it refers to lower dosage strength imiquimod formulations of the present invention that contain the same amount of imiquimod, in the same dosage forms, but not necessarily containing the same inactive ingredients, for the same route of administration and meeting the same or comparable compendia or other applicable standards of identity, strength, quality, and purity, including potency and, where applicable, content uniformity and/or stability.

By "therapeutic equivalence or therapeutically equivalent", it is meant herein to mean those lower dosage strength imiquimod formulations which (a) will produce the same clinical effect and safety profile when practicing the short durations of therapy to treat EGWs in accordance with the present invention and (b) are pharmaceutical equivalents, e.g., they contain imiquimod in the same dosage form, they have the same route of administration; and they have the same imiquimod strength. In other words, therapeutic equivalence means that a chemical equivalent of an imiquimod lower dosage strength imiquimod formulation of the present invention (i.e., containing the same amount of imiquimod in the same dosage form) when administered to the same individuals in the same dosage regimen will provide essentially the same efficacy and toxicity.

By "$T_{max}$", it is meant herein to mean the time when the maximum imiquimod serum concentration is reached at steady state following topical application of a lower dosage strength imiquimod formulation of the present invention, i.e., when the rate of imiquimod absorption equals the rate of imiquimod elimination. In other words, the time that $C_{max}$ is observed for imiquimod.

By "$C_{max}$", it is meant herein to refer to the maximum imiquimod serum concentration that is reached at steady state following topical application of a lower dosage strength imiquimod formulation of the present invention, i.e., when the rate of imiquimod absorption equals the rate of imiquimod elimination. In other words, it is the maximum serum concentration; the highest serum concentration observed during the imiquimod dosing or sampling interval.

By "$C_{min}$", it is meant herein to refer to the minimum measurable imiquimod serum concentration; e.g., imiquimod serum concentration that is observed immediately prior to dosing on Days 7, 14, 21 and 22 (24 hours post-dose).

By "$T_{1/2}$", it is meant herein to mean the time required for half of the quantity of maximum imiquimod serum concentration to be eliminated once steady state is achieved following topical application of a lower dosage strength imiquimod formulation of the present invention. For example, the apparent elimination half-life for imiquimod, that is calculated as about $0.693/\lambda_z$, in accordance with Example 24.

By "$AUC_{0-24}$", it is meant herein to mean the area under the serum imiquimod concentration versus a 24 hour time curve following topical application of a lower dosage strength imiquimod formulation of the present invention, i.e., a measure of imiquimod exposure over a 24 hour period. For example, the area under the imiquimod serum concentration versus time curve, from 0 to 24 hours, that is calculated using the linear trapezoid rule or extrapolated to 24 hours in cases where reportable values are not obtainable up to that time point.

By "$AUC_{0-t}$", it is meant herein to mean the area under the imiquimod serum concentration versus time curve, from 0 to the time of the last non-zero concentration on Day 1; that is calculated using the linear trapezoid rule.

By "$R_{AUC}$", it is meant herein to mean the accumulation ratio; that are calculated as the $AUC_{0-24}$ value during multiple-imiquimod dose administration divided by the $AUC_{0-24}$ value following the first dose (i.e., Day 21/Day 1); or the accumulation ratios that are calculated for an imiquimod metabolite only if sufficient non-zero time points are available to reasonably estimate $AUC_{0-24}$.

By "$AUC_{0-inf}$", it is meant herein to mean the area under the imiquimod serum concentration versus time curve, from 0 to infinity; $AUC_{0-inf}$ that is calculated on Day 1 as $AUC_{(0-inf)}=AUC_{(o-t)}+Ct/K_{et}$ (where $C_t$=the fitted last non-zero concentration, $AUC_{0-t}$=the AUC from time zero to the time of the last non-zero concentration and $K_{et}$=the elimination rate constant).

By "$R_{Cmax}$.", it is meant herein to mean the accumulation ratio; calculated as the $C_{max}$. value during multiple-dose administration divided by the $C_{max}$ value following the first dose (i.e., Day 21/Day 1).

By "$\lambda z_{EFF}$", it is meant herein to mean the effective elimination rate constant, calculated as $-\ln(1-1/R_{Auc})$/tau.

By "$T_{1/2\ EFF}$", it is meant herein to mean the effective half-life for accumulation; calculated as $0.693/\lambda z_{EFF}$.

By "λz", it is meant to refer to an elimination rate constant, i.e., the rate at which imiquimod disappears from the site of measurement once steady state is achieved following topical application of a lower dosage strength imiquimod formulation of the present invention. In other words, the apparent elimination rate constant; that is calculated using linear regression on the terminal portion of the In concentration versus time profile.

By "geometric mean", it refers a statistical average of a set of transformed numbers often used to represent a central tendency in highly variable data. It is calculated from data transformed using powers or logarithms and then transformed back to original scale after averaging.

By "geometric mean ratio", it refers to a ratio of two geometric means, where the "geometric LS mean test" is the numerator of the geometric mean ratio, and the "geometric LS mean reference" is the denominator of the geometric mean ratio.

By "RH", it refers herein to relative humidity.

By "cPs, it refers herein to centipoise.

By "h", it refers herein to hours.

By "ITT", it refers to an intent-to-treat population.

By "Pbo, it refers to placebo.

By "EOS", it refers to End of Study.

By "V", it refers to vehicle.

By "AE", it refers herein to adverse events.

The present invention provides pharmaceutical formulations such as creams, ointments, foams, gels, lotions and adhesive coatings that contain imiquimod and a fatty acid such as isostearic, linoleic, unrefined oleic acid, refined oleic acid, such as Super Refined® oleic acid NF (e.g., a highly purified oleic acid, i.e., an oleic acid which has low polar impurities, such as peroxides, a low peroxide value and is marketed by CRODA; see e.g., www.crodausa.com) and mixtures thereof. The formulations of the invention provide desirable skin penetrability of the imiquimod.

The compound imiquimod is a known antiviral agent that is also known to induce interferon biosynthesis. It can be prepared using the method disclosed in U.S. Pat. No. 4,689,338, the disclosure of which is incorporated herein by reference in its entirety. The compound can be used to treat external genital and perineal wart (EGWs). The amount of imiquimod present in a formulation of the present invention will be an effective amount to treat EGWs to achieve total wart clearance or partial wart reduction or clearance, to prevent the recurrence of such a disease and/or to promote immunity against such a disease with an acceptable safety profile. An example of an effective amount of imiquimod in a formulation of the present invention is between about 1.0 percent and about 4.25 percent by weight based on the total weight of a formulation, more preferably between about 1.5%, 1.75%, 2.0%, 2.25%, 2.5%, 2.75%, 3.0%, 3.25%, 3.5%, 3.75%, 4.0% and 4.25% (between about 1.5% and about 4.25%), even more preferably between about 2.0%, 2.25%, 2.5%, 2.75%, 3.0%, 3.25%, 3.5%, 3.75% and 4.0% (between about 2.0% and about 4.0%), and still even more preferably between about 2.5%, 2.75%, 3.0%, 3.25%, 3.5% and 3.75% (between about 2.5% and about 3.75%). Imiquimod formulations of the present invention that contain about 2.5% imiquimod or about 3.75% imiquimod by weight based on the total weight of the formulation are most preferred.

Likewise, a shortened period or duration, as contemplated by the present invention, will be for reduced periods of time effective to treat EGWs as discussed herein above, e.g., up to eight weeks or less, again depending upon the lower dosage strength imiquimod formulation of the present invention that is selected for daily application, or up to six weeks or less or up to four weeks or less. By way of example, short periods of treatment with lower dosage strength imiquimod formulations for treating EGWs, include:

applying an effective amount of imiquimod, such as via the lower dosage strength imiquimod formulations of the present invention to the area affected with EGWs, as follows: applying an effective amount once per day to the wart treatment area until complete clearance is achieved, for example, between about 28 doses and 56 doses applied once per day, such as applying an effective amount once per day up to about eight weeks or less, up to about six weeks or less, or up to about four weeks or less to thereby treat EGWs.

A fatty acid such as isostearic acid, palmitic acid, stearic acid, linoleic acid, refined oleic acid, such as Super Refined® oleic acid NF (e.g., a highly purified oleic acid, i.e., an oleic acid which has low polar impurities, such as peroxides, a low peroxide value and is marketed by CRODA; see e.g., www.crodausa.com), an unrefined oleic acid blended with effective amounts of antioxidants or mixtures thereof are incorporated into formulations of the present invention. The total amount of fatty acid present in a formulation is preferably between about 3 percent and about 45 percent by weight based on the total weight of a formulation. It should be understood that when oleic acid is selected as a fatty acid, that stability may present issue. Thus, stabilizers, such as anti-oxidants and the like, may be required to preserve pharmaceutical elegance and stability over the life of the oleic acid formulation.

A pharmaceutical formulation of the invention can be in a form such as a cream, an ointment, a foam, a gel, a lotion, a pressure-sensitive adhesive composition, or other forms known to those skilled in the art, each particular form containing imiquimod and fatty acid in particular amounts, and optionally containing various additional elements. The preferred amounts of drug and fatty acid, and the amounts and types of optional elements used in formulations of the invention are discussed below with particular reference to creams, ointments and adhesive compositions.

A cream according to the invention contains 1-isobutyl-1H-imidazo[4,5-c]quinolin-4-amine and fatty acid.

The amount of 1-isobutyl-1H-imidazo[4,5-c]-quinolin-4-amine present in a cream is preferably about 0.5 percent to about 9 percent by weight, and more preferably about 1 percent to about 5 percent by weight, and more preferably about 2.5% to about 3.75%, based on the total weight of the cream.

The total amount of fatty acid present in a cream of the invention is preferably about 3 percent to about 45 percent by weight, and more preferably about 5 percent to about 25 percent by weight, based on the total weight of the cream.

Optionally, a cream of the present invention can contain emollients, emulsifiers, thickeners, and/or preservatives.

Emollients such as long chain alcohols, e.g., cetyl alcohol, stearyl alcohol and cetearyl alcohol; hydrocarbons such as petrolatum and light mineral oil; or acetylated lanolin can be included in a cream of the invention. A cream can contain one or more of these emollients. The total amount of emollient in a cream of the invention is preferably about 5 percent to about 30 percent, and more preferably about 5 percent to about 10 percent by weight based on the total weight of the cream.

Emulsifiers such as nonionic surface active agents, e.g., polysorbate 60 (available from ICI Americas), sorbitan monostearate, polyglyceryl-4 oleate, and polyoxyethylene (4)lauryl ether or trivalent cationic a cream of the invention. A cream can contain one or more emulsifiers. Generally the total amount of emulsifier is preferably about 2 percent to about 14 percent, and more preferably about 2 percent to about 6 percent by weight based on the total weight of the cream.

Pharmaceutically acceptable thickeners, such as Xanthum gum, Guar gum, Veegum Gum™ K (available from R. T. Vanderbilt Company, Inc.), and long chain alcohols (i.e. cetyl alcohol, stearyl alcohol or cetearyl alcohol) can be used. A cream can contain one or more thickeners. The total amount of thickener present is preferably about 3 percent to about 12 percent by weight based on the total weight of the cream.

Preservatives such as methylparaben, propylparaben and benzyl alcohol can be present in a cream of the invention. The appropriate amount of such preservative(s) is known to those skilled in the art.

Optionally, an additional solubilizing agent such as benzyl alcohol, lactic acid, acetic acid, stearic acid, salicylic acid, any alpha-hydroxy acid such as glycolic acid, or hydrochloric acid can be included in a cream of the invention.

If an additional solubilizing agent is used, the amount present is preferably about 1 percent to about 12 percent by weight based on the total weight of the cream.

Optionally, a cream of the invention can contain a humectant such as glycerin, skin penetration enhancers such as butyl stearate, and additional solubilizing agents.

Generally, a cream consists of an oil phase and a water phase mixed together to form an emulsion. Preferably, the amount of water present in a cream of the invention is about 45 percent to about 85 percent by weight based on the total weight of the cream. The oil phase of a cream of the invention can be prepared by first combining the 1-isobutyl-1H-imidazo[4,5-c]quinolin-4-amine or 1-(2-methylpropyl)-1H-imidazo [4,5-c]quinolin-4-amine and the fatty acid (if the cream contains benzyl alcohol it can also be added at this point) and heating with occasional stirring to a temperature of about 50° C. to 85° C. When the 1-isobutyl-1H-imidazo [4,5-c]quinolin-4-amine or 1-(2-methylpropyl)-1H-imidazo [4,5-c]quinolin-4-amine appears to be completely dissolved, the remaining oil phase ingredients are added and heating is continued until dissolution appears to be complete.

The water phase can be prepared by combining all other ingredients and heating with stirring until dissolution appears to be complete.

The creams of the invention are generally prepared by adding the water phase to the oil phase with both phases at a temperature of about 65° C. to 75° C. The resulting emulsion is mixed with a suitable mixer apparatus to give the desired cream.

An ointment of the invention contains an ointment base in addition to 1-isobutyl-1H-imidazo[4,5-c]quinolin-4-amine and fatty acid.

The amount of 1-isobutyl-1H-imidazo[4,5-c]-quinolin-4-amine present in an ointment of the invention is preferably about 0.5 percent to about 9 percent, and more preferably about 0.5 percent to about 5 percent by weight based on the total weight of the ointment.

The total amount of fatty acid present in an ointment of the invention is preferably about 3 percent to about 45 percent, and more preferably about 3 percent to about 25 percent based on the total weight of the ointment.

A pharmaceutically acceptable ointment base such as petrolatum or polyethylene glycol 400 (available from Union Carbide) in combination with polyethylene glycol 3350 (available from Union Carbide) can be used. The amount of ointment base present in an ointment of the invention is preferably about 60 percent to about 95 percent by weight based on the total weight of ointment.

Optionally, an ointment of the invention can also contain emollients, emulsifiers and thickeners. The emollients, emulsifiers, and thickeners and the preferred amounts thereof described above in connection with creams are also generally suitable for use in an ointment of the invention.

An ointment according to the invention can be prepared by combining 1-isobutyl-1H-imidazo[4,5-c]quinolin-4-amine with fatty acid and heating with occasional stirring to a temperature of about 65° C. When the 1-isobutyl-1H-imidazo[4,5-c]-quinolin-4-amine or 1-(2-methylpropyl)-1H-imidazo[4,5-c]quinolin-4-amine appears to be completely dissolved, the remaining ingredients are added and heated to about 65.° C. The resulting mixture is mixed with a suitable mixer while being allowed to cool to room temperature.

A pressure-sensitive adhesive composition of the invention contains 1-isobutyl-1H-imidazo [4,5-c]-quinolin-4-amine or 1-(2-methylpropyl)-1H-imidazo[4,5-c]quinolin-4-amine, fatty acid, and a pressure sensitive adhesive polymer.

The amount of 1-isobutyl-1H-imidazo[4,5-c]-quinolin-4-amine or 1-(2-methylpropyl)-1H-imidazo[4,5-c]quinolin-4-amine present in a pressure sensitive adhesive composition of the invention is preferably about 0.5 percent to about 9 percent by weight, and more preferably about 3 percent to about 7 percent by weight based on the total weight of the adhesive composition. The amount of fatty acid present is preferably about 10 percent to about 40 percent by weight, more preferably about 15 percent to about 30 percent by weight, and most preferably about 20 percent to about 30 percent by weight, based on the total weight of the adhesive composition.

Preferably, the adhesive polymer utilized in a pressure sensitive adhesive composition of the invention is substantially chemically inert to 1-isobutyl-1H-imidazo[4,5-c]-quinolin-4-amine or 1-(2-methylpropyl)-1H-imidazo [4,5-c] quinolin-4-amine. The adhesive polymer is preferably present in an amount of about 55 percent to about 85 percent by weight based on the total weight of the composition. Suitable adhesive polymers include acrylic adhesives that contain, as a major constituent (i.e., at least about 80 percent by weight of all monomers in the polymer), a hydrophobic monomeric acrylic or methacrylic acid ester of an alkyl alcohol, the alkyl alcohol containing 4 to 10 carbon atoms. Examples of suitable monomers are those discussed below in connection with the "A Monomer". These adhesive polymers can further contain minor amounts of other monomers such as the "B Monomers" listed below.

Preferred adhesives include acrylic pressure-sensitive adhesive copolymers containing A and B Monomers as follows: Monomer A is a hydrophobic monomeric acrylic or methacrylic acid ester of an alkyl alcohol, the alkyl alcohol containing 4 to 10 carbon atoms, preferably 6 to 10 carbon atoms, more preferably 6 to 8 carbon atoms, and most preferably 8 carbon atoms. Examples of suitable A Monomers are n-butyl, n-pentyl, n-hexyl, isoheptyl, n-nonyl, n-decyl, isohexyl, 2-ethyloctyl, isooctyl and 2-ethylhexyl acrylates. The most preferred A Monomer is isooctyl acrylate.

Monomer B is a reinforcing monomer selected from the group consisting of acrylic acid; methacrylic acid; alkyl acrylates and methacrylates containing 1 to 3 carbon atoms in the alkyl group; acrylamide; methacrylamide; lower alkyl-substituted acrylamides (i.e., the alkyl group containing 1 to 4 carbon atoms) such as tertiary-butyl acrylamide; diacetone acrylamide; n-vinyl-2-pyrrolidone; vinyl ethers such as vinyl tertiary-butyl ether; substituted ethylenes such as derivatives of maleic anhydride, dimethyl itaconate and monoethyl formate and vinyl perfluoro-n-butyrate. The preferred B Monomers are acrylic acid, methacrylic acid, the above-described alkyl acrylates and methacrylates, acrylamide, methacrylamide, and the above-described lower alkyl substituted acrylamides. The most preferred B Monomer is acrylamide.

In one embodiment of a pressure-sensitive adhesive composition of the invention, the pressure-sensitive adhesive copolymer containing A and B Monomers as set forth above preferably contains the A Monomer in an amount by weight of about 80 percent to about 98 percent of the total weight of all monomers in the copolymer. The A Monomer is more preferably present in an amount by weight of about 88 percent to about 98 percent, and is most preferably present in an amount by weight of about 91 percent to about 98 percent. The B Monomer in such a copolymer is preferably present in the pressure-sensitive adhesive copolymer in an amount by weight of about 2 percent to about 20 percent, more preferably about 2 percent to about 12 percent, and most preferably 2 to 9 percent of the total weight of the monomers in the copolymer.

In another embodiment of a pressure-sensitive adhesive composition of the invention, the adhesive copolymer comprises about 60 to about 80 percent by weight (and preferably about 70 to about 80 percent by weight) of the above-mentioned hydrophobic monomeric acrylic or methacrylic acid ester of an alkyl alcohol (i.e., Monomer A described above) based on the total weight of all monomers in the copolymer; about 4 to about 9 percent by weight based on the total weight of all monomers in the copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower alkyl-substituted acrylamide, diacetone acrylamide and N-vinyl-2-pyrrolidone; and about 15 to about 35 percent by weight (and preferably about 15 to about 25 percent by weight) of vinyl acetate based on the total weight of all monomers in the copolymer. In this embodiment the preferred acrylic or methacrylic acid ester is isooctyl acrylate and the preferred reinforcing monomer is acrylamide.

The above described adhesive copolymers are known, and methods of preparation therefore are well known to those skilled in the art, having been described for example, in U.S. Pat. No. 24,906 (Ulrich), the disclosure of which is incorporated herein by reference. The polymerization reaction can be carried out using a free radical initiator such as an organic peroxide (e.g., benzoylperoxide) or an organic azo compound (e.g., 2,2'-azobis(2,4-dimethylpentanenitrile), available under the trade designation "Vazo 52" from DuPont).

Since pressure-sensitive adhesives such as those described above are inherently rubbery and tacky and are suitably heat and light stable, there is no need to add tackifiers or stabilizers. However, such can be added if desired.

Optionally, a pressure sensitive adhesive composition of the invention can also contain one or more skin penetration enhancers such as glyceryl monolaurate, ethyl oleate, isopropyl myristate, diisopropyl adipate and N,N-dimethyldodecylamine-N-oxide, either as a single ingredient or as a combination of two or more ingredients. The skin penetration enhancer(s) preferably form a substantially homogeneous mixture with the pressure sensitive adhesive polymer or copolymer. The total amount of skin penetration enhancer(s) present in a pressure sensitive adhesive composition of the invention is preferably about 3 percent to about 25 percent by weight, more preferably about 3 percent to about 10 percent by weight based on the total weight of the adhesive composition.

When the skin penetration enhancer is a single ingredient, it is preferably a skin penetration enhancer such as isopropyl myristate, diisopropyl adipate, ethyl oleate, or glyceryl monolaurate.

When a combination skin penetration enhancer is used, it is preferably a combination such as: ethyl oleate with glyceryl monolaurate; ethyl oleate with N,N-dimethyldodecylamine-N-oxide; glyceryl monolaurate with N,N-dimethyldodecylamine-N-oxide; and ethyl oleate with both glyceryl monolaurate and N,N-dimethyldodecylamine-N-oxide.

A pressure-sensitive adhesive composition of the invention can be prepared by combining dry adhesive, 1-isobutyl-1H-imidazo[4,5-c]quinolin-4-amine, fatty acid, and skin penetration enhancer(s) with an organic solvent. The preferred organic solvents are methanol and ethyl acetate. The total solids content of the adhesive coating is preferably in the range of about 15 percent to about 40 percent, and more preferably in the range of about 20 to about 35 percent based on the total weight of the adhesive coating. The resulting mixture is shaken or mixed for a period of about 20 to 72 hours. When this method is used it is preferred that the 1-isobutyl-1H-imidazo[4,5-c]-quinolin-4-amine be in micronized form (i.e., particle size of 1-2 microns in diameter). Optionally, the mixture can be heated during shaking.

In a preferred method, the 1-isobutyl-1H-imidazo[4,5-c]-quinolin-4-amine or 1-(2-methylpropyl)-1H-imidazo[4,5-c] quinolin-4-amine is combined with the fatty acid and shaken at 40° C. until there appears to be complete dissolution. The remaining ingredients are added and the mixture is shaken for a period of about 20 to 72 hours.

The pressure-sensitive adhesive compositions described above are preferably coated onto one surface of a suitable backing of sheet material, such as a film, to form a pressure-sensitive adhesive coated sheet material. A pressure-sensitive adhesive coated sheet material of the invention can be prepared by knife coating a suitable release liner to a predetermined uniform thickness with a wet adhesive formulation. This adhesive coated release liner is then dried and laminated onto a backing using conventional methods. Suitable release liners include conventional release liners comprising a known sheet material, such as a polyester web, a polyethylene web, or a polystyrene web, or polyethylene-coated paper, coated with a suitable silicone-type coating such as that available under the trade designation Daubert 164Z, from Daubert Co. The backing can be occlusive, non-occlusive or a breathable film as desired. The backing can be any of the conventional materials for pressure-sensitive adhesive tapes, such as polyethylene, particularly low density polyethylene, linear low density polyethylene, high density polyethylene, randomly-oriented nylon fibers, polypropylene, ethylene-vinylacetate copolymer, polyurethane, rayon and the like. Backings that are layered, such as polyethylene-aluminum-polyethylene composites are also suitable. The backing should be substantially non-reactive with the ingredients of the adhesive coating. The presently preferred backing is low density polyethylene.

The pressure-sensitive adhesive coated sheet material of the invention can be made in the form of an article such as a tape, a patch, a sheet, a dressing or any other form known to those skilled in the art.

Preferably, an article in the form of a patch is made from an adhesive coated sheet material of the invention and applied to the skin of a mammal. The patch is replaced as necessary with a fresh patch to maintain the particular desired therapeutic effect of the 1-isobutyl-1H-imidazo [4,5-c] quinolin-4-amine.

The inherent viscosity values reported in the examples below were obtained by the conventional method used by those skilled in the art. The measurement of the viscosity of dilute solutions of the adhesive, when compared to controls run under the same conditions, clearly demonstrates the relative molecular weights. It is the comparative values that are significant; absolute figures are not required. In the examples, the inherent viscosity values were obtained using a Cannon-Fenske #50 viscometer to measure the flow time of 10 ml of a polymer solution (0.2 g polymer/deciliter tetrahydrofuran, in a water bath controlled at 25° C.). The examples and the controls were run under identical conditions. The test procedure followed and the apparatus used are explained in detail in the Textbook of Polymer Science, F. W. Billmeyer, Wiley-Interscience, 2nd Edition, 1971 under: Polymer chains and their characterization, D. Solution Viscosity and Molecular Size, pp 84-85, the disclosure and textbook of which is incorporated by reference.

As indicated herein above, and in accordance with the present invention, the present invention contemplates bioequivalent or interchangeable lower dosage strength imiquimod formulations. By way of an example, bioequivalent or interchangeable 3.75% lower dosage strength imiquimod topical formulations, as contemplated by the present invention, include those 3.75% imiquimod formulations that have comparable in-vivo serum profiles, i.e., wherein the following in-vivo parameters are either the same or may vary up to about ±25% or more, when such 3.75% formulations are topically administered daily to the same individuals in the same dosage regimen in accordance with the short durations of therapy of the present invention:

By way of example, a 3.75% imiquimod lower dosage strength formulation of the present invention, when approximately 250 mg of such a formulation' (about 9.375 mg imiquimod) or less is applied daily for 21 days to EGWs in the genital/perianal area with a total wart area of greater than or equal to 100 $mm^2$, achieves steady state by about Day 7, and provides an in-vivo serum profile selected from one or more of the following:

(a) a Day 21 mean $T_{max}$ of about 9.7 hours with a standard deviation ("SD") of about 4.0, a median $T_{max}$ of about 12 hours and a geometric mean $T_{max}$ of about 8.3 hours and a coefficient of variation ("CV") of about 41%;

(b) a Day 21 mean $C_{max}$ of about 0.488 ng/ml with a standard deviation of about 0.368, a median of about 0.45 and a geometric mean $C_{max}$ of about 0.39 ng/mL and a coefficient of variation of about 75%;

(c) a Day 21 $T_{1/2}$, of from about 6.8 to about 54 hours and preferably a mean $T_{1/2}$ of about 24.1 hours with a standard deviation of about 12, a median $T_{1/2}$ of about 22.8 hours and a geometric mean $T_{1/2}$ of about 21 hours and a coefficient of variation of about 51%;

(d) a Day 21 $AUC_{0-24}$ of from about 1.9 to about 14 ng-hr/mL and preferably a mean $AUC_{0-24}$ of about 6.8 ng·hr/mL with a standard deviation of about 3.6, a median $AUC_{0-24}$ of about 6.6 ng·hr/mL, and a geometric mean $AUC_{0-24}$ of about 5.8 ng-hr/mL and a coefficient of variation of about 53%;

(e) a Day 21 λz of from about 0.013 $hr^{-1}$ to about 0.102 $h^{-1}$ and preferably a mean λz of about 0.037 $hr^{-1}$ with a standard deviation of about 0.02, a median λz of about 0.03 $hr^{-1}$ and a geometric mean λz of about 0.03 $hr^{-1}$ and a coefficient of variation of about 60%;

(f) a Day 21 $C_{min}$ of from about 0.025 to about 0.47 and preferably a mean $C_{min}$ of about 0.158 with an SD of about 0.121, a median $C_{min}$ of about 0.14 and a geometric mean $C_{min}$ of about 0.11 and a coefficient of variation of about 77%;

(g) at Day 14/7 (a ratio of the trough concentration at Day 14 over the trough concentration at Day 7), a trough concentration geometric mean ratio of about 1.13 with a 90% confidence interval ("CI") within a range of between about 0.7 and about 1.7;

(h) at Day 21/14 (a ratio of the trough concentration at Day 21 over the trough concentration at Day 14), a trough concentration geometric mean ratio of about 0.84 with a 90% confidence interval ("CI") within a range of between about 0.5 and about 1.3;

(i) at Day 22/21 (a ratio of the trough concentration at Day 22 over the trough concentration at Day 21) a trough concentration geometric mean ratio of about 1.12 with a 90% confidence interval ("CI") within a range of between about 0.7 and about 1.6;

(j) a mean peak imiquimod serum concentration of about 0.488 ng/mL at Day 21;

(k) a Day 21 RAUC of from about 0.6 to about 7 and preferably a mean RAUC of about 2.2 with a standard deviation of about 1.8, a median RAUC of about 1.8 and a geometric mean RAUC of about 1.7 and a coefficient of variation of about 81%;

(l) a Day 21 $RC_{max}$ of from about 0.5 to about 5 and preferably a mean $RC_{max}$ of about 2.3 with a standard deviation of about 1.6, a median $RC_{max}$ of about 1.7 and a geometric mean $RC_{max}$ of about 1.8 and a coefficient of variation of about 70%;

(m) a Day 21 L $\lambda z_{eff}$ of from about 0.006 $h^{-1}$ to about 0.09 $h^{-1}$ and preferably a mean L $\lambda_{zeff}$ of about 0.04 with a standard deviation of about 0.03, a median L $\lambda_{zeff}$ of about 0.03 $h^{-1}$ and a geometric mean LXzeff of about 0.03 $hr^{-1}$ and a coefficient of variation of about 69%;

(n) a Day 21 $T^{1/2}{}_{eff}$ of from about 8 hr to about 111 hr and preferably a mean $T^{1/2}{}_{eff}$ of about 31 hr with a standard deviation of about 30, a median $T^{1/2}{}_{eff}$ of about 22 hr and a geometric mean $T^{1/2}{}_{eff}$ of about 23 $h^{-1}$ and a coefficient of variation of about 97%;

(o) a Day 21 $C_{max}$ in female patients about 61% higher in female subjects than in male subjects (0.676 versus 0.420 ng/mL) and total systemic exposure $AUC_{0-24}$ 8% higher in female subjects than in male subjects (7.192 versus 6.651 ng-hr/mL) when data is not dose normalized;

(p) a Day 21 $C_{max}$ in female patients about 35% higher than in male subjects (0.583 versus 0.431 ng/mL) and $AUC_{0-24}$ about 6% lower in female subjects than in male subjects (6.428 versus 6.858 ng-hr/mL) when using dose normalization to adjust for differences in dosage and reported without subjects who missed an application of study drug during the last week of dosing; and/or (q) a median $T_{max}$ occurring approximately twice as quickly in female subjects (about 6.50 hours) as in male subjects (about 12.0 hours).

In accordance with the present invention, a mean peak serum concentration is achieved with a 3.75% lower dosage strength imiquimod formulation of Examples 23-26. More specifically, a mean peak serum concentration of about 0.488 ng/mL is achieved with a 3.75% lower dosage strength imiquimod formulation of Examples 23-26 after about 9.4 mg of imiquimod is applied to the affected treatment area each day for up to 8 weeks.

Furthermore, this invention provides the following evidence of clinical efficacy: the wart area decreased by about 45% from a mean of about 108.3 mm2 at baseline to about 43.2 mm2 at Day 21, e.g., see Table 145. The P value of <0.0001 for this change from baseline indicated a statistically significant (≤0.050) decrease in wart area after 3 weeks of treatment.

While the lower dosage strength imiquimod pharmaceutical formulations of the present invention can be formulated into any form known to the art, such as a cream, an ointment, a foam, a gel, a lotion or a pressure-sensitive adhesive composition or patch, it should be understood that the creams, ointments, foams, gels and lotions may be packaged into any suitable container, such as unit-dose sachets or packets or multi-dose tubes or containers. A packaged amount of an imiquimod pharmaceutical formulation contemplated by the present invention includes any suitable amount, such as about 250 mg to about 500 mg or more, and preferably about 250 mg, about 300 mg, about 350 mg, about 400 mg, about 450 mg or about 500 mg unit-dose sachets or packets.

Examples of various embodiments of the present invention will now be further illustrated with reference to the following examples. Thus, the following examples are provided to illustrate the invention, but are not intended to be limiting thereof. Parts and percentages are by weight unless otherwise specified. Examples of creams, ointments and pressure sensitive adhesive compositions contemplated by the present invention are described in U.S. Pat. Nos. 4,689,338 and 5,238,944, which are incorporated herein by reference in their entireties. Percent modifications for, e.g., imiquimod and vehicle, to generate imiquimod formulations as described herein are likewise contemplated by the present invention. In addition, the formulations described and disclosed in U.S. Pat. No. 7,655,672, U.S. Patent Publication No. 2007/0123558, Ser. No. 11/276,324, U.S. Patent Publication No. 2007/0264317, U.S. Ser. No. 11/433,471, U.S. Patent Publication No. 2007/0900550 and PCT Publication No. WO2008098232 (A1), are also contemplated by the present invention and are incorporated herein by reference in their entireties.

Preparative Method 1

Laboratory Scale Preparation of Isooctylacrylate/Acrylamide Copolymer

To a 114 gram narrow-mouth glass bottle were added: 18.6 g isooctyl acrylate, 1.4 g acrylamide, 0.04 g benzoyl peroxide, 27.0 g ethyl acetate and 3.0 g methanol. The solution was purged for thirty five seconds with nitrogen at a flow rate of one liter per minute. The bottle was sealed and placed in a rotating water bath at 55° C. for twenty-four hours to effect essentially complete polymerization. The polymer was diluted with ethyl acetate/methanol (90/10) to 23.2 percent solids and had a measured inherent viscosity of 1.26 dl/g in ethyl acetate.

Preparative Method 2

Pilot Plant Scale Preparation of Isooctylacrylate/Acrylamide Copolymer 155 kg isooctylacrylate, 11.6 kg acrylamide, 209.1 kg ethyl acetate and 23.2 kg methanol were charged to a clean, dry reactor. Medium agitation was applied. The batch was deoxygenated with nitrogen while heating to an induction temperature of 55° C. 114 g Lucidol™ 70 initiator (available from Pennwalt Corp.) mixed with 2.3 kg ethyl acetate was charged to the reactor. The temperature was maintained at 55° C. throughout the reaction. After 5.5 hours reaction time, 114 g Lucidol™ 70 mixed with 2.3 kg ethylacetate were charged to the reactor. After 9.0 hours reaction time, an additional 114 g Lucidol™ 70 initiator mixed with 2.3 kg ethyl acetate were charged to the reactor. The reaction was continued until the percent conversion was greater than 98 percent as measured by gas chromatographic evaluation of residual monomer concentration. The resulting polymer solution was diluted to 25-28 percent solids with ethyl acetate/methanol (90/10) and had a measured Brookfield viscosity of 17,000-21,000 centipoises using spindle #4 at 12 rpm. The polymer had a measured inherent viscosity of 1.3-1.4 dllg in ethyl acetate.

The above-mentioned procedure was found to provide a pressure-sensitive adhesive that is equivalent in the practice of the present invention to a pressure-sensitive adhesive prepared according to Preparative Method 1.

A 25-30 percent solids solution of the isooctyl acrylate: acrylamide (93:7) adhesive copolymer in ethyl acetate/methanol (90:10) was coated onto a two-sided release liner using a knife-coater and coating at 0.5 mm in thickness. The adhesive-coated laminate was dried first at 82° C. for 3 minutes and then at 116° C. for 3 minutes. The dried adhesive coating was then stripped off the release liner and placed in a glass bottle. The foregoing procedure results in a reduction of the amount of any residual monomer in the adhesive copolymer.

Preparative Method 3

Preparation of Isooctyl Acrylate:Acrylamide:Vinyl Acetate (75:5:20) Copolymer

The procedure of Preparative Method 1 above acrylate, 8.0 g acrylamide, 32.0 g vinyl acetate, 0.32 g benzoyl peroxide, 216.0 g ethyl acetate and 24.0 g methyl alcohol. The resulting polymer was diluted with the ethyl acetate/methyl alcohol mixture to 21.52% solids. The adhesive polymer had a measured inherent viscosity of 1.40 dl/g in ethyl acetate at a concentration of 0.15 g/dl. Its Brookfield viscosity was 2,300 centipoise.

Preparative Method 4

Preparation of Isooctyl Acrylate Acrylamide:Vinyl Acetate (75:5:20) Copolymer

A master batch was prepared by combining 621.0 g of isooctyl acrylate, 41.4 g of acrylamide, 165.6 g of vinyl acetate, 1.656 g of 2,2'-azobis(2,4-dimethylpentanenitrile) (available from the DuPont Company as Vazo™52), 884.52 g of ethyl acetate and 87.48 g of methanol. A 400 g portion of the resulting solution was placed in an amber quart bottle. The bottle was purged for two minutes with nitrogen at a flow rate of one liter per minute. The bottle was sealed and placed in a rotating water bath at 45° C. for twenty-four hours to effect essentially complete polymerization. The copolymer was diluted with 250 g of ethyl acetate/methanol (90/10) to 26.05% solids and had a measured inherent viscosity of 1.27 dl/g in ethyl acetate at a concentration of 0.15 g/dl. Its Brookfield viscosity was 5580 centipoise.

Example I

A cream according to the present invention is prepared from the following ingredients:

| | % by Weight | Amount |
|---|---|---|
| Oil Phase | | |
| 1-isobutyl-1H-imidazo [4,5-c]-quinolin-4-amine | 1.0 | 40.0 g |
| Isostearic acid | 10.0 | 400.0 g |
| Benzyl alcohol | 2.0 | 80.0 g |
| Cetyl alcohol | 2.2 | 88.0 g |
| Stearyl alcohol | 3.1 | 124.0 g |
| Polysorbate 60 | 2.55 | 102.0 g |
| Sorbitan monostearate | 0.45 | 18.0 g |
| Aqueous Phase Glycerin | 2.0 | 80.0 g |
| Methylparaben | 0.2 | 8.0 g |
| Propylparaben | 0.02 | 0.8 g |
| Purified water | 76.48 | 3059.2 g |

The materials listed above were combined according to the following procedure: The glycerin, methylparaben, propylparaben and water were weighed into a 4 liter glass beaker then heated on a hot plate with stirring until the parabens isostearic acid and 1-isobutyl-1H-imidazo[4,5-c]-quinolin-4-amine were weighed into an 8 liter stainless steel beaker and heated on a hot plate until the amine was in solution (the temperature reached 69° C.). The benzyl alcohol, cetyl alcohol, stearyl alcohol, polysorbate 60 and sorbitan monostearate were added to the isostearic acid solution and heated on a hot plate until all material was dissolved (the temperature reached 75° C.). With both phases at approximately the same temperature (65°-75° C.), the water phase was added to the oil phase. The mixture was mixed with a homogenizer for 13 minutes then put into a cool water bath and mixed with a 3 inch propeller for 40 minutes (the temperature was 29° C.). The resulting cream was placed in glass jars.

Examples 2-9

Using the general method of Example 1, the cream formulations shown in Tables 1 and 2 are prepared.

TABLE 1

| | % by Weight | | | |
|---|---|---|---|---|
| | Example 2 | Example 3 | Example 4 | Example 5 |
| Oil Phase | | | | |
| 1-isobutyl-1H-imidazo-[4,5-c]quinolin-4-amine | 1.0 | 1.0 | 1.0 | 1.0 |
| Isostearic acid | 10.0 | 10.0 | 5.0 | 5.0 |
| Benzyl alcohol | | 2.0 | | |
| Cetyl alcohol | | 1.7 | | |
| Stearyl alcohol | | 2.3 | | |
| Cetearyl alcohol | 6.0 | | 6.0 | 6.0 |
| Polysorbate 60 | 2.55 | 2.55 | 2.55 | 2.55 |
| Sorbitan monostearate | 0.45 | 0.45 | 0.45 | 0.45 |
| Brij ™ 30[a] | | | | 10.0 |
| AqueousPhase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 77.78 | 77.78 | 82.78 | 72.78 |

[a]Brij ™ 30 (polyoxyethylene(4) lauryl ether) is available from ICI Americas, Inc.

TABLE 2

| | % by Weight | | | |
|---|---|---|---|---|
| | Example 6 | Example 7 | Example 8 | Example 9 |
| Oil Phase | | | | |
| 1-isobutyl-1H-imidazo-[4,5-c]quinolin-4-amine | 1.0 | 1.0 | 1.0 | 1.0 |
| Isostearic acid | 10.0 | 25.0 | 10.0 | 6.0 |
| Benzyl alcohol | | 2.0 | | 2.0 |
| Cetyl alcohol | | 2.2 | 1.7 | |
| Stearyl alcohol | | 3.1 | 2.3 | |
| Cetearyl alcohol | 6.0 | | | 6.0 |
| Polysorbate 60 | 2.55 | 3.4 | 2.55 | 2.55 |
| Sorbitan monostearate | 0.45 | 0.6 | 0.45 | 0.45 |
| Brij ™ 30[a] | 10.0 | | | |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 67.78 | 60.48 | 79.78 | 79.78 |

[a]Brij ™ 30 (polyoxyethylene(4) lauryl ether) is available from ICI Americas, Inc.

Example 10

A cream according to the present invention is prepared from the following ingredients in the following Table 3:

TABLE 3

| | % by Weight | Amount |
|---|---|---|
| Oil Phase | | |
| 1-isobutyl-H-1-imidazo [4,5-c]quinolin-4-amine | 1.0 | 3.00 g |
| Isostearic acid | 5.0 | 15.0 g |
| White petrolatum | 15.0 | 45.0 g |
| Light mineral oil | 12.8 | 38.4 g |
| Aluminum stearate | 8.0 | 24.0 g |
| Cetyl alcohol | 4.0 | 12.0 g |
| Witconol ™ 14[a] | 3.0 | 9.00 g |
| Acetylated lanolin | 1.0 | 3.0 g |
| Propylparaben | 0.063 | 0.19 g |
| Aqueous Phase | | |
| Veegum ™ K[b] | 1.0 | 3.0 g |
| Methylparaben | 0.12 | 0.6 g |
| Purified water | 49.017 | 147.05 g |

[a]Witconol ™ 14 (polyglyceryl4 oleate) is available from Witco Chemical Corp. Organics Division
[b]Veegum ™ K (colloidal magnesium aluminum silicate) is available from R. T. Vanderbilt Company Inc.

The materials listed above were combined according to the following procedure:

The 1-isobutyl-1H-imidazo[4,5-c]quinolin-4-amine and the isostearic acid were weighed into a glass jar and heated with occasional stirring until the amine was dissolved (the temperature reached 68° C.). To this solution was added, the petrolatum, mineral oil, aluminum stearate, cetyl alcohol, Witconol™ 14, acetylated lanoline and propylparaben. The mixture was heated to 75° C. In a separate beaker, the methylparaben and water were combined and heated until the paraben dissolved (the temperature reached 61° C.). The Veegum™ K was added to the aqueous solution and heated at 75° C. for 30 minutes while mixing with a homogenizer. With both phases at 75° C., the aqueous phase was slowly added to the oil phase while mixing with a homogenizer. Mixing was continued for 30 minutes while maintaining a temperature to about 80° C. The jar was then capped and the formulation was allowed to cool.

Example 11

An ointment according to the present invention is prepared from the ingredients in the following Table 4:

TABLE 4

| | % by Weight | Amount |
|---|---|---|
| 1-isobutyl-1H-imidazo [4,5-c]quinolin-4-Amine | 1.0 | 0.20 g |
| Isostearic acid | 5.0 | 1.00 g |
| Mineral oil | 12.8 | 2.56 g |
| White petrolatum | 65.2 | 13.04 g |
| Cetyl alcohol | 4.0 | 0.80 g |
| Acetylated lanolin | 1.0 | 0.20 g |
| Witconol ™ | 143.0 | 0.60 g |
| Aluminum stearate | 8.0 | 1.60 g |

The materials listed above are combined according to the following procedure:

The 1-isobutyl-1H-imidazo[4,5-c]quinolin-4-amine and the isostearic acid were placed in a glass jar and heated with stirring until the amine was dissolved. The remaining ingredients were added and the resulting mixture was heated to 65° C. and then mixed while being allowed to cool to room temperature.

Example 12

Using the general procedure of Example 11 an ointment containing the ingredients in the following Table 5 is prepared.

TABLE 5

| | % by Weight | Amount |
|---|---|---|
| 1-Isobutyl-1H-imidazo [4,5-c] quinol in-4-Amine | 1.0 | 0.20 g |
| Isostearic acid | 6.0 | 1.20 g |
| Polyethylene Glycol 400 | 55.8 | 11.16 g |
| Polyethylene Glycol 3350 | 32.6 | 6.52 g |
| Stearyl alcohol | 4.6 | 0.92 g |

Examples 13-15

Creams of the present invention are prepared using the ingredients shown in Table 6. The Example 1 except that benzyl alcohol was used with the isostearic acid to dissolve the 1-isobutyl-1H-imidazo [4,5-c] quinolin-4-amine.

TABLE 6

| | Example 13 Amount % by Weight | Example 14 Amount % by Weight | Example 15 Amount % by Weight |
|---|---|---|---|
| Oil Phase | | | |
| 1-isobutyl-1H-imidazo [4,5-c]quinolin-4-amine | 50 | 5.0 | 4.85 |
| Isotearic acid | 25.0 | 25.0 | 24.3 |
| Benzyl alcohol | 2.0 | 2.0 | 1.94 |
| Cetyl alcohol | 2.2 | 2.2 | 1.16 |
| Stearyl alcohol | 3.1 | 3.1 | 1.75 |
| Petrolatum | 3.0 | | 2.91 |
| Polysorbate 60 | 3.4 | 3.4 | 4.13 |
| Sorbitan monostearate | 0.6 | 0.6 | 0.73 |
| Stearic acid | | | |
| Aqueous Phase | | | |
| Glycerin | 2.0 | 2.0 | 1.94 |
| Methylparaben | 0.2 | 0.2 | 0.19 |
| Propylparaben | 0.02 | 0.02 | 0.02 |

Example 16

A cream according to the present invention is prepared from the ingredients in the following Table 7:

TABLE 7

| | % by Weight Amount | % by Weight Amount |
|---|---|---|
| Oil Phase | | |
| 1-isobutyl-1H-imidazo[4,5-c] quinolin-4-Amine | 4.0 | 0.80 g |
| Isostearic acid | 20.0 | 4.00 g |
| Benzyl alcohol | 2.0 | 0.40 g |
| Cetyl alcohol | 2.2 | 0.49 g |
| Stearyl alcohol | 3.1 | 0.62 g |
| Polysorbate 60 | 3.4 | 0.68 g |
| Sorbitan monostearate | 0.6 | 0.12 g |
| Aqueous Phase | | |
| 1-isobutyl-1H-imidazo [4,5-c] quinolin-4-amine | 1.0 | 0.2 g |

TABLE 7-continued

| | % by Weight Amount | % by Weight Amount |
|---|---|---|
| Glycerin | 2.0 | 0.4 g |
| 85% Lactic acid | 1.0 | 0.22 g |
| Methylparaben | 0.2 | 0.04 g |
| Propylparaben | 0.02 | 0.004 g |
| Purified water | 60.48 | 12.0 g |

The materials listed above are combined according to the following procedure: The isostearic acid and 0.8 g of 1-isobutyl-1H-imidazo[4,5-c]quinolin-4-amine or 1-(2-methylpropyl)-1H-imidazo[4,5-c]quinolin-4-amine were combined in a glass jar and heated with stirring until the amine had dissolved. The remaining oil phase ingredients were added to this solution and the mixture was heated to about 70° C. The aqueous phase ingredients were weighed into a separate beaker and heated with stirring until the amine and the parabens had dissolved. With both phases at about 70° C., the water phase was added to the oil phase and mixed with a propeller until the mixture cooled to room temperature.

Example 17

A mixture of 5.9415 g of the 93:7 isooctyl acrylate: acrylamide adhesive copolymer prepared in PREPARATIVE METHOD 2 above, 1.5126 g isostearic acid, 2.0075 g ethyl oleate, 0.3021 g glyceryl monolaurate, 0.2936 1-isobutyl-1H-imidazo [4,5-c]quinolin-4-amine (micronized) and 23.7 g of 90:10 ethyl acetate:methanol was placed in a small glass jar. The jar was placed on a horizontal shaker and shaken at room temperature for about 13 hours. The formulation was coated at a thickness of 20 mils onto a 5 mil Daubert 164Z liner. The laminate was oven dried for 3 minutes at 105° F., for 2 minutes at 185° F., and for 2 minutes at 210° F. The resulting adhesive coating contained 59.1 percent 93:7 isooctyl acrylate:acylamide adhesive copolymer, 15.0 percent isostearic acid, 20.0 percent ethyl oleate, 3.0 percent glyceryl monolaurate and 2.9 percent 1-isobutyl-1H-imidazo[4,5-c]quinolin-4-amine. The material was then laminated with 3 mil low density polyethylene backing and die cut into 2.056 cm.sup.2 patches.

Examples 18-20

Pressure-Sensitive Adhesive Coated Sheet Materials Prepared Using Unmicronized

1-isobutyl-1H-imidazo [4.5-c] quinolin-4-amine

Using the general method of Example 17 the formulations shown below are prepared. 1-Isobutyl-1H-imidazo[4,5-c] quinolin-4-amine or 1-(2-methylpropyl)-1Himidazo[4,5-c] quinolin-4-amine that had been ground with a mortar and pestle was used. The adhesive was the 93:7 isooctyl acrylate: acrylamide copolymer prepared in Preparative Method 1 above. The solvent was 90:10 ethyl acetate:methanol. All formulations in the following Table 8 were mixed at room temperature.

TABLE 8

| | Example 18 | Example 19 | Example 20 |
|---|---|---|---|
| 1-isobutyl-1H-imidazo [4,5-c]quinolin-4-amine | 5.0 | 3.0 | 3.0 |
| Ethyl oleate | 5.1 | 5.0 | 8.0 |
| Isostearic acid | 10.0 | 10.0 | 6.0 |
| Oleic acid | 20.0 | 20.0 | 13.0 |
| Glyceryl monolaurate | 1.5 | 1.5 | 1.5 |
| N,N-dimethyldodecylamine-N-oxide | 1.0 | 1.1 | 3.0 |
| Adhesive | 57.4 | 59.3 | 65.4 |

Example 21

A formulation with the same components in the same proportions as Example 18 is prepared using a different method. The 1-isobutyl-1H-imidazo[4,5-c]-quinolin-4-amine or 1-(2-methylpropyl)-1H-imidazo[4,5-c]quinolin-4-amine was combined with the oleic and isostearic acids and shaken at 40° C. until there was complete dissolution of the 1-isobutyl-1H-imidazo-[4,5-c]quinolin-4-amine or 1-(2-methylpropyl)-1H-imidazo[4,5-c]quinolin-4-amine. The remaining ingredients were added and shaken a 40° C. for 72 hours. Patches measuring 2.056 cm.sup.2 were prepared by the general method of Example 17.

Example 22

A mixture of 2.4734 g 1-isobutyl-1H-imidazo[4,5-c]-quinolin-4-amine or 1-(2-methylpropyl)-1H-imidazo[4,5-c] quinolin-4-amine, 3.3315 g isostearic acid and 6.6763 g oleic acid is prepared. To 1.8738 g of the above mixture was added 2.8750 g of the 93:7 isooctyl acrylate:acryamide adhesive copolymer prepared in Preparative Method 2 above, 0.2548 g of ethyl oleate, 0.0510 g N,N-dimethyldodecylamine-N-oxide, 0.0820 g glyceryl monolaurate (from Lauricidin, Inc.) and 14.0457 g of 90:10 ethyl acetate/methanol. The above was shaken for 30 hours at room temperature on a horizontal shaker. Transdermal patches were then prepared generally according to the procedures of Example 17.

Example 23

Topical Imiquimod Pharmaceutical Cream Formulations

Creams are prepared in accordance with the present invention using the ingredients shown in this Example 23.

The materials listed below in this Example 23 are combined according to the following procedure to make cream formulations in the following Table 9 of this Example 23:

TABLE 9

| Lower Dosage Strength Imiquimod Formulations | | | | | | |
|---|---|---|---|---|---|---|
| Excipients Formulation | % w/w 1 | % w/w 2 | % w/w 3 | % w/w 4 | % w/w 5 | % w/w 6 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.98 | 66.98 | 64.98 | 61.98 | 60.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients<br>Formulation | % w/w<br>7 | % w/w<br>8 | % w/w<br>9 | % w/w<br>10 | % w/w<br>11 | % w/w<br>12 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.98 | 60.98 | 60.98 | 57.08 | 58.98 | 55.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients<br>Formulation | % w/w<br>13 | % w/w<br>14 | % w/w<br>15 | % w/w<br>16 | % w/w<br>17 | % w/w<br>18 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.48 | 67.08 | 59.98 | 58.98 | 56.98 | 61.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients<br>Formulation | % w/w<br>19 | % w/w<br>20 | % w/w<br>21 | % w/w<br>22 | % w/w<br>23 | % w/w<br>24 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.73 | 66.73 | 64.73 | 61.73 | 60.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients<br>Formulation | % w/w<br>25 | % w/w<br>26 | % w/w<br>27 | % w/w<br>28 | % w/w<br>29 | % w/w<br>30 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.73 | 60.73 | 60.73 | 56.83 | 58.73 | 55.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylaraben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients<br>Formulation | % w/w<br>31 | % w/w<br>32 | % w/w<br>33 | % w/w<br>34 | % w/w<br>35 | % w/w<br>36 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Poly sorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.23 | 66.83 | 59.73 | 58.73 | 56.73 | 61.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients<br>Formulation | % w/w<br>37 | % w/w<br>38 | % w/w<br>39 | % w/w<br>40 | % w/w<br>41 | % w/w<br>42 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.48 | 66.48 | 64.48 | 61.48 | 60.23 | 60.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients<br>Formulation | % w/w<br>43 | % w/w<br>44 | % w/w<br>45 | % w/w<br>46 | % w/w<br>47 | % w/w<br>48 |
|---|---|---|---|---|---|---|
| Fatty acid | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.48 | 60.48 | 60.48 | 56.58 | 58.48 | 55.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients<br>Formulation | % w/w<br>49 | % w/w<br>50 | % w/w<br>51 | % w/w<br>52 | % w/w<br>53 | % w/w<br>54 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.98 | 66.58 | 59.48 | 58.48 | 56.48 | 61.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients<br>Formulation | % w/w<br>55 | % w/w<br>56 | % w/w<br>57 | % w/w<br>58 | % w/w<br>59 | % w/w<br>60 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 1.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.23 | 66.23 | 64.23 | 61.23 | 59.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients<br>Formulation | % w/w<br>61 | % w/w<br>62 | % w/w<br>63 | % w/w<br>64 | % w/w<br>65 | % w/w<br>66 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.23 | 60.23 | 60.23 | 56.33 | 58.23 | 55.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients<br>Formulation | % w/w<br>67 | % w/w<br>68 | % w/w<br>69 | % w/w<br>70 | % w/w<br>71 | % w/w<br>72 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.73 | 66.33 | 59.23 | 58.23 | 56.23 | 61.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients<br>Formulation | % w/w<br>73 | % w/w<br>74 | % w/w<br>75 | % w/w<br>76 | % w/w<br>77 | % w/w<br>78 |
|---|---|---|---|---|---|---|
| Fatty acid* | 10.00 | 12.50 | 25.00 | 10.00 | 15.00 | 20.00 |
| Cetyl alcohol | 2.20 | 2.20 | 2.70 | 4.00 | 4.00 | 2.20 |
| Stearyl alcohol | 3.10 | 3.10 | 3.80 | 2.00 | 2.00 | 3.10 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.00 |
| Sorbitan Monostearate | 0.60 | 0.60 | 0.60 | 1.00 | 1.00 | 1.00 |
| Glycerin | 5.00 | 5.00 | 2.00 | 1.00 | 3.00 | 3.00 |
| Xanthan gum | 0.50 | 0.50 | 0.50 | 0.30 | 0.70 | 0.75 |
| Purified water | 65.98 | 63.48 | 54.78 | 70.28 | 64.28 | 59.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients<br>Formulation | % w/w<br>79 | % w/w<br>80 | % w/w<br>81 | % w/w<br>82 | % w/w<br>83 | % w/w<br>84 |
|---|---|---|---|---|---|---|
| Fatty acid* | 10.00 | 12.50 | 25.00 | 10.00 | 15.00 | 25.00 |
| Cetyl alcohol | 2.20 | 2.20 | 2.70 | 4.00 | 4.00 | 2.70 |
| Stearyl alcohol | 3.10 | 3.10 | 3.80 | 2.00 | 2.00 | 3.80 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.40 |
| Sorbitan Monostearate | 0.60 | 0.60 | 0.60 | 1.00 | 1.00 | 0.60 |
| Glycerin | 5.00 | 5.00 | 2.00 | 1.00 | 3.00 | 2.00 |
| Xanthan gum | 0.50 | 0.50 | 0.50 | 0.30 | 0.70 | 0.50 |
| Purified water | 65.98 | 63.48 | 54.78 | 70.28 | 64.28 | 54.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients<br>Formulation | % w/w<br>85 | % w/w<br>86 | % w/w<br>87 | % w/w<br>88 | % w/w<br>89 | % w/w<br>90 |
|---|---|---|---|---|---|---|
| Fatty acid* | 25.00 | 15.00 | 20.00 | 20.00 | 20.00 | 20.0 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.48 | 66.08 | 58.98 | 57.98 | 55.98 | 60.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients<br>Formulation | % w/w<br>91 | % w/w<br>92 | % w/w<br>93 | % w/w<br>94 | % w/w<br>95 | % w/w<br>96 |
|---|---|---|---|---|---|---|
| Fattty acid* | 15.00 | 12.50 | 25.00 | 15.00 | 10.00 | 20.00 |
| Cetyl alcohol | 2.20 | 2.20 | 2.20 | 2.00 | 2.00 | 2.20 |
| Stearyl alcohol | 3.10 | 3.10 | 3.10 | 2.00 | 2.40 | 3.10 |
| White petrolatum | 6.00 | 5.00 | 3.00 | 3.40 | 2.80 | 3.00 |
| Polysorbate 60 | 3.00 | 3.00 | 3.40 | 3.80 | 3.80 | 3.00 |
| Sorbitan Monostearate | 1.00 | 1.00 | 0.60 | 0.20 | 1.00 | 1.00 |
| Glycerin | 5.00 | 5.00 | 2.00 | 3.00 | 3.00 | 3.00 |
| Xanthan gum | 1.00 | 0.50 | 1.00 | 0.30 | 0.30 | 0.75 |
| Purified water | 60.23 | 63.23 | 55.23 | 66.83 | 70.23 | 59.48 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients<br>Formulation | % w/w<br>97 | % w/w<br>98 | % w/w<br>99 | % w/w<br>100 | % w/w<br>101 | % w/w<br>102 |
|---|---|---|---|---|---|---|
| Fatty acid* | 15.00 | 12.50 | 25.00 | 15.00 | 10.00 | 25.00 |
| Cetyl alcohol | 2.20 | 2.20 | 2.20 | 2.00 | 2.00 | 2.70 |
| Stearyl alcohol | 3.10 | 3.10 | 3.10 | 2.00 | 2.40 | 3.80 |
| White petrolatum | 6.00 | 5.00 | 3.00 | 3.40 | 2.80 | 3.00 |
| Polysorbate 60 | 3.00 | 3.00 | 3.40 | 3.80 | 3.80 | 3.40 |
| Sorbitan Monostearate | 1.00 | 1.00 | 0.60 | 0.20 | 1.00 | 0.60 |
| Glycerin | 5.00 | 5.00 | 2.00 | 3.00 | 3.00 | 2.00 |
| Xanthan gum | 1.00 | 0.50 | 1.00 | 0.30 | 0.30 | 0.50 |
| Purified water | 60.23 | 63.23 | 55.23 | 66.83 | 70.23 | 54.53 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Formulation | 103 | 104 | 105 | 106 | 107 | 108 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.23 | 65.83 | 58.73 | 57.73 | 55.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Formulation | 109 | 110 | 111 | 112 | 113 | 114 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 2.50 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.98 | 65.48 | 63.48 | 60.48 | 59.23 | 59.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 00.00 | 100.00 | 100.00 |

| Excipients | % w/w | % w/w | % w/w | % w/w | % w/w | % w/w |
|---|---|---|---|---|---|---|
| Formulation | 115 | 116 | 117 | 118 | 119 | 120 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 65.48 | 59.48 | 59.48 | 55.58 | 57.48 | 54.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 1100.00 | 100.00 |

| Excipients | % w/w | % w/w | % w/w | % w/w | % w/w | % w/w |
|---|---|---|---|---|---|---|
| Formulation | 121 | 122 | 123 | 124 | 125 | 126 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.98 | 65.58 | 58.48 | 57.48 | 55.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 00.00 | 100.00 |

| Excipients | % w/w | % w/w | % w/w | % w/w | % w/w | % w/w |
|---|---|---|---|---|---|---|
| Formulation | 127 | 128 | 129 | 130 | 131 | 132 |
| Fatty acid* | 15.00 | 18.00 | 15.00 | 20.00 | 12.50 | 20.00 |
| Cetyl alcohol | 2.00 | 2.00 | 2.00 | 2.00 | 2.20 | 2.20 |
| Stearyl alcohol | 2.00 | 2.00 | 2.40 | 2.40 | 3.10 | 3.10 |
| White petrolatum | 3.40 | 2.80 | 3.40 | 2.80 | 5.00 | 3.00 |
| Polysorbate 60 | 3.00 | 3.80 | 3.00 | 3.00 | 3.40 | 3.00 |
| Sorbitan Monostearate | 1.00 | 1.00 | 0.20 | 0.20 | 0.60 | 1.00 |
| Glycerin | 3.00 | 2.00 | 1.00 | 3.00 | 6.00 | 3.00 |
| Xanthan gum | 0.30 | 0.70 | 0.70 | 0.30 | 0.50 | 0.75 |
| Purified water | 65.08 | 62.48 | 67.08 | 61.08 | 61.48 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Formulation | 133 | 134 | 135 | 136 | 137 | 138 |
| Fatty acid* | 15.00 | 18.00 | 15.00 | 20.00 | 12.50 | 25.00 |
| Cetyl alcohol | 2.00 | 2.00 | 2.00 | 2.00 | 2.20 | 2.70 |
| Stearyl alcohol | 2.00 | 2.00 | 2.40 | 2.40 | 3.10 | 3.80 |
| White petrolatum | 3.40 | 2.80 | 3.40 | 2.80 | 5.00 | 3.00 |
| Polysorbate 60 | 3.00 | 3.80 | 3.00 | 3.00 | 3.40 | 3.40 |
| Sorbitan Monostearate | 1.00 | 1.00 | 0.20 | 0.20 | 0.60 | 0.60 |
| Glycerin | 3.00 | 2.00 | 1.00 | 3.00 | 6.00 | 2.00 |
| Xanthan gum | 0.30 | 0.70 | 0.70 | 0.30 | 0.50 | 0.50 |
| Purified water | 65.08 | 62.48 | 67.08 | 61.08 | 61.48 | 53.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Formulation | 139 | 140 | 141 | 142 | 143 | 144 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.48 | 65.08 | 57.98 | 56.98 | 54.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| Excipients | % w/w | % w/w | % w/w | % w/w | % w/w | % w/w |
|---|---|---|---|---|---|---|
| Formulation | 145 | 146 | 147 | 148 | 149 | 150 |
| Fatty acid* | 15.00 | 20.00 | 15.00 | 20.00 | 10.00 | 20.00 |
| Cetyl alcohol | 2.00 | 2.00 | 4.00 | 4.00 | 2.20 | 2.20 |
| Stearyl alcohol | 2.00 | 2.40 | 2.40 | 2.40 | 3.10 | 3.10 |
| White petrolatum | 3.40 | 2.80 | 2.50 | 3.40 | 5.00 | 3.00 |
| Polysorbate 60 | 3.00 | 3.00 | 3.00 | 3.80 | 3.40 | 3.00 |
| Sorbitan Monostearate | 1.00 | 0.20 | 1.00 | 1.00 | 0.60 | 1.00 |
| Glycerin | 3.00 | 3.00 | 1.00 | 3.00 | 5.00 | 3.00 |
| Xanthan gum | 0.30 | 0.30 | 0.30 | 0.70 | 0.50 | 0.75 |
| Purified water | 64.83 | 60.83 | 65.33 | 57.23 | 64.73 | 58.48 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients Formulation | % w/w 151 | % w/w 152 | % w/w 153 | % w/w 154 | % w/w 155 | % w/w 156 |
|---|---|---|---|---|---|---|
| Fatty acid* | 15.00 | 20.00 | 15.00 | 20.00 | 10.00 | 25.00 |
| Cetyl alcohol | 2.00 | 2.00 | 4.00 | 4.00 | 2.20 | 2.70 |
| Steatyl alcohol | 2.00 | 2.40 | 2.40 | 2.40 | 3.10 | 3.80 |
| White petrolatum | 3.40 | 2.80 | 2.50 | 3.40 | 5.00 | 3.00 |
| Polysorbate 60 | 3.00 | 3.00 | 3.00 | 3.80 | 3.40 | 3.40 |
| Sorbitan Monostearate | 1.00 | 0.20 | 1.00 | 1.00 | 0.60 | 0.60 |
| Glycerin | 3.00 | 3.00 | 1.00 | 3.00 | 5.00 | 2.00 |
| Xanthan gum | 0.30 | 0.30 | 0.30 | 0.70 | 0.50 | 0.50 |
| Purified water | 64.83 | 60.83 | 65.33 | 57.23 | 64.73 | 53.53 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients Formulation | % w/w 157 | % w/w 158 | % w/w 159 | % w/w 160 | % w/w 161 | % w/w 162 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.23 | 64.83 | 59.98 | 56.73 | 54.73 | 59.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients Formulation | % w/w 163 | % w/w 164 | % w/w 165 | % w/w 166 | % w/w 167 | % w/w 168 |
|---|---|---|---|---|---|---|
| Fatty acid* | 15.00 | 10.00 | 12.50 | 19.00 | 20.00 | 20.00 |
| Cetyl alcohol | 2.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.00 |
| Sorbitan Monostearate | 0.20 | 0.60 | 0.60 | 0.60 | 0.60 | 1.00 |
| Glycerin | 1.00 | 4.00 | 5.00 | 2.00 | 6.00 | 3.00 |
| Xanthan gum | 0.70 | 0.50 | 0.50 | 0.50 | 0.50 | 0.75 |
| Purified water | 66.58 | 65.48 | 61.38 | 60.48 | 56.48 | 58.23 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients Formulation | % w/w 169 | % w/w 170 | % w/w 171 | % w/w 172 | % w/w 173 | % w/w 174 |
|---|---|---|---|---|---|---|
| Fatty acid* | 15.00 | 10.00 | 12.50 | 19.00 | 20.00 | 25.00 |
| Cetyl alcohol | 2.00 | 2.20 | 2.20 | 2.20 | 2.20 | 2.70 |
| Stearyl alcohol | 2.40 | 3.10 | 3.10 | 3.10 | 3.10 | 3.80 |
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.40 |
| Sorbitan Monostearate | 0.20 | 0.60 | 0.60 | 0.60 | 0.60 | 0.60 |
| Glycerin | 1.00 | 4.00 | 5.00 | 2.00 | 6.00 | 2.00 |
| Xanthan gum | 0.70 | 0.50 | 0.50 | 0.50 | 0.50 | 0.50 |
| Purified water | 66.58 | 65.48 | 61.38 | 60.48 | 56.48 | 53.28 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients Formulation | % w/w 175 | % w/w 176 | % w/w 177 | % w/w 178 | % w/w 179 | % w/w 180 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.98 | 64.58 | 57.48 | 56.48 | 54.48 | 59.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients Formulation | % w/w 181 | % w/w 182 | % w/w 183 | % w/w 184 | % w/w 185 | % w/w 186 |
|---|---|---|---|---|---|---|
| Fatty acid* | 20.00 | 20.00 | 25.00 | 18.75 | 20.00 | 21.2 |
| Cetyl alcohol | 4.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 2.80 | 3.00 | 3.00 | 5.00 | 5.00 | 3.75 |
| Polysorbate 60 | 3.00 | 3.40 | 3.40 | 3.00 | 3.40 | 3.40 |
| Sorbitan Monostearate | 1.00 | 0.60 | 0.60 | 1.00 | 0.60 | 0.60 |
| Glycerin | 1.00 | 2.00 | 2.00 | 5.00 | 5.00 | 5.00 |
| Xanthan gum | 0.30 | 0.50 | 0.50 | 0.05 | 0.50 | 0.50 |
| Purified water | 64.53 | 59.23 | 54.23 | 55.48 | 54.23 | 54.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients Formulation | % w/w 187 | % w/w 188 | % w/w 189 | % w/w 190 | % w/w 191 | % w/w 192 |
|---|---|---|---|---|---|---|
| Fatty acid* | 20.00 | 20.00 | 20.00 | 25.00 | 18.75 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 59.23 | 53.23 | 53.23 | 54.33 | 55.48 | 53.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients Formulation | % w/w 193 | % w/w 194 | % w/w 195 | % w/w 196 | % w/w 197 | % w/w 198 |
|---|---|---|---|---|---|---|
| Fatty acid* | 25.00 | 20.00 | 20.00 | 20.00 | 20.00 | 21.00 |
| Cetyl alcohol | 2.20 | 4.00 | 2.20 | 2.20 | 2.20 | 2.20 |
| Stearyl alcohol | 3.10 | 2.40 | 3.10 | 3.10 | 3.10 | 3.10 |
| White petrolatum | 3.00 | 3.40 | 5.00 | 3.00 | 5.00 | 5.00 |
| Polysorbate 60 | 3.40 | 3.80 | 3.40 | 3.40 | 3.40 | 3.40 |
| Sorbitan Monostearate | 0.60 | 1.00 | 0.60 | 0.60 | 0.60 | 0.60 |
| Glycerin | 2.00 | 3.00 | 2.00 | 5.00 | 5.00 | 5.00 |
| Xanthan gum | 1.00 | 0.70 | 0.50 | 0.50 | 0.50 | 0.50 |
| Purified water | 53.73 | 55.73 | 57.23 | 56.23 | 54.23 | 53.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propylparaben | 0.02 | 0.02 | 0.02 | 0.02 | 0.02 | 0.02 |
| Imiquimod | 3.75 | 3.75 | 3.75 | 3.75 | 3.75 | 3.7 |
| Total | 100.00 | 100.00 | 100.00 | 100.00 | 100.00 | 100.00 |

| Excipients Formulation | % w/w 199 | % w/w 200 | % w/w 201 | % w/w 202 | % w/w 203 | % w/w 204 |
|---|---|---|---|---|---|---|
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients Formulation | % w/w 205 | % w/w 206 | % w/w 207 | % w/w 208 | % w/w 209 | % w/w 210 |
|---|---|---|---|---|---|---|
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylbaraben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients Formulation | % w/w 211 | % w/w 212 | % w/w 213 | % w/w 214 | % w/w 215 | % w/w 216 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.48 | 64.08 | 56.98 | 55.98 | 53.98 | 58.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipient Formulation | % w/w 217 | % w/w 218 | % w/w 219 | % w/w 220 | % w/w 221 | % w/w 222 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.73 | 63.73 | 61.73 | 58.73 | 57.48 | 57.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |

TABLE 9-continued

| | | | | | | |
|---|---|---|---|---|---|---|
| Propyparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients Formulation | % w/w 223 | % w/w 224 | % w/w 225 | % w/w 226 | % w/w 227 | % w/w 228 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 63.73 | 57.73 | 57.73 | 53.83 | 55.73 | 52.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients Formulation | % w/w 229 | % w/w 230 | % w/w 231 | % w/w 232 | % w/w 233 | % w/w 234 |
|---|---|---|---|---|---|---|
| Fatty acid* | 25.00 | 15.00 | 20.00 | 20.00 | 20.0 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.20 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.23 | 63.83 | 56.73 | 55.73 | 53.73 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

*The Fatty acid referenced in this Table 9 can be, for example, linoleic acid (la), stearic acid (sa), palmitic acid (pa), isostearic acid (isa), unrefined oleic acid, (uoa), refined oleic acid, such as super refined oleic acid (roa), or mixtures thereof.

The work area, all vessels and equipment is initially cleaned prior to commencing manufacture. A 2 L glass container and paddle stirrer blade are placed onto a balance and the weight is recorded. The paddle is then removed from the vessel. The isostearic acid and benzyl alcohol are weighed directly into the 2 L glass container. The imiquimod is then weighed into the 2 L glass container and a spatula is used to ensure the imiquimod is wetted with the isostearic acid and benzyl alcohol mixture. The 2 L container is then heated in a water bath to about 55±5° C. while stirring with a Heidolph mixer (Note: aluminum foil is placed around the top of the vessel and the paddle for the mixer, to limit evaporation). The solution is visually inspected to confirm the imiquimod has fully dissolved prior to mixing with cetyl alcohol, stearyl alcohol, white petrolatum, polysorbate 60 and sorbitan monostearate. Cetyl alcohol, stearyl alcohol, white petrolatum, polysorbate 60 and sorbitan monostearate are then weighed directly into the 2 L container and mixing is continued at about 55±5° C. until the oil phase is completely in solution. Separately, about 2 L of water are placed into a beaker and heated to 55±5° C. while stirring with a magnetic follower. Briefly, about 500 ml of the heated water is transferred into a 1 L beaker and placed into the water bath maintained at about 55±f 5° C. Half of the amount of glycerin required for the final formulation is then weighed into the beaker along with the total amount of methylparaben and propylparaben to the water (where both methyl and propyl paraben are weighed into weighing boats first, a pipette is used to remove a portion of the heated water to wash out the weighing boats to ensure total transfer of both the propyl- and methylparaben into the aqueous phase). The mixture is continuously stirred at about 55±5° C. (this is the aqueous phase). The remaining glycerin is then added to a 28 ml vial and the xanthan gum is added and mixed using a small overhead mixer (1KA®-Werke Lab Egg) with paddle attachment for about 10 min. The glycerin and xanthan mixture are then added slowly into the vortex of the aqueous phase, and a further aliquot of about 20 ml of heated water is used to rinse the vessel out into the water phase to ensure complete transfer. The water phase is then heated and mixed at about 55±5° C. until the xanthan gum mixture is fully and evenly dispersed into the aqueous phase. The temperatures of both the water phase and oil phase are both maintained at about 55±5° C. The aqueous phase is then transferred into the oil phase and the speed of the Heidolph mixer is increased during addition. The mixture is then homogenized on high speed for about 3 min and transferred immediately back to the Heidolph mixture; however, the contents of the homogenized sample, about 2 L, are mixed at about room temperature and allowed to cool to about 35° C. The container and contents and the paddle from the overhead mixer are then re-weighed and the weight of the paddle and 2 L beaker, as determined above, are subtracted to determine the total weight of the formulation remaining. The total weight (about 1 kg) of the cream is then made up to weight with heated water (Note: water evaporated during heating, which needs to be corrected at this point). The mixture is then transferred back onto the Heidolph mixer at about room temperature and mixed until the temperature of the formulation is below about 28° C. The lid of the container is then placed onto the vessel and stored at room temperature.

The lower dosage strength formulations of this Example 23 are believed to be stable and consistent with the specifications for the commercially available Aldara® 5% imiquimod cream. More preferably, low dosage formulations of this Example 23, especially as to those lower dosage strength formulations wherein the vehicle comprises an isostearic acid as the fatty acid, are believed to have the following:

(1) Stability. The imiquimod formulations of the present invention, when they are measured on HPLC at 25° C./60% RH, 30° C./65% RH and 40° C./75% RH over, one, two, three and six months, demonstrate stability consistent with the Aid 5% imiquimod cream;

(2) Degradation Products. No degradation products are detected in the formulations of the present invention, at its current recommended storage temperatures of about 4-25° C. In addition, there are no degradation products detected at any of the temperatures or time points mentioned under "Stability" above, when analyzed at about 318 nm.

(3) Homogeneity. The amount of imiquimod that is recovered from the formulations at any of the above-mentioned temperatures and time points is between about 90 to about 110% w/w thereby demonstrating good homogeneity;

(4) Benzyl Alcohol Content. The formulations of the present invention are also within specifications for the Aldara® 5% imiquimod cream, i.e., between 1.0% w/w and 2.1% w/w, at any of the above-mentioned temperatures and time points as to benzyl alcohol content.

(5) Microscopic Stability. There is no change in the particle size and no crystals are detected in the formulations of the present invention when they are stored at 25° C./60% RH and analyzed over a six month period;

(6) Macroscopic Stability. There are no obvious physical changes in the formulations of the present invention when they are stored at 25° C./60% RH and analyzed over a six month period;

(7) Viscosity. The formulations of the present invention are within the range of the specifications for the Aldara® 5% imiquimod cream, i.e., between 2000 cPs and 35,000 cPs, when they are stored at 25° C./60% RH and analyzed over a six month period; pH Stability. The formulations of the present invention are within the range of the specifications for the Aldara® 5% imiquimod cream, i.e., between pH 4.0 and pH 5.5) when they are stored at 25° C./60° % RH and analyzed over a six month period;

(8) Preservative Efficacy Test ("PET"). The formulations of the present invention demonstrate sufficient reductions in colony forming unit counts for each of the organisms with which the formulations are inoculated, i.e., *S. aureus, E. coli, Ps. Aeruginosa, C. albicans*, and *A. niger*, at 2-8° C. and 40° C. over a 28 day test period and meet the requirements specified in both the USP and EP.

(9) Imiquimod In vitro Release. The Aldara® 5% imiquimod cream releases statistically significant ($p<0.05$) higher amounts of imiquimod over a 3 hour time period in comparison to the lower dosage strength formulations of the present invention through a synthetic membrane, e.g., Microporous polyethylene film 3M No. 9711 CoTran™. There is no statistical difference ($p<0.05$) in the total cumulative amount of imiquimod that is released from any of the 3.75% w/w imiquimod formulations. There is no statistical difference ($p<0.05$) in the total cumulative amount of imiquimod that is released from any of the 2.5% w/w imiquimod formulations. The Aldara® 5% imiquimod cream also statistically significantly ($p<0.05$) releases imiquimod at a faster rate over a 3 hour time period in comparison to the lower dosage strength formulations of the present invention through a synthetic membrane, e.g., Microporous polyethylene film 3M No. 9711 CoTran™. There is no statistical difference ($p<0.05$) between the imiquimod release rates for any of the 3.75% w/w imiquimod formulations. There is no statistical difference ($p<0.05$) between the imiquimod release rates for any of the 2.5% w/w imiquimod formulations. Thus, the greater the amount of imiquimod in a formulation, the faster and greater the total amount of imiquimod that is released from such formulation that the amount and rate of release of imiquimod are concentration dependant and that the rates and amounts of release of imiquimod from the formulations of the present invention are linear and dose proportionate to the Aldara® 5% imiquimod cream;

(10) Imiquimod In vitro Skin Permeation (Franz Cell Study). With respect to statistical analyses, there is no statistical difference between the lower dosage strength formulations of the present invention and the Aldara® 5% imiquimod cream as to the amount of imiquimod recovered from the receiver fluid, epidermis and dermis combined, Nonetheless, there is a statistically significant ($p<0.05$) dose proportionate difference between the amount of imiquimod recovered from each of the matrices with respect to the concentration of imiquimod in the lower dosage strength formulations of the present invention and the Aldara® 5% imiquimod cream for both un-absorbed and stratum corneum. Thus there is a linear dose release between the amount of imiquimod that is applied and recovered in each of the matrices, i.e., receiver fluid, unabsorbed dose, stratum corneum, epidermis and dermis.

ANOVA statistical analysis at 95% confidence level is used to analyze the stability data generated, including the data generated for the membrane and skin permeation experiments.

It is also believed that the formulations of the present invention, including the formulations identified in this Example 23, have Hydrophilic-lipophilic balance (HLB) values between about 12 and 15, and more preferably between about 12.4 and about 13.4.

I. Physical Characterization and Testing

The following is conducted for physical characterization of lower dosage strength imiquimod formulations, e.g., formulations identified in Table 12 and Table 18, and for testing lower dosage strength imiquimod formulations, e.g., imiquimod formulations identified in Tables 13-17.

(A) Analytical Method—HPLC Assay

A summary of an HPLC method is provided in Table 10.

TABLE 10

| Summary of HPLC Methodology | |
|---|---|
| HPLC System | HPLC 9. Waters 265 (Alliance Separations module), Water 996 (Photodiode array detector), CPU (Compaq), Software-Microsoft Windows NT Version 4.00.1381 and Analysis software-Millenium[32] Version 4.00.00.00 |
| Column | Supelcosil LC-8-DB (5 mm, 15 × 0.46 cm) |
| Guard Column | Supelguard LC-8-DB 2 cm |
| Detection | UV at 258 nm |
| Sample Temperature | 25° C. |
| Column Temperature | 25° C. |
| Flow Rate | 2 ml/min |
| Mobile Phase | 72:28 aqueous:ACN (1% TEA solution, 0.2% Octyl Sodium Sulfate, adjusted to pH 2.0 with $H_3PO_4$ |
| Injection Volume | 20 µl |
| Run Time | 12 min |
| Needle Wash | 0:90 0.1N HCl:water |

(B) Preparation of HPLC Reagents

Mobile Phase:

About 2.0 g octyl sodium sulfate (OSS) is weighed into a large beaker and is mixed with about 990 ml milli-Q ultrapure water and about 10.0 ml of triethylamine (TEA). The mixture is sonicated and stirred for about 5 min to dissolve the solids. A pH meter is then placed in the mixture and the pH of the OSS/TEA solution is adjusted to about 2.0 with concentrated $H_3PO_4$, stirring continuously during the adjusting procedure. The entire mixture is then filtered through a 0.2 µm filter. The filtrate is mixed with acetonitrile (HPLC grade) in the ratio of about 72:28 aqueous:acetonitrile by volume.

Sample Diluent

About 250 ml acetonitrile (HPLC grade), about 740 ml purified water and about 10 ml of concentrated HCl are mixed together in a 1 L volumetric flask.

Receiver Fluid

About 100 ml of a commercially available standardized 1N HCl solution is diluted to about 1000 ml with Milli-Q ultra pure water.

Standards

Imiquimod standards are prepared, as described under Sample Diluent and Receiver Fluid, for stability test and receiver for membrane release tests. Initially, a stock solution of imiquimod is prepared by dissolving about 25 mg of imiquimod into about 50 ml of solvent (either Sample Diluent or Receiver Fluid) to give a concentration of about 500 µg/ml in Sample Diluent or Receiver Fluid.

A calibration range as shown in Table 11 is prepared for each HPLC run.

TABLE 11

Preparation of Calibration Standards

| Volume of stock solution (ml) | Volume of diluent | Final concentration of Test Item (gg,/ml) |
|---|---|---|
| 10 | 0 | 500 |
| 5 | 5 | 250 |
| 4 | 6 | 200 |
| 2 | 8 | 100 |
| 1 | 9 | 50 |
| 0.5 | 9.5 | 25 |
| 0.2 | 9.8 | 10 |
| 0.1 | 9.9 | 5 |

Combination Standard

The following combination standard solution is also prepared; whereby, about 500 mg of methylparaben and about 50 mg propylparaben are weighed into a single 250 ml volumetric flask and is diluted to volume with sample diluent above, to form the parabens solution. In addition, about 500 mg of imiquimod and about 200 mg benzyl alcohol are also weighed into a single 100 ml volumetric flask and about 10 ml of the parabens solution is then transferred into the imiquimod/benzyl alcohol volumetric which is made up to volume with diluent and is sonicated to dissolve fully.

Impurity Standards

Impurity standards are prepared separately at a concentration of about 50 p·g/ml in Sample Diluent and are analyzed in each HPLC run. The impurity standards that are included in each HPLC run are as follows:

N-propyl imiquimod

N-methyl imiquimod 4-hydroxyimiquimod 4-chloro imiquimod

TABLE 12

| | 2.5% Imiquimod Formulations | | | | | | 3.75% Imiquimod Formulations | | | | | |
|---|---|---|---|---|---|---|---|---|---|---|---|---|
| | 235 % w/w | 236 % w/w | 237 % w/w | 238 % w/w | 239 % w/w | 240 % w/w | 241 % w/w | 242 % w/w | 243 % w/w | 244 % w/w | 181 % w/w | 245 % w/w |
| Excipients | | | | | | | | | | | | |
| Isostearic acid | 15 | 10 | 15 | 10 | 15 | 15 | 15 | 20 | 15 | 20 | 15 | 20 |
| Cetyl alcohol | 2 | 4 | 4 | 2 | 2 | 4 | 2 | 2 | 2 | 2 | 4 | 4 |
| Stearyl alcohol | 2 | 2 | 2 | 2.4 | 2.4 | 2.4 | 2 | 2 | 2.4 | 2.4 | 2.4 | 2.4 |
| White petrolatum | 3.4 | 3.4 | 2.8 | 2.8 | 3.4 | 2.8 | 3.4 | 2.8 | 3.4 | 2.8 | 2.8 | 3.4 |
| Polysorbate 60 | 3.8 | 3.8 | 3 | 3.8 | 3 | 3.8 | 3 | 3.8 | 3 | 3 | 3 | 3.8 |
| Sorbitan Monostearate | 0.2 | 1 | 1 | 1 | 1 | 0.2 | 1 | 1 | 0.2 | 0.2 | 1 | 1 |

TABLE 12-continued

| | 2.5% Imiquimod Formulations | | | | | | 3.75% Imiquimod Formulations | | | | | |
|---|---|---|---|---|---|---|---|---|---|---|---|---|
| | 235 % w/w | 236 % w/w | 237 % w/w | 238 % w/w | 239 % w/w | 240 % w/w | 241 % w/w | 242 % w/w | 243 % w/w | 244 % w/w | 181 % w/w | 245 % w/w |
| Glycerine | 3 | 1 | 3 | 3 | 1 | 1 | 3 | 1 | 1 | 3 | 1 | 3 |
| Xanthan gum | 0.3 | 0.3 | 0.7 | 0.3 | 0.7 | 0.3 | 0.3 | 0.7 | 0.7 | 0.3 | 0.3 | 0.7 |
| Purified water | 65.58 | 69.78 | 63.78 | 69.98 | 66.78 | 65.78 | 64.33 | 60.73 | 66.33 | 60.33 | 64.53 | 55.73 |
| Benzyl alcohol | 2 | 2 | 2 | 2 | 2 | 2 | 2 | 2 | 2 | 2 | 2 | 2 |
| Methylparaben | 0.2 | 0.2 | 0.2 | 0.2 | 0.2 | 0.2 | 0.2 | 0.2 | 0.2 | 0.2 | 0.2 | 0.2 |
| Propylparaben | 0.02 | 0.02 | 0.02 | 0.02 | 0.02 | 0.02 | 0.02 | 0.02 | 0.02 | 0.02 | 0.02 | 0.02 |
| Imiquimod | 2.50 | 2.50 | 2.50 | 2.50 | 2.50 | 2.50 | 3.75 | 3.75 | 3.75 | 3.75 | 3.75 | 3.75 |
| Total amount (g) | 100.00 | 100.00 | 100.00 | 100.00 | 100.00 | 100.00 | 100.00 | 100.00 | 100.00 | 100.00 | 100.00 | 100.00 |
| HLB Values | 14.4 | 12.8 | 12.4 | 12.8 | 12.4 | 14.4 | 12.4 | 12.8 | 14.3 | 14.3 | 12.4 | 12.8 |

In Table 13, fifteen 2.5% w/w imiquimod formulations are manufactured in 100 g batches. Each of the fifteen formulations are assessed for macroscopic and microscopic appearance, as discussed hereinafter.

TABLE 13

| Imiquimod Formulation | 246 % w/w | 110 % w/w | 116 % w/w | 247 % w/w | 117 % w/w | 248 % w/w | 249 % w/w | 250 % w/w |
|---|---|---|---|---|---|---|---|---|
| Excipients | | | | | | | | |
| Isostearic acid | 15.00 | 15.00 | 15.00 | 10.00 | 15.00 | 15.00 | 10.00 | 25.00 |
| Cetyl alcohol | 2.20 | 2.20 | 2.20 | 2.20 | 2.20 | 2.20 | 2.20 | 2.20 |
| Stearyl alcohol | 3.10 | 3.10 | 3.10 | 3.10 | 3.10 | 3.10 | 3.10 | 3.10 |
| White petrolatum | 15.50 | 3.00 | 6.00 | 8.50 | 6.00 | 6.00 | 8.50 | 3.00 |
| Polysorbate 60 | 3.40 | 3.40 | 3.40 | 3.40 | 3.00 | 4.25 | 3.00 | 3.40 |
| Sorbitan Monostearate | 0.60 | 0.60 | 0.60 | 0.60 | 1.00 | 0.75 | 1.00 | 0.60 |
| Glycerine | 2.00 | 2.00 | 5.00 | 5.00 | 5.00 | 5.00 | 5.00 | 2.00 |
| Xanthan gum | 0.50 | 0.50 | 0.50 | 0.50 | 0.50 | 0.50 | 0.50 | 0.50 |
| Purified water | 52.98 | 65.48 | 59.48 | 61.98 | 59.48 | 58.48 | 61.58 | 55.48 |
| Benzyl alcohol | 2.00 | 2.00 | 2.00 | 2.00 | 2.00 | 2.00 | 2.00 | 2.00 |
| Methylparaben | 0.20 | 0.20 | 0.20 | 0.20 | 0.20 | 0.20 | 0.20 | 0.20 |
| Propylparaben | 0.02 | 0.02 | 0.02 | 0.02 | 0.02 | 0.02 | 0.02 | 0.02 |
| Imiquimod | 2.50 | 2.50 | 2.50 | 2.50 | 2.50 | 2.50 | 2.50 | 2.50 |
| Total amount (g) | 100.00 | 100.00 | 100.00 | 100.00 | 100.00 | 100.00 | 100.00 | 100.00 |
| HLB Values | 13.4 | 13.4 | 13.4 | 13.4 | 12.4 | 13.4 | 12.4 | 13.4 |

| Imiquimod Formulation | 113 % w/w | 251 % w/w | 252 % w/w | 253 % w/w | 254 % w/w | 120 % w/w | 121 % w/w |
|---|---|---|---|---|---|---|---|
| Excipients | | | | | | | |
| Isostearic acid | 15.00 | 15.00 | 10.00 | 12.5 | 12.5 | 25.00 | 25.00 |
| Cetyl alcohol | 2.20 | 2.20 | 2.20 | 2.20 | 2.20 | 2.70 | 2.20 |
| Stearyl alcohol | 3.10 | 3.10 | 3.10 | 3.10 | 3.10 | 3.80 | 3.10 |
| White petrolatum | 6.00 | 6.00 | 5.00 | 5.00 | 5.00 | 3.00 | 3.00 |
| Polysorbate 60 | 3.00 | 3.00 | 3.40 | 3.40 | 3.00 | 3.40 | 3.40 |
| Sorbitan Monostearate | 1.00 | 1.00 | 0.60 | 0.60 | 1.00 | 0.60 | 0.60 |
| Glycerine | 5.00 | 5.00 | 5.00 | 5.00 | 5.00 | 2.00 | 2.00 |
| Xanthan gum | 0.75 | 1.00 | 0.50 | 0.50 | 0.50 | 0.50 | 1.00 |
| Purified water | 59.23 | 58.98 | 60.48 | 62.98 | 62.98 | 54.28 | 54.98 |
| Benzyl alcohol | 2.00 | 2.00 | 2.00 | 2.00 | 2.00 | 2.00 | 2.00 |
| Methylparaben | 0.20 | 0.20 | 0.20 | 0.20 | 0.20 | 0.20 | 0.20 |
| Propylparaben | 0.02 | 0.02 | 0.02 | 0.02 | 0.02 | 0.02 | 0.02 |
| Imiquimod | 2.50 | 2.50 | 2.50 | 2.50 | 2.50 | 2.50 | 2.50 |
| Total amount (g) | 100.00 | 100.00 | 100.00 | 100.00 | 100.00 | 100.00 | 100.00 |
| HLB Values | 12.4 | 12.4 | 13.4 | 13.4 | 12.4 | 13.4 | 13.4 |

TABLE 14

| 2.5% Imiquimod Formulations | 110 % w/w | 116 % w/w | 117 % w/w | 250 % w/w | 254 % w/w | 120 % w/w | 121 % w/w | 235 % w/w | 123 % w/w | 124 % w/w | 125 % w/w | 126 % w/w |
|---|---|---|---|---|---|---|---|---|---|---|---|---|
| Excipients | | | | | | | | | | | | |
| Isostearic acid | 15.00 | 15.00 | 15.00 | 25.00 | 12.5 | 25.00 | 25.00 | 15 | 20.00 | 20.00 | 20.00 | 20.00 |
| Cetyl alcohol | 2.20 | 2.20 | 2.20 | 2.20 | 2.20 | 2.70 | 2.2 | 2 | 2.20 | 2.20 | 2.20 | 2.20 |
| Stearyl alcohol | 3.10 | 3.10 | 3.10 | 3.10 | 3.10 | 3.80 | 3.10 | 2 | 3.10 | 3.10 | 3.10 | 3.10 |
| White petrolatum | 3.00 | 6.00 | 6.00 | 3.00 | 5.00 | 3.00 | 3.00 | 3.4 | 5.00 | 3.00 | 5.00 | 3.00 |
| Polysorbate 60 | 3.40 | 3.40 | 3.00 | 3.40 | 3.00 | 3.40 | 3.40 | 3.8 | 3.40 | 3.40 | 3.40 | 3.40 |
| Sorbitan Monostearate | 0.60 | 0.60 | 1.00 | 0.60 | 1.00 | 0.60 | 0.60 | 0.2 | 0.60 | 0.60 | 0.60 | 0.60 |
| Glycerine | 2.00 | 5.00 | 5.00 | 2.00 | 5.00 | 2.00 | 2.00 | 3 | 2.00 | 5.00 | 5.00 | 2.00 |
| Xanthan gum | 0.50 | 0.50 | 0.50 | 0.50 | 0.50 | 0.50 | 1.00 | 0.3 | 0.50 | 0.50 | 0.50 | 0.50 |
| Purified water | 65.48 | 59.48 | 59.48 | 55.48 | 62.98 | 54.28 | 54.98 | 65.58 | 58.48 | 57.48 | 55.48 | 60.48 |
| Benzyl alcohol | 2.00 | 2.00 | 2.00 | 2.00 | 2.00 | 2.00 | 2.00 | 2 | 2.00 | 2.00 | 2.00 | 2.00 |
| Methylparaben | 0.20 | 0.20 | 0.20 | 0.20 | 0.20 | 0.20 | 0.20 | 0.2 | 0.20 | 0.20 | 0.20 | 0.20 |
| Propylparaben | 0.02 | 0.02 | 0.02 | 0.02 | 0.02 | 0.02 | 0.02 | 0.02 | 0.02 | 0.02 | 0.02 | 0.02 |
| Imiquimod | 2.50 | 2.50 | 2.50 | 2.50 | 2.50 | 2.50 | 2.50 | 2.50 | 2.50 | 2.50 | 2.50 | 2.50 |
| Total | 100.00 | 100.00 | 100.00 | 100.00 | 100.00 | 100.00 | 100.00 | 100.00 | 100.00 | 100.00 | 100.00 | 100.00 |
| HLB Values | 13.4 | 13.4 | 12.4 | 13.4 | 12.4 | 13.4 | 13.4 | 14.4 | 13.4 | 13.4 | 13.4 | 13.4 |

TABLE 15

| 3.75% Imiquimod Formulations | 182 % w/w | 188 % w/w | 189 % w/w | 183 % w/w | 184 % w/w | 255 % w/w | 193 % w/w | 245 % w/w | 195 % w/w | 256 % w/w | 197 % w/w |
|---|---|---|---|---|---|---|---|---|---|---|---|
| Excipients | | | | | | | | | | | |
| Isostearic acid | 20.00 | 20.00 | 20.00 | 25.00 | 18.75 | 25.00 | 25.00 | 20 | 20.00 | 20.00 | 20.00 |
| Cetyl alcohol | 2.20 | 2.20 | 2.20 | 2.20 | 2.20 | 2.70 | 2.20 | 4 | 2.20 | 2.20 | 2.20 |
| Stearyl alcohol | 3.10 | 3.10 | 3.10 | 3.10 | 3.10 | 3.80 | 3.10 | 2.4 | 3.10 | 3.10 | 3.10 |
| White petrolatum | 3.00 | 6.00 | 6.00 | 3.00 | 5.00 | 3.00 | 3.00 | 3.4 | 5.00 | 3.00 | 5.00 |
| Polysorbate 60 | 3.40 | 3.40 | 3.00 | 3.40 | 3.00 | 3.40 | 3.40 | 3.8 | 3.40 | 3.40 | 3.40 |
| Sorbitan Monostearate | 0.60 | 0.60 | 1.00 | 0.60 | 1.00 | 0.60 | 0.60 | 1 | 0.60 | 0.60 | 0.60 |
| Glycerine | 2.00 | 5.00 | 5.00 | 2.00 | 5.00 | 2.00 | 2.00 | 3 | 2.00 | 5.00 | 5.00 |
| Xanthan gum | 0.50 | 0.50 | 0.50 | 0.50 | 0.50 | 1.00 | 1.00 | 0.7 | 0.50 | 0.50 | 0.50 |
| Purified water | 59.23 | 53.23 | 53.23 | 54.23 | 55.48 | 53.73 | 53.73 | 55.73 | 57.23 | 58.23 | 54.23 |
| Benzyl alcohol | 2.00 | 2.00 | 2.00 | 2.00 | 2.00 | 2.00 | 2.00 | 2 | 2.00 | 2.00 | 2.00 |
| Methylparaben | 0.20 | 0.20 | 0.20 | 0.20 | 0.20 | 0.20 | 0.20 | 0.2 | 0.20 | 0.20 | 0.20 |
| Propylparaben | 0.02 | 0.02 | 0.02 | 0.02 | 0.02 | 0.02 | 0.02 | 0.02 | 0.02 | 0.02 | 0.02 |
| Imiquimod | 3.75 | 3.75 | 3.75 | 3.75 | 3.75 | 3.75 | 3.75 | 3.75 | 3.75 | 3.75 | 3.75 |
| Total | 100.00 | 100.00 | 100.00 | 100.00 | 100.00 | 100.00 | 100.00 | 100.00 | 100.00 | 100.00 | 100.00 |
| HLB Values | 13.4 | 13.4 | 12.4 | 13.4 | 12.4 | 13.4 | 13.4 | 12.8 | 13.4 | 13.4 | 13.4 |

In Table 16, compositions for Aldara® 5% imiquimod cream and 1% imiquimod cream formulations are shown. Also shown in the Table 16, are four placebo formulations Pbo1, Pbo2, Pbo3 and formulation Pbo4,

TABLE 16

| | 3M Aldara ® (5% | 257 | Placebos | | | |
|---|---|---|---|---|---|---|
| Formulations | Bulk) % w/w | (1%) % w/w | Pbo1 % w/w | Pbo2 % w/w | Pbo3 % w/w | Pbo4 % w/w |
| Excipients | | | | | | |
| Isostearic acid | 25.00 | 25.00 | 20.00 | 20.00 | 20.00 | 20.00 |
| Cetyl alcohol | 2.20 | 2.40 | 2.20 | 2.20 | 2.20 | 2.20 |
| Stearyl alcohol | 3.10 | 3.40 | 3.10 | 3.10 | 3.10 | 3.10 |
| White petrolatum | 3.00 | 3.00 | 5.00 | 3.00 | 5.00 | 3.00 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerine | 2.00 | 2.00 | 2.00 | 5.00 | 5.00 | 2.00 |

TABLE 16-continued

| Formulations | 3M Aldara ® (5% Bulk) % w/w | 257 (1%) % w/w | Placebos Pbo1 % w/w | Pbo2 % w/w | Pbo3 % w/w | Pbo4 % w/w |
|---|---|---|---|---|---|---|
| Xanthan gum | 0.50 | 0.50 | 0.60 | 0.60 | 0.50 | 0.50 |
| Purified water | 52.98 | 58.48 | 80.98 | 59.98 | 57.98 | 62.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 5.00 | 1.00 | 0.00 | 0.00 | 0.00 | 0.00 |
| Total | 100.00 | 100.00 | 100.00 | 100.00 | 100.00 | 100.00 |
| HLB Values | 13.37 | 13.37 | 13.37 | 13.37 | 13.37 | 13.37 |

(C) Uniformity/Homogeneity

Following a 1 kg batch manufacturing process as described in this Example 23, 3×150 mg samples (top, middle and bottom) are removed from each 1 kg bulk batch using a positive displacement pipette and are extracted and are analyzed as described in Section, entitled "imiquimod Content" described hereinafter.

(D) Preparation of Stability Samples

Each of the 1 kg batches are sub-aliquoted individually into 21×60 ml glass powder jars, where:

| | |
|---|---|
| (B) | 5 × 50 g (25° C./60% RH t = 0 h, 1 month, 2 months, 3 months, 6 months) |
| (C) | 5 × 50 g (30° C./65% RH − t = 0 h, 1 month, 2 months, 3 months, 6 months) |
| (D) | 5 × 50 g (40° C./75% RH − t = 0 h, 1 month, 2 months, 3 months, 6 months) |
| (E) | 1 × 60 g (PET sample, placed at 2-8° C.) |
| (F) | 1 × 20 g (placed at 2-8° C.) |
| (G) | 1 × 20 g (placed at −20° C.) |
| (H) | The remaining formulation, is divided into 3 additional aliquots and each is placed at 25° C./60% RH, 30° C./65% RH and 40° C./75% RH. |

All batches are characterised based on the protocols that are shown in Section entitled Protocol for the Assessment of Formulations. Once each aliquot is removed from the relevant stability conditions at each time point; the remaining aliquot from each sample is placed in a fridge at 2-8° C. for future reference if required.

Following the 1 month stability time point, the benzyl alcohol content of the formulations are monitored; for all subsequent time points, the placebo formulations are analyzed by HPLC. Thus, there are no t=0 measurements for benzyl alcohol content for placebo formulations Pbo1, Pbo2 and Pbo3.

(E) Protocol for the Assessment of Formulations

The protocols that are used for the assessment of the formulations are as follows:

(1) Macroscopic Appearance

Macroscopic appearance is determined by visual examination of the physical characteristics which include appearance and texture of each cream. Macroscopic appearance is performed at each time point (t=0, 1, 2, 3 and 6 months) for the 25° C. stability samples, as follows:

(A) Using a medium Granton® pallet knife, a small aliquot of sample (approximately 1 to 2 g) is removed from its container and is placed on the surface of a large Granton® pallet knife.

(B) The medium Granton® pallet knife is then used to smooth the cream over the surface of the large Granton® pallet knife, by using a backward and forward motion of the spatula until a visually uniform layer of cream is obtained on the large Granton® pallet knife.

(C) Visual observations of the cream are recorded which are based on, the presence of lumps, graduals or ease of spread over the surface of the spatula.

(2) Microscopic Appearance

Formulations are viewed under a light microscope (Leica DME FD198536 Light Microscope), to determine particle size, uniformity and the absence of particulates. Digital images of each formulation are taken at each time point (t=0, 1, 2, 3 and 6 months) for the 25° C. stability samples, as follows:

(A) The microscope is set up so that the camera (Nikkon Cool Pix 4500 digital camera) is attached to the relay lens of the microscope and the 40× objective lens is set into place to view the sample. Camera settings: Image size: 1280×960 pixels, Image quality: Fine.

(B) A small droplet of the formulation to be viewed is placed onto a microscope slide (Fisher-brand microscope slides, Cat No. 7101) using a micro-spatula. The microscope slide is then covered using a cover glass (Fisher-brand cover glass, width: 22-32 mm, thickness: 0.13-0.17 mm).

(C) The microscope slide with the formulation is then placed under the 40× objective. Using the fine adjustment knob of the light microscope, the slide is brought into sharper focus to get a clear view.

(D) Once a clear distinct view is obtained, pictures are taken (×400 magnification).

(E) The particle sizes of formulations prepared are determined using a graticule (Olympus, Objective Micrometer, 0.01 mm). Overall uniformity and particle size are measured using the scale on a calibrated graticule. Five random locations on each slide for each formulation are chosen to assess uniformity and particle size.

(3) Imiquimod Content

The imiquimod content of the formulations is measured at each time point (t=0, 1, 2, 3 and 6 months) for the 25° C. and 40° C. stability samples. The 30° C. stability samples are removed from the stability cabinet at each time point and placed at about 2-8° C. for future reference, as follows:

(2) About 150 mg of the formulation is removed from each sample and is transferred into a 50 ml volumetric flask.

(3) About 30-40 ml of diluent (about 250 ml acetonitrile (HPLC grade), about 740 ml purified water and about 10 ml of concentrated HCl are mixed together in a 1 L volumetric flask) is then added to the volumetric flask containing the aliquot of the formulation.

(4) The sample is then vortex mixed for approximately 1 min or until the formulation has visibly completely dispersed into the diluent.

(5) The sample is then sonicated for about 5 min and then is left to cool to room temperature.

(6) The sample is then filled to volume with diluent and is mixed by inverting the volumetric flask.

(7) This step is followed by filtration through a 0.45 mm filter directly into a 2 ml HPLC vial and the cap crimped.

(8) The sample is then analysed on the HPLC using the method described in Section entitled Analytical Method—HPLC Assay described above, with the standard solutions as described above in Sections entitled Standards Combination Standard and Impurity Standard. This method also allows for the detection and measurement of benzyl alcohol.

(4) Related Substances/Degradation Products

Following the extraction and analysis, as described above under Imiquimod Content, the chromatograms for each formulation are compared to those generated for the impurity standards, as described above under Impurity Standards, to identify if there are any degradation peaks present. As the preservatives have similar retention times as the degradation products, the chromatograms are viewed at an absorbance of 318 nm wavelength at which the preservatives do not absorb to confirm the absence of degradation products.

(5) pH Measurements

The pH of the formulations are measured at each time point (t=0, 1, 2, 3 and 6 months), The pH measurement protocol is as follows:

(4) A small sample of the formulation is applied on to the surface of a strip of pH paper (Fisher-brand pH paper: FB33045, Range pH 0.5-5.5) and is spread evenly over the surface using a spatula.

(5) The pH paper with the formulation on it is then left for 10 min to ensure that the paper does absorb the cream (which is confirmed by a color change).

(6) The pH of the formulation is then determined by comparing the color on the strip of pH paper with a range of colors (color chart) that are provided with the Fisher-brand pH paper.

(6) Viscosity from Flow Curve (Rheology Bohlin CVO Measurements)

The rheology of the formulations are measured at each time point (t=0, 1; 2, 3 and 6 months) for the 25° C. stability samples.

(7) Rheology Oscillation Methodology (Bohlin CVO)

The Crossover and $G^I$ values of the ICH stability samples are measured for all the t=0 samples. See e.g., Tables 18 and 26. The 'crossover' point is an indication of the elastic structure of the formulation and a high cross over point indicates that more force is required to breakdown the formulation thus providing an indication for longer term stability of the cream formulations. The $G^I$ value is a measurement of the elastic part of the formulation, whereby a high $G^I$ value indicates a more rigid formulation which 'recovers' more easily from applied shear stress.

(8) Viscosity (Brookfield) Measurements

The viscosity of the formulations is measured at each time point (t=0, 1, 2, 3 and 6 months) for the 25° C. stability samples.

(9) Preservative Efficacy Test Protocol

The preservative efficacy test is performed on formulations 110, 126, Pbo4 and 182 which are stored at about 2-8° C. and about 40° C. for about 3 months. Preservative efficacy testing is carried out according to the procedure described in line with the methodology described in the USP 2007 and EP 2007. The time points, at which the inoculated samples are tested are: 0 h, 24 h, 48 h, 7 days, 14 days, 21 days and 28 days.

Method validation is performed using *Staphylococcus aureus* cultures to confirm the neutralizing effect of DIE broth, for this purpose 110 and 182 are used to confirm neutralization of the preservatives.

II. Test Item Release Studies Through Synthetic Membranes (A) In Vitro Screening of Release Profiles Through Synthetic Membranes The release of imiquimod from 13 formulations (n=4 for each) are compared using methodology based on the principles of the FDA, SUPAC-SS guidelines. The formulations that are tested included: 3M's Aldara® 5% imiquimod cream 1 kg bulk sample, Aldara® 5% imiquimod cream sachet (commercial product), Graceway's Aldara® 5% imiquimod cream 1 kg batch, and formulations 257 (1%), 123, 250, 125, 110, 182, 195, 256, 197 and 183. The protocol for the investigation is as follows:

A synthetic membrane (Microporous polyethylene film 3M No. 9711 CoTran™) is mounted in a small Franz cell (refer to FIG. 1) with a receiver fluid (0.1 N HCl) to ensure sink conditions (is equilibrated for a minimum of 30 min prior to dosing). An infinite dose of formulation (230 to 250 µl is dispensed using a calibrated positive displacement pipette) is applied to the membrane (using the pipette tip to gently spread over the surface) and the diffusion of imiquimod that is measured over time (n=4 per formulation). Briefly 200 µl of the receiver fluid is removed using a 250 µl Hamilton syringe at each time point (0, 15, 30, 60, 120 and 240 min) and is analysed on the HPLC using the method, as described under Analytical Method—HPLC Assay. The sample of receiver fluid is removed at each time point and is replaced with fresh pre-warmed (32° C.) receiver fluid.

III. In Vitro Skin Permeation Study (A) Analytical Methods (1) Liquid Scintillation Method Details Samples are added to a scintillation vial and about 4 ml of scintillation cocktail (Hionic-fluor) is added. The vial is capped and is shaken using a vortex mixer until the sample is mixed with the scintillation cocktail. The scintillation vials are then loaded into racks before analysing on the scintillation counter, using the settings listed as follows.

Model of scintillation counter: Beckman LS 5000 CE
Isotope setting: $C_{14}$
Counting time: 5 min
Calculation mode: SL DPM
Count samples: 1 times
Replicates: 1
Quench monitor: Yes (B) Radioactive Purity of Imiquimod$^{14}$C (1) Preparation of Stock The radio-labelled material is as follows:

Imiquimod stock ($^{C}14$): Specific activity of about 57 mCl/mmol with a radiochemical purity of about 99.2% is supplied as a powder in a borosilicate multi-dose vial with additional screw cap.

Working stock solutions are prepared by addition of 1 ml isostearic acid to the imiquimod powder using a needle and syringe inserted through the septum of the vial. The screw cap is then replaced securely and the vial shaken on a vortex mixer until all the imiquimod dissolves in the isostearic acid.

The homogeneity is also confirmed. This results in a stock solution containing about 1000 Ci/ml.

(C) Preparation of Formulations

The method for the preparation of about a 100 g radioactive batch is as follows:

- The glass container and mixer paddle attachment are placed onto a balance and the weight is recorded before the container and paddle are removed.
- The amount of imiquimod required for the formulation is added by weight and the remaining isostearic acid (minus 1.38 g) and benzyl alcohol are added to the container.
- The entire mixture is heated in a water bath at about 55±5° C. while stirring with a small over head mixer (IKA®-Werke Lab Egg) and paddle attachment.
- Cetyl alcohol, stearyl alcohol, white petrolatum, polysorbate 60 and sorbitan monostearate are added into the beaker and mixed at about 55±5° C. until the oil phase is completely in solution.
- Separately, about 200 ml of water is heated in a beaker to about 55±5° C. while stirring with a magnetic follower.
- About 50 ml of the heated water is transferred into a beaker and is placed in a water bath maintained at about 55±5° C. and half the glycerine, methyl hydroxyparabens and propyl hydroxyparabens are added (where both methyl and propyl parabens are weighed into weighing boats first) to the water and is stirred at about 55±5° C. (this is the aqueous phase).
- The remaining glycerine is added to a 28 mi vial with the xanthan gum and is mixed using a small over head mixer (IKA®-Werke Lab Egg) with paddle attachment for about 10 min.
- The glycerine and xanthan mixture are then added into the vortex of the aqueous phase, using about a 5 ml aliquot of heated water to rinse the vessel out into the water phase.
- Mixing of the water phase is continued for at least about 5 min.
- The aqueous phase is transferred into the oil phase, increasing the stirring speed during addition.
- The mixture is stirred on high speed maintaining the temperature at about 55±5° C. for 30 min.
- The vessel is removed from the mixer and is homogenised using the 1 cm head for about 3 min.
- Mixing is continued while cooling to about 35° C. and the total weight of the cream is made up to weight with heated water. The mixture is transferred to the overhead stirrer and cooling and stirring is continued to about 25° C.
- The formulations are then aliquoted in to screw top vials and are sealed with Parafilm® placed around the screw top lid.
- About 9.862 g of the formulation is weighed into a vial and is placed in a water bath at about 5° C. About 138 mg of radio-labelled working stock solution is then added to the formulation and the formulation is thoroughly mixed using a spatula while cooling.

(D) Homogeneity Control

Following manufacturing of the formulations, the following test is performed:

For each of the formulations, three aliquots (top, middle and bottom of batch) of approximately 5 mg is exactly weighed directly into a scintillation vial, where about 4 ml of scintillation cocktail is added. All of the samples are then directly quantified on the Liquid Scintillation Counter ("LSC") to confirm homogeneity within ±10%.

(E) Franz Cell Study

The method involves the use of full thickness human skin that is mounted in a Franz cell with about a 0.01 N hydrochloric acid as receiver fluid to ensure sink conditions. A dose of formulation equivalent to about 10 mg/cm$^2$ is applied to the membrane and the diffusion of imiquimod is measured over time. Human skin from cosmetic reduction surgery is used. Subcutaneous fat is removed mechanically prior to preparation of the skin section for the study. The formulations (6μ) are applied to the surface of the membrane using a positive displacement pipette. The investigation is performed in several experiments. Two skin donors are used randomly and are assigned across all experiments so that each formulation is tested on both skin donors. Each experiment consists of two randomly assigned formulations (n=6 cells per formulation) and two comparator formulations (n=6 cells per comparator). The receptor compartment of the Franz cells is then filled with the receiver fluid and the cells are fixed in a water bath maintained at about 37° C. The receptor compartment contents are continuously agitated by small magnetic followers. At t=1, 8 and 24 h, samples of receiver fluid are taken from the receptor compartment, and are replaced with fresh receiver fluid and are assayed by scintillation counting.

(F) Mass Balance

At the end of the experiment, a mass balance experiment is carried out, where the amount of $^{14}$Cimiquimod remaining in the donor compartment, surface residue, Stratum corneum (SC), remaining epidermis, dermis and receiver compartment is quantified. This method involves removal of the SC by tape stripping and processing of the remaining epidermal layer and dermis using standard procedures. The protocol for the mass balance is as follows:

Unabsorbed dose: The surface of each Franz cell donor chamber is wiped gently with a cotton bud using 5 clockwise and anti-clockwise movements. This procedure is repeated on 4 occasions using alternate wet (receiver fluid) and dry cotton buds. The cotton buds are added to scintillation cocktail before analysis. Two tape strips are removed from the skin and these are regarded as unabsorbed formulation and included in the total surface activity. The Stratum corneum (SC) is removed by carefully tape stripping the membrane ten times using Scotch adhesive tape. Collectively, each tape is placed into a scintillation vial to which 4 ml of scintillation cocktail are added before analysis. Epidermal layer: The remaining section of the epidermis (following tape stripping) is carefully removed from the dermis with a scalpel. The epidermis is placed into a glass vial containing 2 ml of Soluene 350 and is incubated at about 50° C. for about 72 h before analysis by LSC. The remaining dermal layer is placed in to a glass vial containing about 2 ml of Soluene 350 and is incubated at about 50° C. for about 72 h before analysis by LSC.

(G) Analysis of Data

ANOVA statistical analysis at a 95% confidence level is used to analyse the data generated for the membrane release and skin permeation experiments.

An example of the ANOVA statistical analysis is as follows:

| Level | N | Mean | StDev | Individual 05% CIs For Mean Base on Pooled StDev | | | |
|---|---|---|---|---|---|---|---|
| | | | | +------------ | +------------ | +------------ | +------------ |
| Formulation X | 4 | 4605.5 | 626.9 | | | | (---*---) |
| Formulation Y | 4 | 1862.8 | 185.9 | | (---*---) | | |
| Formulation Z | 4 | 1845.6 | 206.4 | | (---*---) | | |
| | | | | +------------ | +------------ | +------------ | +------------ |
| | | | | 0 1500 | 3000 | 4500 | |

Whereby, no significance (p>0.05) is shown by two overlapping histograms (e.g. Y and Z), whereas a significant difference (P≤0.05) can be identified by two histograms which don't overlap (e.g. X and Y and X and Z). The width of the each histogram is a reflection of the pooled standard deviation from all data sets.

IV Results and Discussion (A) Degradation Product Analysis

It is discovered that the preservatives (benzyl alcohol, methylparaben and propylparaben) at about 318 in the imiquimod formulations can not be detected. Thus, by analysing the imiquimod formulations at this wavelength, it permits the detection of degradation products, if any, in the presence of preservatives. However, no degradation products are identified at about 318 nm for any of the imiquimod formulations tested up to and including the 6 month stability time point at about 25° C. and about 40° C.

Figure 2:
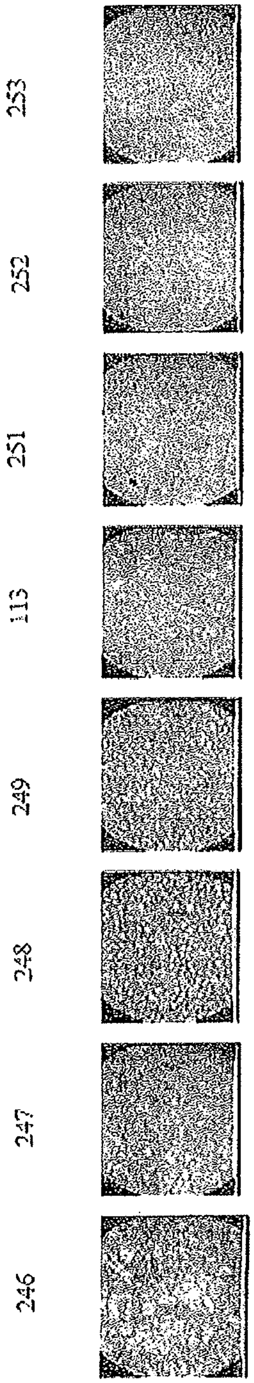
FIG. 2 shows a summary of microscope pictures of eight 2.5% w/w imiquimod formulations, i.e., formulations 113, 246, 247, 248, 249, 251, 252 and 253 (the formulations continued into the stability program are included for the 1 kg batches in TABLE 18 and FIG. 9)

In Table 17 and FIG. 2, they show a summary of the findings, whereby simple microscopic analysis of the imiquimod formulations identify formulations with inconsistent particle size and large aggregation of material. Summary and composition of lower dosage strength imiquimod formulations are listed in Table 13 and Table 14.

TABLE 17

| | 246 % w/w | 110 % w/w | 116 % w/w | 247 % w/w | 117 % w/w | 248 % w/w | 249 % w/w | 250 % w/w | 113 % w/w | 251 % w/w | 252 % w/w | 253 % w/w | 254 % w/w | 120 % w/w | 121 % w/w |
|---|---|---|---|---|---|---|---|---|---|---|---|---|---|---|---|
| Viscosity (visual) | high | High | high | high | high | high | high | low | high | high | high | Medium-high | high | very high | medium low |
| Appearance (spatula) | lumpy | Smooth | smooth | smooth | smooth | smooth | smooth | smooth | slightly textured | Textured | smooth | Smooth | matt, smooth | matt, smooth | smooth |
| pH | 5 | 5 | 5 | 5 | 4.5 | 4.5 | 5 | 4 | 5 | 5 | 5 | 5 | 5 | 4.5 | 4.5 |
| $G^1$ (Pa) | 3639 | 1150.5 | 1504 | 1093 | 1740.5 | 5235 | 1364.5 | 171.5 | 642 | 943 | 626.5 | 567 | 2285.5 | 5231 | 304.5 |
| Cross-over ($o^1$) | 29.5 | 14.5 | 20.5 | 16 | 21.5 | none | 21.5 | 13 | 21.5 | 29.25 | 19 | 15 | 21.5 | 20.5 | 29.75 |
| Microscope | v. bad | Ok | good | bad | good | v.bad | bad | good | bad | bad | ok | Bad | ok | ok | good |

TABLE 18

| Physical Characteristics of 12 Lower Dosage Strength Imiquimod Formulations, i.e., Formulations 181, 235, 236, 237, 238, 239, 240, 241, 242, 243, 244 and 245, | | | | | | | | | | | | |
|---|---|---|---|---|---|---|---|---|---|---|---|---|
| | 235 % w/w | 236 % w/w | 237 % w/w | 238 % w/w | 239 % w/w | 240 % w/w | 241 % w/w | 242 % w/w | 243 % w/w | 244 % w/w | 181 % w/w | 245 % w/w |
| Excipients | | | | | | | | | | | | |
| Isostearic acid | 15 | 10 | 15 | 10 | 15 | 15 | 15 | 20 | 15 | 20 | 15 | 20 |
| Cetyl alcohol | 2 | 4 | 4 | 2 | 2 | 4 | 2 | 2 | 2 | 2 | 4 | 4 |
| Stearyl alcohol | 2 | 2 | 2 | 2.4 | 2.4 | 2.4 | 2 | 2 | 2.4 | 2.4 | 2.4 | 2.4 |
| White petrolatum | 3.4 | 3.4 | 2.8 | 2.8 | 3.4 | 2.8 | 3.4 | 2.8 | 3.4 | 2.8 | 2.8 | 3.4 |
| Polysorbate 60 | 3.8 | 3.8 | 3 | 38 | 3 | 3.8 | 3 | 3.8 | 3 | 3 | 3 | 3.8 |
| Sorbitin Monostearate | 0.2 | 1 | 1 | 1 | 1 | 0.2 | 1 | 1 | 0.2 | 0.2 | 1 | 1 |
| Glycerin | 3 | 1 | 3 | 3 | 1 | 1 | 3 | 1 | 1 | 3 | 1 | 3 |
| Xanthan gum | 0.3 | 0.3 | 0.7 | 0.3 | 0.7 | 0.3 | 0.3 | 0.7 | 0.7 | 0.3 | 0.3 | 0.7 |
| Purified water | 66.58 | 69.79 | 63.78 | 69.98 | 66.78 | 65.78 | 64.33 | 60.73 | 66.33 | 60.33 | 86.53 | 55.73 |
| Benzyl alcohol | 2 | 2 | 2 | 2 | 2 | 2 | 2 | 2 | 2 | 2 | 2 | 2 |
| Methylparaben | 0.2 | 0.2 | 0.2 | 0.2 | 0.2 | 0.2 | 0.2 | 0.2 | 0.2 | 0.2 | 0.2 | 0.2 |
| Propylparaben | 0.02 | 0.02 | 0.02 | 0.02 | 0.02 | 0.02 | 0.02 | 0.02 | 0.02 | 0.02 | 0.02 | 0.02 |
| Imiquimod | 2.50 | 2.50 | 2.50 | 2.50 | 2.50 | 2.50 | 3.75 | 3.75 | 3.75 | 3.75 | 3.75 | 3.75 |
| Total amount (g) | 100.00 | 100.00 | 100.00 | 100.00 | 100.00 | 100.00 | 100.00 | 100.00 | 100.00 | 100.00 | 100.00 | 100.00 |

TABLE 18-continued

Physical Characteristics of 12 Lower Dosage Strength Imiquimod Formulations, i.e., Formulations 181, 235, 236, 237, 238, 239, 240, 241, 242, 243, 244 and 245,

| | 235 % w/w | 236 % w/w | 237 % w/w | 238 % w/w | 239 % w/w | 240 % w/w | 241 % w/w | 242 % w/w | 243 % w/w | 244 % w/w | 181 % w/w | 245 % w/w |
|---|---|---|---|---|---|---|---|---|---|---|---|---|
| HLB Values | 14.39 | 12.78 | 12.35 | 12.79 | 12.35 | 14.39 | 12.35 | 12.78 | 14.26 | 14.26 | 12.35 | 12.78 |
| Modification | multi | multi | multi | multi | multi | multi | multi | multi | multi | multi | multi | multi |
| Viscosity | low/med | high | high | medium | med/high | high | Medium-High | Medium | Medium-Low | Medium-high | Very High | High |
| pH | 4.7 | 4.7 | 4.7 | 6 | 4.7 | 4.7 | 5.0 | 4.7 | 4.7 | 4.5 | 4.7 | 4.5 |
| G | 294.37 | 1527.65 | 639.345 | 467.78 | 552.61 | 924.075 | 116.18 | 416.65 | 8767 | 65.425 | 2514.25 | 1280.05 |
| crossover | 9.5 | 25.25 | 10.5 | 17.75 | 12 | 25.5 | 13.75 | 18.5 | none | 11.75 | 36 | 22.5 |
| microscope | v.good | ok, but particles? | bad | good, but particles? | bad | bad-particles? | good with bubbles | very good | ok | good | very good | good |
| Appearance/Spatula | glossy, v slight texture, matt, does smooth out | smooth matt, slightly aerated | slight texture, matt, does smooth out | glossy, smooth | v. glossy & v. smooth | smooth, matt | glossy, slightly textured with some aeration | glossy, textured with some aeration | glossy, slightly textured, very aerated | glossy, very slightly textured | smooth with a matt appearance | glossy, smooth, with some aeration |

(B) Scale-Up and ICH Stability (1) Homogeneity

In Table 19, formulations 245, 121 and 193 show signs of phase separation. All the other formulations in Table 19 show good homogeneity, and are subsequently sub-aliquoted and placed on stability as described above under Preparation of Stability Samples.

TABLE 19

Homogeneity Results from 1 kg batches, where Samples are Removed from Top Middle and the Bottom of the Batch for Comparison of Homogeneity.

| Formulation | % Recovery | % CV |
|---|---|---|
| 3M Aldara ® 5% Batch | 102.69 ± 2.29 | 2.23 |
| 257 (1%) | 100.29 ± 0.68 | 0.68 |
| 197 | 96.81 ± 2.15 | 2.22 |
| 83 | 97.56 ± 0.48 | 0.50 |
| 245 | 91.08 ± 12.80 | 14.06 |
| 182 | 97.68 ± 0.73 | 0.75 |
| 189 | 98.32 ± 0.92 | 0.94 |
| 184 | 98.37 ± 1.61 | 1.63 |
| 193 | 97.21 ± 0.22 | 0.23 |
| 188 | 98.95 ± 2.48 | 2.51 |
| 195 | 99.66 ± 0.70 | 0.70 |
| 255 | 99.46 ± 0.49 | 0.49 |
| 256 | 98.80 ± 0.75 | 0.76 |
| Graceway Aldara ® 5% Imiquimod | 102.74 ± 1.26 | 1.23 |
| 110 | 101.43 ± 0.63 | 0.62 |
| 116 | 100.39 ± 0.18 | 0.18 |
| 117 | 100.49 ± 0.64 | 0.64 |
| 250 | 99.98 ± 0.37 | 0.37 |
| 254 | 98.70 ± 0.21 | 0.21 |
| 120 | 100.02 ± 0.34 | 0.34 |
| 121 | 106.22 ± 0.09 | 0.09 |
| 235 | 101.04 ± 0.21 | 0.21 |
| 123 | 101.75 ± 0.28 | 0.28 |
| 124 | 95.00 ± 0.32 | 0.34 |
| 125 | 101.12 ± 0.12 | 0.12 |
| 126 | 102.37 ± 0.58 | 0.57 |

TABLE 19-continued

Homogeneity Results from 1 kg batches, where Samples are Removed from Top Middle and the Bottom of the Batch for Comparison of Homogeneity.

| Formulation | % Recovery | % CV |
|---|---|---|
| Pbo1 | N/A | N/A |
| Pbo2 | N/A | N/A |
| Pbo3 | N/A | N/A |
| Pbo4 | N/A | N/A |

(C) Stability (1) Stability of Imiquimod in Formulations

In Table 20, imiquimod in the formulations is stable at both about 25° C. and about 40° C. over an about six month period, although the results for three and six months at both about 25° C. and about 40° C. look consistently higher than previous time points. This could be attributed to a small amount of water evaporation from the containers. In addition, all samples are consistent with the commercially supplied Aldara® 5% imiquimod cream sample. There are no degradation products detected in any of the samples in Table 20 at any of the temperatures and time points when analyzed at about 318 nm With reference to formulation specification, the specification amount of imiquimod that is recovered from the samples in Table 20 is between about 90%-110% w/w, thereby confirming that the samples fall within their target specification. In other words, and by way of example, the specification amount of imiquimod that is recovered from preferred 2.5% imiquimod formulations of the present invention will fall within between about 2.25% and about 2.75% w/w and the amount of imiquimod that is recovered from preferred 3.7.5% imiquimod formulations of the present invention will fall within between about 3.38% and about 4.12% w/w, Thus, in accordance with the present invention, the amount of imiquimod recovery from preferred formulations will fall within about the 100%±10% w/w specification of their target concentrations.

TABLE 20

Percentage of Imiquimod that is Recovered from the Formulations as Compared to Theoretical when the Formulations are Stored at 25° C. and 40° C. over a 6 Month Period. Highlighted Grey Areas Indicate Time Points Which Are Not Tested Due To Rejection/Omission Of Formulations (n = 3 ± sd).

| Imiquimod | T-0 | | | T-1 month 25° C. | | | T-1 month 4° C. | | | T-2 months 25° C. | | | T-2 months 40° C. | | | T-3 months 25° C. | | | T-3 months 40° C. | | | T-6 months 25° C. | | | T-6 months 40° C. | | |
|---|---|---|---|---|---|---|---|---|---|---|---|---|---|---|---|---|---|---|---|---|---|---|---|---|---|---|---|
| Formulations | Mean | | SD | Mean | | SD | Mean | | SD | Mean | | SD | Mean | | SD | Mean | | SD | Mean | | SD | Mean | | SD | Mean | | SD |
| Aldara ® 5% 3M | 100.38 | ± | 0.25 | 100.60 | ± | 0.10 | 100.41 | ± | 0.04 | 100.58 | ± | 0.10 | 101.40 | ± | 0.29 | 104.12 | ± | 0.23 | 104.12 | ± | 0.79 | 106.78 | ± | 4.64 | 105.41 | ± | 0.60 |
| 257 (1%) | 100.29 | ± | 0.12 | 104.36 | ± | 0.18 | 104.98 | ± | 2.41 | 102.31 | ± | 0.46 | 102.42 | ± | 0.10 | 103.16 | ± | 0.37 | 105.79 | ± | 0.27 | 107.09 | ± | 1.63 | 103.76 | ± | 3.59 |
| 197 | 96.81 | ± | 0.17 | 97.74 | ± | 0.20 | 99.22 | ± | 0.33 | 99.28 | ± | 0.14 | 101.47 | ± | 0.22 | 102.69 | ± | 0.92 | 102.69 | ± | 0.92 | 100.39 | ± | 1.04 | 101.11 | ± | 2.66 |
| 183 | 97.69 | ± | 0.21 | 99.73 | ± | 0.32 | 99.43 | ± | 2.77 | 99.61 | ± | 0.33 | 100.01 | ± | 0.05 | 100.80 | ± | 1.07 | 103.70 | ± | 1.58 | 100.75 | ± | 1.82 | 102.19 | ± | 1.33 |
| 245 | | | | | | | | | | | | | | | | | | | | | | | | | | | |
| 182 | 96.76 | ± | 0.25 | 102.01 | ± | 0.01 | 98.46 | ± | 0.15 | 99.00 | ± | 0.12 | 98.07 | ± | 0.10 | 101.48 | ± | 0.27 | 104.39 | ± | 1.55 | 102.91 | ± | 1.16 | 99.21 | ± | 4.25 |
| 189 | 98.73 | ± | 0.19 | 100.72 | ± | 0.17 | 99.20 | ± | 0.25 | | | | | | | | | | | | | | | | | | |
| 184 | 100.09 | ± | 0.08 | 101.71 | ± | 0.14 | 96.86 | ± | 0.20 | | | | | | | | | | | | | | | | | | |
| 193 | | | | | | | | | | | | | | | | | | | | | | | | | | | |
| 188 | 100.28 | ± | 0.02 | 99.39 | ± | 0.17 | 97.04 | ± | 0.21 | | | | | | | | | | | | | | | | | | |
| 195 | 99.39 | ± | 0.32 | 99.33 | ± | 0.07 | 97.84 | ± | 0.25 | 101.13 | ± | 0.10 | 103.13 | ± | 0.10 | 103.00 | ± | 0.15 | 106.25 | ± | 0.99 | 106.84 | ± | 1.38 | 106.28 | ± | 1.22 |
| 255 | 98.87 | ± | 0.42 | 100.67 | ± | 0.02 | 98.73 | ± | 0.13 | | | | | | | | | | | | | | | | | | |
| 256 | 97.58 | ± | 0.03 | 100.06 | ± | 0.22 | 98.05 | ± | 0.12 | 99.74 | ± | 0.07 | 99.28 | ± | 0.24 | 101.74 | ± | 0.37 | 101.71 | ± | 0.44 | 105.42 | ± | 2.10 | 105.55 | ± | 3.20 |
| Graceway Aldara ® 5% Imiquimod | 98.62 | ± | 0.11 | 102.32 | ± | 0.28 | 96.66 | ± | 0.18 | 101.65 | ± | 0.06 | 101.02 | ± | 0.10 | 103.58 | ± | 0.19 | 103.64 | ± | 0.15 | 101.70 | ± | 0.79 | 103.20 | ± | 1.85 |
| 110 | 101.06 | ± | 0.35 | 102.17 | ± | 0.95 | 99.48 | ± | 0.19 | 101.46 | ± | 0.09 | 99.03 | ± | 0.14 | 102.73 | ± | 0.64 | 103.36 | ± | 0.38 | 102.42 | ± | 1.16 | 102.38 | ± | 2.82* |
| 116 | 98.63 | ± | 0.25 | 99.15 | ± | 0.13 | 96.87 | ± | 0.09 | | | | | | | | | | | | | | | | | | |
| 117 | 99.00 | ± | 0.73 | 102.06 | ± | 0.10 | 98.42 | ± | 0.09 | | | | | | | | | | | | | | | | | | |
| 250 | 97.67 | ± | 0.11 | 101.88 | ± | 0.06 | 99.37 | ± | 1.05 | 99.43 | ± | 0.20 | 99.74 | ± | 0.13 | 101.57 | ± | 0.35 | 105.32 | ± | 2.42 | 102.45 | ± | 0.50 | 101.14 | ± | 2.23 |
| 254 | 96.29 | ± | 0.27 | 99.75 | ± | 0.09 | 97.11 | ± | 0.25 | | | | | | | | | | | | | | | | | | |
| 120 | 99.79 | ± | 0.27 | 100.61 | ± | 0.03 | 98.82 | ± | 0.17 | | | | | | | | | | | | | | | | | | |
| 121 | | | | | | | | | | | | | | | | | | | | | | | | | | | |
| 235 | 99.25 | ± | 0.25 | 102.80 | ± | 0.20 | 100.78 | ± | 0.11 | | | | | | | | | | | | | | | | | | |
| 123 | 99.71 | ± | 0.17 | 101.49 | ± | 0.10 | 99.52 | ± | 0.34 | 102.08 | ± | 0.34 | 101.11 | ± | 0.27 | 103.27 | ± | 0.31 | 102.35 | ± | 0.47 | 105.49 | ± | 1.11 | 103.34 | ± | 1.44 |
| 124 | 93.17 | ± | 0.07 | 94.26 | ± | 0.04 | 92.93 | ± | 0.14 | | | | | | | | | | | | | | | | | | |
| 125 | 98.37 | ± | 0.23 | 102.33 | ± | 0.29 | 99.14 | ± | 0.14 | 99.99 | ± | 0.21 | 100.38 | ± | 0.09 | 103.28 | ± | 0.76 | 104.87 | ± | 2.65 | 102.48 | ± | 1.27 | 103.87 | ± | 1.37 |
| 126 | 102.37 | ± | 0.58 | 102.84 | ± | 0.45 | 104.11 | ± | 0.04 | 100.02 | ± | 0.95 | 101.32 | ± | 0.40 | 99.28 | ± | 3.25 | 98.43 | ± | 0.55 | 101.95 | ± | 0.37 | 103.02 | ± | 1.89 |
| PBO4 | 0 | ± | 0 | 0 | ± | 0 | 0 | ± | 0 | 0 | ± | 0 | 0 | ± | 0 | 0 | ± | 0 | 0 | ± | 0 | 0 | ± | 0 | 0 | ± | 0 |
| PBO1 | 0 | ± | 0 | 0 | ± | 0 | 0 | ± | 0 | 0 | ± | 0 | 0 | ± | 0 | 0 | ± | 0 | 0 | ± | 0 | 0 | ± | 0 | 0 | ± | 0 |
| PBO2 | 0 | ± | 0 | 0 | ± | 0 | 0 | ± | 0 | 0 | ± | 0 | 0 | ± | 0 | 0 | ± | 0 | 0 | ± | 0 | 0 | ± | 0 | 0 | ± | 0 |
| PBO3 | 0 | ± | 0 | 0 | ± | 0 | 0 | ± | 0 | 0 | ± | 0 | 0 | ± | 0 | 0 | ± | 0 | 0 | ± | 0 | 0 | ± | 0 | 0 | ± | 0 |

*30° C. sample analysed, as 40° C. had shown signs of phase separation.

(2) Stability of Benzyl Alcohol in Formulations

In Table 21, Benzyl alcohol content is found to fall over the duration of the stability tests. The greatest loss observed is in the placebo's; Pbo4 (1.08±0.02% w/w), Pbo1 (1.01±0.03% w/w), Pbo2 (1.04±0.08% w/w) and Pbo3 (1.11±0.00% w/w) and the active formulation 257 (1%) (1.37±0.01% w/w) which shows a loss in benzyl alcohol at about 40° C. for about 6 months down from 2.0% w/w. The specified range for benzyl alcohol in the Aldara® 5% imiquimod cream formulations (1.0 to 2.1% w/w), are within specification for Aldara® 5% imiquimod cream. The decrease in benzyl alcohol content from the formulations is possibly the result of the formation of an ester (benzyl isostearate), whereby there is a reaction between the excipients of benzyl alcohol and isostearic acid.

TABLE 21

Amount of Benzyl Alcohol that is Recovered from the Formulations when the formulations that are Stored at 25° C. and 40° C. over a 6 Month Period. Highlighted Grey Areas Indicate Time Points Which Are Not Tested Due To Rejection/Omission Of Formulations (N = 3 ± Sd).

| Imiquimod | T-0 | | T-1 month 25° C. | | T-1 month 4° C. | | T-2 months 25° C. | | T-2 months 40° C. | | T-3 months 25° C. | | T-3 months 40° C. | | T-6 months 25° C. | | T-6 months 40° C. | |
|---|---|---|---|---|---|---|---|---|---|---|---|---|---|---|---|---|---|---|
| Formulations | Mean | SD | Mean | SD | Mean | SD | Mean | SD | Mean | SD | Mean | SD | Mean | SD | Mean | SD | Mean | SD |
| Aldara ® 5% 3M | 2.11 | ± 0.02 | 2.04 | ± 0.01 | 1.86 | ± 0.01 | 2.04 | ± 0.01 | 1.84 | ± 0.06 | 1.88 | ± 0.02 | 1.67 | ± 0.02 | 1.76 | ± 0.05 | 1.41 | ± 0.00 |
| 257 (1%) | 2.06 | ± 0.01 | 2.01 | ± 0.01 | 1.74 | ± 0.02 | 2.00 | ± 0.04 | 1.07 | ± 0.03 | 1.74 | ± 0.01 | 1.37 | ± 0.01 | 1.58 | ± 0.01 | 1.02 | ± 0.08 |
| 197 | 2.06 | ± 0.00 | 2.06 | ± 0.01 | 1.86 | ± 0.01 | 2.05 | ± 0.00 | 1.91 | ± 0.02 | 1.85 | ± 0.01 | 1.70 | ± 0.02 | 1.74 | ± 0.05 | 1.47 | ± 0.02 |
| 183 | 2.05 | ± 0.01 | 2.01 | ± 0.01 | 1.85 | ± 0.12 | 2.00 | ± 0.01 | 1.81 | ± 0.00 | 1.78 | ± 0.01 | 1.56 | ± 0.02 | 1.66 | ± 0.04 | 1.24 | ± 0.01 |
| 245 | | | | | | | | | | | | | | | | | | |
| 182 | 2.17 | ± 0.00 | 2.17 | ± 0.00 | 1.95 | ± 0.01 | 2.11 | ± 0.04 | 1.97 | ± 0.00 | 1.94 | 0.01 | 1.82 | ± 0.04 | 1.85 | ± 0.03 | 1.48 | ± 0.05 |
| 189 | 2.11 | ± 0.01 | 2.06 | ± 0.02 | 1.88 | ± 0.02 | | | | | | | | | | | | |
| 184 | 2.13 | ± 0.01 | 2.09 | ± 0.01 | 1.86 | ± 0.01 | | | | | | | | | | | | |
| 193 | | | | | | | | | | | | | | | | | | |
| 188 | 2.15 | ± 0.02 | 2.05 | ± 0.02 | 1.84 | ± 0.01 | | | | | | | | | | | | |
| 195 | 2.12 | ± 0.02 | 2.04 | ± 0.01 | 1.85 | ± 0.02 | 2.07 | ± 0.03 | 1.95 | ± 0.03 | 1.88 | ± 0.01 | 1.74 | ± 0.02 | 1.80 | ± 0.01 | 1.48 | ± 0.01 |
| 255 | 2.09 | ± 0.01 | 2.04 | ± 0.00 | 1.81 | ± 0.02 | | | | | | | | | | | | |
| 256 | 2.07 | ± 0.01 | 2.05 | ± 0.00 | 1.85 | ± 0.00 | 2.06 | ± 0.02 | 1.87 | ± 0.03 | 1.84 | ± 0.01 | 1.88 | ± 0.01 | 1.76 | ± 0.01 | 1.46 | ± 0.01 |
| Graceway Aldara ® 5% Imiquimod | 2.06 | ± 0.01 | 2.06 | ± 0.00 | 1.80 | ± 0.00 | 2.05 | ± 0.00 | 1.91 | ± 0.02 | 1.87 | ± 0.02 | 1.65 | ± 0.01 | 1.73 | ± 0.00 | 1.38 | ± 0.03 |
| 110 | 2.09 | ± 0.01 | 2.04 | ± 0.01 | 1.84 | ± 0.01 | 2.04 | ± 0.02 | 1.91 | ± 0.02 | 1.87 | ± 0.02 | 1.75 | ± 0.01 | 1.78 | ± 0.04 | 1.72 | ± 0.02 |
| 116 | 2.08 | ± 0.01 | 2.05 | ± 0.01 | 1.87 | ± 0.01 | | | | | | | | | | | | |
| 117 | 2.11 | ± 0.01 | 2.06 | ± 0.01 | 1.82 | ± 0.05 | | | | | | | | | | | | |
| 250 | 2.03 | ± 0.01 | 2.00 | ± 0.01 | 1.78 | ± 0.07 | 1.96 | ± 0.02 | 1.70 | ± 0.01 | 1.74 | ± 0.01 | 1.47 | ± 0.03 | 1.59 | ± 0.02 | 1.12 | ± 0.02 |
| 254 | 2.07 | ± 0.01 | 2.04 | ± 0.01 | 1.89 | ± 0.01 | | | | | | | | | | | | |
| 120 | 2.11 | ± 0.00 | 2.00 | ± 0.01 | 1.77 | ± 0.02 | | | | | | | | | | | | |
| 121 | | | | | | | | | | | | | | | | | | |
| 235 | 2.10 | ± 0.00 | 2.10 | ± 0.02 | 1.92 | ± 0.02 | | | | | | | | | | | | |
| 123 | 2.11 | ± 0.01 | 2.05 | ± 0.00 | 1.82 | ± 0.01 | 2.06 | ± 0.01 | 1.85 | ± 0.01 | 1.84 | ± 0.01 | 1.59 | ± 0.00 | 1.73 | ± 0.02 | 1.34 | ± 0.01 |
| 124 | 1.96 | ± 0.01 | 1.89 | ± 0.01 | 1.71 | ± 0.00 | | | | | | | | | | | | |
| 125 | 2.08 | ± 0.01 | 2.06 | ± 0.01 | 1.82 | ± 0.00 | 2.02 | ± 0.01 | 1.82 | ± 0.00 | 1.85 | ± 0.00 | 1.63 | ± 0.04 | 1.73 | ± 0.02 | 1.32 | ± 0.02 |
| 126 | 2.00 | ± 0.02 | 2.02 | ± 0.01 | 1.89 | ± 0.01 | 1.86 | ± 0.02 | 1.65 | ± 0.02 | 2.00 | ± 0.04 | 1.70 | ± 0.04 | 2.01 | ± 0.03 | 1.55 | ± 0.02 |
| PBO4 | 1.93 | ± 0.02 | 1.83 | ± 0.08 | 1.90 | ± 0.03 | 1.91 | ± 0.01 | 1.53 | ± 0.00 | 1.81 | ± 0.01 | 1.39 | ± 0.01 | 1.71 | ± 0.01 | 1.08 | ± 0.02 |
| PBO1 | | | 1.82 | ± 0.01 | 1.65 | ± 0.00 | 1.85 | ± 0.09 | 1.54 | ± 0.10 | 1.93 | ± 0.03 | 1.55 | ± 0.04 | 1.58 | ± 0.02 | 1.01 | ± 0.03 |
| PBO2 | | | 1.83 | ± 0.01 | 1.65 | ± 0.01 | 1.87 | ± 0.19 | 1.70 | ± 0.09 | 2.01 | ± 0.13 | 1.61 | ± 0.08 | 1.65 | ± 0.05 | 1.04 | ± 0.08 |
| PBO3 | | | 1.97 | ± 0.01 | 1.81 | ± 0.01 | 2.09 | ± 0.00 | 1.81 | ± 0.00 | 2.12 | ± 0.04 | 1.70 | ± 0.00 | 1.73 | ± 0.01 | 1.11 | ± 0.00 |

*30° C. sample analysed, as 40° C. had shown signs of phase separation.

(D) Microscopic Stability of the Formulations

Figure 10A:
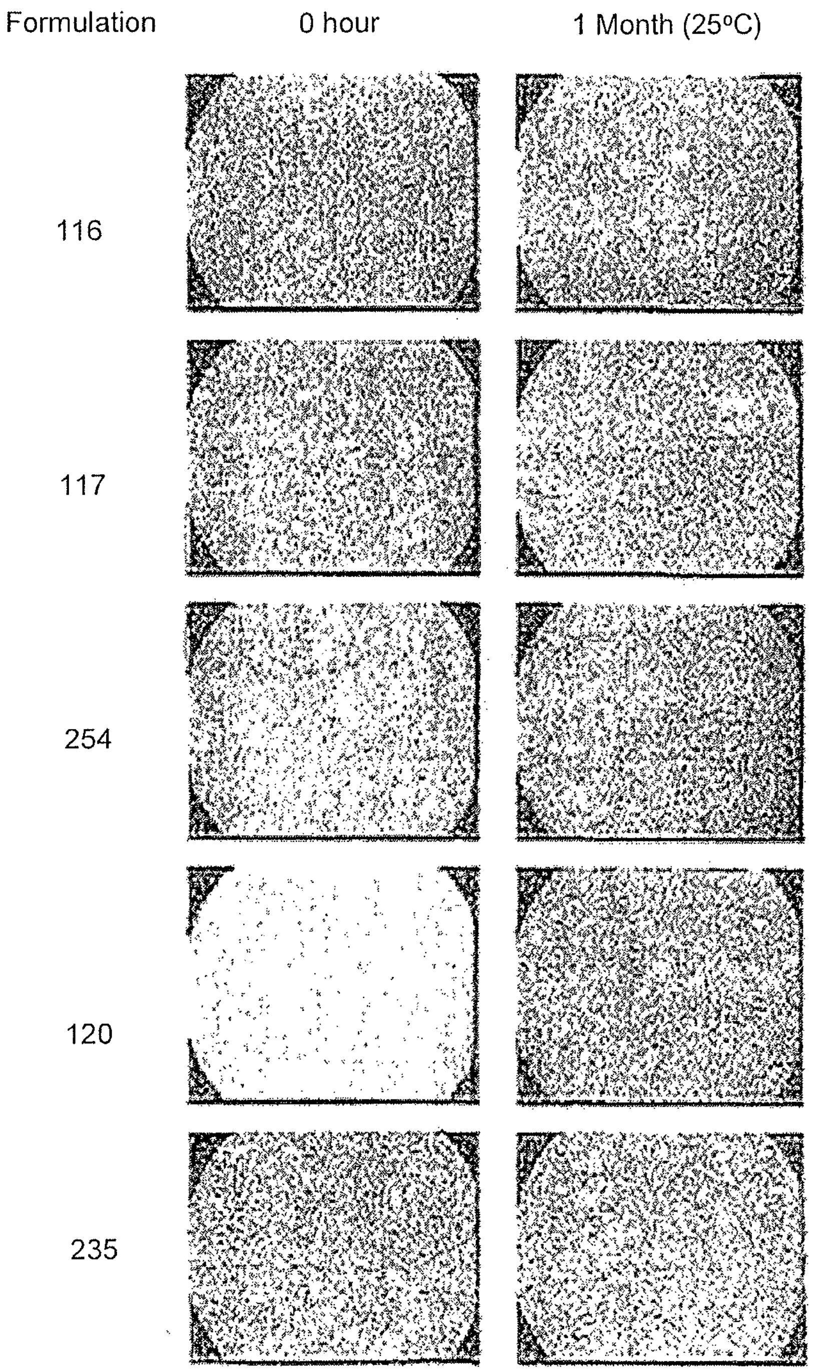
FIGS. 10A-B show microscopic depiction of 10 imiquimod formulations, i.e., formulations, 116, 117, 254, 120, 235, 188, 189, 184, 255, 124, after 1 month stability (t=0 and 1 month)−×400 magnification.
Figure 10B:
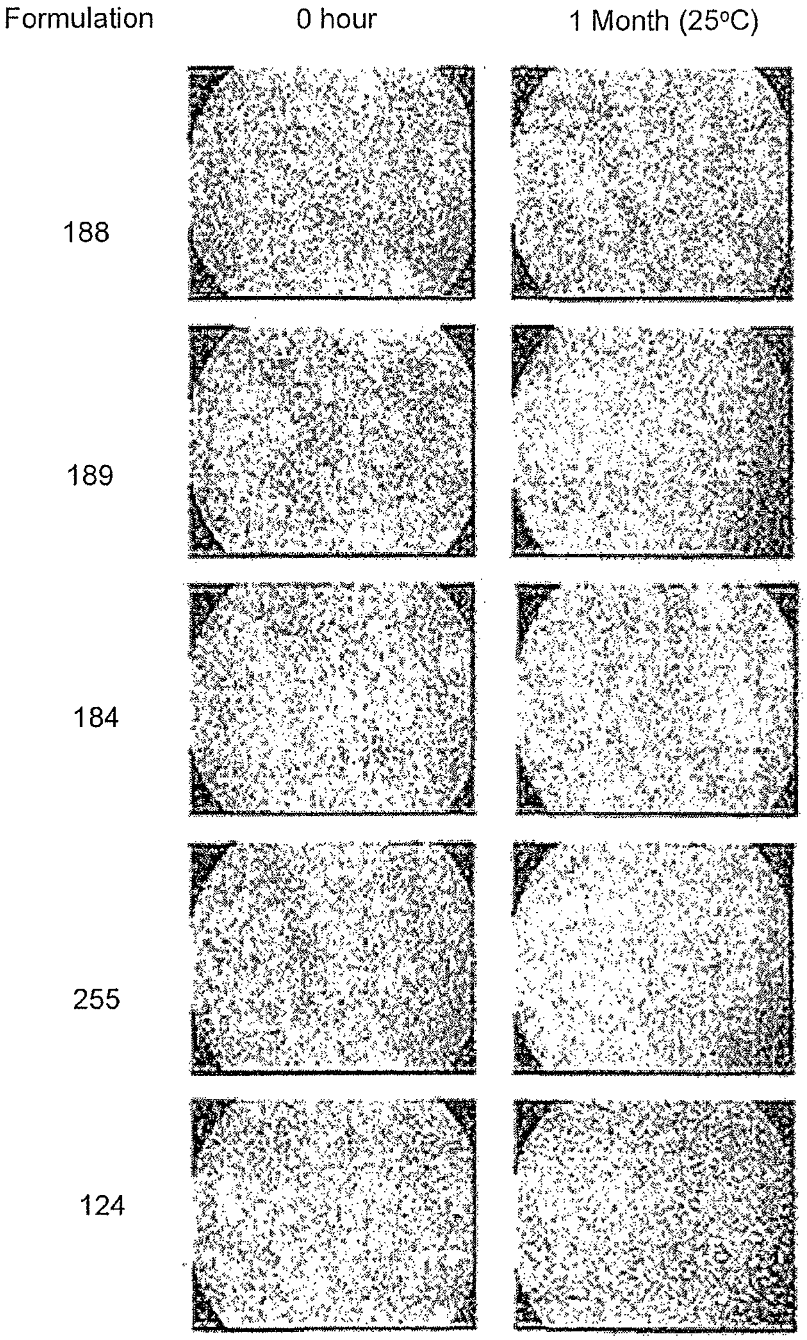

In Table 22, there is no change in the particle size in any of the formulations tested at about 25° C. over about a 6 month period. In addition, and with reference to the microscopic photographs presented in FIGS. 8A-C and 9; no crystals are detected. For completeness and reference, the pictures of the formulations rejected after one month stability are shown in FIGS. 10A-B.

TABLE 22

Results of Particle Size of the Formulations when viewed under a Microscope at 25° C. over a 6 Month Period.

| Formulation | Particle size (μM) T = 0 | t = 1 Month | t = 2 Months | t = 3 Months | t = 6 Months |
|---|---|---|---|---|---|
| 3M Aldara ® 5% | <10 | <10 | <10 | <10 | <10 |
| GRACEWAY Aldara ® 5% | <10 | <10 | <10 | <10 | <10 |
| 257 (1%) | <10 | <10 | <10 | <10 | <10 |
| 110 | <10 | <10 | <10 | <10 | <10 |
| 250 | <10 | <10 | <10 | <10 | <10 |

TABLE 22-continued

Results of Particle Size of the Formulations when viewed under a Microscope at 25° C. over a 6 Month Period.

| Formulation | Particle size (μM) T = 0 | t = 1 Month | t = 2 Months | t = 3 Months | t = 6 Months |
|---|---|---|---|---|---|
| 182 | <10 | <10 | <10 | <10 | <10 |
| 195 | 10 | 10 | 10 | 10 | 10 |
| 123 | 10 | 10 | 10 | 10 | 10 |
| 125 | 10 | 10 | 10 | 10 | 10 |
| 256 | 10 | 10 | 10 | 10 | 10 |
| 197 | 10 | 10 | 10 | 10 | 10 |
| 183 | 10 | 10 | 10 | 10 | 10 |
| 126 | <10 | <10 | <10 | <10 | <10 |
| Pbo1 | <10 | <10 | <10 | <10 | <10 |
| Pbo2 | <10 | <10 | <10 | <10 | <10 |
| Pbo3 | <10 | <10 | <10 | <10 | <10 |
| Pbo4 | <10 | <10 | <10 | <10 | <10 |

(F) Macroscopic Stability of the Formulations

In Table 23, there are no obvious physical changes in' the formulations that are tested over the six month stability program, with the exception of the placebos, which become notably less viscous. See also Tables 24-26.

TABLE 23

Macroscopic Appearance when Imiquimod Formulations are stored at about 25° C. over a 6 Month Period.

| Imiquimod Formulation | Appearance spatula Test (25° C. sample only) t = 0 | t = 1 month | t = 2 months | t = 3 months | t = 6 months | Visual Viscosity (25° C. sample only) t = 0 | t = 1 month | t = 2 months | t = 3 months | t = 6 months |
|---|---|---|---|---|---|---|---|---|---|---|
| 3M Aldera ® 5% Imiquimod | Glossy, very smooth | Glossy, very smooth | Glossy, very smooth | Glossy, very smooth | Glossy, very smooth | High | Medium High | Medium | Medium High | Medium |
| Graceway Aldera ® 5% Imiquimod | Glossy, very smooth | Glossy, very smooth | Glossy, very smooth | Glossy, very smooth | Glossy, very smooth | High | High | Medium High | High | Medium |
| 257(1%) | Glossy, And smooth | Glossy, and smooth | Glossy, very smooth | Glossy, very smooth | Glossy, very smooth | Medium | Medium High | Medium High | Medium High | Low Viscoscity |
| 110 | Glossy, very slightly textured | Glossy, very slightly textured | Glossy, slightly textured | Glossy slightly Textured | Glossy, slightly textured | High | High | High | High | Medium |
| 250 | Glossy and smooth, some aeration | Glossy and textured | Glossy, very slightly textured | Glossy, very slightly textured | Glossy, very slightly textured | Medium | Medium High | Medium High | Medium High | Medium |
| 182 | Very glossy and smooth | Very glossy and smooth | Very glossy and smooth | Very glossy and smooth | Very glossy and smooth | High | Medium High | Medium High | Medium High | High |
| 195 | Glossy, slightly textured | Glossy, slightly textured | Glossy, very slightly textured | Glossy, slightly textured | Glossy, slightly textured | High | High | Medium High | Medium High | High |
| 123 | Glossy, and smooth | Glossy, slightly textured | Glossy slightly textured, smoothed OUT | Glossy, slightly textured, smoothed OUT | Glossy, slightly textured | Medium High | Medium High | Medium High | High | Medium |
| 124 | Glossy and smooth | Glossy and smooth | Glossy, smooth with slight aeration | Glossy, smooth | Glossy, slightly textured | Medium | Medium | Medium | Medium High | Low |
| 256 | Glossy, slightly textured | Glossy, slightly textured | Glossy, slightly textured | Glossy, slightly textured | Glossy, slightly textured | Medium High | Medium High | Medium High | Medium High | High |

TABLE 23-continued

Macroscopic Appearance when Imiquimod Formulations are stored at about 25° C. over a 6 Month Period.

| | Appearance spatula Test (25° C. sample only) | | | | | Visual Viscosity (25° C. sample only) | | | | |
|---|---|---|---|---|---|---|---|---|---|---|
| Imiquimod Formulation | t = 0 | t = 1 month | t = 2 months | t = 3 months | t = 6 months | t = 0 | t = 1 month | t = 2 months | t = 3 months | t = 6 months |
| 197 | Glossy, slightly textured | Glossy, very slightly textured | Glossy and textured | Glossy and slightly textured | Glossy and slightly textured | Medium | Medium High | High | High | High |
| 183 | Glossy, smooth slight aeration | Glossy and smooth | Glossy and smooth | Glossy and smooth | Glossy and smooth | High | Medium High | Medium High | Medium High | Low |
| 126 | Glossy, very slightly textured | Smooth, slightly textured, glossy | Glossy and smooth | Slightly textured, sheen | Glossy | Medium | Medium | Medium | Medium | Low Viscosity |
| Pbo1 | Glossy and smooth | Very glossy and smooth | Very glossy and smooth | Very glossy and smooth | Glossy and smooth | Low | Medium Low | Medium Low | Low | Low |
| Pb02 | Glossy and smooth | Glossy and smooth | Glossy, and smooth | Glossy very slightly textured | Glossy and smooth | Medium Low | Medium | Medium Low | Medium Low | Low |
| Pb03 | Glossy and smooth | Glossy and smooth | Glossy, very slightly textured but smoothed out | Glossy, very slightly textured but smoothed out | Glossy and smooth | Low | Medium Low | Medium Low | Medium Low | Medium |
| Pb04 | Glossy and smooth | Glossy and smooth | Glossy and smooth | Glossy and smooth | Smooth cream high sheen | Medium Low | Medium | Medium Low | Low | Low |

TABLE 24

Stability Data for 10 Formulations, i.e., Formulations 116, 117, 120, 124, 188, 184, 189, 235, 254 and 255, rejected after 1 Month Stability, with respect to the Spatula Test, Visual Viscosity and Particle size (as determined by microscopy).

| | Spatula Test | | Visual Viscosity | | Majority of particle size (μM) | |
|---|---|---|---|---|---|---|
| Formulation | T = 0 | T = 1 Month | T = 0 | T = 1 Month | T = 0 | T = 1 Month |
| 116 | Glossy, textured | Glossy, textured | Medium | Medium-High | 10 | 10 |
| 117 | Glossy, slightly textured | Glossy, slightly textured | Medium-High | Medium-High | <10 | <10 |
| 254 | Smooth with matt appearance | Smooth, matt | High | Medium-High | <10 | <10 |
| 120 | Smooth, matt appearance, some aeration | Smooth, matt | Very High | Very High | <10 | <10 |
| 235 | Glossy, textured but does smooth out | Glossy, very slightly textured but does smooth out | Medium-Low | Medium | <50 | <50 |

TABLE 24-continued

Stability Data for 10 Formulations, i.e., Formulations 116, 117, 120, 124, 188, 184, 189, 235, 254 and 255, rejected after 1 Month Stability, with respect to the Spatula Test, Visual Viscosity and Particle size (as determined by microscopy).

| | Spatula Test | | Visual Viscosity | | Majority of particle size (μM) | |
|---|---|---|---|---|---|---|
| Formulation | T = 0 | T = 1 Month | T = 0 | T = 1 Month | T = 0 | T = 1 Month |
| 188 | Glossy and textured | Glossy and textured | Medium-Low | High | <10 | <10 |
| 189 | Glossy, very slightly textured | Glossy, slightly textured | High | Very High | <10 | <10 |
| 184 | Glossy, slightly textured | Glossy, slightly textured | High | High | <10 | <10 |
| 255 | Glossy and smooth | Glossy and smooth | High | High | 10 | <10 |
| 124 | Glossy, very slightly textured | Glossy, very slightly textured | Medium-High | Medium-High | <10 | <10 |

TABLE 25 pH Stability Data for 10 Imiquimod Formulations, i.e., Formulations 116, 117, 120, 124, 188, 184, 189, 235, 254 and 255, Rejected after 1 Month Stability.

| Formulation | pH | |
|---|---|---|
| Identity | T = 0 | T = 1 Month |
| 116 | 5.0 | 4.7 |
| 117 | 4.5 | 4.5 |
| 254 | 4.7 | 4.7 |
| 120 | 4.5 | 4.5 |
| 235 | 4.5 | 4.5 |
| 188 | 4.7 | 4.7 |
| 189 | 4.7 | 4.7 |
| 184 | 4.7 | 4.7 |
| 255 | 4.5 | 4.5 |
| 124 | 4.5 | 4.5 |

TABLE 26

Viscosity Stability Data for 10 Imiquimod Formulations, i.e., Formulations 116, 117, 120, 124, 188, 184, 189, 235, 254 and 255, Rejected after 1 Month Stability

| | | | Brookfield (cps) | | Bohlin Viscosity (cps) | |
|---|---|---|---|---|---|---|
| Formulation Identity | Crossover T = 0 | G' T = 0 | T = 0 | T = 1 Month | T = 0 | T = 1 Month |
| 116 | 9.0 | 478 | 601867 | 63500 | 15350 | 13300 |
| 117 | 14.0 | 1151 | 1216667 | 1281000 | 17250 | 15600 |
| 254 | 10.3 | 1399 | 1476667 | 1423000 | 19050 | 19000 |
| 120 | 15.3 | 884 | 1416667 | 1393000 | 20250 | 20900 |
| 235 | 6.0 | 134 | 245333 | 313000 | 6350 | 5700 |
| 188 | 14.0 | 708 | 1141333 | 1254000 | 20350 | 20750 |
| 189 | 34.8 | 1037 | 1344333 | 1463000 | 18700 | 18550 |
| 184 | 23.0 | 1054 | 1475667 | 1350000 | 20200 | 21600 |
| 255 | 16.0 | 1488 | 2483333 | 1334000 | 21150 | 25150 |
| 124 | 7.0 | 561 | 849000 | 663000 | 14400 | 14250 |

(F) Brookfield Viscosity Stability Results of Formulations

In Table 27, Brookfield viscosity measurements are notoriously variable and, as such, there are fluctuations in the measurements of the formulations over about a 6 month period when stored at about 25° C. Variations in results are further observed if the spindle or the speed of the spindle rotation is altered. Although the majority of the formulations are measured using the same settings and spindle; the placebo formulations (Pbo1, Pbo2, Pbo3 and Pbo4) result in torque measurements below the threshold required for accurate measurements and subsequently readings are inaccurate. Attempts are made to change the settings and spindles; however, results are vastly different and thus unreliable. See also Tables 24-26.

TABLE 27

Viscosity and Rheology Measurements of Imiquimod Formulations stored at 25° C. over 6 Month Period.

| Formulation Identity | Crossover G(Pa) t = 0 | (o) t = 0 | Brookfield (cPs) | | | | | Bohlin Viscosity (cPs) (based on 3M method) | | | | |
|---|---|---|---|---|---|---|---|---|---|---|---|---|
| | | | t = 0 | t = 1 Month | t = 2 Months | t = 3 Months | t = 6 Months | t = 0 | t = 1 Month | t = 2 Months | t = 3 Months | t = 6 Months |
| 3M Aldera® 5% Imiquimod | 507 | 123 | 660333 | 623000 | 337000 | 428833 | 166233 | 15700 | 17300 | 17600 | 13296 | 12833 |
| Graceway Aldera® 5% Imiquimod | 716 | 10.5 | 1108667 | 1109000 | 587667 | 768566 | 252033 | 18250 | 20250 | 19900 | 18697 | 15100 |
| 257(1%) | 352 | 10.52 | 642667 | 600000 | 220333 | 351566 | * | 13600 | 15050 | 11500 | 6075 | 3139 |
| 110 | 782 | 11.5 | 87100 | 119000 | 782333 | 619300 | 366067 | 16250 | 16400 | 18000 | 16368 | 14076 |
| 250 | 320 | 9 | 695333 | 816000 | 557333 | 394166 | 141400 | 13700 | 16400 | 14950 | 10587 | 5890 |
| 182 | 702 | 8.5 | 693067 | 1097000 | 904667 | 523033 | 273233 | 18050 | 17850 | 18550 | 16820 | 13691 |
| 195 | 692 | 15 | 1141333 | 1293000 | 779333 | 618133 | 381700 | 17000 | 17600 | 16500 | 16208 | 14696 |
| 123 | 510 | 10.8 | 804000 | 773000 | 386333 | 701500 | 199933 | 15800 | 16250 | 15200 | 13095 | 9587 |
| 125 | 485 | 8.5 | 603000 | 707000 | 429667 | 412133 | 127067 | 14900 | 17050 | 15300 | 12069 | 8301 |
| 256 | 667 | 7.3 | 1126000 | 958000 | 697667 | 757523 | 249500 | 18300 | 18750 | 15453 | 12379 | |
| 197 | 646 | 14 | 1082667 | 1377000 | 613667 | 607366 | 274400 | 17750 | 17850 | 17600 | 15861 | 13524 |
| 183 | 719 | 10.3 | 693333 | 839000 | 596000 | 332900 | 188000 | 18700 | 19100 | 18600 | 15906 | 12120 |
| 126 | AP | | 430100 | 235066 | 228104 | 212500 | 105720 | 16783 | 12739 | 14749 | 10856.5 | 8789.5 |
| PB01 | 306 | 11 | 85000 | ** | ** | ** | ** | 12100 | 14450 | 7500 | 7969 | 2508.3 |
| PB02 | 263 | 13 | 79500 | | | | | 14200 | 13950 | 9100 | 6452.5 | 2617.6 |
| PB03 | 305 | 11.5 | 117000 | | | | | 12200 | 13850 | 9000 | 8395 | 3256.5 |
| PB05 | | | 227800 | * | | | | 10350 | 7953 | 5511 | 3550 | 2247 |

Results un-reliable and not presented as the torque was out of range (due to low viscosity) for the Brookfield viscometer using the settings and spindle used for all the other samples.
Alternative spindles and settings were investigated; however, the results were vastly different than previous readings.
** No recorded measurements, as test was only required for initial formulations choice and development.

(G) Bohlin Viscosity Results

Also as shown in Table 27, the Bohlin viscosity results are in contrast to the results of the Brookfield viscosity and appear to be more consistent for all formulations. A fall in the viscosity is observed for 257 (1%) and placebo formulations, Pbo1-4, over the 6 month stability study, whereby the viscosity falls by approximately 50%. All formulations are within the range of the specifications for the Aldara® 5% imiquimod cream formulation (2000 to 35,000 cps), See also Tables 24-26.

(H) pH Stability of Formulations in Table 28, it reports that the specification for all formulations that are tested, fall within the Aldara® 5% imiquimod cream specifications (pH 4.0 to 5.5). A slight variation in pH is observed over the 6 month period for all of the formulations. See also Tables 24-26.

TABLE 28 ph for Imiquimod Formulations when Stored at about 25° C. and about 40° C. over a 6 Month Period. Grey Areas Indicate No Test Is Performed.

| | PH | | | | | | | | |
|---|---|---|---|---|---|---|---|---|---|
| | t = 0 | t = 1 month | | t = 2 months | | t = 3 months | | t = 6 months | |
| Formulation | 25° C. | 25° C. | 40° C. | 25° C. | 40° C. | 25° C. | 40° C. | 25° C. | 40° C. |
| 3m Aldera® 5% Imiquidod | 4.5 | 4.5 | | 4.5 | 4.5 | 4.5 | 4.7 | 4.3 | 4.1 |
| Graceway Aldera® 5% Imiquidod | 4.5 | 4.5 | | 4.5 | 4.5 | 4.5 | 4.5 | 4.3 | 4.5 |
| 257 (1%) | 4.2 | 4.5 | | 4.5 | 4.5 | 4.5 | 4.1 | 4.1 | 3.9 |
| 110 | 5 | 4.7 | | 4.7 | 4.7 | 4.7 | 4.4 | 4.5 | 4.3* |
| 250 | 4.2 | 4.2 | | 4.2 | 4.5 | 4.2 | 4 | 4.2 | 4.1 |
| 182 | 4.5 | 4.5 | | 4.5 | 4.5 | 4.5 | 4.6 | 4.3 | 4.3 |
| 195 | 4.7 | 4.5 | | 4.5 | 4.5 | 4.5 | 4.7 | 4.5 | 4.5 |
| 123 | 4.5 | 4.7 | | 4.7 | 4.7 | 4.7 | 4.3 | 4.1 | 4.3 |
| 125 | 4.5 | 4.5 | | 4.5 | 4.5 | 4.5 | 4.2 | 4.1 | 4.1 |
| 256 | 4.7 | 4.7 | | 4.7 | 4.7 | 4.7 | 4.4 | 4.3 | 4.3 |
| 197 | 4.5 | 4.7 | | 4.7 | 4.7 | 4.7 | 4.6 | 4.5 | 4.3 |
| 183 | 4.5 | 4.5 | | 4.5 | 4.5 | 4.5 | 4.2 | 4.5 | 4.1 |
| 126 | 4.2 | 4.3 | 4.3 | 4.3 | 4.3 | 4.3 | 4.3 | 4.1 | 4.1 |
| Pbo1 | 4.5 | 4.5 | | 4.5 | 4.5 | 4.2 | 4.5 | 4.0 | 4.0 |
| Pbo2 | 4.5 | 4.5 | | 4.2 | 4.1 | 4.2 | 4.2 | 4.1 | 4.1 |

TABLE 28-continued ph for Imiquimod Formulations when Stored at about 25° C. and about 40° C. over a 6 Month Period. Grey Areas Indicate No Test Is Performed.

| | PH | | | | | | | | |
|---|---|---|---|---|---|---|---|---|---|
| | t = 0 | t = 1 month | | t = 2 months | | t = 3 months | | t = 6 months | |
| Formulation | 25° C. | 25° C. | 40° C. | 25° C. | 40° C. | 25° C. | 40° C. | 25° C. | 40° C. |
| Pbo3 | 4.5 | 4.5 | | 4.2 | 4.2 | 4.2 | 4.2 | 4.2 | 4.2 |
| Pho4 | 4.5 | 4.2 | 4.5 | 4.2 | 4.2 | 4.1 | 4.1 | 4.0 | 4.0 |

*30° C. sample analyzed as the 40° C. sample had phase separated (I) Preservative Efficacy Test Table 29 reports final viable counts of organism inoculations that are added to the formulations.

TABLE 29

Total Viable Counts that are obtained for the Organism Inoculates into the Imiquimod Formulations

| Organism | Mimi for 182 and 110 | Cfu/ml for 126 and Pbo4 |
|---|---|---|
| *Staphylococcus aureus* | 2.4E+08 | 3.1E+08 |
| *Escherichia coli* | 1.7E+08 | 2.1E+08 |
| *Pseudomonas aeruginosa* | 9.0E+07 | 1.1E+08 |
| *Candida albicans* | 1.0E+08 | 1.1E+08 |
| *Aspergillus niger* | 1.7E+07 | 1.6E+08 |

Table 30 shows colony forming unit count (cfu) for *Staphylococcus aureus* after PET validation is performed on two formulations stored at about 2-8° C.

TABLE 30

Viable counts that are obtained for *Staphylococcus aureus* that are Inoculated Formulations after PET Validation

| Imiquimod Formulation | Suspension fluid | Dilution | Viable count (cfu/ml) |
|---|---|---|---|
| 110 | DIE broth | 1 ml in 9 ml | 2.20E+08 |
| | | 0.1 ml in 0.9 ml | 2.80E+08 |
| | Ringer's | 1 ml in 9 ml | 1.00E+03 |
| | solution | 0.1 ml in 0.9 ml | 1.50E+03 |
| 182 | D/E broth | 1 ml in 9 ml | 2.30E+08 |
| | | 0.1 ml in 0.9 ml | 2.60E+08 |
| | Ringer's | 1 ml in 9 ml | 1.00E+03 |
| | solution | 0.1 ml in 0.9 ml | 1.40E+03 |

The preservative efficacy test ("PET") is a procedure used to demonstrate antimicrobial activity of a formulation with respect to the preservative system used. In Table 31, cell counts that are recovered from the inoculated formulations at various time points are reported. The data shows that sufficient log reductions are present in the formulations at about 2-8° C. and about 40° C. and meet the requirements that are specified in both the USP and EP.

TABLE 31

Colony Forming Unit Counts that are recovered (Cfu/Ml) for Each Organism from the Imiquimod Formulations over 28 Days.

| | | Organisms recovered-(cfu/ml) | | | | | | | Pass/ |
|---|---|---|---|---|---|---|---|---|---|
| Formulation | Organism | 0 h | 24 h | 48 h | 7 days | 19 days | 21 days | 28 days | Fail |
| Pho4 | *S. aureus* | 3.10E+05 | 0.00E+00 | 0.00E+00 | 0.00E+00 | 0.00E+00 | 0.00E+00 | 0.00E+00 | PASS |
| STORAGE: | *E. coil* | 5.00E+03 | 0.00E+00 | 0.00E+00 | 0.00E+00 | 0.00E+00 | 0.00E+00 | 0.00E+00 | PASS |
| 2-8° C. | *Ps. aeruginosa* | 9.00E+03 | 0.00E+00 | 0.00E+00 | 0.00E+00 | 0.00E+00 | 0.00E+00 | 0.00E+00 | PASS |
| | *A albican* | 5.00E+04 | 1.80E+03 | 0.00E+00 | 0.00E+00 | 0.00E+00 | 0.00E+00 | 0.00E+00 | PASS |
| | *A. niger* | 1.60E+05 | 6.00E+03 | 2.50E+03 | 0.00E+00 | 0.00E+00 | 0.00E+00 | 0.00E+00 | PASS |
| Pho4 | *S. aureus* | 1.70E+06 | 0.00E+00 | 0.00E+00 | 0.00E+00 | 0.00E+00 | 0.00E+00 | 0.00E+00 | PASS |
| STORAGE: | *E. coil* | 6.00E+03 | 0.00E+00 | G.00E+00 | 0.00E+00 | 0.00E+00 | 0.00E+00 | 0.00E+00 | PASS |
| 40° C. | *Ps. aeruginosa* | 1.30E+04 | 0.00E+00 | 0.00E+00 | 0.00E+00 | 0.00E+00 | 0.00E+00 | 0.00E+00 | PASS |
| | *C albican* | 2.60E+04 | 4.10E+03 | 1.30E+03 | 0.00E+00 | 0.00E+00 | 0.00E+00 | 0.00E+00 | PASS |
| | *A. niger* | 3.00E+05 | 1.70E+04 | 3.30E+03 | 0.00E+00 | 0.00E+00 | 0.00E+00 | 0.00E+00 | PASS |
| 126 | *S. aureus* | 5.70E+04 | 0.00E+00 | 0.00E+00 | 0.00E+00 | 0.00E+00 | 0.00E+00 | 0.00E+00 | PASS |
| STORAGE: | *E. coil* | 1.20E+06 | 0.00E+00 | 0.00E+00 | 0.00E+00 | 0.00E+00 | 0.00E+00 | 0.00E+00 | PASS |
| 2-8° C. | *Ps. aeruginosa* | 1.40E+04 | 0.00E+00 | 0.00E+00 | 0.00E+00 | 0.00E+00 | 0.00E+00 | 0.00E+00 | PASS |
| | *C albican* | 3.50E+04 | 5.00E+03 | 400E+02 | 0.00E+00 | 0.00E+00 | 0.00E+00 | 0.00E+00 | PASS |
| | *A. niger* | 1.00E+05 | 2.10E+04 | 2.50E+03 | 0.00E+00 | 0.00E+00 | 0.00E+00 | 0.00E+00 | PASS |
| 126 | *S. aureus* | 2.10E+04 | 0.00E+00 | 0.00E+00 | 0.00E+00 | 0.00E+00 | 0.00E+00 | 0.00E+00 | PASS |
| STORAGE: | *E. coil* | 5.00E+05 | 0.00E+00 | 0.00E+00 | 0.00E+00 | 0.00E+00 | 0.00E+00 | 0.00E+00 | PASS |
| 40° C. | *Ps. aeruginosa* | 1.50E+04 | 0.00E+00 | 0.00E+00 | 0.00E+00 | 0.00E+00 | 0.00E+00 | 0.00E+00 | PASS |
| | *C albican* | 3.80E+04 | 3.60E+03 | 2.50E+03 | 0.00E+00 | 0.00E+00 | 0.00E+00 | 0.00E+00 | PASS |
| | *A. niger* | 1.00E+05 | 2.90E+03 | 1.60E+03 | 0.00E+00 | 0.00E+00 | 0.00E+00 | 0.00E+00 | PASS |
| 110 | *S. aureus* | 1.00E+06 | 0.00E+00 | 0.00E+00 | 0.00E+00 | 0.00E+00 | 0.00E+00 | 0.00E+00 | PASS |
| STORAGE: | *E. coil* | 7.00E+05 | 0.00E+00 | 0.00E+00 | 0.00E+00 | 0.00E+00 | 0.00E+00 | 0.00E+00 | PASS |
| 2-FPG | *Ps. aeruginosa* | 8.00E+04 | 0.00E+00 | 0.00E+00 | 0.00E+00 | 0.00E+00 | 0.00E+00 | 0.00E+00 | PASS |
| | *C albican* | 8.00E+05 | 2.60E+04 | 7.00E+03 | 7.00E+01 | 0.00E+00 | 0.00E+00 | 0.00E+00 | PASS |
| | *A. niger* | 6.00E+04 | 9.00E+04 | 2.30E+04 | 7.00E+03 | 3.70E+02 | 0.00E+00 | 0.00E+00 | PASS |

TABLE 31-continued

Colony Forming Unit Counts that are recovered (Cfu/Ml) for Each Organism from the Imiquimod Formulations over 28 Days.

| Formulation | Organism | Organisms recovered-(cfu/ml) 0 h | 24 h | 48 h | 7 days | 19 days | 21 days | 28 days | Pass/ Fail |
|---|---|---|---|---|---|---|---|---|---|
| 110 | *S. aureus* | 6.00E+05 | 0.00E+00 | 0.00E+00 | 0.00E+00 | 0.00E+00 | 0.00E+00 | 0.00E+00 | PASS |
| STORAGE: | *E. coil* | 8.00E+04 | 0.00E+00 | 0.00E+00 | 0.00E+00 | 0.00E+00 | 0.00E+00 | 0.00E+00 | PASS |
| 40° C. | *Ps. aeruginosa* | 7.00E+05 | 0.00E+00 | 0.00E+00 | 0.00E+00 | 0.00E+00 | 0.00E+00 | 0.00E+00 | PASS |
| | *C albican* | 1.60E+05 | 1.50E+04 | 4.00E+03 | 2.20E+02 | 0.00E+00 | 0.00E+00 | 0.00E+00 | PASS |
| | *A. niger* | 7.00E+04 | 6.00E+04 | 2.50E+03 | 1.90E+04 | 1.90E+02 | 0.00E+00 | 0.00E+00 | PASS |
| 182 | *S. aureus* | 1.70E+06 | 0.00E+00 | 0.00E+00 | 0.00E+00 | 0.00E+00 | 0.00E+00 | 0.00E+00 | PASS |
| STORAGE: | *E. coil* | 1.70E+06 | 0.00E+00 | 0.00E+00 | 0.00E+00 | 0.00E+00 | 0.00E+00 | 0.00E+00 | PASS |
| 2-8° C. | *Ps. aeruginosa* | 7.00E+05 | 0.00E+00 | 0.00E+00 | 0.00E+00 | 0.00E+00 | 0.00E+00 | 0.00E+00 | PASS |
| | *C albican* | 3.00E+05 | 2.10E+04 | 1.90E+03 | 3.00E+03 | 0.00E+00 | 0.00E+00 | 0.00E+00 | PASS |
| | *A. niger* | 4.00E+05 | 5.00E+03 | 2.40E+03 | 3.00E+03 | 0.00E+00 | 0.00E+00 | 0.00E+00 | PASS |
| 182 | *S. aureus* | 1.50E+06 | 0.00E+00 | 0.00E+130 | 0.00E+00 | 0.00E+00 | 0.00E+00 | 0.00E+00 | PASS |
| STORAGE: | *E. coil* | 1.10E+06 | 0.00E+00 | 0.00E+00 | 0.00E+00 | 0.00E+00 | 0.00E+00 | 0.00E+00 | PASS |
| 40° C. | *Ps. aeruginosa* | 6.00E+05 | 0.00E+00 | 0.00E+00 | 0.00E+00 | 0.00E+00 | 0.00E+00 | 0.00E+00 | PASS |
| | *C albican* | 7.00E+05 | 3.00E+04 | 3.00E+03 | 7.00E+03 | 0.00E+00 | 0.00E+00 | 0.00E+00 | PASS |
| | *A. niger* | 7.00E+05 | 6.00E+03 | 2.70E+03 | 1.70E+03 | 1.20E+02 | 0.00E+00 | 0.00E+00 | PASS |

(J) Test Item Release Studies Through Synthetic Membranes

Figure 3:
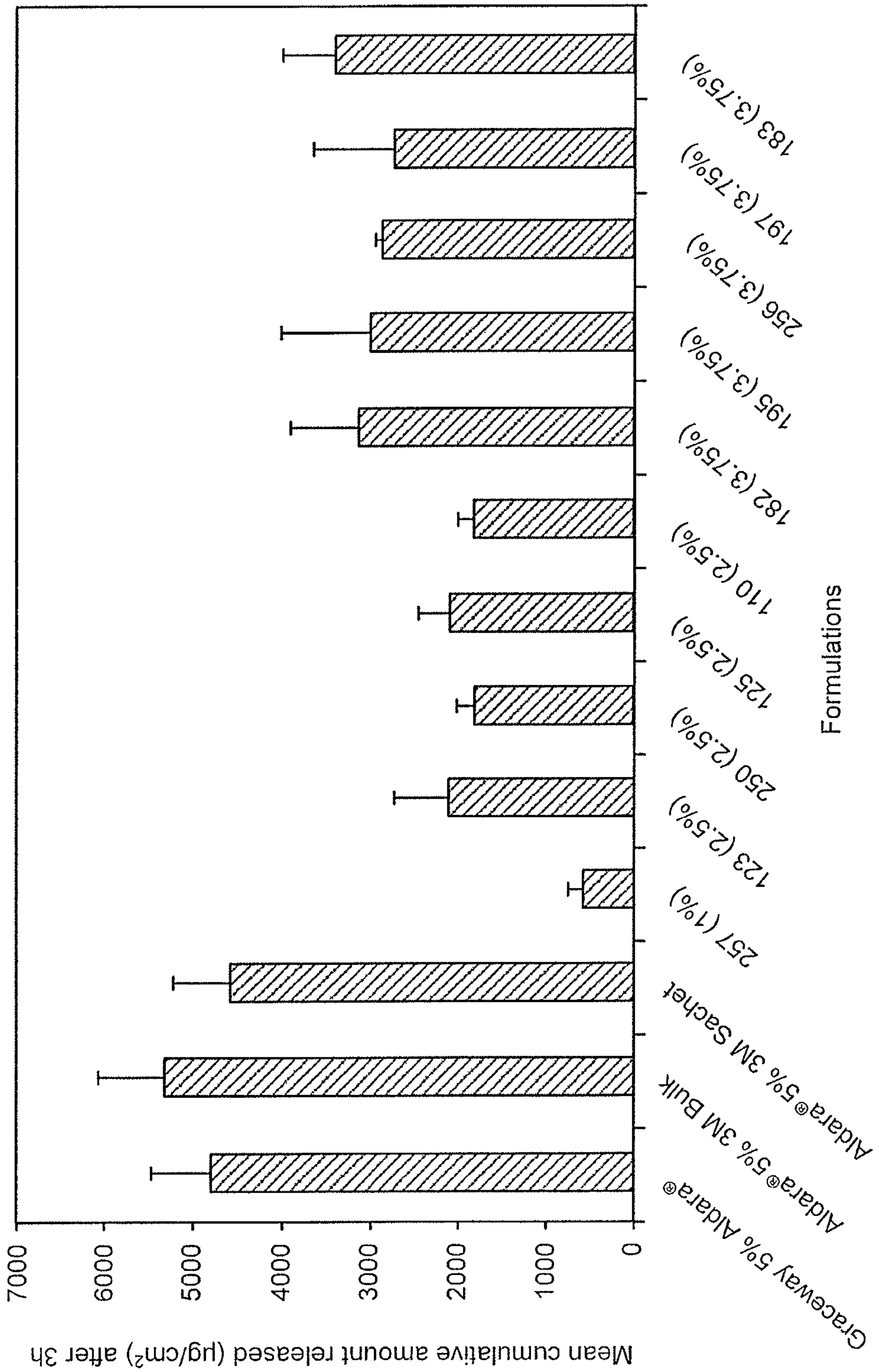
FIG. 3 shows a comparison of the mean cumulative amount of imiquimod released (µg/cm2) after about 3 h for the membrane release studies (for all the formulations selected for Full thickness skin permeation and stability studies) (mean±sd, where n=4)
Figure 4:
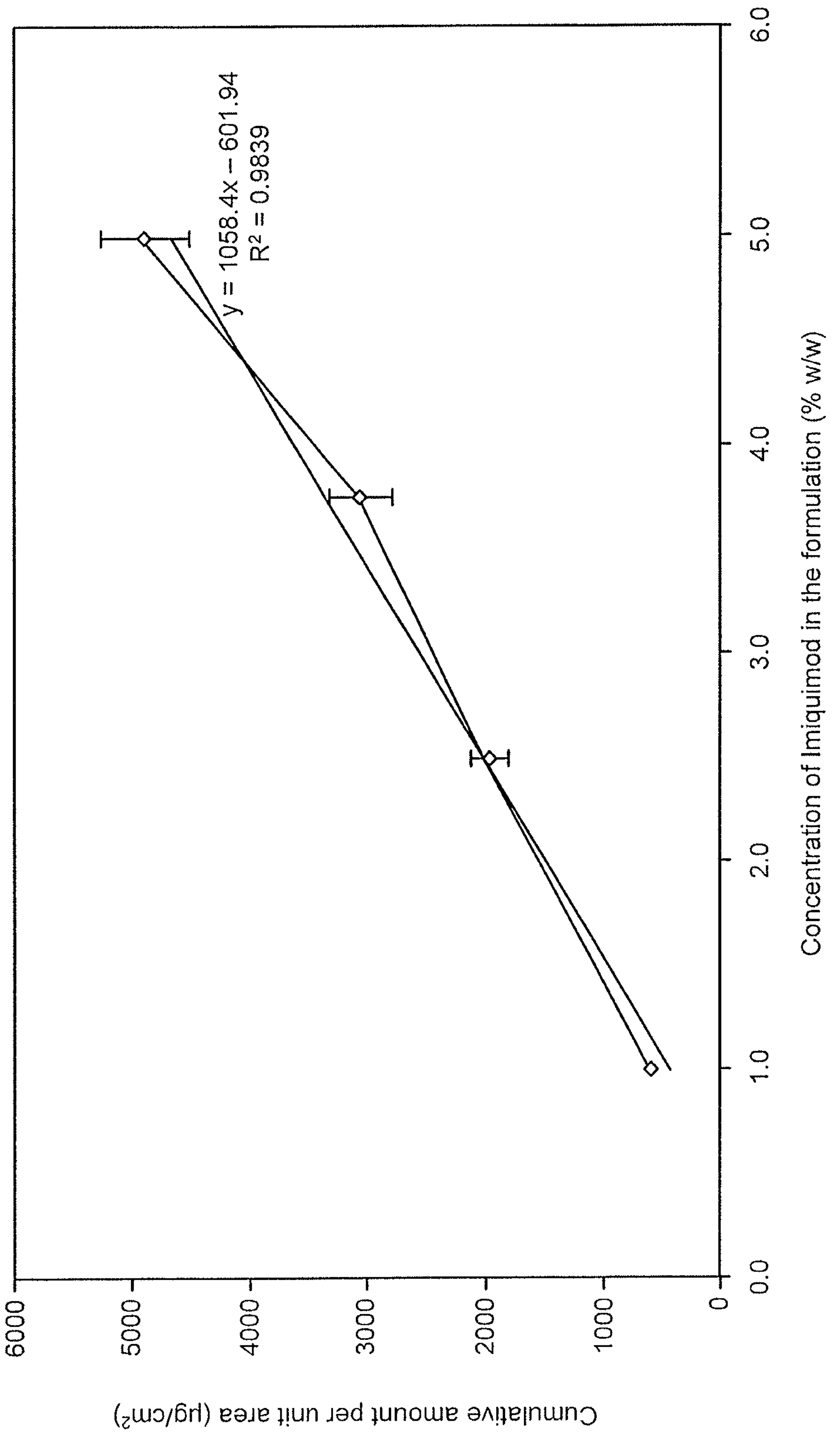
FIG. 4 shows a comparison of the average total cumulative report released (µg/cm2) after 3 h for each concentration of imiquimod in the formulations that are tested (mean±sd, where n=4 for 1%, n=16 for 2.5%, n=20 for 3.75% and n=12 for 5%)

In FIG. 3, it indicates that there is a trend between the concentrations of imiquimod present in the formulation as compared to the amount that is released. This is supported by the results presented in FIG. 4 and the corresponding statistical analysis, where it can be seen that that the higher the imiquimod concentration in the formulation, the greater the release of imiquimod. However, formulation 183 (3.75% w/w imiquimod) gives a statistically (at a 95% confidence level) greater cumulative release of imiquimod when it is compared to the 2.5% w/w formulations. All of the 5% w/w formulations, i.e., Aldara® 5% imiquimod cream batch, Aldara® 5% imiquimod cream Graceway batch, and Aldara® 5% imiquimod cream Sachet), result in significantly ($p<0.05$) higher amounts of imiquimod released over a 3 h time period in comparison to 1%, 2.5% and 3.75% w/w imiquimod formulations. There is no statistical difference ($p>0.05$) in the total cumulative amount of imiquimod that is released from any of the 3.75% w/w imiquimod formulations; likewise there is also no statistical difference ($p>0.05$) from the 2.5% w/w imiquimod formulations.

ANOVA statistical analysis (95% confidence level): mean total cumulative amount that is released (μ/$cm^2$) after 3 h (from results that are presented in FIG. 3):

| Source | DF | SS | MS | F | P |
|---|---|---|---|---|---|
| Formulation | 12 | 86439222 | 7203268 | 19.40 | 0.000 |
| Error | 39 | 14484370 | 371394 | | |
| Total | 51 | 100923592 | | | |
| S = 609.4 | R-Sq = 85.65% | R-Sq (ad) = 81.23% | | | |

| Level | N | Mean | St. Dev | Individual 95% CIs For Mean Based on Pooled StDev +------------ +------------ +------------ +------------ |
|---|---|---|---|---|
| Aldara 3M 5% | 4 | 5332.8 | 734.2 | (---*---) |
| Aldara sachet | 4 | 4605.5 | 626.9 | (---*---) |
| 110 | 4 | 1862.8 | 185.9 | (---*---) |
| 250 | 4 | 1845.6 | 206.4 | (---*---) |
| 182 | 4 | 3161.3 | 774.9 | (---*---) |
| 195 | 4 | 3046.2 | 998.2 | (---*---) |
| 123 | 4 | 2094.9 | 674.6 | (---*---) |
| 125 | 4 | 2134.1 | 369.0 | (---*---) |
| 256 | 4 | 2918.7 | 59.5 | (---*---) |
| 197 | 4 | 2766.0 | 929.1 | (---*---) |
| 183 | 4 | 3453.2 | 564.4 | (---*---) |
| MedPharm Aldara | 4 | 4813.3 | 660.7 | (---*---) |
| 257% | 4 | 586.9 | 170.2 | (---*---) |
| | | | | +------------ +------------ +------------ +------------ |
| | | | | 0 1500 3000 4500 |

Pooled StDev = 609.4

ANOVA statistical analysis (95% confidence level): mean total cumulative amount that is released (ug/cm2) after 3 h for each concentration of imiquimod in the formulations that are tested (from results that are presented in FIG. 4):

| Source | DF | SS | MS | F | P |
|---|---|---|---|---|---|
| Formulation | 3 | 83957708 | 27985903 | 79.18 | 0.000 |
| Error | 48 | 16965878 | 353456 | | |
| Total | 51 | 100923592 | | | |
| S = 594.5 | R-Sq = 83.19% | | R-Sq (adj) = 82.14% | | |

| Level | N | Mean | St. Dev | Individual 95% CIs For Mean Based on Pooled StDev | | | |
|---|---|---|---|---|---|---|---|
| | | | | +------------ | +------------ | +------------ | +------------ |
| 1% | 4 | 586.9 | 170.2 | (---*---) | | | |
| 2.50% | 16 | 1984.4 | 389.9 | | (-*-) | | |
| 3.75% | 20 | 3069.1 | 702.3 | | | (*-) | |
| 5.00% | 12 | 4917.2 | 689.4 | | | | (--*-) |
| | | | | +------------ | +------------ | +------------ | +------------ |
| | | | | 0 | 1500 | 3000 | 4500 |

Pooled StDev = 594.5

Figure 11:
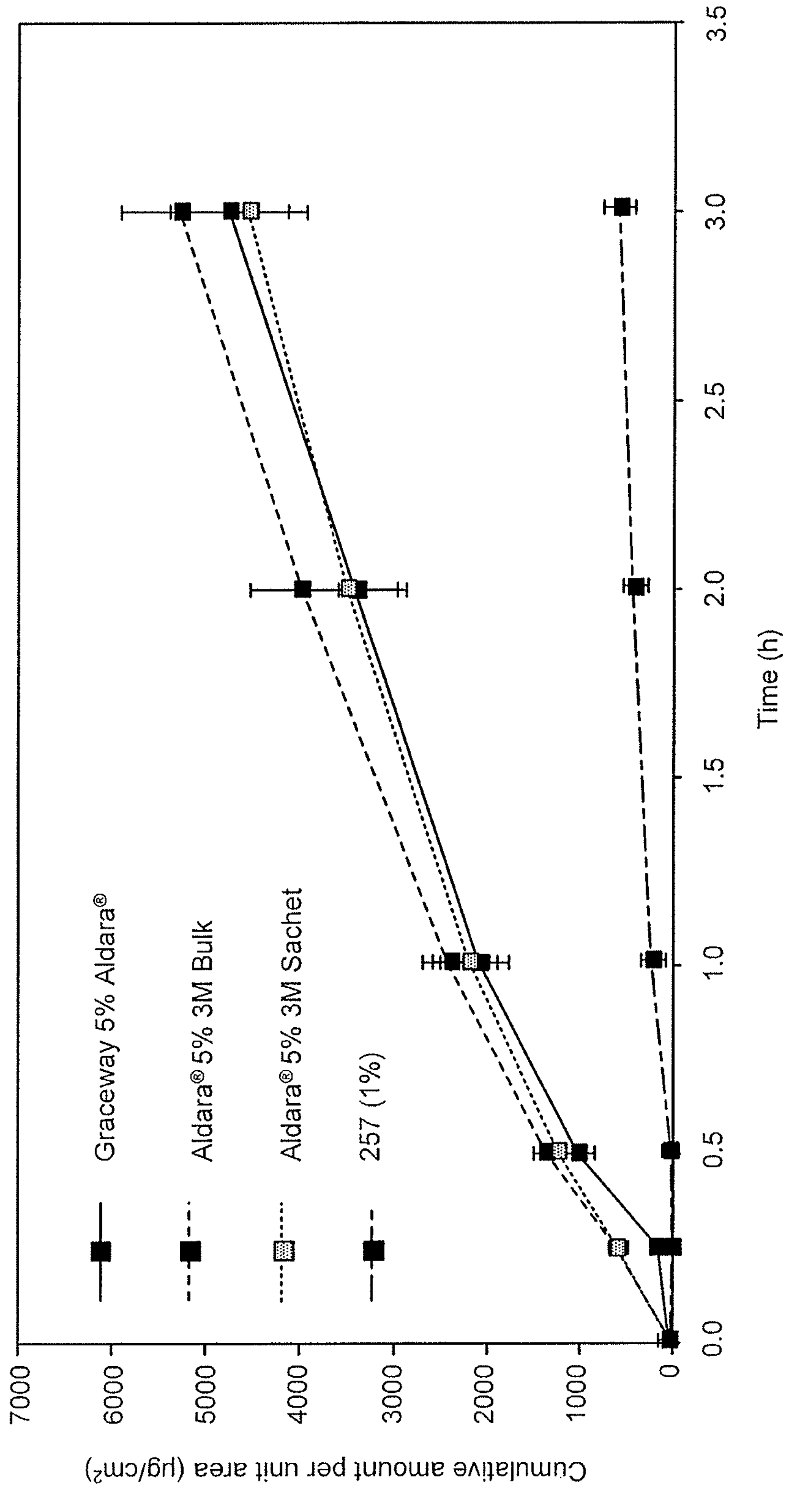
FIG. 11 shows a comparison of the mean amount of imiquimod that is released (µg/cm2) over a 3 hour period for the 3M Aldara® imiquimod cream 1 kg batch, the 3M Aldara® imiquimod cream sachet, the Graceway 3M Aldara® imiquimod cream 1 kg batch and formulation 257, a 1% imiquimod formulation (mean±sd, where n=4)
Figure 12:
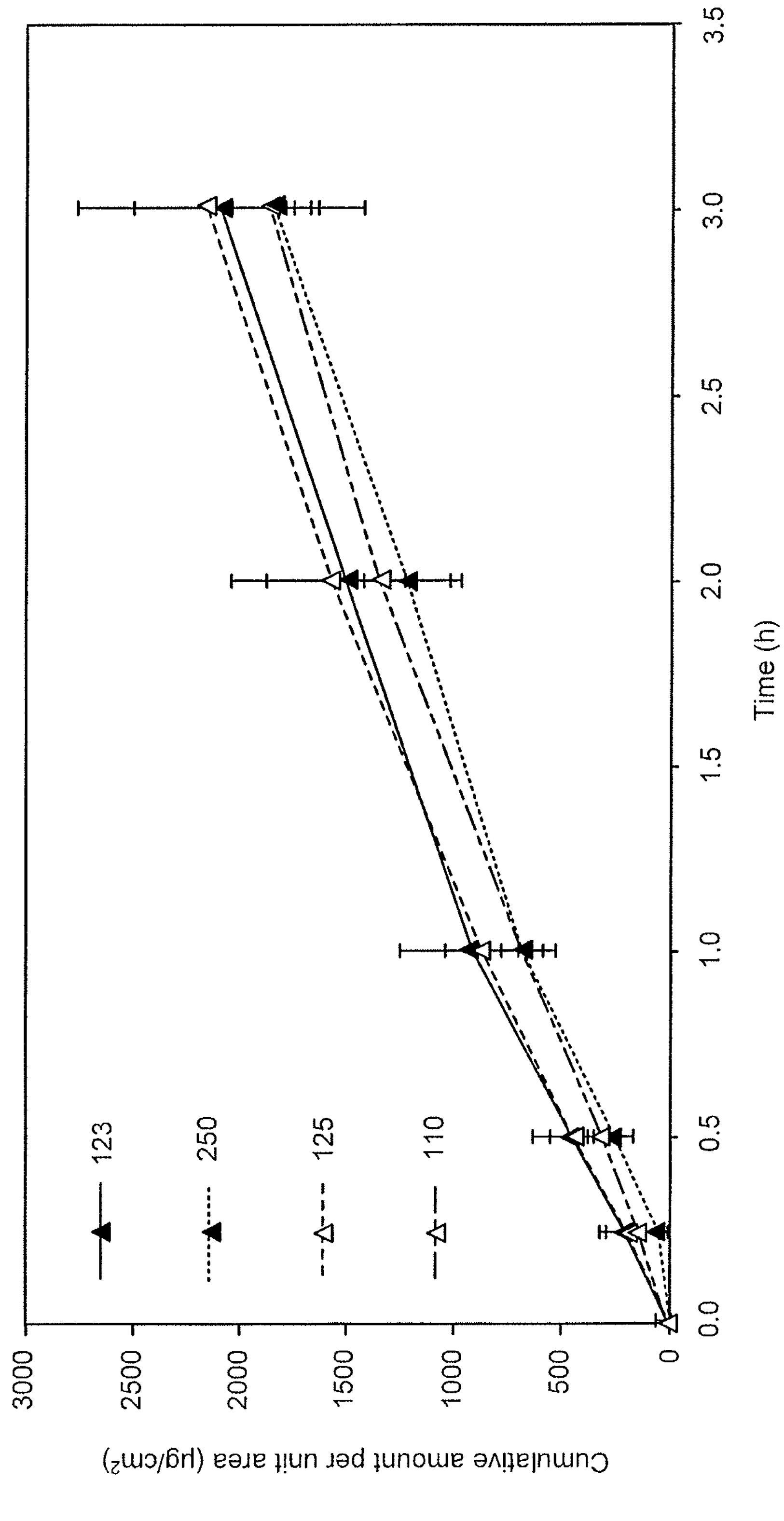
FIG. 12 shows a comparison of the mean amount of imiquimod that is released (µg/cm2) over a 3 hour period for four 2.5% imiquimod formulations, i.e., formulations 110, 123, 125 and 250 (mean±sd, where n=4).
Figure 13:
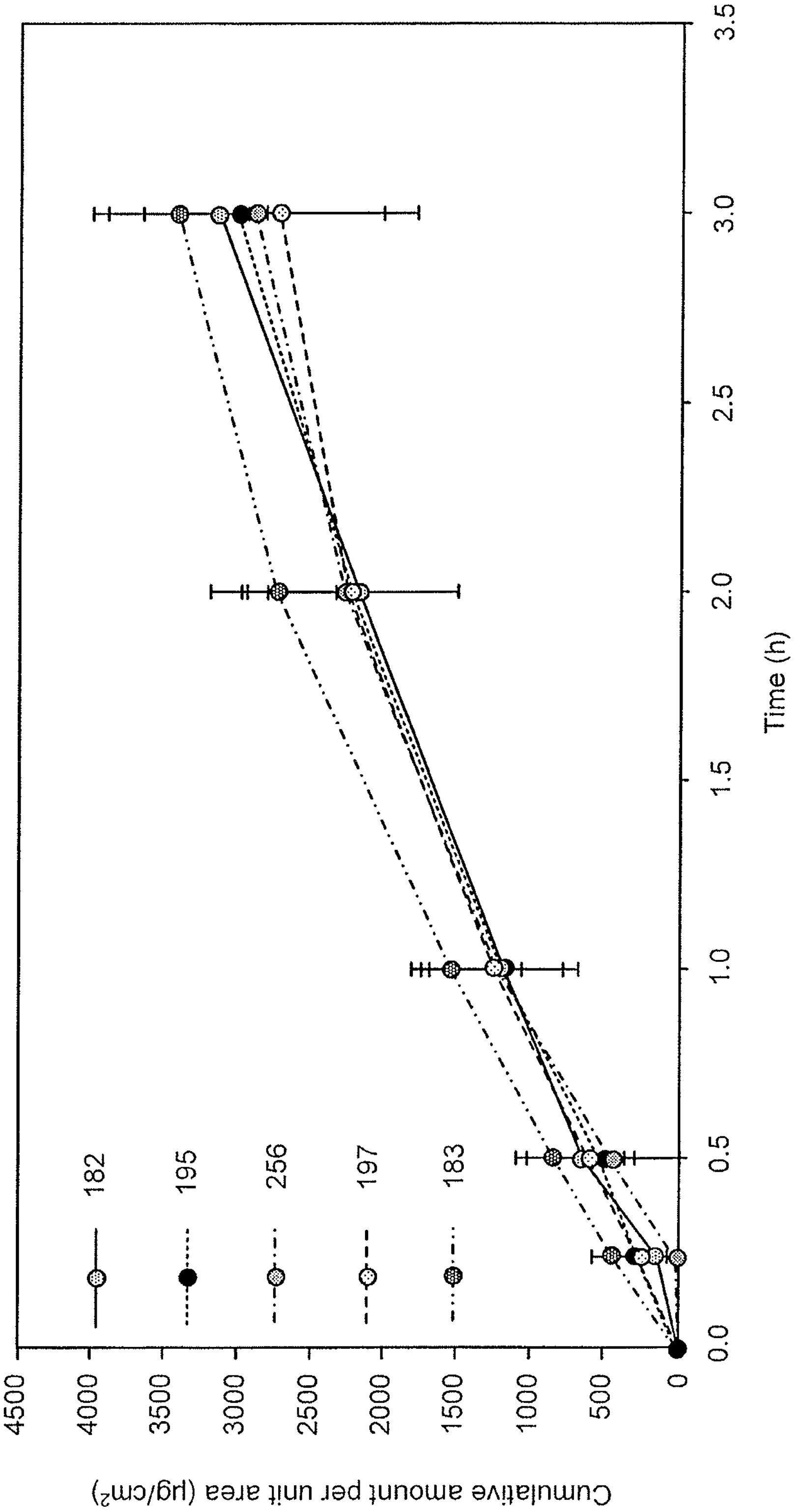
FIG. 13 shows a comparison of the mean amount of imiquimod that is released (ug/cm2) over a 3 hour period for five 3.75% imiquimod formulations, i.e., formulations 182, 183, 195, 197 and 256 (mean±sd, where n=4)

The result for the rate of release presented in Table 32, indicate that the higher the amount of imiquimod in the formulation, the faster the rate of release of imiquimod. Similar to the results of the cumulative amount permeated, there is no statistical difference (p>0.05) between the results for the 2.5% w/w in imiquimod formulations (Table 32 and FIG. 12) and likewise for the 3.75% w/w imiquimod formulations (Table 32 and FIG. 13). See also FIGS. 11 and 14.

TABLE 32

Comparison of Mean Flux of Imiquimod (pg/Cm2) over a 3 11 Period for Membrane Release Tests (Mean ± Sd, Where N = 4) that are Presented as a Function of Time from 15 Min To 3 H. Flux ✓time

| Formulations | Mean ± sd |
|---|---|
| Graceway Aldara ® 5% imiquimod | 3720.65 ± 569.38 |
| 3M Aldara° 5% Imiquimod Cream Bulk | 3873.38 ± 479.64 |
| 3M Aldara 5% Imiquimod Cream sachet | 3319.56 ± 494.32 |

TABLE 32-continued

Comparison of Mean Flux of Imiquimod (pg/Cm2) over a 3 11 Period for Membrane Release Tests (Mean ± Sd, Where N = 4) that are Presented as a Function of Time from 15 Min To 3 H. Flux ✓time

| Formulations | Mean ± sd |
|---|---|
| 257 (1%) | 504.40 ± 148.43 |
| 123 (2.5%) | 1539.39 ± 482.36 |
| 250 (2.5%) | 1396.68 ± 173.65 |
| 125 (2.5%) | 1592.98 ± 324.51 |
| 110 (2.5%) | 1518.29 ± 151.17 |
| 182 (3.75%) | 2410.03 ± 599.08 |
| 195 (3.75%) | 2310.06 ± 597.59 |
| 256 (3.75%) | 2424.87 ± 28.09 |
| 197 (3.75%) | 2116.53 ± 723.60 |
| 183 (3.75%) | 2516.84 ± 357.41 |

ANOVA statistical analysis (95% confidence level): mean amount of imiquimod released (μ/cm$^2$) over a 3 hour period for the membrane release studies (mean±sd, where n=4) presented as a function of √time from 15 min to 3 h (from results presented in Table 32):

| Source | DE | SS | MS | F | P |
|---|---|---|---|---|---|
| Formulation | 12 | 45353042 | 3779420 | 19.05 | 0.000 |
| Error | 39 | 77392670 | 198443 | | |
| Total | 51 | 53092309 | | | |
| S = 445.5 | | R-Sq = 85.42% | | R-Sq (adj) = 80.94% | |

| Level | N | Mean | St. Dev | Individual 95% CIs For Mean Based on Pooled StDev | | | |
|---|---|---|---|---|---|---|---|
| | | | | +------------ | +------------ | +------------ | +------------ |
| 3M Aldara ® 5% Imiquimod Cream Bulk | 4 | 3873.4 | 479.6 | | | | (--*---) |
| 3M Aldara ® 5% Imiquimod Cream Sachet | 4 | 3319.6 | 494.3 | | | | (---*--) |
| 110 | 4 | 1518.3 | 151.2 | | (---*--) | | |
| 250 | 4 | 1396.7 | 173.6 | | (---*--) | | |
| 182 | 4 | 2410.0 | 599.1 | | | (---*---) | |
| 195 | 4 | 2310.1 | 597.6 | | | (---*---) | |
| 123 | 4 | 1539.4 | 482.4 | | (---*---) | | |
| 125 | 4 | 1593.0 | 324.5 | | (--*---) | | |
| 256 | 4 | 2424.9 | 28.1 | | | (---*---) | |
| 197 | 4 | 2116.5 | 723.6 | | | (---*--) | |
| 183 | 4 | 2516.8 | 357.4 | | | (---*---) | |
| Graceway ® 5% Imiquimod Cream | 4 | 3720.6 | 569.4 | | | | (---*---) |

-continued

| | | | | |
|---|---|---|---|---|
| 257 1% | 4 | 504.4 | 148.4 | (---*---) |
| | | | | +------------ +------------ +------------ +------------ |
| | | | | 0 1200 2400 3600 |

Pooled StDev = 445.5

ANOVA statistical analysis (95% confidence level): Comparison of the mean amount of imiquimod released (µg/$cm^2$) over a 3 hour period for the 3M Aldara® 5% imiquimod cream 1 kg batch, the 3M Aldara® 5% imiquimod cream sachet, the Graceway Aldara® 5% imiquimod cream 1 kg batch and 257, 1% Imiquimod formulation (mean±sd, where n=4)—refer to FIG. 11:

| Source | DE | SS | MS | F | P |
|---|---|---|---|---|---|
| Formulation | 3 | 5737855 | 19126285 | 54.74 | 0.000 |
| Error | 12 | 4192460 | 349372 | | |
| Total | 15 | 61571315 | | | |

S = 591.1 R-Sq = 93.19% R-Sq (adj) = 91.49%

| Level | N | Mean | St. Dev | Individual 95% CIs For Mean Based on Pooled StDev<br>+------------ +------------ +------------ +------------ |
|---|---|---|---|---|
| 3M Aldara ® 5% | 4 | 5332.8 | 734.2 | (---*---) |
| Aldara sachet | 4 | 4605.5 | 626.9 | (---*---) |
| MedPharm Alara | 4 | 4813.3 | 660.7 | (---*---) |
| U2F 1% | 4 | 586.9 | 170.2 | (---*---) |
| | | | | +------------ +------------ +------------ +------------ |
| | | | | 0 1600 3200 4800 |

Pooled StDev = 591.1

ANOVA statistical analysis (95% confidence level): Comparison of the mean amount of imiquimod released (µg/$cm^2$) over a 3 hour period for 2.5% imiquimod formulations 123, 250, 125 and 110 (mean±sd, where n=4)—refer to FIG. 12:

| Source | DE | SS | MS | F | P |
|---|---|---|---|---|---|
| Formulation | 3 | 274778 | 91593 | 0.55 | 0.659 |
| Error | 12 | 2004990 | 167083 | | |
| Total | 15 | 2279769 | | | |

S = 408.8 R-Sq = 12.05% R-Sq (adj) = 0.00%

| Level | N | Mean | St. Dev | Individual 95% CIs For Mean Based on Pooled StDev<br>---+----------+-----------+-----------+------- |
|---|---|---|---|---|
| GW002 | 4 | 1862.8 | 185.9 | (---------------*---------------) |
| GW008 | 4 | 1845.6 | 206.4 | (---------------*---------------) |
| GW037 | 4 | 2094.9 | 674.6 | (---------------*---------------) |
| GW039 | 4 | 2134.1 | 369.0 | (---------------*---------------) |
| | | | | ---+-- --------+-----------+-----------+------- |
| | | | | 1500 1800 2100 2400 |

Pooled StDev = 408.8

ANOVA statistical analysis (95% confidence level): Comparison of the mean amount of imiquimod released (µg/$cm^2$) over a 3 hour period for 3.75% imiquimod formulations 182, 195, 256, 197 and 183 (mean±sd, where n=4)—refer to FIG. 13:

| Source | DE | SS | MS | F | P |
|---|---|---|---|---|---|
| Formulation | 4 | 1084063 | 271016 | 0.49 | 0.743 |
| Error | 15 | 8386917 | 552461 | | |
| Total | 19 | 9370981 | | | |

S = 743.3 R-Sq = 11.57% R-Sq (adj) = 0.00%

| Level | N | Mean | St. Dev | Individual 95% CIs For Mean Based on Pooled StDev -------+----------+------------+------------+-- |
|---|---|---|---|---|
| GW030 | 4 | 3161.3 | 774.9 | (---------------*---------------) |
| GW033 | 4 | 3046.2 | 988.2 | (---------------*---------------) |
| GW040 | 4 | 2918.7 | 59.5 | (---------------*---------------) |
| GW041 | 4 | 2766.0 | 929.1 | (---------------*---------------) |
| GW042 | 4 | 3453.2 | 564.4 | -------+----------+------------+------------+-- 2400 3000 3600 4200 |

Pooled StDev = 743.3

Figure 14:
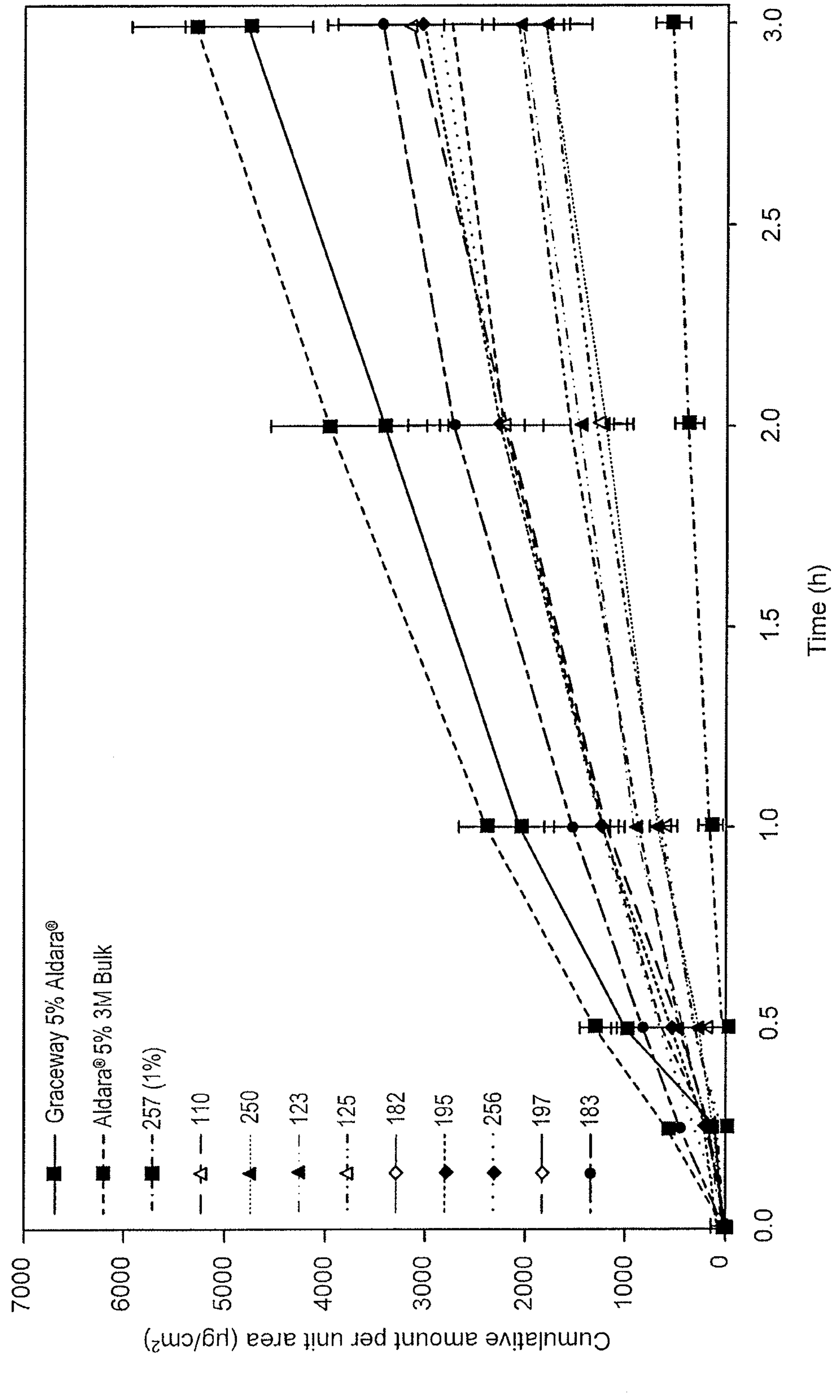
FIG. 14 shows a comparison of the mean amount of imiquimod released (μg/$cm^2$) over a 3 hour period for the 2.5% (▲), 3.75% (·), 3M Aldara® imiquimod cream batch (■), Graceway Aldara® imiquimod cream 1 kg batch (■) and formulation 257 imiquimod formulations (■) (mean±sd, where n=4).

As discussed under FIG. 14 in the Brief Description of the Drawings, FIG. 14 shows a comparison of the mean amount of imiquimod released (μ/cm2) over a 3 hour period for the 2.5% (▲), 3.75% (s), 3M Aldara® imiquimod cream batch (■), Graceway Aldara® imiquimod cream 1 kg batch (■) and formulation 257 Imiquimod formulations (■) (mean±sd, where n=4).

Based on the results; it appears that the greater the amount of imiquimod in the formulation, the faster and greater the total amount of imiquimod that is released, suggesting that the amount and rate of release are concentration dependant.

(K) In vitro Skin Permeation Study (1) Homogeneity

Manufacture of the formulations (about 100 g batches) is first performed, which batches are then mixed with the radioactive labelled material. The batches are prepared by omitting about 1.38 g of isostearic acid which is added with the radio-labelled imiquimod. The homogeneity of the test formulations, see Table 33, is measured as described in under Homogeneity Control above and all compositions are confirmed to meet the criterion (<10% CV).

TABLE 33

Homogeneity of Radioactivity for Imiquimod Formulations

| Formulation | % CV |
|---|---|
| Graceway Aldara ® 5% Imiquimod Cream | 0.93 |
| 3M Aldara ® 5% Imiquimod Cream | 1.50 |
| 182 | 0.80 |
| 195 | 2.39 |
| 256 | 1.17 |
| 197 | 0.07 |
| 183 | 1.54 |
| 110 | 0.71 |
| 250 | 2.53 |
| 123 | 1.89 |
| 125 | 1.53 |
| 126 | 2.55 |
| 257 (1%) | 2.30 |

(2) Franz Cell Study

Figure 5:
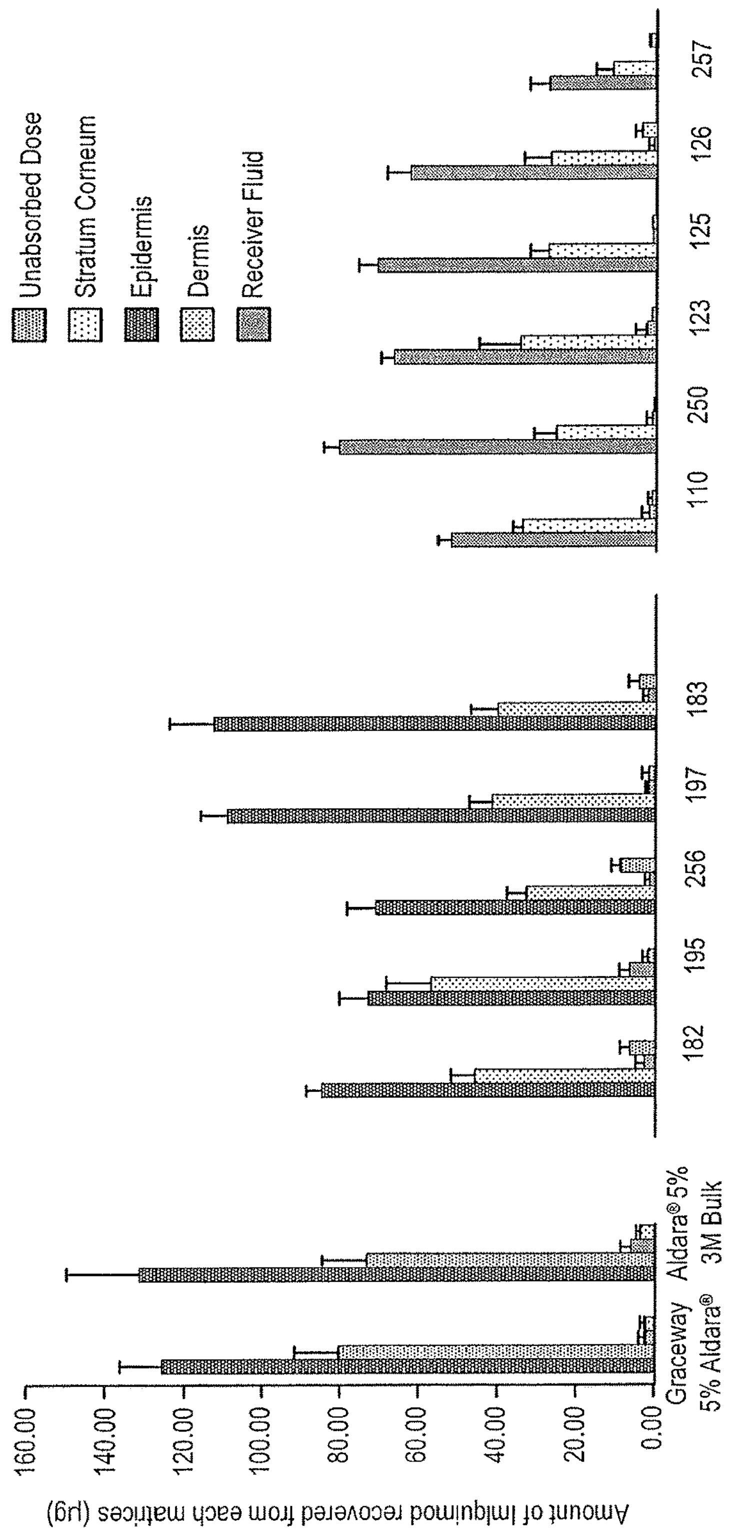
FIG. 5 shows a total amount of imiquimod that is recovered following mass balance for each formulation (See also Tables 35-40 for statistical analysts) (mean±sd, refer to Table 34 for n numbers of each sample)
Figure 6:
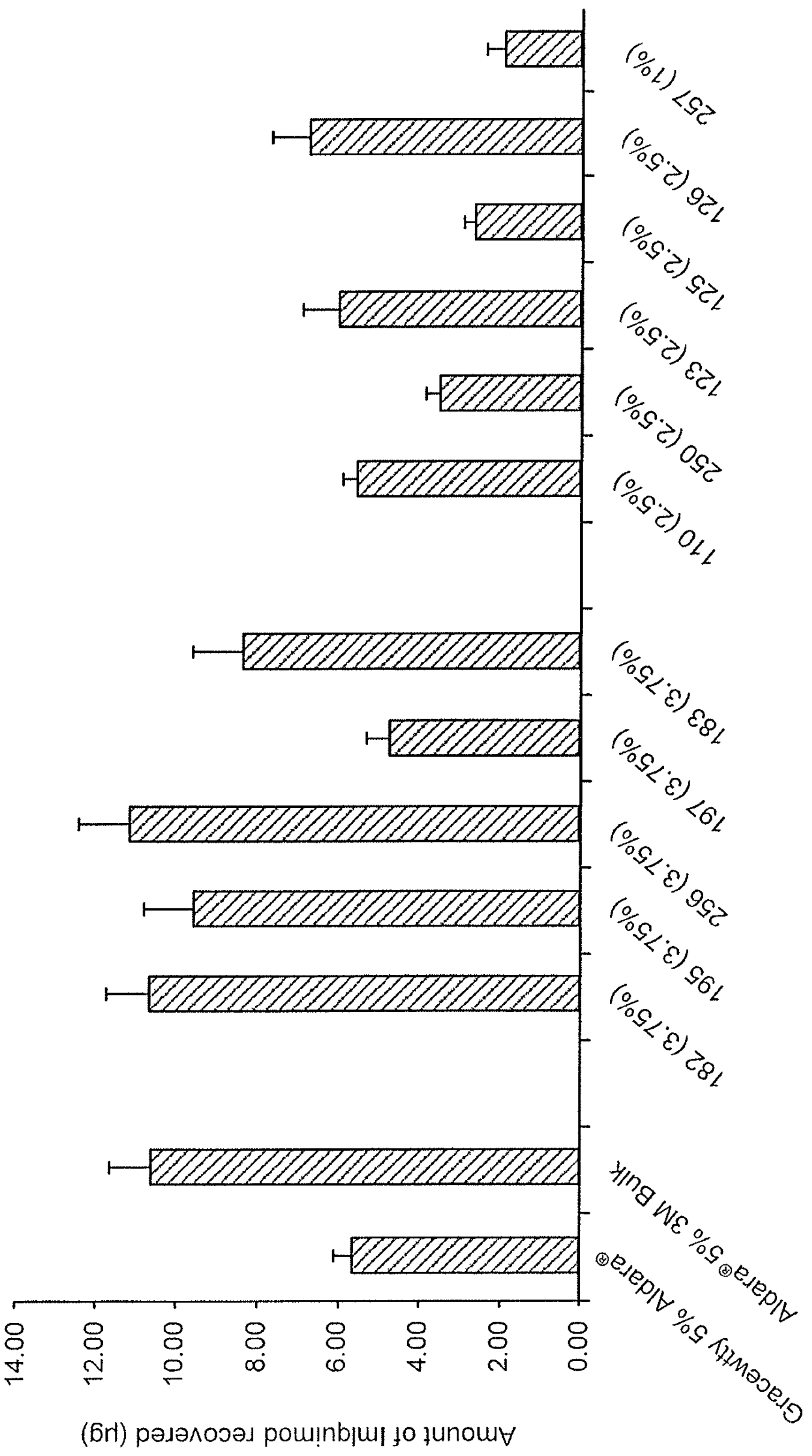
FIG. 6 shows a total amount of imiquimod recovered for each formulation in the receiver fluid, epidermis and dermis combined (mean±sd, refer to Table 34 for n numbers of each sample)

The data that is shown in Table 34 is the actual amount of imiquimod that is recovered for each formulation from the various matrices, which is also represented graphically in FIG. 5. FIG. 6 represents the total amount of imiquimod that is recovered for each formulation in the epidermis, dermis and receiver fluid combined.

TABLE 34

Amount of Imiquimod that is Recovered following Mass Balance Investigation

| | | | Amount of imiquimod recovered ± SEM (ug) | | | | | | | | | | | |
|---|---|---|---|---|---|---|---|---|---|---|---|---|---|---|
| Formulations | Percentage imiquimod | Replicates (n) | Receiver Fluid | | Unabsorbed Dose | | Stratum Corneum | | Epidermis | | Dennis | | Percentage total recovered | |
| Graceway Aldara ® 5% Imiquimod Cream | 5% | 6 | 0.03 | ±0.01 | 127.06 | ±9.58 | 80.78 | ±11.67 | 2.90 | ±0.72 | 2.76 | ±0.70 | 85.24 | ±5.15 |
| 3M Aldara ® % Imiquimod Cream | 5% | 4 | 0.05 | 0.03 | 132.75 | ±17.62 | 74.37 | ±10.59 | 6.60 | ±1.91 | 3.96 | ±0.41 | 86.92 | ±4.16 |

TABLE 34-continued

Amount of Imiquimod that is Recovered following Mass Balance Investigation

| Formulations | Percentage imiquimod | Replicates (n) | Amount of imiquimod recovered ± SEM (ug) Receiver Fluid | | Unabsorbed Dose | | Stratum Corneum | | Epidermis | | Dennis | | Percentage total recovered | |
|---|---|---|---|---|---|---|---|---|---|---|---|---|---|---|
| 182 3.75% | 3.75% | 6 | 0.08 | ±0.06 | 85.75 | ±3.93 | 46.85 | ±5.51 | 3.65 | ±0.85 | 6.94 | 2.22 | 76.25 | 1.82 |
| 195 3.75% | 3.75% | 4 | 0.08 | ±0.07 | 74.19 | ±6.90 | 57.41 | ±11.46 | 7.06 | 2.29 | 2.47 | ±0.87 | 75.16 | 5.12 |
| 256 3.75% | 3.75% | 5 | 0.16 | ±0.06 | 71.73 | ±7.22 | 33.41 | ±4.77 | 1.99 | ±0.71 | 9.03 | ±2.37 | 61.91 | 3.95 |
| 197 3.75% | 3.75% | 5 | 0.06 | ±0.03 | 110.54 | 6.22 | 41.61 | ±6.54 | 2.21 | ±0.36 | 2.53 | ±0.91 | 83.54 | 3.92 |
| 183 3.75% | 3.75% | 4 | 0.02 | ±0.01 | 113.84 | ±11.63 | 40.99 | ±6.99 | 3.26 | ±0.53 | 5.11 | ±2.32 | 86.66 | 6.68 |
| 110 2.5% | 2.5% | 6 | 0.00 | ±0.00 | 52.92 | 3.96 | 33.96 | ±3.43 | 3.25 | ±0.70 | 2.32 | ±0.44 | 73.82 | 4.64 |
| 250 2.5% | 2.5% | 5 | 0.00 | ±0.00 | 82.46 | ±2.94 | 28.30 | ±3.67 | 2.35 | ±0.68 | 1.17 | ±0.30 | 91.25 | 3.93 |
| 123 2.5% | 2.5% | 5 | 0.01 | ±0.01 | 68.33 | ±3.18 | 35.93 | ±10.40 | 4.20 | ±1.69 | 1.80 | ±0.32 | 88.04 | 7.95 |
| 125 2.5% | 2.5% | 6 | 0.02 | ±0.01 | 72.82 | ±3.92 | 28.88 | ±4.41 | 1.12 | ±0.42 | 1.52 | ±0.42 | 83.32 | 2.44 |
| 126 2.5% | 2.5% | 5 | 0.01 | ±0.00 | 64.00 | ±5.27 | 29.59 | ±4.97 | 2.36 | ±0.40 | 4.44 | ±1.62 | 80.15 | 6.61 |
| 257 1% | 1% | 4 | 0.01 | ±0.00 | 28.88 | ±4.60 | 12.49 | ±3.75 | 0.42 | ±0.14 | 1.54 | ±1.05 | 86.98 | 3.40 |

The only data rejected from that presented in Table 34, FIG. 5 and FIG. 6 are obvious outliers that are observed on the basis of cell failure.

Figure 7:
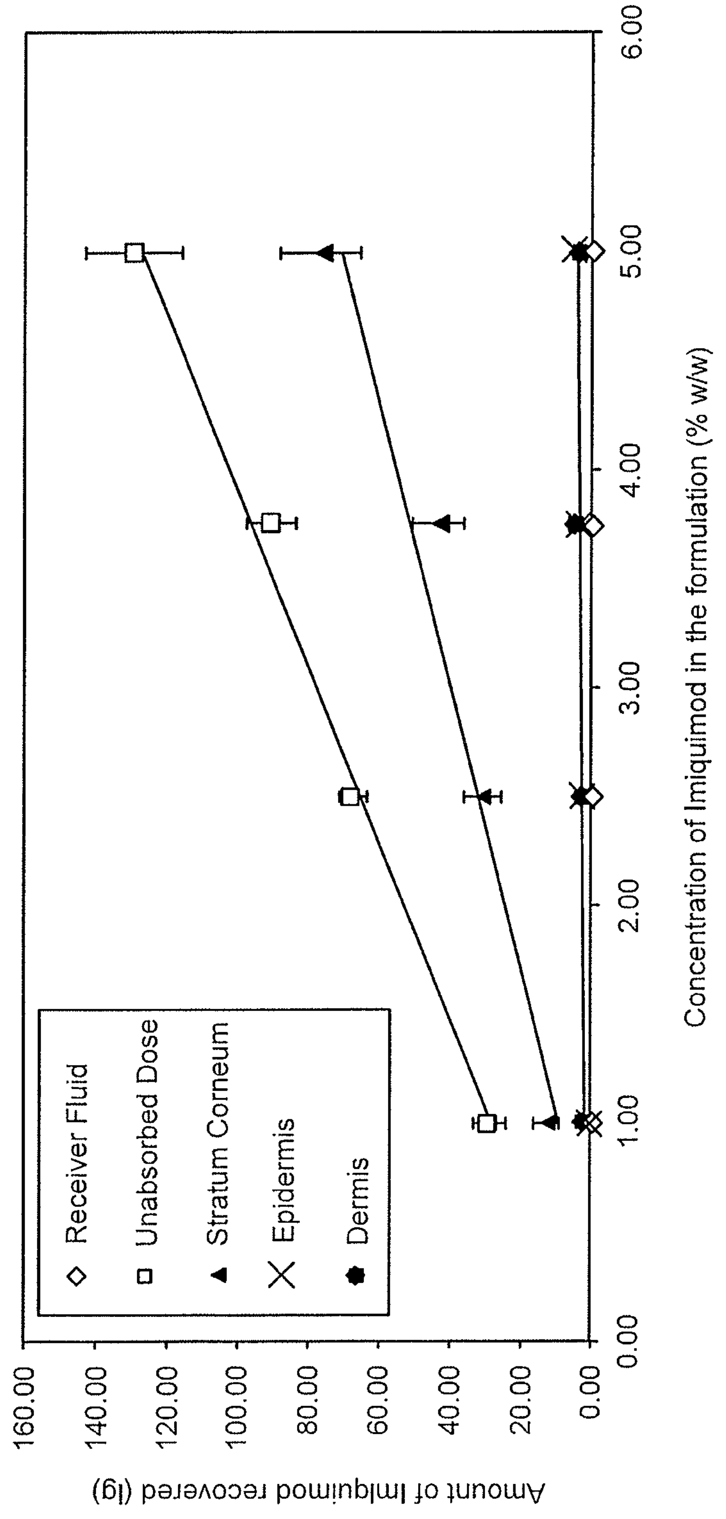
FIG. 7 shows a total amount of imiquimod recovered for the averages of each imiquimod concentration from each of the skin matrices.
Figure 8A:
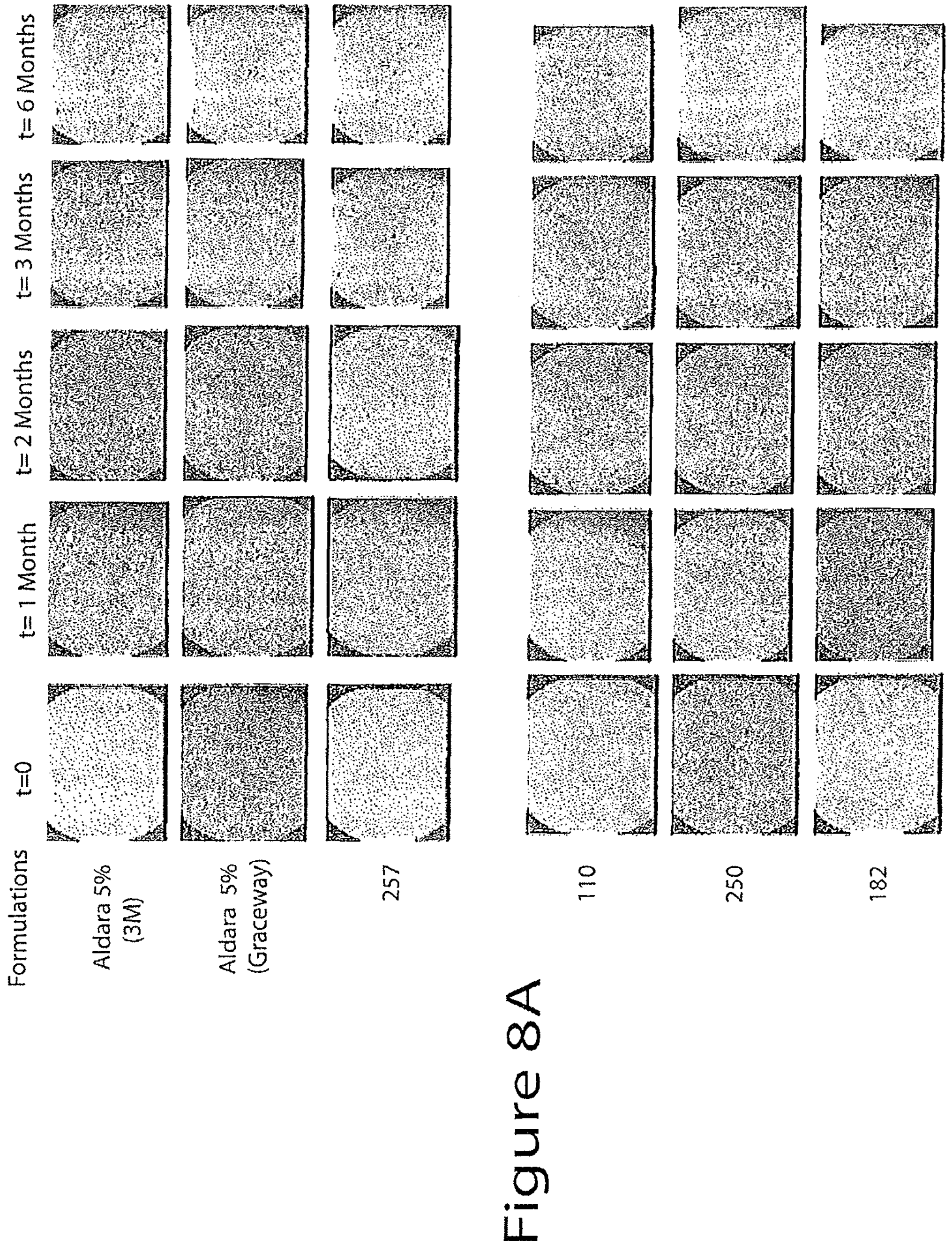
FIGS. 8A-C show microscopic depiction of 13 imiquimod formulations, i.e., 3M Aldara® imiquimod cream 1 kg batch, Graceway 3M Aldara® imiquimod cream 1 kg batch and formulations 110, 123, 125, 126, 182, 183, 195, 197, 250, 256 and 257 (t=0, I., 2, 3 and 6 months)−×400 magnification.
Figure 8B:
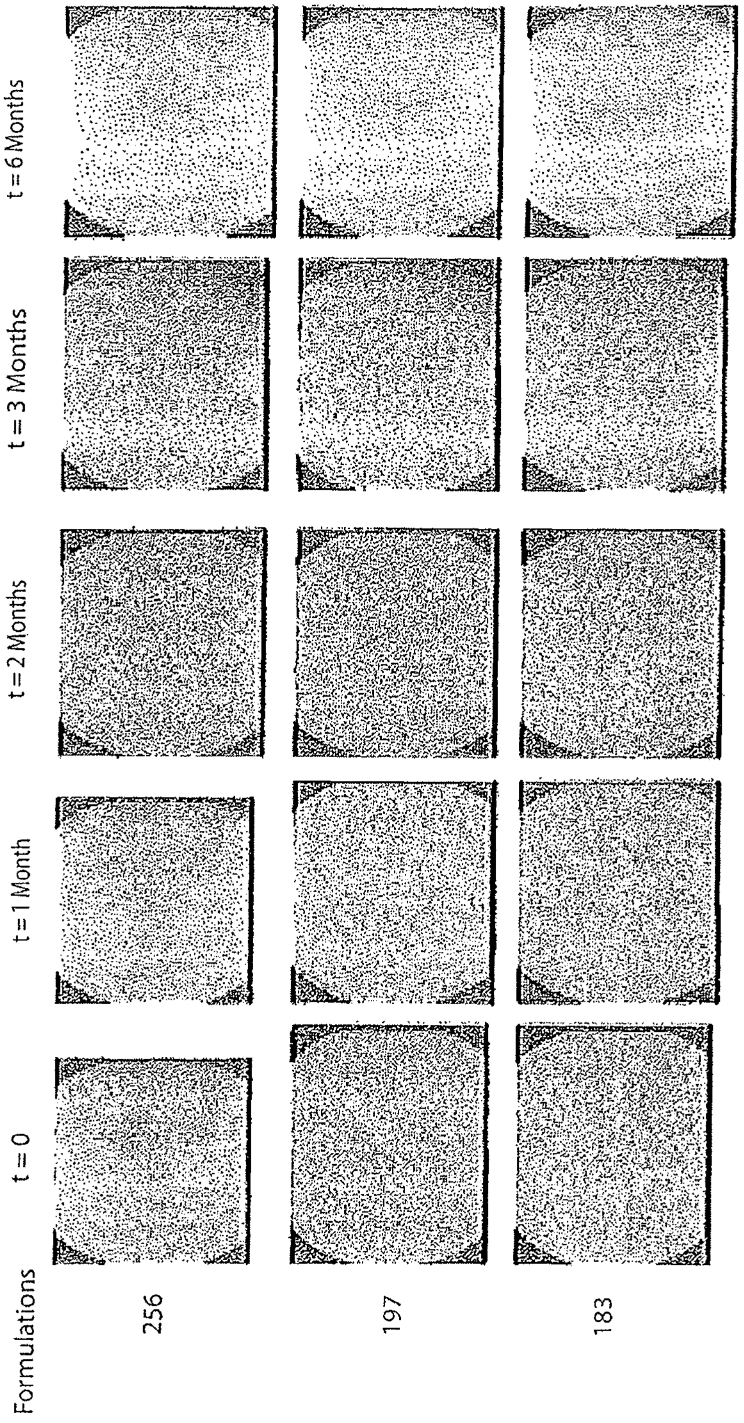
Figure 8C:
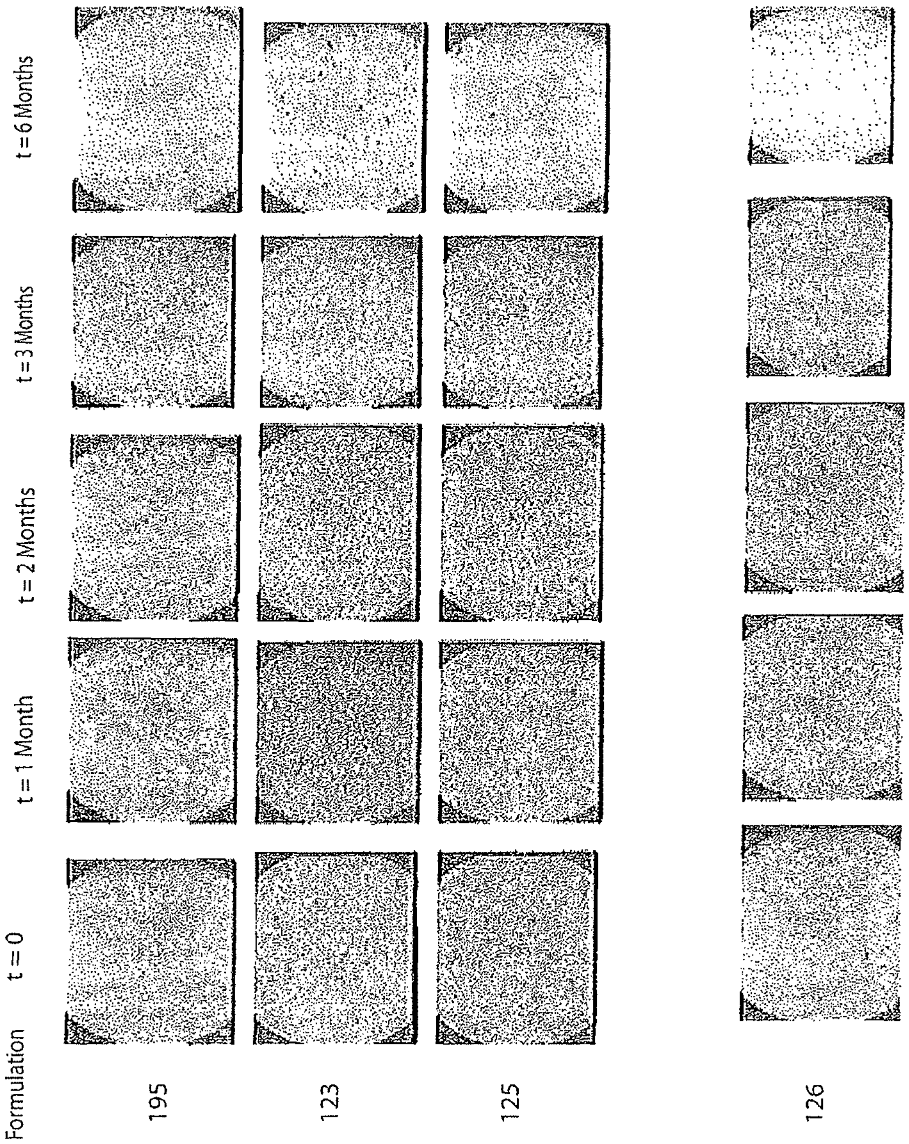
Figure 9:
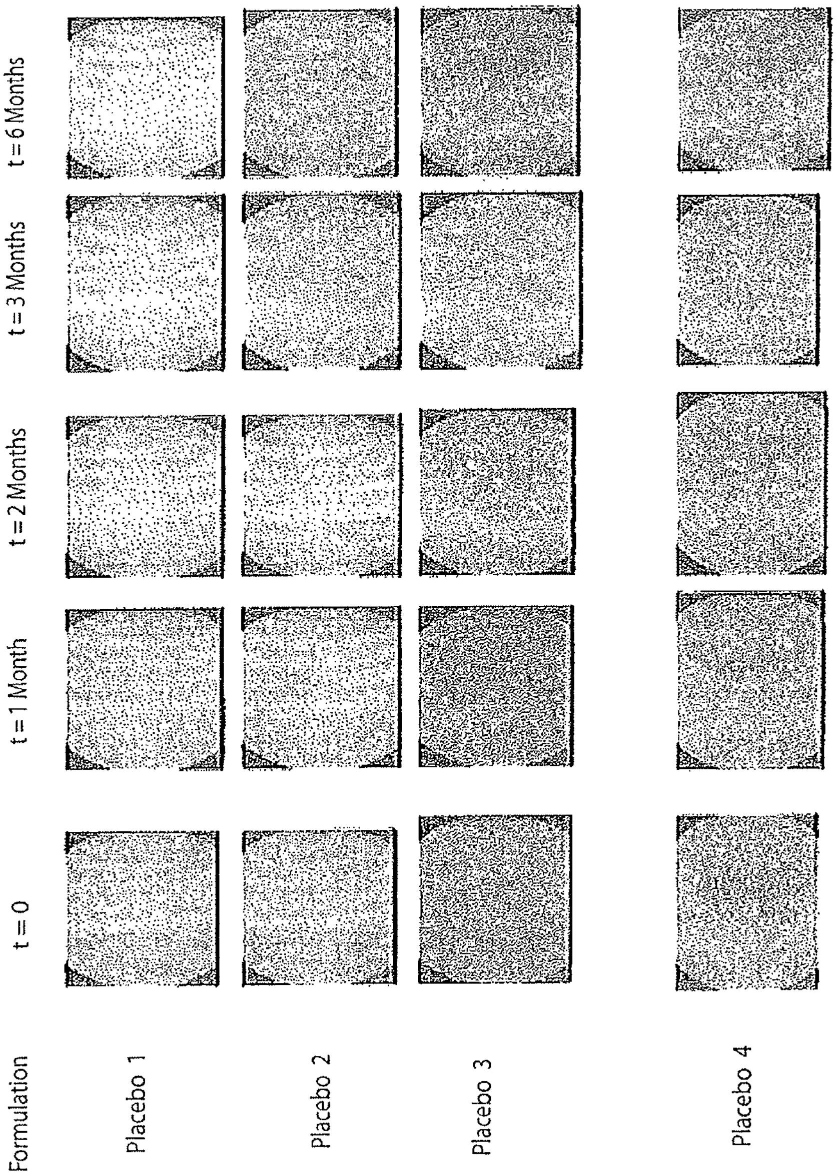
FIG. 9 shows microscopic depiction of placebo formulations Pbo1-Pbo4 (t=0, 1, 2, 3 and 6 months)−×400 magnification.

The average data for the 5%, 1%, 3.75% and 2.5% w/w formulations showing the amount of imiquimod that is recovered from the unabsorbed fraction, in the Stratum corneum and in the epidermis, dermis and receiver fluid combined are shown in FIG. 7. This data shows that there is a linear dose release between the amount of imiquimod applied and recovery in each of the matrices. See also Table 35 for stability of calibration standards in spent receiver fluid and Tables 36-40—for statistical analysis.

TABLE 35

Stability of Calibration Standards in Spent Receiver Fluid (Stored In HPLC Crimp Top Vials at Each Temperature (Where Recovery was Compared To T = 0)

| Standard (ug/ml) | Spent receiver fluid: | 48 h % recovered in Spent receiver fluid Fridge | RT | 37° C. |
|---|---|---|---|---|
| 105.5 | Full thickness + placebo | 88.242 | 88.546 | 91.704 |
| 84.4 | | 84.561 | 84.421 | 85.629 |
| 52.75 | | 91.776 | 92.027 | 93.779 |
| 42.2 | | 83.976 | 84.144 | 86.439 |
| 21.1 | | 84.584 | 85.162 | 88.000 |
| 10.55 | | 88.307 | 86.897 | 90.798 |
| 5.275 | | 90.260 | 87.973 | 86.134 |
| 105.5 | Full thickness | 90.545 | 92.275 | 92.278 |
| 84.4 | | 98.841 | 99.790 | 101.010 |
| 52.75 | | 92.317 | 92.152 | 95.282 |

TABLE 35-continued

Stability of Calibration Standards in Spent Receiver Fluid (Stored In HPLC Crimp Top Vials at Each Temperature (Where Recovery was Compared To T = 0)

| Standard (ug/ml) | Spent receiver fluid: | 48 h % recovered in Spent receiver fluid Fridge | RT | 37° C. |
|---|---|---|---|---|
| 42.2 | | 95.103 | 95.805 | 95.939 |
| 21.1 | | 91.876 | 91.968 | 93.847 |
| 10.55 | | 94.989 | 93.522 | 97.826 |
| 5.275 | | 94.586 | 95.232 | 90.611 |
| 105.5 | Epidermal sheet + placebo | 83.833 | 84.515 | 84.903 |
| 84.4 | | 95.620 | 96.033 | 98.178 |
| 52.75 | | 85.635 | 88.169 | 86.906 |
| 42.2 | | 93.077 | 92.904 | 95.095 |
| 21.1 | | 101.831 | 105.389 | 105.213 |
| 10.55 | | 84.046 | 85.095 | 89.945 |
| 5.275 | | 88.881 | 86.540 | 86.828 |
| 105.5 | Epidermal sheet | 90.465 | 92.089 | 91.501 |
| 84.4 | | 81.350 | 82.276 | 82.694 |
| 52.75 | | 87.669 | 89.096 | 90.943 |
| 42.2 | | 85.716 | 86.340 | 89.641 |
| 21.1 | | 95.828 | 97.098 | 97.470 |
| 10.55 | | 93.180 | 94.971 | 97.099 |
| 5.275 | | 88.938 | 91.447 | 85.995 |

Tables 36-40, Statistical Analysis for Amount of Imiquimod that is Recovered Following Mass Balance Test ANOVA statistical analysis (95% confidence level): Amount of imiquimod that is recovered following mass balance test from receiver fluid (from results that are presented in FIG. 5) is shown in Table 36:

TABLE 36

| Source | DF | SS | MS | F | P |
|---|---|---|---|---|---|
| Cl | 14 | 0.12075 | 0.01006 | 1.84 | 0.066 |
| Error | 52 | 0.28455 | 0.00547 | | |
| Total | 64 | 0.40530 | | | |

S = 0.07397 R-Sq = 29.79% R-Sq (adj) = 13.59%

| Level | N | Mean | St. Dev | Individual 95% CIs For Mean Based on Pooled StDev ----------+----------+----------+----------+ |
|---|---|---|---|---|
| 3M Aldara ® 5% Imiquimod Cream | 4 | 0.05250 | 0.05909 | (----------*----------) |
| 110 2.5% | 6 | 0.00000 | 0.00000 | (----------*----------) |
| 250 2.5% | 5 | 0.00400 | 0.00894 | (----------*----------) |

TABLE 36-continued

| | | | | |
|---|---|---|---|---|
| 182 3.75% | 6 | 0.07833 | 0.14400 | (----------*----------) |
| 195 3.75% | 4 | 0.08250 | 0.14500 | (----------*----------) |
| 123 2.5% | 5 | 0.01200 | 0.01095 | (----------*----------) |
| 125 2.5% | 6 | 0.02333 | 0.02503 | (----------*----------) |
| 256 3.75% | 5 | 0.15600 | 0.14064 | (----------*----------) |
| 197 3.75% | 5 | 0.05800 | 0.06611 | (----------*----------) |
| 183 3.75% | 4 | 0.01750 | 0.01708 | (----------*----------) |
| 126 | 5 | 0.00600 | 0.00894 | (----------*----------) |
| Graceway Aldara ® 5% Imiquimod Cream | 6 | 0.02833 | 0.03312 | (----------*----------) |
| 257 (1%) | 4 | 0.00500 | 0.00577 | (----------*----------) |
| | | | | ----------+----------+----------+----------+ |
| | | | | 0.000 0.080 0.160 0.240 |

Pooled StDev = 0.07397

ANOVA statistical analysis (95% confidence level): Amount of imiquimod that is recovered following mass balance test from unabsorbed dose (from results that are presented in FIG. 5) is shown in Table 37:

TABLE 37

| Source | DF | SS | MS | F | P |
|---|---|---|---|---|---|
| Cl | 12 | 50777 | 4231 | 16.85 | 0.000 |
| Error | 52 | 13071 | 251 | | |
| Total | 64 | 63848 | | | |

S = 15.85 R-Sq = 79.53% R-Sq (adj) = 74.80%

| Level | N | Mean | St. Dev | Individual 95% CIs For Mean Based on Pooled StDev ------------+------------+------------+------------+---- |
|---|---|---|---|---|
| 3M Aldara ® 5% Imiquimod Cream | 4 | 132.75 | 35.25 | (---*---) |
| 110 2.5% | 6 | 52.93 | 9.69 | (---*---) |
| 250 2.5% | 5 | 82.46 | 6.57 | (---*---) |
| 182 3.75% | 6 | 85.75 | 9.63 | (---*---) |
| 195 3.75% | 4 | 74.19 | 13.80 | (---*---) |
| 123 2.5% | 5 | 68.33 | 7.10 | (---*---) |
| 125 2.5% | 6 | 72.82 | 9.61 | (---*---) |
| 256 3.75% | 5 | 71.73 | 16.15 | (---*---) |
| 197 3.75% | 5 | 110.54 | 13.91 | (---*---) |
| 183 3.75% | 4 | 113.85 | 23.27 | (---*---) |
| 126 | 5 | 63.98 | 11.78 | (---*---) |
| Graceway Aldara ® 5% Imiquimod Cream | 6 | 127.06 | 23.46 | (---*---) |
| 257 (1%) | 4 | 28.88 | 9.20 | (---*---) |
| | | | | ------------+------------+------------+------------+--- |
| | | | | 35 70 105 140 |

Pooled StDev = 15.85

ANOVA statistical analysis (95% confidence level): Amount of imiquimod that is recovered following mass balance test from Stratum corneum (from results that are presented in FIG. 5) is shown in Table 38:

TABLE 38

| Source | DF | SS | MS | F | P |
|---|---|---|---|---|---|
| Cl | 12 | 21479 | 1790 | 6.72 | 0.000 |
| Error | 52 | 13848 | 266 | | |
| Total | 64 | 35327 | | | |

S = 16.32 R-Sq = 60.80% R-Sq (adj) = 51.75%

Individual 95% CIs For Mean Based on Pooled StDev

TABLE 38-continued

| Level | N | Mean | St. Dev | --+--------------+---------------+---------------+---------- |
|---|---|---|---|---|
| 3M Aldara ® 5% Imiquimod Cream | 4 | 74.38 | 21.17 | (-----*-----) |
| 110 2.5% | 6 | 33.96 | 8.41 | (----*----) |
| 250 2.5% | 5 | 28.30 | 8.21 | (------*-----) |
| 182 3.75% | 6 | 46.85 | 13.50 | (------*-----) |
| 195 3.75% | 4 | 57.41 | 22.92 | (------*-----) |
| 123 2.5% | 5 | 35.93 | 23.25 | (------*-----) |
| 125 2.5% | 6 | 28.88 | 10.80 | (------*-----) |
| 256 3.75% | 5 | 33.41 | 10.67 | (------*-----) |
| 197 3.75% | 5 | 41.61 | 14.62 | (------*-----) |
| 183 3.75% | 4 | 41.00 | 13.97 | (------*-----) |
| 126 | 5 | 29.59 | 11.11 | (------*-----) |
| Graceway Aldara ® 5% Imiquimod Cream | 6 | 80.78 | 28.60 | |
| 257 (1%) | 4 | 12.49 | 7.49 | (------*-----) |
| | | | | --+--------------+---------------+---------------+---------- |
| | | | | 0 25 50 75 |

Pooled StDev = 16.32

ANOVA statistical analysis (95% confidence level): Amount of imiquimod that is recovered following mass balance test from epidermis (from results that are presented in FIG. 5) is shown in Table 39:

TABLE 39

| Source | DF | SS | MS | F | P |
|---|---|---|---|---|---|
| Cl | 12 | 187.78 | 15.65 | 3.26 | 0.002 |
| Error | 52 | 249.79 | 4.80 | | |
| Total | 64 | 437.57 | | | |

S = 2.192 R-Sq = 42.91% R-Sq (adj) = 29.74%

| Level | N | Mean | St. Dev | Individual 95% CIs For Mean Based on Pooled StDev<br>--------+----------+-----------+-----------+--- |
|---|---|---|---|---|
| 3M Aldara ® 5% Imiquimod Cream | 4 | 6.600 | 3.823 | (------*-----) |
| 110 2.5% | 6 | 3.248 | 1.717 | (------*------) |
| 250 2.5% | 5 | 2.350 | 1.514 | (------*------) |
| 182 3.75% | 6 | 3.643 | 2.083 | (------*------) |
| 195 3.75% | 4 | 7.055 | 4.580 | (------*------) |
| 123 2.5% | 5 | 4.196 | 3.782 | (------*-----) |
| 125 2.5% | 6 | 1.123 | 1.039 | (------*-----) |
| 256 3.75% | 5 | 1.990 | 1.588 | (------*-----) |
| 197 3.75% | 5 | 2.208 | 0.797 | (------*-----) |
| 183 3.75% | 4 | 3.260 | 1.053 | (------*-----) |
| 126 | 5 | 2.360 | 0.903 | (------*-----) |
| Graceway Aldara ® 5% Imiquimod Cream | 6 | 2.895 | 1.752 | (------*------) |
| 257 (1%) | 4 | 0.415 | 0.273 | (------*-----) |
| | | | | --------+----------+-----------+-----------+--- |
| | | | | 0.0 3.0 6.0 9.0 |

Pooled StDev = 2.192

ANOVA statistical analysis (95% confidence level): Amount of imiquimod that is recovered following mass balance test from dermis (from results that are presented in FIG. 5) is shown in Table 40:

TABLE 40

| Source | DF | SS | MS | F | P |
|---|---|---|---|---|---|
| Cl | 12 | 340.72 | 28.39 | 3.29 | 0.001 |
| Error | 52 | 448.34 | 8.62 | | |
| Total | 64 | 789.06 | | | |

S = 2.936 R-Sq = 43.18% R-Sq (adj) = 30.07%

| Level | N | Mean | St. Dev | Individual 95% CIs For Mean Based on Pooled StDev --------+-----------+--------------+--------------+--- |
|---|---|---|---|---|
| 3M Aldara ® 5% Imiquimod Cream | 4 | 3.960 | 0.825 | (--------*-------) |
| 110 2.5% | 6 | 3.323 | 1.068 | (------*------) |
| 250 2.5% | 5 | 1.164 | 0.663 | (--------*-------) |
| 182 3.75% | 6 | 6.937 | 5.445 | (------*------) |
| 195 3.75% | 4 | 2.473 | 1.733 | (--------*-------) |
| 123 2.5% | 5 | 1.796 | 0.715 | (--------*-------) |
| 125 2.5% | 6 | 1.518 | 1.020 | (--------*-------) |
| 256 3.75% | 5 | 9.030 | 5.305 | (------*------) |
| 197 3.75% | 5 | 2.532 | 2.036 | (--------*-------) |
| 183 3.75% | 4 | 5.110 | 4.638 | (--------*-------) |
| 126 | 5 | 4.436 | 3.626 | (-------*------) |
| Graceway Aldara ® 5% Imiquimod Cream | 6 | 2.758 | 1.721 | (------*------) |
| 257 (1%) | 4 | 1.533 | 2.099 | (--------*------) |
| | | | | --------+-----------+--------------+--------------+--- 0.0 3.5 7.0 10.5 |

Pooled StDev = 2.936

The results that are presented in FIG. 6, indicate that the delivery of the imiquimod into the receiver fluid, epidermis and dermis combined from formulations 182, 195 and 256 are similar to the Aldara® 5% imiquimod cream formulation when comparing averages. With respect to the statistical analysis, there is no statistical difference (p>0.05) between 110 (2.5%), 126 (2.5%), 123 (2.5%), 182, (3.75%), 195 (3.75%), 256 (3.75%), 197 (3.75%) and 183 (3.75%) when compared to Aldara® 5% imiquimod cream formulation in the amount of imiquimod that is recovered from the receiver fluid, epidermis and dermis combined.

In Table 41, ANOVA statistical analysis (95% confidence level) are presented: Total amount of imiquimod that is recovered for each formulation in the receiver fluid, epidermis and dermis combined (from the results that are presented in FIG. 6:

TABLE 41

| Source | DF | SS | MS | F | P |
|---|---|---|---|---|---|
| Cl | 12 | 340.72 | 28.39 | 3.29 | 0.001 |
| Error | 52 | 448.34 | 8.62 | | |
| Total | 64 | 789.06 | | | |

S = 3.819 R-Sq = 43.05% R-Sq (adj) = 29.91%

| Level | N | Mean | St. Dev | Individual 95% CIs For Mean Based on Pooled StDev ----+---------+---------+---------+---- |
|---|---|---|---|---|
| 257 (1%) | 4 | 1.958 | 2.357 | (------*------) |
| 110 2.5% | 6 | 5.572 | 2.706 | (------*------) |
| 250 2.5% | 5 | 3.524 | 1.445 | (------*--------) |
| 123 2.5% | 5 | 6.010 | 4.296 | (------*------) |
| 125 2.5% | 6 | 2.663 | 0.837 | (---------*-------) |
| 126 2.5% | 5 | 6.804 | 3.538 | (---------*-------) |
| 182 3.75% | 6 | 10.662 | 6.441 | (------*------) |
| 195 3.75% | 4 | 9.608 | 5.392 | (--------*------) |
| 256 3.75% | 5 | 11.180 | 5.770 | (------*------) |
| 197 3.75% | 5 | 4.800 | 1.749 | (------*------) |
| 183 3.75% | 4 | 8.388 | 3.666 | (--------*--------) |
| | | | | Individual 95% CIs For Mean Based on Pooled StDev |
| Level | N | Mean | St. Dev | ----+---------+---------+---------+---- |
| Graceway Aldara ® 5% Imiquimod Cream | 6 | 5.682 | 2.671 | (--------*--------) |

TABLE 41-continued

| | | | | |
|---|---|---|---|---|
| 257 (1%) | 4 | 10.613 | 4.211 | (---------*---------) |
| | | | | ----+----------+---------+---------+----- |
| | | | | 0.0 5.0 10.0 15.0 |

Pooled StDev = 3.819

The results that are presented in FIG. 7 and statistical analysis in Tables 42-46 indicate that there is a distinct dose proportionate trend between the amount of imiquimod that is recovered from each of the matrices with respect to the concentration of imiquimod in the formulation for both unabsorbed and Stratum corneum. The trend in this data, is also observed for the epidermis (with respect to average values in the statistical analysis).

In Tables 42-46, statistical analysis for the total amount of imiquimod recovered from each of the matrices (1%, 2.5%, 3.75% and 5% w/w formulations)

ANOVA statistical analysis (95% confidence level): Total amount of imiquimod that is recovered for imiquimod concentration combined from each of the matrices from unabsorbed dose (from results presented in FIG. 7) in Table 42:

TABLE 42

| Source | DF | SS | MS | F | P |
|---|---|---|---|---|---|
| Cl | 3 | 44198 | 14733 | 35.53 | 0.000 |
| Error | 61 | 25293 | 415 | | |
| Total | 64 | 69491 | | | |
| S = 20.36 R-Sq = 63.60% R-Sq (adj) = 61.81% | | | | | |

| Level | N | Mean | St. Dev | Individual 95% CIs For Mean Based on Pooled StDev<br>---------------+------------+------------+----------- +- |
|---|---|---|---|---|
| 1% | 4 | 28.88 | 9.20 | (-------*-------) |
| 2.5% | 27 | 64.08 | 16.24 | (-*--) |
| 3.75% | 24 | 90.75 | 22.48 | (-*-) |
| 5% | 10 | 129.33 | 26.99 | (---*---) |
| | | | | ---------------+------------+------------+----------+-<br>35 70 105 140 |

Pooled StDev = 20.36

ANOVA statistical analysis (95% confidence level): Total amount of imiquimod that is recovered, for imiquimod concentration combined from each of the matrices from Strateum corneum (from results presented in FIG. 7) in Table 43:

TABLE 43

| Source | DF | SS | MS | F | P |
|---|---|---|---|---|---|
| Cl | 3 | 19744 | 6581 | 25.76 | 0.000 |
| Error | 61 | 15583 | 255 | | |
| Total | 64 | 35327 | | | |
| S = 15.98 | | R-Sq = 55.89% | | R-Sq (adj) = 53.72% | |

| Level | N | Mean | St. Dev | Individual 95% CIs For Mean Based on Pooled StDev<br>--+----------------+------------+--------------+------- |
|---|---|---|---|---|
| 1% | 4 | 12.49 | 7.49 | (------*------) |
| 2.5% | 27 | 31.34 | 12.57 | (--*-) |
| 3.75% | 24 | 43.74 | 15.85 | (-*--) |
| 5% | 10 | 78.79 | 24.79 | (---*---) |
| | | | | --+---------------+-------------+------------+-----------<br>0 25 50 75 |

Pooled StDev = 15.98

ANOVA statistical analysis (95% confidence level): Total amount of imiquimod that is recovered for imiquimod concentration combined from each of the matrices from epidermis (from results presented in FIG. 7) in Table 44:

TABLE 44

| Source | DF | SS | MS | F | P |
|---|---|---|---|---|---|
| Cl | 3 | 55.25 | 18.42 | 2.97 | 0.040 |
| Error | 61 | 382.32 | 6.27 | | |
| Total | 64 | 437.57 | | | |

| | | |
|---|---|---|
| S = 2.504 | R-Sq = 12.63% | R-Sq (adj) = 8.33% |

| Level | N | Mean | St. Dev | Individual 95% CIs For Mean Based on Pooled StDev ------------+-----------+----------+---------+- |
|---|---|---|---|---|
| 1% | 4 | 0.415 | 0.273 | (-------------*------------) |
| 2.5% | 27 | 2.621 | 2.137 | (--*---) |
| 3.75% | 24 | 3.505 | 2.729 | (---*---) |
| 5% | 10 | 4.37 | 3.200 | (-----*-----) |
| | | | | ------------+-----------+----------+---------+- |
| | | | | 0.0 2.5 5.0 7.5 |

Pooled StDev = 2.504

ANOVA statistical analysis (95% confidence level): Total amount of imiquimod that is recovered for imiquimod concentration combined from each of the matrices from dermis (from results presented in FIG. 7) in Table 45:

TABLE 45

| Source | DF | SS | MS | F | P |
|---|---|---|---|---|---|
| Cl | 3 | 147.4 | 49.1 | 4.67 | 0.005 |
| Error | 61 | 641.7 | 10.5 | | |
| Total | 64 | 789.1 | | | |

| | | |
|---|---|---|
| S = 3.243 | R-Sq = 18.68% | R-Sq (adj) = 14.68% |

| Level | N | Mean | St. Dev | Individual 95% CIs For Mean Based on Pooled StDev ---------+------------+------------+------------+-- |
|---|---|---|---|---|
| 1% | 4 | 1.533 | 2.099 | (----------------*-------------------) |
| 2.5% | 27 | 2.223 | 1.974 | (----*----) |
| 3.75% | 24 | 5.407 | 4.694 | (-----*----) |
| 5% | 10 | 3.239 | 1.502 | (-------*-------) |
| | | | | ---------+------------+-----------+------------+-- |
| | | | | 0.0 2.5 5.0 7.5 |

Pooled StDev = 3.243

ANOVA statistical analysis (95% confidence level): Total amount of imiquimod that is recovered for imiquimod concentration combined from each of the matrices from receiver fluid (from results presented in FIG. 7) in Table 46:

TABLE 46

| Source | DF | SS | MS | F | P |
|---|---|---|---|---|---|
| Cl | 3 | 0.07047 | 0.02349 | 4.28 | 0.008 |
| Error | 61 | 6.33483 | 0.00549 | | |
| Total | 64 | 0.40530 | | | |

TABLE 46-continued

| S = 0.07409 | R-Sq = 17.39% | R-Sq (adj) = 13.32% |
|---|---|---|

| Level | N | Mean | St. Dev | Individual 95% CIs For Mean Based on Pooled StDev<br>----+---------+---------+---------+----- |
|---|---|---|---|---|
| 1% | 4 | 0.00577 | 0.00577 | (-----------------*------------------) |
| 2.5% | 27 | 0.00926 | 0.01542 | (-----*-----) |
| 3.75% | 24 | 0.08083 | 0.11632 | (-----*-----) |
| 5% | 10 | 0.03800 | 0.04392 | (---------*---------) |
| | | | | -----+------------+------------+-----------+---- |
| | | | | −0.050 0.000 0.050 0.100 |

Pooled StDev = 0.07409

The following Tables 47-59 summarize results for formulations 126, 182 and Pbo4.

TABLE 47

Stability of Imiquimod in the Formulations. Percentage of imiquimod that is recovered from each formulation compared to theoretical when stored at 25° C. and 40° C. over a 6 month period.

| | | t = 1 month | 2 months | | t = 3 months | | | t = 6 months | |
|---|---|---|---|---|---|---|---|---|---|
| Formulations | t = 0 h | 25° C. | 40° C. | 25° C. | 40° C. | 25° C. | 40° C. | 25° C. | 40° C. |
| 182 | 96.76 ± 025 | 102.01 ± 0.01 | 98.46 ± 0.15 | 99.00 ± 0.12 | 98.07 ± 0.10 | 101.48 ± 0.27 | 104.39 ± 1.55 | 102.91 ± 1.16 | 99.12 ± 0.45 |
| PBO4 | 0 | 0 | 0 | 0 | 0 | 0 | 0 | 0 | 0 |
| 126 | 102.37 ± 0.58 | 102.84 ± 0.45 | 204.11 ± 0.04 | 100.02 ± 0.95 | 101.32 ± 040 | 99.28 ± 3.25 | 98.43 ± 0.55 | 101.95 ± 037 | 103.02 ± 1.89 |

TABLE 48

Stability of Imiquimod in the Formulations. Identification of Imiquimod when the formulations are stored at 25° C. and 40° C. over a 6 month period (confirmed by HPLC).

| | | T = 1 month | | T = 2 months | | T = 3 months | | T = 6 months | |
|---|---|---|---|---|---|---|---|---|---|
| Formulations | T = 0 | 25° C. | 40° C. | 25° C. | 25° C. | 40° C. | 40° C. | 25° C. | 40° C. |
| 182 | Complies | Complies | Complies | Complies | Compile | Complies | Complie | Comp les | Complie |
| 126 | Complies | Complies | Complies | Complies | Compile | Complies | Complie | Complies | Complie |
| GWO3OP | Complies | Complies | Complies | Complies | Complie | Complies | Complie | Complies | Complie |

TABLE 49

Stability of Benzyl Alcohol in the Formulations. Amount of benzyl alcohol that is recovered from each of the formulations when the formulations are stored at 25° C. and 40° C. over a 6 month period.

| | | t = 1 month | | 2 months | | t = 3 months | | t = 6 months | |
|---|---|---|---|---|---|---|---|---|---|
| Formulations | t = 0 h | 25° C. | 40° C. | 25° C. | 40° C. | 25° C. | 40° C. | 25° C. | 40° C. |
| 182 | 2.07 ± 0.00 | 2.17 ± 0.00 | 1.95 ± 0.01 | 2.11 ± 0.04 | 1.97 ± 0.00 | 1.94 ± | 1.82 ± 0.04 | 1.85 ± 0.03 | 1.48 ± 0.05 |
| PB04 | 1.93 ± 0.02 | 1.83 ± 0.06 | 1.90 ± 0.03 | 1.91 ± 0.03 | 1.53 ± 0.00 | 1.81 ± | 1.39 ± 0.01 | 1.71 ± 0.01 | 1.08 ± 0.02 |
| 126 | 2.00 ± 0.02 | 2.02 ± 0.01 | 1.89 ± 0.01 | 1.86 ± 0.02 | 1.65 ± 0.02 | 2.00 ± | 1.70 ± 0.04 | 2.01 ± 0.03 | 1.55 ± 0.02 |

TABLE 50

Stability of Benzyl Alcohol in the Formulations. Identification of Benzyl alcohol when the formulations are stored at 25° C. and 40° C. over a 6 month period (confirmed by HPLC.

| | | T = 1 month | | T = 2 months | | T = 3 months | | T = 6 months | |
|---|---|---|---|---|---|---|---|---|---|
| Formulations | T = 0 | 25° C. | 40° C. | 25° C. | 25° C. | 40° C. | 40° C. | 25° C. | 40° C. |
| 182 | Complies | Complies | Complies | Complies | Compile | Complies | Complie | Compiles | Complie |
| 126 | Complies | Complies | Complies | Complies | Complie | Complies | Complie | Compiles | Complie |
| PB04 | Complies | Complies | Complies | Complies | Complie | Complies | Complie | Complies | Complie |

TABLE 51

| Stability of Methylparabens in the Formulations. Amount of Methylparabens that are recovered from each of the formulations when the formulations are stored at 25° C. and 40° C. over a 6 month period. | | | | | | | | | |
|---|---|---|---|---|---|---|---|---|---|
| | | t = 1 month | | t = 2 months | | t = 3 months | | t = 6 months | |
| Formulations | t = 0 h | 25° C. | 40° C. | 25° C. | 40° C. | 25° C. | 40° C. | 25° C. | 40° C. |
| 182 | 0.18 ± 0.001 | 0.18 ± 0.000 | 0.19 ± 0.001 | 020 ± 0.001 | 0.20 ± 0.000 | 0.19 ± 0.000 | 0.20 ± 0.004 | 0.19 ± 0.002 | 0.19 ± 0.001 |
| PB04 | 0.19 ± 0.00 | 0.19 ± 0.003 | 0.18 ± 0.002 | 0.20 ± 0.001 | 0.20 ± 0.000 | 0.20 ± 0.001 | 0.20 ± 0.001 | 0.20 ± 0.001 | 0.20 ± 0.002 |
| 126 | 0.20 ± 0.002 | 0.20 ± 0.001 | 0.19 ± 0.000 | 0.19 ± 0.001 | 0.21 ± 0.00 | 0.21 ± 0.001 | 0.20 ± 0.001 | 0.20 ± 0.001 | 0.20 ± 0.001 |

TABLE 52

| Stability of Methylparabens in the Formulations. Identification of Methylparabens when the formulations are stored at 25° C. and 40° C. over a 6 month period (confirmed by HPLC). | | | | | | | | | |
|---|---|---|---|---|---|---|---|---|---|
| | | T = 1 month | | T = 2 months | | T = 3 months | | T = 6 months | |
| Formulation | T = 0 | 25° C. | 40° C. | 25° C. | 25° C. | 40° C. | 40° C. | 25° C. | 40° C. |
| 182 | Complies | Complies | Complies | Complies | Complies | Complies | Complies | Complies | Complies |
| 126 | Complies | Complies | Complies | Complies | Complies | Complies | Complies | Complies | Complies |
| PB04 | Complies | Complies | Complies | Complies | Complies | Complies | Complies | Complies | Complies |

TABLE 53

| Stability of Propylparabens in the Formulations. Amount of Propylparabens that are recovered from each of the formulations when the formulations are stored at 25° C. and 40° C. over a 6 month period. | | | | | | | | | |
|---|---|---|---|---|---|---|---|---|---|
| | | t = 1 month | | t = 2 months | | t = 3 months | | t = 6 months | |
| Formulations | t = 0 h | 25° C. | 40° C. | 25° C. | 40° C. | 25° C. | 40° C. | 25° C. | 40° C. |
| 182 | 0.019 ± 0.000 | 0.020 ± 0.001 | 0.018 ± 0.000 | 0.018 ± 0.000 | 0.018 ± 0.000 | 0.021 ± 0.002 | 0.022 ± 0.001 | 0.019 ± 0.000 | 0.019 ± 0.0010 |
| PB04 | 0.018 ± 0.001 | 0.018 ± 0.001 | 0.16 ± 0.001 | 0.19 ± 0.000 | 0.020 ± 0.000 | 0.020 ± 0.002 | 0.020 ± 0.002 | 0.018 ± 0.000 | 0.020 ± 0.001 |
| 126 | 0.018 ± 0.000 | 0.019 ± 0.001 | 0.021 ± 0.001 | 0.018 ± 0.000 | 0.019 ± 0.001 | 0.020 ± 0.001 | 0.010 ± 0.001 | 0.020 ± 0.000 | 0.020 ± 0.001 |

TABLE 54

| Stability of Propylparabens in the Formulations. Identification of Propylparabens when the formulations are stored at 25° C. and 40° C. over a 6 month period (confirmed by HPLC). | | | | | | | | | |
|---|---|---|---|---|---|---|---|---|---|
| | | T = 1 month | | T = 2 months | | T = 3 months | | T = 6 months | |
| Formulation | T = 0 | 25° C. | 40° C. | 25° C. | 25° C. | 40° C. | 40° C. | 25° C. | 40° C. |
| 182 | Complies | Complies | Complies | Complies | Complies | Complies | Complies | Complies | Complies |
| 126 | Complies | Complies | Complies | Complies | Complies | Complies | Complies | Complies | Complies |
| PB04 | Complies | Complies | Complies | Complies | Complies | Complies | Complies | Complies | Complies |

TABLE 55

Microscopic Stability of the Formulations. The results of the particle size for each formulation which is determined by optical microscopy at 25° C. over a 6 month period.

| | Particle size (μM) | | | | |
|---|---|---|---|---|---|
| Formulation | t = 0 | t = 1 Month | t = 2 Months | t = 3 Months | t = 6 Months |
| 182 | <10 | <10 | <10 | <10 | <10 |
| PBO4 | <10 | <10 | <10 | <10 | <10 |
| 126 | <10 | <10 | <10 | <10 | <10 |

TABLE 56 pH stability of the Formulations. The results of the pH test for each of the formulations when the formulations are stored at 25° C. and 40° C. over a 6 month period. Grey area indicate no test was performed.

| | pH | | | | | | | | |
|---|---|---|---|---|---|---|---|---|---|
| | t=0 | t = 1 month | | t = 2 months | | t = 3 months | | t = 6 months | |
| Formulation | 25° C. | 25° C. | 40° C. | 25° C. | 40° C. | 25° C. | 40° C. | 25° C. | 40° C. |
| 182 | 4.5 | 4.5 | | 4.5 | 4.5 | 4.5 | 4.6 | 4.3 | 4.3 |
| PBO4 | 4.5 | 4.2 | 4.5 | 4.2 | 4.2 | 4.1 | 4.1 | 4.0 | 4.0 |
| 126 | 4.2 | 4.3 | 4.3 | 4.3 | 4.3 | 4.3 | 4.3 | 4.1 | 4.1 |

TABLE 57

Macroscopic stability of the Formulations. The results of the macroscopic appearance test when the formulations are stored at 25° C. over a 6 month period.

| | Appearance spatula Test (25° C. sample only) | | | | | Visual Viscosity (25° C. sample only) | | | | |
|---|---|---|---|---|---|---|---|---|---|---|
| Formulation | t = 0 | 1 = 1 month | t = 2 months | t = 3 months | 1 = 6 months | t = 0 | t = 1 month | t = 2 months | t = months | t = 6 months |
| 182 | Very glossy and smooth | Very glossy and smooth | Very glossy and smooth | Very glossy and smooth | Very glossy and smooth | High | Medium-High | Medium-High | Medium-High | High |
| 126 | Glossy, very slightly textured | Smooth, slightly textured, glossy | Glassy and smooth | Slightly textured, sheen | Glossy | Medium | Medium | Medium | Medium | Low viscosity |
| PB04 | Glossy and smooth | Glossy and smooth | Glossy and smooth | Glossy and smooth | Smooth cream high sheen | Medium-Low | Medium | Medium-Low | Low | Low |

TABLE 58

Brookfield and Bohlin Viscosity. The results of the viscosity and rheology measurements for the formulations that are stored at 25° C. over a 6 month period.

| | | Crossover | Brookfield (cPs) | | | | | Bohlin Viscosity (cps) (based on 3M method) | | | | |
|---|---|---|---|---|---|---|---|---|---|---|---|---|
| Formulation Identity | G*(Pa) t = 0 | (o*) t = 0 | t = 0 | t = 1 Month | t = 2 Months | t = 3 Months | t = 6 Months | t = 0 | t = 1 Month | t = 2 Months | t = 3 Months | t = 6 Months |
| 182 | 702 | 8.5 | 693067 | 1097000 | 904667 | 523033 | 273233 | 18050 | 17850 | 18550 | 16820 | 13691 |
| 126 | ** | ** | 430100 | 235066 | 228104 | 212500 | 105720 | 16783 | 12739 | 14749 | 108565 | 87895 |
| PB04 | ** | ** | 227800 | * | * | * | * | 10350 | 7953 | 5511 | 3550 | 2247 |

*Results not presented as the torque is out of range (due to low viscosity) for the Brookfields viscometer based on the setting and spindle that are used for all the other samples. Alternative spindles and settings are investigated; however, the results are vastly different compared to previous readings.
**no recorded measurements.

TABLE 59

Identification of 4-hydroxy Imiquimod when the formulations are stored at 25° C. and 40° C. over a 6 month period (confirmed by HPLC at 318 nm).

| | t = 0 | t = 1 month | | t = 2 months | | T = 3 months | | t = 6 months | |
|---|---|---|---|---|---|---|---|---|---|
| Formulations | 25° C. | 25° C. | 40° C. | 25° C. | 40° C. | 25° C. | 40° C. | 25° C. | 40° C. |
| 182 | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| PBO4 | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| 126 | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |

Example 24

Two Phase 3, Randomized, Double-Blind, Placebo-Controlled, Multi-Center, Efficacy and Safety Studies of 2.5% and 3.75% Imiquimod Creams in the Treatment of External Genital Warts This Example 24 will study a shorter duration treatment regimen utilizing lower concentrations of imiquimod to allow for more frequent dosing. The lower concentrations of imiquimod should permit daily dosing such that the overall short treatment regimen (up to 8 weeks of treatment) could still provide adequate clearing of external genital/perianal warts.

The clinical development program for the formulations of lower strengths of imiquimod will investigate a patient population similar to that evaluated in the development program for Aldara®. In addition to lower strengths, the key modification is to the treatment regimen itself, as the treatment with the 2.5% and 3.75% imiquimod creams will be once daily for a maximum of 8 weeks, rather than the currently approved regimen of 3 times per week with Aldara for up to 16 weeks. Each strength will be evaluated vs. placebo to determine the benefit risk profile with each of these treatment regimen.

Study Objective

The primary objective of this Example is to compare the efficacy and safety of 2.5% imiquimod cream and 3.75% imiquimod cream to placebo cream, applied once daily for up to 8 weeks, in the treatment of external genital warts (EGW).

The secondary objective of this study is to provide information on recurrence of EGW.

Description of Study

This is a randomized, double-blind, placebo-controlled, multicenter Phase 3 study of 2.5% and 3.75% imiquimod creams in the treatment of EGW. Two investigational treatments will be studied: 2.5% imiquimod cream once-a-day application for a maximum of 8 weeks and 3.75% imiquimod cream once-a-day for a maximum of 8 weeks. The study will consist of a Screening visit and an Evaluation Period including a maximum 8-week Treatment Period and a maximum 8-week No-treatment Period. Subjects with complete clearance at the end of study (EOS) will be followed for a maximum of 12 weeks for recurrence. During the Evaluation Period, subjects will be followed until they have achieved complete clearance of all warts. Any subject determined to have achieved complete wart clearance at any time through the Week 16 visit will enter the maximum 12-week Follow-up Period for evaluation of recurrence. The total study duration is a maximum of 28 weeks from randomization.

Approximately 450 subjects with at least 2 and up to 30 external genital/perianal warts will be randomized. Subjects will be screened for study eligibility during the 4 weeks prior to randomization. During the Screening Period, the medical history, including genital/perianal wart history and wart treatment history, and demographic information, including sex, age, and race will be recorded. In addition, a physical examination, including vital signs and clinical safety laboratory tests, will be performed for each subject. If clinically indicated, a sexually transmitted diseases (STD) screen may be performed. Subjects with a positive screen for STD may participate in the study if they otherwise meet the required Inclusion/Exclusion Criteria. For female subjects, a pelvic exam/Pap smear will be performed unless a normal (negative) Pap smear result is available and was performed within 6 months of enrollment.

Qualified subjects will be randomized to receive one of 3 treatments: 2.5% imiquimod cream, 3.75% imiquimod cream, or placebo cream. Subjects will apply study cream once daily for a maximum of 8 weeks. Subjects will be stratified by gender and will be randomized to treatment with an allocation ratio of 2:2:1 in favor of the active treatments. All subjects will be seen every 2 weeks for up to 16 weeks, depending on complete clearance of all baseline and new warts.

In the Evaluation Period, subjects will apply investigative cream to the identified treatment area for a maximum of 8 weeks. If the subject has not achieved complete wart clearance by the Week 8 visit (end of treatment, EOT), the subject will be followed for an additional maximum of 8 weeks. Subjects determined to have achieved clearance of all warts at any time through Week 16 will complete procedures for the EOS visit and will immediately enter the Follow-up Period for determination of recurrence. In the Follow-up Period, subjects will be followed every 4 weeks for up to 12 weeks or until the recurrence of warts. The 2.5% and 3.75% imiquimod creams that will be used this Example 24 have the same formulations as the 2.5% and 3.75% imiquimod creams that were used in the EGWs studies reported in Examples 23-26, which are described in application for U.S. patent, Ser. No. 12/636,613 filed Dec. 11, 2009, which is incorporated herein by reference in its entirety.

Clinical evaluations, including count of warts and assessment of local skin reactions, and recording of adverse events (AEs) and concomitant medications will be performed. Safety laboratory tests will also be performed prior to treatment and at the EOS visit.

Study Number: GW01-0805 of 2.5% imiquimod cream and 3.75% imiquimod cream with that of placebo cream, applied once daily for up to 8 weeks, in the treatment of EGW. The secondary objective of this study was to provide information on the recurrence of EGW.

Methodology: This was a randomized, double-blind, placebo-controlled, multicenter study that compared the efficacy and safety of 2.5% imiquimod cream and 3.75% imiquimod cream with that of placebo in the treatment of EGW. The study consisted of a screening visit and an evaluation period that included a maximum 8-week treatment period and a maximum 8-week no-treatment period. Subjects who achieved complete clearance at End of Study (EOS) entered a maximum 12-week follow-up period for evaluation of recurrence. The total study duration was a maximum of 28 weeks from randomization.

Subjects determined to be eligible during the screening period were stratified by gender and randomized in a 2:2:1 ratio to 2.5% imiquimod cream, 3.75% imiquimod cream, or placebo cream. Subjects were scheduled for 1 prestudy screening visit, and then were scheduled for visits every 2 weeks for up to 16 weeks during the evaluation period, depending on complete clearance of all baseline and new warts. During the evaluation period, subjects applied investigative cream to the identified treatment area for a maximum of 8 weeks. If the subject did not achieve complete wart clearance by the Week 8 visit (End of Treatment, EOT), the subject was monitored for an additional maximum of 8 weeks. Subjects determined to have achieved clearance of all warts at any time through Week 16 completed procedures for the EOS visit and were eligible to immediately enter the follow-up period for determination of recurrence. During the follow-up period, subjects were monitored every 4 weeks for up to 12 weeks or until the recurrence of warts.

Clinical evaluations included counts of the number of warts, assessments of local skin reactions (LSRs), and recordings of adverse events (AEs) and concomitant medications. At selected centers, photography was performed at designated visits: Laboratory tests were also performed prior to treatment and at the EOS visit to assess safety.

The study design is presented schematically in Tables 60 and 61 below.

in the treatment of EGW, a placebo-control group was included in the study design. The study medications were identical with the exception of the absence of imiquimod in the placebo cream and the concentration of imiquimod (2.5% or 3.75%) in the active formulations.

The double-blind study design, in which the treatment assignment was concealed from the subjects, investigators, and all individuals involved in study execution, monitoring, and data collection, was chosen to provide an unbiased evaluation of the study medications. Comparison of each imiquimod group to the placebo group provides an unbiased test of the effect of imiquimod.

The 8-week treatment period was selected based on market experience of the use of Aldara to treat EGW, in which treatment duration greater than 8 weeks appears to be rare. Subjects who did not experience clearance during the treatment period were observed for an additional no-treatment period of up to 8 weeks. Once clearance was achieved at any time during the study, subjects were observed during a 12-week follow-up period to determine if the EGW recurred.

Selection of Study Population

It was planned to enroll approximately 450 subjects in a 2:2:1 ratio: approximately 180 in each active-treatment group and 90 in the placebo group. Forty-five investigative study centers in the United States (US) participated in the study, although 2 centers did not enroll any subjects. Study centers could enroll a maximum of 30 subjects per center. Enrollment was stopped at all centers when the study enrollment goal was reached.

Inclusion Criteria

Subjects could participate in the study if they met the following inclusion criteria:

1. Were willing and able to give informed consent—for subjects under 18, the parent/legal guardian was required to give written informed consent and the subject was required to provide written assent in accordance with local regulations;
2. Were at least 12 years of age at the time of initial screening;

TABLE 60

| Study Design-Evaluation Period | | | | | | | | | |
|---|---|---|---|---|---|---|---|---|---|
| Screening | Treatment Period | | | | | No-treatment Period | | | |
| Week −4 to 0 | Week 0 Day 1 | Week 2 | Week 4 | Week 6 | Week 8/ EOT | Week 10 | Week 12 | Week 14 | Week 16/ EOS |
| Visit 1 | Visit 2 | Visit 3 | Visit 4 | Visit 5 | Visit 6 | Visit 7 | Visit 8 | Visit 9 | Visit 10 |

Note:
At any time during the Evaluation Period (i.e., any time after Visit 2), a subject who achieved clearance of all warts concluded the evaluation period and was eligible to enter the Follow-up for Recurrence Period.

TABLE 61

| Study Design—Follow-up for Recurrence Period Follow-up Period (Only in subjects with clearance of all warts) | | |
|---|---|---|
| Week 4 Post-EOS | Week 8 Post-EOS | Week 12 Post-EOS |
| Follow-up Visit 1 | Follow-up Visit 2 | Follow-up Visit 3 |

Discussion of Study Design, Including the Choice of Control Groups

This was a randomized, double-blind, placebo-controlled, multicenter study. In order to assess the effect of imiquimod 3. Were willing and able to participate in the study as outpatients, making frequent visits to the study center during the treatment and follow-up periods, and to comply with all study requirements;
4. Had a diagnosis of external genital/perianal warts with at least 2 warts and no more than 30 warts located in one or more of the following anatomic locations:

In both sexes: inguinal, perineal, and perianal areas;

In men: over the glans penis, penis shaft, scrotum, and foreskin;

In women: on the vulva;
5. Had total wart areas of at least 10 $mm^2$;

6. Were judged to be in good health based upon the results of a medical history, physical examination, and safety laboratory profile;
7. If female and of childbearing potential, had a negative serum pregnancy test at Screening and a negative urine pregnancy test prior to randomization and were willing to use effective contraception; and
8. If male or a male partner of a female subject, were willing to use condoms for sexual activities during the study.

Exclusion Criteria

Subjects were excluded from the study if they met any of the following criteria:

1. Had received any topical and/or destructive treatments for external genital warts within 4 weeks (within 12 months for imiquimod, and within 12 weeks for sinecatechins) prior to enrollment (i.e., the randomization visit);
2. Had received any of the following treatments within the indicated time intervals prior to enrollment:

| Medication/Treatment | Washout |
|---|---|
| Any marketed or investigational HPV vaccines | 12 months |
| Imiquimod | 12 months |
| Sinecatechins (Veregen ®) | 12 weeks |
| Interferon/Interferon inducer | 4 weeks |
| Cytotoxic drugs | 4 weeks |
| Immunomodulators or immunosuppressive therapies | 4 weeks |
| Oral antiviral drugs (with the exception of oral acyclovir and acyclovir related drugs for suppressive or acute therapy herpes; or oseltamivir for prophylaxis or acute therapy of influenza) | 4 weeks |
| Topical antiviral drugs (including topical acyclovir and acyclovir related drugs) in the wart areas | 4 weeks |
| Podophyllotoxin/Podofilox in the wart areas | 4 weeks |
| Oral and parenteral corticosteroids (inhaled/intranasal steroids are permitted) | 4 weeks |
| Any topical prescription therapy for any conditions in the wart areas | 4 weeks |
| Dermatologic/cosmetic procedures or surgeries in the wart areas | 4 weeks |

3. Had any evidence (physical or laboratory) of clinically significant or unstable disease and/or any condition that might have interfered with the response to the study treatment or altered the natural history of EGW;
4. Were currently participating in another clinical study or had completed another clinical study with an investigational drug or device within the past 4 weeks;
5. Had known or active chemical dependency or alcoholism as assessed by the investigator;
6. Had known allergies to study drug or any excipient in the study cream;
7. Were currently immunosuppressed or had a history of immunosuppression;
8. Had a planned surgery that would cause an interruption of study treatment;
9. Had sexual partners currently in treatment with an approved or investigational treatment for EGW;
10. Had any current or recurrent malignancies in the genital or treatment area;
11. Had any untreated or unstable genital infections (other than genital warts);
12. Had any of the following conditions:
    known human immunodeficiency virus (HIV) infection;
    current or past history of high risk HPV infection (e.g., HPV 16, 18, etc);
    an outbreak of herpes genitalis in the wart areas within 4 weeks prior to enrollment;
    internal (rectal, urethral, vaginal/cervical) warts that required or were undergoing treatment;
    a dermatological disease (e.g., psoriasis) or skin condition in the wart areas which may have caused difficulty with examination;
13. If female, had clinically significant abnormalities on pelvic examination or had laboratory test results showing high-grade pathology (e.g., high-grade squamous intraepithelial lesion, moderate or severe dysplasia, squamous cell carcinoma);
14. If female, were nursing or pregnant or planned to become pregnant during the study.

Removal of Patients from Therapy or Assessment

Subjects could withdraw from the study or be withdrawn by the investigator at any time without prejudice to their future medical care. Any subject who did not comply with the inclusion/exclusion criteria could be withdrawn from further participation in the study.

Subjects could also be discontinued if the investigator determined that LSRs or AEs were of such severe intensity, serious events, or of a duration sufficient to warrant discontinuation, or if a subject required treatment for a suspected malignancy or other condition within the treatment or surrounding area. If a subject discontinued due to an LSR, the LSR was recorded as an AE, and the subject was monitored until the AE resolved to the investigator's satisfaction.

Any subject who received study drug and discontinued prematurely from the study was to return to the study center for EOS procedures. Subjects who discontinued prematurely from the study for any reasons were not replaced.

Treatments Administered

The test products were 2.5% imiquimod cream and 3.75% imiquimod cream. The reference therapy was placebo cream. Subjects applied the study drug in a thin layer once daily to each wart identified at Baseline and any new wart that appeared during the treatment period. A maximum of 1 packet (250 mg) of study drug was applied for a given dose (250 mg of 3.75% cream is equivalent to 9.375 mg imiquimod, and 250 mg of 2.5% cream is equivalent to 6.25 mg imiquimod). Study drug was applied prior to normal sleeping hours and removed approximately 8 hours later with mild soap and water. Subjects were to continue to apply study cream to all identified wart/wart areas until all warts were cleared.

The investigational products, 2.5% imiquimod cream and 3.75% imiquimod cream, contained imiquimod, isostearic acid, benzyl alcohol, cetyl alcohol, stearyl alcohol, polysorbate 60, sorbitan monostearate, white petrolatum, glycerin, methyl paraben, propyl paraben, purified water, and xanthan gum. The placebo cream contained the same ingredients as the active formulations with the exception of imiquimod.

Method of Assigning Patients to Treatment Groups

Subjects were randomly assigned to study treatments in a 2:2:1 ratio (2.5% imiquimod cream:3.75% imiquimod cream:placebo cream).

Selection of Doses in the Study

The approved dosing regimen for Aldara® (imiquimod) Cream, 5% for EGW is 3 times per week until warts are cleared, up to 16 weeks of treatment. This protocol studied a treatment regimen shorter in duration, and used lower concentrations of imiquimod to allow for more frequent dosing. The lower concentrations of imiquimod used in this study were chosen to permit daily dosing such that the overall shortened treatment regimen (8 weeks compared with a 16-week treatment regimen for Aldara) could still provide adequate clearing of EGW.

Selection and Timing of Dose for Each Patient

Subjects meeting all inclusion and no exclusion criteria were randomly assigned in a 2:2:1 ratio to 1 of the 3 treatment groups (2.5% imiquimod cream:3.7% imiquimod cream:or placebo cream).

Each dose of study drug was to be applied by the subject at approximately the same time of day. To reduce the risk of study drug removal from daily hygienic or physical activities, study drug was to be applied just prior to the subject's normal sleeping hours.

Subjects were to wash the treatment area with mild soap and water before applying the study medication, allow the area to dry thoroughly, and then apply the study medication once daily. Subjects were to apply a thin layer of study cream to each wart identified at Baseline and any new wart that appeared during the treatment period. Only up to one packet of study cream was to be applied per application.

The subjects were encouraged to leave study cream on for approximately 8 hours, preferably during normal sleeping hours, and were not to wash the treatment area, swim, shower or bathe, or have sexual contacts while the study medication was on the skin. Subjects could wash the study cream off with soap and water any time after approximately 8 hours of application. Subjects were to continue applying the study cream for a maximum of 8 weeks or until the investigator determined that they had achieved complete clearance of all (baseline and new) warts. Subjects were not to make up any missed doses.

Rest periods, or temporary interruptions of dosing due to intolerable local skin reactions, were allowed during the study if the investigator or subject (or legal parent or guardian) decided that study drug application should be interrupted. Subjects who were placed on a rest period were to be seen by the investigator prior to resuming treatment with study drug in order to assess if the recovery of the treatment site was sufficient. Doses missed due to a rest period were not counted as missed doses in the assessment of subject compliance with the treatment regimen. The study visit schedule and procedures were not to be altered due to missed doses or rest periods. If a subject experienced a strong local reaction in one treatment area but not in other treated areas, the subject could temporarily stop applying study cream in that affected area while continuing study treatment in the other areas.

Treatment of New Warts

During treatment period, any new warts appearing in any of the protocol-defined anatomic locations were treated with the study cream. Neither the warts present at Baseline nor new warts were allowed to be treated during the no-treatment period (i.e., from the Week 8/EOT visit to the Week 16 visit).

Blinding

This study was conducted as a double-blind study, i.e., the treatment assignment was concealed from the subjects, the investigators and their staff, and the clinical research team.

Treatment supplies for each subject included treatment kits for 8 weeks of treatment. Each treatment kit contained 4 supply boxes of study cream and one emergency box, each box containing a 2-week supply of study cream. At the randomization/Day 1 visit, a randomization number was assigned to each subject. Each subject was assigned the next available treatment kit number available at the site, starting from the lowest number for each gender and proceeding in numerical order to the highest number.

The randomization code for each subject could be accessed via the double-blind tear-off label, but was to be broken for an individual subject only in an emergency situation such as a serious adverse event (SAE). The study monitor or project manager was to be informed prior to any emergency unblinding. If the code for a subject was broken, the investigator was to document promptly the premature unblinding of the investigational product in the electronic case report form (eCRF) system.

No premature unblinding was performed. The treatment assignments were unblinded approximately 3 months after the last subject contact after all data queries had been answered and the database had been locked.

Prior and Concomitant Therapy

At each visit, prior and concomitant medications and therapies were reviewed. The name of the medication (trade or generic name), indication for use, and start and stop dates were recorded for any medication used.

Restricted Medications/Treatments

The following medications, preparations, and treatments that could potentially affect the study results were prohibited during the study:

1. Imiquimod 5% cream (Aldara®);
2. Any marketed or investigational HPV vaccines;
3. Sinecatechins (Veregen);
4. Interferon or interferon inducers;
5. Cytotoxic drugs;
6. Immunomodulators or immunosuppressive therapies;
7. Oral or parenteral corticosteroids (inhaled/intranasal steroids are permitted);
8. Oral antiviral drugs (with the exception of oral acyclovir and acyclovir related drugs for suppressive or acute therapy herpes; or oseltamivir for prophylaxis or acute therapy of influenza);
9. Topical antiviral drugs (including topical acyclovir and acyclovir related drugs) in the treatment areas;
10. Podophyllotoxin/Podofilox in the treatment areas;
11. Any topical prescription medications in the treatment areas;
12. Dermatologic/cosmetic procedures or surgeries in the treatment areas.

Treatment Compliance

Study center personnel carefully queried each subject and reviewed the study diary at each treatment study visit to make sure the subject was dosing with study drug as indicated. The numbers of returned used and unused study packets were counted and recorded, and any discrepancies were discussed with the subject. During the treatment period, the study center personnel continued to instruct the subject on dosing procedures until the subject demonstrated compliance with study drug application. If at any time the investigator felt that a subject had missed a significant number of doses (exclusive of rest periods) or was not compliant with the study requirements, the investigator was to contact the project manager or study monitor to review the subject's compliance status and to determine a course of action.

Efficacy and Safety Variables

Efficacy and Safety Measurements Assessed

A schedule of study visits and procedures is presented in the Table below. Source documentation was completed at each subject's visit, and the data captured in the source documents was subsequently entered into eCRFs by the investigator or designee. The evaluator who performed the EGW count and LSR assessment at Baseline was to perform these assessments at the subsequent visits if possible.

Photographs were taken of the treatment area at selected centers, for informational purposes only. Only subjects who had signed a photographic consent form were to be photographed. No subjects under the age of 18 years (19 in Nebraska, Alabama, Alaska, or Wyoming) were photographed. The majority of subjects who participated in this trial did not have photographs of the treatment area taken. Cameras, detailed instructions on taking the photographs, and related items for photography were provided to the study centers by Canfield Scientific, Inc.

Criteria for Evaluation:

Efficacy Assessments

Count of External Genital/Perianal Warts (EGWS)

In order to qualify for this study, subjects had to have at least 2 warts and no more than 30 warts in the genital/perianal area at the screening and randomization/Day 1 visits. At each study visit including Screening, the number of warts, including new warts, was documented on the source documents and eCRF for each of the following anatomic locations:

In both sexes: inguinal, perineal, and perianal areas;

In men: over the glans penis, penis shaft, scrotum, and foreskin (if circumcised, the foreskin area was marked as "not applicable");

In women: on the vulva.

Any warts that were visible to the naked eye were included in the lesion count as separate lesions.

In the event that the margins or boundaries of some warts could not be discerned due to local skin reactions obscuring the field, the best estimate by clinical assessment of the number of warts in each anatomic location was made and the count included.

If possible, the same investigator who counted the warts at Baseline completed wart counts at subsequent study visits.

Measurement of Baseline Wart Area

At the screening and randomization/Day 1 visits, the size of each wart or wart cluster was measured by length and width. The total wart areas were to equal at least 10 $mm^2$ in order to qualify for this study. The investigator measured the total baseline wart area to be treated in $mm^2$. The total baseline wart area was the sum of individual areas for each wart or cluster of warts. It was preferred that each subject's wart areas be measured by the same investigator at both visits. If the wart areas were not continuous, the total areas were to be calculated and recorded on the source documents and eCRF.

Treatment of New Warts

During the treatment period, any new warts that appeared in any of the protocol defined anatomic locations were treated with study cream. Treatment for any warts, Baseline or new, was not allowed during the no-treatment period (i.e., from the EOT visit to the Week 16 visit).

Safety Assessments

Safety assessments included visual assessments of local skin reactions (LSRs) at each study visit after the screening visit, including any temporary interruptions of dosing (i.e., rest periods) required in response to LSRs; all reports of AEs and SAEs, with their severity and relationship to study drug; results of clinical laboratory tests (including urine pregnancy tests for women of childbearing potential); pelvic examinations with Pap smears in women; findings of a general physical examination at the screening visit, and intercurrent dermatologic conditions occurring within or outside of the treatment area.

Full information about the definition of AEs and SAEs, the procedure for reporting them, and the assessment of other safety parameters is given in the protocol.

Adverse Events

Subjects were queried indirectly regarding AEs during each study visit. All AEs that occurred during the study period were recorded on the appropriate eCRF. The description of the AE included the dates of onset and resolution (duration), severity, relationship to study treatment or other therapy, action taken (if any), and outcome. If the investigator considered it necessary, he or she was to contact the sponsor with regard to any AE that occurred after a subject ended study participation. Any treatment-related AEs or LSRs that were ongoing at the end of the study were followed to the investigator's satisfaction. The study period for the purpose of AE reporting was defined as the period from the prestudy screening or the initiation of any study procedures to the end of the follow-up period.

An adverse event was defined as any untoward medical occurrence in a patient or clinical investigation subject that was temporally related to protocol procedures, including the administration of a pharmaceutical product at any dose, but that did not necessarily have a causal relationship with the treatment. Laboratory values or results of other diagnostic procedures considered by the investigator to be clinically significant were captured as AEs and summarized accordingly.

Local skin reactions were not recorded as AEs unless they extended beyond the anatomic treatment area, if they required any medical interventions, or if the LSR resulted in subject discontinuation from the study. Application site reactions other than those described as LSRs (eg, vesicles, burning, itching, bleeding, soreness, and induration) were recorded as AEs.

Severity:

Terms used to describe the severity of an AE were mild, moderate, and severe. These terms were defined as follows:

Mild—The subject was aware of the signs and symptoms but the signs and symptoms were easily tolerated.

Moderate—The signs and symptoms were sufficient to restrict, but did not prevent, usual daily activity for the subject.

Severe—The subject was unable to perform usual daily activity.

Serious Adverse Events:

An SAE was any AE that, at any dose, resulted in any of the following outcomes: death, life-threatening AE, inpatient hospitalization or prolongation of existing hospitalization, persistent or significant disability/incapacity, or a congenital anomaly/birth defect.

An event was considered serious when, based upon appropriate medical judgment, it jeopardized the subject and may have required medical or surgical intervention to prevent one of the outcomes listed above.

A life-threatening AE was any AE that, at any dose, placed the subject, in the view of the investigator, at immediate risk of death from the reaction as it occurred. It did not include a reaction or event that, had it occurred in a more severe form, might have caused death.

Local Skin Reactions

Local skin reactions in the treatment and/or immediate surrounding area were clinically identified by the following categories: erythema, edema, weeping/exudate, flaking/scaling/dryness, scabbing/crusting, and erosion/ulceration. At each study visit after the screening visit, the investigator visually assessed the treatment and immediate surrounding areas and graded the intensity of each LSR category using the scales in Tables 62 and 63.

TABLE 62

| Local Skin Reaction Scale | | | | |
|---|---|---|---|---|
| Local Skin | Severity Definitions | | | |
| Reaction | 0 | 1 (Mild) | 2 (Moderate) | 3 (Severe) |
| Erythema | None | Faint to mild redness | Moderate redness | Intense redness |
| Edema | None | Mild visible or barely palpable swelling/ induration | Easily palpable swelling/ induration | Gross swelling/ induration |
| Weeping/ exudate | None | Minimal exudate | Moderate exudate | Heavy exudate |
| Flaking/ scaling/ dryness | None | Mild dryness/ flaking | Moderate dryness/ flaking | Severe dryness/ flaking |
| Scabbing/ crusting | None | Crusting | Serous scab | Eschar |

TABLE 63

| Local Skin Reaction Scale (erosion/ulceration) | | | |
|---|---|---|---|
| Local Skin | Severity Definitions | | |
| Reactions | 0 | 2 | 3 |
| Erosion/ulceration | None | Erosion | Ulceration |

Erosion/ulceration intensity was originally collected as 0 None, 1=Erosion, and 2=Ulceration. For consistency in the analysis of LSR intensities and sum score, these were recoded as 0=None, 2=Erosion, and 3=Ulceration.

Local skin reactions were assessed independently from AEs, and were recorded as AEs only if they extended beyond the immediate surrounding area, if they required any medical interventions, or if the LSR resulted in subject discontinuation from the study. Other application site reactions not listed above (eg, vesicles, burning, itching, bleeding, soreness, and induration) were recorded as AEs.

Intercurrent Dermatological Conditions

Occurring Within the Treatment Area

Dermatological Conditions—Subjects who experienced dermatological conditions within the treatment area that were unrelated to or may have been exacerbated by study cream could be discontinued from the study if these conditions impaired wart count and LSR assessments. In such a circumstance, the EOS procedures were to be completed.

Herpes Genitalis—A subject who had an outbreak of herpes genitalis that required treatment during the study in the genital wart areas could remain in the study but was to stop dosing with study cream. If the outbreak of herpes was distal from the wart areas and did not interfere with study drug application or wart evaluation, the subject was to remain in the study and could continue dosing with study cream. Subjects could receive treatment for herpes genitalis with oral acyclovir, famciclovir, and valaciclovir.

Occurring Outside the Treatment Area

Dermatological Conditions—Subjects who experienced dermatological conditions outside the treatment area or area immediately surrounding the treatment area could receive treatments for these conditions with the exception of treatments listed above.

Vaginal and/or Cervical Warts During the study, subjects who developed vaginal and/or cervical warts were to be monitored by the investigator throughout the. treatment period. These diseases could be treated after the subject exited the study.

Vulvar Intraepithelial Neoplasia or Vaginal Intraepithelial Neoplasia—If vulvar or vaginal intraepithelial neoplasia was diagnosed during the study, the investigator was to consult with the medical monitor regarding the subject's continued participation in the study.

Rectal Mucosal or Urethral Warts—Rectal and urethral warts could be treated with conventional therapy only after the subject exited the study.

Rest Periods

A rest period was a temporary interruption of dosing due to intolerable LSRs. Doses that were missed due to a subject's noncompliance with the treatment regimen were not considered a rest period. Rest periods from daily treatment were instituted by the investigator as needed, with resumption of treatment at the investigator's discretion.

Clinical Laboratory Tests

Laboratory Tests:

Subjects had samples taken at the prestudy screening visit and at the EOS visit for analysis of the following parameters:

Hematology: hemoglobin, hematocrit, red blood cell count (RBC), white blood count (WBC) with differential, and platelet count;

Serum chemistry: glucose (non-fasting), blood urea nitrogen (BUN), creatinine, cholesterol, total bilirubin, aspartate aminotransferase (AST), alanine aminotransferase (ALT), lactate dehydrogenase (LDH), alkaline phosphatase (AP), potassium, sodium, calcium, chloride, total protein, albumin, and phosphorous;

Serum pregnancy test: females of childbearing potential underwent a serum pregnancy test at the screening visit, and the test result had to be negative for the subject to participate in the study;

Urinalysis: color/appearance, glucose, pH, ketones, specific gravity, microscopic examination, and protein;

The samples were analyzed at a central laboratory, Covance Central Laboratory Services, 8211 Scicor Drive, Indianapolis, Ind. 46214. Any laboratory test result that the investigator considered to be clinically significant was recorded as an AE.

Urine Pregnancy Tests: Females of childbearing potential underwent a urine pregnancy test (UPT) at Screening (in addition to a serum pregnancy test), the randomization/Day 1 visit, every 4 weeks during the evaluation period, and at the EOT visit. If either the UPT or the serum pregnancy test was positive prior to randomization, the subject was not permitted to enroll in the study. Any subject who became pregnant during treatment was discontinued from further treatment. If there was a suspicion of pregnancy at any time during the treatment period, a urine sample was obtained and tested. All pregnancies were to be immediately reported to the medical monitor and followed through to resolution. Subjects were to continue with follow-up visits.

Sexually transmitted disease (STD) Screen: If applicable or if clinically indicated, an STD screen was performed at the screening visit. This was not considered part of the protocol.

General Physical Examination

At the screening visit, the investigator completed a general physical examination that included measurement of blood pressure, pulse rate, temperature, weight, and respiration rate.

Pelvic Examination and PAP Smear

For female subjects, a pelvic examination including a Pap smear was performed at the screening visit unless a normal (negative) Pap smear result was available and had been performed within 6 months of enrollment. Subjects with Pap smear results which were negative (normal) could be enrolled. Subjects with atypical squamous cells of undetermined significance (ASCUS) or low grade squamous intraepithelial lesion (LSIL) may have been eligible for enrollment if per usual clinical follow-up there was no suspicion of high grade pathology. Subjects with results showing high-grade pathology were not to be enrolled in the study and were to be followed appropriately or referred to their primary care physician for further care. The ThinPrep® Pap (ie, Papanicolaou) test was the only test that was performed in this study. The samples were analyzed at a central laboratory, South Bend Medical Foundation, Inc., 530 N. Lafayette Blvd., South Bend, Ind. 46601. Subjects with a (negative/normal) Pap smear result obtained within 6 months prior to enrollment did not need to have the test repeated.

Appropriateness of Measurements

External genital warts are clinically diagnosed and treated in North America and elsewhere. A count of the number of clinically visible EGWs by a qualified investigator is an appropriate measurement of the efficacy of a treatment for EGW. The safety assessments, which included AE monitoring and clinical laboratory testing and which followed standard medical practice guidelines, are accepted measures that provide general health assessments. Because imiquimod therapy has been known to be associated with LSRs, the type and severity of these were monitored separately from other AEs. These measures are generally recognized as appropriate for the purposes of this study.

Efficacy Analyses

Primary Efficacy Variable

The primary efficacy variable was the subject status with respect to complete clearance of all warts (baseline and new) in all anatomic areas at EOS (Week 16), as determined by the investigator.

Secondary and Tertiary Efficacy Variables

Secondary efficacy variables were the following:

- Subject status with respect to partial clearance of baseline warts, defined as at least a 75% reduction in the number of baseline warts, at EOS/Week 16.
- Percent change from Baseline to EOS in the total number of warts.
- Subject status with respect to complete clearance of all warts at EOS and remained cleared in all anatomic areas, as determined by the investigator, through the end of the follow-up for recurrence period.
- Time from Baseline to complete clearance of all warts, as determined by the investigator.

The tertiary efficacy variables are the following:

- Subject status with respect to complete clearance of all warts (baseline and new) in all anatomic areas, at EOT/Week 8.
- Subject status with respect to at least a 50% reduction in the number of baseline warts at EOS/Week 16.

Statistical Methods for Efficacy Analyses

Efficacy analyses were conducted on the ITT population and on the PP population. For the primary efficacy variable, imputations were made for missing data points using last observation carried forward (LOCF, primary analysis), taking all missed observations as failure (sensitivity analysis), and using observed cases (supportive analysis). For the ITT population, subjects who had no post-baseline data were included in the analysis carrying forward the baseline data. The PP population analysis used observed cases, except for complete clearance and for recurrence.

Analysis of the Primary Efficacy Variable

The primary efficacy endpoint, complete clearance rate at the EOS, was analyzed using Cochran-Mantel-Haenszel (CMH) statistics, stratifying by gender and site. All pairwise comparisons of active treatment versus placebo were made using Hochberg's modified Bonferroni procedure. If either test was significant at a 0.025 level of significance, then that test was considered significant. Otherwise, if both tests were significant at 0.05, then both tests were considered significant. The 3.75% and 2.5% treatment groups were compared to each other at the 0.05 level of significance if at least one of these treatment groups was found to be different than the placebo using the Hochberg's test.

In the primary analysis of complete clearance rate, the Breslow-Day statistic was tested at the 10% level for heterogeneity of the odds ratios across analysis sites. A finding of statistical significance in this test was followed by exploratory analyses to characterize the source of the heterogeneity.

Analysis of Secondary Efficacy Variables

The secondary efficacy variable partial clearance rate was analyzed using Cochran-Mantel-Haenszel (CMH) statistics, stratifying by gender and site. The percent change from baseline to EOS in wart count was analyzed using analysis of covariance (ANCOVA), controlling for baseline wart count, gender, and analysis site. The proportion of subjects who were clear prior to or at EOS and remained clear at the end of the follow-up for recurrence period was summarized by frequency count and 95% confidence interval. The time to complete clearance was analyzed using the log rank test in the context of a Kaplan-Meier survival analysis. For analysis of secondary efficacy variables, only the LOCF method was used for the ITT population, and observed cases for the PP population. All data from interim visits were analyzed using visit windows.

The secondary efficacy variables were compared pairwise using Hochberg's modified Bonferroni procedure.

- If at least one of the active arms was found to be superior to placebo in the primary efficacy variable of complete clearance according to Hochberg's modified Bonferroni procedure, the secondary efficacy variable of partial (>75%) clearance was compared between each of the active arms and placebo.
- If the secondary efficacy variable of partial (>75%) clearance was found to be superior to placebo in either of the active treatment groups, then the secondary efficacy variable of percent change from Baseline to EOS in wart count was tested.
- If the secondary efficacy variable of percent change from Baseline to EOS in wart count was found to be superior to placebo in either of the active treatment groups, then the secondary efficacy variable of complete clearance at EOS and remained clear at the end of follow-up for recurrence period was tested.
- If the secondary efficacy variable of complete clearance at EOS and remained clear at the end of follow-up for recurrence period was found to be superior to placebo in either of the active treatment groups, then the secondary efficacy variable of time from Baseline to complete clearance was tested.

The percent change from Baseline in EGW count at each post-baseline visit was summarized by mean, standard deviation, median, and range by treatment group. The recurrence rate of warts was summarized by treatment group and study visit using visit windows.

Analysis of Tertiary Efficacy Variables

The tertiary efficacy endpoints, complete clearance rate at EOT and subject status with respect to at least a 50% reduction in baseline wart count, were analyzed using Cochran-Mantel-Haenszel (CMH) statistics, stratifying on gender and site.

Visit Windows

For the analysis of wart counts, the data were summarized by analysis visits. Analysis visits were assigned according to the actual study day of the evaluation as illustrated in Table 64.

TABLE 64

Visit Windows

| Evaluation Period Analysis Visit | Target Study Day | Day Range |
|---|---|---|
| Baseline | 1 | Study Day ≤1 |
| Week 2 | 15 | 1 < Study Day ≤ 22 |
| Week 4 | 29 | 22 < Study Day ≤ 36 |
| Week 6 | 43 | 36 < Study Day ≤ 50 |
| Week 8 | 57 | 50 < Study Day ≤ 64 |
| End of Treatment (EOT) | — | Study Day ≤64 |
| Week 10 | 71 | 64 < Study Day ≤ 78 |
| Week 12 | 85 | 78 < Study Day ≤ 92 |
| Week 14 | 99 | 92 < Study Day ≤ 106 |
| Week 16 | 113 | 106 < Study Day ≤ 127 |
| End of Study (EOS) | — | Study Day ≤127 |
| **Follow-up Period Analysis Visit** | **Target Study Day Post EOS** | **Day Range** |
| Follow-up Week 4 | 29 | 1 < Study Day ≤ 43 |
| Follow-up Week 8 | 57 | 43 < Study Day ≤ 71 |
| Follow-up Week 12 | 85 | 71 < Study Day ≤ 99 |

All visits (scheduled or unscheduled) were mapped to an analysis visit. If more than 1 evaluation was assigned to an analysis visit, the evaluation with the lowest wart count within the window was used for analysis. Study day was calculated as the date of evaluation minus the date of randomization plus one except for the follow up visits. For the follow up visits, study day was calculated as the date of evaluation minus the date of End of Study (EOS) visit plus one.

Safety Analyses

All safety variables were analyzed using the safety population. Safety variables included the following:

- Local skin reactions.
- Rest periods during the treatment period:
  - The number and percentage by treatment group of subjects who required a rest period (1 or more).
  - The number of dosing days missed due to rest periods.
  - The number of dosing days prior to the beginning of the first rest period.
- Adverse events.
- Clinical laboratory test results.

Adverse Events

Adverse events were coded using Medical Dictionary for Regulatory Activities (MedDRA, version 11.0) terminology. A treatment-emergent AE was defined as an AE that began or worsened in severity after Day 1 and no more than 30 days after the last application of study drug. If an AE had a completely missing start date, it was considered a "treatment emergent" event, unless the stop date was prior to the date of randomization.

Treatment-emergent AEs and all AEs were summarized for each treatment group by the overall incidence of at least one event, incidence by system organ class, and incidence by system organ class and preferred term. Each subject contributed only once to each of the rates, regardless of the number of occurrences (events) the subject experienced.

Treatment-emergent AEs were summarized by severity (mild, moderate, or severe) and by relationship to study product (related, not related). Events were considered not related to study product if the relationship was "not related" or "probably not related".

Similarly, related events were those that were "probably related" or "related". An AE was assumed to be related to study drug if the relationship to study drug was unknown. For AEs that occurred more than once, the AE that was most related to study drug in that period was used in the summary of AEs by relationship to study drug categories. Similarly, the AE with the maximum intensity in that period was used in the summary of AEs by severity. If severity was missing or unknown, it was assumed to be severe.

The incidence of AEs was summarized for subgroup analysis by gender, by age subgroup, and by number of anatomic locations (i.e., one location versus multiple). Serious AEs (SAES) and AEs that led to discontinuation from the study were listed by subject.

Local Skin Reactions

The LSR intensities were summarized by frequency counts and mean score by treatment group and study visit for each LSR type. The LSRs were graded as follows:

- Erythema (0=None, 1=Faint to mild redness, 2-Moderate redness, 3=Intense redness),
- Edema (O=None, 1=Mild visible or barely palpable swelling/induration, 2=Easily palpable swelling/induration 3=Gross swelling/induration),
- Weeping/Exudate (O=None, 1=Minimal exudate, 2-Moderate exudate, 3=Heavy exudate),
- Flaking/Scaling/Dryness (O=None, 1=Mild dryness/flaking, 2=Moderate dryness/flaking, 3=Severe dryness/flaking),
- Scabbing/Crusting (0=None, 1=Crusting, 2=Serous scab, 3-Eschar),
- Erosion/Ulceration (O=None, 2=Erosion, 3-Ulceration).

Erosion/ulceration intensity was originally collected as 0=None, 1=Erosion, and 2=Ulceration. For consistency in the analysis of LSR intensities and sum score, these were recoded as 0=None, 2=Erosion, and 3=Ulceration.

The most intense reaction (post-baseline) and incidence of any reaction (post-baseline) for each LSR type were also presented by frequency distribution and mean score by treatment group. Data were analyzed using visit windows.

The LSR sum score (addition of 6 scores) was computed and summarized by treatment group at each study visit.

Rest Periods

A rest period was a temporary interruption of dosing due to intolerable LSRs or other AEs. Doses missed due to a subject's noncompliance with the treatment regimen were not considered a rest period. The start of a rest period was the first date on which the study medication was not applied for the reason of "rest period". The end of the rest period was the first date of application following the start of the rest period. The number and percentage of subjects who required a rest period (1 or more) were analyzed by treatment group using CMH statistics. The number of dosing days missed due to rest periods and the number of dosing days prior to the beginning of the first rest period were analyzed using the Wilcoxon test. In this analysis, only subjects who experienced a rest period were included.

Study Patients

Disposition of Subjects

Evaluation Period

Subject disposition for the evaluation period is displayed in Table 65 below.

TABLE 65

Subject Disposition - Evaluation Period (ITT Population)

| Total Subjects, n (%) | Imiquimod Cream 3.75% | Imiquimod Cream 2.5% | Placebo | Overall |
|---|---|---|---|---|
| Randomized | 204 | 202 | 105 | 511 |
| Completed evaluation[a] | 149 (73.0) | 139 (68.8) | 77 (73.3) | 365 (71.4) |
| Not Cleared | 89 (43.6) | 90 (44.6) | 68 (64.8) | 247 (48.3) |
| Cleared, Ended Study | 7 (3.4) | 6 (3.0) | 2 (1.9) | 15 (2.9) |
| Cleared, Entered Follow- | 53 (26.0) | 43 (21.3) | 7 (6.7) | 103 (20.2) |
| Discontinued evaluation period | 55 (27.0) | 63 (31.2) | 28 (26.7) | 146 (28.6) |
| Reasons for discontinuation during evaluation period, n (%) | | | | |
| Safety reasons (AEs) | 3 (1.5) | 4 (2.0) | 0 | 7 (1.4) |
| Investigator's request | 2 (1.0) | 0 | 1 (1.0) | 3 (0.6) |
| Subject's request (not AE) | 11 (5.4) | 10 (5.0) | 4 (3.8) | 25 (4.9) |
| Lack of efficacy | 0 | 0 | 0 | 0 |
| Noncompliance | 2 (1.0) | 3 (1.5) | 3 (2.9) | 8 (1.6) |
| Use of concomitant | 0 | 1 (0.5) | 0 | 1 (0.2) |
| Lost to follow-up | 35 (17.2) | 40 (19.8) | 19 (18.1) | 94 (18.4) |
| Other (not AE)[b] | 2 (1.0) | 5 (2.5) | 1 (1.0) | 8 (1.6) |

AE = adverse event

[a]Based on investigator assessment (CRF page 31), includes subjects who (1) cleared prior to or at EOS/Week 16, (2) not cleared at Week 16.

One subject in 2.5% treatment group had a wart count of zero at EOS but reason for discontinuation was 'Subject's request' due to concomitant cryotherapy. Another subject in the 2.5% treatment group had a wart count of zero at Week 8 visit but not cleared at EOS. One subject was randomized to the 2.5% treatment group, but included in the 3.75% group for safety analysis. One subject in the 2.5% imiquimod group, who discontinue from the study at the subject's request was also recorded as discontinued from the study due to an adverse event.

Of 911 subjects who were screened, 511 (56.1%) were randomized and 400 (43.9%) failed screening. The most frequent reason for screen failure (194 subjects [48.5% out of 400 screen failures]) was that the subject did not have a clinical diagnosis of external genital/perianal warts and did not have between 2 and 30 warts located in the inguinal, perineal and perianal areas.

Two hundred and four (204) subjects were randomized into the 3.75% imiquimod treatment group, 202 subjects were randomized into the 2.5% imiquimod treatment group, and 105 subjects were randomized into the placebo group. Overall, 71.4% of the subjects completed the evaluation study, and in the individual treatment groups 73.0%, 68.8%, and 73.3% in the 3.75% imiquimod, 2.5% imiquimod, and placebo groups, respectively, completed the study. Lost to follow-up, was the most common reason for discontinuation from the evaluation period and accounted for withdrawal of at least 17% of the subjects in each treatment group. There was no appreciable difference in the percentages of subjects who were lost to follow-up or the times at which they became lost to follow-up. Of the subjects who withdrew from the study, a sizable number of subjects discontinued early, i.e., had no post-Baseline visit: 16 of 55 (29.1%) in the 3.75% imiquimod group, 21 of 63 (33.3%) in the 2.5% imiquimod group, and 7 of 28 (25%) in the placebo group. No subjects were discontinued from the study due to lack of efficacy.

Of the 511 subjects randomized into treatment groups, 222 were male and 289 were female. Similar percentages of subjects of males and females in each treatment group completed the evaluation period. With the exception of subjects showing EGW clearance (a higher percentage of females compared with males cleared of EGW), disposition characteristics within genders were similar to those in the overall population.

Follow-Up for Recurrence Period

Subject disposition for the follow-up period is displayed in Table 66 below.

TABLE 66

Subject Disposition - Follow-Up Period (ITT Population)

| Total Subjects, n (%) | Imiquimod Cream 3.75% | Imiquimod Cream 2.5% | Placebo | Overall |
|---|---|---|---|---|
| Entered follow-up period | 53 (100) | 43 (100) | 7 (100) | 103 (100) |
| Completed study, no recurrence | 36 (67.9) | 30 (69.8) | 7 (100) | 73 (70.9) |
| Subjects with EGW recurrence | 11 (20.8) | 8 (18.6) | 0 | 19 (18.4) |
| Discontinued follow-up period[a] | 6 (11.3) | 5 (11.6) | 0 | 11 (10.7) |
| Reasons for discontinuation during follow-up, n (%) | | | | |
| Subject's request (not AE) | 1 (1.9) | 1 (2.3) | 0 | 2 (1.9) |
| Lost to follow-up | 5 (9.4) | 3 (7.0) | 0 | 8 (7.8) |
| Other (not AE)[b] | 0 | 1 (2.3) | 0 | 1 (1.0) |

AE - adverse event.

[a]Excludes subjects discontinued due to recurrence of external genital warts.

Overall, 103 subjects entered the follow-up for recurrence period, 53 subjects in the 3.75%® imiquimod treatment group, 43 subjects in the 2.5% imiquimod treatment group, and 7 subjects in the placebo group.

Overall, 11 subjects were discontinued from the follow-up period. Of the 6 (11.3%) subjects in the 3.75% imiquimod treatment group, 5 (9.4%) subjects were lost to follow-up and 1 (1.9%) was due to the subject's request. Five subjects were discontinued from the follow-up period in the 2.5% imiquimod treatment group, 3 (7.0%) subjects were lost to follow-up, and 1 (2.3%) each were due to the subject's request or 'other' (both non-AE). No subjects in the placebo group discontinued from the follow-up period.

Protocol Deviations

Final determination of each subject's status with respect to inclusion in the PP evaluation was made in a joint data review by clinical and statistical staff prior to unblinding the treatment codes.

A total of 142 subjects had major protocol deviations and were excluded from the PP population; 60 in the 3.75% imiquimod treatment group, 58 in the 2.5% imiquimod treatment group, and 24 in the placebo group). A total of 140 subjects were excluded due to lost to follow-up (accounting for approximately two-thirds of the subjects excluded from the PP population) and treatment noncompliance. Three subjects who were noncompliant were also excluded from the PP population for additional reasons: one subject (2.5% imiquimod group) had taken exclusionary medication, one subject (3.75%) had a wart area <10 $mm^2$ and one subject (placebo) had used imiquimod as a prior EGW treatment within the exclusionary period. One subject was excluded from the PP population because the subject received kits from each of the imiquimod treatment groups and 1 subject was excluded because they had taken exclusionary medication.

A total of 4 subjects (all females) received study medication kits from the incorrect gender strata. Subject 10-001 received study medication kit # M5341 (2.5%), Subject 10-009 received study medication kit # M5426 (placebo), Subject 10-011 received study medication kit M5427 (3.75%), and Subject 22-013 received study medication kit M5314 (3.75%) instead of the next available female kit. For all analyses, these 4 subjects were analyzed according to their actual gender (female).

Efficacy Evaluation

Datasets Analyzed

The number of subjects in each analysis population is presented in Table 67 below.

TABLE 67

Number (%) of Subjects in Analysis Populations

| | Imiquimod Cream | | | |
|---|---|---|---|---|
| Populations | 3.75% | 2.5% | Placebo | Overall |
| ITT population | 204 | 202[a] | 105 | 511 |
| PP population | 144 | 144 | 81 | 369 |
| Safety population | 205[a] | 201[a] | 105 | 511 |
| Follow-up for Recurrence population | 51 | 43 | 7 | 103 |

[a]Subject 04/025 was originally randomized to the 2.5% imiquimod treatment group; however, at Week 2, the subject incorrectly received a 3.75% imiquimod treatment group kit assigned to another subject. For the safety analysis the highest dose received (3.75%) is used and for the efficacy analysis, the original randomized treatment of 2.5% is used.

A total of 511 subjects were included in the ITT and safety population. Of these, 369 subjects were included in the PP population. A total of 103 subjects elected to enter the follow-up period and comprised the follow-up for recurrence population.

Demographic and Other Baseline Characteristics

Prestudy/Baseline Demographics

Demographic and baseline characteristics for the ITT population are presented in Table 68 below.

TABLE 68

Demographic Summary by Treatment Group—ITT Population

| | Imiquimod Cream | | | |
|---|---|---|---|---|
| | 3.75% (N = 204) | 2.5% (N = 202) | Placebo (N = 105) | Overall (N = 511) |
| Age in years | | | | |
| Mean (SD) | 32.8 (11.0) | 33,1 (10.1) | 33.3 (10.8) | 33.1 (10.6) |
| Median | 29.5 | 31.0 | 30.0 | 30.0 |
| Minimum, Maximum | 15.0, 70.0 | 18.0, 60.0 | 19.0, 66.0 | 15.0, 70.0 |
| Sex, n (%) | | | | |
| Male | 88 (43.1) | 85 (42.1) | 49 (46.7) | 222 (43.4) |
| Female | 116 (56.9) | 117 (57.9) | 56 (53.3) | 289 (56.6) |
| Race, n (%) | | | | |
| White | 141 (69.1) | 133 (65.8) | 76 (72.4) | 350 (68.5) |
| Black/African American | 55 (27.0) | 66 (32.7) | 27 (25.7) | 148 (29.0) |
| Other | 8 (4.0%) | 3 (1.5%) | 2 (2.0%) | 13 (2.5%) |
| Ethnicity, n (%) | | | | |
| Hispanic | 12 (5.9) | 21 (10.4) | 8 (7.6) | 41 (8.0) |
| Non-Hispanic | 192 (94.1) | 181 (89.6) | 97 (92.4) | 470 (92.0) |

SD = standard deviation.

Demographic characteristics were similar among the 3 treatment groups. Slightly more than half of the subjects were female. Overall, 68.5% of the subjects were White and more than 89% of the subjects in every treatment group were non-Hispanic. The mean age ranged from 32.8 years in the 3.75% imiquimod treatment group to 33.3 years in the placebo group. Demographic characteristics in the PP population were similar to those in the 1 population.

Medical History

The most frequently reported conditions were hypertension (53 subjects), depression (42 subjects), and seasonal allergies (35 subjects).

External Genital Warts Treatment History

Previous EGW treatment was reported by 50.5%, 52.5%, and 47.6% of subjects in the 3.75% imiquimod, 2.5% imiquimod, and placebo groups, respectively. Cryotherapy, the most frequently reported treatment, had been performed in 51 (25.0%) subjects in the 3.75% imiquimod treatment group, in 46 (22.8%) of the subjects in the 2.5% treatment group, and in 22 (21.0%) of the subjects in the placebo group. Other treatments included imiquimod (in a total of 45 subjects), acetic acid (in a total of 33 subjects), laser therapy (in a total of 29 subjects), "other" treatments (in 24 subjects), podophyllin (in 23 subjects), podophyllotoxin (in 21 subjects) and surgical excision (23 subjects), and electrodessication (13 subjects).

Prior and Concomitant Medications

Seventeen subjects (8.3%) in the 3.75% imiquimod treatment group, 20 subjects (9.9%©) in the 2.5% treatment group, and 6 subjects (5.7%) in the placebo group were taking prior medications, i.e., medications that were discontinued prior to the date of randomization. The most common prior medications were antibacterials for systemic use in 2.9% of the 3.75% imiquimod treatment group, 2.5% of the 2.5% imiquimod treatment group, and 3.8% of the placebo group.

One hundred thirty-four (65.4%) subjects in the 3.75% imiquimod treatment group, 121 (60.2%) subjects in the 2.5% imiquimod treatment group, and 63 (60.0%) subjects in the placebo group received one or more concomitant medications during this study. The following classes of concomitant medication were received by more than 10% of the subjects in one or more of the treatment groups:

- Analgesics, received by 20.5% of the 3.75% imiquimod treatment group, 20.4% of the 2.5% imiquimod treatment group, and 20.0% of the placebo group;

Antibacterials for systemic use, received by 15.1% of the 3.75% imiquimod treatment group, 17.4% of the 2.5% imiquimod treatment group, and 14.3% of the placebo group;

Anti-inflammatory and anti-rheumatic products, received by 14.1% of the 3.75% imiquimod treatment group, 11.9% of the 2.5% imiquimod treatment group, and 13.3% of the placebo group;

Sex hormones and modulators of the genital system, received by 12.7% of the 3.75% imiquimod treatment group, 10.0% of the 2.5% imiquimod treatment group, and 12.4% of the placebo group;

Psychoanaleptics, received by 10.2% of the 3.75% imiquimod treatment group, 8.0% of the 2.5% imiquimod treatment group, and 8.6% of the placebo group.

Baseline Number of External Genital Warts

A summary of the external genital wart counts at Baseline and other baseline data relevant to subjects' EGW are presented in the Table 69 for the ITT population.

TABLE 69

Baseline External Genital Warts Data by Treatment Group - ITT Population

| | Imiquimod Cream | | | |
|---|---|---|---|---|
| | 3.75% (N = 204 | 2.5% (N = 202) | Placebo (N = 105) | Overall (N = 511) |
| Total wart area ($mm^2$) | | | | |
| Mean (SD) | 150.2 (321.9) | 161.1 (367.4) | 200.7 (374.9) | 164.9 (351.4) |
| Median | 61 | 53 | 61 | 57 |
| Minimum, Maximum | 9, 3419 | 10, 4000 | 10, 1950 | 9, 4000 |
| Total wart count | | | | |
| Mean (SD) | 8.7 (7.5) | 7.7 (6.3) | 7.7 (6.3) | 8.1 (6.8) |
| Media | 6 | 5 | 6 | 6 |
| Minimum, Maximum | 2, 48 | 2, 30 | 2, 29 | 2, 48 |
| Years Since Diagnosis | | | | |
| Mean | 4.9 | 5.8 | 5.5 | 5.4 |
| Standard Deviation | 7.4 | 7.6 | 7.9 | 7.6 |
| Median | 2.0 | 2.3 | 2.2 | 2.2 |
| Minimum, Maximum | 0.0, 39.4 | 0.0, 33.4 | 0.0, 33.4 | 0.0, 39.4 |
| Anatomic location, Males[a], n | 88 | 85 | 49 | 222 |
| Inguinal | 24 (27.3) | 17 (20.0) | 19 (38.8) | 60 (27.0) |
| Perineal | 6 (6.8) | 8 (9.4) | 3 (6.1) | 17 (7.7) |
| Perianal | 8 (9.1) | 6 (7.1) | 5 (10.2) | 19 (8.6) |
| Glans Penis | 9 (10.2) | 11 (12.9) | 5 (10.2) | 25 (11.3) |
| Penis Shaft | 71 (80.7) | 76 (89.4) | 39 (79.6) | 186 (83.8) |
| Scrotum | 19 (21.6) | 16 (18.8) | 14 (28.6) | 49 (22.1) |
| Foreskin | 0 | 2 (2.4) | 2 (4.1) | 4 (1.8) |
| Anatomic location, Females[b], n | 116 | 117 | 56 | 289 |
| Inguinal | 11 (9.5) | 19 (16.2) | 4 (7.1) | 34 (11.8) |
| Perineal | 61 (52.6) | 53 (45.3) | 29 (51.8) | 143 (49.5) |
| Perianal | 53 (45.7) | 51 (43.6) | 26 (46.4) | 130 (45.0) |
| Vulva | 86 (74.1) | 78 (66.7) | 31 (55.4) | 195 (67.5) |
| Number of treatment anatomic areas, n (%)-Males[a] | | | | |
| Total Males | 88 (100) | 85 (100) | 49 (100) | 222 (100) |
| 1 | 49 (55.7) | 48 (56.5) | 25 (51.0) | 122 (55.0) |
| 2 | 30 (34.1) | 25 (29.4) | 12 (24.5) | 67 (30.2) |
| 3 | 8 (9.1) | 10 (11,8) | 10 (20.4) | 28 (12.6) |
| 4 | 1 (1.1) | 2 (2.4) | 2 (4.1) | 5 (2.3) |
| Number of treatment anatomic areas, n (%)-Females[b] | | | | |
| Total Females | 116 (100) | 117 (100) | 56 (100) | 289 (100) |
| 1 | 47 (40.5) | 53 (45.3) | 28 (50.0) | 128 (44.3) |
| 2 | 46 (39.7) | 48 (41.0) | 23 (41.1) | 117 (40.5) |
| 3 | 20 (17.2) | 12 (10.3) | 4 (7.1) | 36 (12.5) |
| 4 | 3 (2.6) | 4 (3.4) | 1 (1.8) | 8 (2.8) |

SD = standard deviation.

[a]Denominator based on the number of males in treatment group.

[b]Denominator based on the number of females in treatment group.

The mean total wart area was 164.9 $mm^2$ overall, and ranged from 150.2 $mm^2$ in the 3.75% imiquimod treatment group to 200.7 $mm^2$ in the placebo group. The mean total wart count was 8.1 overall, and ranged from 7.7 in the 2.5% imiquimod treatment group and placebo to 8.7 in the 3.75% imiquimod treatment group.

In males, the most commonly affected areas were the penis shaft (83.8%), the inguinal area (27.0%), and the scrotum (22.1%). In females, the most commonly-affected areas were the vulva (67.5%), the perineal area (49.5%), and the perianal area (45.0%). More than 50% of subjects in the female subgroup and more than 40% of subjects in the male subgroup had two or more anatomic locations affected with warts at Baseline.

Measurements of Treatment Compliance

Compliance was based on the number of applications received (where a rest period day was counted as an application) divided by the number of intended applications, or by the number of packets used (where a rest period day was counted as a packet used) divided by the number of packets intended to be used per the protocol-defined treatment regimen, whichever was greater. Noncompliance with the treatment regimen was defined as compliance less than 75% or greater than 125%.

The overall mean treatment compliance was 83.2% in the 3.75% imiquimod treatment group, 86.5% in the 2.5% imiquimod treatment group, and 91.1% in the placebo group). Of the 142 subjects excluded from the PP population, 140 were the result of noncompliance with the treatment regimen, including many subjects who were lost to follow-up. Compliance rates were slightly higher in subjects who cleared their EGW during the study (87.7%, 91.8%, and 97.8% in the 3.75% imiquimod, 2.5% imiquimod, and placebo group, respectively) compared with subjects who did not clear (81.1%, 84.5%, and 90.4% in the 3.75% imiquimod, 2.5% imiquimod, and placebo group, respectively).

Analysis of Efficacy

Complete Clearance Rate of all Warts

Complete Clearance Rates at End of Study

The primary efficacy variable in this study was the proportion of subjects with complete clearance of all warts (those present at Baseline and new warts) at EOS (ie, 8 weeks after EOT). The primary analysis was performed on the ITT population with imputation (LOCF) for missing data points. The PP population analysis used observed cases only. The results of these analyses for the ITT population are shown in Table 70. Results are presented graphically for the ITT population in FIG. 15.

TABLE 70

Proportion of Subjects with Complete Clearance of Warts at the Week 16/End of Study Visit

| | Imiquimod Cream | | |
|---|---|---|---|
| | 3.75% | 25% | Placebo |
| ITT Population (LOCF) | | | |
| n/N[a] (%) | 60/204 (29.4) | 50/202 (24.8) | 9/105 (8.6) |
| 95% CI | 23.3, 36.2 | 19.0, 31.3 | 4.0, 15.6 |
| P value vs placebo | <0.001** | <0.001** | — |
| P value vs 2.5% imiquimod cream | 0.187 | | |

TABLE 70-continued

Proportion of Subjects with Complete Clearance of Warts at the Week 16/End of Study Visit

| | Imiquimod Cream | | |
|---|---|---|---|
| | 3.75% | 25% | Placebo |
| Males | | | |
| n/N[a] (%) | 15/88 (17.0) | 13/85 (15.3) | 2/49 (4.1) |
| 95% CI | 9.9, 26.6 | 8.4, 24.7 | 0.5, 14.0 |
| P value vs placebo | 0.019** | 0.034** | |
| P value vs 2.5% imiquimod cream | 0.639 | | |
| Females | | | |
| n/N[a] (%) | 45/116 (38.8) | 37/117 (31.6) | 7/56 (12.5) |
| 95% CI | 29.9, 48.3 | 23.3, 40.9 | 5.2, 24.1 |
| P value vs placebo | <0.001** | 0.012** | |
| P value vs 2.5% imiquimod cream | 0.204 | | |

LOCF = last observation carried forward,

95% CI = 95% confidence interval

[a]n/N = number of subjects with complete clearance at end of study divided by the number of subjects analyzed.

P values are from Cochran-Mantel-Haenszel test, stratified by gender and analysis site (overall population) or stratified by analysis site (gender subgroups, taking 2 treatment groups at a time. P values marked with

**are statistically significant using Hochberg's modified Bonferroni procedure. Confidence intervals were calculated using the exact binomial statistics.

Breslow-Day P values for ITT Population (LOCF,) males, are 3.75% Imiquimod Cream vs Placebo = 0.933, 2.5% Imiquimod Cream vs Placebo = 0.691, and 3.75% Imiquimod Cream vs 2.5% Imiquimod Cream = 0.773.

Breslow-Day P values for ITT Population (LOCF), females, are 3.75% Imiquimod Cream vs Placebo = 0.731, 2.5% Imiquimod Cream vs Placebo = 0.757, and 3.75% Imiquimod Cream vs 2.5% Imiquimod Cream = 0.942.

In the ITT population, the rate of complete clearance of EGW at EOS was significantly higher (P<0.001) in the active treatment groups; 29.4% in the 3.75% imiquimod group and 24.8% in the 2.5% imiquimod group, compared with placebo (8.6%). As shown in the Table above, subjects in the 335% imiquimod group had a higher rate of complete clearance than subjects in the 2.5% imiquimod group. However, the difference between the 2 active treatment groups was not statistically significant (P=0.187).

Results were similar in the by-gender analyses. The complete clearance rates at EOS were statistically significantly higher in the 2 active treatment groups compared with placebo for both genders. In all treatment groups, the complete clearance rates were consistently higher in females than in males.

Due to deviations from GCP, an additional analysis was run in which 2 study sites (Sites 13 and 18) were excluded from the primary analysis. Removal of the efficacy data from these 2 sites does not materially impact the results: the primary analyses, complete clearance rates of actives compared to placebo are numerically increased.

Figure 15:
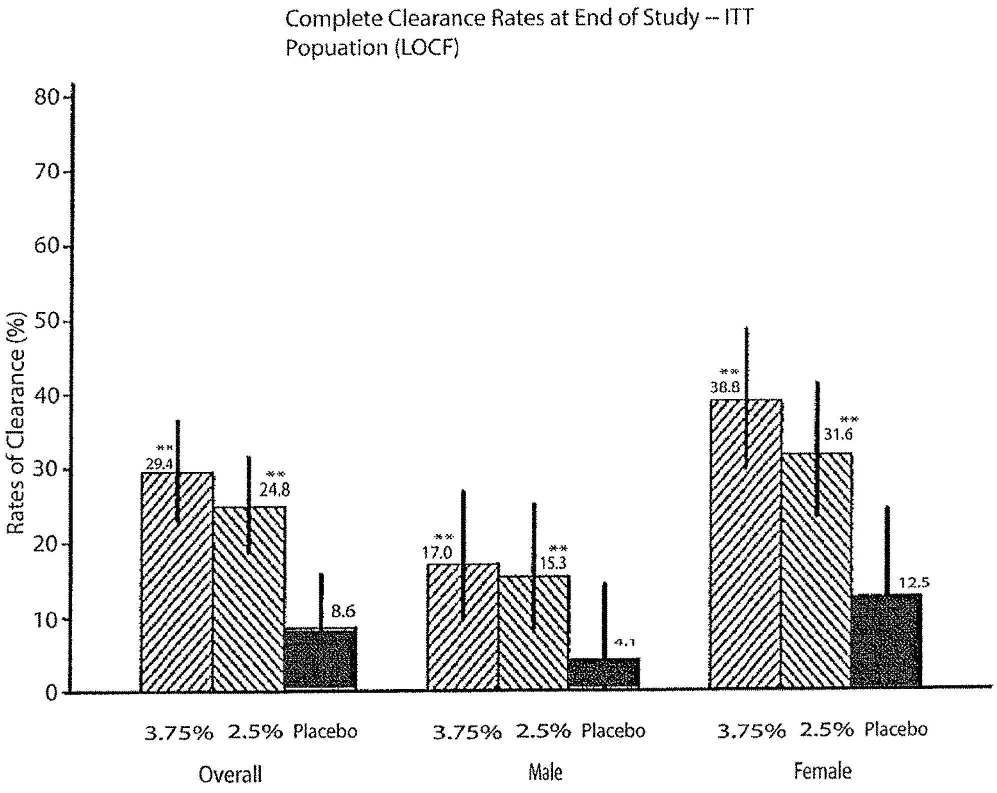
FIG. 15 shows complete clearance rates observed in the intent-to-treat (111) population at the end of one study of a lower-dose imiquimod treatment of genital warts. Subjects received treatment for 8 weeks or until complete clearance, whichever occurred sooner. Bars Marked with ** show statistically significant difference from placebo. The vertical lines represent 95% confidence intervals.

Rates of complete clearance at EOS in the ITT population are illustrated in FIG. 15.

The primary efficacy variable was analyzed for the PP population, overall and by gender, using observed cases (OC). Results for the PP population are shown in Table 71.

TABLE 71

Proportion of Subjects with Complete Clearance of Warts at the Week 16/End of Study Visit - PP Population (Observed Cases)

| | Imquimod Cream | | |
|---|---|---|---|
| | 3.75% | 2.5% | Placebo |
| PP population (OC), at EOS | | | |
| n/N[a] (%) | 49/144 (34.0) | 43/144 (29.9) | 9/81 (11.1) |
| 95% confidence interval | 26.3, 42.4 | 22.5, 38.0 | 5.2, 20.0 |

TABLE 71-continued

Proportion of Subjects with Complete Clearance of Warts at the Week 16/End of Study Visit - PP Population (Observed Cases)

| | Imquimod Cream | | |
|---|---|---|---|
| | 3.75% | 2.5% | Placebo |
| P value vs placebo | <0.001** | <0.001** | — |
| P value vs 2.5% imiquimod cream | 0.243 | — | |
| Males | | | |
| n/N[a] (%) | 12/59 (20.3) | 12/64 (18.8) | 2/36 (5.6) |
| 95% confidence interval | 11.0, 32.8 | 10.13, 30.5 | 0.7, 18.7 |
| P value vs placebo | 0.026** | 0.011** | |
| P value vs 2.5% imiquimod cream | 0.568 | | |
| Females | | | |
| n/N[a] (%) | 37/85 (43.5) | 31/80 (38.8) | 7/45 (15.6) |
| 95% confidence interval | 32.8, 54.7 | 28.1, 50.3 | 6.5, 29.5 |
| P value vs placebo | 0.002** | 0.009** | |
| P value vs 2.5% imiquimod cream | 0.424 | | |

95% CI 95% confidence interval,

OC = observed cases.

[a]n/N = number of subjects with complete clearance at end of study divided by the number of subjects analyzed.

P values are from Cochran-Mantel-Haenszel test, stratified by gender and analysis site (overall population) or stratified by analysis site (gender subgroups, taking 2 treatment groups at a time. P values marked with

**are statistically significant using Hochberg's modified Bonferroni procedure. Confidence intervals were calculated using the exact binomial distribution. Complete clearance was carried forward once achieved.

In the PP population, overall, the complete clearance rates at EOS were higher than those in the ITT population for all treatment groups: 34.0% in the 3.75% imiquimod group, 29.9% in the 2.5% imiquimod group, and 11.1% in the placebo group. The larger responses in the active treatment groups were statistically significant compared with placebo (P<0.001 for the active treatment groups). As was the case in the ITT population, the rate of complete clearance was larger in the 3.75% imiquimod group than in the 2.5% imiquimod group, but the difference between the 2 active treatment groups was not statistically significant.

Results were similar in the by-gender analyses. In all treatment groups in the PP population, the complete clearance rates at EOS were consistently higher in females than in males. Complete clearance rates were statistically significantly higher in the 2 active treatment groups compared with placebo for both genders.

Figure 16:
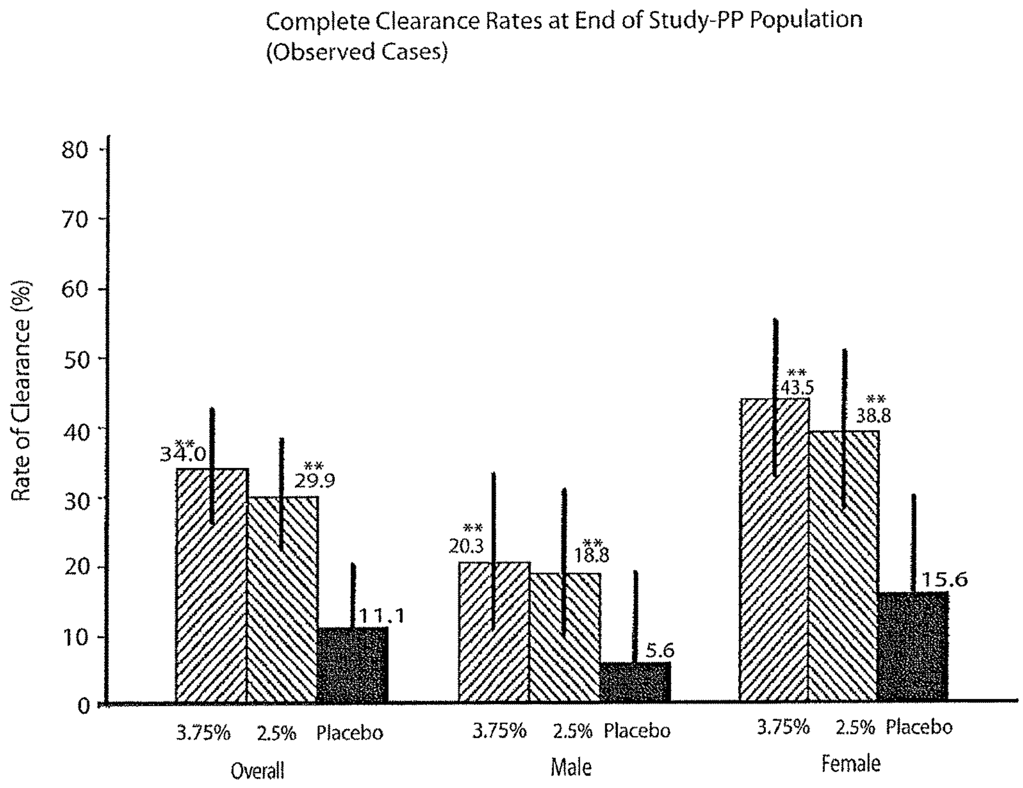
FIG. 16 shows complete clearance rates observed in the Per Protocol (PP) population at the end of one study of a lower-dose imiquimod treatment of genital warts. Bars Marked with ** show statistically significant difference from placebo. The thick vertical lines represent 95% confidence intervals.

Rates of complete clearance at EOS in the PP population are illustrated in FIG. 16.

Complete Clearance Rates at End of Treatment

A summary of the complete clearance rate at EOT for the ITT population, overall and by gender, is provided in Table 72.

TABLE 72

Proportion of Subjects with Complete Clearance of Warts at End of Treatment - ITT Population (LOCF)

| | Imiquimod Cream | | |
|---|---|---|---|
| | 3.75% | 2.5% | Placebo |
| ITT Population (LOCF) | | | |
| n/N[a] (%) | 32/204 (15.7) | 28/202 (13.9) | 4/10 5 (3.8) |
| 95% CI | 11.0, 21.4 | 9.4, 19.4 | 1.0, 9.5 |
| P value vs placebo | 0.002** | 0.012** | — |
| P value vs 2.5% imiquimod cream | 0.460 | — | — |

TABLE 72-continued

Proportion of Subjects with Complete Clearance of Warts at End of Treatment - ITT Population (LOCF)

| | Imiquimod Cream | | |
|---|---|---|---|
| | 3.75% | 2.5% | Placebo |
| Males | | | |
| n/N[a] (%) | 8/88 (9.1) | 6/85 (7.1) | 1/49 (2.0) |
| 95% CI | 4.0, 17.1 | 2.6, 14.7 | 0.1, 10.9 |
| P value vs placebo | 0.092 | 0.222 | — |
| P value vs 2.5% imiquimod cream | 0.547 | — | — |
| Females | | | |
| n/N[a] (%) | 24/116 (20.7) | 22/117 (18.8) | 3/56 (5,4) |
| 95% CI | 137, 29.2 | 12.2, 27.1 | 1.1, 14.9 |
| P value vs placebo | 0.009** | 0.028** | — |
| P value vs 2.5% imiquimod cream | 0.616 | — | — |

LOCF = last observation carried forward,

95% CI = 95% confidence interval.

[a]n/N = number of subjects with complete clearance at end of treatment divided by the number of subjects analyzed.

P values are from Cochran-Mantel-Haenszel test, stratified by gender and analysis site (overall population) or stratified by analysis site (gender subgroups), taking 2 treatment groups at a time. P values marked with

**are statistically significant using Hochberg's modified Bonferroni procedure. Confidence intervals were calculated using the exact binomial distribution.

At Week 8/EOT, 15.7% of subjects in the 3.75% imiquimod group, 13.9% of subjects in the 2.5% imiquimod group, and 3.8% of subjects in the placebo group had attained complete clearance. The overall complete clearance rate at EOT was significantly higher in the 3.75% imiquimod group (P=0.002) and in the 2.5% imiquimod group (P 0.012) compared with the placebo group. The clearance rate in the 3.75% imiquimod group was slightly higher than in the 2.5% imiquimod group; however, the difference was not statistically significant.

The complete clearance rate at EOT was significantly higher in the active treatment groups compared with placebo only in the female subgroup. In all treatment groups, the complete clearance rates were consistently higher in females than in males. Slightly higher percentages of males in the 3.75% imiquimod group achieved complete clearance than those in the 2.5% imiquimod group.

A summary of the complete clearance at EOT for the PP population is provided in Table 73.

TABLE 73

Proportion of Subjects with Complete Clearance of Warts at End of Treatment - PP Population (Observed Cases)

| | Imiquimod Cream | | |
|---|---|---|---|
| | 3.75% | 2.5% | Placebo |
| PP Population (QC), at EOT | | | |
| nfli[a] (%) | 26/144 (18.1) | 24/144 (16.7) | 4/81 (4.9) |
| 95% CI | 12.1, 25.3 | 11.0, 23.8 | 1.4, 12.2 |
| P value vs placebo | 0.010** | 0.019** | — |
| P value vs 2.5% imiquimod cream | 0.602 | — | — |
| Males | | | |
| n/N[a] (%) | 7/59 (11.9) | 6/64 (9,4) | 1/36 (2.8) |
| 95% CI | 4.9, 22.9 | 3.5, 19.3 | 0.1, 14.5 |
| P value vs placebo | 0.206 | 0.250 | — |
| P value vs 2.5% imiquimod cream | 0.400 | — | — |

TABLE 73-continued

Proportion of Subjects with Complete Clearance of Warts at End of Treatment - PP Population (Observed Cases)

| | Imiquimod Cream | | |
|---|---|---|---|
| | 3.75% | 2.5% | Placebo |
| Females | | | |
| n/N[a] (%) | 19/85 (22.4) | 18/80 (22.5) | 3/45 (6.7) |
| 95% CI | 14.0, 32.7 | 13.9, 33.2 | 1.4, 18.3 |
| P value vs placebo | 0.024** | 0.041** | — |
| P value vs 2.5% imiquimod cream | 0.934 | — | — |

95% CI = 95% confidence interval,

OC = observed cases

[a]n/N = number of subjects with complete clearance at end of treatment divided by the number of subjects analyzed.

P values are from Cochran-Mantel-Haenszel test, stratified by gender and analysis site (overall population) or stratified by analysis site (gender subgroups), taking 2 treatment groups at a time. P values marked with

**are statistically significant using Hochberg's modified Bonferroni procedure. Confidence intervals were calculated using the exact binomial distribution. Complete clearance was carried forward once achieved.

In the PP population, the EOT complete clearance rate was significantly higher in both active treatment groups compared with placebo (P=0.010 for 3.75% imiquimod vs placebo; and P=0.019 for 2.5% imiquimod vs placebo). The difference between the active treatment groups was not statistically significant.

In the PP population, complete clearance rates for males and females were higher than those in the population. Complete clearance rates in the female subgroup in both active treatment groups were essentially the same and were significantly higher compared with those in the placebo group. A slightly higher percentage of males in the 3.75% imiquimod group achieved complete clearance than those in the 2.5% imiquimod group. In both treatment groups in males, the difference in clearance rate was not statistically significant when compared to placebo. In all treatment groups, the complete clearance rates were consistently higher in females than in males.

Complete Clearance Rates by Visit Week

Figure 17:
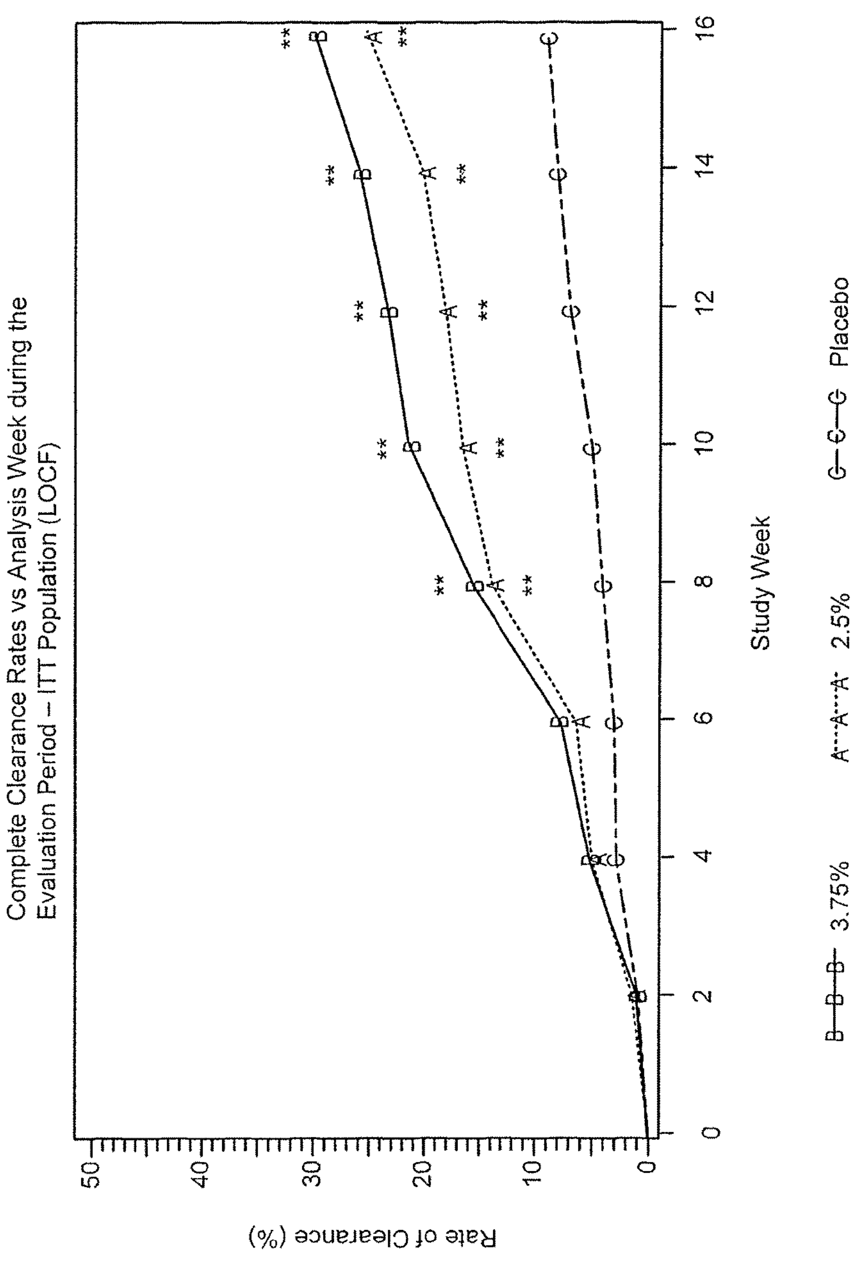
FIG. 17 shows complete clearance rates vs analysis week during the evaluation period observed in the intent-to-treat (ITT) population in one study of a lower-dose imiquimod treatment of genital warts.

A by-visit summary of complete clearance rates in the ITT population during the evaluation period is shown graphically in FIG. 17.

As shown in FIG. 17, the complete clearance rate was higher in the imiquimod treatment groups compared with placebo at all assessment time points after Week 4, and the differences were statistically significant at Week 8 (EOT) and thereafter. This includes the Week 8/end of treatment assessment and the Week 16/end of study assessment.

In female subjects, the complete clearance rate was significantly higher in the 3.75% imiquimod group compared with placebo at all assessment time points after Week 6. The complete clearance rate was significantly higher in the 2.5% imiquimod group compared with placebo at Weeks 8, 10 and 16. The difference between the active treatment groups was not statistically significant at any time point during the evaluation period. In male subjects, the complete clearance rate was significantly higher in the 3.75% group compared with placebo at all assessment time point from Week 10 to Week 16. The complete clearance rate was significantly higher in the 2.5% imiquimod group compared with placebo at Weeks 14 and 16. The difference between the active treatment groups was not statistically significant at any time point during the evaluation period.

Figure 18:
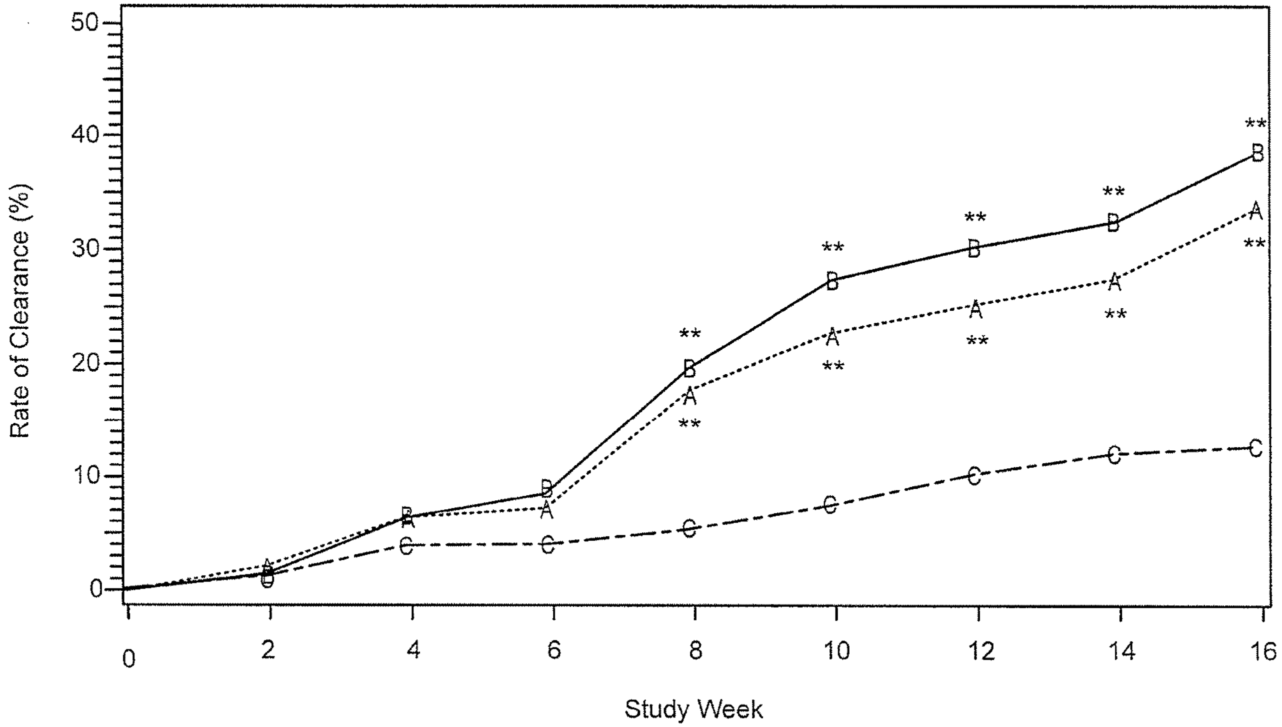
FIG. 18 shows complete clearance rates vs analysis week during the evaluation period observed in the Per Protocol (PP) population in one study of a lower-dose imiquimod treatment of genital warts.

A by-visit summary of complete clearance rates in the PP population during the evaluation period is shown in FIG. 18.

Results in the PP population were similar to those in the ITT population. The complete clearance rate was significantly higher in the active treatment groups compared with placebo at all assessment time points after Week 6. The difference in clearance rate between the 2 active treatments was not statistically significant.

In female subjects, the complete clearance rate was significantly higher in the 3.75% and 2.5% imiquimod groups compared with placebo at Week 8 and Week 16. The difference between the active treatment groups was not statistically significant at any time point during the evaluation period. In male subjects, the complete clearance rate was significantly higher in the 3.75% group compared with placebo at Week 10, Week 14 and Week 16. The complete clearance rate was significantly higher in the 2.5% imiquimod group compared with placebo at Week 16. The difference between the active treatment groups was not statistically significant at any time point during the evaluation period.

Partial Clearance Rates

Partial (≥75%) Clearance Rates at End of Study

The proportion of subjects, overall and by gender, who had a partial clearance (≥75% reduction from Baseline in wart count) during the study is summarized in Table 74 for the ITT population. Partial clearance was defined as at least a 75% reduction in the number of warts in the treatment area compared with Baseline.

TABLE 74

Proportion of Subjects with Partial (≥75%) Clearance at End of Study, ITT Population

| | Imiquimod Cream | | |
|---|---|---|---|
| | 3.75% | 2.5% | Placebo |
| ITT Population (LOCF) at EOS | | | |
| n/N[a] (%) | 79/204 (38.7) | 63/202 (31.2) | 11/105 (10.5) |
| 95% CI | 32.0, 45.8 | 24.9, 38.1 | 5.3, 18.0 |
| P value vs Placebo | <0.001** | <0.001** | — |
| P value vs 2.5% Imiquimod Cream | 0.078 | — | — |
| Males | | | |
| n/N[a] (%) | 21/88 (23.9) | 19/85 (22.4) | 3/49 (6.1) |
| 95% CI | 15.4, 34.1 | 14.0, 32.7 | 1.3, 16.9 |
| P value vs Placebo | 0.008** | 0.013** | |
| P value vs 2.5% Imiquimod Cream | 0.776 | | |
| Females | | | |
| n/N[a] (%) | 58/116 (50.0) | 44/117 (37.6) | 8/56 (14.3) |
| 95% CI | 40.6, 59.4 | 28.8, 47.0 | 6.4, 26.2 |
| P value vs Placebo | <0.001** | 0.002** | |
| P value vs 2.5% Imiquimod Cream | 0.050** | | |

95% CI = 95% confidence interval

[a]n/N = number of subjects with complete clearance at end of study divided by the number of subjects analyzed.

Partial clearance was defined as at least a 75% reduction in the number of warts in the treatment area compared with Baseline. P values are from Cochran-Mantel-Haenszel test, stratified by gender and analysis site (gender subgroups), or stratified by analysis site (gender subgroups) taking 2 treatment groups at a time. The P values marked with ** are statistically significant using Hochberg's modified Bonferroni procedure. Confidence intervals were calculated using the exact binomial distribution.

In the ITT population, the difference in the partial (≥75%) clearance rate at EOS between each of the imiquimod treatment groups and placebo was statistically significant (P≤0.001). The partial (≥75%) clearance rate was higher in the 3.75% imiquimod group than in the 2.5% imiquimod group, but the difference between the 2 active treatment groups was not statistically significant.

In the by-gender analyses, the ≥75% clearance rate at EOS was significantly higher in both of the active treatment groups compared with placebo for both males and females. The ≥75% clearance rate in the female subgroup was significantly higher in the 3.75% imiquimod group than in the 2.5% imiquimod group. In all treatment groups, the ≥75% clearance rates were consistently higher in females than in males.

Figure 19:
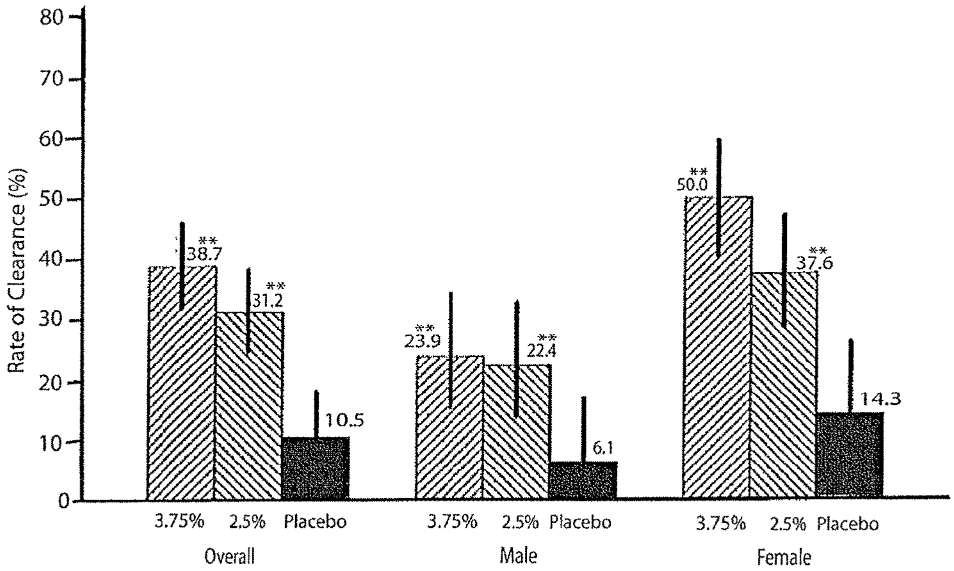
FIG. 19 shows partial (≥75%) clearance rates observed in the intent-to-treat (ITT) population at the end of one study of a lower-dose imiquimod treatment of genital warts. Partial clearance was defined as at least a 75% reduction in the number of EGW lesions compared to baseline at anytime point during the study. Bars marked with the ** show statistically significant difference from placebo. Bars marked with ## show statistically significant difference from 2.5%. The vertical lines represent 95% confidence intervals.

Rates of partial (≥75%) clearance at EOS in the ITT population are illustrated in FIG. 19.

A summary of the partial (≥75%) clearance rate at EOS for the PP population, overall and by gender, is presented in Table 75. The ≥75% clearance rates at EOS are presented graphically in FIG. 20 for the PP population.

TABLE 75

Proportion of Subjects with Partial (>75%) Clearance at End of Study-PP Population (Observed Cases)

| | Imiquimod Cream | | |
|---|---|---|---|
| | 3.75% | 2.5% | Placebo |
| PP Population (OC), at EOS | | | |
| n/N[a] (%) | 65/144 (45.1) | 55/144 (38.2) | 11/81 (13.6) |
| 95% CI | 36.8, 53.6 | 30.2, 46.7 | 7.0, 23.0 |
| P value vs placebo | <0.001.** | <0.001** | — |
| P value vs 2.5% imiquimod cream | 0.128 | — | — |
| Males | | | |
| n/N[a] (%) | 16/59 (27.1) | 18/64 (28.1) | 3/36 (8.3) |
| 95% CI | 16.4, 40.3 | 17.6, 40.8 | 1.8, 22.5 |
| P value vs placebo | 0.011** | 0.014** | — |
| P value vs 2.5% imiquimod cream | 0.696 | — | — |
| Females | | | |
| n/N[a] (%) | 49/85 (57.6) | 37/80 (46.3) | 8/45 (17.8) |
| 95% CI | 46.4, 68.3 | 35.0, 57.8 | 8.0, 32.1 |
| P value vs placebo | <0.001** | 0.001** | — |
| P value vs 2.5% imiquimod cream | 0.112 | — | — |

95% CI = 95% confidence interval,

OC = observed cases

[a]n/N = number of subjects with complete clearance at end of study divided by the number of subjects analyzed.

Partial clearance was defined as at least a 75% reduction in the number of warts in the treatment area compared with Baseline. P values are from Cochran-Mantel-Haenszel test, stratified by gender and analysis site (overall population) or stratified by analysis site (gender subgroups), taking 2 treatment groups at a time. P values marked with ** are statistically significant using Hochberg's modified Bonferroni procedure. Confidence intervals were calculated using the exact binomial distribution statistics.

In the PP population, the partial (≥75%) clearance rate at EOS was higher in the active treatment groups than in the placebo group. The difference between each of the imiquimod treatment groups and placebo was statistically significant (P<0.001). There was no statistically significant difference in partial (≥75%) clearance rate between the active treatment groups. The partial (≥75%) clearance rates were statistically significantly higher in the 3.75% imiquimod group compared with placebo at all analysis time points after Week 4; results of the analysis over time are presented below.

As in the overall PP population, the ≥75% clearance rate was significantly higher with 3.75% imiquimod and with 2.5% imiquimod versus placebo in either gender. There was no statistically significant difference between the active treatment groups in either gender.

Figure 20:
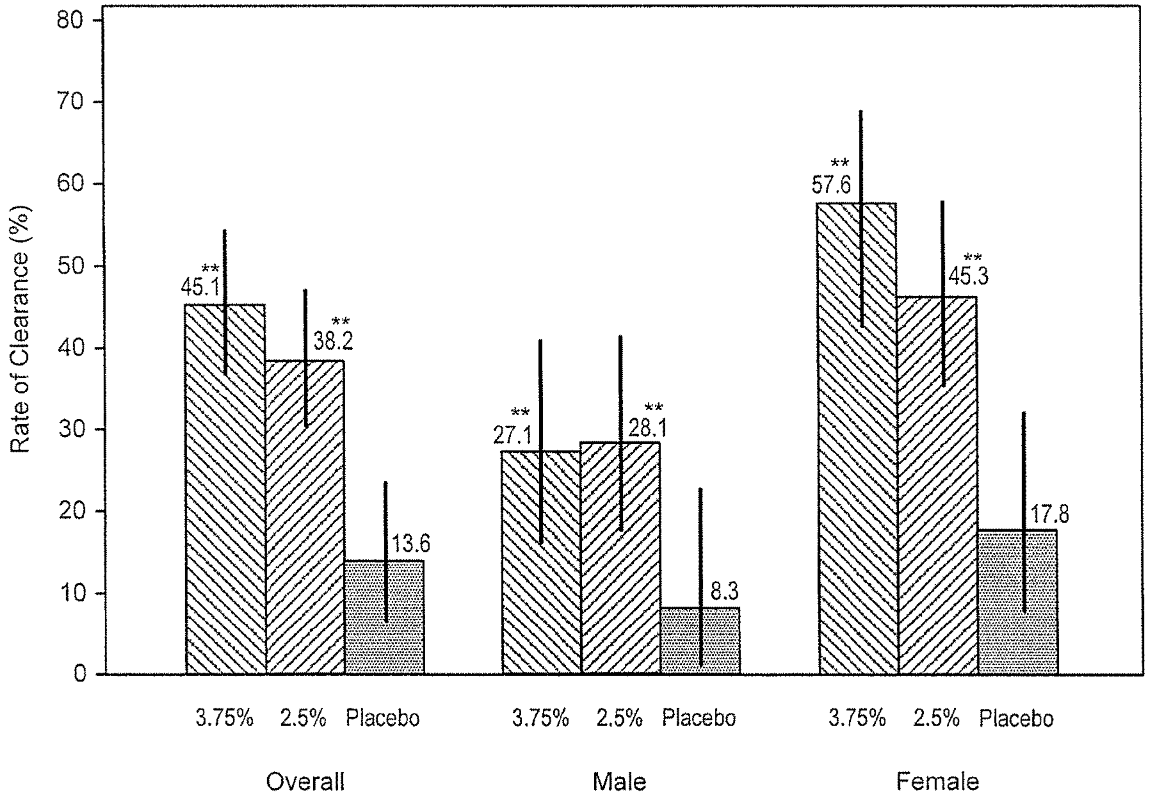
FIG. 20 shows partial (≥75%) clearance rates observed in the Per Protocol (PP) population at the end of one study of a lower-dose imiquimod treatment of genital warts.

Rates of partial (≥75%) clearance at EOS in the PP population are illustrated in FIG. 20.

Partial (≥75%) Clearance Rates at End of Treatment

The proportion of subjects who had a 75% or greater reduction from Baseline in wart count at EOT is summarized in Table 76 for the ITT population.

TABLE 76

Proportion of Subjects with Partial (≥75%) Clearance at End of Treatment-ITT Population (LOCF)

| | Imiquimod Cream | | |
|---|---|---|---|
| | 3.75% | 2.5% | Placebo |
| ITT Population (LOCF) at EOT | | | |
| n/N[a] (%) | 60/204 (29.4) | 44/202 (21.8) | 8/105 (7.6) |
| 95% CI | 23.3, 36.2 | 16.3, 28.1 | 3.3, 14.5 |
| P value vs placebo | <0.001** | 0.003** | — |
| P value vs 2.5% imiquimod cream | 0.054 | — | — |
| Males | | | |
| n/N[a] (%) | 19/88 (21.6) | 11/85 (12.9) | 1/49 (2.0) |
| 95% CI | 13.5, 31.6 | 6.6, 22.0 | 0.1, 10.9 |
| P value vs placebo | 0.002** | 0.029** | |
| P value vs 2.5% imiquimod cream | 0.134 | | |
| Females | | | |
| n/N[a] (%) | 41/116 (35.3) | 33/117 (28.2) | 7/56 (12.5) |
| 95% CI | 26.7, 44.8 | 20.3, 37.3 | 5.2, 24.1 |
| P value vs placebo | 0.001** | 0.027** | |
| P value vs 2.5% imiquimod cream | 0.193 | | |

LOCF = last observation carried forward,

95% CI = 95% confidence interval.

[a]n/N—number of subjects with complete clearance at end of treatment divided by the number of subjects analyzed.

Partial clearance was defined as at least a 75% reduction in the number of warts in the treatment area compared with Baseline. P values are from Cochran-Mantel-Haenszel test, stratified by gender and analysis. site (overall population) or stratified by analysis site (gender subgroups), taking 2 treatment groups at a time. P values marked with ** are statistically significant using Hochberg's modified Bonferroni procedure. Confidence intervals were calculated using the exact binomial statistics.

In the overall ITT population, the ≥75% clearance rate at EOT was significantly higher in the active treatment groups than in the placebo group. The difference between the active treatment groups was not statistically significant.

The ≥75% clearance rate at EOT was significantly higher with both active treatment groups compared with placebo in either gender. There was no significant difference between 3.75% and 2.5% imiquimod in either gender subgroup.

The partial (≥75%) clearance rate at EOT for the PP population is provided in Table 77.

TABLE 77

Proportion of Subjects with Partial (≥75%) Clearance at End of Treatment-PP Population (Observed Cases)

| | Imiquimod Cream | | |
|---|---|---|---|
| | 3.75% | 2.5% | Placebo |
| PP Population (OC), EOT | | | |
| n/N[a] (%) | 51/144 (35.4) | 39/144 (27.1) | 8/81 (9.9) |
| 95% CI | 27.6, 43.8 | 20.0, 35.1 | 4.4, 18.5 |
| P value vs placebo | <0.001** | 0.003** | — |
| P value vs 2.5% imiquimod cream | 0.047** | — | — |
| Males | | | |
| n/N[a] (%) | 16/59 (27.1) | 11/64 (17.2) | 1/36 (2.8) |
| 95% CI | 16.4, 40.3 | 8.9, 28.7 | 0.1, 14.5 |
| P value vs placebo | 0.007** | 0.031** | — |
| P value vs 2.5% imiquimod cream | 0.090 | — | — |

TABLE 77-continued

Proportion of Subjects with Partial (≥75%) Clearance at End of Treatment-PP Population (Observed Cases)

| | Imiquimod Cream | | |
|---|---|---|---|
| | 3.75% | 2.5% | Placebo |
| Females | | | |
| n/N[a] (%) | 35/85 (41.2) | 28/80 (35.0) | 7/45 (15.6) |
| 95% CI | 30.6, 52.4 | 24.7, 46.5 | 6.5, 29.5 |
| P value vs placebo | 0.003** | 0.036** | — |
| P value vs 2.5% imiquimod cream | 0.220 | — | — |

95% CI = 95% confidence interval,
OC = observed cases,
EOT = end of treatment
[a]n/N = number of subjects with complete clearance at end of treatment divided by the number of subjects analyzed.
Partial clearance was defined as at least a 75% reduction in the number of warts in the treatment area compared with Baseline. P values are from Cochran-Mantel-Haenszel test, stratified by gender and analysis site (overall population) or stratified by analysis site (gender subgroups), taking 2 treatment groups at a time. The P values marked with ** are statistically significant using Hochberg's modified Bonferroni procedure. Confidence intervals were calculated using the exact binomial distribution statistics.

In the overall PP population, the ≥75% clearance rate at EOT was significantly higher in the active treatment groups than in the placebo group. The partial (≥75%) clearance rate in the 3.75% imiquimod group was significantly higher (P=0.047) than that in the 2.5% imiquimod treatment group.

The ≥75% clearance rate at EOT was significantly higher with both active treatment groups compared with placebo for both genders. There was no significant difference between 3.75% and 2.5% imiquimod groups in either gender.

Partial (≥75%) Clearance Rates by Analysis Visit

Over the course of the study, the partial (≥75%) clearance rates were statistically significantly higher in the 3.75% and 2.75% imiquimod group compared with placebo at all analysis time points after Week 6, and were significantly higher for 3.75% compared with 2.5% imiquimod at Weeks 6, 12, and 14.

In both genders, the difference between each of the imiquimod treatment groups and placebo was statistically significant at Week 16. In the female subgroup, the difference between the active treatment groups was statistically significant (P=0.050).

The partial (≥75%) clearance rates were statistically significantly higher in the 3.75% and 2.75% imiquimod groups compared with placebo at all analysis time points after Week 8, and were significantly higher for 3.75% imiquimod group compared with 2.5% imiquimod at Weeks 6 and 10.

Subjects with at Least a 50% Reduction in Wart Count at End of Study

Figure 21:
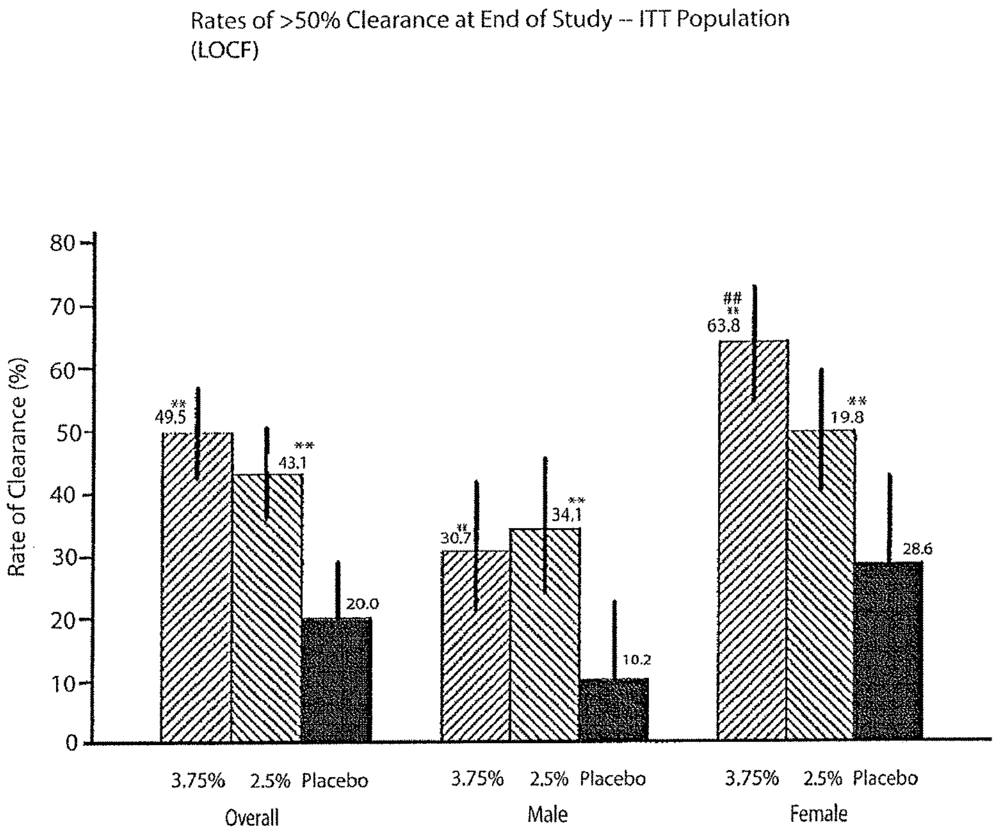
FIG. 21 shows ≥50% clearance rates observed in the intent-to-treat (ITT) population at the end of one study of a lower-dose imiquimod treatment of genital warts. Bars marked with the ** show statistically significant difference from placebo. Bars marked with show statistically significant difference from 2.5%. The thick vertical lines represent 95% confidence intervals.

Table 78 provides a summary of the ≥50% clearance rate at EOS for the ITT population (overall and by gender). The results are presented graphically in FIG. 21.

TABLE 78

Proportion of Subjects with ≥50% Clearance at End of Study-ITT Population (LOCF)

| | Imiquimod Cream | | |
|---|---|---|---|
| | 3.75% | 2.5% | Placebo |
| ITT Population (LOCF) at EOS | | | |
| n/N[a] (%) | 101/204 (49.5) | 87/202 (43.1) | 21/105 (20.0) |
| 95% CI | 42.5, 56.6 | 36.1, 50.2 | 12.8, 28.9 |
| P value vs placebo | <0.001** | <0.001** | — |
| P value vs 2.5% imiquimod cream | 0.154 | — | — |
| Males | | | |
| n/N[a] (%) | 27/88 (30.7) | 29/85 (34.1) | 5/49 (10.2) |
| 95% CI | 21.3, 41.4 | 24.2, 45.2 | 3.4, 22.2 |
| P value vs placebo | 0.007** | 0.002** | |
| P value vs 2.5% imiquimod cream | 0.617 | | |
| Females | | | |
| n/N[a] (%) | 74/116 (63.8) | 58/117 (49.6) | 16/56 (28.6) |
| 95% CI | 54.4, 72.5 | 40.2, 59.0 | 17.3, 42.2 |
| P value vs placebo | <0.001** | 0.009** | |
| P value vs 2.5% imiquimod cream | 0.027** | | |

LOCF—last observation carried forward,
95% CI = 95% confidence interval.
[a]n/N—number of subjects with complete clearance at end of study divided by the number of subjects analyzed.
50% clearance is defined as at least a 50% reduction in the number of warts in the treatment area compared with Baseline. P values are from Cochran-Mantel-Haenszel test, stratified by gender and analysis site (overall population) or stratified by analysis site (gender subgroups), taking 2 treatment groups at a time. P values marked with ** are statistically significant using Hochberg's modified Bonferroni procedure. Confidence intervals were calculated using the exact binomial distribution statistics.

In the overall ITT population, the rate of ≥50% clearance of EGW at EOS was significantly higher in each of the imiquimod treatment groups compared with placebo. The ≥50% clearance rate was higher in the 3.75% imiquimod group than in the 2.5% imiquimod group, but the difference between the 2 active treatment groups was not statistically significant.

The ≥50% clearance rate at EOS was significantly higher with both active treatment groups compared with placebo for both genders. The ≥50% clearance rate at EOS was significantly higher in the 3.75% imiquimod group compared with the 2.5% imiquimod group for females only. In males, the ≥50% clearance rate was higher in the 2.5% imiquimod group than in the 3.75% imiquimod group. However, the difference was not statistically significant.

Results in the PP population (overall and by gender) were similar to results in the ITT population.

Subjects with ≥50% Reduction in Wart Count at End of Treatment

Table 79 provides a summary of the ≥50% clearance rate at EOT for the ITT population (overall and by gender).

TABLE 79

Proportion of Subjects with ≥50% Clearance at End of Treatment-ITT Population (LOCF)

| | Imiquimod Cream | | |
|---|---|---|---|
| | 3.75% | 2.5% | Placebo |
| ITT Population (LOCF) at EOT | | | |
| n/N[a] (%) | 89/204 (43.6) | 74/202 (36.6) | 18/105 (17.1) |
| 95% CI | 36.7, 50.7 | 30.0, 43.7 | 10.5, 25.7 |
| P value vs placebo | <0.001** | <0.001** | |
| P value vs 2.5% imiquimod cream | 0.103 | | |

TABLE 79-continued

Proportion of Subjects with ≥50% Clearance at End of Treatment-ITT Population (LOCF)

| | Imiquimod Cream | | |
|---|---|---|---|
| | 3.75% | 2.5% | Placebo |
| Males | | | |
| n/N[a] (%) | 31/88 (35.2) | 25/85 (29.4) | 5/49 (10.2) |
| 95% CI | 25.3, 46.1 | 20.0, 40.3 | 3.4, 22.2 |
| P value vs placebo | <0.001** | 0.012** | |
| P value vs 2.5% imiquimod cream | 0.412 | | |
| Females | | | |
| n/N[a] (%) | 58/116 (50.0) | 49/117 (41.9) | 13/56 (23.2) |
| 95% CI | 40.6, 59.4 | 32.8, 51.4 | 13.0, 36.4 |
| P value vs placebo | <0.001** | 0.016** | |
| P value vs 2.5% imiquimod cream | 0.152 | | |

LOCF = last observation carried forward,
95% CI = 95% confidence interval.
[a]n/N of subjects with complete clearance at end of treatment divided by the number of subjects analyzed.
50% clearance was defined as at least a 50% reduction in the number of warts in the treatment area compared with Baseline. P values are from Cochran-Mantel-Haenszel test, stratified by gender and analysis site (overall population) or stratified by analysis site (gender subgroups), taking 2 treatment groups at a time. The P values marked with ** are statistically significant using Hochberg's modified Bonferroni procedure. Confidence intervals were calculated using the exact binomial distribution statistics.

In the overall ITT population, the ≥50% clearance rate at EOT was significantly higher in the active treatment groups than in the placebo group. The difference between the active treatment groups was not statistically significant. The ≥50% clearance rate at EOT was significantly higher with both active treatment groups compared with placebo for both gender subgroups. There was no significant difference between 3.75% and 2.5% imiquimod in either gender. In all treatment groups, the ≥50% clearance rates at EOT were higher in females than in males.

Results were similar in the PP population. In the overall PP population, the rate of ≥50% clearance of EGW at EOT was significantly higher in the active treatment groups compared to placebo. In both the male and female subgroups, the ≥50% clearance rate was significantly higher in both of the active treatment groups compared with placebo.

Subjects with ≥50% Reduction in Wart Count by Analysis Week

Figure 22:
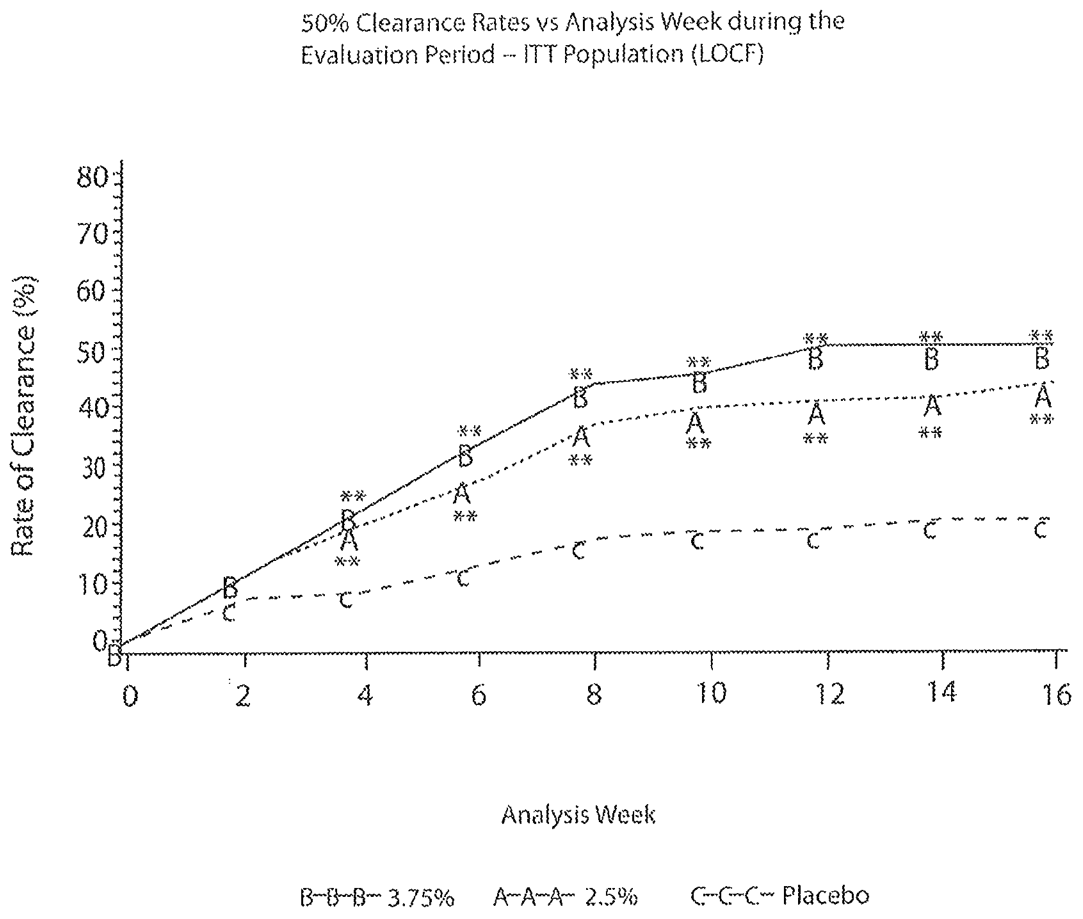
FIG. 22 shows ≥50% clearance rates vs analysis week during the evaluation period observed in the intent-to-treat (ITT) population in one study of a lower-dose imiquimod treatment of genital warts. 50% clearance is defined as at least a 50% reduction in the number of warts in the treatment area compared with Baseline. Points marked with ** show statistically significant difference from placebo. Subjects received treatment for 8 weeks or until complete clearance, whichever was sooner.

As shown in FIG. 22 for the overall ITT population, the difference between each of the imiquimod treatment groups and placebo was statistically significant at Week 16 (P<0.001 for 3.75% imiquimod and 2.5% imiquimod vs placebo), and at all post-Baseline assessment time points after Week 4. The ≥50% clearance rate in the 3.75% imiquimod group was higher than that in the 2.5% imiquimod treatment group at End of Study however the difference was not statistically significant.

In both genders, the difference between each of the imiquimod treatment groups and placebo was statistically significant at Week 16. In the female subgroup, the difference between the active treatment groups was statistically significant (P=0.027).

Results in the PP population were similar to those in the ITT population. Compared with placebo, the ≥50% clearance rate was significantly higher in both active treatment groups at all analysis time points after Week 4. The ≥50% clearance rate in the 3.75% imiquimod group was higher than that in the 2.5% imiquimod treatment group at End of Study however the difference was not statistically significant.

Wart Counts and Change and Percent Change from Baseline in Wart Counts

Summaries of the EGW counts, change from Baseline in EGW counts, and percent change from Baseline in EGW counts over the course of the study are presented in Table 80 below. The mean percent changes in EGW counts over time are presented graphically in FIG. 23.

TABLE 80

Summary of External Genital Wart Count from Baseline to End of Treatment/End of Study-ITT Population (LOCF)

| | Imiquimod Cream | | |
|---|---|---|---|
| | 3.75% (N = 204) | 2.5% (N = 202) | Placebo (N = 105) |
| Baseline | | | |
| Mean | 8.7 (7.5) | 7.7 (6.3) | 7.7 (6.3) |
| Median | 6 | 5 | 6 |
| Min, Max | 2, 48 | 2, 30 | 2, 29 |
| P value vs Placebo | 0.180 | 0.727 | |
| P value vs 2.5% Imiquimod | 0.158 | | |
| Week 8/EOT | | | |
| Mean | 5.5 (7.2) | 5.3 (5.6) | 7.2 (6.6) |
| Median | 3 | 3 | 5 |
| Min, Max | 0, 51 | 0, 25 | 0, 30 |
| Week 16/EOS | | | |
| Mean | 5.0 (7.3) | 4.7 (5.7) | 7.1 (6.8) |
| Median | 3 | 3 | 4 |
| Min, Max | 0, 65 | 0, 29 | 0, 31 |
| Change from Baseline to EOS | | | |
| Mean | −3.7 (7.1) | −3.0 (4.9) | −0.6 (3.7) |
| Median | −2 | −1 | 0 |
| Min, Max | −43, 40 | −30, 7 | −15, 11 |
| P value vs Placebo | <0.001** | <0.001** | |
| P value vs 2.5% Imiquimod | 0.643 | | |
| Percent Change from Baseline to EOS | | | |
| Mean | −40.9 (56.9) | −37.7 (46.2) | −7.8 (46.8) |
| Median | −46.8 | −19.1 | 0.0 |
| Min, Max | −100, 160 | −100, 67 | −100, 183 |
| P value vs Placebo | <0.001** | <0.001** | |
| P value vs 2.5% Imiquimod | 0.641 | | |

P values are from Cochran-Mantel-Haenszel test, stratified by gender and analysis site, taking 2 treatment groups at a time. Change from Baseline is calculated as the post-Baseline value minus the Baseline value. Change from Baseline P values are from analysis of covariance (ANCOVA), controlling for Baseline wart count, gender, and analysis site. The P values marked with ** are statistically significant using Hochberg's modified Bonferroni procedure.

The mean EGW count at Baseline was similar between all the treatment groups for the ITT population. At EOT the EGW counts were lowest in the 3.75% imiquimod group and highest in the placebo group. At EOS the EGW counts were lowest in the 2.5% imiquimod group and highest in the placebo group. At EOS, the mean change from Baseline was significantly greater in the active treatment groups compared with placebo. The difference in mean change between the active treatment groups was not statistically significant.

In the gender subgroups, the Baseline EGW counts were higher in the 3.75% imiquimod group and 2.75% imiquimod group in both genders compared with placebo however the difference was not statistically significant. The mean change and mean percent change from Baseline in EGW count was significantly larger for both active treatment groups versus placebo in males and in females.

Figure 23:
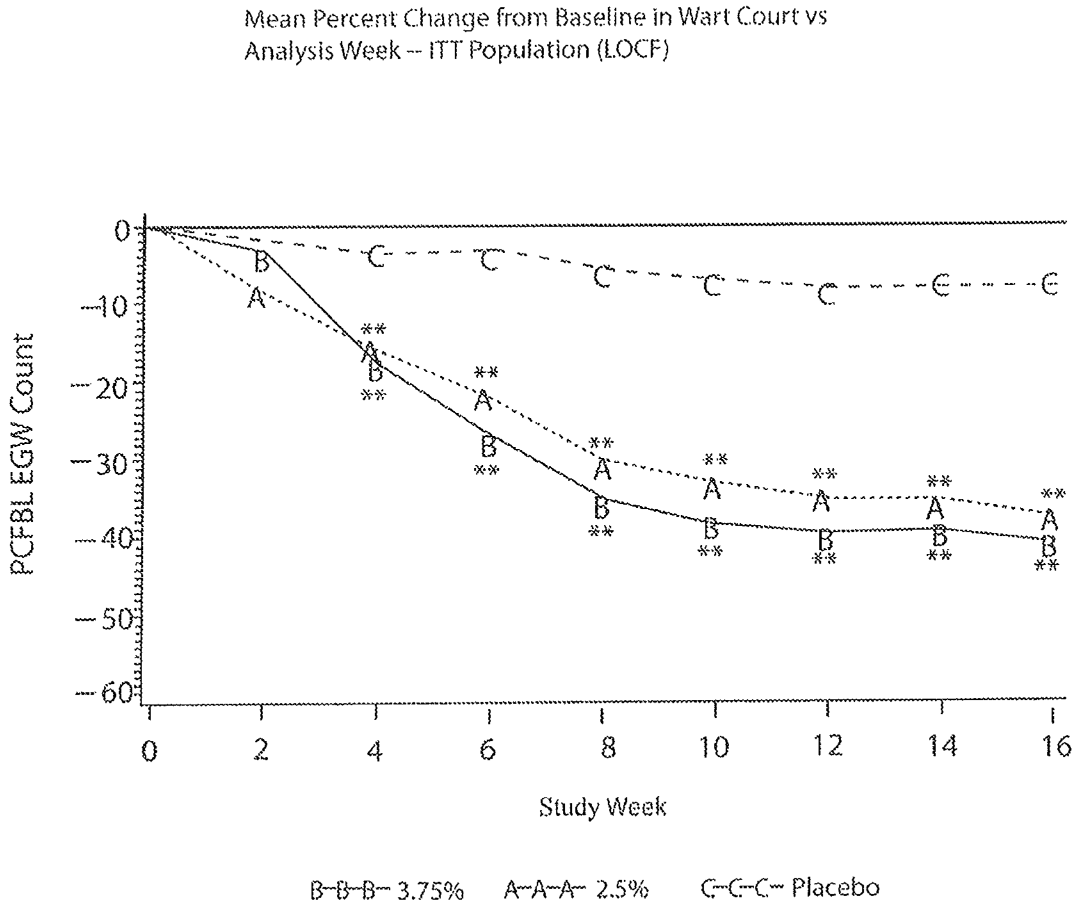
FIG. 23 shows mean percent change from baseline in wart count vs. analysis week observed in the intent-to-treat (ITT) population in one study of a lower-dose imiquimod treatment of genital warts. PCFBL=Percent Change from Baseline. Points marked with the ** show statistically significant difference from placebo. Subjects received treatment for 8 weeks or until complete clearance, whichever was sooner.

As shown in FIG. 23 for the ITT population, the mean percent decrease from Baseline in wart count in the 2 active treatment groups was consistently larger than placebo, and the differences between the 2 active treatment groups compared with placebo were statistically significant at all post-Baseline analysis time points after Week 4. The differences between the 3.75% imiquimod and 2.5% imiquimod groups were not statistically significant at any time during the study.

For the PP population, summaries of the EGW counts, change from Baseline in EGW counts, and percent change from Baseline in EGW counts over the course of the study are presented in Table 81.

TABLE 81

Summary of External Genital Wart Count from Baseline to End of Treatment and End of Study-PP Population (Observed Cases)

| | Imiquimod Cream | | |
|---|---|---|---|
| | 3.75% | 2.5% | Placebo |
| **Baseline** | | | |
| N | 144 | 144 | 81 |
| Mean | 8.4 (7.2) | 7.6 (6.4) | 7.8 (6.3) |
| Median | 6 | 5 | 6 |
| MM, Max | 2, 32 | 2, 30 | 2, 29 |
| P value vs Placebo | 0.174 | 0.726 | |
| P value vs 2.5% Imiquimod | 0.340 | | |
| **End of Treatment (EOT)** | | | |
| N | 119 | 125 | 72 |
| Mean | 5.3 (7.7) | 4.7 (5.2) | 7.3 (6.3) |
| Median | 3 | 3 | 5 |
| Min, Max | 0, 51 | 0, 25 | 0, 23 |
| **End of Study (EOS)** | | | |
| N | 87 | 93 | 65 |
| Mean | 6.4 (9.0) | 5.2 (5.8) | 7.8 (7.0) |
| Median | 4 | 3 | 6 |
| Min, Max | 0, 65 | 0, 29 | 0, 31 |
| **Change from Baseline at EOS** | | | |
| N | 87 | 93 | 65 |
| Mean | −3.1 (7.3) | −3.0 (5.5) | 0.2 (3.7) |
| Median | −2 | −1 | 0 |
| Min, Max | −25, 40 | −30, 5 | −15, 11 |
| P value vs Placebo | 0.024** | <0.001** | |
| P value vs 2.5% Imiquimod | 0.208 | | |
| **Percent Change from Baseline at EOS** | | | |
| N | 87 | 93 | 65 |
| Mean | −30.6 (56.2) | −28.9 (40.8) | 2.9 (45.9) |
| Median | −33.3 | −20.8 | 0.0 |
| Min, Max | −100, 160 | −100, 67 | −100, 183 |
| P value vs Placebo | <0.001** | <0.001** | |
| P value vs 2.5% Imiquimod | 0.346 | | |

P values are from Cochran-Mantel-Haenszel test, stratified by gender and analysis site, taking 2 treatment groups at a time. Change from Baseline is calculated as the post-Baseline value minus the Baseline value. Change from Baseline P values are from analysis of covariance (ANCOVA), controlling for Baseline wart count, gender, and analysis site. The P values marked with ** are statistically significant using Hochberg's modified Bonferroni procedure.

The mean EGW count at Baseline was similar across the treatment groups for the PP population. At both EOT and EOS, the EGW counts were lowest in the 2.5% imiquimod group and highest in the placebo group in the PP population. At EOS, the mean change and mean percent change from Baseline in EGW count was significantly greater in the active treatment groups compared with placebo, however the difference between the active treatment groups was not statistically significant.

In the female subgroup only, the mean change and mean percent change from Baseline in EGW count at EOS was significantly lower in both active treatment groups compared with placebo, and there was no significant difference between the active treatment groups. In males, the mean change and mean percent change was lower in both active treatment groups compared with placebo; the difference in mean change was significant only for the 2.5% imiquimod group, but the difference in mean percent change was significant for both the 3.75% and 2.5% imiquimod groups.

The mean percent decrease from Baseline in wart count in the 2 active treatment groups was consistently larger than placebo. The differences between the active treatment groups and placebo were statistically significant at all post-Baseline time points after Week 4 with the exception of the 2.5% imiquimod group at Week 12, The differences between the 3.75% imiquimod and 2.5% imiquimod groups were not statistically significant at any analysis time point.

Time to Complete Clearance

Summaries of the time to complete clearance are shown in Table 82 below.

TABLE 82

Time to Clearance (days) for the ITT population

| | Imiquimod Cream | | |
|---|---|---|---|
| | 3.75% (N = 204) | 2.5% (N = 202) | Placebo (N = 105) |
| **All Subjects (Kaplan-Meier)** | | | |
| N | 204 | 202 | 105 |
| $1^{st}$ Quartile | 71.0 | 101.0 | >57 |
| Median time to complete clearance, including all subjects, days | 123.0 | ≥101 | ≥112.0 |
| P value vs Placebo | <0.001 | <0.001 | — |
| P value vs 2.5% imiquimod cream | 0.474 | — | |
| **Only Subjects Who Attained Clearance** | | | |
| N | 60 | 50 | 9 |
| $1^{st}$ Quartile | 47.0 | 43.0 | 34.0 |
| Median time to complete clearance, including only subjects who attained clearance, days | 60.0 | 63.0 | 71.0 |
| $3^{rd}$ Quartile | 81.5 | 100.0 | 91.0 |

P values are from the log rank test comparing survival curves in the Kaplan-Meier framework, taking 2 treatment groups at a time.

Although the median time to complete clearance for the ITT treatment group was not reached, the median time to complete clearance in the ITT population was statistically significantly shorter in the 2 active treatment groups compared with placebo (P≤0.001 using the log-rank test). The difference between the 2 imiquimod treatment groups was not statistically significant (P=0.474).

For those subjects who attained complete clearance, the median time to complete clearance was 60 days in the 3.75% imiquimod group, 63 days in the 2.75% imiquimod group, and 71 days in the placebo group.

Results in the PP population were similar to those in the ITT population. Among the subset of subjects who achieved complete clearance in the PP population, the median time to clearance was 64 days in the 3.75% imiquimod group, 63 days in the 2.5% imiquimod group, and 71 days in the placebo group.

Complete clearance was achieved more rapidly in female subjects compared with males in both the ITT and PP populations.

Sustained Complete Clearance Rate at Week 12 of the Follow-Up for Recurrence Period The numbers of subjects who remained clear in the follow-up period or who had a recurrence of EGW are presented in Table 83 below.

TABLE 83

Wart Recurrence Rate-Follow-up for Recurrence Population (LOCF)

| | Imiquimod Cream | | |
|---|---|---|---|
| | 3.75% (N = 5) | 2.5% (N = 43) | Placebo (N = 7) |
| Recurrence Follow-up-Week 12 | | | |
| Subjects who remained clear[a], n/N (%) | 34/53 (64.2) | 29/43 (67.4) | 7/7 (100.0) |
| Subjects who had a recurrence, n/N (%) | 10/53 (18.9) | 7/43 (16.3) | 0 |
| Missed at Week 12 Visit | 9/53 (17.0) | 7/43 (16.3) | 0/7 (0.0) |
| 95% Confidence interval | 9.4, 32.0 | 6.8, 30.7 | — |

[a]Includes those who had a visit within window with no warts

Thirty-four subjects (64.2%) in the 3.75% imiquimod group, 29 subjects (67.4%) in the 2.5% imiquimod group, and 7 subjects (100%) in the placebo group achieved complete clearance at EOS that was sustained throughout the 12-week follow-up period. Data were missing for 9 subjects (17.0%) in the 3.75% imiquimod group and 7 subjects (16.3%) in the 2.5% imiquimod group, so their recurrence status was not known, but at least 18.9% of the 3.75% imiquimod group and 16.3% of the 2.5% imiquimod group in the follow-up for recurrence population are known to have shown recurrence of EGW within 12 weeks of the initial clearance.

Statistical/Analytical Issues

Adjustments for Covariates

The primary efficacy analysis was based on a CMH test, stratified by gender and analysis site. Secondary analyses were performed in a number of subgroups. No other adjustments for covariates were planned.

Handling of Dropouts or Missing Data

For the primary ITT analysis, missing observations due to early discontinuation were imputed using the LOCF. Screening data were carried forward if no baseline data existed for the subject. Baseline data were carried forward if no post-baseline data existed for the subject. Additional analyses of the primary efficacy variable were performed in which (1) all missing observations were considered as failures and (2) using only observed cases, without imputations. The results of these additional analyses are presented in the Table 84 below.

TABLE 84

Proportion of Subjects with Complete Clearance at End of Study (Sensitivity and Supporting Analyses)-ITT Population

| | Imiquimod Cream | | |
|---|---|---|---|
| | 3.75% (N = 204) | 2.5% (N = 202) | Placebo (N = 105) |
| ITT Population (all subjects with missing data were counted as failures) | | | |
| n/N[a] (%) | 60/204 (29.4) | 51/202 (25.2) | 9/105 (8.6) |
| 95% CI | 23.3, 36.2 | 19.4, 31.8 | 4.0, 15.6 |
| P value vs Placebo | <0.001** | <0.001** | — |
| P value vs 2.5% Imiquimod Cream | 0.231 | — | |
| ITT Population (observed cases) | | | |
| n/N[a] (%) | 60/204 (29.4) | 50/202 (24.8) | 9/105 (8.6) |
| 95% CI | 23.3, 36.2 | 19.0, 31.8 | 4.0, 15.6 |
| P value vs Placebo | <0.001** | 0.001** | — |
| P value vs 2.5% Imiquimod Cream | 0.231 | — | |

95% CI = 95% confidence interval

[a]n/N = number of subjects with complete clearance at end of study divided by the number of subjects analyzed.

P values are from Cochran-Mantel-Haenszel test, stratified by gender and analysis site, taking 2 treatment groups at a time. P-values marked with ** are statistically significant using Hochberg's modified Bonferroni procedure. Confidence intervals were calculated using the exact binomial distribution.

Results of these additional analyses are identical to those obtained based upon LOCF for all treatment groups.

Multicenter Studies

In order to obtain at least 6 subjects per site per active treatment group, investigational sites yielding fewer than 15 subjects were combined in order of geographic proximity. The exact composition of these "analysis sites" was determined and documented prior to breaking the study blind. The stratification for CMH analyses was based on the analysis sites, not on the actual investigational sites.

Multiple Comparison/Multiplicity

The primary efficacy endpoint, complete clearance rate at the End of Study, was analyzed using Cochran-Mantel-Haenszel (CMH) statistics, stratifying on gender and site. As mentioned above, all pairwise comparisons of active treatment versus placebo were made using Hochberg's modified Bonferroni procedure. If either test was significant at a 0.025 level of significance, then that test was considered significant. Otherwise, if both tests were significant at 0.05, then both tests were considered significant. The 3.75% and 2.5% treatment groups were compared to each other at the 0.05 level of significance if at least one of these treatment groups was found to be different than the placebo using the Hochberg's test.

The 4 secondary efficacy variables were to be tested hierarchically using Hochberg's modified Bonferroni procedure to conserve Type 1 error. First, only if the primary endpoint showed statistical significant could the first secondary efficacy variable be tested. If the prior secondary efficacy variable showed statistical significance then the next secondary efficacy variable could be tested, etc.

Use of an "Efficacy Subset" of Subjects

Efficacy variables were analyzed for a Per Protocol (PP) subset of subjects. The PP population included all subjects in the ITT population who had no major protocol violations: 144 subjects in the 3.75% imiquimod treatment group, 144 subjects in the 2.5% imiquimod treatment group, and 81 subjects in the placebo group. The demographic and baseline characteristics in the PP population were similar to those in the population, although the mean total wart area decreased in the 3.75% imiquimod group.

In the analysis of the primary efficacy variable, the results in the PP population were similar to those in the ITT population. The proportion of subjects with complete clearance at Week 16/EOS was statistically significantly greater in the active treatment groups compared with placebo.

Results in the PP population for the other efficacy variables were also similar to those from the ITT population.

Examination of Subgroups

The primary efficacy variable was summarized without statistical testing by, investigator site, by analysis site, by investigator medical specialty, by gender, by age subgroup, by race subgroup, by baseline EGW count subgroup, by baseline wart areas, by anatomic locations (inguinal, perineal, perianal, glans penis, penis shaft, scrotum, foreskin, or vulva), by number of anatomic locations affected by EGW (ie, one location versus multiple), by whether first EGW episode, by duration from first diagnosis of EGW, by rest periods (yes or no), and by previous treatment with imiquimod (yes or no).

In general, the complete clearance rates increased in a dose-dependent manner regardless of subgroup. The most striking subgroup effect was observed in the analysis by gender. Complete clearance at EOS was attained by 17.0%, 15.3%, and 4.1% of male subjects, and by 38.8%, 31.6%, and 12.5% of females in the 3.75%, 2.5%, and placebo groups, respectively.

The complete clearance tended to be higher in the following subgroups:

- Females;
- Lower baseline wart count (≤7 compared with >7);
- Baseline wart area ≤70 $mm^2$;
- Subjects with baseline warts in the perianal, perineal and glans penis;
- Subjects who took a rest period (noted in the imiquimod groups but not placebo);
- No previous imiquimod treatment (noted in the imiquimod groups but not placebo).

In the 3.75% imiquimod group, the complete clearance rate was higher in older subjects (>35 years) compared with younger subjects.

When analyzed by analysis site or investigative site subgroups, the complete clearance rate was highest in the 3.75% imiquimod group at 12/24 analysis sites and 17/43 investigative sites.

When analyzed by investigator site specialty subgroups, the highest overall complete clearance rates were observed at sites specializing in gynecology (sites where more females were enrolled) or infectious disease. At sites specializing in dermatology and urology, the clearance rates decreased with increasing imiquimod dose. Few subjects in any treatment group attained complete clearance at sites specializing in dermatology or urology (sites at which only male subjects were enrolled) or infectious disease.

Additional Analysis by Gender

Additional analyses of the data were performed to explore the possible effect of gender on efficacy. Of the 511 subjects randomized into the trial, 222 (43.4%) were male and 289 (56.6%) were female. Similar percentages of males and females completed the evaluation period. Lost to follow-up and subject's request were the most common reasons for study discontinuation in both genders. The time to loss of follow-up was similar in the active treatment groups for both genders. However, in males, the highest percentage of subjects lost to follow-up were in the 3.75% imiquimod group, and in females, the highest percentage of subjects lost to follow-up were in the 2.5% imiquimod group.

As in the overall population, the response with 3.75% imiquimod cream was significantly superior to that with placebo in both genders. The complete clearance rates were consistently higher in females compared with males in all treatment groups for both the ITT and PP populations, including the sensitivity and supporting analyses of the ITT population.

A summary of complete clearance of all anatomic sites at EOS by baseline involvement of anatomic locations is presented in Table 85 below. Of note, a majority of subjects of each gender had involvement of more than one anatomic site at baseline.

TABLE 85

Complete Clearance at End of Study by Baseline Anatomic Location,-ITT Population (LOCF)

| | Imiquimod Cream | | |
|---|---|---|---|
| Baseline anatomic location | 3.75% (N = 204) | 2.5% (N = 202) | Placebo (N = 105) |
| Both genders-n/N (%)[a] | | | |
| Inguinal | 3/35 (8.6) | 7/36 (19.4) | 1/23 (4.3) |
| Perinea] | 26/67 (38.8) | 18/61 (29.5) | 2/32 (6.3) |
| Perianal | 28/61 (45.9) | 19/57 (33.3) | 4/31 (12.9) |
| Males-n/N (%)[a] | | | |
| Inguinal | 1/24 (4.2) | 2/17 (11.8) | 1/19 (5.3) |
| Perinea] | 1/6 (16.7) | 1/8 (12.5) | 0/3 (0.0) |
| Perianal | 3/8 (37.5) | 0/6 (0.0) | 0/5 (0.0) |
| Glans Penis | 4/9 (44.4) | 3/11 (27.3) | 0/5 (0.0) |
| Penis Shaft | 10/71 (14.1) | 12/76 (15.8) | 2/39 (5.1) |
| Scrotum | 0/19 (0.0) | 1/16 (6.3) | 0/14 (0.0) |
| Foreskin | — | 0/2 (0.0) | 0/2 (0.0) |
| Females-n/N (%)[a] | | | |
| Inguinal | 2/11 (18.2) | 5/19 (263) | 0/4 (0.0) |
| Perineal | 25/61 (41.0) | 17/53 (32.1) | 2/29 (6.9) |
| Perianal | 25/53 (47.2) | 19/51 (37.3) | 4/26 (15.4) |
| Vulva | 31/86 (36.0) | 22/78 (28.2) | 5/31 (16.1) |

[a]Subjects with complete clearance are included in the numerator.

In the anatomic areas common to both genders, perineal and perianal involvements were relatively common in females: few males had baseline disease in those areas. Females with perineal or perianal EGW at Baseline demonstrated relatively high rates of complete clearance at EOS. The third most common anatomic site, the inguinal area, was present in more males in the 3.75% imiquimod and placebo groups but comparable in both genders in the 2.5% imiquimod group. Females in the active treatment groups had a higher rate of complete clearance than males. The lowest clearance rates occurred in subjects with inguinal area involvement (at Baseline) in all treatment groups. The complete clearance rates at EOS by baseline anatomic location for each gender are shown in Table 85.

The anatomic areas most commonly affected with EGW at Baseline in males were the penis shaft, inguinal, and scrotum area. The complete clearance rates were highest in the subjects whose EGW at Baseline was in the glans penis and perianal area for the 3.75% imiquimod group compared with the 2.5% imiquimod group and placebo. In females, the vulva, perineal, and perianal areas were the areas most commonly affected with EGW at Baseline. The complete clearance rates were highest with 3.75% imiquimod for all baseline anatomic areas with the exception of the inguinal area in females.

In both genders, complete clearance rates were higher in subjects who took a rest period from imiquimod treatment compared with those who did not take a rest period. The complete clearance rates in males and females were higher for subjects >35 years of age than in younger subjects. Females with a first EGW diagnosis within one year had higher clearance rates than those with a longer EGW history. Males with a first EGW diagnosis after one year had higher clearance rates than those with a shorter EGW history.

Exploratory Analysis of Anatomic Specific Complete Clearance

In this study, subjects applied study medication to individual warts in various anatomic areas identified at Baseline. Some subjects developed new warts during the study. These new warts may have appeared within anatomic areas already displaying EGW at Baseline and/or these new warts may have appeared in 'new' anatomic areas that had not been exposed to study medication at initiation of treatment. New warts were treated with study medication when they appeared, but received less than a full course of treatment, because treatment was not extended beyond 8 weeks from randomization.

An exploratory analysis of complete clearance within the specific anatomic areas affected with EGW at Baseline was performed for the overall ITT population and by gender.

Drug Dose, Drug Concentration, and Relationships to Response

This study examined the efficacy of 2.5% imiquimod cream and 3.75% imiquimod cream, that was applied once daily for a maximum of 8 weeks. Subjects self-applied a maximum of 1 packet (250 mg) of study drug per application. No sample collection for pharmacokinetic determinations was planned in this study; therefore, no analysis of drug concentration was done.

A dose response was observed in this study. The 3.75% imiquimod cream consistently demonstrated higher efficacy rates compared with the 2.5% imiquimod cream for all primary and secondary efficacy measures, in both the ITT and PP populations. The difference between the 2 active treatment groups was not statistically significant for primary efficacy analysis, secondary and tertiary efficacy variables.

Efficacy Conclusions

The investigational products 3.75% imiquimod cream and 2.5% imiquimod cream met the criteria for efficacy as defined in this protocol.

For the primary endpoint (the rate of complete clearance of EGW at Week 16/EOS), results with 3.75% imiquimod cream and 2.5% imiquimod cream were statistically significantly superior to results with the placebo cream ($P<0.001$). This effect was observed in both the ITT and PP populations. In the ITT population, the complete clearance rates were 29.4% and 24.8%, respectively, in the 3.75% and 2.5% imiquimod treatment groups, compared with 8.6% in the placebo group. Results in the 3.75% imiquimod group were numerically but not statistically higher than in the 2.5% imiquimod group.

The complete clearance rate at end of treatment (EOT) was statistically significantly superior with both active treatment groups compared with placebo overall and in the female subgroup in both the ITT and PP populations.

Over the course of the study, the complete clearance rates were significantly superior with both active treatment groups compared with placebo at every analysis time point after Week 8 in both the ITT and PP populations. Clearance rates were higher in the 3.75% imiquimod group than in the 2.5% imiquimod group however the difference was not statistically significant at any time point during the evaluation period.

The partial (≥75%) clearance rate in both active treatment groups was statistically significantly superior to the placebo cream at Week 16/EOS for the ITT population and PP population (overall and in both genders). Results were significantly higher for the active treatment groups at all analysis time points after Week 4 for the ITT and PP populations.

Over the course of the study, the partial (≥75%) clearance rates were significantly superior with both active treatment groups at every analysis time point after Week 6 (ITT population) and Week 8 (PP population). Results were significantly higher for the 3.75% imiquimod vs 2.5% imiquimod at Weeks 6, 12, and 14.

The ≥50% clearance rate at EOS was significantly greater in both active treatment groups compared with placebo in both the ITT and PP populations, Results were higher in the 3.75% imiquimod group vs 2.5% imiquimod however the difference was not statistically significant.

Over the course of the study, the ≥50% clearance rates were significantly superior with both active treatment groups compared with placebo at every analysis time point after Week 4 in both the ITT and PP populations.

The complete and partial clearance rates were consistently higher in the female subgroup compared with the male subgroup in all treatment groups. Mean change and percent change from Baseline in EGW counts were consistently higher in females compared with males in the active treatment groups.

At EOS, the mean percent change from Baseline in wart count with 3.75% imiquimod cream and 2.5% imiquimod cream was statistically significantly greater than with placebo ($P\leq0.001$) in the ITT and PP populations.

Although the median time to complete clearance for the ITT treatment group was not reached, the median time to complete clearance in the ITT population was statistically significantly shorter in the 2 active treatment groups compared with placebo ($P\leq0.001$ using the log-rank test). The difference between the 2 imiquimod treatment groups was not statistically significant ($P=0.474$). For those subjects who attained complete clearance, the median time to complete clearance was 60 days in the 3.75% imiquimod group, 63 days in the 2.75% imiquimod group, and 71 days in the placebo group.

Thirty-four of 53 subjects (64.2%) in the 3.75% imiquimod group remained completely clear of EGW through the 12-week follow-up period, while 10/53 subjects had wart recurrence. The status is unknown for 9/53 subjects. Twenty-nine of 43 subjects (67.4%) in the 2.5% imiquimod group (with 7 missing subjects), and 7 of 7 subjects in the placebo group remained clear through the follow-up period, Thus, at least 64.2% of the 3.75% imiquimod group and 67.4% of the 2.5% imiquimod group in the follow-up for recurrence population are known to have sustained clearance of all anatomic sites for at least 12 weeks from initial clearance.

Safety Evaluation

Extent of Exposure

An overall summary of study drug exposure for the ITT population is presented in Table 86 below. One subject was originally randomized to the 2.5% imiquimod treatment group; however, at Week 2, the subject incorrectly received a 3.75% imiquimod treatment group kit assigned to another subject. For the safety analysis the highest dose received (3.75% imiquimod) was used and the subject was considered as part of the safety population instead of the ITT population.

TABLE 86

Overall Study Drug Exposure-ITT Population

| | Imiquimod Cream | | |
|---|---|---|---|
| | 3.75% (N = 204) | 2.5% (N = 202) | Placebo (N = 105) |
| Treatment duration, days[a]-All subjects | | | |
| N | 172 | 163 | 89 |
| Mean ± SD | 50.0 (15.6) | 50.8 (15.3) | 54.7 (10.9) |
| Median | 56 | 56 | 56 |
| MM, Max | 1, 89 | 3, 97 | 13, 73 |
| Total number of packets used | | | |
| N | 164 | 159 | 86 |
| Mean ± SD | 43.8 (14.4) | 45.1 (14.2) | 52.7 (9.5) |
| Median | 48 | 51 | 56 |
| Min, Max | 6, 72 | 3, 65 | 13, 76 |
| Number of days treated[b] | | | |
| N | 172 | 163 | 89 |
| Mean ± SD | 43.7 (15.4) | 45.6 (15.5) | 52.0 (10.9) |
| Median | 50 | 52 | 55 |
| Min, Max | 1, 74 | 3, 92 | 13, 69 |
| Percent of Treatment Compliance[c] | | | |
| N | 191 | 180 | 97 |
| Mean ± SD | 83.2 (26.7) | 86.5 (23.2) | 91.1 (20.8) |
| Median | 95 | 96 | 98 |
| MM, Max | 0, 116 | 13, 118 | 25, 123 |

SD—standard deviation,
min = minimum,
max = maximum.
[a]Duration of treatment is date of last dose minus date of first dose plus 1. Last dose is defined as last date on study medication.
[b]Days treated is the duration of treatment minus rest period days and missed doses.
[c]Based on either packet use compliance or treatment days compliance whichever is greater.

The mean treatment duration, number of study medication packets, and number of days were numerically highest in the placebo group compared with the 3.75% and 2.5% imiquimod treatment groups.

Based on the available data, on average, the subjects used 43.8 packets of 3.75% imiquimod, 45.1 packets of 2.5% imiquimod, and 52.7 packets of placebo. Mean treatment duration was 50.0 days in the 3.75% imiquimod treatment group, 50.8 days in the 2.5% imiquimod treatment group, and 54.7 days in the placebo group. When rest periods and missed doses were subtracted, the total number of days treated was reduced to 43.7, 45.6, and 52.0 days in the 3.75% imiquimod, 2.5% imiquimod, and placebo groups, respectively.

The mean number of packets used, number of days treated, and percent treatment compliance were higher in the males than in females in the active treatment groups in the ITT and safety populations. Mean treatment duration was higher in males than in females for the 2.5% imiquimod group in the ITT population. There was no difference between genders in the placebo group.

Adverse Events (AEs)

Brief Summary of Adverse Events

A summary of the overall incidence of AEs is provided in Table 87 below for the safety population.

TABLE 87

Summary of Adverse Events-Safety Population

| | Imiquimod Cream | | |
|---|---|---|---|
| | 3.75% (N = 205) | 2.5% (N = 201) | Placebo (N = 105) |
| Subjects with any AE, n (%) | 103 (50.2) | 101 (50.2) | 43 (41.0) |
| Number of AEs | 286 | 227 | 75 |
| Subjects with any: | | | |
| Treatment-related[a] AE, n (%) | 40 (19.5) | 37 (18.4) | 3 (2.9) |
| SAE, n (%) | 7 (3.4) | 2 (1.0) | 1 (1.0) |
| AEs of severe intensity, n (%) | 15 (7.3) | 10 (5.0) | 4 (3.8) |
| AE leading to study discontinuation, n (%) | 3 (1.5) | 5 (2.5) | 0 |

AE—adverse event,
SAE—serious adverse event
[a]Includes "Probably related" and "Related" AEs.
Counts reflect numbers of subjects in each treatment group reporting one or more adverse events that map to the MedDRA system organ class. A subject may be counted once only in each row of the table. A treatment-emergent AE is an AE that began or worsened in severity after Day I and no more than 30 days after the last application of study drug. Subject 03/012 in the 2.5% imiquimod group, who discontinued from the study at the subject's request (CRF page 31) was also recorded as discontinued from the study due to an adverse event.

The number of subjects who experienced any AE (including those not considered treatment emergent) was similar in the active treatment groups (103 [50.2%] and 101 [50.2%] in the 3.75% and 2.5% imiquimod groups, respectively) and lower in the placebo group (43, [41.0%]). The number of subjects with AEs considered treatment-related or severe in intensity was similar in the active treatment groups and lower in the placebo group. Seven (3.4%) of subjects in the 3.75% imiquimod group experienced an SAE. The number of subjects with an SAE or who withdrew from the study due to an AE was low in the other 2 treatment groups.

An overall summary of the incidence of treatment-emergent AEs is provided in Table 88 below.

TABLE 88

Summary of Treatment-Emergent Adverse Events-Safety Population

| | Imiquimod Cream | | |
|---|---|---|---|
| | 3.75% (N = 205) | 2.5% (N = 201) | Placebo (N = 105) |
| Subjects with any AE, n (%) | 91 (44.4) | 82 (40.8) | 34 (32.4) |
| Number of AEs | 216 | 167 | 51 |
| Subjects with any: | | | |
| Treatment-related[a] AE, n (%) | 40 (19.5) | 37 (18.4) | 3 (2.9) |
| Application site AE, n (%) | 35 (17.1) | 33 (16.4) | 3 (2.9) |
| SAE, n (%) | 6 (2.9) | 2 (1.0) | 1 (1.0) |
| AEs of severe intensity, n (%) | 14 (6.8) | 9 (4.5) | 3 (2.9) |
| AE leading to study discontinuation, n (%) | 3 (1.5) | 5 (2.5) | 0 |

AE = adverse event,
SAE = serious adverse event
[a]Includes "Probably related" and "Related" AEs.
Counts reflect numbers of subjects in each treatment group reporting one or more adverse events that map to the MedDRA system organ class. A subject may be counted once only in each row of the table. A treatment-emergent AE is an AE that began or worsened in severity after Day f and no more than 30 days after the last application of study drug.

The number of subjects with treatment-emergent AEs was similar in the active treatment groups (91 [44.4%] and 82 [40.8%] in the 3.75% and 2.5% imiquimod groups, respectively) and lower in the placebo group (34, [32.4%]). The number of subjects with AEs considered treatment-emergent or severe in intensity was similar in the active treatment groups and lower in the placebo group. A higher percentage of subjects in the active treatment groups had application site reactions compared with placebo. The number of subjects with an SAE or who withdrew from the study due to an AE was relatively low in all treatment groups.

Most Frequent Adverse Events

A treatment-emergent AE was defined as an AE that began or worsened in severity after the first application of the study drug and no more than 30 days after the last application of the study drug. The incidence of the most commonly-occurring treatment-emergent AEs is presented by preferred term in Table 89 below.

TABLE 89

Number (%) of Subjects with Most Frequent TreatmentEmergent Adverse Events (≥1% in any active treatment group)-Safety Population

| | Imiquimod Cream | | |
|---|---|---|---|
| | 3.75% (N = 205) | 2.5% (N = 201) | Placebo (N = 105) |
| Subjects with any AE, n (%) | 91 (44.4) | 82 (40.8) | 34 (32.4) |
| Application site pain | 17 (8.3) | 8 (4.0) | 0 |
| Application site pniritus | 8 (3.9) | 14 (7.0) | 1 (1.0) |
| Application site irritation | 12 (5.9) | 8 (4.0) | 1 (1.0) |
| Nasopharyngitis | 4 (2.0) | 7 (3.5) | 6 (5.7) |
| Upper respiratory tract infection | 5 (2.4) | 4 (2.0) | 2 (1.9) |
| Urinary tract infection | 4 (2.0) | 3 (1.5) | 2 (1.9) |
| Vaginal candidiasis | 1 (0.5) | 7 (3.5) | 1 (1.0) |
| Nasal congestion | 2 (1.0) | 5 (2.5) | 1 (1.0) |
| Headache | 3 (1.5) | 3 (1.5) | 1 (1.0) |
| Pruritus genital | 4 (2.0) | 2 (1.0) | 1 (1.0) |
| Scrotal erythema | 2 (1.0) | 5 (2.5) | 0 |
| Influenza | 1 (0.5) | 3 (1.5) | 2 (19) |
| Application site rash | 2 (1.0) | 3 (1.5) | 0 |
| Application site ulcer | 2 (1.0) | 3 (1.5) | 0 |
| Nausea | 3 (1.5) | 1 (0.5) | 1 (1.0) |
| Rash | 3 (1.5) | 1 (0.5) | 1 (1.0) |
| Scrotal ulcer | 2 (1.0) | 3 (1.5) | 0 |
| Sinusitis | 3 (1.5) | 0 | 2 (1.9) |
| Application site infection | 1 (0.5) | 3 (1.5) | 0 |
| Application site vesicles | 3 (1.5) | 1 (0.5) | 0 |
| Sinus congestion | 3 (1.5) | 1 (0.5) | 0 |
| Anxiety | 3 (15) | 0 | 0 |
| Influenza like illness | 0 | 3 (1.5) | 0 |
| Musculoskeletal pain | 3 (1.5) | 0 | 0 |
| Scrota/pain | 3 (1.5) | 0 | 0 |

AE = adverse event

Counts reflect numbers of subjects in each treatment group reporting one or more adverse events that map to the MedDRA system organ class. A subject may be counted once only in each row of the table.

A treatment-emergent AE is an AE that began or worsened in severity after the first application of the study drug and no more than 30 days after the last application of the study drug.

The AE reported with the greatest overall incidence was application site pain, reported in 8.3% of subjects in the 3.75% imiquimod group, 4.0% of subjects in the 2.5% imiquimod group, and 0.0% of subjects in the placebo group.

Application site pruritus occurred with a higher frequency in the 2.5% imiquimod group (7.0%) compared with the 3.75% imiquimod group (3.9%) and placebo 0.0% groups. Nasopharyngitis occurred with a higher frequency in the placebo group (5.7%) compared with the 3.75% imiquimod group (2.0%), and 2.5% imiquimod group (3.5%). With these exceptions, the incidence of the individual AEs was similar in the 2 active treatment groups and lower in the placebo group.

Flu-like symptoms and certain other systemic effects have been reported with 5% imiquimod treatment. The incidence of these AEs was very low in the current study. These events were reported in this study in the 3.75% imiquimod, 2.5% imiquimod, and placebo groups, respectively, as follows:

- nausea was reported in 3 (1.5%), 1 (0.5%), and 1 (0.5%) subjects;
- influenza was reported in 1 (0.5%), 3 (1.5%), and 2 (1.9%) subjects;
- influenza-like illness was reported in 0, 3 (1.5%), and 0 subjects;
- myalgia was reported in 1 (0.5%), 1 (0.5%), and 0 subjects;
- pyrexia was reported in 1 (0.5%), 1 (0.5%), and 0 subjects;
- chills were reported in 0, 1 (0.5), and 0 subjects.

Adverse Events by System Organ Class

The incidence of AEs is presented by system organ class in Table 90 below.

TABLE 90

Number (%) of Subjects with Treatment-Emergent Adverse Events by System Organ Class-Safety Population

| | Imiquimod Cream | | |
|---|---|---|---|
| | 3.75% (N = 205) | 2.5% (N = 201) | Placebo (N = 105) |
| General disorders and administration site disorders | 42(20.5) | 37(18.4) | 5(4.8) |
| Infections and infestations | 36(17.6) | 37(18.4) | 20(19.0) |
| Respiratory, thoracic, and mediastinal disorders | 11(5.4) | 10(5.0) | 4(3.8) |
| Gastrointestinal disorders | 11(5.4) | 6(3.0) | 3(2.9) |
| Skin and subcutaneous tissue disorders | 11(5.4) | 3(1.5) | 2(1.9) |
| Reproductive system and breast disorders | 10(4.9) | 13(6.5) | 2(1.9) |
| Musculoskeletal and connective tissue disorders | 7(3.4) | 4(2.0) | 1(1.0) |
| Injury, poisoning, and connective tissue disorders | 6(2.9) | 3(1.5) | 4(3.8) |
| Psychiatric disorders | 4(2.0) | 1(0.5) | 1(1.0) |
| Nervous system disorders | 3(1.5) | 5(2.5) | 1(1.0) |
| Investigations | 2(1.0) | 0 | 1(1.0) |
| Renal and urinary disorders | 2(1.0) | 0 | 1(1.0) |
| Neoplasms benign, malignant, and unspecified (incl cysts and polyps) | 2(1.0) | 0 | 0 |
| Immune system disorders | 1(0.5) | 1(0.5) | 1(1.0) |
| Surgical and medical procedures | 1(0.5) | 1(0.5) | 1(1.0) |
| Endocrine disorders | 1(0.5) | 0 | 0 |
| Metabolism and nutrition disorders | 1(0.5) | 0 | 0 |
| Vascular disorders | 1(0.5) | 0 | 0 |
| Blood and lymphatic disorders | 0 | 2(1.0) | 0 |

AE = adverse event

Counts reflect numbers of subjects in each treatment group reporting one or more AEs that map to the MedDRA system organ class. A subject was counted only once in each row of the table.

System organ classes in which AEs were reported with an incidence of ≥5% in at least one treatment group were general disorders and administrative site disorders, infections and infestations, gastrointestinal disorders, reproductive system and breast disorders, respiratory, thoracic, and mediastinal disorders, and skin and subcutaneous tissue disorders.

Adverse Events by Intensity

Most of the AEs were of mild or moderate intensity. Four AEs were rated as severe in at least 2 subjects in any treatment group:

- application site pruritus, reported in 1 subject (0.5%) in the 3.75% imiquimod treatment group, 2 subjects (1.0%) in the 2.5% imiquimod treatment group, and 0 subjects in the placebo group;
- application site irritation, reported in 2 subjects (1.0%) in the 3.75% imiquimod treatment group, 2 subjects (1.0%) in the 2.5% imiquimod treatment group, and 0 subjects in the placebo group;

application site rash, reported in 2 subjects (1.0%) in the 3.75% imiquimod treatment group, 0 subjects in the 2.5% imiquimod treatment and placebo groups;

scrotal erythema, reported in 2 subjects (1.0%®) in the 3.75% imiquimod treatment group, 1 subject (0.5%) in the 2.5% imiquimod treatment group, and 0 subjects in the placebo group.

Adverse Events by Relationship to Treatment

Treatment-emergent AEs are summarized by treatment group and relationship to study treatment in Table 91 below.

TABLE 91

Number (%) of Subjects with Treatment-Emergent Adverse Events Related to Treatment-Safety Population

| | Imiquimod Cream | | Placebo |
|---|---|---|---|
| | 3.75% (N = 205) | 2.5% (N = 201) | (N = 105) |
| Subjects with any treatment-related AE, n (%) | 40 (19.5) | 37 (18.4) | 3 (2.9) |
| Subjects with any treatment-related: | | | |
| SAE, n (%) | 0 | 0 | 0 |
| AE of severe intensity, n (%) | 9 (4.4) | 9 (4.5) | 1 (1.0) |
| AE leading to study drug discontinuation, n (%) | 1 (0.5) | 3 (1.5) | 0 |
| Application site pain | 16 (7.8) | 8 (4.0) | 0 |
| Application site pruritus | 7 (3.4) | 14 (7.0) | 1 (1.0) |
| Application site irritation | 11 (5.4) | 8 (4.0) | 1 (1.0) |
| Application site rash | 2 (1.0) | 3 (1.5) | 0 |
| Application site ulcer | 2 (1.0) | 3 (1.5) | 0 |
| Application site bleeding | 2 (1.0) | 1 (0.5) | 1 (1.0) |
| Application site vesicles | 3 (1.5) | 1 (0.5) | 0 |
| Secretion discharge | 2 (1.0) | 2 (1.0) | 0 |
| Application site reaction | I (0.5) | 2 (1.0) | 0 |
| Application site dermatitis | 1 (0.5) | 1 (0.5) | 0 |
| Application site discharge | 1 (0.5) | 1 (0.5) | 0 |
| Application site erythema | 0 | 2 (1.0) | 0 |
| Application site erosion | 0 | 1 (0.5) | 0 |
| Application site paraesthesia | 0 | 0 | 1 (1.0) |
| Application site swelling | 1 (0.5) | 0 | 0 |
| Scrotal erythema | 2 (1.0) | 4 (2.0) | 0 |
| Scrotal ulcer | 2 (1.0) | 3 (1.5) | 0 |
| Scrotal oedema | 2 (1.0) | 2 (1.0) | 0 |
| Pruritus genital | 2 (1.0) | 1 (0.5) | 0 |
| Scrotal pain | 3 (1.5) | 0 | 0 |
| Genital rash | 0 | 1 (0.5) | 0 |
| Pelvic pain | 0 | 1 (0.5) | 0 |
| Penis disorder | 0 | 1 (0.5) | 0 |
| Prostatitis | 1 (0.5) | 0 | 0 |
| Scrotal irritation | 1 (0.5) | 0 | 0 |
| Vulval disorder | 0 | 1 (0.5) | 0 |
| Vulval ulceration | 0 | 1 (0.5) | 0 |
| Vulvovaginal pruritus | 1 (0.5) | 0 | 0 |
| Application site infection | 1 (0.5) | 3 (1.5) | 0 |

TABLE 91

Number (%) of Subjects with Treatment-Emergent Adverse Events Related to Treatment-Safety Population

| | Imiquimod Cream | | |
|---|---|---|---|
| | 3.75% (N = 205)5 | 2.5% (N = 201) | Placebo (N = 105) |
| Application site cellulitis | 1 (0.5) | 0 | 0 |
| Application site pustules | 0 | 1 (0.5) | 0 |

TABLE 91-continued

Number (%) of Subjects with Treatment-Emergent Adverse Events Related to Treatment-Safety Population

| | Imiquimod Cream | | |
|---|---|---|---|
| | 3.75% (N = 205)5 | 2.5% (N = 201) | Placebo (N = 105) |
| Cellulitis | 0 | 1 (0.5) | 0 |
| Folliculitis | 0 | 1 (0.5) | 0 |
| Fungal infection | 1 (0.5) | 0 | 0 |
| Influenza | 1 (0.5) | 0 | 0 |
| Scrotal infection | 1 (0.5) | 0 | 0 |
| Staphylococcal abscess | 0 | 1 (0.5) | 0 |
| Haemorrhoidal haemorrhage | 1 (0.5) | 0 | 0 |
| Haemorrhoids | 0 | 1 (0.5) | 0 |
| Nausea | 0 | 1 (0.5) | 0 |
| Groin pain | 0 | 1 (0.5) | 0 |
| Myalgia | 1 (0.5) | 0 | 0 |
| Pain in extremity | 0 | 1 (0.5) | 0 |
| Rash | 1 (0.5) | 0 | 0 |
| Scab | 0 | 1 (0.5) | 0 |
| Skin exfoliation | 1 (0.5) | 0 | 0 |
| Lymph node pain | 0 | 1 (0.5) | 0 |
| Burning sensation | 0 | 1.(0.5) | 0 |
| Dysuria | 1 (0.5) | 0 | 0 |

AE = adverse event

Counts reflect numbers of subjects in each treatment group reporting one or more AEs that map to the MedDRA system organ class. A subject was counted only once in each row of the table. Treatment-related includes Probably Related and Related.

Adverse events considered to be treatment-related were reported in 40 subjects (19.5%) in the 3.75% imiquimod treatment group, 37 (18.4%) in the 2.5% imiquimod treatment group, and 3 (2.9%) in the placebo group. The most frequently reported treatment-related AEs were application site pain and application site pruritus. Application site AEs were the most frequently reported treatment-related AEs followed by AEs involving the scrotum. Application site pruritus, application site irritation, application site bleeding and paraesthesia, each in 1 subject (1.0%), were the only treatment-related AEs reported in the placebo group.

Treatment-related AEs of severe intensity were reported by 9 subjects in the 3.75% imiquimod group, 9 subjects in the 2.5% imiquimod group, and 1 subject in the placebo group. The majority of the AEs were application site reactions and all resolved without sequelae.

Adverse Events by Subgroup

Treatment-emergent AEs were analyzed by gender, by age, by number of anatomic areas affected by EGW, and by baseline wart count. As in the overall population, application site reactions were the most commonly-reported AEs and treatment-related AEs in all subgroups for all treatment groups.

Adverse Events by Gender

Summaries of the analysis by gender are provided in Table 92 below.

TABLE 92

Treatment-emergent Adverse Events by Gender-Safety Population

| | Male | | | Female | | |
|---|---|---|---|---|---|---|
| | 3.75% Imiquimod n = 88 | 2.5% Imiquimod n = 85 | Placebo n = 49 | 3.75% Imiquimod n = 117 | 2.5% Imiquimod n = 116 | Placebo n = 56 |
| Subjects with any AE, n (%) | 37 (42.0) | 28 (32.9) | 8 (16.3) | 54 (46.2) | 54 (46.6) | 26 (46.4) |
| Number of AEs | 104 | 60 | 11 | 112 | 107 | 40 |
| Number (%) of subjects with: | | | | | | |
| Any Treatment-related AE | 16 (18.2) | 13 (15.3) | 0 (0.0) | 24 (20.5) | 24 (20.7) | 3 (5.4) |
| Any SAE | 2 (2.3) | I. (1.2) | 0 (0.0) | 4 (3.4) | 1 (0.9) | I (1.8) |
| Any Severe AE | 10 (11.4) | 2 (2.4) | 0 (0.0) | 4 (3.4) | 7 (6.0) | 3 (5.4) |
| Any AE leading to Study Discontinuation | 1 (1.1) | 2 (2.4) | 0 (0.0) | 2 (1.7) | 3 (2.6) | 0 (0.0) |
| Any Application site Reaction | 14 (15.9) | 9 (10.6) | 0 (0.0) | 21 (17.9) | 24 (20.7) | 3 (5.4) |

The overall incidence of AEs was higher in females than in males in all treatment groups. Treatment-related AEs and SAEs were reported in a higher percentage of females than in males in the 3.75% imiquimod and placebo treatment groups but not in the 2.5% imiquimod group. Severe AEs were reported in a higher percentage of females in the 2.5% imiquimod and placebo groups, but not in the 3.75% imiquimod group. The incidence of SAEs and AEs leading to study discontinuation was low in all treatment groups regardless of gender. Application site reactions were the most commonly reported AEs in the 2 imiquimod treatment groups. Severe AEs and application site reactions were each reported in 3 female subjects (5.4%) in the placebo group.

Adverse Events by Age:

As in the overall population, application site reactions were the most commonly-reported treatment-emergent AEs in both age groups for the 2 imiquimod treatment groups.

In the active treatment groups, the incidence of treatment-emergent AEs was similar in younger (≤35 years) and older (>35 years) subjects within each treatment group. Treatment-emergent AEs were reported in 45.1%, 40.8%, and 31.8%, respectively, of younger subjects in the 3.75% imiquimod, 2.5% imiquimod, and placebo groups compared with 43.1%, 40.8%, and 33.3%, respectively, of the older subjects in the 3.75% imiquimod, 2.5% imiquimod, and placebo groups.

In the active treatment groups, the incidence of treatment-related AEs and application site reactions was slightly higher in younger subjects than in older subjects; however, within each age subgroup, there was little difference between the active treatments. Few treatment-related AEs or application site reactions were reported in subjects in either age subgroup who received placebo.

Adverse Events by Number of Anatomic Areas:

As in the overall population, the most commonly-reported treatment-emergent AEs and treatment-related AEs in both subgroups for all treatment groups were application site reactions.

In the 2 active treatment groups, similar percentages of subjects in the single-area and multiple-area subgroups reported a treatment-emergent AE. In the placebo group, subjects in the multiple-area subgroup reported a higher percentage of treatment-emergent AEs than those in the single-area subgroup (36.5% versus 28.3%, respectively). For treatment-related AEs and application site reactions, there was little difference in AE incidence between the subgroups in any of the treatment groups.

Adverse Events by Baseline Wart Count:

In the subjects with 7 or fewer warts at Baseline, the incidence of AEs was 43.9%, 39.5%, and 32.8%, respectively, in the 3.75% imiquimod, 2.5% imiquimod, and placebo groups, whereas in subjects with more than 7 warts at. Baseline, the incidence of AEs was 45.1%, 42.9%, and 31.6%, respectively, in the 3.75% imiquimod, 2.5% imiquimod, and placebo groups.

In the subjects with 7 or fewer warts at Baseline, the incidence of treatment-related AEs was 19.5%, 16.9%, and 4,5%, respectively, in the 3.75% imiquimod, 2.5% imiquimod, and placebo groups, whereas in subjects with more than 7 warts at Baseline, the incidence of treatment-related AEs was 19.5%, 20.8%, and 0%, respectively, in the 3.75% imiquimod, 2.5% imiquimod, and placebo groups.

There was little difference in the incidence of treatment-emergent AEs, treatment-related AEs, and application site reactions between the subgroups in any of the active treatment groups. In the placebo group, subjects with 7 or fewer warts had a higher incidence of application site reactions than subjects with more than 7 warts.

Local Skin Reactions

Local skin reactions were assessed by the investigator at each visit including Baseline (pretreatment). At Baseline, 5.4%®, 6.0%, and 8.6% of subjects in the 3.75% imiquimod, 2.5% imiquimod, and placebo groups, respectively, had at least one LSR reaction (LSR intensity score ≥0). The most intense post-Baseline LSRs (ie, those with the highest intensity rating) in the treatment area that were assessed by the investigator over the course of the study are summarized in the Table below (Table 93). The potential maximum sum of LSR scores was 18 (six types of LSRs each with maximum potential score of 3).

TABLE 93

Frequency Distribution of Most Intense Post-baseline Local Skin Reactions in the Treatment Area-Safety Population

| | | Number (%) of Subjects | | |
|---|---|---|---|---|
| | | Imiquimod | | |
| Type of Reaction | Intensity | 3.75% (N = 205) | 2.5% (N = 201) | Placebo (N = 105) |
| Erythema | N | 189 (100) | 180 (100) | 98 (100) |
| | 0 = None | 50 (26.5) | 64 (35.6) | 67 (68.4) |
| | 1 = Faint to mild redness | 49 (25.9) | 49 (27.2) | 19 (19.4) |

TABLE 93-continued

Frequency Distribution of Most Intense Post-baseline Local Skin Reactions in the Treatment Area-Safety Population

| Type of Reaction | Intensity | Number (%) of Subjects Imiquimod 3.75% (N = 205) | 2.5% (N = 201) | Placebo (N = 105) |
|---|---|---|---|---|
| | 2 = Moderate redness | 71 (37.6) | 47 (26.1) | 11 (11.2) |
| | 3 = Intense redness | 19 (10.1) | 20 (11.1) | 1 (1.0) |
| | >0 (any reaction) | 139 (73.5) | 116 (64.4) | 31 (31.6) |
| | Mean score (SD) | 1.31 (0.97) | 1.13 (1.02) | 0.45 (0.73) |
| Edema | N | 189 (100) | 180 (100) | 98 (100) |
| | 0 = None | 108 (57.1) | 111 (61.7) | 89 (90.8) |
| | 1 = Mild visible/ barely palpable swelling/induration | 59 (31.2) | 47 (26.1) | 8 (8.2) |
| | 2 = Easily palpable | 19 (10.1) | 16 (8.9) | 1 (1.0) |
| | 3 = Gross swelling/ induration | 3 (1.6) | 6 (3.3) | 0 |
| | >0 (any reaction) | 81 (42.9) | 69 (38.3) | 9 (9.2) |
| | Mean score (SD) | 0.56 (0.74) | 0.54 (0.79) | 0.10 (0.34) |
| Weeping/ Exudate | N | 189 (100) | 180 (100) | 98 (100) |
| | 0 = None | 124 (65.6) | 125 (69.4) | 95 (96.9) |
| | 1 = Minimal exudate | 49 (25.9) | 41 (22.8) | 3 (3.1) |
| | 2 = Moderate exudate | 12 (6.3) | 12 (6.7) | 0 |
| | 3 = Heavy exudate | 4 (2.1) | 2 (1.1) | 0 |
| | >0 (any reaction) | 65 (34.4) | 55 (30.6) | 3 (3.1) |
| | Mean score (SD) | 0.45 (0.71) | 0.39 (0.66) | 0.03 (0.17) |
| Flaking/ Scaling/ Dryness | N | 189 (100) | 180 (100) | 98 (100) |
| | 0 = None | 129 (68.3) | 144 (80.0) | 87 (88.8) |
| | 1 = Mild dryness/ flaking | 52 (27.5) | 28 (15.6) | 11 (11.2) |
| | 2 = Moderate dryness/flaking | 8 (4.2) | 6 (3.3) | 0 |
| | 3 = Severe dryness/flaking | 0 | 2 (1.1) | 0 |
| | >0 (any reaction) | 60 (31.7) | 36 (20.0) | 11 (11.2) |
| | Mean score (SD) | 0.36 (0.56) | 0.26 (0.57) | 0.11 (0.32) |
| Scabbing/ Crusting | N | 189 (100) | 180 (100) | 98 (100) |
| | 0 = None | 141 (74.6) | 141 (78.3) | 93 (94.9) |
| | 1 = Crusting | 41 (21.7) | 30 (16.7) | 5 (5.1) |
| | 2 = Serious scab | 6 (3.2) | 8 (4.4) | 0 |
| | 3 = Eschar | 1 (0.5) | 1 (0.6) | 0 |
| | >0 (any reaction) | 48 (25.4) | 39 (21.7) | 5 (5.1) |
| | Mean score | 0.30 (0.55) | 0.27 (0.57) | 0.05 (0.22) |
| Erosion/ Ulceration | N | 189 (100) | 180 (100) | 98 (100) |
| | 0 = None | 116 (61.4) | 118 (65.6) | 92 (93.9) |
| | 2 = Erosion | 51 (27.0) | 40 (22.2) | 5 (5.1) |
| | 3 = Ulceration | 22 (11.6) | 22 (12.2) | 1 (1.0) |
| | >0 (any reaction) | 73 (38.6) | 62 (34.4) | 6 (6.1) |
| | Mean score (SD) | 0.89 (1.16) | 0.81 (1.16) | 0.13 (0.53) |

SD = Standard deviation.

Note:

For purposes of analysis, 'Erosion' is categorized as 2 = Moderate, and 'Ulceration' is categorized as 3 = Severe. Denominator for the most intense reaction is the number of subjects with at least one post-baseline assessment.

As displayed in the Table above, the incidence of each type of LSR was higher in the active treatment groups compared with placebo. For each LSR, the percentage of subjects with any reaction and the mean intensity score were highest in the 3.75% imiquimod treatment group, somewhat lower in the 2.5% imiquimod group, and lowest in the placebo group. The incidence of severe LSRs was similar between the active treatment groups within each LSR category, and lower in the placebo group.

Erythema was the LSR reported with the greatest frequency and the greatest mean intensity in all 3 treatment groups. Severe erythema was reported in 10.1% of subjects in the 3.75% imiquimod group, 11.1% of subjects in the 2.5% imiquimod group, and 1.0% of subjects in the placebo group. The mean intensity score was higher in the active treatment group (1.31 and 1.13 in the 3.75% and 2.5% imiquimod groups, respectively) compared with placebo.

Edema rated as severe was reported in 1.6% and 3.3% of subjects in the 3.75% and 2.5% imiquimod groups, respectively, compared with no subjects in the placebo group. The mean intensity scores were higher in the active treatment groups (0.56 and 0.54 in the 3.75% and 2.5% imiquimod groups, respectively) compared with 0.10 in the placebo group.

For erosion/ulceration severe reactions (ulceration) were reported in 11.6% and 12.2% of subjects in the 3.75% and 2.5% imiquimod groups, respectively, compared with 1.0% of subjects in the placebo group. The mean intensity scores were higher in the active treatment groups (0.89 and 0.81 in the 3.75% and 2.5% imiquimod groups, respectively) compared with 0.13 in the placebo group.

The majority of cases of weeping/exudate, flaking/scaling, and scabbing/crusting were mild in intensity. Few subjects in any treatment group had a reaction considered to be severe.

A summary of subjects who had any post-baseline local skin reaction is presented in Table 94 below.

TABLE 94

Summary of Subjects Who Had Any Local Skin Reaction During the Study-Safety Population

| Most Intense Reaction (post-Baseline) | Number (%) of Subjects Imiquimod 3.75% (N = 205) | 2.5% (N = 201) | Placebo (N = 105) |
|---|---|---|---|
| N | 189 | 180 | 98 |
| 0 = None | 41 (21.7) | 57 (31.7) | 57 (58.2) |
| 1 = Mild | 41 (21.7) | 42 (23.3) | 26 (26.5) |
| 2 = Moderate | 74 (39.2) | 48 (26.7) | 13 (133) |
| 3 = Severe | 33 (17.5) | 33 (18.3) | 2 (2.0) |
| >0 (any reaction) | 148 (78.3) | 123 (68.3) | 41 (41.8) |
| Mean score (SD) | 1.5 (1.0) | 1.3 (1.1) | 0.6 (0.8) |

SD = Standard deviation.

Note:

For purposes of analysis, 'Erosion' is categorized as 2 = Moderate, and 'Ulceration' is categorized as 3 = Severe. Denominator for the most intense reaction is the number of subjects with at least 1 post-baseline assessment.

As noted for the individual LSRs, the percentage of subjects reporting an LSR at each intensity category was higher in the active treatment group compared with placebo, and was somewhat higher with 3.75% imiquimod than with 2.5% imiquimod. Severe reactions were reported by 17.5% of subjects in the 3.75% imiquimod group and 18.3% of subjects in the 2.5% imiquimod group compared with 2.0% of subjects in the placebo group. The mean score for the most intense LSR reaction was slightly higher in the 3.75% imiquimod group (1.5) than in the 2.5% imiquimod group (1.3).

Figure 24:
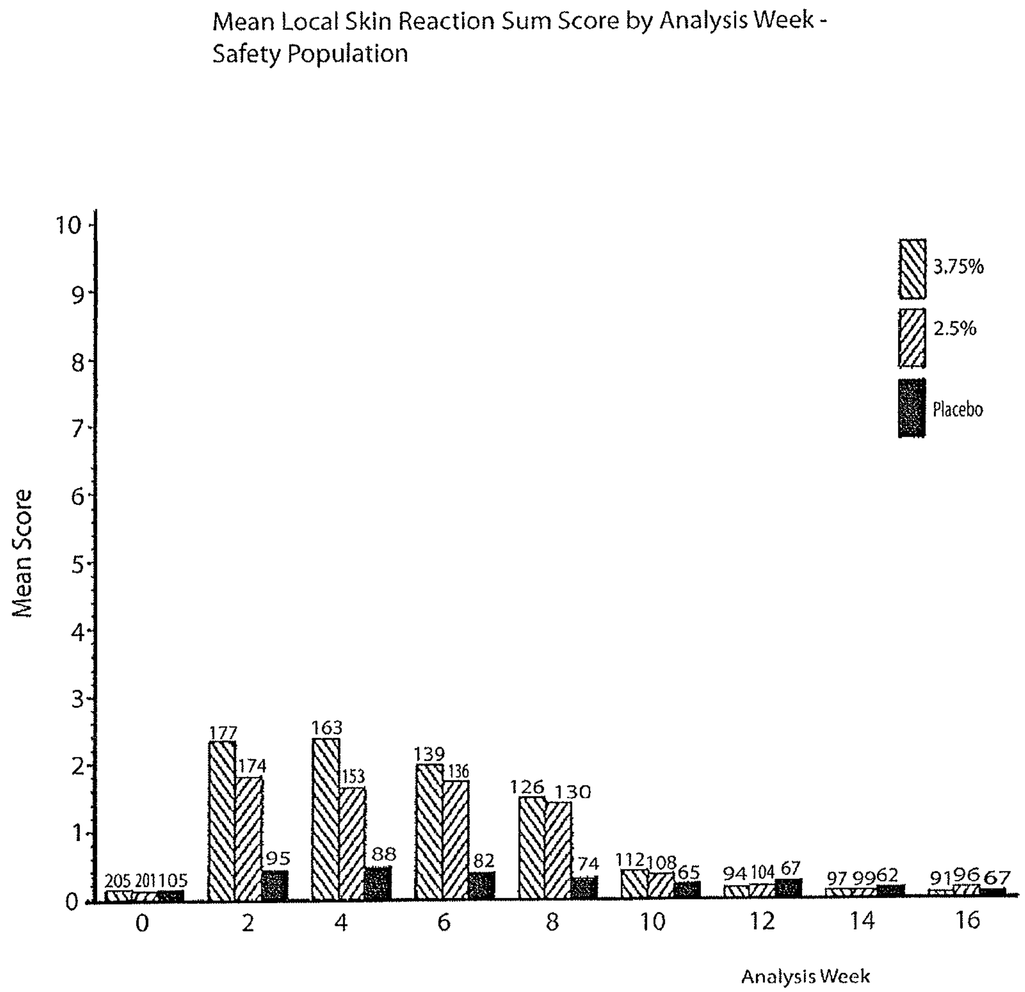
FIG. 24 shows mean local skin reaction sum score by analysis week, safety population, in one study of a lower-dose imiquimod treatment of genital warts.

The mean LSR sum score is shown by study week in FIG. 24.

Erythema was the major contributor to the LSR sum score in all treatment groups, as determined by visual inspection. In the imiquimod treatment groups, the mean LSR sum score peaked at Week 2, decreased slightly during the treatment period, and rapidly decreased when treatment was discontinued. Mean LSR scores in the placebo group were highest at Week 4 but were considerably lower than those seen with active treatment.

Rest Periods

Summaries of the rest periods for the safety population are presented in Table 95 below.

TABLE 95

Summary of Rest Periods-Safety Population

| | Imiquimod Cream | | |
|---|---|---|---|
| | 3.75% (N = 205) | 2.5% (N = 201) | Placebo (N = 105) |
| Subjects requiring rest period, n/N (%)[a] | 67 (32.7) | 55 (27.4) | 3 (2.9) |
| P value vs Placebo | <0.001 | <0.001 | NA |
| P value vs 2.5% imiquimod cream | 0.234 | NA | NA |
| No. of dosing days missed due to rest period[b] | | | |
| N | 67 | 55 | 3 |
| Mean (SD) | 10.3 (8.1) | 9.3 (6.7) | 6.7 (4.7) |
| Median | 7 | 7 | 5 |
| P value vs Placebo | 0.522 | 0.526 | NA |
| P value vs 2.5% cream | 0.714 | NA | NA |
| No. of dosing days prior to the beginning of the first rest period[b°] | | | |
| N | 67 | 55 | 3 |
| Mean (SD) | 18.3 (11.5) | 18.9 (13.7) | 25.7 (4.0) |
| Median | 14 | 14 | 28 |
| P value vs Placebo | 0.151 | 0.192 | NA |
| P value vs 2.5% cream | 0.924 | NA | NA |

No. = number;
SD = standard deviation;
NA = not applicable
[a]P values are from Cochran-Mantel-Haenszel test, stratified by gender and analysis site, taking 2 treatment groups at a time.
[b]P values are from the Wilcoxon Rank Sum test, taking 2 treatment groups at a time.

Significantly larger percentages of subjects in the active treatment groups compared with placebo took a rest period during the study (P<0.001). There was no significant difference between the active treatments in the percentage of subjects who took a rest period (32.7% and 27.4% in the 3.75% and 2.5% imiquimod groups, respectively). There were no statistically significant differences between the treatment groups in the mean duration of rest periods or the mean number of dosing days prior to the rest periods.

Analysis of Adverse Events

Application site reactions are commonly reported for topically applied products. An additional analysis of these events is presented below.

Application site reactions reported in this study are displayed in Table 96 below.

TABLE 96

Number (%) of Subjects with Treatment-Emergent Application Site Adverse Events-Safety Population

| | Imiquimod Cream 3.75% (N = 205) | 2.5% (N = 201) | Placebo (N = 105) |
|---|---|---|---|
| Subjects with any application site reaction, n (%) | 35 (17.1) | 33 (16.4) | 3 (2.9) |
| Number of application site reactions | 59 | 54 | 4 |

TABLE 96-continued

Number (%) of Subjects with Treatment-Emergent Application Site Adverse Events-Safety Population

| | Imiquimod Cream 3.75% (N = 205) | 2.5% (N = 201) | Placebo (N = 105) |
|---|---|---|---|
| Number (%) of subjects with any: | | | |
| Related Application Site Reaction [a], n (%) | 33 (16.1) | 32 (15.9) | 3 (2.9) |
| Serious Application Site Reaction, n (%) | 0 | 0 | 0 |
| Severe Application Site Reaction, n (%) | 6 (2.9) | 6 (3.0) | 1 (1.0) |
| Application Site Reaction Leading to Study Discontinuation, n (%) | 1 (0.5) | 3 (1.5) | 0 |
| General disorders and administration site conditions, n (%) | 35 (17.1) | 32 (15.9) | 3 (2.9) |
| Application site pain | 17 (8.3) | 8 (4.0) | 0 |
| Application site pruritus | 8 (3.9) | 14 (7.0) | 1 (1.0) |
| Application site irritation | 12 (5.9) | 8 (4.0) | 1 (1.0) |
| Application site rash | 2 (1.0) | 3 (1.5) | 0 |
| Application site ulcer | 2 (1.0) | 3 (1.5) | 0 |
| Application site bleeding | 2 (1.0) | 1 (0.5) | 1 (1.0) |
| Application site vesicles | 3 (1.5) | 1 (0.5) | 0 |
| Application site reaction | 1 (0.5) | 2 (1.0) | 0 |
| Application site dermatitis | 1 (0.5) | 1 (0.5) | 0 |
| Application site discharge | 1 (0.5) | 1 (0.5) | 0 |
| Application site erythema | 0 | 2 (1.0) | 0 |
| Application site dryness | 1 (0.5) | 0 | 0 |
| Application site erosion | 0 | 1 (0.5) | 0 |
| Application site hypersensitivity | 0 | 1 (0.5) | 0 |
| Application site reaction | 1 (0.5) | 0 | 0 |
| Application site paraesthesia | 0 | 0 | 1 (1.0) |
| Application site swelling | 1 (0.5) | 0 | 0 |
| Infections and infestations, n (%) | 2 (1.0) | 4 (2.0) | 0 |
| Application site infection | 1 (0.5) | 3 (1.5) | 0 |
| Application site cellulitis | 1 (0.5) | 0 | 0 |
| Application site pustules | 0 | 1 (0.5) | 0 |

[a] Includes 'Probably related' and 'Related' adverse events.
Note:
Counts reflect numbers of subjects in each treatment group reporting 1 or more AEs that map to the MedDRA system organ class. A subject may be counted once only in each row of the table.

The incidence of application site AEs and treatment-related application site AEs was similar in the 3.75% and 2.5% imiquimod treatment study groups. Few subjects in any of the treatment groups reported severe application site events or application site events that led to study withdrawal. No serious application site reactions were reported in any study group.

Listing of Deaths, Other Serious Adverse Events and Other Significant Adverse Events Deaths There was one death in the study (a 28-year old White male randomized to the 3.75% imiquimod group). The subject was undergoing treatment for EGW on the glans penis and penis shaft and in the inguinal area. At the time of the event (gunshot wound to the chest) the subject had applied an unknown number of packets of 3.75% imiquimod cream. The fatal gunshot wound to the chest occurred on Study Day 40. The subject was receiving paracetamol 650 mg po prn and topical Benzamycing 90 g qhs at the time he was hospitalized.

Other Serious Adverse Events

Serious adverse events are presented in Table 97 below.

TABLE 97

Number (%) of Subjects with Serious Adverse Events-Safety Population

| | Imiquimod Cream | | |
|---|---|---|---|
| | 3.75% (N = 205) | 2.5% (N = 201) | Placebo (N = 105) |
| Subjects with any serious adverse event, n (%) | 7 (3.4) | 2 (1.0) | 1 (1.0) |
| Subjects with any treatment-emergent SAE, n (%) | 6 (2.9) | 2 (1.0) | 1 (1.0) |
| Subjects with any treatment-related SAE, n (%) | 0 | 0 | 0 |
| Serious adverse events | | | |
| Malignant melanoma | 2 (1.0) | 0 | 0 |
| Anxiety | 1 (0.5) | 0 | 0 |
| Suicidal ideation | 0 | 1 (0.5) | 0 |
| Chest pain | 1 (0.5) | 0 | 0 |
| Diverticulitis | 1 (0.5) | 0 | 0 |
| Gun shot wound | 1 (0.5) | 0 | 0 |
| Diabetes mellitus inadequate control | 1 (0.5) | 0 | 0 |
| Arthritis | 0 | 0 | 1 (1.0) |
| Dyspnoea | 1 (0.5) | 0 | 0 |
| Ovarian cystectomy | 0 | 1 (0.5) | 0 |
| Gall bladder disorder[a] | 1 (0.5) | NA | NA |
| Pancreatic carcinoma[a] | 1 (0.5) | NA | NA |
| Ovarian epithelial cancer[a] | 1 (0.5) | NA | NA |
| Bile duct obstruction[a] | 1 (0.5) | NA | NA |
| Abdominal pain[a] | 1 (0.5) | NA | NA |
| Abdominal distension[a] | 1 (0.5) | NA | NA |
| Pneumothorax[a] | 1 (0.5) | NA | NA |
| Catheter related infection[a] | 1 (0.5) | NA | NA |
| Obstruction gastric[a] | 1 (0.5) | NA | NA |

Counts reflect numbers of subjects in each treatment group reporting one or more adverse events that map to the MedDRA system organ class. A subject was counted only once in each row of the table.
[a]Subject 03/014 was diagnosed with cancer during screening. All events reported for this subject were classified as non treatment-emergent SAEs.

Few SAEs were reported during the study. The overall incidence of SAEs was higher in the 3.75% imiquimod group than in the 2.5% imiquimod and placebo groups. Treatment-emergent SAEs occurred in 6 subjects (2.9%) in the 3.75% imiquimod group, 2 subjects (1.0%) in the 2.5% imiquimod group, and 1 subject (1.0%) in the placebo group. No trends were evident. No treatment-related SAEs were reported by subjects in any of the treatment groups. Two SAEs (anxiety and suicidal ideation) were recorded as ongoing, 2 SAEs (diabetes and ovarian cystectomy) resolved with sequelae, and all other SAEs resolved without sequelae.

Other Significant Adverse Events

Treatment-emergent AEs that led to discontinuation from the study are presented in Table 98.

TABLE 98

Number (%) of Subjects with Treatment-Emergent Adverse Events Leading to Study Discontinuation-Safety Population

| | Imiquimod Cream | | |
|---|---|---|---|
| | 3.75% (N = 205) | 2.5% (N = 201) | Placebo (N = 105) |
| Subjects with an AE leading to study discontinuation, n (%) | 3 (1.5) | 5 (2.5) | 0 |
| Subjects with a treatment-related AE leading to study discontinuation, n (%) | 1 (0.5) | 3 (1.5) | 0 |

TABLE 98-continued

Number (%) of Subjects with Treatment-Emergent Adverse Events Leading to Study Discontinuation-Safety Population

| | Imiquimod Cream | | |
|---|---|---|---|
| | 3.75% (N = 205) | 2.5% (N = 201) | Placebo (N = 105) |
| Adverse events leading to discontinuation, n (%) | | | |
| Application site pain | 1 (0.5) | 2 (1.0) | 0 |
| Gunshot wound | 1 (0.5) | 0 | 0 |
| Malignant melanoma right breast | 1 (0.5) | 0 | 0 |
| Malignant melanoma right lower lateral extremity | 1 (0.5) | 0 | |
| Hypersensitivity | | | |
| Application site erythema | 0 | 1 (0.5) | |
| Application site irritation | 0 | 1 (0.5) | 0 |
| Application site pruritus | 0 | 1 (0.5) | 0 |
| Scrotal erythema | 0 | 1 (0.5) | 0 |
| Scrotal ulcer | 0 | 1 (0.5) | 0 |
| Lymph node pain | 0 | 1 (0.5) | 0 |
| Pelvic pain | 0 | 1 (0.5) | 0 |
| Groin pain | 0 | 1 (0.5) | 0 |
| Application site ulcer | 0 | 1 (0.5) | 0 |
| Cellulitis | 0 | 1 (0.5) | 0 |
| Application site infection | 0 | 1 (0.5) | 0 |
| Suicidal ideation | 0 | 1 (0.5) | 0 |

Counts reflect numbers of subjects in each treatment group reporting one or more adverse events that map to the MedDRA system organ class. A subject was counted only once in each row of the table.
A treatment-emergent AE is an AE that began or worsened in severity after the first application of the study drug and no more than 30 days after the last application of the study drug. Treatment-related includes Probably Related and Related.

The incidence of AEs that led to study discontinuation was low in all treatment groups. The number of subjects with any AE leading to study discontinuation was higher in the 2.5% imiquimod group than in the 3.75% imiquimod group. No subjects in the placebo group discontinued the study because of AEs. Only 1 subject in the 3.75% imiquimod group and 3 subjects in the 2.5% imiquimod group reported treatment-related AEs that led to study discontinuation. Subject 06/021 (3.75% imiquimod) discontinued the study because of application site pain. In the 2.5% imiquimod treatment group, Subject 04/022 discontinued the study because of application site pain, Subject 12/010 discontinued the study because of application site erythema, application site irritation, application site pain and application site pruritus, and Subject 18/016 discontinued the study because of scrotal erythema and scrotal ulcer in a non-treatment area, lymph node pain, pelvic pain, groin pain, and application site ulcer. All (except scrotal erythema and scrotal ulcer in a non-treatment area) were application site reactions. All of these AEs resolved without sequelae.

Analysis and Discussion of Serious Adverse Events, and Other Significant Adverse Events One death (3.75% imiquimod group) occurred among the subjects in this study. The incidence of SAEs was low in this study. No SAE was considered related to study treatment. Few subjects discontinued the study as a result of an AE. Treatment-related application site reactions accounted for less than half of the AEs leading to study withdrawal. Only two SAEs (anxiety and suicidal ideation) were noted as ongoing and 2 SAEs (diabetes and ovarian cystectomy) resolved with sequelae.

Clinical Laboratory Evaluation

For most of the hematological, chemistry, and urinalysis variables, the majority of the subjects were normal at Screening and at EOS. Occasional shifts from normal at Screening to above or below the limits of the normal range were observed; however, no dose-response relationship was evident.

For the clinical chemistry determinations, shifts from normal to high were most frequently recorded for ALT (15/155 in the 3.75% imiquimod group, 11/146 in the 2.5% imiquimod group, and 2/80 in the placebo group), AST (11/155 in the 3.75% imiquimod group, 4/144 in the 2.5% imiquimod group, and 3/79 in the placebo group), and glucose (8/156 in the 3.75% imiquimod group, 10/146 in the 2.5% imiquimod group, and 4/79 in the placebo group). Low cholesterol was noted in 6/156 in the 3.75% imiquimod group, 8/146 in the 2.5% imiquimod group, and 5/82 in the placebo group. High cholesterol was also noted in 9/156 in the 3.75% imiquimod group, 6/146 in the 2.5% imiquimod group, and 6/82 in the placebo group. Shifts from normal to low were most frequently recorded for cholesterol (9/156 in the 3.75% imiquimod group, 7/146 in the 2.5% imiquimod group, and 3/82 in the placebo group).

In the hematology analyses, shifts from normal to high were most frequently reported for neutrophils (5/155 in the 3.75% imiquimod group, 7/147 in the 2.5% imiquimod group, and 6/80 in the placebo group). Shifts from normal to low were most frequently reported for WBCs (6/155 in the 3.75% imiquimod group, 6/147 in the 2.5% imiquimod group, and 4/80 in the placebo group).

The most commonly-reported shift observed in the study was a shift from normal to high in urine protein (37/156 in the 3.75% imiquimod group, 35/143 in the 2.5% imiquimod group, and 17/79 in the placebo group). However, at screening, 24.4%, 20.3%, and 16.5% in the 3.75% imiquimod group, 2.5% imiquimod group, and placebo group, respectively, had high concentrations of urinary protein. Other findings from urinalysis included shifts from normal to high for leukocyte esterase (12/156 in the 3.75% imiquimod group, 13/143 in the 2.5% imiquimod group, and 2/79 in the placebo group) and blood in the urine (11/156 in the 3.75% imiquimod group, 6/143 in the 2.5% imiquimod group, and 2/79 in the placebo group).

Pregnancies and Outcome

Five women became pregnant during the study, 2 in the 3.75% imiquimod group, 2 in the 2.5% imiquimod group, and 1 in the placebo group. All of the pregnancies were discovered after the subject had taken her last dose of study medication. The exposure to study medication was 45 packets and unknown of 3.75% imiquimod cream, unknown and 24 packets of 2.5% imiquimod cream, and 55 packets of placebo cream. The outcomes of the pregnancies are to be determined.

In addition, one subject in the 2.5% group reported that she was pregnant, just after a negative urine test result was reported at the Week 8 visit. The exposure to study medication was 55 packets.

Safety Conclusions

- Mean exposure to study medication was approximately 44 packets, 45 packets, and 53 packets of study medication in the 3.75% imiquimod, 2.5% imiquimod, and placebo groups respectively. Mean treatment duration was similar among the study groups and ranged from 50.0 days in the 3.75% imiquimod group to 54.7 days in the placebo group.
- Treatment-emergent AEs were reported in 44.4%, 40.8%, and 32.4% of subjects in the 3.75% imiquimod, 2.5% imiquimod, and placebo groups, respectively. Most AEs were mild or moderate in intensity. Application site reactions were the most frequently reported AEs. Adverse events of the system organ classes "general disorders and administration site conditions" and "infections and infestations" were the most frequently reported. Incidences of these events were similar in the active treatment groups.
- The incidence of systemic symptoms (ie, flu-like symptoms, etc) previously noted with 5% imiquimod was low (1%) in this study.
- Treatment-emergent SAEs were reported in 6 subjects in the 3.75% imiquimod group, 2 subjects in the 2.5% imiquimod group, and 1 subject in the placebo group. None of the SAEs were considered treatment-related.
- Treatment-emergent AEs that led to study discontinuation were reported in 3 subjects, 5 subjects, and no subjects in the 3.75% imiquimod, 2.5% imiquimod, and placebo groups, respectively. Of those TEAEs leading to discontinuation, 4 subjects withdrew from the study for TEAEs considered treatment-related: 1 subject in the 3.75% imiquimod group and 3 subjects in the 2.5% imiquimod group. All (except scrotal erythema and scrotal ulcer in a non-treatment area) were application site reactions.
- The incidence of TEAEs and severe AEs was higher in females than in males across all treatment groups, and the incidence of application site reactions was higher in females than in males in the active treatment groups.
- Adverse events leading to study discontinuation were rare in all treatment groups regardless of gender.
- Local skin reactions were reported in 78.3%, 68.3%, and 41.8% of subjects in the 3.75% imiquimod, 2.5% imiquimod, and placebo groups, respectively. The incidence and severity of LSRs was higher in the active treatment groups than in the placebo group. Erythema was the LSR reported with the greatest frequency and the greatest mean intensity in all treatment groups. Local skin reactions were coincident with the treatment period and rapidly decreased when treatment was concluded. Severe intensity LSRs were similar in the active groups.
- Rest periods were taken by 67 subjects (32.7%), 55 subjects (27.4%), and 3 subjects (2.9%©) in the 3.75% imiquimod, 2.5% imiquimod, and placebo groups, respectively. The frequency, duration, and number of dosing days prior to the rest period were similar in the active treatment group and lower in the placebo group.
- There was no evidence of clinically meaningful trends in vital sign measurements or clinical laboratory measurements. One subject in the placebo group reported laboratory AEs that were considered clinically significant, the AEs were considered not related to treatment.

Discussion and Overall Conclusions

Discussion

In this double-blind, placebo controlled clinical study, 511 subjects with EGW diagnosed by clinical examination were randomized to receive treatment with 3.75% imiquimod cream, 2.5% imiquimod cream, or a matching placebo cream. During the evaluation period, subjects applied study medication once daily to the identified treatment area(s) for a maximum of 8 weeks. If the subject did not achieve complete wart clearance by the Week 8 visit (end of treatment [EOT]), the subject was monitored for an additional maximum 8 weeks of no treatment. Subjects determined to have achieved complete clearance of all warts at any time until Week 16 (end of study [EOS]) completed procedures for the end-of-study visit and were eligible to immediately enter the follow-up period for determination of wart recurrence. During the follow-up period, subjects were monitored every 4 weeks for up to 12 weeks or until the recurrence of warts. The 3.75% imiquimod cream and 2.5% imiquimod cream demonstrated efficacy and tolerability as compared with placebo for treatment of EGW. Overall, 71.1% of subjects completed the evaluation period, and the discontinuation rates were similar in all treatment groups. Compliance with the daily treatment regimen ranged from 83.2% in the 3.75% imiquimod group to 91.1% in the placebo group.

Imiquimod has been demonstrated to be a safe and effective treatment for EGW. The dosing regimen for the currently approved product, 5% imiquimod cream, is 3 times per week for up to 16 weeks. Clinical experience has shown compliance with this regimen is challenging, as the treatment duration is long and the application schedule is non-intuitive. The current study was designed to evaluate imiquimod cream in lower concentrations to permit a more intuitive daily-dosing regimen and a shortened treatment regimen (up to 8 weeks).

Efficacy

Efficacy was demonstrated for the primary efficacy measure as well as for the secondary and tertiary efficacy measures for the 3.75% imiquimod cream and 2.5% imiquimod cream. Results for all efficacy measures for which statistical testing was performed were highly statistically significant in both of the active treatment groups as compared with placebo in both the ITT and PP populations.

Measures of wart reduction showed pronounced treatment effects for the higher concentration product (complete clearance rates of 29.4%, 24.8% and 8.6%; ≥75% clearance rates of 38.7%, 31.2%, and 10.5%; mean percent change in wart count of −40.9%, −37.7%, and −7.8%; and at least 50% reduction in wart count in 49.5%, 43.1%, and 20.0% of subjects in the 3.75% imiquimod, 2.5% imiquimod, and placebo groups, respectively, in the ITT population).

It should be noted that the primary efficacy variable used in this study (complete clearance of all warts, both Baseline and newly emerged, in all assessed anatomic areas) was very conservative. Warts were counted in all assessed anatomic areas without distinction as to those warts identified at baseline or those newly identified. In this study, subjects applied study medication to individual warts in various anatomic areas identified at Baseline. Some subjects developed new warts during the study, and these new warts may have appeared in anatomic areas involved at Baseline as well as in newly involved anatomic areas. New warts were treated with study medication when they appeared, but received less than a full course of treatment, because treatment was not extended beyond 8 weeks from randomization/Day 1 visit. Subjects who did not completely clear all warts by the Week 8/EOT visit were followed for a maximum 8 week no treatment period. As with evaluations during the daily treatment phase, subjects were evaluated for the presence of EGW in all anatomic areas, and no distinction was made between baseline and newly evident warts. As efficacy measures were based on complete clearance of all warts, not just warts presented at Baseline, development of new warts would potentially lower the complete and partial clearance rates.

Subgroup analyses were performed for the primary efficacy variable. In general, the complete clearance rates increased in a dose-dependent manner regardless of subgroup. The most striking subgroup effect was observed in the analysis by gender; the complete clearance rates were consistently higher in females than in males in all treatment groups. The higher absolute clearance rates in females than in males have been seen previously with 5% imiquimod cream as well as with other topical treatments and may be due in part to the distribution of warts on females (eg, less keratinized skin).

In addition to gender subgroup, the complete clearance rates tended to be higher in subjects with ≤7 warts at Baseline, in subjects with a Baseline wart area ≤70 $mm^2$, in subjects who took a rest period, in subjects with no previous imiquimod treatment, in subjects whose EGW was first diagnosed within I year, and in subjects with baseline warts in the anatomic areas with less keratinized skin such as the (perianal area, the perineal area, on the glans penis, or on the vulva). Of note, baseline demographics for the population as a whole suggest that EGWs in this study cohort were of relatively longstanding duration (mean/median years since diagnosis of 5.4/2.2 years).

Safety

Daily application of 3.75% or 2.5% imiquimod cream was generally well tolerated in this study. Few subjects discontinued the study due to adverse events. Very few serious adverse events were reported, and none were considered treatment related. The proportion of subjects with treatment-related AEs was higher in the active treatment groups (19.5% and 18.4% in the 3.75% and 2.5% imiquimod, respectively) than with placebo (2.9%), but there was no difference in the incidence rates between imiquimod groups. Most AEs were mild or moderate in intensity, and resolved without sequelae.

The majority of AEs considered treatment-related occurred in the system organ class "General Disorders and Administrative Site Conditions", and are not unanticipated with imiquimod. For the most part, these represented various application site reaction symptoms such as pain, irritation, and pruritus. The proportion of subjects with any application site reaction was similar in the active treatment groups.

Anticipated reactions in the application area were also captured separately as local skin reactions (LSRs). The frequency and intensity of LSRs were higher in the active treatments compared with placebo. Erythema was the LSR reported with the greatest frequency and the greatest mean intensity in all treatment groups. Severe intensity LSRs were similar between the active groups. Local skin reactions were coincident with the treatment period and rapidly decreased when treatment was concluded.

There was no evidence of clinically meaningful trends in vital sign measurements or clinical laboratory measurements.

Conclusion

The 3.75% and 2.5% cream formulations of imiquimod demonstrated substantial efficacy for the treatment of EGW. All efficacy measures for which statistical testing was performed were significantly superior in the 3.75% and 2.5% imiquimod treatment groups compared with placebo in both the ITT and PP populations. The difference between 3.75% imiquimod and 2.5% imiquimod did not reach statistical significance at any time during the study. Treatment with either imiquimod formulation resulted in greater increases in local skin reactions compared with the placebo cream: erythema was the LSR reported with the greatest frequency and the greatest mean intensity in all treatment groups. For both active creams, the number and severity of local skin reactions decreased rapidly after the completion of treatment. The most frequently reported adverse events were application site reactions observed in the active treatment groups; however, few subjects discontinued the study as a result of adverse events, indicating that these events were manageable and generally well tolerated.

Study Number: GW01-0801

Objectives: The primary objective of this study is to compare the efficacy and safety of 2.5% imiquimod cream and 3.75% imiquimod cream to placebo cream, applied once daily for up to 8 weeks, in the treatment of external genital warts (EGW). The secondary objective of this study is to provide information on recurrence of EGW.

Methodology:

This was a randomized, double-blind, placebo-controlled, multicenter study that compared the efficacy and safety of 2.5% imiquimod cream and 3.75% imiquimod cream with that of placebo in the treatment of EGW. Subjects determined to be eligible during the screening period were stratified by gender and randomized in a 2:2:1 ratio to 2.5% imiquimod cream, 335% imiquimod cream, or placebo cream. Subjects were scheduled for 1 prestudy screening visit, and then were scheduled for visits every 2 weeks for up to 16 weeks during the evaluation period, depending upon clearance of all baseline and new warts. During the evaluation period, subjects applied investigative cream to the identified treatment area for a maximum of 8 weeks. If the subject did not achieve complete wart clearance by the Week 8 visit (end of treatment, EOT), the subject was monitored for an additional maximum of 8 weeks. Subjects determined to have achieved clearance of all warts at any time until Week 16 completed procedures for the end-of-study (FOS) visit and were eligible to immediately enter the follow-up period for determination of recurrence: During the follow-up period, subjects were monitored every 4 weeks for up to 12 weeks or until the recurrence of warts.

Clinical evaluations included counting of warts and assessment of local skin reactions (LSRs), and recording of adverse events (AEs) and concomitant medications. At selected centers, photography was performed at designated visits. Laboratory tests were also performed prior to treatment and at the EOS visit to assess safety.

Number of Subjects (Total and for Each Treatment):

It was planned to enroll approximately 450 subjects in a 2:2:1 ratio. Actual enrollment was 470 subjects, and the ITT population and safety population comprised 470 subjects (195 imiquimod 3.75%, 178 imiquimod 2.5%, and 97 placebo). The per protocol (PP) population comprised 347 subjects (137 imiquimod 3.75%, 134 imiquimod 2.5%, and 76 placebo).

Inclusion Criteria:

Subjects could participate in the study if they met the following inclusion criteria:

1. Were willing and able to give informed consent—for subjects under 18, the parent/legal guardian was required to give written informed consent and the subject was required to provide written assent in accordance with local regulations;
15. Were at least 12 years of age at the time of initial screening:
16. Were willing and able to participate in the study as outpatients, making frequent visits to the study center during the treatment and follow-up periods, and to comply with all study requirements;
17. Had a diagnosis of external genital/perianal warts with at least 2 warts and no more than 30 warts located in one or more of the following anatomic locations:
   In both sexes: inguinal, perineal, and perianal areas;
   In men: over the glans penis, penis shaft, scrotum, and foreskin;
   In women: on the vulva;
18. Had total wart areas of at least 10 $mm^2$;
19. Were judged to be in good health based upon the results of a medical history, physical examination, and safety laboratory profile;
20. If female and of childbearing potential, had a negative serum pregnancy test at Screening and a negative urine pregnancy test prior to randomization and were willing to use effective contraception; and
21. If male or a male partner of a female subject, were willing to use condoms for sexual activities during the study.

Exclusion Criteria:

Subjects were excluded from the study if they met any of the following criteria:

1. Had received any topical and/or destructive treatments for external genital warts within 4 weeks (within 12 months for imiquimod and within 12 weeks for sinecatechins) prior to enrollment (ie, the randomization visit);
22. Had received any of the following treatments within the indicated time intervals prior to enrollment:

| Medication/Treatment | Washout Interval |
|---|---|
| Any marketed or investigational HPV vaccines | 12 months |
| Imiquimod | 12 months |
| Sinecatechins (Veregen ®) | 12 weeks |
| Interferon/Interferon inducer | 4 weeks |
| Cytotoxic drugs | 4 weeks |
| Immunomodulators or immunosuppressive therapies | 4 weeks |
| Oral antiviral drugs (with the exception of oral acyclovir and acyclovir related drugs for suppressive or acute therapy herpes; or oseltamivir for prophylaxis or acute therapy of influenza) | 4 weeks |
| Topical antiviral drugs (including topical acyclovir and acyclovir related drugs) in the wart areas | 4 weeks |
| Podophyllotoxin/Podofilox in the wart areas | 4 weeks |
| Oral and parenteral corticosteroids (inhaled/intranasal steroids are permitted) | 4 weeks |
| Any topical prescription therapy for any conditions in the wart areas | 4 weeks |
| Dermatologic/cosmetic procedures or surgeries in the wart areas | 4 weeks |

23. Had any evidence (physical or laboratory) of clinically significant or unstable disease and/or any condition that might have interfered with the response to the study treatment or altered the natural history of EGW;
24. Were currently participating in another clinical study or had completed another clinical study with an investigational drug or device within the past 4 weeks;
25. Had known or active chemical dependency or alcoholism as assessed by the investigator;
26. Had known allergies to study drug or any excipient n the study cream;
27. Were currently immunosuppressed or had a history of immunosuppression;
28. Had a planned surgery that would cause an interruption of study treatment;
29. Had sexual partners currently in treatment with an approved or investigational treatment for EGW;
30. Had any current or recurrent malignancies in the genital or treatment area;
31. Had any untreated or unstable genital infections (other than genital warts);
32. Had any of the following conditions:
   known human immunodeficiency virus (HIV) infection;
   current or past history of high risk HPV infection (eg, HPV 16, 18, etc);

an outbreak of herpes genitalis in the wart areas within 4 weeks prior to enrollment;

internal (rectal, urethral, vaginal/cervical) warts that required or were undergoing treatment;

a dermatological disease (eg, psoriasis) or skin condition in the wart areas which may have caused difficulty with examination;

33. If female, had clinically significant abnormalities on pelvic examination or had laboratory test results showing high-grade pathology (eg, high-grade squamous intraepithelial lesion, moderate or severe dysplasia, squamous cell carcinoma);

34. If female, were nursing or pregnant or planned to become pregnant during the study.

Test Product, Dose and Mode of Administration:

The test products were 2.5% imiquimod cream and 3.75% imiquimod cream. The reference therapy was placebo cream. Subjects applied the study drug in a thin layer once daily to each wart identified at Baseline and any new wart that appeared during the treatment period.

A maximum of 1 packet (250 mg) of study drug was applied for a given dose (250 mg of 3.75% cream is equivalent to 9.375 mg imiquimod, and 250 mg of 2.5% cream is equivalent to 6.25 mg imiquimod). Study drug was applied prior to normal sleeping hours and removed approximately 8 hours later with mild soap and water. Subjects were to continue to apply study cream to all identified wart/wart areas until all warts were cleared.

The investigational products, 2.5% imiquimod cream and 3.75% imiquimod cream, contained imiquimod, isostearic acid, benzyl alcohol, cetyl alcohol, stearyl alcohol, polysorbate 60, sorbitan monostearate, white petrolatum, glycerin, methyl paraben, propyl paraben, purified water, and xanthan gum. The placebo cream contained the same ingredients as the active formulations with the exception of imiquimod.

Subjects meeting all inclusion and no exclusion criteria were randomly assigned in a 2:2:1 ratio to 1 of the 3 treatment groups (2.5% imiquimod cream:3.7% imiquimod cream:or placebo cream).

Each dose of study drug was to be applied by the subject at approximately the same time of day. To reduce the risk of study drug removal from daily hygienic or physical activities, study drug was to be applied just prior to the subject's normal sleeping hours.

Subjects were to wash the treatment area with mild soap and water before applying the study medication, allow the area to dry thoroughly, and then apply the study medication once daily. Subjects were to apply a thin layer of study cream to each wart identified at Baseline and any new wart that appeared during the treatment period. Only up to one packet of study cream was to be applied per application.

The subjects were encouraged to leave study cream on for approximately 8 hours, preferably during normal sleeping hours, and were not to wash the treatment area, swim, shower or bathe, or have sexual contacts while the study medication was on the skin. Subjects could wash the study cream off with soap and water any time after approximately 8 hours of application. Subjects were to continue applying the study cream for a maximum of 8 weeks or until the investigator determined that they had achieved complete clearance of all (baseline and new) warts. Subjects were not to make up any missed doses.

Rest periods, or temporary interruptions of dosing due to intolerable local skin reactions, were allowed during the study if the investigator or subject (or legal parent or guardian) decided that study drug application should be interrupted. Subjects who were placed on a rest period were to be seen by the investigator prior to resuming treatment with study drug in order to assess if the recovery of the treatment site was sufficient. Doses missed due to a rest period were not counted as missed doses in the assessment of subject compliance with the treatment regimen. The study visit schedule and procedures were not to be altered due to missed doses or rest periods. If a subject experienced a strong local reaction in one treatment area but not in other treated areas, the subject could temporarily stop applying study cream in that affected area while continuing study treatment in the other areas.

During treatment period, any new warts appearing in any of the protocol-defined anatomic locations were treated with the study cream. Neither the warts present at Baseline nor new warts were allowed to be treated during the no-treatment period (ie, from the Week 8/EOT visit to the Week 16 visit).

Criteria for Evaluation:

Primary Efficacy Variables:

The primary efficacy variable was subject status with respect to complete clearance of all warts (baseline and new) in all anatomic areas at Week 16 (End of Study, EOS), as determined by the investigator.

Secondary and Tertiary Efficacy Variables

Secondary efficacy variables were the following:

Subject status with respect to partial clearance of baseline warts, defined as at least 75% reduction in the number of baseline warts at EOS/Week 16.

Percent change from Baseline to EOS in total number of warts.

Subject status with respect to complete clearance of all warts at EOS, remaining cleared in all anatomic areas, as determined by the investigator, through the end of the follow-up for recurrence period, and Time from Baseline to complete clearance of all warts, as determined by the investigator.

Tertiary efficacy variables were the following:

Subject status with respect to complete clearance of all warts (baseline and new) in all anatomic areas at EOT/Week 8, and Subject status with respect to at least 50% reduction in the number of baseline warts at EOS/Week 16.

Statistical Methods for Efficacy Analyses

Efficacy analyses were conducted on the ITT population and on the PP population. For the primary efficacy variable, imputations were made for missing data points using last observation carried forward (LOCF, primary analysis), taking all missed observations as failure (sensitivity analysis), and using observed cases (supportive analysis). For the ITT population, subjects who had no post-baseline data were included in the analysis carrying forward the baseline data. The PP population analysis used observed cases except for complete clearance and recurrence.

Analysis of the Primary Efficacy Variable

The primary efficacy endpoint, complete clearance rate at the EOS, was analyzed using Cochran-Mantel-Haenszel (CMH) statistics, stratifying by gender and site.

All pairwise comparisons of active treatment versus placebo were made using Hochberg's modified Bonferroni procedure. If either test was significant at a 0.025 level of significance, then that test was considered significant. Otherwise, if both tests were significant at 0.05, then both tests were considered significant. The 3.75% and 2.5% treatment groups were compared to each other at the 0.05 level of significance if at least one of these treatment groups was found to be different than the placebo using the Hochberg's test.

In the primary analysis of complete clearance rate, the Breslow-Day statistic was tested at the 10% level for heterogeneity of the odds ratios across analysis sites. A finding of statistical significance in this test was followed by exploratory analyses to characterize the source of the heterogeneity.

Analysis of Secondary Efficacy Variables

The secondary efficacy variable partial clearance rate was analyzed using Cochran-Mantel-Haenszel (CMH) statistics, stratifying by gender and site. The percent change from baseline to EOS in wart count was analyzed using analysis of covariance (ANCOVA), controlling for baseline wart count, gender, and analysis site. The proportion of subjects who were clear prior to or at EOS and remained clear at the end of the follow-up for recurrence period was summarized by frequency count and 95% confidence interval. The time to complete clearance was analyzed using the log rank test in the context of a Kaplan-Meier survival analysis.

For analysis of secondary efficacy variables, only the LOCF method was used for the ITT population, and observed cases for the PP population. All data from interim visits were analyzed using visit windows.

The secondary efficacy variables were to be compared pairwise using Hochberg's modified Bonferroni procedure.

- If at least one of the active arms was found to be superior to placebo in the primary efficacy variable of complete clearance according to Hochberg's modified Bonferroni procedure, the secondary efficacy variable of partial (≥75%) clearance was compared between each of the active arms and placebo.
- If the secondary efficacy variable of partial (≥75%) clearance was found to be superior to placebo in either of the active treatment groups, then the secondary efficacy variable of percent change from Baseline to EOS in wart count was tested.
- If the secondary efficacy variable of percent change from Baseline to EOS in wart count was found to be superior to placebo in either of the active treatment groups, then the secondary efficacy variable of complete clearance at EOS and remained clear at the end of follow-up for recurrence period was tested.
- If the secondary efficacy variable of complete clearance at EOS and remained clear at the end of follow-up for recurrence period was found to be superior to placebo in either of the active treatment groups, then the secondary efficacy variable of time from Baseline to complete clearance was tested.

The percent change from Baseline in EGW count at each post-baseline visit was summarized by mean, standard deviation, median, and range by treatment group. The recurrence rate of warts was summarized by treatment group and study visit using visit windows.

Analysis of Tertiary Efficacy Variables

The tertiary efficacy endpoints, complete clearance rate at EOT and subject status with respect to at least a 50% reduction in baseline wart count, were analyzed using Cochran-Mantel-Haenszel (CMH) statistics, stratifying on gender and site.

Visit Windows

For the analysis of wart counts, the data were summarized by analysis visits. Analysis visits were assigned according to the actual study day of the evaluation as illustrated in Table 98 below.

TABLE 98

Visit Windows

| Evaluation Period Analisis Visit | Target Study Day | Day Range |
|---|---|---|
| Baseline | 1 | Study Day ≤ 1 |
| Week 2 | 15 | 1 < Study Day ≤ 22 |
| Week 4 | 29 | 22 < Study Day ≤ 36 |
| Week 6 | 43 | 36 < Study Day ≤ 50 |
| Week 8 | 57 | 50 < Study Day ≤ 64 |
| End of Treatment (EOT) | — | Study Day ≤ 64 |
| Week 10 | 71 | 64 < Study Day ≤ 78 |
| Week 12 | 85 | 78 < Study Day ≤ 92 |
| Week 14 | 99 | 92 < Study Day ≤ 106 |
| Week 16 | 113 | 106 < Study Day ≤ 127 |
| End of Study EOS) | — | Study Day ≤ 127 |
| **Follow-up Period Analysis Visit** | **Target Study Day Post EOS** | **Day Range** |
| Follow-up Week 4 | 29 | 1 < Study Day ≤ 43 |
| Follow-up Week 8 | 57 | 43 < Study Day ≤ 71 |
| Follow-up Week_12 | 85 | 71 < Study Day ≤ 99 |

All visits (scheduled or unscheduled) were mapped to an analysis visit. If more than 1 evaluation was assigned to an analysis visit, the evaluation with the lowest wart count within the window was used for analysis. Study day was calculated as the date of evaluation minus the date of randomization plus one except for the follow up visits. For the follow up visits, study day was calculated as the date of evaluation minus the date of End of Study (EOS) visit plus one.

Safety Analyses

All safety variables Were analyzed using the safety population. Safety variables included the following:

- Local skin reactions.
- Rest periods during the treatment period:
  - The number and percentage by treatment group of subjects who required a rest period (1 or more).
  - The number of dosing days missed due to rest periods.
  - The number of dosing days prior to the beginning of the first rest period.
- Adverse events.
- Clinical laboratory test results.

Adverse Events

Adverse events were coded using Medical Dictionary for Regulatory Activities (MedDRA, version 11.0) terminology. A treatment-emergent AE was defined as an AE that began or worsened in severity after Day 1 and no more than 30 days after the last application of study drug. If an AE had a completely missing start date, it was considered a "treatment emergent" event, unless the stop date was prior to the date of randomization.

Treatment-emergent AEs and all AEs were summarized for each treatment group by the overall incidence of at least one event, incidence by system organ class, and incidence by system organ class and preferred term. Each subject contributed only once to each of the rates, regardless of the number of occurrences (events) the subject experienced.

Treatment-emergent AEs were summarized by severity (mild, moderate, or severe) and by relationship to study product (related, not related). Events were considered not related to study product if the relationship was "not related" or "probably not related." Similarly, related events were those that were "probably related" or "related." An AE was assumed to be related to study drug if the relationship to study drug was unknown. For AEs that occurred more than once, the AE that was most related to study drug in that period was used in the summary of AEs by relationship to study drug categories. Similarly, the AE with the maximum intensity in that period was used in the summary of AEs by severity. If severity was missing or unknown, it was assumed to be severe.

The incidence of AEs was summarized for subgroup analysis by gender, by age subgroup, and by number of anatomic locations (ie, one location versus multiple). Serious AEs (SAES) and AEs that led to discontinuation from the study were listed by subject.

Local Skin Reactions

The LSR intensities were summarized by frequency counts and mean score by treatment group and study visit for each LSR type. The LSRs were graded as follows:

Erythema (0=None, 1=Faint to mild redness, 2=Moderate redness, 3=Intense redness), Edema (0=None, 1=Mild visible or barely palpable swelling/induration, 2=Easily palpable swelling/induration, 3=Gross swelling/induration), Weeping/Exudate (0=None, 1=Minimal exudate, 2=Moderate exudate, 3=Heavy exudate), Flaking/Scaling/Dryness (0=None, 1=Mild dryness/flaking, 2=Moderate dryness/flaking, 3=Severe dryness/flaking), Scabbing/Crusting (0=None, 1=Crusting, 2=Serous scab, 3=Eschar), Erosion/Ulceration (0=None, 2=Erosion, 3=Ulceration).

Erosion/ulceration intensity was originally collected as 0=None, 1=Erosion, and 2=Ulceration. For consistency in the analysis of LSR intensities and sum score, these were recoded as 0=None, 2=Erosion, and 3=Ulceration.

The most intense reaction (post-baseline) and incidence of any reaction (post-baseline) for each LSR type were also presented by frequency distribution and mean score by treatment group. Data were analyzed using windows.

The LSR sum score (addition of 6 scores) was computed and summarized by treatment group at each study visit.

Rest Periods

A rest period was a temporary interruption of dosing due to intolerable LSRs or other AEs. Doses missed due to a subject's noncompliance with the treatment regimen were not considered a rest period. The start of a rest period was the first date on which the study medication was not applied for the reason of "rest period" on CRF page 20. The end of the rest period was the first date of application following the start of the rest period. The number and percentage of subjects who required a rest period (I or more) were analyzed by treatment group using CMH statistics. The number of dosing days missed due to rest periods and the number of dosing days prior to the beginning of the first rest period were analyzed using the Wilcoxon test. In this analysis, only subjects who experienced a rest period were included.

Disposition of Subjects

The disposition of subjects for the evaluation period is shown in Table 99 below:

TABLE 99

Subject Disposition-Evaluation Period (ITT Population)

| Total Subjects, n (%) | Imiquimod Cream 3.75% | 2.5% | Placebo | Overall |
|---|---|---|---|---|
| Randomized | 195 | 178 | 97 | 470 |
| Completed evaluation periods[a] | 136 (69.7) | 121 (68.0) | 66 (68.0) | 323 (68.7) |
| Not Cleared | 82 (42.1) | 87 (48.9) | 56 (57.7) | 225 (47.9) |
| Cleared, Ended Study | 4 (2.1) | 3 (1.7) | 4 (4.1) | 11 (2.3) |
| Cleared, Entered Follow-up | 50 (25.6) | 31 (17.4) | 6 (6.2) | 87 (18.5) |
| Discontinued evaluation period | 59 (30.3) | 57 (32.0) | 31 (32.0) | 147 (31.3) |
| Reasons for discontinuation during evaluation period, n (%) | | | | |
| Safety reasons (AEs) | 3 (1.5) | 2 (1.1) | 1 (1.0) | 6 (1.3) |
| Investigator's request | 1 (0.5) | 0 | 0 | 1 (0.2) |
| Subject's request (not AE) | 10 (5.1) | 8 (4.5) | 7 (7.2) | 25 (5.3) |
| Lack of efficacy | 0 | 1 (0.6) | 0 | 1 (0.2) |
| Noncompliance | 1 (0.5) | 4 (2.2) | 0 | 5 (1.1) |
| Use of concomitant therapy | 0 | 0 | 0 | 0 |
| Lost to follow-up | 39 (20.0) | 37 (20.8) | 19 (19.6) | 95 (20.2) |
| Other (not AE) | 5 (2.6) | 5 (2.8) | 4 (4.1) | 14 (3.0) |

AE = adverse event.

[a]Based on investigator assessment (CRF page 31), includes subjects who (1) cleared prior to or at EOS/Week 16, (2) not cleared at Week 16.

Of the 794 subjects who were screened, 470 (59.2%) were randomized and 324 (40.8%) were screen failures. The most frequent reason for screen failure (170 subjects [52.5%] out of 324 screen failures) was that subjects did not have a clinical diagnosis of EGW with at least 2 warts and no more than 30 warts in one or more of the protocol-specified anatomic locations.

One hundred ninety five (195) subjects were randomized into the 3.75% imiquimod treatment group, 178 subjects were randomized into the 2.5% imiquimod treatment group, and 97 subjects were randomized into the placebo group. Overall, 68.7% of subjects completed the study, and in the individual treatment groups, 69.7%, 68.0%, and 68.0% in the 3.75% imiquimod, 2.5% imiquimod, and placebo groups, respectively, completed the study. Lost to follow-up was the most common reason for discontinuation from the evaluation period, and accounted for withdrawal of approximately 20% of subjects in each treatment group. Among the treatment groups, there was no appreciable difference in the percentages of subjects who were lost to follow-up or the times at which they became lost to follow-up. A sizeable number of subjects discontinued early, ie, had no post-Baseline visit: 15 of 59 (25.4%) in the 3.75% imiquimod group, 16 of 57 (28.1%) in the 2.5% imiquimod group, and 5 of 31 (16.1%) in the placebo group.

Follow-Up for Recurrence Period

Subject disposition for the follow-up period is shown in Table 100 below:

TABLE 100

Subject Disposition-Follow-up Period (ITT Population)

| Total Subjects, n (%) | Imiquimod Cream 3.75% | 2.5% | Placebo | Overall |
|---|---|---|---|---|
| Entered follow-up period | 50 (100) | 31 (100) | 6 (100) | 87 (100) |
| Completed study, no recurrence | 41 (82.0) | 20 (64.5) | 6 (100) | 67 (77.0) |
| Subjects with EGW recurrence | 7 (14.0) | 7 (22.6) | 0 | 14 (16.1) |
| Discontinued follow-up period[a] | 2 (4.0) | 4 (12.9) | 0 | 6 (6.9) |

TABLE 100-continued

Subject Disposition-Follow-up Period (ITT Population)

| | Imiquimod Cream | | | |
|---|---|---|---|---|
| Total Subjects, n (%) | 3.75% | 2.5% | Placebo | Overall |
| Reasons for discontinuation during follow-up, n (%) | | | | |
| Subject's request (not AE) | 0 | 1 (3.2) | 0 | 1 (1.1) |
| Lost to follow-up | 2 (4.0) | 3 (9.7) | 0 | 5 (5.7) |
| Other (not AE) | 0 | 0 | 0 | 0 |

AE = adverse event.
[a]Excludes subjects discontinued due to recurrence of external genital warts.

Overall, 87 subjects entered the follow-up for recurrence period; 50 from the 3.75% imiquimod treatment group, 31 from the 2.5% imiquimod treatment group, and 6 from the placebo group. Only 6 subjects (2 and 4 in the 3.75% and 2.5% imiquimod groups, respectively) discontinued the follow-up for evaluation period. Of these, 5 subjects were lost to follow-up and 1 subject was discontinued at his request.

Efficacy Evaluation

Datasets Analyzed

The number of subjects in each analysis population is presented in Table 101 below.

TABLE 101

Number (%) of Subjects in Analysis Populations

| | Imiquimod Cream | | | |
|---|---|---|---|---|
| Populations | 3.75% | 2.5% | Placebo | Overall |
| ITT population | 195 | 178 | 97 | 470 |
| PP population | 137 | 134 | 76 | 347 |
| Safety population | 195 | 178 | 97 | 470 |
| Follow-up for Recurrence population | 50 | 31 | 6 | 87 |

A total of 470 subjects were included in the ITT and safety populations. Of these, 347 subjects were included in the PP population. A total of 87 subjects elected to enter the follow-up period and comprised the follow-up for recurrence population.

Demographic and Other Baseline Characteristics

Prestudy/Baseline Demographics

Demographic and baseline characteristics for the ITT population are shown in Table 102 below.

TABLE 102

Demographic Summary by Treatment Group-ITT Population

| | Imiquimod Cream | | | |
|---|---|---|---|---|
| | 3.75% (N = 195) | 2.5% (N = 178) | Placebo (N = 97) | Overall (N = 470) |
| Age in years | | | | |
| Mean (SD) | 32.5 (11.6) | 32.7 (11.3) | 30.5 (10.6) | 32.2 (11.3) |
| Median | 29.0 | 30.0 | 27.0 | 29.0 |
| Minimum, Maximum | 18.0, 81.0 | 17.0, 78.0 | 18.0, 75.0 | 17.0, 81.0 |
| Sex, n (%) | | | | |
| Male | 95 (48.7) | 83 (46.6) | 47 (48.5) | 225 (47.9) |
| Female | 100 (51.3) | 95 (53.4) | 50 (51.5) | 245 (52.1) |

TABLE 102-continued

Demographic Summary by Treatment Group-ITT Population

| | Imiquimod Cream | | | |
|---|---|---|---|---|
| | 3.75% (N = 195) | 2.5% (N = 178) | Placebo (N = 97) | Overall (N = 470) |
| Race, n (%) | | | | |
| White | 147 (75.4) | 122 (68.5) | 66 (68.0) | 335 (71.3) |
| Black/African American | 41 (21.0) | 47 (26.4) | 28 (28.9) | 116 (24.7) |
| Other | 7 (3.6) | 9 (5.1) | 3 (3.1) | 19 (4.0) |
| Ethnicity, n (%) | | | | |
| Hispanic | 31 (15.9) | 25 (14.0) | 11 (11.3) | 67 (14.3) |
| Non-Hispanic | 164 (84.1) | 153 (86.0) | 86 (88.7) | 403 (85.7) |

SD = standard deviation.

Demographic characteristics were similar among the 3 treatment groups. Slightly more than half of the subjects were female. Overall, 71.3% of subjects were White, and more than 84% of subjects in every treatment group were non-Hispanic. The mean age ranged from 30.5 years in the placebo group to 32.7 years in the 2.5% imiquimod treatment group.

Medical History

The most frequently-reported concomitant medical conditions were hypertension/high blood pressure (42 subjects), seasonal allergies (27 subjects), and depression (21 subjects).

External Genital Warts Treatment History

Previous EGW treatment was reported by 493%, 42.7%, and 33.0% of subjects in the 3.75% imiquimod, 2.5% imiquimod, and placebo groups, respectively. Cryotherapy was the most frequently reported treatment, and had been performed in 28.2% of the subjects in the 3.75% imiquimod treatment group, 18.5% of subjects in the 2.5% imiquimod treatment group, and 13.4% of subjects in the placebo group. Other treatments included acetic acid (in a total of 42 subjects), imiquimod (in 33 subjects), podophyllotoxin (in 23 subjects), laser therapy (in 22 subjects), "other" treatments (in 20 subjects), surgical excision (in 12 subjects), podophyllin (in 9 subjects), and electrodessication (in 3 subjects).

Prior and Concomitant Medications

Sixteen subjects (8.2%) in the 3.75% imiquimod treatment group, 12 subjects (6.7%) in the 2.5% imiquimod treatment group, and 4 subjects (4.1%) in the placebo group were taking prior medications, ie, medications that were discontinued prior to the date of randomization. The most common prior medications were antibacterials for systemic use in 3.6% of the 3.75% imiquimod treatment group, 3.9% of the 2.5% imiquimod treatment group, and 2.1% of the placebo group.

Ninety-two subjects (47.2%) in the 3.75% imiquimod treatment group, 94 subjects (52.8%) in the 2.5% imiquimod treatment group, and 45 subjects (46.4%) in the placebo received one or more concomitant medications during the study. The following classes of concomitant medications were received by more than 10% of the subjects in one or more treatment groups:

Analgesics, received by 18.5% of the 3.75% imiquimod treatment group, 13.5% of the 2.5% imiquimod treatment group, and 20.6% of the placebo group;

Anti-inflammatory and anti-rheumatic products, received by 10.3% of the 3.75% imiquimod treatment group, 13.5% of the 2.5% imiquimod treatment group, and 12.4% of the placebo group;

Sex hormones and modulators of the genital system, by 7.7% of the 3.75%® imiquimod treatment group, 10.1% of the 2.5% imiquimod treatment group, and 9.3% of the placebo group.

Baseline Number of External Genital Warts

A summary of the external genital wart counts at Baseline and other baseline data relevant to subjects' EGW are presented in Table 103 below:

TABLE 103

Baseline External Genital Warts Data by Treatment Group-ITT Population

| | Imiquimod Cream | | | |
|---|---|---|---|---|
| | 3.75% (N = 195) | 2.5% (N = 178) | Placebo (N = 97) | Overall (N = 470) |
| Total wart area ($mm^2$) | | | | |
| Mean (SD) | 150.9 (458.7) | 160.2 (334.8) | 140.7 (248.6) | 152.3 (377.0) |
| Median | 52 | 68 | 73 | 61 |
| Minimum, Maximum | 10, 5579 | 10, 3212 | 6, 1969 | 6, 5579 |
| Total wart count | | | | |
| Mean (SD) | 8.6 (6.4) | 9.2 (6.7) | 11.6 (8.8) | 9.4 (7.1) |
| Median | 7 | 7 | 8 | 7 |
| Minimum, Maximum | 2, 30 | 2, 30 | 2, 30 | 2, 30 |
| Years Since Diagnosis | | | | |
| Mean | 4.2 | 4.8 | 3.6 | 4.3 |
| Standard Deviation | 6.6 | 7.8 | 6.1 | 7.0 |
| Median | 1.4 | 1.5 | 1.3 | 1.4 |
| Minimum, Maximum | 0.0, 33.3 | 0.0, 53.7 | 0.0, 33,7 | 0.0, 53.7 |
| Anatomic location, Males[a], n | 95 | 83 | 47 | 225 |
| Inguinal | 29 (30.5) | 20 (24.1) | 13 (27.7) | 62 (27.6) |
| Perineal | 7 (7.4) | 6 (7.2) | 4 (8.5) | 17 (7.6) |
| Perianal | 6 (6.3) | 8 (9.6) | 2 (4.3) | 16 (7.1) |
| Glans penis | 9 (9.5) | 6 (7.2) | 5 (10.6) | 20 (8.9) |
| Penis shaft | 77 (81.1) | 71 (85.5) | 42 (89.4) | 190 (84.4) |
| Scrotum | 27 (28.4) | 29 (34.9) | 8 (17.0) | 64 (28.4) |
| Foreskin | 3 (3.2) | 4 (4.8) | 1 (2.1) | 8 (3.6) |
| Anatomic location, Females[b], n | 100 | 95 | 50 | 245 |
| Inguinal | 17 (17.0) | 11 (11.6) | 6 (12.0) | 34 (13.9) |
| Perineal | 48 (48.0) | 43 (45.3) | 22 (44.0) | 113 (46.1) |
| Perianal | 44 (44.0) | 52 (54.7) | 22 (44.0) | 118 (48.2) |
| Vulva | 59 (59.0) | 60 (63.2) | 32 (64.0) | 151 (61.6) |
| Number of treatment anatomic areas, n (%)-Males[a] | | | | |
| Total Males | 95 (100) | 83 (100) | 47 (100) | 225 (100) |
| 1 | 47 (49.5) | 38 (45.8) | 25 (53.2) | 110 (48.9) |
| 2 | 34 (35.8) | 31 (37.3) | 16 (34.0) | 81 (36.0) |
| 3 | 13 (13.7) | 12 (14.5) | 6 (12.8) | 31 (13.8) |
| 4 | 1 (1.1) | 2 (2.4) | 0 | 3 (1.3) |
| Number of treatment anatomic areas, n (%)-Females[b] | | | | |
| Total Females | 100 (100) | 95 (100) | 50 (100) | 245 (100) |
| 1 | 49 (49.0) | 40 (42.1) | 26 (52.0) | 115 (46.9) |
| 2 | 36 (36.0) | 40 (42.1) | 17 (34.0) | 93 (38.0) |
| 3 | 13 (13.0) | 14 (14.7) | 6 (12.0) | 33 (13.5) |
| 4 | 2 (2.0) | 1 (1.1) | 1 (2.0) | 4 (1.6) |

SD = standard deviation.

[a]Denominator based on the number of males in treatment group.

[b]Denominator based on the number of females in treatment group.

The mean total wart area was 152.3 $mm^2$ overall, and ranged from 140.7 $mm^2$ in the placebo group to 160.2 $mm^2$ in the 2.5% imiquimod treatment group. The mean total wart count was 9.4 warts overall, and ranged from 8.6 warts in the 3.75% imiquimod treatment group to 11.6 warts in the placebo group. In males, the most commonly affected anatomic areas were the penis shaft (84.4%), the scrotum (28.4%), and the inguinal area (27.6%). In females, the most commonly affected anatomic areas were the vulva (61.6%), the perianal area (48.2%), and the perineal area (46.1%). The anatomic distribution of warts was fairly consistent across the treatment groups. More than 50% of subjects in both gender subgroups had two or more anatomic locations affected with warts at Baseline.

Measurements of Treatment Compliance

Treatment compliance data was collected and analyzed. Compliance was based on the number of applications received (where a rest period day was counted as an application) divided by the number of intended applications, or by the number of packets used (where a rest period day was counted as a packet used) divided by the number of packets intended to be used per the protocol-defined treatment regimen, whichever was greater. Noncompliance with the treatment regimen was defined as compliance less than 75% or greater than 125%.

The overall mean treatment compliance was 84.3% in the 3.75% imiquimod group, 84.7% in the 2.5% imiquimod group, and 86.8% in the placebo group. Of the 123 subjects excluded from the PP population in this study, 122 exclusions were the result of noncompliance with the treatment regimen, including many subjects who were lost to follow-up. Compliance rates were slightly higher in subjects who cleared their EGW during the study (90.9%, 88.5%, and 87.2% in the 3.75% imiquimod, 2.5% imiquimod, and placebo groups, respectively) compared with, subjects who did not clear (81.5%, 83.8%, and 86.8% in the 3.75% imiquimod, 2.5% imiquimod, and placebo groups, respectively).

Efficacy Results

Complete Clearance of all Warts

Complete Clearance Rates at End of Study

The primary efficacy variable in this study was the proportion of subjects with complete clearance of all warts (those present at Baseline and new warts) at EOS (ie, 8 weeks after EOT). The primary analysis was performed on the ITT population with imputation (LOCF) for missing data points. The results of the analyses on the population, overall and by gender, are shown in Table 104 below. Results are presented graphically for the ITT population in FIG. 25.

TABLE 104

Proportion of Subjects with Complete Clearance of Warts at the Week 16/End of Study (EOS) Visit

| | Imiquimod Cream | | |
|---|---|---|---|
| | 3.75% | 2.5% | Placebo |
| ITT Population (LOCF) | | | |
| n/N[a] (%) | 53/195 (27.2) | 34/178 (19.1) | 10/97 (10.3) |
| 95% CI | 21.1, 34.0 | 13.6, 25.7 | 5.1, 18.1 |
| P value vs placebo | <0.001** | 0.065 | — |
| P value vs 2.5% Imiquimod Cream | 0.061 | — | — |
| Males | | | |
| n/N[a] (%) | 19/95 (20.0) | 11/83 (13.3) | 2/47 (4.3) |
| 95% confidence interval | 12.5, 29.5 | 6.8, 22.5 | 0.5, 14.5 |
| P value vs Placebo | 0.015** | 0.110 | — |
| P value vs 2.5% Imiquimod Cream | 0.236 | — | — |
| Females | | | |
| n/N[a] (%) | 34/100 (34.0) | 23/95 (24.2) | 8/50 (16.0) |
| 95% confidence interval | 24.8, 44.2 | 16.0, 34.1 | 7.2, 29.1 |
| P value vs Placebo | 0.017** | 0.255 | — |
| P value vs 2.5% Imiquimod Cream | 0.147 | — | — |

LOCF = last observation carried forward, 95% CI = 95% confidence interval.

[a]n/N = number of subjects with complete clearance at end of study divided by the number of subjects analyzed.

P values are from Cochran-Mantel-Haenszel test, stratified by gender and analysis site (overall population) or stratified by analysis site (gender subgroups), taking 2 treatment groups at a time.

The P values marked with ** are statistically significant using Hochberg's modified Bonferroni procedure.

Confidence intervals are calculated using exact binomial statistics.

Breslow-Day P values for ITT Population (LOCF), males, are 3.75% Imiquimod Cream vs Placebo = 0.357, 2.5% Imiquimod Cream vs Placebo = 0.245, and 3.75% Imiquimod Cream vs 2.5% Imiquimod Cream = 0.708. Breslow-Day P values for ITT Population (LOCF), females, are 3.75% Imiquimod Cream vs Placebo = 0.358, 2.5% Imiquimod Cream vs Placebo = 0.310, and 3.75% Imiquimod Cream vs 2.5% Imiquimod Cream = 0.178.

In the ITT population, the rate of complete clearance of EGW at EOS was significantly higher (P<0.001) in the 3.75% imiquimod group (27.2%) compared with placebo (10.3%); the difference in rate of complete clearance between the 2.5% imiquimod group (19.1%) and the placebo group (10.3%) did not attain statistical significance (P=0.065). The 3.75% imiquimod group had a higher rate of complete clearance than the 2.5% imiquimod group, but the difference between the 2 active treatment groups was not statistically significant (P=0.061).

Results were similar in the by-gender analyses. Complete clearance rates at EOS were statistically significantly higher with 3.75% imiquimod than with placebo in both genders. There was no significant difference in complete clearance rates at EOS between 2.5% imiquimod and placebo in either gender. In all treatment groups, the complete clearance rates were consistently higher in females than in males.

Figure 25:
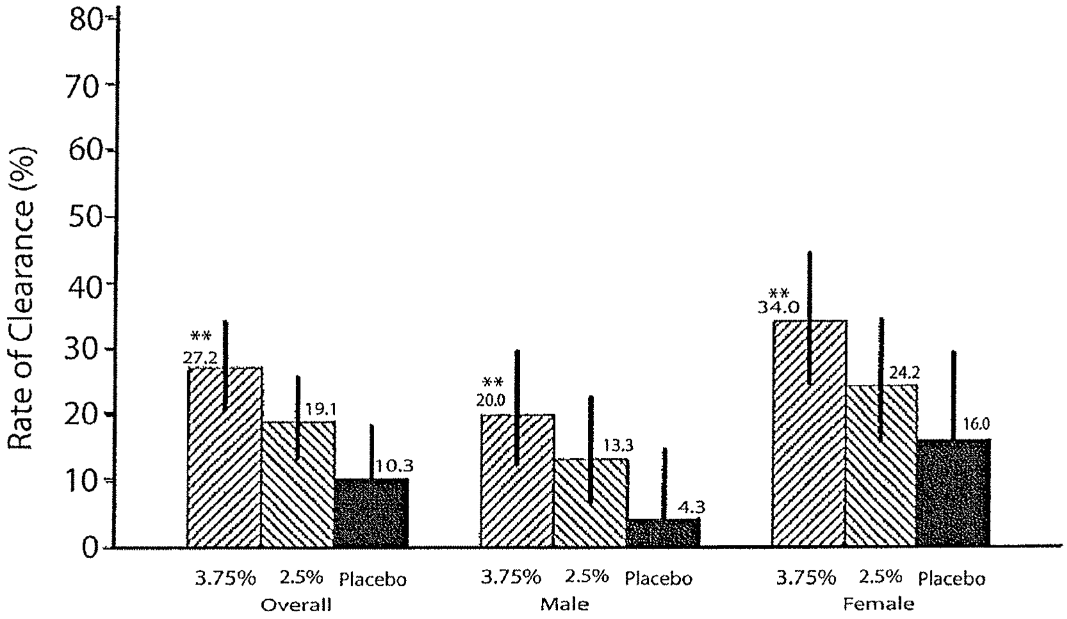
FIG. 25 shows complete clearance rates observed in the intent-to-treat (ITT) population at the end of one study of a lower-dose imiquimod treatment of genital warts.

Rates of complete clearance at EOS in the ITT population are illustrated in FIG. 25.

The primary efficacy variable was analyzed for the PP population, overall and by gender, using observed cases (OC). Results for the PP population are shown in Table 105 below.

TABLE 105

Proportion of Subjects with Complete Clearance of Warts at the Week 16/End of Study (EOS) Visit-PP Population (Observed Cases)

| | Imiquimod Cream | | |
|---|---|---|---|
| | 3.75% | 2.5% | Placebo |
| PP Population (OC), at EOS | | | |
| N | 137 | 134 | 76 |
| n/N[a] (%) | 46/137 (33.6) | 32/134 (23.9) | 9/76 (11.8) |
| 95% CI | 25.7, 42.1 | 16.9, 32.0 | 5.6, 21.3 |
| P value vs placebo | <0.001** | 0.044** | — |
| P value vs 2.5% Imiquimod Cream | 0.060 | — | — |
| Males | | | |
| n/N[a] (%) | 17/69 (24.6) | 10/63 (15.9) | 2/34 (5.9) |
| 95% confidence interval | 15.1, 36.5 | 7.9, 27.3 | 0.7, 19.7 |
| P value vs Placebo | 0.023** | 0.161 | — |
| P value vs 2.5% Imiquimod Cream | 0.286 | — | — |
| Females | | | |
| n/N[a] (%) | 29/68 (42.6) | 22/71 (31.0) | 7/42 (16.7) |
| 95% confidence interval | 30.7, 55.2 | 20.5, 43.1 | 7.0, 31.4 |

TABLE 105-continued

Proportion of Subjects with Complete Clearance of Warts at the Week 16/
End of Study (EOS) Visit-PP Population (Observed Cases)

| | Imiquimod Cream | | |
|---|---|---|---|
| | 3.75% | 2.5% | Placebo |
| P value vs Placebo | 0.005** | 0.140 | — |
| P value vs 2.5% Imiquimod Cream | 0.121 | — | — |

95% CI = 95% confidence interval,
OC = observed cases.
$^a$n/N = number of subjects with complete clearance at end of study divided by the number of subjects analyzed.
P values are from Cochran-Mantel-Haenszel test, stratified by gender and analysis site (overall population) or stratified by analysis site (gender subgroups), taking 2 treatment groups at a time.
P values marked with ** are statistically significant using Hochberg's modified Bonferroni procedure.
Confidence intervals were calculated using the exact binomial distribution.
Complete clearance was carried forward once achieved.

In the PP population, the complete clearance rates at EOS were higher than those in the ITT population for all treatment groups: 33.6% in the 3.75% imiquimod group, 23.9% in the 2.5% imiquimod group, and 11.8% in the placebo group. The larger responses in the active treatment groups were statistically significant compared with placebo (P<0.001 for 3.75% imiquimod vs placebo; P=0.044 for 2.5% imiquimod vs placebo). As was the case in the ITT population, the complete clearance rate was larger in the 3.75% imiquimod group than in the 2.5% imiquimod group, but the difference between the 2 active treatment groups was not statistically significant.

Results were similar in the by-gender analyses. Complete clearance rates at EOS were statistically significantly higher with 3.75% imiquimod than with placebo in both genders. There was no significant difference in complete clearance rates at EOS between 2.5% imiquimod and placebo in either gender. In all treatment groups, the complete clearance rates were consistently higher in females than in males.

Figure 26:
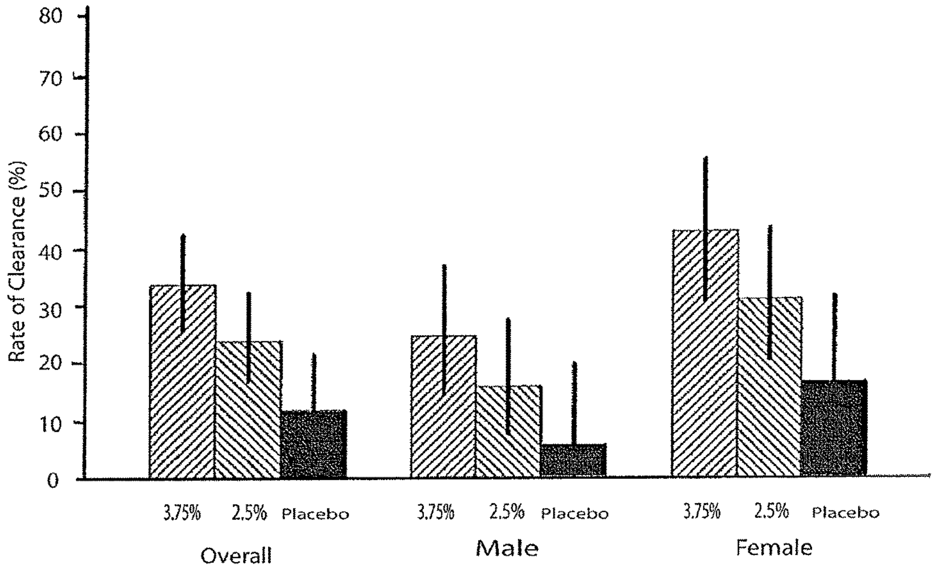
FIG. 26 shows complete clearance rates observed in the Per Protocol (PP) population at the end of one study of a lower-dose imiquimod treatment of genital warts.

Rates of complete clearance at EOS in the PP population are illustrated in FIG. 26.

Complete Clearance Rates at End of Treatment

A summary of the complete clearance at EOT for the ITT population, overall and by gender, is provided in Table 106.

TABLE 106

Proportion of Subjects with Complete Clearance of Warts at End of
Treatment-ITT Population (LOCF)

| | Imiquimod Cream | | |
|---|---|---|---|
| | 3.75% | 2.5% | Placebo |
| ITT Population (LOCF) | | | |
| n/N$^a$ (%) | 43/195 (22.1) | 20/178 (11.2) | 5/97 (5.2) |
| 95% CI | 16.4, 28.5 | 7.0, 16.8 | 1.7, 11.6 |
| P value vs placebo | <0.001** | 0.090 | — |
| P value vs 2.5% imiquimod cream | 0.004** | — | — |
| Males | | | |
| n/N$^a$ (%) | 14/95 (14.7) | 6/83 (7.2) | 1/47 (2.1) |
| 95% CI | 8.3, 23.5 | 2.7, 15.1 | 0.1, 11.3 |
| P value vs placebo | 0.027 | 0.227 | — |
| P value vs 2.5% imiquimod cream | 0.123 | — | — |
| Females | | | |
| n/N$^a$ (%) | 29/100 (29.0) | 14/95 (14.7) | 4/50 (8.0) |
| 95% CI | 20.4, 38.9 | 8.3, 23.5 | 2.2, 19.2 |

TABLE 106-continued

Proportion of Subjects with Complete Clearance of Warts at End of
Treatment-ITT Population (LOCF)

| | Imiquimod Cream | | |
|---|---|---|---|
| | 3.75% | 2.5% | Placebo |
| P value vs placebo | 0.003** | 0.215 | — |
| P value vs 2.5% imiquimod cream | 0.017** | — | — |

LOCF = last observation carried forward,
95% CI = 95% confidence interval.
$^a$n/N = number of subjects with complete clearance at end of treatment divided by the number of subjects analyzed.
P values are from Cochran-Mantel-Haenszel test, stratified by gender and analysis site (overall population) or stratified by analysis site (gender subgroups), taking 2 treatment groups at a time.
P values marked with ** are statistically significant using Hochberg's modified Bonferroni procedure.
Confidence intervals were calculated using the exact binomial distribution.

At Week 8/EOT, 22.1% of subjects in the 3.75% imiquimod group, 11.2% of subjects in the 2.5% imiquimod group, and 5.2% of subjects in the placebo group had attained complete clearance. The overall complete clearance rate at EOT was significantly higher in the 3.75% imiquimod group compared with placebo (P<0.001) and compared with 2.5% imiquimod (P=0.004). The difference between 2.5% imiquimod and placebo was not statistically significant.

The complete clearance rate at EOT was significantly higher in the 3.75% imiquimod group compared with placebo and compared with 2.5% imiquimod only in the female subgroup. The difference between 2.5% imiquimod and placebo was not statistically significant in either gender subgroup. In all treatment groups, the complete clearance rates were consistently higher in females than in males.

A summary of the complete clearance at Ear for the PP population, overall and by gender, is provided in Table 107.

TABLE 107

Proportion of Subjects with Complete Clearance of Warts at End of
Treatment-PP Population (Observed Cases)

| | Imiquimod Cream | | |
|---|---|---|---|
| | 3.75% | 23% | Placebo |
| PP Population (OC) at EOT | | | |
| n/N$^a$ (%) | 36/137 (26.3) | 19/134 (14.2) | 4/76 (5.3) |
| 95% CI | 19.1, 34.5 | 8.8, 21.3 | 1.5, 12.9 |
| P value vs placebo | <0.001** | 0.038** | — |
| P value vs 2.5% imiquimod cream | 0.015** | — | — |

TABLE 107-continued

Proportion of Subjects with Complete Clearance of Warts at End of Treatment-PP Population (Observed Cases)

| | Imiquimod Cream | | |
|---|---|---|---|
| | 3.75% | 23% | Placebo |
| Males | | | |
| n/N[a] (%) | 12/69 (17.4) | 6/63 (9.5) | 1/34 (2.9) |
| 95% CI | 9.3, 28.4 | 3.6, 19.6 | 0.1, 15.3 |
| P value vs placebo | 0.069 | 0.267 | — |
| P value vs 2.5% imiquimod cream | 0.290 | — | — |
| Females | | | |
| n/N[a] | 24/68 (35.3) | 13/71 (18.3) | 3/42 (7.1) |
| 95% CI | 24.1,47.8 | 10.1,29.3 | 1.5, 19.5 |
| P value vs placebo | <0.001** | 0.079 | — |
| P value vs 2.5% imiquimod cream | 0.025** | — | — |

95% CI = 95% confidence interval,
OC = observed cases.
[a]n/N = number of subjects with complete clearance at end of treatment divided by the number of subjects analyzed.
P values are from Cochran-Mantel-Haenszel test, stratified by gender and analysis site (overall population) or stratified by analysis site (gender subgroups), taking 2 treatment groups at a time.
P values marked with ** are statistically significant using Hochberg's modified Bonferroni procedure.
Confidence intervals were calculated using the exact binomial distribution.
Complete clearance was carried forward once achieved.

In the PP population, the EOT complete clearance rate was significantly higher in both active treatment groups compared with placebo (P<0.001 for 3.75% imiquimod vs placebo; and P=0.038 for 2.5% imiquimod vs placebo), The complete clearance rate at EOT was significantly greater with 3.75% imiquimod than with 2.5% imiquimod (P=0.015).

In the female subgroup, the complete clearance rate at EOT was significantly higher in the 3.75% imiquimod group compared with placebo and compared with 2.5% imiquimod. In the male subgroup, there was no significant difference between any of the treatment groups. In all treatment groups, the complete clearance rates were consistently higher in females than in males.

Complete Clearance Rates by Visit Week

Figure 27:
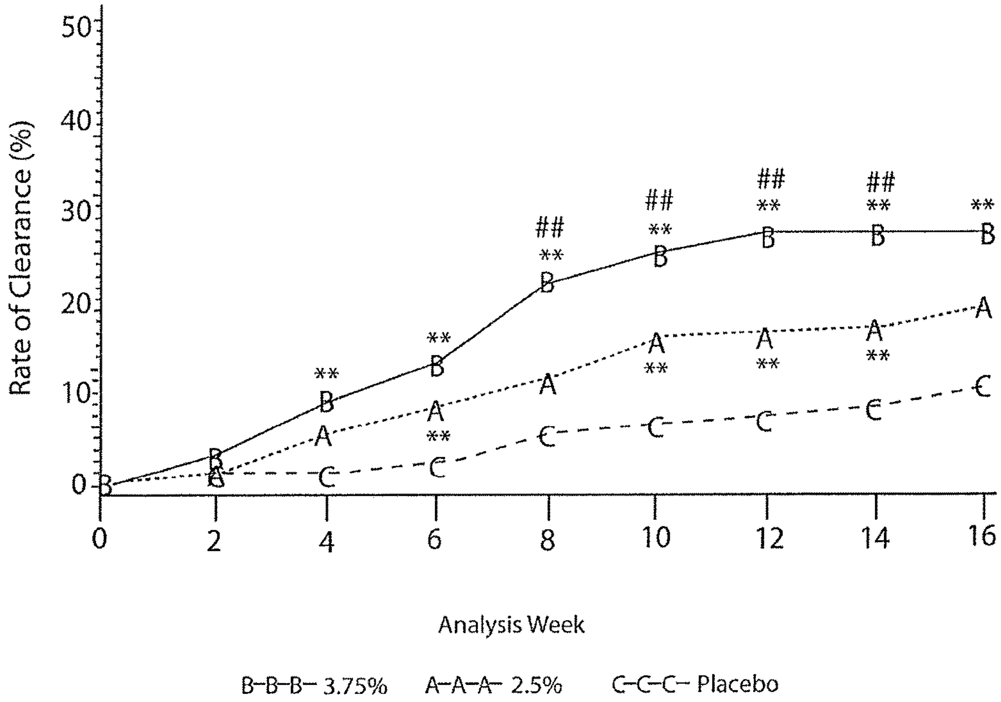
FIG. 27 shows complete clearance rates vs analysis week during the evaluation period observed in the intent-to-treat (ITT) population in one study of a lower-dose imiquimod treatment of genital warts, Points marked with the ** show statistically significant difference from placebo. Points marked with the ## show statistically significant difference from 2.5%. Subjects received treatment for 8 weeks or until complete clearance, whichever was sooner.

A by-visit summary of complete clearance rates in the ITT population during the evaluation period is shown graphically in FIG. 27.

As shown in FIG. 27, the complete clearance rate was significantly higher in the 3.75% imiquimod group compared with placebo at all assessment time points after Week 2; this includes the Week 8/end of treatment assessment and the Week 16/end of study assessment. The complete clearance rate was significantly higher in the 2.5% imiquimod group compared with placebo at Weeks 6, 10, 12, and 14. The clearance rate was higher in the 3.75% imiquimod group than in the 2.5% imiquimod group and the difference was statistically significant at Week 8 (end of treatment), and at Weeks 10, 12, and 14.

In female subjects, the complete clearance rate was significantly higher in the 3.75% imiquimod group compared with placebo at all assessment time points after Week 2, and was significantly higher compared with 2.5% imiquimod at Weeks 4, 6, 8, 12, and 14. In male subjects, the complete clearance rate was significantly higher in the 3.75% imiquimod group compared with placebo at Weeks 10, 12, 14, and 16. There was no statistically significant difference in complete clearance rate between 2.5% imiquimod and placebo in either gender.

Figure 28:
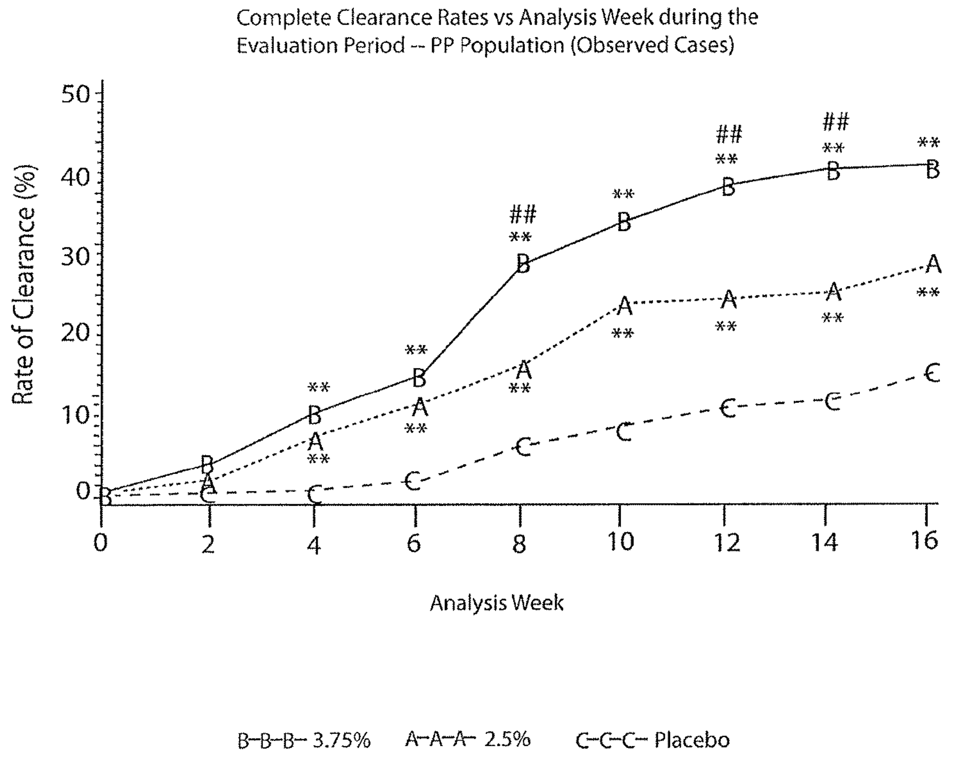
FIG. 28 shows complete clearance rates vs analysis week during the evaluation period observed in the Per Protocol (PP) population in one study of a lower-dose imiquimod treatment of genital warts. Points marked with the ** show statistically significant difference from placebo. Points marked with the ## show statistically significant difference from 2.5%. Subjects received treatment for 8 weeks or until complete clearance, whichever was sooner.

A by-visit summary of complete clearance rates in the PP population during the evaluation period is shown in FIG. 28.

Results in the PP population were similar to those in the ITT population. The complete clearance rate was significantly higher in the 3.75% imiquimod and 2.5% imiquimod groups compared with placebo at all assessment time points after Week 2. The clearance rate was higher in the 3.75% imiquimod group than in the 2.5% imiquimod group and the difference was statistically significant at Weeks 8, 12, and 14.

In female subjects, the complete clearance rate was significantly higher in the 3.75% imiquimod group compared with placebo at all assessment time points after Week 2, and was significantly higher compared with 2.5% imiquimod at Weeks 8 and 12. In male subjects, the complete clearance rate was significantly higher in the 3.75% imiquimod group compared with placebo at, Weeks 10, 12, 14, and 16. The only significant difference in complete clearance rate between 2.5% imiquimod and placebo occurred in females at Week 10.

Partial Clearance Rates

Partial (≥75%) Clearance Rates at End of Study

Figure 29:
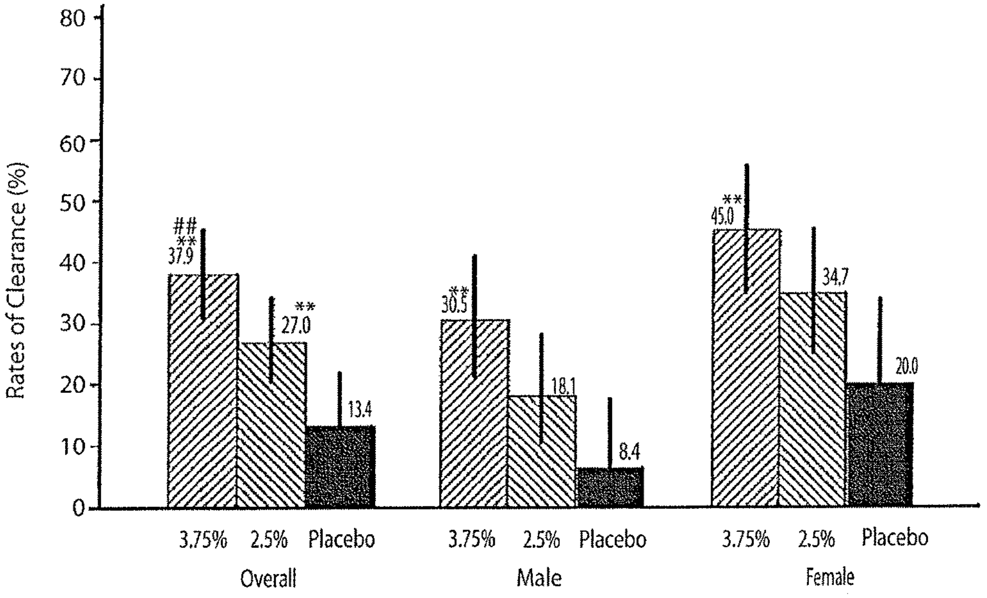
FIG. 29 shows partial (≥75%) clearance rates observed in the intent-to-treat (ITT) population at the end of one study of a lower-dose imiquimod treatment of genital warts. Partial clearance was defined as at least a 75% reduction in the number of EGW lesions compared to baseline at anytime point during the study. Bars marked with the ** show statistically significant difference from placebo. Bars marked with ## show statistically significant difference from 2.5%. The thick vertical lines represent 95% confidence intervals.

The proportion of subjects, overall and by gender, who had a partial clearance (≥75% reduction from Baseline in wart count) during the study is summarized in Table 108 and FIG. 29 for the ITT population. Partial clearance was defined as at least a 75% reduction in the number of warts in the treatment area compared with Baseline.

TABLE 108

Proportion of Subjects with Partial (≥75%) Clearance at End of Study-ITT Population

| | IMIQUIMOD CREAM | | |
|---|---|---|---|
| | 3.75% | 2.5% | PLACEBO |
| ITT Population (LOCF) at EOS | | | |
| n/N[a] (%) | 74/195 (37.9) | 48/178 (27.0) | 13/97 (13.4) |
| 95% CI | 31.1, 45.2 | 20.6, 34.1 | 7.3, 21.8 |
| P value vs Placebo | <0.001** | 0.010** | — |
| P value vs 2.5% Imiquimod Cream | 0.023** | — | — |
| Males | | | |
| n/N[a] (%) | 29/95 (30.5) | 15/83 (18.1) | 3/47 (6.4) |
| 95% CI | 21.5, 40.8 | 10.5, 28.0 | 1.3, 17.5 |
| P value vs Placebo | 0.001** | 0.060 | — |
| P value vs 2.5% Imiquimod Cream | 0.067 | — | — |
| Females | | | |
| n/N[a] (%) | 45/100 (45.0) | 33/95 (34.7) | 10/50 (20.0) |
| 95% CI | 35.0, 55.3 | 25.3, 45.2 | 10.0, 33.7 |
| P value vs Placebo | 0.002** | 0.071 | — |
| P value vs 2.5% Imiquimod Cream | 0.150 | — | — |

95% CI = 95% confidence interval.
[a]n/N = number of subjects with complete clearance at end of study divided by the number of subjects analyzed
Partial clearance was defined as at least a 75% reduction in the number of warts in the treatment area compared with Baseline.
P values are from Cochran-Mantel-Haenszel test, stratified by gender and analysis site (overall population) or stratified by analysis site (gender subgroups), taking 2 treatment groups at a time.
The P values marked with ** are statistically significant using Hochberg's modified Bonferroni procedure.
Confidence intervals were calculated using the exact binomial distribution In the ITT population, the difference in the partial (≥75%©) clearance rate at EOS between each of the imiquimod treatment groups and placebo was statistically significant. The partial (≥75%) clearance rate in the 3.75% imiquimod group was significantly higher than that in the 2.5% imiquimod treatment group.

In the by-gender analyses, the ≥75% clearance rate at EOS was significantly higher in the 3.75% imiquimod group compared with placebo for both males and females. There was no significant difference between 2.5% imiquimod and placebo, or between the 3.75% and 2.5% imiquimod groups. In all treatment groups, the ≥75% clearance rates were consistently higher in females than in males.

Figure 30:
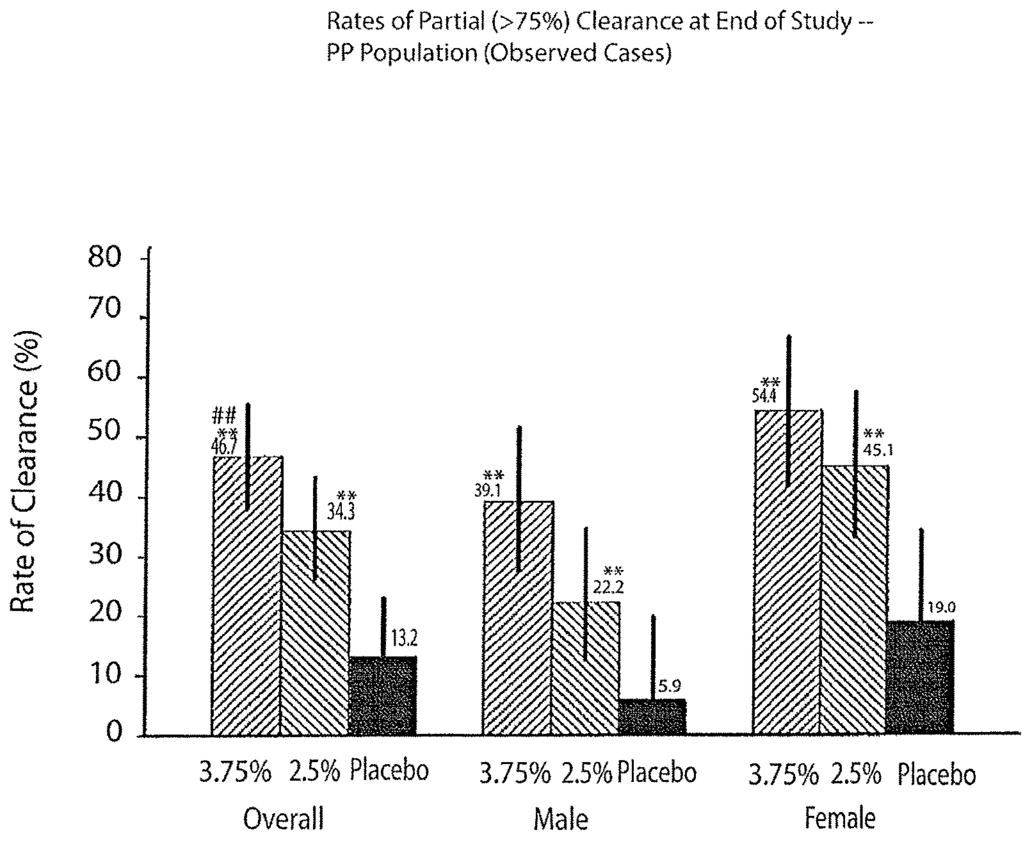
FIG. 30 shows partial (≥75%) clearance rates observed in the Per Protocol (PP) population at the end of one study of a lower-dose imiquimod treatment of genital warts. Bars marked with the ** show statistically significant difference from placebo. Bars marked with ## show statistically significant difference from 2.5%. The thick vertical lines represent 95% confidence intervals.

A summary of the partial (≥75%) clearance rate at EOS for the PP population, overall and by gender, is presented in Table 109. The ≥75% clearance rates at EOS are presented graphically in FIG. 30.

TABLE 109

Proportion of Subjects with Partial (≥75%) Clearance at End of Study-PP Population (Observed Cases)

| | IMIQUIMOD CREAM | | |
|---|---|---|---|
| | 3.75% | 2.5% | PLACEBO |
| PP Population (OC), at EOS | | | |
| n/N[a] (%) | 64/137 (46.7) | 46/134 (34.3) | 10/76 (13.2) |
| 95% CI | 38.1, 55.4 | 26.3, 43.0 | 6.5, 22.9 |
| P value vs Placebo | <0.001** | <0.001** | — |
| P value vs 2.5% Imiquimod Cream | 0.048** | — | — |
| Males | | | |
| n/N[a] (%) | 27/69 (39.1) | 14/63 (22.2) | 2/34 (5.9) |
| 95% CI | 27.6, 51.6 | 12.7, 34.5 | 0.7, 19.7 |
| P value vs Placebo | <0.001** | 0.041** | — |
| P value vs 2.5% Imiquimod Cream | 0.090 | — | — |
| Females | | | |
| n/N[a] (%) | 37/68 (54.4) | 32/71 (45,1) | 8/42 (19.0) |
| 95% CI | 41.9, 66.5 | 33.2, 57.3 | 8.6, 34.1 |
| P value vs Placebo | <0.001** | 0.009** | — |
| P value vs 2.5% Imiquimod Cream | 0.257 | — | — |

95% CI = 95% confidence interval.
[a]n/N = number of subjects with complete clearance at end of study divided by the number of subjects analyzed
Partial clearance was defined as at least a 75% reduction in the number of warts in the treatment area compared with Baseline.
P values are from Cochran-Mantel-Haenszel test, stratified by gender and analysis site (overall population) or stratified by analysis site (gender subgroups), taking 2 treatment groups at a time.
The P values marked with ** are statistically significant using Hochberg's modified Bonferroni procedure.
Confidence intervals were calculated using the exact binomial statistics.

In the PP population, the partial (≥75%) clearance rate at EOS was higher in the active treatment groups than in the placebo group. The difference between each of the imiquimod treatment groups and placebo was statistically significant (P<0.001). The partial (≥75%) clearance rate in the 3.75% imiquimod group was significantly higher (P=0.048) than that in the 2.5% imiquimod treatment group. The partial (≥75%) clearance rates were statistically significantly higher in the 3.75% imiquimod group compared with placebo at all analysis time points after Week 0.

As in the overall PP population, the ≥75% clearance rate was significantly higher with 3.75% imiquimod and with 2.5% imiquimod versus placebo in either gender. There was no statistically significant difference between the active treatment groups in either gender.

Partial (≥75%) Clearance Rates at End of Treatment

The proportion of subjects who had a 75% or greater reduction from Baseline in wart count at EOT is shown in Table 110.

TABLE 110

Proportion of Subjects with Partial (≥75%) Clearance at End of Treatment-ITT Population (LOCF)

| | IMIQUIMOD CREAM | | |
|---|---|---|---|
| | 3.75% | 2.5% | PLACEBO |
| ITT Population (LOCF) at EOT | | | |
| N | 195 | 178 | 97 |
| n/N[a] (%) | 62/195 (31.8) | 40/178 (22.5) | 9/97 (9.3) |
| 95% CI | 25.3, 38.8 | 16.6, 29.3 | 4.3, 16.9 |
| P value vs Placebo | <0.001** | 0.008** | — |
| P value vs 2.5% Imiquimod Cream | 0.037** | — | — |
| Males | | | |
| n/N[a] (%) | 24/95 (25.3) | 14/83 (16.9) | 3/47 (6.4) |
| 95% CI | 16.9, 35.2 | 9.5, 26.7 | 1.3, 17.5 |
| P value vs Placebo | 0.007** | 0.093 | — |
| P value vs 2.5% Imiquimod Cream | 0.174 | — | — |
| Females | | | |
| n/N[a] (%) | 38/100 (38.0) | 26/95 (27.4) | 6/50 (12.0) |
| 95% CI | 28.5, 48.3 | 18.7, 37.5 | 4.5, 24.3 |
| P value vs Placebo | 0.001** | 0.040** | — |
| P value vs 2.5% Imiquimod Cream | 0.114 | — | — |

LOCF = last observation carried forward,
95% CI = 95% confidence interval.
[a]n/N = number of subjects with complete clearance at end of study divided by the number of subjects analyzed
Partial clearance was defined as at least a 75% reduction in the number of warts in the treatment area compared with Baseline.
P values are from Cochran-Mantel-Haenszel test, stratified by gender and analysis site (overall population) or stratified by analysis site (gender subgroups), taking 2 treatment groups at a time.
The P values marked with ** are statistically significant using Hochberg's modified Bonferroni procedure.
Confidence intervals were calculated using the exact binomial statistics.

In the overall ITT population, the ≥75% clearance rate at EOT was significantly higher in the active treatment groups than in the placebo group, and was significantly higher with 3.75% than with 2.5% imiquimod.

The ≥75% clearance rate at EOT was significantly higher with 3.75% imiquimod compared with placebo in either gender, and for 2.5% imiquimod versus placebo in the female subgroup. There was no significant difference between 3.75% and 2.5% imiquimod in either gender.

The ≥75% clearance rate at EOT for the PP population is provided in Table 111.

TABLE 111

Proportion of Subjects with Partial (≥75%) Clearance at End of Treatment-PP Population (Observed Cases)

| | IMIQUIMOD CREAM | | |
|---|---|---|---|
| | 3.75% | 2.5% | PLACEBO |
| PP Population (OC), at EOT | | | |
| n/N[a] (%) | 54/137 (39.4) | 39/134 (29.1) | 6/76 (7.9) |
| 95% CI | 31.2, 48.1 | 21.6, 37.6 | 3.0, 16.4 |
| P value vs Placebo | <0.001** | <0.001** | — |
| P value vs 2.5% Imiquimod Cream | 0.062 | — | — |
| Males | | | |
| n/N[a] (%) | 21/69 (30.4) | 14/63 (22.2) | 2/34 (5.9) |
| 95% CI | 19.9, 42.7 | 12.7, 34.5 | 0.7, 19.7 |
| P value vs Placebo | 0.010** | 0.050** | — |
| P value vs 2.5% Imiquimod Cream | 0.429 | — | — |

TABLE 111-continued

Proportion of Subjects with Partial (≥75%) Clearance at End of Treatment-PP Population (Observed Cases)

| | IMIQUIMOD CREAM | | |
|---|---|---|---|
| | 3.75% | 2.5% | PLACEBO |
| Females | | | |
| n/N[a] (%) | 33/68 (48.5) | 25/71 (35.2) | 4/42 (9.5) |
| 95% CI | 36.2, 61.0 | 242, 47.5 | 2.7, 22.6 |
| P value vs Placebo | <0.001** | 0.006** | — |
| P value vs 2.5% Imiquimod Cream | 0.077 | — | — |

95% CI = 95% confidence interval,

OC = observed cases,

EOT = end of treatment

[a]n/N = number of subjects with complete clearance at end of study divided by the number of subjects analyzed Partial clearance was defined as at least a 75% reduction in the number of warts in the treatment area compared with Baseline.

P values are from Cochran-Mantel-Haenszel test, stratified by gender and analysis site (overall population) or stratified by analysis site (gender subgroups), taking 2 treatment groups at a time.

The P values marked with ** are statistically significant using Hochberg's modified Bonferroni procedure.

Confidence intervals were calculated using the exact binomial statistics.

In the overall PP population, the ≥75% clearance rate at EOT was significantly higher in the active treatment groups than in the placebo group. There was no significant difference between the active treatment groups.

The ≥75% clearance rate at EOT was significantly higher with both active treatments compared with placebo in both genders. There was no significant difference between the 3.75% and 2.5% imiquimod groups in either gender.

Partial (≥75%) Clearance Rails by Analysis Visit

Over the course of the study, the partial (≥75%) clearance rates were statistically significantly higher in the 3.75% imiquimod group compared with placebo at all analysis time points after Week 2, and were significantly higher for 3.75% compared with 2.5% imiquimod at all analysis time points after Week 4. The partial (≥75%) clearance rates were significantly higher for 2.5% imiquimod vs placebo at Weeks 4, 6, 8, 10, 14, and 16.

In both genders, the difference between each of the imiquimod treatment groups and placebo was statistically significant at Week 16. The partial (≥75%) clearance rates were statistically significantly higher in the 3.75% imiquimod group compared with placebo at Week 6 and thereafter in males, and at Week 4 and thereafter in females.

The partial (≥75%) clearance rates were statistically significantly higher in the 3.75% imiquimod group compared with placebo at all analysis time points after Week 0.

Subjects with at Least a 50% Reduction in Wart Count at End of Study

Figure 31:
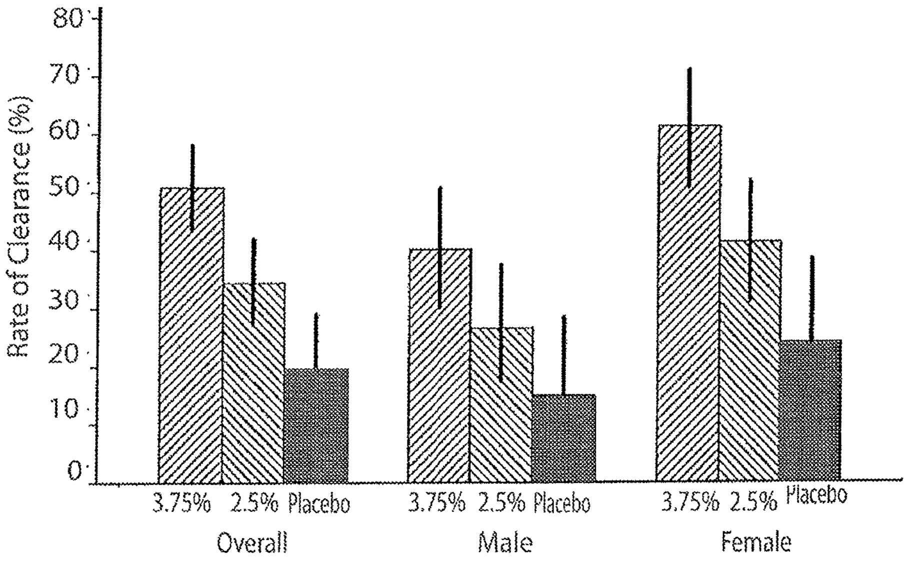
FIG. 31 shows ≥50% clearance rates observed in the intent-to-treat (ITT) population at the end of one study of a lower-dose imiquimod treatment of genital warts. Bars marked with the statistically significant difference from placebo. Bars marked with ## show statistically significant difference from 2.5%. The thick vertical lines represent 95% confidence intervals.

Table 112 provides a summary of the ≥50% clearance rate at EOS for the In population (overall and by gender). These data are shown graphically in FIG. 31.

TABLE 112

Proportion of Subjects with ≥50% Clearance at End of Study-ITT Population (LOCF)

| | IMIQUIMOD CREAM | | |
|---|---|---|---|
| | 3.75% (N = 195) | 2.5% (N = 178) | PLACEBO (N = 97) |
| ITT Population (LOCF) at EOS | | | |
| n/N[a] (%) | 99/195 (50.8) | 61/178 (34.3) | 19/97 (19.6) |
| 95% CI | 43.5, 58.0 | 27.3, 41.7 | 12.2, 28.9 |
| P value vs Placebo | <0.001** | 0.015** | — |
| P value vs 2.5% Imiquimod Cream | <0.001** | — | — |
| Males | | | |
| n/N[a] (%) | 38/95 (40.0) | 22/83 (26.5) | 7/47 (14.9) |
| 95% CI | 30.1, 50.6 | 17.4, 37.3 | 6.2, 28.3 |
| P value vs Placebo | 0.003** | 0.136 | — |
| P value vs 2.5% Imiquimod Cream | 0.066 | — | — |
| Females | | | |
| n/N[a] (%) | 61/100 (61.0) | 39/95 (41.1) | 12/50 (24.0) |
| 95% CI | 50.7, 70.6 | 31.1, 51.6 | 13.1, 38.2 |
| P value vs Placebo | <0.001** | 0.053 | — |
| P value vs 2.5% Imiquimod Cream | 0.005** | — | — |

LOCF = last observation carried forward,

95% CI= 95% confidence interval.

[a]n/N = number of subjects with complete clearance at end of study divided by the number of subjects analyzed 50% clearance was defined as at least a 50% reduction in the number of warts in the treatment area compared with Baseline.

P values are from Cochran-Mantel-Haenszel test, stratified by gender and analysis site (overall population) or stratified by analysis site (gender subgroups), taking 2 treatment groups at a time.

The P values marked with ** are statistically significant using Hochberg's modified Bonferroni procedure.

Confidence intervals were calculated using the exact binominal statistics.

In the overall ITT population, the rate of ≥50% clearance of EGW at EOS was significantly higher in the active treatment groups compared with placebo, and in the 3.75% imiquimod group compared with 2.5% imiquimod. In both the male and female subgroups, the ≥50% clearance rate is significantly higher with 3.75% imiquimod than with placebo, but there was no significant difference between 2.5% imiquimod and placebo. There was a significant difference between 3.75% and 2.5% imiquimod for females but not for males. In all treatment groups, the ≥50% clearance rates at EOS were higher in females than in males.

Results were similar in the PP population. In the overall PP population, the rate of ≥50% clearance of EGW at EOS was significantly higher in the active treatment groups compared with placebo, and in the 3.75% imiquimod group compared with 2.5% imiquimod. In both the male and female subgroups, the ≥50% clearance rate is significantly higher with 3.75% imiquimod than with placebo. There was a significant difference between 2.5% imiquimod and placebo, and between 3.75% and 2.5% imiquimod for females but not for males. In all treatment groups, the ≥50% clearance rates at EOS were higher in females than in males.

Subjects with ≥50% Reduction in Wart Count at End of Treatment

Table 113 provides a summary of the ≥50% clearance rate at EOT for the ITT population (overall and by gender).

TABLE 113

Proportion of Subjects with >50% Clearance at End of Treatment-ITT Population (LOCF)

| | IMIQUIMOD CREAM | | |
|---|---|---|---|
| | 3.75% | 2.5% | PLACEBO |
| ITT Population (LOCF) at EOT | | | |
| n/N[a] (%) | 93/195 (47.7) | 58/178 (32.6) | 15/97 (15.5) |
| 95% CI | 40.5, 54.9 | 25.8, 40.0 | 8.9, 24.2 |
| P value vs Placebo | <0.001** | 0.004** | — |
| P value vs 2.5% Imiquimod Cream | 0.002** | — | — |
| Males | | | |
| n/N[a] (%) | 36/95 (37.9) | 20/83 (24.1) | 7/47 (14.9) |
| 95% CI | 28.1, 48.4 | 15.4, 34.7 | 6.2, 28.3 |
| P value vs Placebo | 0.007** | 0.299 | — |
| P value vs 2.5% Imiquimod Cream | 0.050** | — | — |
| Females | | | |
| n/N[a] (%) | 57/100 (57.0) | 38/95 (40.0) | 8/50 (16.0) |
| 95% CI | 46.7, 66.9 | 30.1, 50.6 | 7.2, 29.1 |
| P value vs Placebo | <0.001** | 0.003** | — |
| P value vs 2.5% Imiquimod Cream | 0.017** | — | — |

LOCF = last observation carried forward,
95% CI = 95% confidence interval.
[a]n/N = number of subjects with complete clearance at end of study divided by the number of subjects analyzed
50% clearance was defined as at least a 50% reduction in the number of warts in the treatment area compared with Baseline.
P values are from Cochran-Mantel-Haenszel test, stratified by gender and analysis site (overall population) or stratified by analysis site (gender subgroups), taking 2 treatment groups at a time.
The P values marked with ** are statistically significant using Hochberg's modified Bonferroni procedure.
Confidence intervals were calculated using the exact binominal statistics.

In the overall ITT population, the rate of ≥50% clearance of EGW at EOT was significantly higher in the active treatment groups compared with placebo, and in the 3.75% imiquimod group compared with 2.5% imiquimod. In both the male and female subgroups, the ≥50%® clearance rate was significantly higher with 3.75% imiquimod than with placebo and with 3.75% imiquimod than with 2.5% imiquimod. There was a significant difference between 2.5% imiquimod and placebo for females but not for males. In all treatment groups, the ≥50% clearance rates at EOT were higher in females than in males.

Results were similar in the PP population. In the overall PP population, the rate of ≥50% clearance of EGW at EOT was significantly higher in the active treatment groups compared with placebo, and in the 3.75% imiquimod group compared with 2.5% imiquimod. In both the male and female subgroups, the ≥50% clearance rate was significantly higher with 3.75% imiquimod than with placebo, and was significantly higher with 2.5% imiquimod versus placebo in females but not males. There was no significant difference between 3.75% and 2.5% imiquimod in either gender subgroup.

Subjects with ≥50% Reduction in Wart Count by Analysis Week

Figure 32:
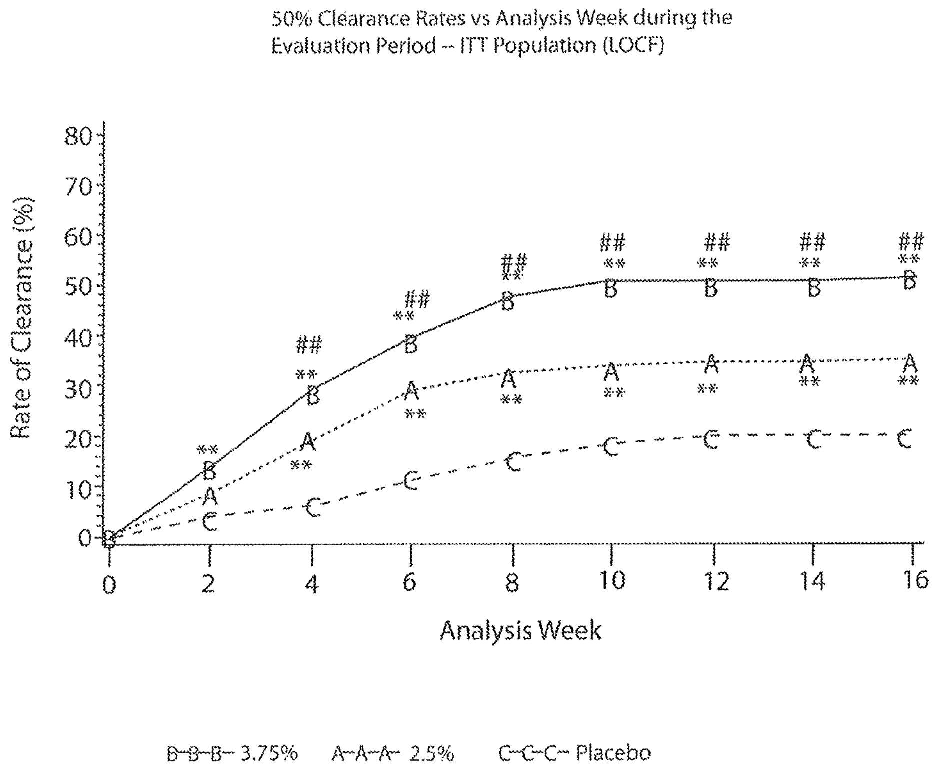
FIG. 32 shows ≥50% clearance rates vs analysis week during the evaluation period observed in the intent-to-treat (ITT) population in one study of a lower-dose imiquimod treatment of genital warts. 50% clearance was defined as at least a 50% reduction in the number of warts in the treatment area compared with Baseline. Points marked with ** show statistically significant difference from placebo. Points marked with ## show statistically significant difference from 2.5%. Subjects received treatment for 8 weeks or until complete clearance, whichever was sooner.

As shown in FIG. 32 for the overall ITT population, the difference between each of the imiquimod treatment groups and placebo was statistically significant at Week 16 (P<0.001 for 3.75% imiquimod vs placebo; P=0.015 for 2.5% imiquimod vs placebo), and at all post-Baseline assessment time points, with the exception of Week 2 in the 2.5% imiquimod group. The ≥50% clearance rate in the 3.75% imiquimod group was significantly higher than that in the 2.5% imiquimod treatment group at End of Study (LOCF) (P<0.001) and at all assessment time points after the Week 2 assessment.

The ≥50% clearance rates were statistically significantly higher in the 3.75% imiquimod group compared with placebo at Week 4 and thereafter in both genders. The differences between 2.5% imiquimod and placebo were significant at Weeks 4 and 6 in males, and at Weeks 6, 8, 10, and 14 in females.

Results in the PP population were similar to those in the ITT population. Compared with placebo, the ≥50% clearance rate was significantly higher in the 3.75% imiquimod group at all analysis time points after Week 0, and was significantly higher with 2.5% imiquimod at all analysis time points except Weeks 12 and 14.

Wart Counts and Change and Percent Change from Baseline in Wart Counts

Summaries of the EGW counts, change from Baseline in EGW counts, and percent change from Baseline in EGW counts over the course of the study are presented in Table 114 for the overall ITT population. The mean percent changes in EGW count over time are presented graphically in FIG. 33 for the ITT population.

TABLE 114

Summary of External Genital Wart Count from Baseline to End of Treatment and End of Study-ITT Population (LOCF)

| | Imiquimod Cream | | |
|---|---|---|---|
| | 3.75% (N = 195) | 2.5% (N = 178) | Placebo (N = 97) |
| Baseline | | | |
| Mean (SD) | 8.6 (6.4) | 9.2 (6.7) | 11.6 (8.8) |
| Median | 7 | 7 | 8 |
| Min, Max | 2, 30 | 2, 30 | 2, 30 |
| P value vs Placebo | <0.001** | 0.009** | — |
| P value vs 2.5% Imiquimod | 0.347 | — | — |
| End of Treatment (Week 8) | | | |
| Mean (SD) | 4.8 (5.7) | 7.1 (7.5) | 10.4 (9.6) |
| Median | 3 | 5 | 7 |
| Min, Max | 0, 30 | 0, 44 | 0, 43 |

TABLE 114-continued

Summary of External Genital Wart Count from Baseline to End of Treatment and End of Study-ITT Population (LOCF)

| | Imiquimod Cream | | |
|---|---|---|---|
| | 3.75% (N = 195) | 2.5% (N = 178) | Placebo (N = 97) |
| End of Study/Week 16 | | | |
| Mean (SD) | 4.5 (5.8) | 6.8 (7.6) | 10.1 (9.9) |
| Median | 3 | 5 | 7 |
| Min, Max | 0, 30 | 0, 47 | 0, 43 |
| Change from Baseline to EOS | | | |
| Mean (SD) | −4.1 (5.6) | −2.4 (5.8) | −1.5 (6.4) |
| Median | −9 | −1 | 0 |
| Min, Max | −29, 7 | −22, 21 | −28, 15 |
| P value vs Placebo | <0.001** | 0.021** | |
| P value vs 2.5% Imiquimod | <0.001** | | — |
| Percent Change from Baseline to | | | |
| Mean (SD) | −45.8 (47.3) | −26.6 (55.8) | −9.4 (57.0) |
| Median | −50.0 | −14.6 | 0.0 |
| Min, Max | −100, 100 | −100, 222 | −100, 350 |
| P value vs Placebo | <0.001** | 0.008** | — |
| P value vs 2.5% Imiquimod | <0.001** | — | — |

P values are from Cochran-Mantel-Haenszel test, stratified by gender and analysis site, taking 2 treatment groups at a time.
Change from Baseline is calculated as the post-Baseline value minus the Baseline value.
Change from Baseline P values are from analysis of covariance (ANCOVA), controlling for Baseline wart count, gender, and analysis site.
The P values marked with ** are statistically significant using Hochberg's modified Bonferroni procedure.

The mean EGW count at Baseline was significantly lower in the active treatment groups compared with placebo at Baseline for the overall ITT population. At both EOT and EOS, the EGW counts were lowest n the 3.75% imiquimod group and highest in the placebo group. At EOS, the mean change from Baseline in EGW count was significantly greater in the active treatment groups compared with placebo, and was significantly greater in the 3.75% imiquimod group compared with 2.5% imiquimod.

In the gender subgroups, the Baseline EGW counts were significantly lower in the 3.75% imiquimod group compared with placebo for females, and were significantly lower in both active treatment groups compared with placebo in males. The mean change and mean percent change from Baseline at BUS in EGW count was significantly larger for 3.75% imiquimod versus placebo in males and in females. The mean percent change from Baseline at EOS in EGW count was significant for 2.5% imiquimod versus placebo only in females.

Figure 33:
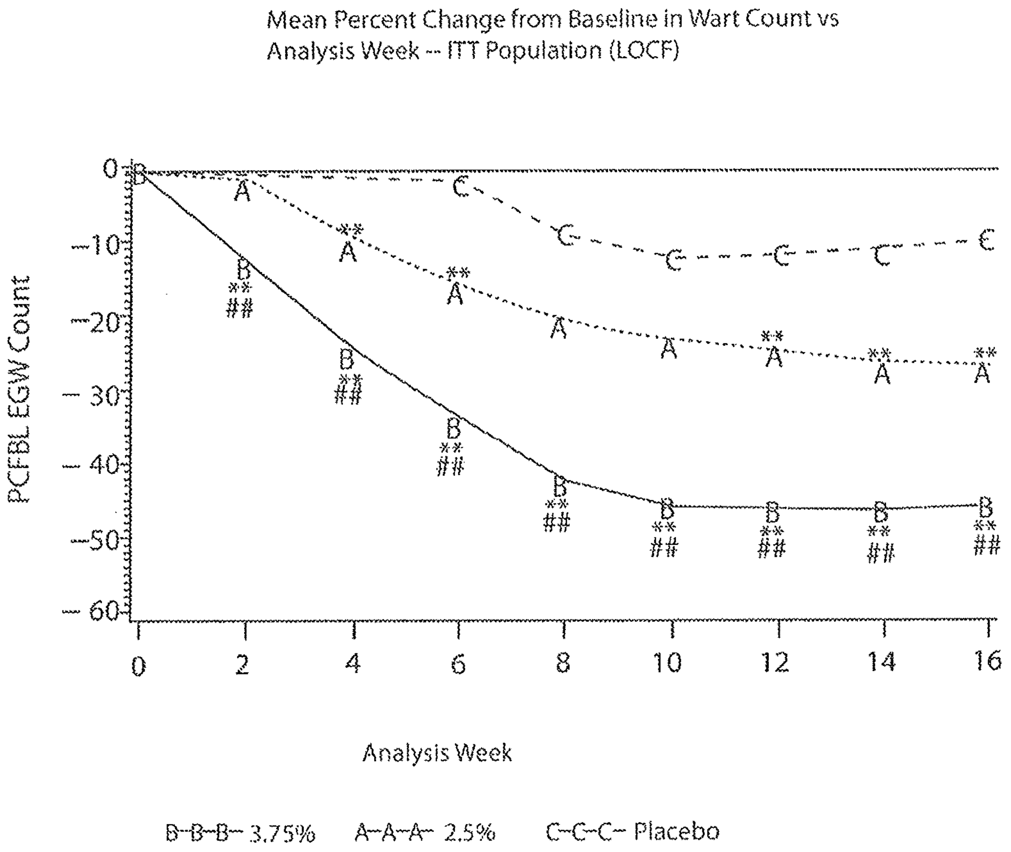
FIG. 33 shows mean percent change from baseline in wart count vs. analysis week observed in the intent-to-treat (ITT) population in one study of a lower-dose imiquimod treatment of genital warts. PCFBL=Percent Change from Baseline. Points marked with the ** show statistically significant difference from placebo. Points marked with ## show statistically significant difference from 2.5%, Subjects received treatment for 8 weeks or until complete clearance, whichever was sooner.

As shown in FIG. 33 for the overall ITT population, the mean percent decrease from Baseline in wart count in the 3.75% imiquimod treatment group was consistently larger than that with 2.5% imiquimod or placebo, and the differences were statistically significant at all post-Baseline analysis time points. The mean percent decrease in the 2.5% imiquimod group was larger compared with placebo, and the difference was statistically significant at Weeks 4, 6, 12, 14, and 16.

For the PP population, summaries of the EGW counts, change from Baseline in EGW counts, and percent change from Baseline in EGW counts over the course of the study are presented in Table 115.

TABLE 115

Summary of External Genital Wart Count from Baseline to End of Treatment and End of Study-PP Population (Observed Cases)

| | IMIQUIMOD CREAM | | |
|---|---|---|---|
| | 3.75% | 2.5% | PLACEBO |
| Baseline | | | |
| N | 137 | 133 | 76 |
| Mean (SD) | 8.7 (6.4) | 9.1 (6.5) | 11.6 (8.8) |
| Median | 7 | 8 | 9 |
| Min, Max | 2, 30 | 2, 30 | 2, 30 |
| P value vs Placebo | <0.001** | 0.005** | — |
| P value vs 2.5% Imiquimod | 0.540 | — | — |
| End of Treatment (EOT) | | | |
| N | 137 | 134 | 76 |
| Mean (SD) | 4.2 (5.4) | 6.3 (7.5) | 10.6 (9.7) |
| Median | 3 | 4 | 7 |
| Min, Max | 0, 30 | 0, 44 | 0, 43 |
| End of Study (EOS) | | | |
| N | 137 | 134 | 76 |
| Mean (SD) | 3.8 (5.5) | 5.9 (7.7) | 10.4 (10.0) |
| Median | 2 | 4 | 7 |
| Min, Max | 0, 30 | 0, 47 | 0, 43 |
| Change from Baseline at EOS | | | |
| N | 137 | 134 | 76 |
| Mean (SD) | −4.9 (6.0) | −3.1 (6.4) | −1.2 (6.9) |
| Median | −3 | −2 | 0 |
| Min, Max | −29, 7 | −22, 21 | −28.15 |
| P value vs Placebo | <0.001** | <.001** | — |
| P value vs 2.5% Imiquimod | 0.015** | — | — |

TABLE 115-continued

Summary of External Genital Wart Count from Baseline to End of Treatment and End of Study-PP Population (Observed Cases)

| | IMIQUIMOD CREAM | | |
|---|---|---|---|
| | 3.75% | 2.5% | PLACEBO |
| Percent Change from Baseline at EOS | | | |
| N | 137 | 134 | 76 |
| Mean (SD) | −54.0 (48.5) | −34.4 (60.6) | −5.2 (61.1) |
| Median | −66.7 | −38.8 | 0.0 |
| Min, Max | −100, 100 | −100, 222 | −100, 350 |
| P value vs Placebo | <0.001** | <0.001** | — |
| P value vs 2.5% Imiquimod | 0.16** | — | — |

P values are from Cochran-Mantel-Haenszel test, stratified by gender and analysis site, taking 2 treatment groups at a time.
Change from Baseline is calculated as the post-Baseline value minus the Baseline value.
Change from Baseline P values are from analysis of covariance (ANCOVA), controlling for Baseline wart count, gender, and analysis site.
The P values marked with ** are statistically significant using Hochberg's modified Bonferroni procedure.

The mean EGW count at Baseline was significantly lower in the active treatment groups compared with placebo at Baseline for the PP population, At both EOT and EOS, the EGW counts were lowest in the 3.75% imiquimod group and highest in the placebo group in the PP population. At EOS, the mean change from Baseline in EGW count was significantly greater in the active treatment groups compared with placebo, and was significantly greater in the 3.75% imiquimod group compared with 2.5% imiquimod.

In both genders, the mean change and mean percent change from Baseline in EGW count at EOS was significantly larger in both active treatment groups compared with placebo, and there was no significant difference between the active treatment groups. At EOS, both the mean change and mean percent change from Baseline in EGW counts were significantly larger in the active treatment groups compared with placebo.

The mean percent decrease from Baseline in wart count in the 3.75% imiquimod treatment group was consistently larger than that with 2.5% imiquimod or placebo. The differences between 3.75% imiquimod and placebo were statistically significant at all post-Baseline assessment time points, while the differences between 3.75% and 2.5% imiquimod were significant at Weeks 2, 6, 8, EOT, 12, and EOS. The mean percent decrease in the 2.5% imiquimod group was larger than that with placebo, but the difference was statistically significant only at EOT and EOS.

Time to Complete Clearance

Summaries of the time to complete clearance are shown in Table 116 for the ITT population.

TABLE 116

Time to Clearance (days) for the ITT population

| | Imiquimod Cream | | |
|---|---|---|---|
| | 3.75% (N = 195) | 2.5% (N = 178) | Placebo (N = 97) |
| All Subjects Kaplan-Meier | | | |
| N | 195 | 178 | 97 |
| $1^{st}$ Quartile | 58.0 | 117.0 | >58 |
| Median time to complete clearance ($2^{nd}$ quartile) | >71 | >102 | >112 |
| 3rd Quartile | >113 | >113 | >113 |
| P value vs Placebo | <0.001 | 0.035 | — |
| P value vs 2.5% imiquimod cream | 0.052 | — | |
| Only Subjects Who Attained Clearance | | | |
| N | 53 | 34 | 10 |
| $1^{st}$ Quartile | 31.0 | 32.0 | 51.0 |
| Median time to complete clearance (2" Quartile) | 52.0 | 56.5 | 67.0 |
| $3^{rd}$ Quartile | 58.0 | 76.0 | 106.0 |

P values are from the log rank test comparing survival curves in the Kaplan-Meier framework, taking 2 treatment groups at a time.

Although the time to complete clearance in the ITT treatment groups was not reached, the median time to clearance was statistically significantly shorter in the 3.75% imiquimod group compared with placebo (P<0.001 using the log-rank test) and in the 2.5% imiquimod group compared with placebo (P=0.035). The difference between the 2 imiquimod treatment groups approached statistical significant (P=0.052).

For those subjects who attained complete clearance, the median time to complete clearance was 52 days in the 3.75% imiquimod group, 56 days in the 2.5% imiquimod group, and 67 days in the placebo group.

Results in the PP population were similar to those in the ITT population, Among the subset of subjects who achieved complete clearance in the PP population, the median time to clearance was 57 days in the 3.75% imiquimod group, 56.5 days in the 2.5% imiquimod group, and 72 days in the placebo group.

Complete clearance was achieved more rapidly in female subjects compared with males in both the ITT and PP populations.

Sustained Complete Clearance Rate at Week 12 of the Follow-Up for Recurrence Period The numbers of subjects who remained clear in the follow-up period or who had a recurrence of EGW are presented in Table 117.

TABLE 117

Wart Recurrence Rate-Follow-up for Recurrence Population (LOCF)

| | Imiquimod Cream | | |
|---|---|---|---|
| | 3.75% (N = 49) | 2.5% (N = 31) | Placebo (N = 6) |
| Recurrence Follow-up- | | | |
| Subjects who remained clear[a], n/N | 37/49 (75.5) | 15/31 (48.4) | 5/6 (83.3) |
| Subjects who had a recurrence, n/N | 7/49 (14.3) | 6/31 (19.4) | 0 |
| Missing | 5/49 (10.2) | 10/31 (32.3) | 1/6 (16.7) |
| 95% Confidence interval | 5.9, 27.2 | 7.5, 37.5 | — |

[a]Includes those who had a visit within window with no warts.

Thirty-seven subjects (75.5%) in the 3.75% imiquimod group, 15 subjects (48.4%) in the 2.5% imiquimod group, and 5 subjects (83.3%) in the placebo group achieved complete clearance at EOS that was sustained throughout the 12-week follow-up period. Data were missing for 5 subjects (10.2%) in the 3.75% imiquimod group, 10 subjects (32.3%) in the 2.5% imiquimod group, and 1 subject (16.7%) in the placebo group so their recurrence status was not known, but at least 14.3% of the 3.75% imiquimod group and 19.4% of the 2.5% imiquimod group in the follow-up for recurrence population are known to have shown recurrence of EON within 12 weeks of the initial clearance.

Statistical/Analytical Issues

Adjustments for Covariates

The primary efficacy analysis was based on a CMH test, stratified by gender and analysis site. Secondary analyses were performed in a number of subgroups. No other adjustments for covariates were planned.

Handling of Dropouts or Missing Data

For the primary In analysis, missing observations due to early discontinuation were imputed using the LOCF. Screening data were carried forward if no baseline data existed for the subject—Baseline data were carried forward if no post-baseline data existed for the subject. Additional analyses of the primary efficacy variable were performed in which (1) all missing observations were considered as failures and (2) using only observed cases, without imputations. The results of these additional analyses are presented in Table 118 below.

TABLE 118

Proportion of Subjects with Complete Clearance at End of Study (Sensitivity and Supporting Analyses)-ITT Population

| | Imiquimod Cream | | |
|---|---|---|---|
| | 3.75% (N = 195) | 2.5% (N = 178) | Placebo (N = 97) |
| ITT Population (all subjects with missing data were counted as failures) | | | |
| n/N[a] (%) | 53/195 (27.2) | 34/178 (19.1) | 10/97 (10.3) |
| 95% CI | 21.1, 34.0 | 13.6, 25,7 | 5.1, 18.1 |
| P value vs Placebo | <0.001 ** | 0.065 | — |
| P value vs 2.5% Imiquimod Cream | 0.061 | — | — |

TABLE 118-continued

Proportion of Subjects with Complete Clearance at End of Study (Sensitivity and Supporting Analyses)-ITT Population

| | Imiquimod Cream | | |
|---|---|---|---|
| | 3.75% (N = 195) | 2.5% (N = 178) | Placebo (N = 97) |
| ITT Population (observed cases) | | | |
| n/N[a] (%) | 53/195 (27.2) | 34/178 (19.1) | 10/97 (10.3) |
| 95% CI | 21.1, 34.0 | 13.6, 25.7 | 5.1, 18.1 |
| P value vs Placebo | <0.001** | 0.065 | — |
| P value vs 2.5% Imiquimod Cream | 0.061 | — | — |

95% CI = 95% confidence interval.

[a]n/N = number of subjects with complete clearance at end of study divided by the number of subjects analyzed.

P values are from Cochran-Mantel-Haenszel test, stratified by gender and analysis site, taking 2 treatment groups at a time.

P-values marked with ** are statistically significant using Hochberg's modified Bonferroni procedure.

Confidence intervals were calculated using the exact binomial distribution.

Results of these additional analyses are identical to those obtained based upon LOCF for all treatment groups.

Multicenter Studies

In order to obtain at least 6 subjects per site per active treatment group, investigational sites yielding fewer than 15 subjects were combined in order of geographic proximity. The exact composition of these "analysis sites" was determined and documented prior to breaking the study blind. The stratification for CMH analyses was based on the analysis sites, not on the actual investigational sites.

Multiple Comparison/Multiplicity

The primary efficacy endpoint, complete clearance rate at the End of Study, was analyzed using Cochran-Mantel-Haenszel (CMH) statistics, stratifying on gender and site. All pairwise comparisons of active treatment versus placebo were made using Hochberg's modified Bonferroni procedure. If either test was significant at a 0.025 level of significance, then that test was considered significant. Otherwise, if both tests were significant at 0.05, then both tests were considered significant. The 3.75% and 2.5% treatment groups were compared to each other at the 0.05 level of significance if at least one of these treatment groups was found to be different than the placebo using the Hochberg's test.

The 4 secondary efficacy variables were to be tested hierarchically using Hochberg's modified Bonferroni procedure to conserve Type 1 error. First, only if the primary endpoint showed statistical significant could the first secondary efficacy variable be tested. If the prior secondary efficacy variable showed statistical significance then the next secondary efficacy variable could be tested, etc.

Use of an "Efficacy Subset" of Subjects

Efficacy variables were analyzed for a Per Protocol (PP) subset of subjects. The PP population included all subjects in the ITT population who had no major protocol violations: 137 subjects in the 3.75% imiquimod treatment group, 134 subjects in the 2.5% imiquimod treatment group, and 76 subjects in the placebo group. The demographic and baseline characteristics in the PP population were similar to those in the ITT population, although the mean total wart area was slightly less in the 3.75% imiquimod group, and slightly greater in the 2.5% imiquimod and placebo groups for the PP population.

In the analysis of the primary efficacy variable, the results in the PP population were similar to those in the ITT population. The proportion of subjects with complete clearance at Week 16/EOS was statistically significantly greater in the 3.75% imiquimod treatment group than in the placebo group; and larger but not significantly greater than in the 2.5% imiquimod group. While the complete clearance rate with 2.5% imiquimod was larger than that with placebo, the difference was statistically significant only in the analyses of the PP population.

Results in the PP population for the other efficacy variables were also similar to those from the ITT population.

Examination of Subgroups

The primary efficacy variable was summarized by investigator site, by analysis site, by investigator medical specialty, by gender, by age subgroup, by race subgroup, by baseline EGW count subgroup, by baseline wart areas, by anatomic locations (inguinal, perineal, perianal, glans penis, penis shaft, scrotum, foreskin, or vulva), by number of anatomic locations affected by EGW (ie, one location versus multiple), by whether first EGW episode, by duration from first diagnosis of EGW, by rest periods (yes or no), and by previous treatment with imiquimod (yes or no).

In general, the complete clearance rates increased in a dose-dependent manner regardless of subgroup. The most striking subgroup effect was observed in the analysis by gender. The complete clearance rates were consistently higher in females than in males in all treatment groups. Complete clearance at EOS was attained by 20.0%, 13.3%, and 4.3% of male subjects and by 34.0%, 24.2%, and 16.0% of female subjects in the 3.75% imiquimod, 2.5% imiquimod, and placebo groups, respectively.

The complete clearance rates tended to be higher in the following subgroups:

- Females;
- Lower baseline wart count (≤7 compared with >7);
- More recent first EGW diagnosis (≤1 year compared with >1 year);
- Subjects with baseline warts in the perineal area, the perianal area, on the foreskin, or on the vulva;
- Subjects who took a rest period (noted in the imiquimod groups but not placebo);
- No previous imiquimod treatment (noted in the imiquimod groups but not placebo).

In the 3.75% imiquimod group only, the complete clearance rate was higher in older subjects (>35 years) compared with younger subjects, and in baseline wart areas >70 and ≤150 $mm^2$ compared with baseline wart areas ≤70 $mm^2$ or >150 $mm^2$.

When analyzed by analysis site or investigative site subgroups, the complete clearance rate was highest in the 3.75% imiquimod group at 14/20 analysis sites and 17/30 investigational sites. When analyzed by investigator site specialty subgroups, the highest overall complete clearance rates were observed at sites specializing in gynecology or family/general practice, where more female subjects were enrolled. At sites specializing in dermatology, gynecology, or family practice/general practice, the complete clearance rates increased in a dose-dependent manner. Few subjects in any treatment group attained complete clearance in sites specializing in urology (sites at which only male subjects were enrolled) or infectious disease.

Additional Analyses by Gender

Additional analyses of the data were performed to explore the possible effect of gender on efficacy. Of the 470 subjects randomized into the trial, 225 (47.9%) were male and 245 (52.1%) were female. Similar percentages of males and females completed the evaluation period. Lost to follow-up and subject's request were the most common reasons for study discontinuation in both genders, and similarly low proportions of males (0.4%) and females (2.0%) withdrew for safety reasons. The time to lost to follow-up was similar in the active treatment groups for both genders.

As in the overall population, the response with 3.75% imiquimod cream was significantly superior to that with placebo in both genders. The complete clearance rates were consistently higher in females compared with males in all treatment groups for both the ITT and PP populations, including the sensitivity and supporting analyses of the ITT population.

A summary of complete clearance of all anatomic sites at EOS by baseline involvement of anatomic locations is presented in Table 119, below. Of note, a majority of subjects of each gender had involvement of more than one anatomic site at Baseline.

TABLE 119

Complete Clearance at End of Study by Baseline Anatomic Location-ITT Population (LOCF)

| | Imiquimod Cream | | |
|---|---|---|---|
| Baseline anatomic location | 3.75% (N = 195) | 2.5% (N = 178) | Placebo (N = 97) |
| Both genders-n/N (%)[a] | | | |
| Inguinal | 9/46 (19.6) | 5/31 (16.1) | 1/19 (5.3) |
| Perineal | 21/55 (38.2) | 12/49 (24.5) | 5/26 (19.2) |
| Perianal | 17/50 (34.0) | 11/60 (18.3) | 5/24 (20.8) |
| Males-n/N (%) | | | |
| Inguinal | 5/29 (17.2) | 5/20 (25.0) | 1/13 (7.7) |
| Perineal | 1/7 (14.3) | 0/6 (0.0) | 0/4 (0.0) |
| Perianal | 1/6 (16.7) | 0/8 (0.0) | 0/2 (0.0) |
| Glans Penis | 2/9 (22.2) | 0/6 (0.0) | 0/5 (0.0) |
| Penis Shall | 14/77 (18.2) | 11/71 (15.5) | 2/42 (4.8) |
| Scrotum | 4/27 (14.8) | 5/29 (17.2) | 0/8 (0.0) |
| Foreskin | 1/3 (33.3) | 2/4 (50.0) | 0/1 (0.0) |
| Females-n/N | | | |
| (%) Inguinal | 4/17 (23.5) | 0/11 (0.0) | 0/6 (0.0) |
| Perineal | 20/48 (41.7) | 12/43 (27.9) | 5/22 (22.7) |
| Perianal | 16/44 (36.4) | 11/52 (21.2) | 5/22 (22.7) |
| Vulva | 18/59 (30.5) | 13/60 (21.7) | 3/32 (9.4) |

[a]Subjects with complete clearance are included in the numerator.

In the anatomic areas common to both genders, perineal and perianal involvement was relatively common in females; few males had baseline disease in those areas. Females with perineal or perianal EGW at Baseline demonstrated relatively high rates of complete clearance at EOS. The third common anatomic site, the inguinal area, was involved in 27.6% of males and 13.9% of females at Baseline. The lowest clearance rates occurred in subjects with inguinal area involvement (at Baseline) in all treatment groups.

The anatomic areas most commonly affected with EGW at Baseline in males were the penis shaft, scrotum, and inguinal area. The complete clearance rates in subjects whose EGW included these areas at Baseline were similar for the 3.75% imiquimod and 2.5% imiquimod groups. In females, the vulva, perianal area, and perineal area were the areas most commonly affected with EGW at Baseline. The complete clearance rates were highest with 3.75% imiquimod for all baseline anatomic areas in female subjects.

In both genders, complete clearance rates were higher in subjects who took a rest period from imiquimod treatment compared with those who did not take a rest period. The complete clearance rates in males were higher for subjects >35 years of age than in younger subjects but no age trend was observed in females. Females with a first EGW diagnosis within one year and those experiencing their first EGW episode had higher clearance rates than those with a longer EGW history or with previous EGW outbreaks, but no trend was observed in males.

Exploratory Analysis of Anatomic Specific Complete Clearance

In this study, subjects applied study medication to individual warts in various anatomic areas identified at Baseline. Some subjects developed new warts during the study. These new warts may have appeared within anatomic areas already displaying EGW at Baseline and/or these warts may have appeared in 'new' anatomic areas that had not been exposed to study medication at initiation of treatment. New warts were treated with study medication when they appeared, but received less than a full course of treatment, because treatment was not extended beyond 8 weeks from randomization.

An exploratory analysis of complete clearance within the specific anatomic areas affected with EGW at Baseline was performed for the overall ITT population and by gender.

Drug Dose, Drug Concentration, and Relationships to Response

This study examined the efficacy of 2.5% imiquimod cream and 3.75% imiquimod cream, that was applied once daily for a maximum of 8 weeks. Subjects self-applied a maximum of 1 packet (250 mg) of study drug per application. No sample collection for pharmacokinetic determinations was planned in this study; therefore, no analysis of drug concentration was done.

A dose response was observed in this study. The 3.75% imiquimod cream consistently demonstrated higher efficacy rates compared with the 2.5% imiquimod cream for all primary and secondary efficacy measures, in both the ITT and PP populations. The difference between the 2 active treatment groups was not statistically significant for the primary efficacy analysis, but was significant for several secondary and tertiary efficacy variables.

Drug-Drug and Drug-Disease Interactions

No drug-drug interactions with respect to drug disposition and/or metabolism were evaluated in the study.

Efficacy Conclusions

The investigational product 3.75% imiquimod cream met the criteria for efficacy as defined in this protocol. For the 2.5% imiquimod cream, efficacy measures were consistently higher than those for placebo, but the values were not consistently significantly different compared with placebo.

For the primary endpoint (the rate of complete clearance of EGW at Week 16/E0S), results with the 3.75% imiquimod cream were statistically significantly superior to results with the placebo cream. This effect was observed in both the ITT and PP populations, overall and in both genders. In the ITT population, the rates of complete clearance were 27.2% and 19.1%, respectively, in the 3.75% and 2.5% imiquimod treatment groups, compared with 10.3% in the placebo group. Results in the 3.75% imiquimod group were numerically but not statistically higher than those in the 2.5% imiquimod group.

The complete clearance rate at end of treatment (EOT) was statistically significantly superior with 3.75% imiquimod compared with placebo and with 2.5% imiquimod overall and in the female subgroup in both the ITT and PP populations.

Over the course of the study, the complete clearance rates were significantly superior with 3.75% imiquimod compared with placebo at every analysis time point after Week 2 in both the ITT and PP populations. Results were significantly higher for 3.75% imiquimod vs 2.5% imiquimod at Weeks 8, 10, 12, and 14 (ITT population) and at Weeks 8, 12, and 14 (PP Population).

The partial (≥75%) clearance rate with the 3.75% imiquimod cream was statistically significantly superior to the placebo cream at Week 16/EOS for the ITT population (overall and in both genders), and at Week 16 and EOS for, the PP population (overall and in both genders). Results were significantly higher for 3.75% imiquimod vs placebo at all analysis time points after Week 2 (ITT population) and Week 0 (PP population).

Over the course of the study, the partial (≥75%) clearance rates were significantly superior with 3.75% imiquimod compared with placebo at every analysis time point after Week 4 (ITT population) and Week 2 (PP population). Results were significantly higher for 3.75% imiquimod vs 2.5% imiquimod at every time point after Week 4 in the ITT population.

The ≥50% clearance rate at EOS was significantly greater in the 3.75% imiquimod group compared with placebo in both the ITT and PP populations, overall and in both genders. Results were significant for 3.75% imiquimod versus 2.5% imiquimod at EOS overall and in the female subgroup in the ITT and PP populations.

Over the course of the study, the ≥50% clearance rates were significantly superior with 3.75% imiquimod compared with placebo at every analysis time point after Week 0 in both the ITT and PP populations. Results were significantly higher for 3.75% imiquimod vs 2.5% imiquimod at all analysis time points after Week 2 in the ITT population.

The complete and partial clearance rates were consistently higher in the female subgroup compared with the male subgroup in all treatment groups. Mean change and percent change from Baseline in EGW counts were consistently higher in females compared with males in the active treatment groups.

At EOS, the percent change from Baseline in wart count with, the 3.75% imiquimod cream was statistically significantly greater than with placebo cream or with 2.5% imiquimod cream in both the ITT and PP populations.

Although the median time to complete clearance for the ITT treatment groups was not reached, the time to clearance was statistically significantly shorter in the 3.75% imiquimod group compared with placebo (P<0.001) and in the 2.5% imiquimod group compared with placebo (P=0.035). For those subjects who attained complete clearance, the median time to complete clearance was 52 days, 56.5 days, and 67 days for the 3.75% imiquimod, 2.5% imiquimod, and placebo groups, respectively.

Thirty-seven of 49 subjects (75.5%) in the 3.75% imiquimod group remained completely clear of EGW through the 12-week follow-up period, while 7/49 subjects had wart recurrence and the status is unknown for 5/49 subjects. Fifteen of 31 subjects (48.4%) in the 2.5% imiquimod group (with 10 missing subjects), and 5 of 6 subjects in the placebo group (with 1 missing subject) remained clear through the follow-up period. Thus, at least 75.5% of the 3.75% imiquimod group and 48.4% of the 2.5% imiquimod group in the follow-up for recurrence population are known to have sustained clearance of all anatomic sites for at least 12 weeks from the initial clearance.

Safety Evaluation

Extent of Exposure

An overall summary of study drug exposure for the ITT population is presented in Table 120. In this study, the ITT and safety populations are identical.

TABLE 120

Overall Study Drug Exposure-ITT Population

| | Imiquimod Cream | | |
|---|---|---|---|
| | 3.75% (N = 195) | 2.5% (N = 178) | Placebo (N = 97) |
| Treatment duration, days[a]-All subjects | | | |
| N | 167 | 145 | 87 |
| Mean ± SD | 47.8 (15.8) | 50.2 (14.9) | 52.8 (12.1) |
| Median | 56 | 56 | 56 |
| Min, Max | 6, 78 | 6, 87 | 1, 70 |
| Total number of packets used | | | |
| N | 159 | 132 | 81 |
| Mean ± SD | 43.3 (16.1) | 46.0 (13.2) | 51.7 (10.8) |
| Median | 48 | 51 | 55 |
| Min, Max | 0, 64 | 6, 66 | 1, 63 |
| Number of Days Treated [b] | | | |
| N | 167 | 145 | 87 |
| Mean ± SD | 43.1 (15.8) | 44.3 (14.2) | 50.3 (12.0) |
| Median | 48 | 49 | 54 |
| Min, Max | 6, 69 | 6, 63 | 1, 67 |
| Percent of Treatment Compliance[c] | | | |
| N | 182 | 163 | 93 |
| Mean ± SD | 84.3 (25.0) | 84.7 (25.0) | 86.8 (23.8) |
| Median | 95 | 95 | 96 |
| Min, Max | 0, 127 | 16, 120 | 8, 111 |

SD-standard deviation,
min = minimum,
max-maximum.
[a]Duration of treatment is date of last dose minus date of first dose plus 1. Duration of treatment is missing if either the date of first dose or the date of last dose is partial or missing. Last dose is defined as last date on study medication.
[b] Days treated is the duration of treatment minus rest period days and missed doses.
[c]Based on either packet use compliance or treatment days compliance whichever is greater.

The mean treatment duration, number of study medication packets used, and number of days treated were lowest in the 3.75% imiquimod treatment group and highest in the placebo group.

Based on the available data, on average, the subjects used 43.3 packets of 3.75% imiquimod, 46.0 packets of 2.5% imiquimod, and 51.7 packets of placebo. Mean treatment duration was 47.8 days in the 3.75% imiquimod treatment group, 50.2 days in the 2.5% imiquimod treatment group, and 52.8 days in the placebo group. When rest periods and missed doses were subtracted, the numbers of treated days were reduced to 43.1, 44.3, and 50.3 days—in the 3.75% imiquimod, 2.5% imiquimod, and placebo groups, respectively.

The mean number of packets used, number of days treated, and percent treatment compliance were higher in the males than in females in the active treatment groups in the ITT and safety populations. Mean treatment duration was higher in males than in females for the 3.75% imiquimod group. There was no difference between genders in the placebo group.

Adverse Events (AEs)

Brief Summary of Adverse Events

A summary of the overall incidence of AEs is provided in Table 121 for the safety population.

TABLE 121

Summary of Adverse Events-Safety Population

| | Imiquimod | | |
|---|---|---|---|
| | 3.75% (N = 195) | 2.5% (N = 178) | Placebo (N = 97) |
| Subjects with any AE, n (%) | 61 (31.3) | 55 (30.9) | 25 (25.8) |
| Number of AEs | 146 | 124 | 43 |
| Subjects with any: | | | |
| Treatment-related[a] AE, n (%) | 30 (15.4) | 27 (15.2) | 2 (2.1) |
| SAE, n (%) | 2 (1.0) | 2 (1.1) | 0 |
| AEs of severe intensity, n (%) | 10 (5.1) | 12 (6.7) | 1 (1.0) |
| AE leading to study discontinuation, n (%) | 3 (1.5) | 2 (1.1) | 1 (1.0) |

AE = adverse event,
SAE = serious adverse event
[a]Includes "Probably related" and "Related" AEs. Counts reflect numbers of subjects in each treatment group reporting one or more adverse events that map to the MedDRA system organ class. A subject may be counted once only in each row of the table. A treatment-emergent AE is an AE that began or worsened in severity after Day 1 and no more than 30 days after the last application of study drug.

The number of subjects who experienced any AE (including those not considered treatment emergent) was similar in the active treatment groups (31.3% and 30.9% in the 3.75% and 2.5% imiquimod groups, respectively) and slightly lower in the placebo group (25.8%). The number of subjects with AEs considered treatment related or severe in intensity was similar in the active treatment groups and lower in the placebo group. The number of subjects with an SAE or who withdrew from the study due to an AE was low in all treatment groups.

An overall summary of the incidence of treatment-emergent AEs is provided in Table 122 for the safety population.

TABLE 122

Summary of Treatment-Emergent Adverse Events-Safety Population

| | IMIQUIMOD CREAM | | |
|---|---|---|---|
| | 3.75% (N = 195) | 2.5% (N = 178) | PLACEBO (N = 97) |
| Subjects with any AE, n (%) | 53 (27.2) | 52 (29.2) | 22 (22.7) |
| Number of AEs | 123 | 102 | 36 |
| Subjects with any: | | | |
| Treatment-related[a] AE, n (%) | 30 (15.4) | 27 (15.2) | 2 (2.1) |
| SAE, n (%) | 1 (0.5) | 2 (1.1) | 0 |
| AEs of severe intensity, n (%) | 7 (3.6) | 11 (6.2) | 1 (1.0) |
| AE leading to study Discontinuation, n (%) | 3 (1.5) | 2 (1.1) | 1 (1.0) |

TABLE 122-continued

Summary of Treatment-Emergent Adverse Events-Safety Population

|  | IMIQUIMOD CREAM | | PLACEBO (N = 97) |
| --- | --- | --- | --- |
|  | 3.75% (N = 195) | 2.5% (N = 178) |  |
| Subjects with any application Site reaction, n (%) | 29 (14.9) | 25 (14.0) | 2 (2.1) |

AE = adverse event,
SAE = serious adverse event
[a]Includes "Probably related" and "Related" AEs. Counts reflect numbers of subjects in each treatment group reporting one or more adverse events that map to the MedDRA system organ class. A subject may be counted once only in each row of the table. A treatment-emergent AE is an AE that began or worsened in severity after Day 1 and no more than 30 days after the last application of study drug.

The number of subjects with treatment-emergent AEs was similar in the active treatment groups (27.2% and 29.2% in the 3.75% and 2.5% imiquimod groups, respectively) and slightly lower in the placebo group (22.7%). The number of subjects with treatment-emergent AEs considered treatment related or severe in intensity was similar in the active treatment groups and lower in the placebo group. A higher percentage of subjects in the active treatment groups had application site reactions compared with placebo. The number of subjects with an SAE or who withdrew from the study due to an AE was low in all treatment groups.

Most Frequent Adverse Events

A treatment-emergent AE was defined as an AE that began or worsened in severity after the first application of the study drug and no more than 30 days after the last application of the study drug. The incidence of the most commonly-occurring treatment-emergent AEs is presented by preferred term in Table 123.

TABLE 123

Number (%) of Subjects with Most Frequent Treatment-Emergent Adverse Events (≥1% in any active treatment group)-Safety Population

|  | IMIQUIMOD CREAM | | PLACEBO (N = 97) |
| --- | --- | --- | --- |
|  | 3.75% (N = 195) | 2.5% (N = 178) |  |
| Subjects with any treatment-emergent AE, n (%) | 53 (27.2) | 52 (29.2) | 22 (22.7) |
| Subjects with any AE, n (%) |  |  |  |
| Application site pain | 11 (5.6) | 12 (6.7) | 1 (1.0) |
| Application site irritation | 12 (6.2) | 5 (2.8) | 1 (1.0) |
| Nasopharyngitis | 7 (3.6) | 7 (3.9) | 3 (3.1) |
| Application site pruritus | 3 (1.5) | 3 (1.7) | 1 (1.0) |
| Application site reaction | 3 (1.5) | 3 (1.7) | 0 |
| Back pain | 2 (1.0) | 3 (1.7) | 1 (1.0) |
| Vaginitis bacterial | 4 (2.1) | 2 (1.1) | 0 |
| Application site discharge | 3 (1.5) | 2 (1.1) | 0 |

TABLE 123-continued

Number (%) of Subjects with Most Frequent Treatment-Emergent Adverse Events (≥1% in any active treatment group)-Safety Population

|  | IMIQUIMOD CREAM | | PLACEBO (N = 97) |
| --- | --- | --- | --- |
|  | 3.75% (N = 195) | 2.5% (N = 178) |  |
| Application site erythema | 3 (1.5) | 2 (1.1) | 0 |
| Upper respiratory tract infection | 2 (1.0) | 2 (1.1) | 1 (1.0) |
| Pyrexia | 2 (1.0) | 1 (0.6) | 1 (1.0) |
| Application site erosion | 2 (1.0) | 1 (0.6) | 0 |
| Application site oedema | 2 (1.0) | 1 (0.6) | 0 |
| Ear infection | 2 (1.0) | 1 (0.6) | 0 |
| Headache | 3 (1.5) | 0 | 0 |
| Influenza | 2 (1.0) | 1 (0.6) | 0 |
| Vaginal candidiasis | 0 | 2 (1.1) | 1 (1.0) |
| Application site bleeding | 2 (1.0) | 0 | 0 |
| Application site excoriation | 2 (1.0) | 0 | 0 |
| Application site rash | 2 (1.0) | 0 | 0 |
| Application site ulcer | 2 (1.0) | 2 (1.1) | 0 |
| Rash | 2 (1.0) | 0 | 0 |
| Urinary tract infection | 0 | 2 (1.1) | 0 |

AE = adverse event
Counts reflect numbers of subjects in each treatment group reporting one or more adverse events that map to the MedDRA system organ class. A subject may be counted once only in each row of the table.
A treatment-emergent AE is an AE that began or worsened in severity after the first application of the study drug and no more than 30 days after the last application of the study drug.

The AE reported with the greatest overall incidence was application site pain, reported in 5.6% of subjects in the 3.75% imiquimod group, 6.7% of subjects in the 2.5% imiquimod group, and 1.0% of subjects in the placebo group.

Application site irritation occurred with a higher frequency in the 3.75% imiquimod group (6.2%) compared with the 2.5% imiquimod (2.8%) and placebo (1.0%©) groups. With this exception, the incidence of the individual AEs was similar in the 2 active treatment groups and lower in the placebo group.

Flu-like symptoms and certain other systemic effects have been reported with 5% imiquimod treatment. The incidence of these AEs was very low in the current study. These events were reported in this study in the 3.75% imiquimod, 2.5% imiquimod, and placebo groups, respectively, as follows:

pyrexia was reported in 2 (1.0%), 1 (0.6%), and 1 (1.0%) subjects;
nausea was reported in 1 (0.5%), 1 (0.6%), and 1 (1.0%©) subjects;
chills were reported in 0, 1 (0.6%), and 0 subjects;
influenza-like illness was reported in 1 (0.5%), 0, and 0 subjects;
myalgia was reported in 1 (0.5%), 0, and 0 subjects.

Adverse Events by System Organ Class

The incidence of AEs is presented by system organ class in Table 124.

TABLE 124

Number (%) of Subjects with Treatment-Emergent Adverse Events by System Organ Class-Safety Population

|  | IMIQUIMOD CREAM | | PLACEBO (N = 97) |
| --- | --- | --- | --- |
|  | 3.75% (N = 195) | 2.5% (N = 178) |  |
| General disorders and administration site conditions | 30 (15.4) | 26 (14.6) | 3 (3.1) |
| Infections and infestations | 22 (11.3) | 17 (9.6) | 11 (11.3) |
| Musculoskeletal and connective tissue disorders | 6 (3.1) | 4 (2.2) | 2 (2.1) |
| Gastrointestinal disorders | 3 (1.5) | 5 (2.8) | 3 (3.1) |
| Injury, poisoning and procedural complications | 3 (1.5) | 5 (2.8) | 1 (1.0) |

TABLE 124-continued

Number (%) of Subjects with Treatment-Emergent Adverse Events by System Organ Class-Safety Population

| | IMIQUIMOD CREAM | | |
|---|---|---|---|
| | 3.75% (N = 195) | 2.5% (N = 178) | PLACEBO (N = 97) |
| Skin and subcutaneous tissue disorders | 5 (2.6) | 3 (1.7) | 0 |
| Nervous system disorders | 4 (2.1) | 2 (1.1) | 1 (1.0) |
| Reproductive system and breast disorders | 4 (2.1) | 2 (1.1) | 1 (1.0) |
| Respiratory, thoracic and mediastinal disorders | 1 (0.5) | 3 (1.7) | 3 (3.1) |
| Psychiatric disorders | 0 | 1 (0.6) | 2 (2.1) |
| Renal and urinary disorders | 1 (0.5) | 1 (0.6) | 0 |
| Blood and lymphatic system disorders | 0 | 1 (0.6) | 0 |
| Cardiac disorders | 0 | 1 (0.6) | 0 |
| Eye disorders | 0 | 0 | 1 (1.0) |
| Immune system disorders | 0 | 0 | 1 (1.0) |
| Investigations | 0 | 1 (0.6) | 0 |
| Surgical and medical procedures | 0 | 1 (0.6) | 0 |

AE = adverse event

Counts reflect numbers of subjects in each treatment group reporting one or more AEs that map to the MedDRA system organ class. A subject was counted only once in each row of the table.

General disorders and administration site conditions, as well as infections and infestations, were the only system organ classes in which AEs were reported with an incidence of ≥5% in at least one treatment group.

Adverse Events by Intensity

Most of the AEs were of mild or moderate intensity. Two AEs were rated as severe in at least 2 subjects: application site pain, reported in 2 subjects (1.0%) in the 3.75% imiquimod treatment group, 3 subjects (1.7%) in the 2.5% imiquimod group, and 0 placebo subjects; and application site reaction, reported in 1 subject (0.5%) in the 3.75% imiquimod group, 2 subjects (1.1%) in the 2.5% imiquimod group, and 0 placebo subjects.

Adverse Events by Relationship to Treatment

Treatment-emergent AEs are summarized by treatment group and relationship to study treatment in Table 125.

TABLE 125

Number (%) of Subjects with Treatment-Emergent Adverse Events Related to Treatment-Safety Population

| | IMIQUIMOD CREAM | | |
|---|---|---|---|
| | 3.75% (N = 195) | 2.5% (N = 178) | PLACEBO (N = 97) |
| Subjects with any treatment-related AE, n (%) | 30 (15.4) | 27 (15.2) | 2 (2.1) |
| Subjects with any treatment related: | | | |
| SAE, n (%) | 0 | 0 | 0 |
| AE of severe intensity, n (%) | 3 (1.5) | 6 (3.4) | 0 |
| AE leading to study discontinuation, n (%) | 2 (1.0) | 2 (1.1) | 0 |
| Application site pain | 11 (5.6) | 12 (6.7) | 1 (1.0) |
| Application site irritation | 12 (6.2) | 5 (2.8) | 1 (1.0) |
| Application site pruritus | 3 (1.5) | 3 (1. ) | 1 (1.0) |
| Application site reaction | 3 (1.5) | 3 (1.7) | 0 |
| Application site discharge | 3 (1.5) | 2 (1.1) | 0 |
| Application site erythema | 3 (1.5) | 2 (1.1) | 0 |
| Application site erosion | 2 (1.0) | 1 (0.6) | 0 |
| Application site oedema | 2 (1.0) | 1 (0.6) | 0 |
| Application site bleeding | 2 (1.0) | 0 | 0 |
| Application site excoriation | 2 (1.0) | 0 | 0 |
| Application site rash | 2 (1.0) | 0 | 0 |
| Pyrexia | 1 (0.5) | 1 (0.6) | 0 |
| Application site dermatitis | 0 | 1 (0.6) | 0 |
| Application site discomfort | 0 | 1 (0.6) | 0 |
| Application site ulcer | 0 | 1 (0.6) | 0 |

TABLE 125-continued

Number (%) of Subjects with Treatment-Emergent Adverse Events Related to Treatment-Safety Population

| | IMIQUIMOD CREAM | | |
|---|---|---|---|
| | 3.75% (N = 195) | 2.5% (N = 178) | PLACEBO (N = 97) |
| Chills | 0 | 1 (0.6) | 0 |
| Pain | 1 (0.5) | 0 | 0 |
| Swelling | 1 (0.5) | 0 | 0 |
| Deriztal cyst | 1 (0.5) | 0 | 0 |
| Pruritus | 1 (0.5) | 0 | 0 |
| Rash | 1 (0.5) | 0 | 0 |
| Skin discolouration | 0 | 1 (0.6) | 0 |
| Application site cellulitis | 1 (0.5) | 0 | 0 |
| Vaginitis bacterial | 0 | 1 (0.6) | 0 |
| Excoriation | 0 | 1 (0.6) | 0 |
| Dysuria | 1 (0.5) | 0 | 0 |

AE = adverse event

Counts reflect numbers of subjects in each treatment group reporting one or more AEs that map to the MedDRA system organ class. A subject was counted only once in each row of the table.

Treatment-related includes Probably Related and Related.

Adverse events considered to be treatment related were reported in 30 subjects (15.4%) in the 3.75% imiquimod treatment group, 27 subjects (15.2%) in the 2.5% imiquimod treatment group, and 2 subjects (2.1%) in the placebo group. The most frequently reported treatment-related AEs were application site pain and application site irritation. Application site adverse events were the only treatment-related AEs that occurred in more than 1 subject in any treatment group. Application site pain, application site irritation, and application site pruritus, each in 1 subject (1.0%), were the only treatment-related AEs reported in the placebo group.

Treatment-related AEs of severe intensity were reported by 3 subjects in the 3.75% imiquimod group and 6 subjects in the 2.5% imiquimod group. All were application site AEs and all resolved without sequelae. In the 3.75% imiquimod group, 2 subjects had severe application site pain, and 1 subject discontinued the study due to a severe application site reaction. In the 2.5% imiquimod group, 2 subjects had severe application site pain, 1 subject had a severe application site reaction, 1 subject had a severe application site irritation, 1 subject had both severe application site pain and reaction and discontinued the study, and 1 subject discontinued the study due to severe application site dermatitis.

Adverse Events by Subgroup

Treatment-emergent AEs were analyzed by gender, by age, by number of anatomic areas affected by EGW, and by baseline wart count. As in the overall population, application site reactions were the most commonly-reported AEs and treatment-related AEs in all subgroups for all treatment groups.

Adverse Events by Gender

Summaries of the analysis by gender are provided in Table 126.

TABLE 126

Treatment-emergent Adverse Events by Gender-Safety Population

| | Male | | | Female | | |
|---|---|---|---|---|---|---|
| | 3.75% Imiquimod n = 95 | 2.5% Imiquimod n = 83 | Placebo n = 47 | 3.75% Imiquimod n = 100 | 2.5% Imiquimod n = 95 | Placebo n = 50 |
| Subjects with any AE, n (%) | 22 (23.2) | 18 (21.7) | 9 (19.1) | 31 (31.0) | 34 (35.8) | 13 (26.0) |
| Number of AEs | 48 | 33 | 10 | 75 | 69 | 26 |
| Number (%) of subjects with: | . | | | | | |
| Any Treatment-related AE | 12 (12.6) | 10 (12.0) | 1 (2.1) | 18 (18.0) | 17 (17.9) | 1 (2.0) |
| Any SAE | 0 (0.0) | 1 (1.2) | 0 (0.0) | 1 (1.0) | 1 (1.1) | 0 (0.0) |
| Any Severe AE | 0 (0.0) | 3 (3.6) | 0 (0.0) | 7 (7.0) | 8 (8.4) | 1 (2.0) |
| Any AE leading to Study Discontinuation | 0 (0.0) | 1 (1.2) | 0 (0.0) | 3 (3.0) | 1 (1.1) | 1 (2.0) |
| Any Application Site Reaction | 12 (12.6) | 10 (12.0) | 1 (2.1) | 17 (17.0) | 15 (15.8) | 1 (2.0) |

The overall incidence of treatment-emergent AEs was higher in females than in males in all treatment groups. Treatment-related AEs, severe AEs, and application site reactions were reported in a higher percentage of females than males in both imiquimod groups but were rare for both genders in the placebo group. The incidence of SAEs and AEs leading to study discontinuation was low in all treatment groups regardless of gender.

Within each gender subgroup, the percentage of subjects reporting AEs in the 3.75% and 2.5% imiquimod treatment groups was similar.

Adverse Events by Age:

As in the overall population, application site reactions were the most commonly-reported treatment-emergent AEs and treatment-related AEs in both age groups for all treatment groups.

In the active treatment groups, the incidence of treatment-emergent AEs was greater in older subjects (>35 years) than in younger (535 years) subjects; however, the proportions were similar in the placebo group. Treatment-emergent AEs were reported in 22.7%, 27.8%, and 22.2%, respectively, of younger subjects in the 3.75% imiquimod group, 2.5% imiquimod group, and placebo group compared with 36.5%, 31.7%, and 24.0%, respectively, of the older subjects in the 3.75% imiquimod group, 2.5% imiquimod group, and placebo group.

In the younger subgroup, the incidence of treatment-related AEs and application site reactions was similar between the 2 active treatment groups. In older subjects, the incidence of treatment-related AEs and application site reactions was slightly higher in the 3.75% imiquimod group than in the 2.5% imiquimod group. Few treatment-related AEs or application site reactions were reported in subjects in either age group who received placebo.

Adverse Events by Number of Anatomic Areas:

As in the overall population, the most commonly-reported treatment-emergent AEs and treatment-related AEs in both subgroups for all treatment groups were application site reactions.

In the 3.75% imiquimod group, higher percentages of subjects in the multiple-area subgroup than in the single-area subgroup reported any AE (30.3% and 24.0%, respectively), a treatment-related AE (22.2% and 8.3%, respectively), or an application site reaction (22.2% and 7.3%, respectively). There was little difference in AE incidence between the subgroups in the 2.5% imiquimod and placebo treatment groups.

The proportion of subjects with a treatment-related AE or an application site reaction in the multiple-area subgroup was higher in the 3.75% imiquimod group than in the 2.5% imiquimod group, whereas in the single-area subgroup, the proportion of subjects with a treatment-related AE or an application site reaction was higher in the 2.5% imiquimod group compared with the 3.75% imiquimod group.

Adverse Events by Baseline Wart Count:

As in the overall population, application site reactions were the most commonly-reported treatment-emergent AEs in both subgroups for all treatment groups. No trends in AE incidence with regard to baseline wart count were observed.

In the subjects with 7 or fewer warts at Baseline, the incidence of AEs was 29.0%, 18.7%, and 22.2%, respectively, in the 3.75% imiquimod, 2.5% imiquimod, and placebo groups, whereas in subjects with more than 7 warts at Baseline, the incidence of AEs was 25.0%, 40.2%, and 23.1%, respectively, in the 3.75% imiquimod, 2.5% imiquimod, and placebo groups.

In the subjects with 7 or fewer warts at Baseline, the incidence of treatment-related AEs was 15.9%, 9.9%, and 2.2%, respectively, in the 3.75% imiquimod, 2.5% imiquimod, and placebo groups, whereas in subjects with more than 7 warts at Baseline, the incidence of treatment-related AEs was 14.8%, 20.7%, and 1.9%, respectively, in the 3.75% imiquimod, 2.5% imiquimod, and placebo groups.

The incidence of treatment-related AEs or application site reactions was generally similar in the active treatment groups and lower in the placebo group.

Local Skin Reactions

Local skin reactions were assessed by the investigator at each visit including Baseline (pretreatment). At Baseline, 3.6%, 2.8%, and 3.1% of subjects in the 3.75% imiquimod, 2.5% imiquimod, and placebo groups, respectively, had at least one LSR reaction (LSR intensity score >0). The most intense post-Baseline LSRs (ie, those with the highest intensity rating) in the treatment areas that were assessed by the investigator over the course of the study are summarized in Table 127. The potential maximum sum of LSR scores was 18 (six types of LSRs each with a maximum potential score of 3).

TABLE 127

Frequency Distribution of Most Intense Post-baseline Local Skin Reactions in the Treatment Area-Safety Population

| Type of Reaction | Intensity | Number (%) of Subjects Imiquimod 3.75% (N = 195) | 2.5% (N = 178) | Placebo (N = 97) |
|---|---|---|---|---|
| Erythema | N | 180 (100) | 162 (100) | 92 (100) |
| | 0 = None | 39 (21.7) | 56 (34.6) | 68 (73.9) |
| | 1 = Faint to mild redness | 54 (30.0) | 48 (29.6) | 20 (21.7) |
| | 2 = Moderate redness | 70 (38.9) | 42 (25.9) | 4 (4.3) |
| | 3 = Intense redness | 17 (9.4) | 16 (9.9) | 0 |
| | >0 (any reaction) | 141 (78.3) | 106 (65.4) | 24 (26.1) |
| | Mean score (SD) | 1.36 (0.93) | 1.11 (1.00) | 0.30 (0.55) |
| Edema | N | 180 (100) | 162 (100) | 92 (100) |
| | 0 = None | 98 (54.4) | 95 (58.6) | 85 (92.4) |
| | 1 = Mild visible/barely palpable swelling/induration | 54 (30.0) | 42 (25.9) | 6 (6.5) |
| | 2 = Easily palpable swelling/induration | 23 (12.8) | 22 (13.6) | 1 (1.1) |
| | 3 = Gross swelling/induration | 5 (2.8) | 3 (1.9) | 0 |
| | >0 (any reaction) | 82 (45.6) | 67 (41.4) | 7 (7.6) |
| | Mean score (SD) | 0.64 (0.81) | 0.59 (0.79) | 0.09 (0.32) |
| Weeping/Exudate | N | 180 (100) | 162 (100) | 92 (100) |
| | 0 = None | 110 (61.1) | 111 (68.5) | 90 (97.8) |
| | 1 = Minimal exudate | 45 (25.0) | 36 (22.2) | 1 (1.1) |
| | 2 = Moderate exudate | 22 (12.2) | 13 (8.0) | 1 (1.1) |
| | 3 = Heavy exudate | 3 (1.7) | 2 (1.2) | 0 |
| | >0 (any reaction) | 70 (38.9) | 51 (31.5) | 2 (2.2) |
| | Mean score (SD) | 0.54 (0.77) | 0.42 (0.69) | 0.03 (0.23) |
| Flaking/Scaling/Dryness | N | 180 (100) | 162 (100) | 92 (100) |
| | 0 = None | 122 (67.8) | 121 (74.7) | 82 (89.1) |
| | 1 = Mild dryness/flaking | 52 (28.9) | 32 (19.8) | 9 (9.8) |
| | 2 = Moderate dryness/flaking | 6 (3.3) | 8 (4.9) | 1 (1.1) |
| | 3 = Severe dryness/flaking | 0 | 1 (0.6) | 0 |
| | >0 (any reaction) | 58 (32.2) | 41 (25.3) | 10 (10.9) |
| | Mean score (SD) | 0.36 (0.55) | 0.31 (0.59) | 0.12 (0.36) |
| Scabbing/Crusting | N | 180 (100) | 162 (100) | 92 (100) |
| | 0 = None | 135 (75.0) | 131 (80.9) | 89 (96.7) |
| | 1 = Crusting | 33 (18.3) | 21 (13.0) | 1 (1.1) |
| | 2 = Serous scab | 10 (5.6) | 8 (4.9) | 2 (2.2) |
| | 3 = Eschar | 2 (1.1) | 2 (1.2) | 0 |
| | >0 (any reaction) | 45 (25.0) | 31 (19.1) | 3 (3.3) |
| | Mean score | 0.33 (0.63) | 0.27 (0.61) | 0.05 (0.31) |
| Erosion/Ulceration | N | 180 (100) | 162 (100) | 92 (100) |
| | 0 = None | 110 (61.1) | 108 (66.7) | 89 (96.7) |
| | 2 = Erosion | 49 (27.2) | 39 (24.1) | 3 (3.3) |
| | 3 = Ulceration | 21 (11.7) | 15 (9.3) | 0 |
| | >0 (any reaction) | 70 (38.9) | 54 (33.3) | 3 (3.3) |
| | Mean score (SD) | 0.89 (1.16) | 0.76 (1.11) | 0.07 (0.36) |

SD = Standard deviation.

Note:

For purposes of analysis, ‘Erosion’ is categorized as 2 = Moderate, and ‘Ulceration is categorized as 3 = Severe. Denominator for the most intense reaction is the number of subjects with at least one post-baseline assessment.

As displayed in Table 127, the incidence of each type of LSR was higher in the active treatment groups compared with placebo. For each LSR, the percentage of subjects with any reaction and the mean intensity score were highest in the 3.75% imiquimod treatment group, somewhat lower in the 2.5% imiquimod group, and lowest in the placebo group. The incidence of severe LSRs was similar between the active treatment groups within each. LSR category, and lower in the placebo group.

Erythema was the LSR reported with the greatest frequency and the greatest mean intensity in all 3 treatment groups. Severe erythema was reported in 9.4% and 9.9% of subjects in the 3.75% and 2.5% imiquimod groups, respectively, and in no subjects in the placebo group. The mean intensity score was higher in the active treatment groups (1.36 and 1.11 in the 3.75% and 2.5% imiquimod groups, respectively) compared with placebo (0.30). Edema rated as severe was reported in 2.8% and 1.9% of subjects in the 3.75% and 2.5% imiquimod groups, respectively, and in no subjects in the placebo group. The mean intensity scores were higher in the active treatment groups (0.64 and 0.59 in the 3.75% and 2.5% imiquimod groups, respectively) compared with 0.09 in the placebo group.

For erosion/ulceration, severe reactions (ulceration) were reported in 11.7% and 9.3% of subjects in the 3.75% and 2.5% imiquimod groups, respectively, and in no subjects in the placebo. The mean intensity scores were higher in the active treatment groups (0.89 and 0.76 in the 3.75% and 2.5% imiquimod groups, respectively) compared with 0.07 in the placebo group.

The majority of cases of weeping/exudate, flaking/scaling, and scabbing/crusting were mild in intensity. Few subjects in any treatment group had a reaction considered to be severe.

A summary of subjects who had any local skin reaction is presented in Table 128.

TABLE 128

Summary of Subjects Who Had Any Local Skin Reaction During the Study-Safety Population

| Most Intense Reaction (post-Baseline) | Number (%) of Subjects Imiquimod 3.75% (N = 195) | 2.5% (N = 178) | Placebo (N = 97) |
|---|---|---|---|
| N | 180 | 162 | 92 |
| 0 = None | 36 (20.0) | 52 (32.1) | 63 (68.5) |
| 1 = Mild | 48 (26.7) | 37 (22.8) | 22 (23.9) |
| 2 = Moderate | 64 (35.6) | 49 (30.2) | 7 (7.6) |
| 3 = Severe | 32 (17.8) | 24 (14.8) | 0 |
| >0 (any reaction) | 144 (80.0) | 110 (67.9) | 29 (31.5) |
| Mean score (SD) | 1.5 (1.0) | 1.3 (1.1) | 0.4 (0.6) |

SD = Standard deviation.

For purposes of analysis, ‘Erosion’ is categorized as 2 = Moderate and ‘Ulceration’ is categorized as 3 = Severe. Denominator for the most intense reaction is the number of subjects with at least one post-baseline assessment.

As noted for the individual LSRs, the percentage of subjects reporting an LSR at each intensity category was higher in the active treatment groups compared with placebo, and was somewhat higher with 3.75% imiquimod than with 2.5% imiquimod. Severe reactions were reported by 17.8% of subjects in the 3.75% imiquimod group and 14.8% of subjects in the 2.5% imiquimod group compared with no subjects in the placebo group. The mean score for most intense LSR reaction was slightly higher in the 3.75% imiquimod group (1.5) than in the 2.5% imiquimod group (1.3).

Figure 34:
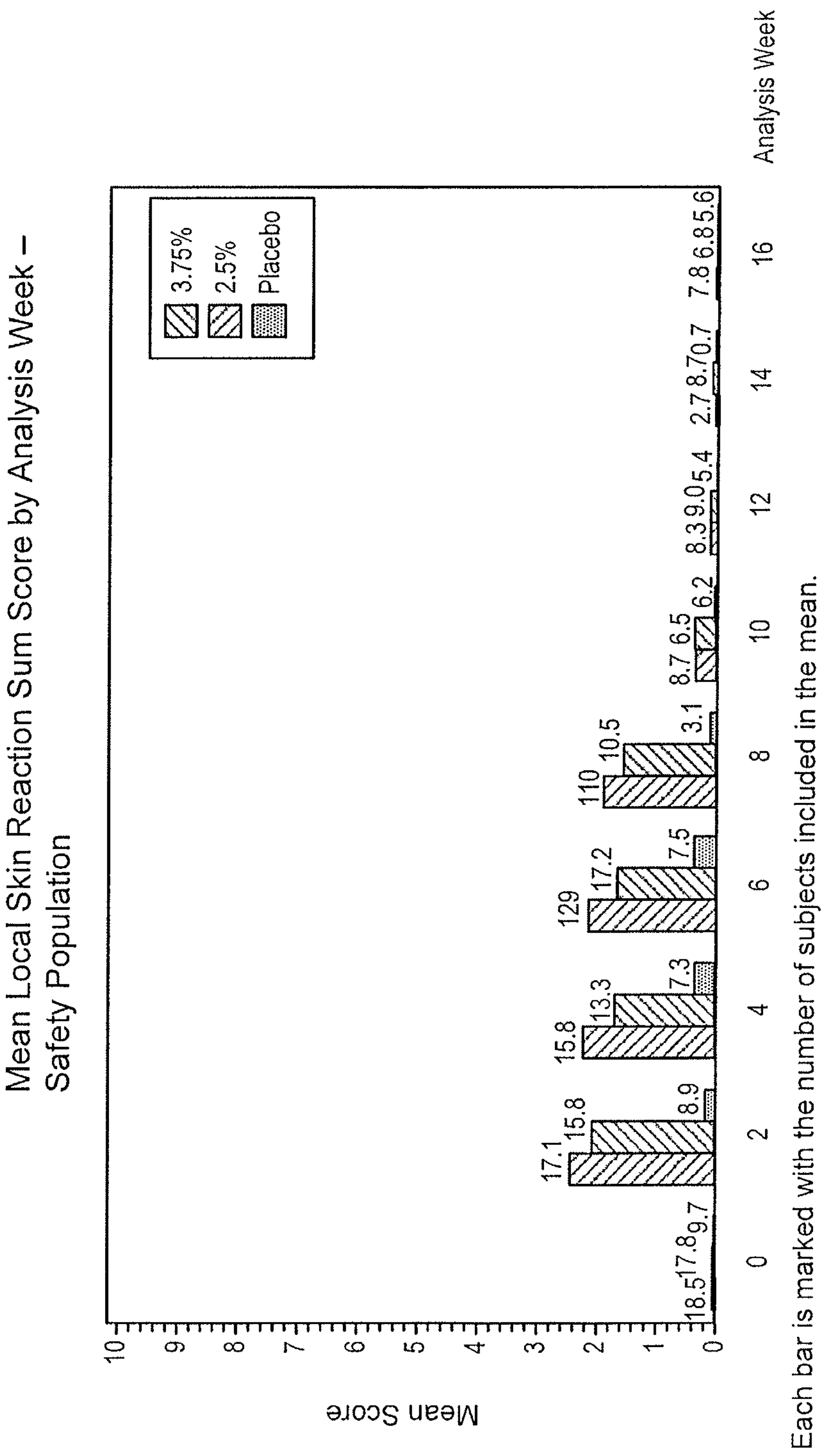
FIG. 34 shows mean local skin reaction sum score by analysis week, safety population, in one study of a lower-dose imiquimod treatment of genital warts.

The mean LSR sum score is shown by study week in FIG. 34. Erythema was the major contributor to the LSR sum score in all treatment groups, as determined by visual inspection. In the imiquimod treatment groups, the mean LSR sum score peaked at Week 2, decreased slightly during the treatment period, and rapidly decreased when treatment was discontinued. Mean LSR scores in the placebo group were highest at Week 4 and Week 6, but were considerably lower than those seen with active treatment.

Rest Periods

Summaries of the rest periods for the safety population are presented in Table 129.

TABLE 129

| Summary of Rest Periods-Safety Population | | | |
|---|---|---|---|
| | IMIQUIMOD CREAM | | |
| | 3.75% (N = 195) | 2.5% (N = 178) | PLACEBO (N = 97) |
| Subjects requiring rest period, n/N (%)[a] | 59 (30.3) | 49 (27.5) | 1 (1.0) |
| P value vs Placebo | <0.001 | <0.001 | NA |
| P value vs 2.5% imiquimod cream | 0.567 | NA | NA |
| No. of dosing days missed due to rest period[b] | | | |
| N | 59 | 49 | 1 |
| Mean (SD) | 7.9 (6.2) | 10.0 (7.0) | 3.0 |
| Median | 7 | 8 | 3 |
| P value vs Placebo | 0.310 | 0.224 | NA |
| P value vs 2.5% cream | 0.105 | NA | NA |
| No. of dosing days rior to the beginning of the first rest period[b] | | | |
| N | 57 | 49 | 1 |
| Mean (SD) | 17.8 (12.4) | 19.3 (11.9) | 15.0 |
| Median | 14 | 14 | 15 |
| P value vs Placebo | 0.631 | 0.945 | NA |
| P value vs 2.75% cream | 0.455 | NA | NA |

No. = number;
SD = standard deviation;
NA = not applicable
[a]P values are from Cochran-Mantel-Haenszel test, stratified by gender and analysis site, taking 2 treatment groups at a time.
[b]P values are from the Wilcoxon Rank Sum test, taking 2 treatment groups at a time.

Significantly larger percentages of subjects in the active treatment groups compared with placebo took a rest period during the study (P<0.001). There was no significant difference between the active treatments in the percentage of subjects who took a rest period (30.3% and 27.5% in the 3.75% and 2.5% imiquimod groups, respectively). There were no statistically significant differences between the treatment groups in the mean duration of rest periods or the mean number of dosing days prior to the rest periods.

Analysis of Adverse Events

Application site reactions are commonly reported for topically applied products. An additional analysis of these events is presented below. Application site reactions reported in this study are displayed in Table 130 below:

TABLE 130

| Number (%) of Subjects with Treatment-Emergent Application Site Adverse Events-Safety Population | | | |
|---|---|---|---|
| | Imiguimod Cream | | |
| | 3.75% (N = 195) | 2.5% (N = 178) | Placebo (N = 97) |
| Subjects with any application site reaction, n (%) | 29 (14.9) | 25 (14.0) | 2 (2.1) |
| Number of application site reactions | 57 | 36 | 3 |
| Number (%) of subjects with any: | | | |
| Related Application Site Reaction[a], n (%) | 29 (14.9) | 24 (13.5) | 2 (2.1) |
| Serious Application Site Reaction, n (%) | 0 | 0 | 0 |
| Severe Application Site Reaction, n (%) | 3 (1.5) | 6 (3.4) | 0 |
| Application Site Reaction Leading to Study Discontinuation, n (%) | 2 (1.0) | 2 (1.1) | 0 |

TABLE 130-continued

| Number (%) of Subjects with Treatment-Emergent Application Site Adverse Events-Safety Population | | | |
|---|---|---|---|
| General disorders and administration site conditions, n (%) | 28 (14.4) | 25 (14.0) | 2 (2.1) |
| Application site pain | 11 (5.6) | 12 (6.7) | 1 (1.0) |
| Application site irritation | 12 ( 6.2) | 5 (2.8) | 1 (1.0) |
| Application site pruritus | 3 (1.5) | 3 (1.7) | 1 (1.0) |
| Application site reaction | 3 (1.5) | 3 (1.7) | 0 |
| Application site discharge | 3 (1.5) | 2 (1.1) | 0 |
| Application site erythema | 3 (1.5) | 2 (1.1) | 0 |
| Application site erosion | 2 (1.0) | 1 (0.6) | 0 |
| Application site oedema | 2 (1.0) | 1 (0.6) | 0 |
| Application site bleeding | 2 (1.0) | 0 | 0 |
| Application site excoriation | 2 (1.0) | 0 | 0 |
| Application site rash | 2 (1.0) | 0 | 0 |
| Application site ulcer | 0 | 2 (1.1) | 0 |
| Application site dermatitis | 0 | 1 (0.6) | 0 |
| Application site discomfort | 0 | 1 (0.6) | 0 |
| Infections and infestations, n (%) | 1 (0.5) | 0 | 0 |
| Application site cellulitis | 1 (0.5) | 0 | 0 |

[a]Includes 'Probably related' and 'Related' adverse events.
Counts reflect numbers of subjects in each treatment group reporting 1 or more AEs that map to the MedDRA system organ class. A subject may be counted once only in each row of the table.

The incidence of application site adverse events and treatment-related application site events was similar in the 3.75% and 2.5% imiquimod treatment study groups. Few subjects in the active treatment groups and no subjects in the placebo group reported severe application site events or application site events that led to study withdrawal. No serious application site reactions were reported in any study group.

The most commonly reported application site reactions were application site pain and application site irritation.

TABLE 131

| Number (%) of Subjects with Serious Adverse Events-Safety Population | Imiquimod Cream | | |
|---|---|---|---|
| | 3.75% (N = 195) | 2.5% (N = 178) | Placebo (N = 97) |
| Subjects with any SAE, n (%) | 2 (1.0) | 2 (1.1) | 0 |
| Subjects with any treatment-emergent SAE, n (%) | 1 (0.5) | 2 (1.1) | 0 |
| Subjects with any related SAE, n (%) | 0 | 0 | 0 |
| Serious adverse events | | | |
| Iron deficiency anemia | 0 | 1 (0.6) | 0 |
| Acute abdomen | 1 (0.5) | 0 | 0 |
| Pelvic mass | 1 (0.5) | 0 | 0 |
| Migraine | 0 | 1 (0.6) | 0 |
| Syncope | 0 | 1 (0.6) | 0 |
| Cholecystolithiasis[a] | 1 (0.5) | 0 | 0 |

Counts reflect numbers of subjects in each treatment group reporting one or more adverse events that map to the MedDRA system organ class. A subject was counted only once in each row of the table.
[a]One subject had an SAE that was not considered treatment-emergent.

Few SAEs were reported during the study. Treatment-emergent SAEs occurred in 1 subject (0.5%) in the 3.75% imiquimod group, 2 subjects (1.1%) in the 2.5% imiquimod group, and no placebo subjects. One additional subject in the 3.75% imiquimod group had an SAE (cholecystolithiasis) that occurred during the follow-up for recurrence period and was not considered treatment-emergent. None of the SAEs were considered related to study treatment and all resolved with no sequelae.

Other Significant Adverse Events

Treatment-emergent AEs that led to discontinuation from the study are presented in Table 132 below:

TABLE 132

| Number (%) of Subjects with Treatment-Emergent Adverse Events Leading to Study Discontinuation-Safety Population | Imiquimod Cream | | |
|---|---|---|---|
| | 3.75% (N = 195) | 2.5% (N = 178) | Placebo (N = 97) |
| Subjects with an AE leading to study discontinuation, n (%) | 3 (1.5) | 2 (1.1) | 1 (1.0) |
| Subjects with a treatment-related AE leading to study discontinuation, n (%) | 2 (1.0) | 2 (1.1) | 0 |
| Adverse events leading to discontinuation | | | |
| Application site erythema | 1 (0.5) | 0 | 0 |
| Application site reaction | 1 (0.5) | 1 (0.6) | 0 |
| Application site discharge | 1 (0.5) | 0 | 0 |
| Application site dermatitis | 0 | 1 (0.6) | 0 |
| Pelvic mass | 1 (0.5) | 0 | 0 |
| Acute abdomen | 1 (0.5) | 0 | 0 |
| Bronchitis | 0 | 0 | 1 (1.0) |

Counts reflect numbers of subjects in each treatment group reporting one or more adverse events that map to the MedDRA system organ class. A subject was counted only once in each row of the table.
A treatment-emergent AE is an AE that began or worsened in severity after the first application of the study drug and no more than 30 days after the last application of the study drug.
Treatment-related includes Probably Related and Related.

The incidence of AEs that led to study discontinuation was low in all treatment groups. Two subjects (1.0%) in the 3.75% imiquimod group and 2 subjects (1.1%) in the 2.5% imiquimod group withdrew from the study for AEs that were considered related to study treatment; all of these were application site reactions. Two subjects discontinued the study for AE considered not related to study treatment; a pelvic mass and an acute abdomen in 1 subject in the 3.75% imiquimod group and bronchitis in one placebo subject. The AEs that led to study withdrawal resolved without sequelae, with the exception of 2 application site AEs, each in 1 subject. As the EOS/early termination visit was the last contact with both subjects, the events were recorded as "ongoing."

Analysis and Discussion of Serious Adverse Events, and Other Significant Adverse Events No deaths occurred among the subjects in this study. The incidence of SAEs was low in this study. No SAE was considered related to study treatment and all resolved with no sequelae. Few subjects discontinued the study as a result of an AE. All of the treatment-related AEs leading to study withdrawal were application site reactions. Only two AEs (both application site reactions) were noted as ongoing at EOS.

Clinical Laboratory Evaluation

For most of the hematology, chemistry, and urinalysis variables, results in the majority of the subjects were normal at Screening and at EOS. Occasional shifts from normal at Screening to above or below the normal range were observed; however, no dose-response relationship was evident.

For the clinical chemistry determinations, shifts from normal to high were most frequently recorded for glucose (9/140 in the 3.75% imiquimod group, 10/125 in the 2.5% imiquimod group, and 10/70 in the placebo group), AST (8/140 in the 3.75% imiquimod group, 10/125 in the 2.5% imiquimod group, and 1/69 in the placebo group), and ALT (9/140 in the 3.75% imiquimod group, 11/125 in the 2.5% imiquimod group, and 4/70 in the placebo group). Low cholesterol was noted in 9/141 subjects in the 3.75% imiquimod group, 9/125 in the 2.5% imiquimod group, and 2/70 in the placebo group).

In the hematology analyses, shifts from normal to high were most frequently recorded for white blood cell counts (4/138 in the 3.75% imiquimod group, 6/124 in the 2.5% imiquimod group, and 6/68 in the placebo group). Shifts from normal to low were most frequently recorded for red blood cell counts (7/138 in the 3.75% imiquimod group, 6/124 in the 2.5% imiquimod group, and 2/68 in the placebo group).

The most commonly-reported shift observed in the study was a shift from normal to high in urine protein (34/134 subjects [25.4%] in the 3.75% imiquimod group, 22/120 subjects [18.3%] in the 2.5% imiquimod group, and 18/69 subjects [26.1%] in the placebo group). However, 34% of subjects (46/134) in the 3.75% imiquimod group, 38% of subjects (45/120) in the 2.5% imiquimod group, and 46% of subjects (32/69) in the placebo group had high concentrations of urinary protein at Screening. Other findings from urinalysis included shifts from normal to high for blood in the urine (10/134 subjects in the 3.75% imiquimod group, 7/120 subjects in the 2.5% imiquimod group, and 2/69 subjects in the placebo group).

Safety Conclusions

Mean exposure to study medication was approximately 43 packets, 46 packets, and 52 packets of study medication in the 3.75% imiquimod, 2.5% imiquimod, and placebo groups, respectively. Mean treatment duration was similar among the study groups and ranged from 47.8 days in the 3.75% imiquimod group to 52.8 days in the placebo group.

Treatment-emergent AEs were reported in 27.2%, 29.2%, and 22.7% of subjects in the 3.75% imiquimod, 2.5% imiquimod, and placebo groups, respectively. Most AEs were mild or moderate in intensity. Application site reactions were the most frequently reported AEs. Adverse events of the system organ classes "general disorders and administration site conditions" and "infections and infestations" were the most frequently reported, and the incidence of these events was similar in the active treatment groups. The incidence of severe LSRs was similar in the active treatment groups.

The incidence of systemic symptoms (ie, flu-like symptoms, etc) previously noted with 5% imiquimod was low (≤1%) in this study.

Treatment-emergent SAEs were reported in 1 subject in the 3.75% imiquimod group, 2 subjects in the 2.5% imiquimod group, and no placebo-treated subjects; none were considered treatment-related.

Treatment-emergent AEs that led to study discontinuation were reported in 3 subjects, 2 subjects, and 1 subject in the 3.75% imiquimod, 2.5% imiquimod, and placebo groups, respectively. Four subjects (2 in each of the imiquimod groups) withdrew from the study for TEAEs considered related or probably related to study treatment, and all were application site reactions.

The incidence of TEAEs and severe AEs was higher in females than in males across all treatment groups, and the incidence of application site reactions was higher in females than in males in the active treatment groups. Serious AEs and AEs leading to study discontinuation were rare in all treatment groups regardless of gender.

Local skin reactions were reported in 80.0%, 67.9%, and 31.5% of subjects in the 3.75% imiquimod, 2.5% imiquimod, and placebo groups, respectively. The incidence and severity of LSRs was higher in the active treatment groups than in the placebo group. Erythema was the LSR reported with the greatest frequency and the greatest mean intensity in all treatment groups. Local skin reactions were coincident with the treatment period and rapidly decreased when treatment was concluded. The incidence of severe intensity LSRs was similar in the active treatment groups.

Rest periods were taken by 59 subjects (30.3%), 49 subjects (27.5%), and 1 subject (1.0%) in the 3.75% imiquimod, 2.5% imiquimod, and placebo groups, respectively. The frequency, duration, and number of dosing days prior to the rest period were similar in the active treatment groups and lower in the placebo group.

There was no evidence of clinically meaningful trends in vital sign measurements or clinical laboratory measurements. Two subjects, both in the 2.5% imiquimod group, had abnormal laboratory values that were reported as AEs; only 1 (a moderate increase in blood lactate dehydrogenase) was considered probably related to study treatment.

Discussion

In this double-blind, placebo controlled clinical study, 470 subjects with EGW diagnosed by clinical examination were randomized to receive treatment with 3.75% imiquimod cream, 2.5% imiquimod cream, or a matching placebo cream. During the evaluation period, subjects applied study medication once daily to the identified treatment area(s) for a maximum of 8 weeks. If the subject did not achieve complete wart clearance by the Week 8 visit (end of treatment [EM]), the subject was monitored for an additional maximum 8 weeks of no treatment. Subjects determined to have achieved complete clearance of all warts at any time until Week 16 (end of study [EOS]) completed procedures for the end-of-study visit and were eligible to immediately enter the follow-up period for determination of wart recurrence. During the follow-up period, subjects were monitored every 4 weeks for up to 12 weeks or until the recurrence of warts. The 3.75% imiquimod cream demonstrated efficacy and tolerability as compared with placebo for treatment of EGW. Efficacy variables for the 2.5% imiquimod treatment group were superior compared with placebo, but the differences versus placebo were not consistently statistically significant. Overall, 68.7% of subjects completed the evaluation period, and the discontinuation rates were similar in all treatment groups. Compliance with the daily treatment regimen ranged from 84.3% in the 3.75% imiquimod group to 86.8% in the placebo group.

Imiquimod has been demonstrated to be a safe and effective treatment for EGW. The dosing regimen for the currently approved product, 5% imiquimod cream, is 3 times per week for up to 16 weeks. Clinical experience has shown compliance with this regimen is challenging, as the treatment duration is long and the application schedule is non-intuitive. The current study was designed to evaluate imiquimod cream in lower concentrations to permit a more intuitive daily-dosing regimen and a shortened treatment regimen (up to 8 weeks) that provides acceptable efficacy and tolerability.

Efficacy

Efficacy was demonstrated for the primary efficacy measure as well as for the secondary and tertiary efficacy measures for the 3.75% imiquimod cream. Results for all efficacy measures for which statistical testing was performed were highly statistically significant in the 3.75% imiquimod treatment group as compared with placebo in both the ITT and PP populations. For the 2.5% imiquimod cream, the efficacy measurements were superior to those with placebo, but the differences were not consistently statistically significant.

Measures of wart reduction showed pronounced treatment effects for the higher concentration product (complete clearance rates of 27.2%, 19.1% and 10.3%; ≥75% clearance rates of 37.9%, 27.0%, and 13.4%; mean percent change in wart count of −45.8%, −26.6%, and −9.4%; and at least 50% reduction in wart count in 50.8%, 34.3%, and 19.6% of subjects in the 3.75% imiquimod, 2.5% imiquimod, and placebo groups, respectively, in the ITT population).

It should be noted that the primary efficacy variable used in this study (complete clearance of all warts, both Baseline and newly emerged, in all assessed anatomic areas) was very conservative. Warts were counted in all assessed anatomic areas without distinction as to those warts identified at Baseline or those newly identified. In this study, subjects applied study medication to individual warts in various anatomic areas identified at Baseline. Some subjects developed new warts during the study, and these new warts may have appeared in anatomic areas involved at Baseline as well as in newly involved anatomic areas. New warts were treated with study medication when they appeared, but received less than a full course of treatment, because treatment was not extended beyond 8 weeks from randomization/Day 1 visit. Subjects who did not completely clear all warts by the Week 8/EOT visit were followed for a maximum 8 week no treatment period. As with evaluations during the daily treatment phase, subjects were evaluated for the presence of EGW in all anatomic areas, and no distinction was made between baseline and newly evident warts. As efficacy measures were based on complete clearance of all warts, not just warts presented at Baseline, development of new warts would potentially lower the complete and partial clearance rates.

Subgroup analyses were performed for the primary efficacy variable. In general, the complete clearance rates increased in a dose-dependent manner regardless of subgroup. The most striking subgroup effect was observed in the analysis by gender; the complete clearance rates were consistently higher in females than in males in all treatment groups. The higher absolute clearance rates in females than in males have been seen previously with 5% imiquimod cream as well as with other topical treatments and may be due in part to the distribution of warts on females (eg, less keratinized skin). In addition to gender subgroup, the complete clearance rates tended to be higher in subjects with ≤7 warts at Baseline, in subjects whose EGW was first diagnosed less than 1 year, in subjects who took a rest period, and in subjects with baseline warts in the anatomic areas with less keratinized skin such as the perineal area, the perineal area, the foreskin, or the vulva. Of note, baseline demographics for the population as a whole suggest that EGWs in this study cohort were of relatively longstanding duration (mean/median years since diagnosis of 4.3/1.4 years).

Safety

Daily application of 3.75% or 2.5% imiquimod cream was generally well tolerated in this study. Few subjects discontinued the study due to adverse events. Very few serious adverse events were reported, and none were considered treatment related. The proportion of subjects with treatment-related AEs was higher in the active treatment groups (15.4% and 15.2% in the 3.75% and 2.5% imiquimod, respectively) than with placebo (2.1%), but there was no difference in the incidence rates between imiquimod groups. Most AEs were mild or moderate ill intensity, and resolved without sequelae.

The majority of AEs considered treatment related occurred in the system organ class General Disorders and Administrative Site Conditions, and are not unanticipated with imiquimod. For the most part, these represented various application site reaction symptoms such as pain, irritation, pruritus, etc. The proportion of subjects with any application site reaction was similar in the active treatment groups.

Anticipated reactions in the application area were also captured separately as local skin reactions (LSRs). The frequency and intensity of LSRs were higher in the active treatments compared with placebo. Erythema was the LSR reported with the greatest frequency and the greatest mean intensity in all treatment groups. The incidence of severe intensity LSRs was similar in the active treatment groups. Local skin reactions were coincident with the treatment period and rapidly decreased when treatment was concluded.

There was no evidence of clinically meaningful trends in vital sign measurements or clinical laboratory measurements.

Conclusion

The 3.75% cream formulation of imiquimod demonstrated substantial efficacy for the treatment of EGW. All efficacy measures for which statistical testing was performed were significantly superior in the 3.75% imiquimod treatment group compared with placebo in both the ITT and PP populations. Consistently greater efficacy was observed with the 3.75% imiquimod product compared with 2.5% imiquimod, and the safety profiles were similar. Treatment with either imiquimod formulation resulted in greater increases in local skin reactions compared with the placebo cream: erythema was the LSR reported with the greatest frequency and the greatest mean intensity in all treatment groups. For both active creams, the number and severity of local skin reactions decreased rapidly after the completion of treatment. The most frequently reported adverse events were application site reactions observed in the active treatment groups; however, few subjects discontinued the study as a result of adverse events, indicating that these events were manageable and generally well tolerated.

Example 25

The Combined Two Phase 3, Randomized, Double-Blind, Placebo-Controlled, Multi-Center, Efficacy and Safety Studies of 3.75% Imiquimod Creams in the Treatment of External Genital Warts, as Reported in Example 24 and in the Draft U.S. Label and the Canadian Product Monograph Incorporated Herein by Reference in their Entireties and Filed Contemporaneously Herewith In two double-blind, randomized, placebo-controlled clinical studies, 601 subjects with EGW were treated with 3.75% imiquimod cream, or a matching placebo cream-studies enrolled subjects aged from 15 to 81 years. The baseline wart area ranged from 6 to 5579 mm2 and the baseline wart count ranged from 2 to 48 warts. Most subjects had two or more treated anatomic areas at Baseline. Anatomic areas included: inguinal, perineal, and perianal areas (both genders); the glans penis, penis shaft, scrotum, and foreskin (in men); and the vulva (in women). Up to one packet of study cream was applied once daily to each wart identified at Baseline and any new wart that appeared during the treatment period. The study cream was applied to all warts prior to normal sleeping hours and left on for approximately 8 hours. Subjects continued applying the study cream for up to 8 weeks or until they achieved complete clearance of all (baseline and new) warts in all anatomic areas. Subjects not achieving complete wart clearance by the Week 8 visit (end of treatment. EOT), were evaluated for up to 8 weeks or until they achieved complete clearance during an additional 8, week no-treatment period. Subjects who achieved complete clearance of all warts at any time until the Week 16 visit entered a 12 week follow-up for recurrence period.

Efficacy was assessed by wart counts (those present at Baseline and new warts appearing during the study) at EOS (i.e., up to 16 weeks from Baseline). Complete clearance required clearance of all warts in all anatomic areas. Partial clearance rate was defined as the proportion of subjects with at least a 75% reduction in the number of baseline warts at EOS. Percent reductions were measured relative to the numbers of warts at Baseline. Complete and partial clearance rates, and percent reductions in wart counts from baseline are shown in the Table 133 below (by overall rate and by gender).

TABLE 133

| Efficacy End Points | | |
|---|---|---|
| | TRADENAME ™ Cream, 3.75% | Placebo Cream |
| Complete Clearance Rate | | |
| Overall | 28.3% (113/399) | 9.4% (19/202) |
| Females | 36.6% (79/216) | 14.2% (15/106) |
| Males | 18.6% (34/1 83) | 4.2% (4/96) |
| Partial Clearance Rate | | |
| Overall | 38.3% (153/399) | 11.9% (24/202) |
| Females | 47.7% (103/216) | 17.0% (18/106) |
| Males | 27.3% (50/183) | 6.3% (6/96) |
| Percent Reduction of EGW | | |
| Overall | 50.0% | 0.0 |
| Females | 70.7% | 0.0 |
| Males | 23.3% | 0.0 |

The numbers of subjects who remained clear of EGW at the end of 12 week follow-up for recurrence period are shown in Table 134 below:

TABLE 134

| Sustained Complete Clearance | | |
|---|---|---|
| | TRADENAME ™ Cream, 3.75% | Placebo Cream |
| Cleared and entered Follow-up | 102 | 13 |
| Remained Clear | 71 | 12 |

Systemic absorption of imiquimod (up to 9.4 mg [one packet]) across the affected skin of 18 subjects with EGW was observed with once daily dosing for 3 weeks. The mean peak serum drug concentration at Day 21 was about 0.488 ng/mL.

Acute dermal toxicity studies in rabbits with unformulated imiquimod under occlusion did not reveal any toxic effects at very high dose levels—5000 mg/kg. When administered orally, intraperitoneally, subcutaneously or intravenously, single dose studies revealed that imiquimod produced central nervous system (CNS) stimulation and convulsions at lethal doses. However, signs of CNS toxicity did not occur when animals were given lower repeat doses (100 mg/kg or lower) as shown in Table 135.

TABLE 135

| Species | Route | $LD_{50}$ (mg/kg) |
|---|---|---|
| Mouse | Oral | 403 |
| | Intraperitoneal | 879 |
| Rat | Oral | 1665 |
| | Intraperitoneal | 763 |
| | Subcutaneous | ≈20 |
| Rabbit | Dermal | >5000 |
| Monkey | Oral | >200 |
| | intravenous infusion | ≈8 |
| | intravenous bolus | >6 |

As indicated above, in two double-blind, placebo-controlled studies for genital warts, 602 subjects applied up to one packet of a cream of the present invention or placebo daily for up to 8 weeks. The most frequently reported adverse reactions were local skin and application site reactions.

Overall, fewer than 1% (3/400) of the subjects treated with a cream of the present invention discontinued due to local skin application site reactions. The incidence and severity of local skin reaction during controlled clinical studies are shown in Table 136.

TABLE 136

Local Skin Reactions in the Treatment Area Assessed by the Investigator

| | TRADENAME Cream | | | | Placebo | | | |
|---|---|---|---|---|---|---|---|---|
| | Females n = 217 | | Males n = 183 | | Females n = 106 | | Males n = 96 | |
| | All Grades* | Severe | All Grades* | Severe | All Grades* | Severe | All Grades* | Severe |
| Erythema | 74% | 10% | 78% | 10% | 23% | 0% | 37% | 1% |
| Edema (induration | 41% | 2% | 48% | 2% | 8% | 0% | 9% | 0% |
| Weeping! Exudate | 35% | 1% | 39% | 3% | 5% | 0% | 0% | 0% |
| Flaking! Scaling! nrwile.cc | 26% | 0% | 39% | 0% | 11% | 0% | 11% | 0% |
| Scabbing! Crusting | 18% | <1% | 34% | 1% | 6% | 0% | 2% | 0% |
| Erosion! Ulceration | 36% | 13% | 42% | 10% | 7% | 1% | 2% | 0% |

*Mild, Moderate, or Severe

Local skin reactions were recorded as adverse events if they extended beyond the treatment area, if they required any medical intervention, or they resulted in patient discontinuation from the study.

Selected treatment related adverse reactions are listed below.

TABLE 137

Treatment Related Adverse Reactions Occurring in >1% of a Cream of Present Invention Treated Subjects and at a Greater Frequency than with Placebo in either Gender

| | Females | | Males | |
|---|---|---|---|---|
| Preferred Term | TRADE-NAME Cream n = 217 | Placebo n = 106 | TRADE-NAME Cream n = 183 | Placebo n = 96 |
| Application site pain | 7.8% | 0% | 5.5% | 1.0% |
| Application site irritation | 5.5% | 0.9% | 6.0% | 1.0% |
| Application site pruritus | 3.2% | 1.9% | 1.6% | 0% |
| Application site bleeding | 1.4% | 0.9% | 1.5% | 0% |
| Application site discharge | 1.4% | 0% | 0.5% | 0% |
| Application site erythema | 1.4% | 0% | 0% | 0% |
| Application site reaction | 0.9% | 0% | 1.1% | 0% |
| Application site rash | 0.9% | 0% | 1.1% | 0% |
| Scrotal pain | 0% | 0% | 1.6% | 0% |
| Application site excoriation | 0% | 0% | 1.1% | 0% |
| Secretion discharge | 0% | 0% | 1.1% | 0% |
| Scrotal erythema | 0% | 0% | 1.1% | 0% |
| Scrotal ulcer | 0% | 0% | 1.1% | 0% |
| Scrotal edema | 0% | 0% | 1.1% | 0% |
| Pruritus genital | 0% | 0% | 1.1% | 0% |
| Application site cellulitis | 0% | 0% | 1.1% | 0% |

Systemic adverse reactions considered treatment related in clinical trials involving a cream of the present invention included pain, pyrexia (fever), influenza, and myalgia.

Adverse reactions seen in clinical trials for external genital warts involving 5% imiquimod cream included: tinea cruris, application site soreness, hypopigmentation, sensitivity, stinging and tenderness.

Other systemic adverse reactions considered treatment related in clinical trials for external genital warts involving 5% imiquimod cream included: headache, influenza-like symptoms, fatigue, malaise, nausea, and diarrhea.

Example 26

An Open Label, Single Center, Non-Randomized Pharmacokinetic Study to Evaluate Safety of and Systemic Exposure to Multiple Applications of Imiquimod Cream in Subjects with External Genital Warts Objectives To quantify the pharmacokinetics of imiquimod and its metabolites during 3 weeks of daily applications of 3.75% imiquimod cream in subjects with external genital warts (EGW) under maximal use conditions. Secondary objectives include subject tolerability and safety assessments.

Methodology

In this open-label, single-center, non-randomized, pharmacokinetic (PK) study, approximately 18 adult subjects (a target of at least 5 subjects of each gender) with at least 8 warts in the genital/perianal area or a total wart area of ≥100 $mm^2$ applied once daily applications of up to 1 packet of 3.75% imiquimod cream for 3 continuous weeks (21 days). The study was conducted under the maximal use conditions (dose, disease severity, and wart area) anticipated in Phase III studies.

Subjects stayed at the study center overnight during the treatment initiation visit (Day 1, first evening application) and the end-of-treatment visit (Day 21, last evening application). On Days 1 and 21, serum PK samples were collected pre-application and at planned time points for 24 hour post application; samples were also collected at 48 and 72 hours after application on Day 21. In addition, serum PK samples were collected in the evening prior to application on Days 7 and 14 to determine trough concentrations for steady-state analysis.

Adverse events (AEs), local skin reactions (LSRs), number of warts, wart area measurements, concomitant medication use, study medication accountability, and subject compliance were reviewed at each visit. Routine clinical laboratory assessments (serum chemistry, hematology, and urinalysis) were performed at screening and 72 hours after the last application on Day 21.

This study was performed primarily to determine the pharmacokinetics of 3.75% imiquimod cream during 3 weeks of once daily application in subjects with EGW; consequently, an open-label, non-randomized study design was chosen. Since the pharmacokinetics of imiquimod have been evaluated in several studies, a control group was considered unnecessary, and since mean urinary recoveries of imiquimod and its metabolites were low in a previous study of EGW subjects (Study 1253-IMIQ$_9$), urinary pharmacokinetic analyses imiquimod and its metabolites were not performed in this study. Local skin reactions (LSRs) were assessed independently of adverse events (AEs). Standard safety assessments used in clinical research were included for the evaluation of safety and tolerability.

The 3-week treatment duration was selected to confirm that steady-state conditions would exist with a relatively constantly applied dose/wart area. Steady-state conditions for thrice weekly dosing of 5% imiquimod were previously attained within 2 weeks of dosing in subjects with EGWs. A pharmacokinetic study was conducted in subjects with EGWs (Study 1253-IMIQ), during which 12 subjects received 5% imiquimod cream administered 3-times weekly for 16 weeks. While the trough levels in this study were insufficient to determine whether steady-state conditions were achieved (virtually all results were below the lower limit of quantification, LLOQ), the mean $C_{max}$ values at Weeks 4 and 16 were within the range of those observed after the first dose, and the measured half-life values ranged from 3.4 to 33.4 hours. As a result, steady-state conditions would exist after 7 days of treatment at the longest measured half-life value (33.4 hours). Following 21 days of once daily administration, steady-state conditions would be achieved if the half-life value was ≤100 hours (3 times the highest value observed in Study 1253-LMIQ). Since the measured elimination half-life values previously observed in EGWs subjects were consistent with shorter times to steady state (i.e., 1 to 2 weeks), subjects were expected to attain steady-state conditions within the 3 weeks of this study.

Inclusion Criteria

Subjects could participate in the study if they

1. Were willing and able to give informed consent.
2. Were at least 18 years of age.
3. Were willing and able to participate in the study with two overnight stays and frequent visits to the study center and to comply with all study requirements.
4. Had a negative pregnancy test result prior to the first application of test medication (for women of childbearing potential) and agreed to use an approved method of birth control while enrolled in the study.
5. Had a diagnosis of external genital/perianal warts with at least 8 warts or a total wart area of at least 100 mm2 in any of the following anatomic locations:

Both Sexes: In the inguinal, perineal, and perianal areas;

Men: Over the glans penis, penis shaft, scrotum, and foreskin, including the base of the penis; and Women: On the vulva, including the mons.

6. Were in good general health as confirmed by a medical history, physical examination, and laboratory tests at the screening visit.

Exclusion Criteria

Subjects who met any of the following criteria were excluded from the study if they:

1. Were women of childbearing potential who were pregnant, lactating, or planning to become pregnant during the course of the study
2. Had any topical and/or destructive treatments for EGW within 4 weeks prior to first treatment
3. Had received any of the following treatments within 4 weeks prior to the first treatment:
   a. Imiquimod
   b. Interferon/interferon inducer
   c. Cytotoxic drugs
   d. Immunomodulators or immunosuppressive therapies
   e. Oral antiviral drugs (with the exception of oral acyclovir and acyclovir-related drugs for suppressive or acute therapy of herpes or oseltamivir for prophylaxis or acute therapy of influenza)
   f. Topical antiviral drugs (including topical acyclovir and acyclovir-related drugs) in the treatment areas
   g. Podophyllotoxin/podofilox in the treatment areas
   h. Oral and parenteral corticosteroids (inhaled/intranasal steroids were permitted)
   i. Topical steroids if greater than 2 g/day
   j. Any other topical prescription therapy for any conditions in the treatment areas k. Dermatologic/cosmetic procedures or surgeries in the treatment areas
4. Had any evidence (physical or laboratory) of clinically significant or unstable disease and/or any condition (e.g., renal disease) that might interfere with the pharmacokinetic response to the study treatment or alter the natural history of EGW
5. Were currently participating in another clinical study or had completed another clinical study with an investigational drug or device within the past 30 days
6. Had known or active chemical dependency or alcoholism as assessed by the investigator
7. Had known allergies to study drug or any excipient in the study cream
8. Were currently immunosuppressed or had a history of immunosuppression
9. Had a planned surgery that would cause an interruption of study treatment
10. Had sexual partners currently being treated with an approved or investigational treatment for EGW
11. Had any current or recurrent malignancies in the genital or wart area
12. Had any untreated or unstable genital infections (other than genital warts)
13. Had any of the following conditions:
    Known human immunodeficiency virus (HIV) infection
    An outbreak of herpes genitalis in the wart areas within 4 weeks prior to Enrollment
    Internal (rectal, urethral, vaginal/cervical) warts requiring or undergoing treatment
    A dermatological disease (e.g., psoriasis) or skin condition in the wart areas that might cause difficulty with examination
14. Females with clinically significant abnormalities on pelvic examination or laboratory results showing high-grade pathology (e.g., high-grade squamous intraepithelial lesion, moderate or severe dysplasia, squamous cell carcinoma).

Removal of Subjects from Therapy or Assessment

Subjects could choose to withdraw from the study or be withdrawn by the investigator at any time without prejudice to their future medical care. Any subject who did not comply with the inclusion/exclusion criteria could be withdrawn from further participation in the study.

Subjects were also discontinued from the study for the following reasons:

The investigator determined that the subject experienced local skin reactions (LSRs) of severe enough intensity or duration to warrant discontinuation. If a subject discontinued due to an LSR, the LSR was recorded as an adverse event (AE), and the subject was followed until the AE resolved to the investigator's satisfaction.

The subject took any prohibited medications or underwent any prohibited treatments or procedures as described below.

The subject developed a dermatological condition within the wart area unrelated to study cream that interfered with treatment compliance.

The subject developed a malignancy within the wart area that required intervention.

The subject became pregnant during the study.

Subjects who discontinued from the study were to complete the appropriate end-of-study procedures.

Prohibited medications/treatments or procedures:

a. Imiquimod 5% cream (Aldara®)

b. Interferon/interferon inducer c. Cytotoxic drugs d. Immunomodulators or immunosuppressive therapies e. Oral or parenteral corticosteroids (inhaled/intranasal steroids are permitted)

f. Oral antiviral drugs (with the exception of oral acyclovir and acyclovir-related drugs for suppressive or acute therapy of herpes or oseltamivir for prophylaxis or acute therapy of influenza)

g. Topical antiviral drugs (including topical acyclovir and acyclovir-related drugs) in the treatment areas h. Podophyllotoxin/podofilox in the treatment areas i. Any topical prescription medications in the application areas j. Dermatologic/cosmetic procedures or surgeries in the application areas A total of 18 subjects, 13 male subjects and 5 female subjects, were enrolled (18 planned) who met the inclusion and exclusion criteria and were able to participate within the time frame of this study. All subjects completed the study.

Criteria and Methods for Evaluation:

Efficacy was not evaluated in this study.

Primary Assessments:

The pharmacokinetics of imiquimod and its metabolites during 3 weeks of daily application with 3.75% imiquimod cream under the maximal use conditions (up to 1 packet of the cream applied to least 8 genital/perianal warts or in an area of at least 100 $mm^2$) were quantified.

During the 3-week treatment period, blood samples for determination of the concentrations of imiquimod (R-837)

and two metabolites combined (S-26704 and S-27700) were collected at 9 time points on Day 1 (first application) within approximately 30 minutes of pre-application (0 hour) and 1, 2, 4, 6, 9, 12, 16, and 24 hours after application of study cream and on Day 21 (last application) at pre-application and 1, 2, 4, 6, 9, 12, 16, and 24 hours after application of study cream, Pharmacokinetic (PK) blood samples were also collected 48 hours after the last application on Day 21, and End-of-Study (EOS) PK blood samples were collected 72 hours after the final application. In addition, single blood draws for PK analysis of trough concentrations to determine steady state were obtained on Day 7 and Day 14 (in the evening prior to application). Blood samples could be obtained within ±5 minutes of the target sampling time.

Urine samples for PK analysis were not obtained during this study.

Serum PK samples were analyzed for concentrations of imiquimod (R-837) and two major metabolites (S-267046-27700) using validated analytical methods.

Secondary Assessments:

Adverse events and local skin reactions were evaluated during the study.

Severity, relationship to study medication and timing of adverse events were recorded.

Routine clinical laboratory assessments (serum chemistry, hematology and urinalysis) will be performed at Screening, Day 1, and the end of study visits.

Pharmacokinetic and Statistical Methods:

The concentration of imiquimod and its 2 metabolites combined (S-26704 and S-27700) in serum over time will be used to calculate pharmacokinetic parameter estimates, when. sufficient data are present Pharmacokinetic variables will be calculated from the serum concentration data using standard, non-compartmental methods.

Results

Pharmacokinetics Analysis

Serum Concentrations

Mean serum concentrations of imiquimod and two of its metabolites combined are shown using the linear and semi-log scales on Day 1 in FIG. 35 and Day 21 in FIG. 36 below.

Figure 35:
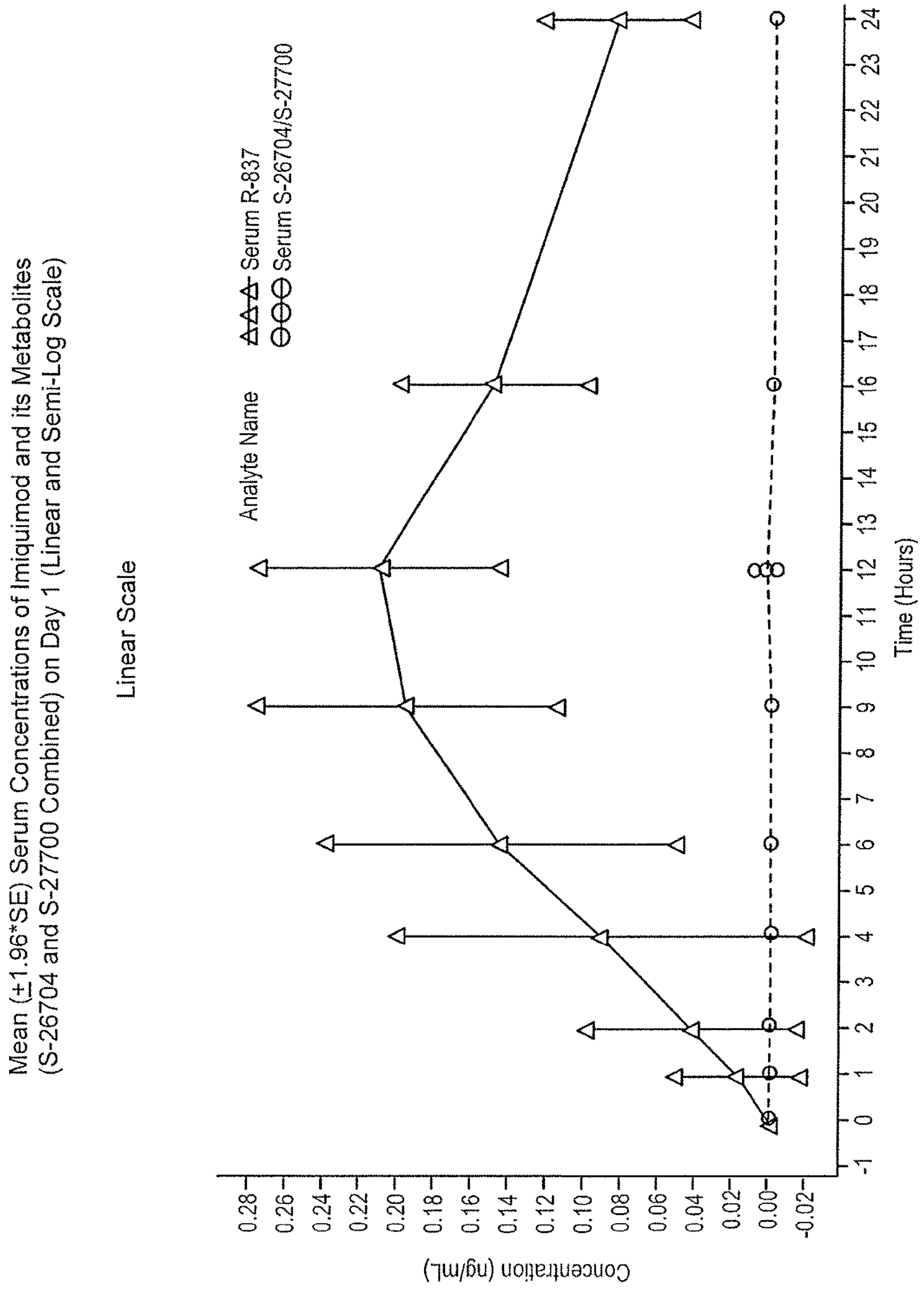
FIG. 35 shows mean serum concentrations of imiquimod and imiquimod metabolites on Day 1 (linear and semi-log scale).
Figure 35:
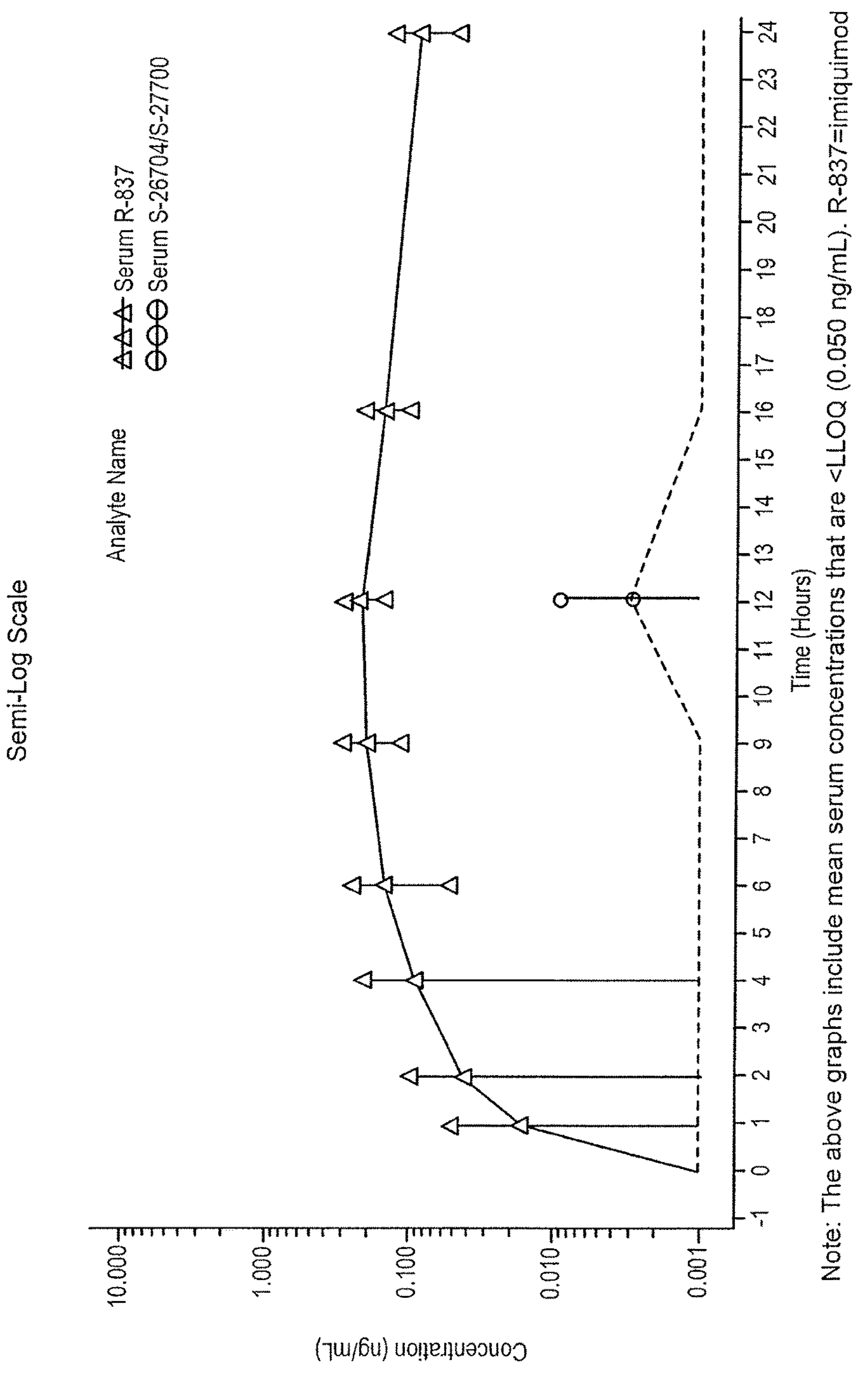

As shown in FIG. 35, the mean serum concentration of imiquimod (R-837) on Day 1 increased steadily until reaching a peak concentration of approximately 0.20 ng/mL at approximately 12 hours after the first application of imiquimod 3.75% cream. By 24 hours after application, the mean serum concentration of imiquimod had decreased to approximately half the peak concentration. Subject 001-411 had no concentrations above BLQ on Day 1; consequently, no pharmacokinetic parameters could be calculated for this subject on Day 1. Subject 001-408 had an imiquimod concentration above BLQ (0.058 ng/mL) only at 12 hours on Day 1, limiting the pharmacokinetics that could be calculated. Serum concentrations of the two imiquimod metabolites (S-26704 and S-27700 combined) were undetectable on Day 1 except for Subject 001-418 who had a concentration of 0.056 ng/mL at 12 hours after application.

Figure 36:
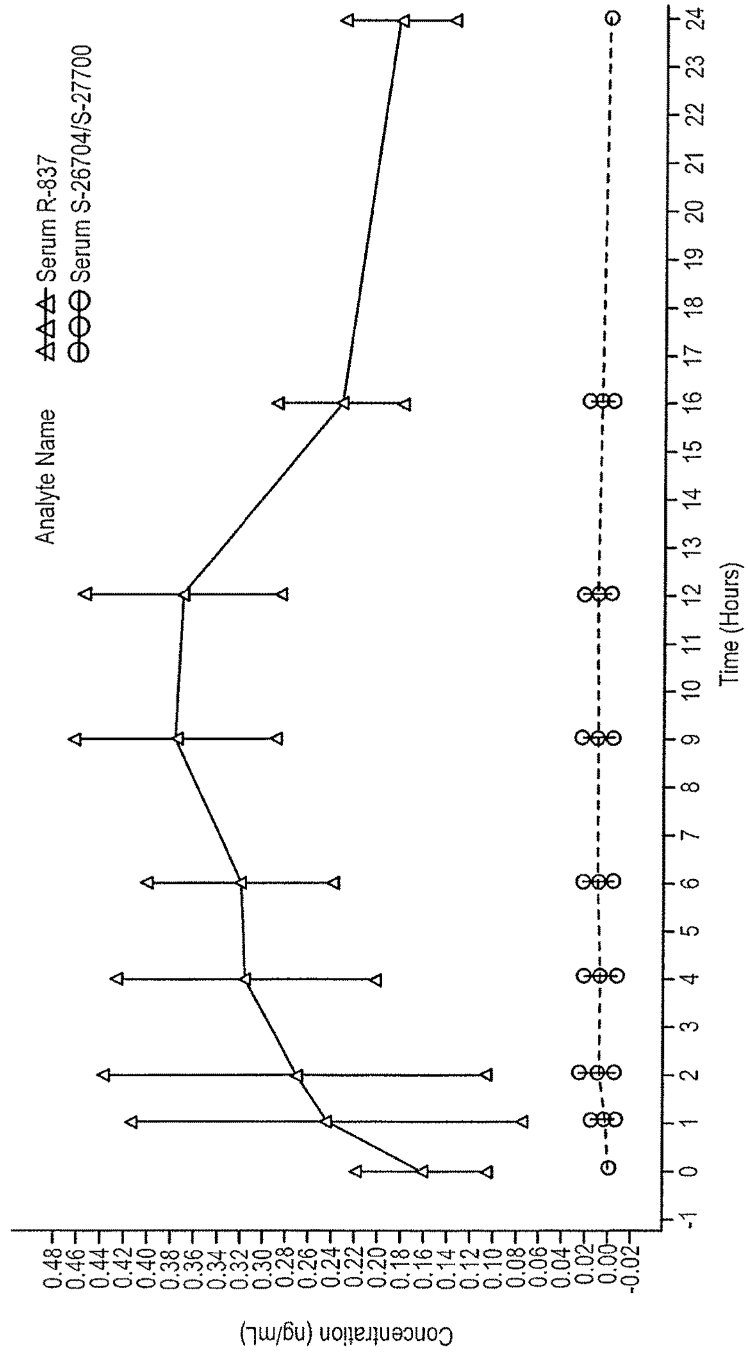
FIG. 36 shows mean serum concentrations of imiquimod and imiquimod metabolites on Day 21 (linear and semi-log scale).
Figure 36:
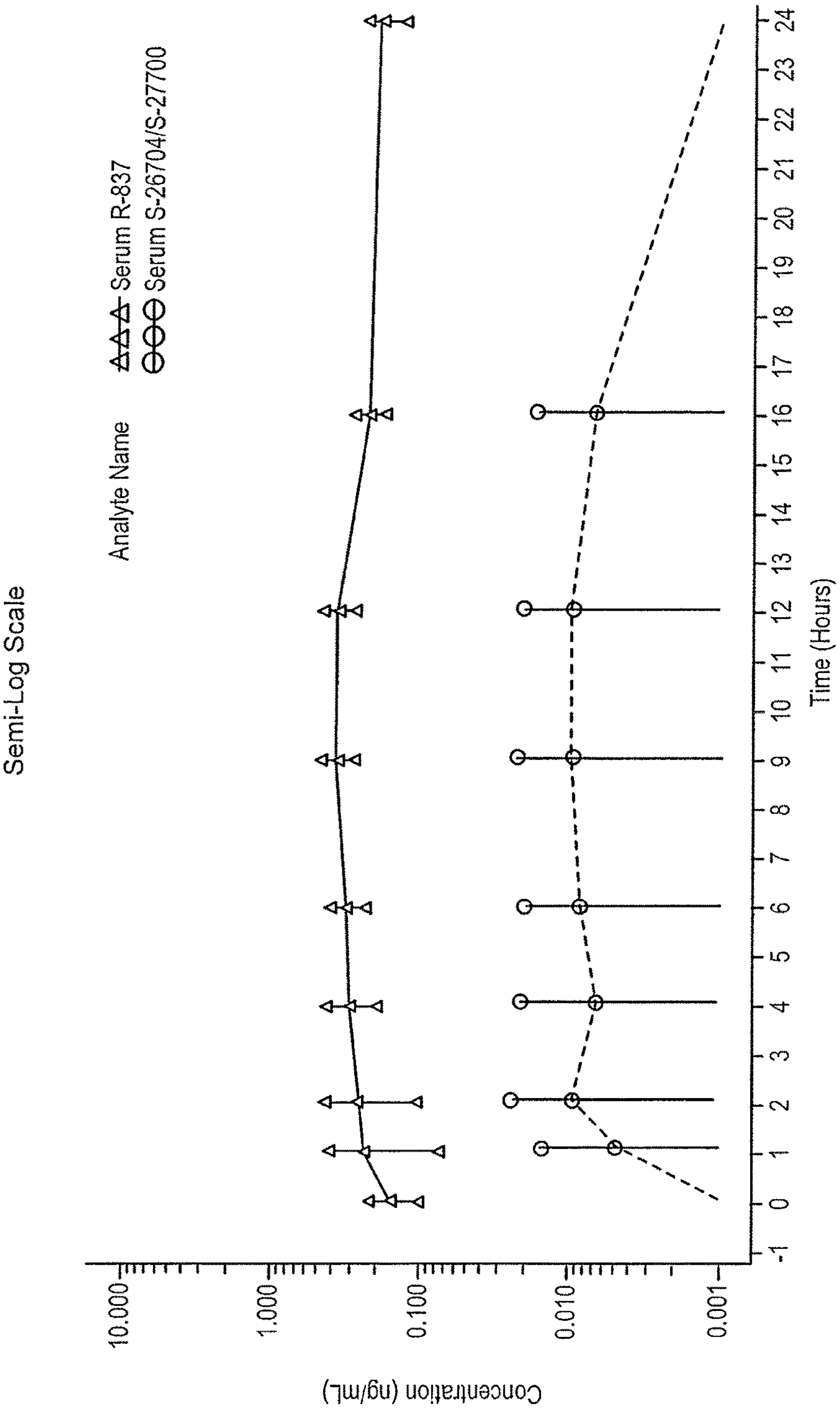

As shown in FIG. 36, mean serum concentrations of imiquimod on Day 21 ranged from approximately 0.16 to 0.37 ng/mL over the 24-hour period after study drug application. Serum concentrations of two imiquimod metabolites (S-26704 and S-27700 combined) were reported for only 4 subjects on Day 21; the few concentrations that were reported tended to be low (0.050 ng/mL to 0.133 ng/mL).

| Pharmacokinetic Abbreviations and Definitions of Terms | |
|---|---|
| $AUC_{0-inf}$ | Area under the serum concentration versus time curve, from 0 to infinity; $AUC_{0-inf}$ calculated as Day 1 as $AUC(_{0-inf}) = AUC(_{0-inf}) + Ct/\lambda_z$ (where $AUC_{0-t}$ = AUC from time zero to the time of the last non-zero concentration, $C_t$ = the fitted last non-zero concentration, and $\lambda_z$ = the elimination rate constant) |
| $AUC_{0-t}$ | Area under the serum concentration versus time curve, from 0 to the time of the last non-zero concentration on Day 1; calculated using the linear trapezoid rule |
| $AUC_{0-24}$ | Area under the serum concentration versus time curve, from 0 to 24 hours, calculated using the linear trapezoid rule or extrapolated to 24 hours in cases where reportable values were not obtainable up to that time point |
| $C_{max}$ | Maximum serum concentration; the highest serum concentration observed during the dosing or sampling interval |
| $C_{min}$ | Minimum measurable serum concentration; serum concentration observed immediately prior to dosing on Days 7, 14, 21, and 22 (24 hours post-dose) |
| $\lambda_{zEFF}$ | Effective elimination rate constant, calculated as $-\ln(1-1/R_{AUC})$/tau |
| $\lambda_z$ | Apparent elimination rate constant; calculated using linear regression on the terminal portion of the in-concentration versus time profile |
| $R_{AUC}$ | Accumulation ratio; calculated as the $AUC_{0-24}$ value during multiple-application administration divided by the $AUC_{0-24}$ value following the first application (ie., Day 21/Day 1); accumulation ratios calculated for the metabolite only if sufficient non-zero time points were available to reasonably estimate $AUC_{0-24}$ |
| $R_{Cmax}$ | Accumulation ratio; calculated as the $C_{max}$ value during multiple-application administration divided by the $C_{max}$. value following the first application (i.e., Day 21/Day 1) |
| $T_{1/2}$ | The apparent elimination half-life, calculated as $0.693/\lambda_z$ |
| $T_{1/2\ EFF}$ | Effective half-life for accumulation; calculated as $0.693/\lambda_{z\ EFF}$ |
| $T_{max}$ | Time that $C_{max}$ was observed |

Pharmacokinetic Results

TABLE 137

Summary of Serum Pharmacokinetics for Imiquimod (R-837) on Day 1 and Day 21

| Parameter | N | Mean (SD) Day 1[a] | N | Mean (SD) Day 21[b] |
|---|---|---|---|---|
| $C_{max}$ (n/mL) | 18 | 0.259 (0.223) | 15 | 0.488 (0.368) |
| $C_{max}$ (n/mL) | — | NA | 15 | 0.158 (0.121) |
| $T_{max}$ (hr)[c] | 17 | 12.00 (4.00-16.00) | 15 | 12.00 (1.00-16.00) |
| $AUC_{0-24}$ (ng · hr/mL) | 15 | 3.748 (2.541) | 15 | 6.795 (3.591) |
| $AUC_{0-t}$ (ng · hr/mL) | 18 | 3.123 (2.665) | — | NA |
| $AUC_{0-inf}$ (ng · hr/mL) | 12 | 5.352 (2.636) | — | NA |
| $\lambda_z$ (1/hr) | 12 | 0.0756 (0.0416) | 14 | 0.0370 (0.0222) |
| $T_{1/2}$ (hr) | 12 | 12.450 (8.249) | 14 | 24.135 (12.402) |
| $R_{Cmax}$ | — | NA | 14 | 2.260 (1.579) |
| $R_{AUC}$ | — | NA | 12 | 2.169 (1.752) |
| $\lambda_{z\ EFF}$ ($hr^{-1}$) | — | NA | 10 | 0.0380 (0.0261) |
| $T_{1/2\ EFF}$ ($h^{-1}$) | — | NA | 10 | 31.328 (30.308) |

NA = Not applicable

[a]Day 1 results include all PK population subjects.

[b]Day 21 PK results include all PK population subjects except Subject 001-404 (missed applications on Days 8 and 18), Subject 001-407 (missed an application on Day 20), and Subject 001-416 (missed an application on Day 17).

[c]Median (minimum-maximum)

TABLE 139

Summary of Individual Serum Pharmacolinetic Parameters-Cmin (Ng/Ml) by Day for Imiquimod, PK Population
TREATMENT: IMIQUIMOD 3.75% CREAM QD
ANALYTE: Serum R-837 (imiquimod)

| Subject ID/ Statistics | Day 7 | Day 14 | Day 21 | Day 22 |
|---|---|---|---|---|
| 001-401 | 0.059 | 0.052 | 0.025 | 0.073 |
| 001-402 | 0.097 | 0.277 | 0.263 | 0.240 |
| 001-403 | 0.142 | 0.315 | 0.075 | 0.099 |
| 001-404 | 0.194 | 0.199 | | |
| 001-405 | 0.480 | 0.467 | 0.088 | 0.181 |
| 001-406 | 0.115 | 0.025 | 0.025 | 0.090 |
| 001-407 | 0.214 | 0.276 | | |
| 001-408 | 0.073 | 0.125 | 0.137 | 0.099 |
| 001-409 | 0.237 | 0.376 | 0.221 | 0.272 |
| 001-410 | 0.194 | 0.247 | 0.467 | 0.348 |
| 001-411 | 0.142 | 0.076 | 0.081 | 0.287 |
| 001-412 | 0.287 | 0.025 | 0.269 | 0.370 |
| 001-413 | 0.025 | 0.025 | 0.025 | 0.077 |
| 001-414 | 0.207 | 0.159 | 0.102 | 0.086 |
| 001-415 | 0.244 | 0.054 | 0.150 | 0.123 |
| 001-416 | 0.025 | 0.224 | | |
| 001-417 | 0.126 | 0.196 | 0.192 | 0.228 |
| 001-418 | 0.111 | 0.165 | 0.246 | 0.145 |
| N | 18 | 18 | 15 | 15 |
| MEAN | 0.165 | 0.182 | 0.158 | 0.181 |
| SD | 0.109 | 0.129 | 0.121 | 0.102 |
| CV % | 66.167 | 70.793 | 76.926 | 56.495 |
| GEOMETRICMEAN | 0.130 | 0.129 | 0.113 | 0.156 |
| MIN | 0.025 | 0.025 | 0.025 | 0.073 |

To calculate Cmin values on Days 7, 14, 21, and 22. BLQ was input in the database with the ½ lower limit of quantification value of 0.05 ng/ml (i.e., 0.025). During the last week, 3 subjects missed applications (404 on Day 18, 407 on Day 20, and 416 on Day 17) and are excluded from Days 21 and 22 results to provide data with subjects who applied all applications.

TABLE 138

Summary Of Individual Serum Pharmacokinetic Parameters At Day 21 For Imiquimod-Without Subjects 404, 407 And 416 Pk Population
TREATMENT: 3.75 IMIQUIMOD CREAM QD
ANALYTE: Serum R-837

| SUBJECT/ STATISTICS | Cmax (ng/mL) | Tmax (hr.) | AUC(0-24) (hr*ng/mL) | RAUC | RCmax | Lz (1/hr) | Lzeff ($hr^{-1}$) | T ½ (hr) | T½, eff (hr) |
|---|---|---|---|---|---|---|---|---|---|
| 001-401 | 0.140 | 12.000 | 2.201 | 1.148 | 0.933 | 0.0516 | 0.0855 | 13.436 | 8.111 |
| 001-402 | 0.492 | 12.000 | 8.096 | 7.209 | 5.407 | | 0.0062 | | 111.398 |
| 001-403 | 0.202 | 12.000 | 3.244 | 1.958 | 1.656 | 0.0293 | 0.0298 | 23.686 | 23.273 |
| 001-405 | 0.215 | 12.000 | 3.949 | 0.641 | 0.495 | 0.0128 | | 53.990 | |
| 001-406 | 0.444 | 9.000 | 4.682 | 2.235 | 3.171 | 0.1022 | 0.0247 | 6.784 | 28.044 |
| 001-408 | 0.281 | 4.000 | 3.723 | | 4.845 | 0.0454 | | 15.275 | |
| 001-409 | 0.518 | 12.000 | 8.606 | 1.844 | 1.609 | 0.0252 | 0.0326 | 27.514 | 21.294 |
| 001-410 | 0.659 | 9.000 | 10.296 | | 4.393 | 0.0219 | | 31.695 | |
| 001-411 | 0.359 | 9.000 | 6.732 | | | 0.0262 | | 26.470 | |
| 001-412 | 0.651 | 12.000 | 11.536 | 3.178 | 1.876 | 0.0374 | 0.0157 | 18.51 | 44.024 |
| 001-413 | 0.107 | 16.000 | 1.924 | 0.817 | 0.498 | 0.0163 | | 42.622 | |
| 001-414 | 0.446 | 4.000 | 6.232 | 1.820 | 1.735 | 0.0408 | 0.0332 | 16.971 | 20.867 |
| 001-415 | 0.485 | 9.000 | 6.599 | 1.337 | 1.394 | 0.0506 | 0.0574 | 13.712 | 12.077 |
| 001-417 | 0.692 | 12.000 | 10.379 | 2.639 | 2.029 | 0.0317 | 0.0199 | 21.887 | 34.919 |
| 001-418 | 1.632 | 1.000 | 13.735 | 1.199 | 1.597 | 0.0274 | 0.0748 | 25.337 | 9.270 |
| N | 15 | 15 | 15 | 12 | 14 | 14 | 10 | 14 | 10 |
| MEAN | 0.488 | 9.667 | 6.795 | 2.169 | 2.260 | 0.0370 | 0.0380 | 24.135 | 31.328 |
| SD | 0.368 | 3.958 | 3.591 | 1.752 | 1.579 | 0.0222 | 0.0261 | 12.402 | 30.308 |
| CV % | 75.318 | 40.946 | 52.843 | 80.774 | 69.857 | 59.9435 | 68.6301 | 51.384 | 96.746 |
| GEOMETRIC MEAN | 0.392 | 8.291 | 5.834 | 1.755 | 1.783 | 0.0324 | 0.0299 | 21.386 | 123.196 |
| MIN | 0.107 | 1.000 | 1.924 | 0.641 | 0.495 | 0.0128 | 0.0062 | 6.784 | 8.111 |
| MEDIAN | 0.446 | 12.000 | 6.599 | 1.832 | 1.696 | 0.0305 | 0.0312 | 22.786 | 22.284 |
| MAX | 1.632 | 16.000 | 13.735 | 7.209 | 5.407 | 0.1022 | 0.0855 | 53.99 | 111.398 |

During the last week, 3 subjects missed applications (404 on Day 18, 407 on Day 20, and 416 on Day 17) and are excluded from Day 21 results to provide data with subjects who applied all applications.

TABLE 140

| Summary of Serum Pharmacokinetic Parameters- Cmin (ng/mL) by Day for Imiquimod, PK Population TREATMENT: IMIQUIMOD 3.75% CREAM QD ANALYTE: Serum R-837 (Imiquimod) | | | | |
|---|---|---|---|---|
| Subject ID/ Statistics | Day 7 | Day 14 | Day 21 | Day 22 |
| MEDIAN | 0.142 | 0.181 | 0.137 | 0.145 |
| MAX | 0.480 | 0.467 | 0.467 | 0.370 |

To calculate Cmin values on Days 7, 14, 21, and 22, BLQ was input in the database with ½ the lower limit of quantification value of 0.05 ng/ml (i.e., 0.025). During the last week, 3 subjects missed applications (404 on Day 18, 407 on Day 20, and 416 on Day 17) and are excluded from Days 21 and 22 results to provide data with subjects who applied all applications.

As shown above in Table 137, imiquimod peak exposure ($C_{max}$) and total exposure (AUC) increased in serum over the 21 days of once daily applications. Mean $C_{max}$ increased from 0.259 ng/mL on Day 1 to 0.488 ng/mT on Day 21. Between Day 1 and Day 21, mean $AUC_{0-24}$ increased from 3.748 to 6.795 ng·hr/mL. Imiquimod median $T_{max}$ was 12 hours on Days 1 and 21.

Mean accumulation ratios for imiquimod reflect the increase in peak and total exposure between Day 1 and Day 21. The ratio of peak exposure ($RE_{max}$) of 2.260 and the ratio of overall systemic exposure ($R_{AUC}$) of 2.169 indicated an approximate 2-fold increase in both peak exposure and total exposure over 21 days. The mean effective half-life for accumulation, $T_{1/2EFF}$, was 31.328 hours; 5 times $T_{1/2EFF}$ divided by 24 hours would indicate that imiquimod should reach steady state on approximately Day 6 or 7 after repeated once daily administration.

The apparent elimination rate constant, $\lambda_z$, was 0.0756 on Day 1 and 0.0370 on Day 21. The imiquimod mean half-lives, $T_{1/25}$ were 12.5±8.2 hours on Day 1 (sampling through 24 hours) and 24.1±12.4 hours on Day 21 (sampling through 72 hours). This apparent increase in half-life most likely represented a better estimate on Day 21 due to the longer sampling duration and fewer BLQ concentrations. Five times the apparent elimination half-life measured on Day 21 divided by 24 hours indicated that steady-state conditions should be reached on Day 5 following once daily administration.

No significant differences in imiquimod (R-837) pharmacokinetic parameters were observed on Day 21 when data excluding Subject 001-404 (missed Day 8 and Day 18 applications), Subject 001-407 (missed Day 20 application), and Subject 001-416 (missed Day 17 application) were compared to data including these 3 subjects the inclusion/exclusion of these 3 subjects did not affect the conclusions.

Serum concentrations of two imiquimod metabolites (S-26704 and S-27700 combined) were measured, but the data were too sparse to assess.

TABLE 141

Comparison of Female and Male Subject Non-Dose-Normalized and Dose-Normalized Pharmacokinetic Parameters on Day 21

| | Mean (SD) Day 21 | | | | | | | |
|---|---|---|---|---|---|---|---|---|
| | Female[a] | | | | Male[b] | | | |
| Parameter | N | Not Dose Normalized | N | Dose Normalized | N | Not Dose Normalized | N | Dose Normalized |
| $C_{max}$ (ng/mL) | 4 | 0.676 (0.656) | 4 | 0.583 (0.484) | 11 | 0.420 (0.203) | 11 | 0.431 (0.198) |
| $AUC_{0-24}$ (ng•hr/mL) | 4 | 7.192 (4.796) | 4 | 6.428 (3.791) | 11 | 6.651 (3.327) | 11 | 6.858 (3.351) |
| $T_{max}$ (hr)[c] | 4 | 6.50 (1.00-12.00) | — | — | 11 | 12.00 (4.00-16.00) | — | — |

[a]Results do not include Subject 001-416 (missed an application on Day 17).

[b]Results do not include Subject 001-404 (missed applications on Days 8 and 18) and Subject 001-407 (missed an application on Day 20).

[c]Median (minimum-maximum)

As shown in Tables 141 and 142, when not dose normalized, peak exposure, $C_{max}$, was 61% higher in female subjects than in male subjects (0.676 versus 0.420 ng/mL), and total systemic exposure, $AUC_{0-24}$, was 8% higher in female subjects than in male subjects (7.192 versus 6.65 1 ng hr/mL). When dose normalized and reported without subjects who missed an application of study drug during the last week of dosing, $C_{max}$ was 35% higher in female subjects than in male subjects (0.583 versus 0.431 ng/mL) while $AUC_{0-24}$ was 6% lower in female subjects than in male subjects (6.428 versus 6.85 8 nglr/mL). Median $T_{max}$ occurred approximately twice as quickly in female subjects (6.50 hours) as in male subjects (12.00 hours).

TABLE 142

Mean (SD) Cmax (ng/mL) and Mean (SD) $AUC_{0-24}$ (ng · hr/mL)

| | Dose Normalized | Female (n = 4) | Male (n = 11) |
|---|---|---|---|
| Mean (SD) Cmax (ng/mL) | No | 0.676 (0.656) | 0.420 (0.203) |
| | Yes | 0.583 (0.484) | 0.431 (0.198) |
| Mean (SD) AUC0-24 (ng · hr/mL) | No | 7.192 (4.796) | 6.651 (3.327) |
| | Yes | 6.428 (3.791) | 6.858 (3.351) |

TABLE 143

Primary Analysis of Steady State for Imiquimod Trough Serum Concentrations (PK Population)

| Trough (Pre-Dose) | Geometric LS Mean[a] | | | Geometric Mean | 90% Confidence |
|---|---|---|---|---|---|
| Comparison | N | Test | Reference | Ratio[b] | Interval |
| Day 14 vs. Day 7 | 13 | 0.1749 | 0.1543 | 1.1335 | 0.7364-1.7446 |
| Day 21 vs. Day 14 | 11 | 0.1571 | 0.1874 | 0.8384 | 0.5308-1.3243 |
| Day 22 vs. Day 21 | 12 | 0.1839 | 0.1643 | 1.1194 | 0.7640-1.6402 |

Note:

Primary steady-state analysis only included subjects with paired and non-zero serum concentration data on the days being compared and subjects who applied all 7 applications in the preceding week and applied at least 80% of the prescribed applications in all prior weeks.

[a]Point estimate for geometric least-squares (LS) mean was based on an ANOVA model, including study day as a fixed effect.

[b]Steady-state conditions were considered to exist during an interval if the point estimate for the geometric mean ratio was <1.43.

TABLE 144

Secondary Analysis of Steady State for Imiquimod Trough Serum Concentrations (PK Population)

| Trough (Pre-Dose) | Geometric LS Mean[a] | | | Geometric Mean | 90% Confidence |
|---|---|---|---|---|---|
| Comparison | N | Test | Reference | Ratio[b] | Interval |
| Day 14 vs. Day 7 | 17 | 0.1259 | 0.1270 | 0.9915 | 0.5876-1.6729 |
| Day 21 vs. Day 14 | 15 | 0.1127 | 0.1150 | 0.9805 | 0.5344-1.7992 |
| Day 22 vs. Day 21 | 15 | 0.1556 | 0.1127 | 1.3800 | 0.8537-2.2309 |

Note:

Secondary steady-state analysis only included subjects with paired serum concentration data in which BLQ values were replaced with LLOQ/2 values on the days being compared and subjects who applied all 7 applications in the preceding week and applied at least 80% of the prescribed applications in all prior weeks.

[a]Point estimate for geometric least-squares (LS) mean was based on an ANOVA model, including study day as a fixed effect.

[b]Steady-state conditions were considered to exist during an interval if the point estimate for the geometric mean ratio was <1.43.

As shown above in Tables 143 and 144 the geometric mean ratios for all steady-state comparison intervals were <1.43, indicating that steady state was achieved by Day 7. In the primary analysis, the geometric mean ratio during the Day 21 versus Day 14 interval was lower than might be expected (0.83 84), but the geometric mean ratio for the Day 22 versus Day 21 interval (1.1194) and the geometric mean ratio for the Day 14 versus Day 7 interval (1.1335) were both close to 1.00, indicating that steady-state conditions were likely achieved by Day 7. This conclusion is consistent with the estimated time to steady state calculated from the observed mean elimination half-life and the mean effective half-life for accumulation. The decrease in the geometric mean ratio during the Day 21 versus Day 14 interval may have been a consequence of inpatient versus outpatient application. Overall, it appears that steady-state conditions were achieved by Day 7.

TABLE 145

Summary of External Genital Wart Area ($mm^3$) by Visit
Compound: Imiquimod 3.75% Cream QD
Protocol: GW01-0804

| | 3.75% (N = 18) |
|---|---|
| Baseline (Day 1) | |
| N | 18 |
| Mean (SD) | 108.3 (138.7) |
| Median | 60.0 |
| Minimum, Maximum | 15.0, 620.0 |
| Day 7 | |
| N | 18 |
| Mean (SD) | 101.3 (125.3) |
| Minimum, Maximum | 15.0, 554.0 |
| Percent Change from Baseline | |
| N | 18 |
| Mean (SD) | −6.8 (20.8) |
| Median | −4.1 |
| Minimum, Maximum | −59.5, 49.3 |
| P. Value | 0.1836 |
| Day 14 | |
| N | 18 |
| Mean (SD) | 73.8 (59.8) |
| Median | 65.5 |
| Minimum, Maximum | 2.0, 248.0 |
| Percent Change from Baseline | |
| N | 18 |
| Mean (SD) | −19.7 (30.3) |
| Median | −17.6 |
| Minimum, Maximum | −94.6, 42.4 |
| P Value | 0.0133 |
| Day 21 | |
| N | 18 |
| Mean (SD) | 43.2 (28,1) |
| Median | 41.5 |
| Minimum, Maximum | 0.0, 90.0 |
| Percent Change from Baseline | |
| N | 18 |
| Mean (SD) | −45.0 (27.6) |
| Median | −43.0 |
| Minimum, Maximum | −100.0, 8.0 |
| P Value | <.0001 |

Note:

P values are from t-test against no change from baseline.

Pharmacokinetics Conclusions

Serum concentrations of imiquimod were low in subjects with EGWs treated with up to one packet of imiquimod 3.75% cream once daily for 21 days. Mean serum concentrations ranged from approximately 0.16 to 0.37 ng/mL on Day 21. Serum concentrations of two imiquimod metabolites (S-26704 and S-27700 combined) were measured, but the data were too sparse to assess (only 4 subjects had any concentrations above the LLOQ on Day 21). In the pharmacokinetic population, imiquimod mean peak ($C_{max}$) and total exposure ($AUC_{0-24}$) increased between Day 1 and Day 21. The accumulation ratios based on peak exposure, and overall systemic exposure, $R_{AUC}$, indicated an approximate 2-fold accumulation (2.260 and 2.169, respectively) at steady state. Imiquimod median $T_{max}$ was 12 hours on Days 1 and 21. The mean effective half-life for accumulation, $T_{1/2EFF}$, was 31.328 hours, and the observed mean elimination half-life, $T^{1/2}$, was 24.1±2.4 hours on Day 21. Analysis of trough concentrations over time indicated that steady-state conditions were achieved by Day 7, which was consistent with the time to steady state predicted from the observed mean elimination half-life (approximately 5 days) and the mean effective half-life for accumulation (approximately 6 to 7 days).

On Day 21, non-dose-normalized mean peak exposure, $C_{max}$ was 61% higher in female subjects than in male subjects and dose-normalized (adjustment for differences in dosage) mean $C_{max}$, was 35% higher in female subjects. Non-dose-normalized mean total systemic exposure, $AUC_{0-24}$, was 8% higher in female subjects than in male subjects while dose-normalized mean $AUC_{0-24}$ was 6% lower in female subjects on Day 21. Median $T_{max}$ occurred approximately twice as quickly in female subjects (6.5 hours) as in male subjects (12.0 hours). Due to the controlling influence of a single female subject and the disparity in the number of female and male subjects (4/11), female/male comparative results appeared somewhat skewed, but mean $C_{max}$ values were low for both female and male subjects (<1.0 ng/mL) Overall, peak exposure ($C_{max}$) appeared higher and reached more quickly in female subjects than in male subjects, and total systemic exposure ($AUC_{0-24}$) appeared comparable in female and male subjects.

Brief Summary of Adverse Events

A total of 14 treatment-emergent adverse events (TEAEs) were experienced by 10 of 18 subjects (55.6%) treated with imiquimod 3.75% cream in this study. Of the 14 TEAEs reported, 4 TEAEs experienced by 3 of 18 subjects (16.7%) were considered probably related or related to treatment—application site ulcer experienced by 2 subjects (11.1%) and application site irritation and application site pruritus experienced by the same subject (5.6%). Dosing was interrupted for 2 days for 1 subject (5.6%) due to an application site ulcer. All TEAEs were mild in intensity except moderate application site ulcer experienced by 2 subjects (11.1%) and moderate upper respiratory tract infection experienced by 1 subject (5.6%). No deaths, serious adverse events (SAEs), or discontinuations due to AEs were reported.

Analysis of Adverse Events

Approximately half the subjects, 10 of 18 (55.6%), treated with up to 1 packet imiquimod 3.75% cream once daily for 21 days in this study experienced TEAEs. The most commonly reported TEAEs were headache in 4 of 18 subjects (22.2%) and application site ulcer in 2 of 18 subjects (11.1%), All other TEAEs were experienced by 1 of 18 subjects (5.6%) and included vomiting, application site irritation, application site pruritus, fatigue, upper respiratory tract infection, excoriation, and phlebitis. All of these TEAEs were mild in intensity except moderate application site ulcer experienced by 2 subjects (11.1%) (one male and one female) and moderate upper respiratory tract infection experienced by 1 female subject (5.6%).

Only a small number of subjects—3 of 18 (16.7%)—experienced TEAEs considered probably related or related to treatment. The most frequently occurring treatment-related TEAE was application site ulcer, which was experienced by 2 subjects (11.1%). Application site irritation (burning) and application site pruritus were experienced by the same male subject (5.6%).

Analysis of Local Skin Reactions (LSRs)

LSRs, including erythema, edema, weeping/exudate, flaking/scaling/dryness, and scabbing/crusting were evaluated for severity (mild, moderate, or severe) on Days 1 (pre-application), 7, 14, and 21 and at 48 and 72 hours post last application. The occurrence of erosion and ulceration were also reported. The majority of LSRs were mild or moderate and were first noticeable on Day 14. Severe LSRs were experienced by 22.2% of the subjects (4 of 18): three experienced severe erythema, two experienced severe weeping/exudate, and one experienced severe scabbing/crusting (the same subject had experienced severe weeping/exudate). The only LSR reported as an adverse event was moderate ulceration that required medical intervention and was considered related or probably related to treatment in 11.1% of the subjects (2 of 18).

Safety Conclusions imiquimod 3.75% cream applied once daily for up to 21 days was well tolerated. Treatment-emergent adverse events (TEAEs) were experienced by 10 of 18 subjects (55.6%). TEAEs considered probably related or related to treatment included 4 TEAEs reported by 3 of 18 subjects (16.7%): application site ulcer experienced by 2 subjects (11.1%) and application site irritation and application site pruritus experienced by the same subject (5.6%).

Dosing was interrupted for 2 days for 1 subject (5.6%) due to an application site ulcer. All TEAEs were mild in intensity except for moderate application site ulcer experienced by 2 subjects (11.1%) and moderate upper respiratory tract infection experienced by 1 subject (5.6%). No deaths, SAEs, or discontinuations due to AEs were reported.

Expected local skin reactions were generally mild to moderate, observed primarily on or after Day 14, and rarely interrupted treatment. Erythema was the most frequently reported local skin reaction (13 of 18 subjects, 72.2%), followed by edema (9 subjects, 50%); weeping/exudate and scabbing/crusting (7 subjects each, 38.9%); flaking/scaling/dryness (6 subjects, 33.3%), erosion (6 subjects, 33.3%), and ulceration (5 subjects, 27.8%). Overall, 7 of 18 subjects (38.9%) experienced all or most of the local skin reactions, with 4 of these subjects (22.2%) experiencing severe reactions. LSRs generally resolved or lessened in severity during the 72 hours after the last application of the study drug was applied. Clinical laboratory values were generally within reference ranges for all parameters in this study. Vital signs and physical examinations did not reveal any significant safety concerns.

Discussion and Overall Conclusions

In this open-label, single-center, non-randomized study, pharmacokinetic (PK) and safety were evaluated in 18 subjects with at least 8 external genital warts (EGWs) in the genital/perianal area or a total wart area of ≥100 $mm^2$ who applied imiquimod 3.75% cream to the affected areas once daily for up to 21 days.

Serum concentrations of imiquimod (R-837) were low in subjects treated with daily applications of imiquimod 3.75% cream (mean of 0.16 to 0.37 ng/mL on Day 21). The maximum serum concentrations were 1.632 ng/mL for female subjects (Day 21) and 0.659 ng/mL for male subjects (Day 22). Serum concentrations of two imiquimod metabolites (S-26704 and S-27700 combined) were measured, but the non-zero data were too sparse to assess.

Peak exposure ($C_{max}$) and total exposure ($AUC_{0-24}$) for imiquimod (R-837) were higher on Day 21 than Day 1 when analyzing all subjects in the pharmacokinetic population except 3 subjects who missed an application during the last week of dosing. The mean accumulation ratios, $R_{Cmax}$ and $R_{AUC}$, were 2.260 and 2.169, respectively. On Day 21, the serum concentration profile showed minor fluctuations during the 24 hours after application—mean $C_{max}$ (0.488±0.368 ng/mL) was approximately 3 times the level of mean $C_{min}$ (0.158±0.121 ng/mL). Imiquimod (R-837) median $T_{max}$ was 12 hours on Days 1 and 21. The mean effective half-life for accumulation was 31.33 hours, and the observed mean elimination half-life was 24.14 hours on Day 21. Analysis of trough concentrations over time indicated that steady-state conditions were achieved by Day 7, which was consistent with the time to steady state predicted from the mean observed elimination half-life (approximately 5 days) and the mean effective half-life for accumulation (approximately 6 or 7 days).

In a comparison of female and male subjects who applied imiquimod 3.75% cream to EGWs, analyses of the female and male groups were limited by wide variability in the data, small overall numbers, a large disparity in group sizes (female/male comparison of 4 versus 11 subjects), and the controlling influence of a single female subject. Dose normalization was employed to adjust for differences in dosage. When not dose normalized, mean $C_{max}$ was 61% higher in female subjects than in male subjects, and mean $AUC_{0-24}$ was 8% higher in female subjects than in male subjects. When dose normalized, mean Cm. was 35% higher in female subjects than in male subjects while mean $AUC_{0-24}$ was 6% lower in female subjects than in male subjects. Overall, mean $C_{max}$ and $AUC_{0-24}$ were low and generally comparable on Day 21 for female subjects, male subjects, and the entire pharmacokinetic population—mean $C_{max}$: 0.583, 0.431, and 0.488 ng/mL, respectively, and mean $AUC_{0-24}$: 6.428, 6.858, and 6.795 ng/hr/mL, respectively. Median $T_{max}$ occurred approximately twice as quickly in female subjects (6.50 hours) as in male subjects (12.00 hours).

Safety evaluations demonstrated that imiquimod 3.75% cream was well tolerated when applied once daily for up to 21 days. Treatment-emergent adverse events (TEAEs) were experienced by 10 of 18 subjects (55.6%), and all but 3 of the TEAEs were mild moderate application site ulcer experienced by 2 subjects (11.1%) and moderate upper respiratory tract infection experienced by 1 subject (5.6%). Only 3 subjects (16.7%) experienced TEAEs that were considered probably related or related to treatment application site ulcer experienced by 2 subjects (11.1%) and application site irritation and application site pruritus experienced by the same subject (5.6%). Dosing was interrupted for 2 days for 1 subject (5.6%) due to an application site ulcer. The TEAEs observed in this study were consistent with TEAEs previously observed with the currently marketed 5% imiquimod cream product (Aldara®).[7] No deaths, SAEs, or discontinuations due to AEs were reported.

Expected local skin reactions were generally mild to moderate and were observed primarily on or after Day 14. Erythema was the most frequently reported local skin reaction (13 of 18 subjects, 72.2%), followed by edema (9 subjects, 50%); weeping/exudate and scabbing/crusting (7 subjects each, 38.9%); flaking/scaling/dryness (6 subjects, 33.3%), erosion (6 subjects, 33.3%), and ulceration (5 subjects, 27.8%). Overall, 7 of 18 subjects (38.9%) experienced all or most of the local skin reactions, with 4 of these subjects (22.2%) experiencing severe reactions. Once observed during treatment, an LSR appeared to either last 1 week, or if persisting, often continued throughout the study at a lower severity. LSRs generally resolved or lessened in severity during the 72 hours after the last application of the study drug was applied. No severe LSRs were observed at the end of the, study (the visit at 72 hours after the last application of the study cream).

Clinical laboratory values, vital signs, and physical examinations did not reveal any significant safety concerns.

In conclusion, the amount of imiquimod (R-837) absorbed into systemic circulation after topical application of imiquimod 3.75% cream to external genital warts once daily for up to 21 days was low; $C_{max}$ (peak exposure) and $AUC_{0-24}$ (total systemic exposure) increased approximately 2-fold between Day 1 and Day 21. $T^{1/2}$, was 12.5±8.2 hours on Day 1 (sampling through 24 hours) and 24.1±12.4 hours on Day 21 (sampling through 72 hours). Steady state was achieved by Day 7. Peak exposure ($C_{max}$) appeared higher and reached more quickly ($C_{max}$) in female subjects than in male subjects, and total systemic exposure ($AUC_{0-24}$) appeared comparable in female and male subjects. The degree of difference in results between female and male subjects did not indicate any reason for safety concerns.

Imiquimod 3.75% cream applied to external genital warts once daily for up to 21 days was well-tolerated. Treatment-related adverse events only occurred in a small percentage of subjects (16.7%), and with the exception of three of moderate intensity, all treatment-emergent adverse events were mild. The majority of local skin reactions were generally mild to moderate in intensity and were observed primarily on or after Day 14. Severe reactions were only observed for erythema in 3 subjects, weeping/exudate in 2 subjects, and scabbing/crusting in 1 subject.

Example 27

Study of in vitro Effects of Imiquimod on QT, QRS, APD, Tp-e and Arrhythmogenesis in Rabbit Left Ventricular Wedge Preparation 1. Drug and Concentrations Tested Imiquimod (n=6, MW 240): 0.5 nM, 5 nM, 50 nM and 150 nM. Cisapride as a positive control compound (n=4, MW 483.96): 5 nM, 50 nM, 150 nM and 500 nM.

2. Objectives

The purpose of this project was to examine the effects of imiquimod on QRS duration, QT interval, $T_{p-e}$, interval, an index of transmural dispersion of repolarization and proarrhythmias including early after depolarization (EAD) in the isolated rabbit left ventricular wedge preparation. In addition, the relative TdP risk of imiquimod was estimated using a score table. More importantly, the effects of imiquimod were compared with those of a positive control cisapride, which has been reported to induce QT prolongation and Torsades de Pointes (TdP).

3. Materials and Methods 3.1 Arterially Perfused Rabbit Left Ventricular Wedge Preparations New Zealand White rabbits, either sex weighing 2.3-2.8 kg were anticoagulated with heparin and anesthetized with ketamine/xylazine (40-50 mg/0.5-1.0 mg, per kg, i.v.). The chest was opened via a left thoracotomy, and the heart was excised and placed in a cardioplegic solution consisting of cold (4° C.) normal Tyrode's solution. Transmural wedges with dimensions of approximately 1.5 cm wide and 2-3 cm long were dissected from the left ventricle as described before (Liu et al, Heart Rhythm 2006; 3:948-956). The tissue was cannulated via a small branch of the left anterior descending artery and perfused with cardioplegic solution. The preparation was then placed in a small tissue bath and arterially perfused with Tyrode's solution containing 4 mM K+ buffered with 95% 02 and 5% CO2 (Temperature: 35.7±0.1° C., perfusion pressure: 40-50 mmHg). The ventricular wedge was allowed to equilibrate in the tissue bath until electrically stable for one hour. The preparations were stimulated at basic cycle lengths (BCL) of 1000 and 2000 ms using bipolar silver electrodes insulated except at the tips and applied to the endocardial surface.

3.2 Electrophysiologic Recordings from Rabbit Ventricular Wedge Preparations

A transmural ECG signal was recorded via a HP ECG amplifier (model 8811A) using extracellular silver/silver chloride electrodes placed in the Tyrode's solution, bathing the preparation 1.0 to 1.5 cm from the epicardial and endocardial surfaces, along the same vector as the transmembrane recordings (Epi: "+" pole). The QT interval was defined as the time from the onset of the QRS to the point at which the final downslope of the T wave crosses the isoelectric line. Transmembrane action potential from the endocardium (Endo) was recorded for identification of EADs only when QT prolongation >30% via a customer-made amplifier. Transmural dispersion of repolarization (TDR) was defined as the interval between the end and the peak of T wave ($T_{p-e}$).

All measured biological signals including ECG and transmembrane action potentials were sampled via a D/A converter (CED 1401, England) and stored in electronic media (CD) and external hard drives. The raw signals of ECG and transmembrane action potentials were analysed using Spike 2 software (CED, England).

3.3 Formulation

Imiquimod and cisapride in dimethyl sulfoxide (DMSO) were prepared on each experimental day. The maximal concentration of DMSO was ≤0.1%.

3.4 Study Designs (1) Imiquimod was tested at concentrations of 0.5 nM, 5 nM, 50 nM and 150 nM in 6 wedge preparations. The positive control cisapride was tested in 5 nM, 50 nM, 150 nM and 500 nM in 4 wedge preparations.

(2) The preparation was exposed to imiquimod and cisapride at each concentration for ≥30 minutes.

(3) Two BCLs of 1000 and 2000 ms were used.

(4) Action potentials from Endo in the rabbit wedge preparation were recorded for identification of EAD-dependent phenomena only when QT prolongation was greater than 30%.

(5) The QT and QRS intervals and the interval of $T_{p-e}$, an index of transmural dispersion of repolarization (TDR), were measured. The ratio of $T_{p-e}$ to QT was calculated.

(6) Arrhythmic phenomena, including spontaneous R-on-T ectopic beats and TdP, were recorded if they occurred.

3.5 To Estimate Relative TdP Risk

The relative TdP risk of each compound was estimated according in which the $T_{p-e}$/QT ratio and LAD-dependent phenomena were emphasized.

3.6 Data Analysis

Results were presented as mean±SEM. Statistical analysis was performed using the Student's t-test. A $p<0.05$ is considered as statistically significant when compared the values at control perfusion.

4. Results 4.1 Effect on QRS Duration

Imiquimod had no significant effect on QRS duration in the concentration ranges tested.

On the other hand, the positive control cisapride produced a small but statistically significant increase in QRS duration at concentration of 0.5 uM.

4.2 Effects on QT

Imiquimod exhibited a trend to produce a small QT increase (4%) at concentrations of 150 nM only at a BCL of 2000 ms. However, previous validation data (data from Main Line Health Heart Center) using DMSO as a vehicle control group revealed comparable QT prolongation. There was no statistical significance in QT between imiquimod and vehicle groups.

On the other hand, the positive control drug cisapride exhibited marked concentration-dependent QT prolongation.

4.3 Effects on $T_{p-e}$, Interval

Imiquimod had no significant effect on $T_{p-e}$ Interval in the concentration range tested (n=6).

On the other hand, the positive control drug cisapride exhibited marked concentration-dependent $T_{p-e}$ prolongation.

4.4 Proarrhythmias

Imiquimod did not cause any proarrhythmic events in any preparation at any concentration. The estimated TdP scores are either zero or negative.

Cisapride caused an equivocal EAD in 1 of 4 preparations at concentration of 0.5 uM. Its maximal TdP score is 6.5±0.5 at concentration of 0.5 uM.

5. Comments and Conclusions

Imiquimod does not have a significant effect on the QT interval, $T_{p-e}$ (an index of transmural dispersion of repolarization) and QRS, indicating that imiquimod possesses little risk of TdP (TdP score<0) and other proarrhythmias like ventricular tachycardia in the concentration range tested.

The positive control Cisapride produced marked concentration-dependent QT and $T_{p-e}$ prolongation in the concentration range from 0.005 to 0.5 uM. The maximal TdP score in the rabbit left ventricular wedge preparation is 6.5. This indicates that the rabbit left ventricular wedge preparation has a sufficient sensitivity to detect even a weak QT prolonging liability.

Thus, this clinical case as summarized in Examples 24-26 and as illustrated in FIGS. 1-36, further demonstrates efficacy without treatment limiting local skin reactions or adverse events and further demonstrates that complete clearance is achieved with a 3.75% imiquimod formulation of Example 23 when applied to the treatment areas diagnosed with EGWs of a subject following a treatment regimen described in those Examples 24-26. In Example 23 herein above, formulations 126 and 182, wherein the fatty acid is isa, are the formulations that are used in Examples 24-26 and in FIGS. 1-36 discussed and described herein above. In addition, isa formulations 126 and 182 pass the PET tests when stored at about 40° C. for about 3 months.

The following are a draft of the U.S. Label and the Canadian Product Monograph referenced in Example 25 above.

Draft U.S. Label (referred to in Example 25)

Highlights of Prescribing Information

These highlights do not include all the information needed to use Zyclara™ safe effectively. See full prescribing information for Zyclara Cream.

ZYCLARA (imiquimod), Cream, 3.75%

For topical use only

Initial U.S. Approval:

Indications and Usage

Zyclara Cream is indicated for the treatment of external genital and perianal warts/condyloma acuminate in patients 12 years or older (11)

Dosage and Administration

Zyclara Cream is not for oral, opthamalic, intra-anal or intravaginal use. (2)

External Genital Warts: daily to the external genital/perianal warts until total clearance or up to 8 weeks (2.1)

Dosage Forms and Strengths

Zyclara (imiquimod Cream, 3.75% is supplied in single-use packets (28 per Dose Pack), each of which contains 250 mg or the cream, equivalent to 9.4 mg of imiquimod. (3)

Contraindictions

None (4)

Warnings and Precautions

Intense local inflammatory reactions can occur (e.g. skin weeping, erosion). Dosing interruption may be required (2, 5.1, 6)

Flu-like signs and symptoms way accompany or even precede, local skin reactions, and may include fatigue, fever, myalgia, malaise and nausea. Dosing interruption may be required (2, 5.2, 6)

Avoid exposure to sunlight and sunlamps to the affected areas (5.3).

Treatment of urethral, intra-vaginal, cervical, rectal or intra-anal viral disease is not recommended. (5.)

Adverse Reactions

Table 1: Local Skin Reactions in the Treatment Area Assessed by the Investigator; Table 1: Local Skin Reactions in the Treatment Area Assessed by the Investigator Table 2: Treatment Related Adverse Reactions Occurring in >1% of Zyclara-Treated Subjects and at a Greater Frequency that with Placebo in either gender. (6)

To report SUSPECTED ADVERSE REACTIONS, contact Graceway Pharmaceuticals, LLC at 1-800-328-0255 or FDA at 1-800-FDA-1088 or www.fda.gov/medwatch.

See 17 for PATIENT COUNSELING INFORMATION and FDA-approved patient labeling.

Full Prescribing Information: Contents*

*Sections or subsections omitted from the Full Prescribing information are not listed.

1. INDICATIONS AND USAGE
1.1 Unevaluated Populations
2. DOSAGE AND ADMINISTRATION
3. DOSAGE FORMS AND STRENGTHS
4. CONTRAINDICTIONS
5. WARNINGS AND PRECAUTIONS
5.1 Local Skin Reactions
5.2 Systemic Reactions
5.3 Ultraviolet Light Exposure
5.4 Unevaluated Uses: External Genital Warts
6. ADVERSE REACTIONS
6.1 Clinical Trials Experience
6.2 Dermal Safety Trials Experience
6.3 Postmarketing Experience
7. USE IN SPECIFIC POPULATIONS
8.1 Pregnancy
8.3 Nursing Mothers
8.4 Pediatric Use
8.5 Geriatric Use
Overdosage
Description
Clinical Pharmacology
12.1 Mechanism of Action
12.2 Pharmacodynamics
12.3 Pharmacokinetics
Nonclinical Toxicology
13.1 Carcinogenesis, Mutagenesis, Impairment of Fertility
8. CLINICAL STUDIES
How Supplied/storage and Handling
Patient Counseling Information
17.1 Instructions for Administration
17.2 Local Skin Reactions
17.3 Systemic Reactions
17.4 Recommended Administration
17.7 FDA—Approved Patient Labeling Full Prescribing Information

1 INDICATIONS AND USAGE

Zyclara Cream is indicated for the treatment of external genital and perianal warts/condyloma acuminata, whether present at the start of therapy or emerging during therapy, in patients 12 years or older.

1.1 Unevaluated Populations

The safety and efficacy of Zyclara Cream in immunosuppressed patients have not been established.

Zyclara Cream should be used with caution in patients with pre-existing autoimmune conditions.

2 Dosage and Administration

Zyclara Cream is not for oral, ophthalmic, infra-anal, or intravaginal use. Zyclara Cream should be applied once-a-day to the external genital/perianal warts. Zyclara Cream should be used for up to 8 weeks. Zyclara Cream should be applied prior to normal sleeping hours and left on the skin for approximately 8 hours, after which time the cream should be removed by washing the area with mild soap and water. The prescriber should demonstrate the proper application technique to maximize the benefit of Zyclara Cream therapy.

It is recommended that patients wash their hands before and after applying Zyclara Cream.

A thin layer of Zyclara Cream should be applied to the areas of existing and emerging warts and rubbed in until the cream is no longer visible. The application site should not be occluded. Following the treatment period the cream should be removed by washing the treated area with mild soap and water.

Local skin reactions at the treatment site are common. [see Adverse Reactions (6.2)] A rest period of several days may be taken if required by the patient's discomfort or severity of the local skin reaction. Treatment may resume once the reaction subsides. Non-occlusive dressings such as cotton gauze or cotton underwear may be used in the management of skin reactions.

Zyclara Cream is packaged in single-use packets with 28 packets supplied per box, which contain sufficient cream to cover the wart areas; use of excessive amounts of cream should be avoided. Patients should be prescribed no more than 2 Dose Packs (56 packets) for the treatment course. Unused packets should be discarded. Partially-used packets should be discarded and not reused.

3 Dosage Forms and Strengths

Zyclara (imiquimod) Cream, 3.75%, is supplied in single-use packets each of which contains 250 mg of the cream, equivalent to 9.4 mg of imiquimod. Zyclara Cream is supplied in a Dose Pack of 28 packets each.

4 Contraindications

None.

5 Warnings and Precautions 5.1 Local Skin. Reactions

Intense local skin reactions including skin weeping or erosion can occur after a few applications of Zyclara Cream and may require an interruption of dosing. [see Dosage and Administration (2) and Adverse Reactions (6)]. Zyclara Cream has the potential to exacerbate inflammatory conditions of the skin, including chronic graft versus host disease.

Administration of Zyclara Cream is not recommended until the skin is healed from any previous drug or surgical treatment.

5.2 Systemic Reactions

Flu-like signs and symptoms may accompany, or even precede, local skin reactions and may include fatigue, fever, myalgia, malaise and nausea. An interruption of dosing and an assessment of the patient should be considered. [see Adverse Reactions (6)]

5.3 Ultraviolet Light Exposure

In an animal photo-carcinogenicity study, imiquimod cream shortened the time to skin tumor formation [see Nonclinical Toxicology (13.1)]. The enhancement of ultraviolet carcinogenicity is not necessarily dependent on phototoxic mechanisms. Therefore, patients should minimize or avoid natural or artificial sunlight exposure to the affected areas.

5.4 Unevaluated Uses

Zyclara Cream has not been evaluated for the treatment of urethral, intra-vaginal, cervical, rectal, or intra-anal human papilloma viral disease.

6 Adverse Reactions

Clinical trials are conducted under widely varying conditions. Adverse reaction rates observed in the clinical trials of a drug cannot be directly compared to rates in the clinical trials of another drug and may not reflect the rates observed in practice.

6.1 Clinical Trials Experience

In two double-blind, placebo-controlled studies for genital warts, 602 subjects applied up to one packet of Zyclara Cream or placebo daily for up to 8 weeks. The most frequently reported adverse reactions were local skin and application site reactions.

Overall, fewer than 1% (3/400) of the subjects treated with Zyclara cream discontinued due to local skin/application site reactions. The incidence and severity of local skin reaction during controlled clinical studies are shown in Table 1 below.

TABLE 1

Local Skin Reactions in the Treatment Area Assessed by the Investigator

| | Zyclara Cream | | | | Placebo | | | |
|---|---|---|---|---|---|---|---|---|
| | Females n = 217 | | Males n = 183 | | Females n = 106 | | Males n = All | |
| | All Grades* | Severe | All Grades* | Severe | All Grades* | Severe | All Grades* | Severe |
| Erythema | 74% | 10% | 78% | 10% | 23% | 0% | 37% | 1% |
| Edema (induration) | 41% | 2% | 48% | 2% | 8% | 0% | 9% | 0% |
| Weeping/Exudate | 35% | 1% | 39% | 3% | 5% | 0% | 0% | 0% |
| Flaking/Scaling/ Dryness | 26% | 0% | 39% | 0% | 11% | 0% | 11% | 0% |
| Scabbing/Crusting | 18% | <1% | 34% | 1% | 6% | 0% | 2% | 0% |
| Erosion/Ulceration | 36% | 13% | 42% | 10% | 7% | 1% | 2% | 0% |

*Mild, Moderate, or Severe

Local skin reactions were recorded as adverse events if they extended beyond the treatment area, if they required any medical intervention, or they resulted in patient discontinuation from the study.

Selected treatment related adverse reactions are listed below.

TABLE 2

Treatment Related Adverse Reactions Occurring in >1% of Zyclara-Treated Subjects and at a Greater Frequency than with Placebo in either gender

| | Females | | Males | |
|---|---|---|---|---|
| Preferred Term | Zyclara Cream n = 217 | Placebo n = 106 | Zyclara Cream n = 183 | Placebo n = 96 |
| Application site pain | 7.8% | 0% | 5.5% | 1.0% |
| Application site irritation | 5.5% | 0.9% | 6.0% | 1.0% |
| Application site pruritus | 3.2% | 1.9% | 1.6% | 0% |
| Application site bleeding | 1.4% | 0.9% | 1.5% | 0% |
| Application site discharge | 1.4% | 0% | 0.5% | 0% |
| Application site erythema | 1.4% | 0% | 0% | 0% |
| Application site reaction | 0.9% | 0% | 1.1% | 0% |
| Application site rash | 0.9% | 0% | 1.1% | 0% |
| Scrotal pain | 0% | 0% | 1.6% | 0% |
| Application site excoriation | 0% | 0% | 1.1% | 0% |
| Secretion discharge | 0% | 0% | 1.1% | 0% |
| Scrotal erythema | 0% | 0% | 1.1% | 0% |
| Scrotal ulcer | 0% | 0% | 1.1% | 0% |
| Scrotal edema | 0% | 0% | 1.1% | 0% |
| Pruritus genital | 0% | 0% | 1.1% | 0% |
| Application site cellulitis | 0% | 0% | 1.1% | 0% |

Systemic adverse reactions considered treatment related in clinical trials involving Zyclara Cream included pain, pyrexia (fever), influenza, and myalgia.

Adverse reactions seen in clinical trials for external genital warts involving 5% imiquimod cream included: tinea cruris, application site soreness, hypopigmentation, sensitivity, stinging and tenderness.

Other systemic adverse reactions considered treatment related in clinical trials for external genital warts involving 5% imiquimod cream included: headache, influenza-like symptoms, fatigue, malaise, nausea, and diarrhea.

6.2 Dermal Safety Trials Experience

Provocative repeat insult patch test studies involving induction and challenge phases produced no evidence that imiquimod cream causes photoallergenicity or contact sensitization in healthy skin; however, cumulative irritancy testing revealed the potential for imiquimod cream to cause irritation, and application site reactions were reported in the clinical studies. [see Adverse Reactions (6)]

6.3 Postmarketing Experience

The following adverse reactions have been identified during post-approval use of Aldara (imiquimod) Cream, 5%©. Because these reactions are reported voluntarily from a population of uncertain size, it is not always possible to reliably estimate their frequency or establish a causal relationship to drug exposure.

Application Site Disorders: tingling at the application site.

Body as a Whole: angioedema.

Cardiovascular: capillary leak syndrome, cardiac failure, cardiomyopathy, pulmonary edema, arrhythmias (tachycardia, atrial fibrillation, palpitations), chest pain, ischemia, myocardial infarction, syncope.

Endocrine: thyroiditis.

Gastro-Intestinal System Disorders: abdominal pain.

Hematological: decreases in red cell, white cell and platelet counts (including idiopathic thrombocytopenic purpura), lymphoma.

Hepatic: abnormal liver function.

Infections and Infestations: herpes simplex.

Musculo-Skeletal System Disorders: arthralgia.

Neuropsychiatric: agitation, cerebrovascular accident, convulsions (including febrile convulsions), depression, insomnia, multiple sclerosis aggravation, paresis, suicide.

Respiratory: dyspnea.

Urinary System Disorders: proteinuria.

Skin and Appendages: exfoliative dermatitis, erythema multiforme, hyperpigmentation, hypertrophic scar.

Vascular: Henoch-Schonlein purpura syndrome.

8 Use in Specific Populations 8.1 Pregnancy

Pregnancy Category C:

There are no adequate and well-controlled studies in pregnant women. Zyclara Cream should be used during pregnancy only if the potential benefit justifies the potential risk to the fetus.

Note: The animal multiples of human exposure calculations were based on daily dose comparisons in this label. For the animal multiple of human exposure ratios presented in this label, the Maximum Recommended Human Dose (MRHD), was set at 1 packet (250 mg cream) per treatment of Zyclara Cream (imiquimod 3.75%, 9.375 mg imiquimod).

Systemic embryofetal development studies were conducted in rats and rabbits. Oral doses of 1, 5 and 20 mg/kg/day imiquimod were administered during the period of organogenesis (gestational days 6-15) to pregnant female rats. In the presence of maternal toxicity, fetal effects noted at 20 mg/kg/day (375×MRHD based on AUC comparisons) included increased resorptions, decreased fetal body weights, delays in skeletal ossification, bent limb bones, and two fetuses in one litter (2 of 1567 fetuses) demonstrated exencephaly, protruding tongues and low-set ears. No treatment related effects on embryofetal toxicity or teratogenicity were noted at 5 mg/kg/day (73×MRHD based on AUC comparisons)

Intravenous doses of 0.5, 1 and 2 mg/kg/day imiquimod were administered during the period of organogenesis (gestational days 6-18) to pregnant female rabbits. No treatment related effects on embryofetal toxicity or teratogenicity were noted at 2 mg/kg/day (2.1×MRHD based on BSA comparisons), the highest dose evaluated in this study, or 1 mg/kg/day (234×MRHD based on AUC comparisons).

A combined fertility and peri- and post-natal development study was conducted in rats. Oral doses of 1, 1.5, 3 and 6 mg/kg/day imiquimod were administered to male rats from 70 days prior to mating through the mating period and to female rats from 14 days prior to mating through parturition and lactation. No effects on growth, fertility, reproduction or post-natal development were noted at doses up to 6 mg/kg/day (50×MRHD based on AUC comparisons), the highest dose evaluated in this study. In the absence of maternal toxicity, bent limb bones were noted in the Fl fetuses at a dose of 6 mg/kg/day (50×MRHD based on AUC comparisons). This fetal effect was also noted in the oral rat embryofetal development study conducted with imiquimod. No treatment related effects on teratogenicity were noted at 3 mg/kg/day (24×MRHD based on AUC comparisons).

8.3 Nursing Mothers

It is not known whether imiquimod is excreted in human milk following use of Zyclara Cream. Because many drugs are excreted in human milk, caution should be exercised when Zyclara Cream is administered to nursing women.

8.4 Pediatric Use

Safety and efficacy in patients with external genital/perianal warts below the age of 12 years have not been established.

8.5 Geriatric Use

Of the 399 subjects treated with Zyclara Cream in the EGW clinical studies, 5 subjects (1%) were 65 years or older. Data were too sparse to evaluate treatment effects in this population. No other clinical experience has identified differences in responses between the elderly and younger subjects, but greater sensitivity of some older individuals cannot be ruled out.

10 Overdosage

Topical overdosing of Zyclara Cream could result in an increased incidence of severe local skin reactions and may increase the risk for systemic reactions.

The most clinically serious adverse event reported following multiple oral imiquimod doses of >200 mg (equivalent to imiquimod content of >21 packets of Zyclara) was hypotension, which resolved following oral or intravenous fluid administration.

11 Description

Zyclara Cream is a toll-like receptor agonist for topical administration. Each gram contains 37.5 mg of imiquimod in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Chemically, imiquimod is 1-(2-methylpropyl)-1H-imidazo [4,5-c] quinolin-4-amine. Imiquimod has a molecular formula of Cid-116N.; and a molecular weight of 240.3. Its structural formula is:

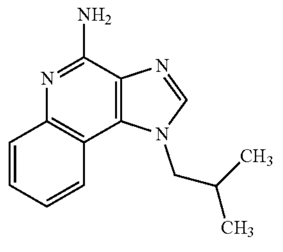 [SMILES: CC(C)Cn1cnc2c(N)nc3ccccc3c21]

12 Clinical Pharmacology 12.1 Mechanism of Action

The mechanism of action of Zyclara Cream is unknown.

12.2 Pharmacodynamics

Imiquimod has no direct antiviral activity in cell culture. A study in 22 subjects with genital/perianal warts comparing imiquimod cream 5% and vehicle shows that imiquimod induces mRNA encoding cytokines including interferon-α at the treatment site. In addition HPVL1 mRNA and HPV DNA are significantly decreased following treatment. However, the clinical relevance of these findings is unknown.

12.3 Pharmacokinetics

Systemic absorption of imiquimod (up to 9.4 mg [one packet]) across the affected skin of 18 subjects with EGW was observed with once daily dosing for 3 weeks. The mean peak serum drug concentration at Day 21 was 0.488 ng/mL.

13 Nonclinical Toxicology 13.1 Carcinogenesis, Mutagenesis, Impairment of Fertility In an oral (gavage) rat carcinogenicity study, imiquimod was administered to Wistar rats on a 2×/week (up to 6 mg/kg/day) or daily (3 mg/kg/day) dosing schedule for 24 months. No treatment related tumors were noted in the oral rat carcinogenicity study up to the highest doses tested in this study of 6 mg/kg administered 2×/week in female rats (50×MRHD based on AUC comparisons), 4 mg/kg administered 2×/week in male rats (40×MRHD) or 3 mg/kg administered 7×/week to male and female rats (25×MRHD).

In a dermal mouse carcinogenicity study, imiquimod cream (up to 5 mg/kg/application imiquimod or 0.3% imiquimod cream) was applied to the backs of mice 3×/week for 24 months. A statistically significant increase in the incidence of liver adenomas and carcinomas was noted in high dose male mice compared to control male mice (96×MIRED based on AUC comparisons). An increased number of skin papillomas was observed in vehicle cream control group animals at the treated site only.

In a 52-week dermal photo-carcinogenicity study, the median time to onset of skin tumor formation was decreased in hairless mice following chronic topical dosing (3×/week; 40 weeks of treatment followed by 12 weeks of observation) with concurrent exposure to UV radiation (5 days per week) with vehicle alone. No additional effect on tumor development beyond the vehicle effect was noted with the addition of the active ingredient, imiquimod, to the vehicle cream.

Imiquimod revealed no evidence of mutagenic or clastogenic potential based on the results of five in vitro genotoxicity tests (Ames assay, mouse lymphoma L5178Y assay, Chinese hamster ovary cell chromosome aberration assay, human lymphocyte chromosome aberration assay and SHE cell transformation assay) and three in vivo genotoxicity tests (rat and hamster bone marrow cytogenetics assay and a mouse dominant lethal test).

Daily oral administration of imiquimod to rats, throughout mating, gestation, parturition and lactation, demonstrated no effects on growth, fertility or reproduction, at doses up to 57×MRHD based on AUC comparisons.

Clinical Studies

In two double-blind, randomized, placebo-controlled clinical studies, 601 subjects with EGW were treated with 3.75% imiquimod cream, or a matching placebo cream. Studies enrolled subjects aged from 15 to 81 years. The baseline wart area ranged from 6 to 5579 $mm^2$ and the baseline wart count ranged from 2 to 48 warts. Most subjects had two or more treated anatomic areas at Baseline. Anatomic areas included: inguinal, perineal, and perianal areas (both genders); the glans penis, penis shaft, scrotum, and foreskin (in men); and the vulva (in women). Up to one packet of study cream was applied once daily to each wart identified at Baseline and any new wart that appeared during the treatment period. The study cream was applied to all warts prior to normal sleeping hours and left on for approximately 8 hours. Subjects continued applying the study cream for up to 8 weeks or until they achieved complete clearance of all (baseline and new) warts in all anatomic areas. Subjects not achieving complete wart clearance by the Week 8 visit (end of treatment, EOT), were evaluated for up to 8 weeks or until they achieved complete clearance during an additional 8 week no-treatment period. Subjects who achieved complete clearance of all warts at any time until the Week 16 visit entered a 12 week follow-up for recurrence period.

Efficacy was assessed by wart counts (those present at Baseline and new warts appearing during the study) at EOS (i.e., up to 16 weeks from Baseline).

Complete clearance required clearance of all warts in all anatomic areas. Partial clearance rate was defined as the proportion of subjects with at least a 75% reduction in the number of baseline warts at EOS. Percent reductions were measured relative to the numbers of warts at Baseline. Complete and partial clearance rates, and percent reductions in wart counts from baseline are shown in the table below (by overall rate and by gender).

TABLE 3

Efficacy Endpoints

| | Zyclara Cream 3.75% | Placebo Cream |
|---|---|---|
| Complete Clearance Rate | | |
| Overall | 28.3% (113/399) | 9.4% (19/202) |
| Females | 36.6% (79/216) | 14.2% (15/106) |
| Males | 18.6% (34/183) | 4.2% (4/96) |
| Partial Clearance Rate | | |
| Overall | 38.3% (153/399) | 11.9% (24/202) |
| Females | 47.7% (103/216) | 17.0% (18/106) |
| Males | 27.3% (50/183) | 6.3% (6/96) |
| Percent Reduction of EGW (Median) | | |
| Overall | 50.0% | 0.0 |
| Females | 70.7% | 0.0 |
| Males | 23.3% | 0.0 |

The numbers of subjects who remained clear of EGW at the end of 12 week follow-up for recurrence period are shown in Table 4 below:

TABLE 4

Sustained Complete Clearance

| | Zyclara Cream 3.75% | Placebo Cream |
|---|---|---|
| Cleared and entered Follow-up | 102 | 13 |
| Remained Clear | 71 | 12 |

16 How Supplied/storage And Handling

Zyclara (imiquimod) Cream, 3.75%, is supplied in single-use packets which contain 250 mg of the cream. Available as: Dose Pack of 28 packets NDC 29336-710-28. Store at 25° C. (77° F.); excursions permitted to 15° to 30° C. (59° to 86° F.) [See USP Controlled Room Temperature].

Avoid Freezing.

Keep out of reach of children.

17 Patient Counseling Information

See FDA-Approved Patient Labeling (17.7)

17.1 Instructions for Administration:

Zyclara Cream should be used as directed by a physician. [see Dosage and Administration (2)] Zyclara Cream is for external use only. Contact with the eyes, lips and nostrils should be avoided. [see Indications and Usage (1) and Dosage and Administration (2)].

The treatment area should not be bandaged or otherwise occluded. Partially-used packets should be discarded and not reused. The prescriber should demonstrate the proper application technique to maximize the benefit of Zyclara Cream therapy.

It is recommended that patients wash their hands before and after applying Zyclara Cream.

17.2 Local Skin Reactions:

Patients may experience local skin reactions during treatment with Zyclara Cream. Potential local skin reactions include erythema, edema, erosions/ulcerations, weeping/exudate, flaking/scaling/dryness, and scabbing/crusting. These reactions can range from mild to severe in intensity and may extend beyond the application site onto the surrounding skin. Patients may also experience application site reactions such as itching, irritation or pain. [see Adverse Reactions (6)]

Local skin reactions may be of such an intensity that patients may require rest periods from treatment. Treatment with Zyclara Cream can be resumed after the skin reaction has subsided, as determined by the physician. Treatment should not be extended beyond 8 weeks due to missed doses or rest periods. Patients should contact their physician promptly if they experience any sign or symptom at the application site that restricts or prohibits their daily activity or makes continued application of the cream difficult.

Because of local skin reactions, during treatment and until healed, the treatment area is likely to appear noticeably different from normal skin. Localized hypopigmentation and hyperpigmentation have been reported following use of imiquimod cream. These skin color changes may be permanent in some patients.

17.3 Systemic Reactions:

Patients may experience flu-like systemic signs and symptoms during treatment with Zyclara Cream. Systemic signs and symptoms may include fatigue, fever, myalgia, malaise, and nausea. [see Adverse Reactions (6)] An interruption of dosing and assessment of the patient should be considered.

17.4 Recommended Administration

Dosing is once daily before bedtime to the skin of the affected wart areas. Zyclara Cream treatment should continue until there is total clearance of the genital/perianal warts or for up to 8 weeks.

It is recommended that the treatment area be washed with mild soap and water approximately 8 hours following Zyclara Cream application.

It is common for patients to experience local skin reactions such as erythema, erosion, excoriation/flaking, and edema at the site of application or surrounding areas. Most skin reactions are mild to moderate.

Sexual (genital, anal, oral) contact should be avoided while Zyclara Cream is on the skin. Application of Zyclara Cream in the vagina is considered internal and should be avoided. Female patients should take special care if applying the cream at the opening of the vagina because local skin reactions on the delicate moist surfaces can result in pain or swelling, and may cause difficulty in passing urine.

Uncircumcised males treating warts under the foreskin should retract the foreskin and clean the area daily.

New warts may develop during therapy, as Zyclara Cream is not a cure.

The effect of Zyclara Cream on the transmission of genital/perianal warts is unknown. Zyclara Cream may weaken condoms and vaginal diaphragms, therefore concurrent use is not recommended.

Should severe local skin reaction occur, the cream should be removed by washing the treatment area with mild soap and water.

17.7 FDA-Approved Patient Labeling 17.8 Patient Information

Zyclara [imiquimod] Cream, 3.75%

(Imiquimod)

IMPORTANT: Not for Mouth, Eye, or Vaginal Use

Read the Patient Information that comes with Zyclara Cream before you start using it and each time you get a refill. There may be new information. This leaflet does not take the place of talking with your healthcare provider about your medical condition or treatment. If you do not understand the information, or have any questions about Zyclara Cream, talk with your healthcare provider or pharmacist.

What is Zyclara Cream?

Zyclara Cream is a skin use only (topical) medicine used to treat external genital and perianal warts in people 12 years and older.

Zyclara Cream does not work for everyone. Zyclara Cream may not completely cure your genital or perianal warts. New warts may develop during treatment with Zyclara Cream. It is not known if Zyclara Cream can stop you from spreading genital or perianal warts to other people. For your own health and the health of others, it is important to practice safer sex. Talk to your healthcare provider about safer sex practices.

Who should not use Zyclara Cream?

Zyclara Cream has not been studied in children under 12 years old for external genital and perianal warts.

Before using Zyclara Cream, tell your healthcare provider:

- about all your medical conditions, including if you
  - are pregnant or planning to become pregnant. It is not known if Zyclara Cream can harm your unborn baby.
  - are breastfeeding. It is not known if Zyclara Cream passes into your milk and if it can harm your baby.
- about all the medicines you take including prescription and non-prescription medicines, vitamins and herbal supplements. Especially tell your healthcare provider if you have had other treatments for genital or perianal warts. Zyclara Cream should not be used until your skin has healed from other treatments.

How should I use Zyclara Cream?

- Use Zyclara Cream exactly as prescribed by your healthcare provider. Zyclara Cream is for skin use only. Do not take by mouth and do not get Zyclara Cream in or near your eyes, lips or nostrils. Do not use Zyclara Cream unless your healthcare provider has taught you the right way to use it. Talk to your healthcare provider if you have any questions.
- Your healthcare provider will tell you where to apply Zyclara Cream and how often and for how long to apply it for your condition. Do not use Zyclara Cream longer than prescribed, Using too much Zyclara Cream, or using it too often, or for too long can increase your chances for having a severe skin reaction or other side effect. Talk to your healthcare provider if Zyclara Cream does not work for you.
- Zyclara Cream is applied once a day. Zyclara Cream is usually left on the skin for approximately 8 hours. Treatment should continue until the warts are completely gone or for up to 8 weeks.

Applying Zyclara Cream

Zyclara Cream should be applied just before your bedtime.

Wash the area to be treated with mild soap and water. Allow the area to dry.

Uncircumcised males treating warts under their penis foreskin must pull their foreskin back and clean before treatment and clean daily during the weeks of treatment.

Wash your hands

Open a new packet of Zyclara Cream just before use.

Apply a thin layer of Zyclara Cream only to the affected area or areas to be treated. Do not use more Zyclara cream than is needed to cover the treatment area. Do not use more than one packet for each application.

Rub the cream in all the way to the affected area or areas.

Do not get Zyclara Cream in or around your eyes or mouth.

Do not get Zyclara in the anus when applying to perianal warts.

Female patients treating genital warts must be careful when applying Zyclara Cream around the vaginal opening. Female patients should take special care if applying the cream at the opening of the vagina because local skin reactions on the delicate moist surfaces can cause pain or swelling, and may cause problems passing urine. Do not put Zyclara Cream in your vagina.

Do not cover the treated area with an airtight bandage. Cotton gauze dressings can be used. Cotton underwear can be worn after applying Zyclara Cream to the genital or perianal area.

Safely throw away the open packet of Zyclara Cream so that children and pets cannot get it. The open packet should be thrown away even if all the Zyclara Cream was not completely used.

After applying Zyclara Cream, wash your hands well.

Leave the cream on the affected area or areas for the time prescribed by your healthcare provider. Do not bathe or get the treated area wet before the right time has passed. Do not leave Zyclara Cream on your skin longer than prescribed.

After about 8 hours, wash the treated area or areas with mild soap and water. If you forget to apply Zyclara Cream, continue on your regular schedule and do not make up the missed dose(s).

If you get Zyclara Cream in your mouth or in your eyes rinse well with water right away.

What should I avoid while using Zyclara Cream?

Do not cover the treated site with bandages or other closed dressings. Cotton gauze dressings are okay to use, if needed. Cotton underwear can be worn after treating the genital or perianal area.

Do not get Zyclara Cream in or near the eyes, lips or nostrils,

Do not put Zyclara Cream in your vagina or anus.

Do not use sunlamps or tanning beds, and avoid sunlight to the treated area as much as possible during treatment with Zyclara Cream.

Do not have sexual contact including genital, anal, or oral sex when Zyclara Cream is on your genital or perianal skin. Zyclara Cream may weaken condoms and vaginal diaphragms. This means they may not work as well to prevent pregnancy. For your own health and the health of others, it is important to practice safer sex. Talk to your healthcare provider about safer sex practices.

What are the possible side effects of Zyclara Cream?Side effects with Zyclara Cream may include skin reactions at the treatment site such as:

redness swelling a sore, blister, or ulcer skin that becomes hard or thickened skin peeling scabbing and crusting itching burning changes in skin color that do not always go away During treatment and until the skin has healed, your skin in the treatment area is likely to appear noticeably different from normal skin. Side effects, such as redness, scabbing, itching and burning are common at the site where Zyclara Cream is applied, and sometimes the side effects go outside of the area where Zyclara Cream was applied. Swelling, small open sores and drainage may also be experienced with use of Zyclara Cream. You may also experience itching, irritation or pain. Patients should be aware that new warts may develop during treatment, as Zyclara Cream may not be a cure. Many people see reddening or swelling on or around the application site during the course of treatment. If you have questions regarding treatment or local skin reactions, please talk with your healthcare provider.

You have a higher chance for severe skin reactions if you use too much Zyclara Cream or use it the wrong way. Stop Zyclara Cream right away and call your healthcare provider if you get any skin reactions that affect your daily activities, or that do not go away, Sometimes, Zyclara Cream must be stopped for a while to allow your skin to heal, Talk to your healthcare provider if you have questions about your treatment or skin reactions.

Other side effects of Zyclara Cream include pain, fever, muscle aches, and may also include headache, back pain, joint aches, tiredness, flu-like symptoms, nausea, and diarrhea.

If the reactions seem excessive, if either skin breaks down or sores develop during the first week of treatment, if flu-like symptoms develop or if you begin to not feel well at anytime, stop applying Zyclara Cream and contact your healthcare provider.

These are not all the side effects of Zyclara Cream. For more information, ask your healthcare provider or pharmacist.

How do I store Zyclara Cream?

Store Zyclara Cream at 77° F. (25° C.). [59° to 86° F.; 15° to 30° C.] Do not freeze.

Safely throw away Zyclara Cream that is out of date or that you do not need.

Keep Zyclara Cream and all medicines out of the reach of children.

General information about Zyclara Cream

Medicines are sometimes prescribed for conditions that are not mentioned in patient information leaflets. Do not use Zyclara Cream for a condition for which it was not prescribed. Do not give Zyclara Cream to other people, even if they have the same symptoms you have.

This leaflet summarizes the most important information about Zyclara Cream. If you would like more information, talk with your healthcare provider. You can ask your pharmacist or healthcare provider for information about Zyclara Cream that is written for the healthcare provider. If you have other questions about Zyclara Cream, call 1-800-328-0255.

What are the ingredients in Zyclara Cream?

Active Ingredient: imiquimod

Inactive ingredients: isostearic acid, cetyl alcohol, stearyl alcohol, white petrolatum, polysorbate 60, sorbiran monostearate, glycerin, xanthan gum, purified water, benzyl alcohol, methylparaben, and propylparaben.

Manufactured by:

3M Health Care Limited, Loughborough LE11 IEP England

Distributed by:

Graceway Pharmaceuticals, LLC, Bristol, Tenn. 37620

Canadian Product Monograph (referred to in Example 25)

PRODUCT MONOGRAPH

$^{Pr}$TRADENAME$^{TM}$

(imiquimod) Cream, 3.75%

9.4 mg per 250 mg single-dose packet

Immune response modifier

GRACEWAY PHARMACEUTICALS
252 PALL MALL ST., SUITE 302
LONDON, ONTARIO
CANADA
N6A 5P6

DATE OF PREPARATION:
MARCH 24, 2010

SUBMISSION CONTROL NO.:

TABLE OF CONTENTS

PART I: HEALTH PROFESSIONAL INFORMATION ..... 3
SUMMARY PRODUCT INFORMATION ..... 3
INDICATIONS AND CLINICAL USE ..... 3
CONTRAINDICATIONS ..... 4
WARNINGS AND PRECAUTIONS ..... 4
ADVERSE REACTIONS ..... 6
DRUG INTERACTIONS ..... 8
DOSAGE AND ADMINISTRATION ..... 8
OVERDOSAGE ..... 10
ACTION AND CLINICAL PHARMACOLOGY ..... 10
STORAGE AND STABILITY ..... 11
DOSAGE FORMS, COMPOSITION AND PACKAGING ..... 11

PART II: SCIENTIFIC INFORMATION ..... 12
PHARMACEUTICAL INFORMATION ..... 12
CLINICAL TRIALS ..... 13
DETAILED PHARMACOLOGY ..... 15
TOXICOLOGY ..... 16
REFERENCES ..... 19

PART III: CONSUMER INFORMATION ..... 21

PrTRADENAME™

(imiquimod) Cream, 3.75%

PART I: HEALTH, PROFESSIONAL INFORMATION

SUMMARY PRODUCT INFORMATION

| ROUTE OF ADMINISTRATION | DOSAGE FORM / STRENGTH | CLINICALLY RELEVANT NONMEDICINAL INGREDIENTS |
|---|---|---|
| TOPICAL | CREAM / 9.4 MG IMIQUIMOD PER 250 MG SINGLE-DOSE PACKET (3.75 % W/W) | *FOR A COMPLETE LISTING SEE DOSAGE FORMS, COMPOSITION AND PACKAGING SECTION.* |

INDICATIONS AND CLINICAL USE

TRADENAME cream is indicated for the treatment of external genital and perianal warts/condyloma acuminata, whether present at the start of therapy or emerging during therapy, in patients 12 years or older.

Geriatrics (>65 Years of Age)

Data from EGW clinical trials was too sparse to evaluate treatment effects in this population (see WARNINGS AND PRECAUTIONS, Geriatrics).

Pediatrics

Safety and efficacy in patients below the age of 12 years have not been established (See WARNINGS AND PRECAUTIONS, Pediatrics).

Immunosuppressed

The safety and efficacy of TRADENAME cream in immunosuppressed patients have not been established (See WARNINGS AND PRECAUTIONS, Immune)

CONTRAINDICATIONS

TRADENAME cream is contraindicated in individuals with a history of sensitivity reactions to imiquimod or to any of the components in the formulation. It should be discontinued if hypersensitivity to any of its ingredients is noted (See WARNINGS AND PRECAUTIONS, Sensitivity).

WARNINGS AND PRECAUTIONS

General

TRADENAME Cream has not been evaluated for the treatment of urethral, infra-vaginal, cervical, rectal, or intra-anal human papilloma viral disease.

Systemic Reactions

Flu-like signs and symptoms may accompany, or even precede, local skin reactions and may include fatigue, nausea, fever, myalgias, arthralgias, and chills. An interruption of dosing or dose adjustment and an assessment of the patient should be considered (See ADVERSE REACTIONS).

Carcinogenesis and Mutagenesis

In a hairless mouse photocarcinogenicity study with solar ultraviolet light irradiation, imiquimod cream enhanced UVR-induced skin tumour development, but not beyond that of the vehicle cream. Vehicle cream alone enhanced ultraviolet induced skin tumour development (See TOXICOLOGY, Carcinogenicity). It is recommended that patients minimize or avoid natural or artificial sunlight exposure to the treatment area(s) during treatment with TRADENAME.

Immune

The safety and efficacy of TRADENAME cream in immunosuppressed patients have not been established.

TRADENAME topical cream should be used with caution in patients with preexisting autoimmune conditions (including thyroiditis, multiple sclerosis, spondyloarthropathy, psoriasis, ulcerative colitis) (See ADVERSE REACTIONS, Post-Market Adverse Drug Reactions).

Sensitivity

Hypersensitivity reactions (urticaria) and erythema multiforme have been reported in patients receiving imiquimod cream, however causality has not been established. TRADENAME cream should be discontinued immediately if these events occur.

Skin

Local skin reactions such as erythema, scabbing/crusting, flaking/scaling/dryness, and edema are common.

Intense local skin reactions including erythema, scabbing/crusting and erosion/ulceration can occur after a few applications of TRADENAME cream and may require an interruption of dosing (See ADVERSE REACTIONS and DOSAGE AND ADMINISTRATION)

TRADENAME cream has the potential to exacerbate inflammatory conditions of the skin, including chronic graft versus host disease.

Administration of TRADENAME cream is not recommended until the skin is healed from any previous drug or surgical treatment.

Should a severe local skin reaction occur, the cream should be removed by washing the treatment area with mild soap and water and drying the area thoroughly. Treatment with TRADENAME cream can be resumed after consultation with the treating physician, and once the skin reaction has subsided.

Special Populations

Pregnant Women: Imiquimod was not teratogenic in rat or rabbit teratology studies. In rats at a high maternally toxic dose (28 times human dose on a mg/$m^2$ basis), reduced pup weights and delayed ossification were observed. However, there are no adequate and well-controlled studies in pregnant women. Because animal reproduction studies are not always predictive of human response, this drug should be used during pregnancy only if the potential benefit justifies the potential risk to the fetus.

Nursing Women: It is not known whether topically applied imiquimod is excreted in human milk. Because many drugs are excreted in human milk, caution should be exercised when TRADENAME cream is administered to nursing women.

Pediatrics (< 18 years of age):
Safety and efficacy in patients with external genital/perianal warts below the age of 12 years have not been established.

Geriatrics (>65 years of age):
Of the 399 subjects treated with TRADENAME Cream in the EGW clinical studies, 5 subjects (1%) were 65 years or older. Data were too sparse to evaluate treatment effects in this population. No other clinical experience has identified differences in responses between the elderly and younger subjects, but greater sensitivity of some older individuals cannot be ruled out.

ADVERSE REACTIONS

Adverse Drug Reaction Overview

Clinical Trial Adverse Drug Reactions

In two double-blind, placebo-controlled studies for genital warts, 602 subjects applied up to one packet of TRADENAME Cream or placebo daily for up-to 8 weeks. The most frequently reported adverse reactions were local skin and application site reactions.

Overall, fewer than 1% (3/400) of the subjects treated with TRADENAME cream discontinued due to local skin/application site reactions. The incidence and severity of local skin reaction during controlled clinical studies are shown in Table 1.

Table 1: Local Skin Reactions in the Treatment Area Assessed by the Investigator

| | TRADENAME CREAM | | | | PLACEBO | | | |
|---|---|---|---|---|---|---|---|---|
| | FEMALES N=217 | | MALES N=183 | | FEMALES N=106 | | MALES N=96 | |
| | ALL GRADES * | SEVERE | ALL GRADES * | SEVERE | ALL GRADES * | SEVERE | ALL GRADES * | SEVERE |
| ERYTHEMA | 74% | 10% | 78% | 10% | 23% | 0% | 37% | 1% |
| EDEMA (INDURATION) | 41% | 2% | 48% | 2% | 8% | 0% | 9% | 0% |
| WEEPING/EXUDATE | 35% | 1% | 39% | 3% | 5% | 0% | 0% | 0% |
| FLAKING/ SCALING/DRYNESS | 26% | 0% | 39% | 0% | 11% | 0% | 11% | 0% |
| SCABBING/ CRUSTING | 18% | <1% | 34% | 1% | 6% | 0% | 2% | 0% |
| EROSION/ ULCERATION | 36% | 13% | 42% | 10% | 7% | 1% | 2% | 0% |

* Mild, Moderate, or Severe

Local skin reactions were recorded as adverse events if they extended beyond the treatment area, if they required any medical intervention, or they resulted in patient discontinuation from the study.

Selected treatment related adverse reactions are listed below.

Table 2: Treatment Related Adverse Reactions Occurring in >1% of TRADENAME-Treated Subjects and at a Greater Frequency than with Placebo in either gender.

| PREFERRED TERM | FEMALES TRADENAME CREAM N=217 | FEMALES PLACEBO N=106 | MALES TRADENAME CREAM N=183 | MALES PLACEBO N=96 |
|---|---|---|---|---|
| APPLICATION SITE PAIN | 7.8% | 0% | 5.5% | 1.0% |
| APPLICATION SITE IRRITATION | 5.5% | 0.9% | 6.0% | 1.0% |
| APPLICATION SITE PRURITUS | 3.2% | 1.9% | 1.6% | 0% |
| APPLICATION SITE BLEEDING | 1.4% | 0.9% | 1.5% | 0% |
| APPLICATION SITE DISCHARGE | 1.4% | 0% | 0.5% | 0% |
| APPLICATION SITE ERYTHEMA | 1.4% | 0% | 0.5% | 0% |
| APPLICATION SITE REACTION | 0.9% | 0% | 1.1% | 0% |
| APPLICATION SITE RASH | 0.9% | 0% | 1.1% | 0% |
| SCROTAL PAIN | 0% | 0% | 1.6% | 0% |
| APPLICATION SITE EXCORIATION | 0% | 0% | 1.1% | 0% |
| SECRETION DISCHARGE | 0% | 0% | 1.1% | 0% |

| | | | | |
|---|---|---|---|---|
| SCROTAL ERYTHEMA | 0% | 0% | 1.1% | 0% |
| SCROTAL ULCER | 0% | 0% | 1.1% | 0% |
| SCROTAL EDEMA | 0% | 0% | 1.1% | 0% |
| PRURITUS GENITAL | 0% | 0% | 1.1% | 0% |
| APPLICATION SITE CELLULITIS | 0% | 0% | 1.1% | 0% |

Systemic adverse reactions considered treatment related in clinical trials involving TRADENAME Cream included pain, pyrexia (fever), influenza, and myalgia.

Adverse reactions seen in clinical trials for external genital warts involving 5% imiquimod cream included: tinea cruris, application site soreness, hypopigmentation, sensitivity, stinging and tenderness.

Other systemic adverse reactions considered treatment related in clinical trials for external genital warts involving 5% imiquimod cream included: headache, influenza-like symptoms, fatigue, malaise, nausea, and diarrhea.

Dermal Safety Trial Experience

Provocative repeat insult patch test studies involving induction and challenge phases produced no evidence that imiquimod cream causes photoallergenicity or contact sensitization in healthy skin; however, cumulative irritancy testing revealed the potential for imiquimod cream to cause irritation, and application site reactions were reported in the clinical studies.

Post-Market Adverse Drug Reactions

Rare reports have been received of either the onset or exacerbation of autoimmune conditions (including thyroiditus, multiple sclerosis, spondyloarthropathy, psoriasis, ulcerative colitis) in association with imiquimod 5% cream therapy.

The following adverse reactions have beenidentified during post-approval use of Aldara (imiquimod) Cream, 5%. Because these reactions are reported voluntarily from a population of uncertain size; it is not always possible to reliably estimate their frequency or establish a causal relationship to drug exposure.

Application Site Disorders: tingling, at the application site.
Body as a Whole: angioedema.
Cardiovascular: capillary leak syndrome, cardiac failure, cardiomyopathy, pulmonary edema, arrhythmias (tachycardia, atrial fibrillation, palpitations), chest pain, ischemia, myocardial infarction, syncope.
Endocrine: thyroiditis.
Gastro-Intestinal System Disorders: abdominal pain.
Hematological: decreases in red cell, white cell and platelet counts (including idiopathic thrombocytopenic purpura), lymphoma.
Hepatic: abnormal liver function.
Infections and Investations: herpes simplex.
Musculo-Skeletal System Disorders: arthralgia.
Neuropsychiatric: agitation, cerebrovascular accident, convulsions (including febrile convulsions), depression, insomnia, multiple sclerosis aggravation, paresis, suicide.
Respiratory: dyspnea.
Urinary System Disorders: proteinuria.
Skin and Appendages: exfoliative dermatitis, erythema multiforme, hyperpigmentation, hypertrophic scar.
Vascular: Henoch-Schonlein purpura syndrome.

DRUG INTERACTIONS

Overview

Interactions between TRADENAME cream with other drugs have not been established.

DOSAGE AND ADMINISTRATION

Recommended Dose and Dosage Adjustment

TRADENAME Cream should be applied once-a-day to the external genital/perianal warts. TRADENAME Cream should be used for up to 8 weeks.

Up to 1 packet of TRADENAME Cream should be applied to the treatment area t each application.

Missed Dose

If a dose is missed, the regular schedule should be continued. Do not make up the missed dose(s).

Each treatment cycle should not be extended due to missed doses or rest periods.

Administration

TRADENAME Cream should be used as directed by a physician. TRADENAME Cream is for external use only. Contact with the eyes, lips and nostrils should be avoided.

It is recommended that patients wash their hands before and after applying TRADENAME Cream.

TRADENAME Cream is not for oral, ophthalmic, intra-anal, intravaginal use. TRADENAME Cream should be applied once-a-day to the external genital/perianal warts. TRADENAME Cream should be used for up to 8 weeks. TRADENAME Cream should be applied prior to normal sleeping hours and left on the skin for approximately 8 hours, after which time the cream should be removed by washing the area with mild soap and water. The prescriber should deomonstrate the proper application technique to maximize the benefit of TRADENAME Cream therapy.

A thin layer of TRADENAME Cream should be applied to the areas of existing and emerging warts and rubbed in until the cream is no longer visible. The application site should not be occluded. Following the treatment period the cream should be removed by washing the treated area with mild soap and water. Unused packets should be discarded. Partially-used packets should be discarded and not reused.

Local skin reactins at the treatment site are common (see Adverse Reactions). A est period of several days may be taken if required by the patient's discomfort or severity of the local skin reaction. Treatment may resume once the reaction subsides. Non-occlusive dressings such as cotton gauze or cotton underwear may be used in the management of skin reactions.

Sexual (genital, anal, oral) contact should be avoided while TRADENAME Cream is on the skin. Application of TRADENAME Cream in the vagina is considered internal and should be avoided. Female patients should take special care if applying the cream at the opening of the vagina because local skin reactions on the delicate moist surfaces can result in pain or swelling, and may cause difficulty in passing urine.

Uncircumcised males treating warts under the foreskin should retract the foreskin and clean the area daily.

New warts may develop during therapy, as TRADENAME Cream is not a cure.

The effect of TRADENAME Cream on the transmission of genital/perianal warts is unknown.

TRADENAME Cream may weaken condoms and vaginal diaphragms, therefore concurrent use is not recommended.

Should severe local skin reaction occur, the cream should be removed by washing the treatment area with mild soap and water.

OVERDOSAGE

Overdosage of TRADENAME cream in humans is unlikely due to minimal percutaneous absorption. Animal studies reveal a rabbit dermal lethal imiquimod dose of greater than 5000 mg/kg. Persistent topical overdosing of TRADENAME cream could result in an increased incidence of severe local skin reactions and may increase the risk for systemic reactions.

The most clinically serious adverse event reported following multiple oral imiquimod doses of ≥200 mg was hypotension which resolved following oral or intravenous fluid administration.

ACTION AND CLINICAL PHARMACOLOGY

Mechanism of Action

*In vitro* studies have demonstrated.that imiquimod induces the release of interferon alpha (IFN-α) and other cytokines from human monocytes/macrophages and keratinocytes. The panel of cytokines induced varied with the cell's tissues origin. Topical *in vivo* applicationof imiquimod cream on mouse skin resulted in increased concenrations of IFN and tumour necrosis factor (TNF) compared with skin of untreated mice.

Pharmacodynamics

Imiquimod has no direct antiviral activity in cell culture. A study in 22 subjects with genital/perianal warts comparing imiquimod cream 5% and vehicle shows that imiquimod induces mRNA encoding cytokines including interferon-α at the treatment site. In addition HPVL1 mRNA and HPV DNA are significantly decreased following treatment. Howeer, the clinical relevance of these findings is unknown.

Pharmacokinetics

Percutaneous absorption of imiquimod has been studied through intact healthy skin, the skin of genital warts, and lesions of sun damaged skin. Percutaneous absorption of [$^{14}$C]imiquimod was minimal in a study involving six healthy subjects treated with a single topical application of (5 mg) of [$^{14}$C]imiquimod in cream formulation. No radioactivity [$^{14}$C] was deteted in the serum (lower limit of quantitation is 1 ng/mL) and <0.9% of the radiolabelled does was excreted in the urine and feces following topical application.

Systemic absorption of imiquimod (up to 9.4 mg [one 250 mg packet of 3.75% imiquimod cream]) across the affected skin of 18 subjects with EGW was observed with once daily dosing for 3 weeks. The mean peak serum drug concentration at Day 21 was 0.488 ng/mL.

Special Populations and Conditions

Age: No formal pharmacokinetic study was conducted to examine age related differences in the pharmacokinetic profile of TRADENAME cream.

Gender: During 3 weeks of treatment, the AUC $_{0-24}$ on Day 21 appeared to be similar in female and male subjects bu $C_{max}$ was higherand reached more quickly in female subjects who applied TRADENAME cream to external genital warts.

STORAGE AND STABLITY

Store between 15°C and 25°C. Avoid freezing.

DOSAGE FORMS, COMPOSITION AND PACKAGING

TRADENAME cream is supplied in single-use packets which contain 250 mg of the cream. Available as a box of 28 packets.

Each gram of TRADENAME cream contains 37.5 mg of imiquimod in an off-white to faintly yellow oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

PART II: SCIENTIFIC INFORMATION

PHARMACEUTICAL INFORMATION

Drug Substance

Common name: Imiquimod (USAN, INN)

Chemical. name: 1-(2-methylpropyl)-1*H*-imidazo[4,5-*c*]quinolin-4-amine

Molecular formula and molecular mass: $C_{14}H_{16}N_4$;MW = 240.3

Structural formula:

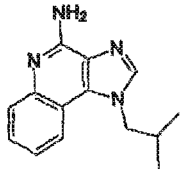

Physicochemical properties:

| | |
|---|---|
| Physical Form | Crystalline solid that varies in colour from white to off-white or buff. The compound has no odour. |
| Solubility: | Practically insoluble in most common organic solvents and in aqueous systems except at extremely low pH conditions. It can be made soluble to the extent of at least 100 mg/mL in methanol (as a salt) upon the addition of a few drops of hydrochloric or acetic acid. Soluble in fatty acids such as oleic acid and isostearic acid. |
| pKa Value: | The ionization constant for imiquimod was determined by ultraviolet (UV) spectroscopy and pH-solubility to be about 7.5. |
| Melting point: | 297-299°C with sublimation. |

CLINICAL TRIALS

In two double-blind, randomized, placebo-controlled clinical studies, 601 subjects with EGW were treated with 3.75% imiquimod cream, or a matching placebo cream. Studies enrolled subjects aged from 15 to 81 years. The baseline wart area ranged from 6 to 5579 $mm^2$ and the baseline wart count ranged from 2 to 48 warts. Most subjects had two or more treated anatomic areas at Baseline. Anatomic areas included: inguinal, perineal, and perianal areas (both genders); the glans penis, penis shaft, scrotum, and foreskin (in men); and the vulva (in women). Up to one packet of study cream was applied once daily to each wart identified at Baseline and any new wart that appeared during the treatment period. The study cream was applied to all warts prior to normal sleeping hours and left on for approximately 8 hours. Subjects continued applying the study cream for up to 8 weeks or until they achieved complete clearance of all (baseline and new) warts in all anatomic areas. Subjects not achieving complete wart clearance by the Week 8 visit (end of treatment, EOT), were evaluated for up to 8 weeks or until they achieved complete clearance during an additional 8 week no-treatment period. Subjects who achieved complete clearance of all warts at any time until the Week 16 visit entered a 12 week follow-up for recurrence period.

Efficacy was assessed by wart counts (those present at Baseline and new warts appearing during the study) at EOS (i.e.,up to 16 weeks from Baseline). Complete clearance required clearance of all warts in all anatomic areas. Partial clearance rate was defined as the proportion of subjects with at least a 75% reduction in the number of baseline warts at EOS. Percent reductions were measured relative to the numbers of warts at Baseline. Complete and partial clearance rates, and percent reductions in wart counts from baseline are shown in the table below (by overall rate and by gender).

Table 3: Efficacy Endpoints

| | TRADENAME™ CREAM, 3.75% | PLACEBO CREAM |
|---|---|---|
| COMPLETE CLEARANCE RATE | | |
| OVERALL | 28.3% (113/399) | 9.4% (19/202) |
| FEMALES | 36.6% (79/216) | 14.2% (15/106) |
| MALES | 18.6% (34/183) | 4.2% (4/96) |
| PARTIAL CLEARANCE RATE | | |
| OVERALL | 38.3% (153/399) | 11.9% (24/202) |
| FEMALES | 47.7% (103/216) | 17.0% (18/106) |
| MALES | 27.3% (50/183) | 6.3% (6/96) |
| PERCENT REDUCTION OF EGW (MEDIAN) | | |
| OVERALL | 50.0% | 0.0 |
| FEMALES | 70.7% | 0.0 |
| MALES | 23.3% | 0.0 |

The numbers of subjects who remained clear of EGW at the end of 12 weeks follow-up for recurrence period are shown in Table 4 below:

Table 4: Sustained Complete Clearance

| | TRADENAME™ CREAM 3.75% | PLACEBO CREAM |
|---|---|---|
| CLEARED AND ENTERED FOLLOW-UP | 102 | 13 |
| REMAINED CLEAR | 71 | 12 |

DETAILED PHARMACOLOGY

Pharmacodynamics: Imiquimod is an immune response modifier that is not a nucleoside analogue. Imiquimod is a Toll-like receptor 7 agonist that activates immune cells. Topical application to skin is associated with increases in markers for cytokines and immune cells. Saturable binding studies suggest a membrance receptor for imiquimod exists on responding cells. *In vitro* studies have demonstrated that imiquimod induces the production of IFN and other cytokines from a variety of human and animal cells. In addition, cytokines were produced following dermal application and oral administration in various laboratory animals and in human studies following oral administration of imiquimod. In animal models imiquimod is an effective antiviral and antitumour agent whose activity is principally due to induction of alpha interferon but other cytokines are also involved.

*In vitro* studies using isolated guinea pig myocardium, showed tipulation with tachyphylaxis development after multiple doses. Moderate to marked inhibition of agonist-induced contractions was observed in isolated guinea pig tracheal strips. Intravenous administration of a bolus dose of imiquimod caused CNS and cardiac stipulation in dogs. Little activity was found in inflammatory rat models. Some local anaesthetic activity, slight effect on locomotor,a nd slight effect on hexobarbital induced sleep time were observed in the mouse.

Pharmacokinetics and Metabolism: Animal and human dermal pharmacokinetic results indicate that minimal, if any, systemic absorption occurs following dermal application if imiquimod cream. Imiquimod was not quantifiable in the serum of rats dosed topically three times per week at 5 mg/kg for 4 weeks; low levels of metabolite were quantifiable after the last, but not after the first dose. In guinea pigs, after a single large (21 mg/kg) topical does of [$^{14}$C]imiquimod as a 5% cream, only low concentrations of imiquimod were quantifiable in plasma.

Oral ADME (absorption, distribution, metabolism, elimination) studies in laboratory animals, revealed extensive biotransformation followed by both urinary and biliary excretion of metabolites. Tissue distribution is rapid with clearance after 2 to 3 days with the exceptions of pigmented tissues - skin and uveal tract of the eye. No evidence of ocular toxicity was found in six month oral rat and monkey imiquimod toxicity studies conducted at high daily doses.

Systemic absorption of imiquimod (up to 9.4 mg [one packet]) across the affected skin of 18 subjects with EGW was observed with once daily dosing for 3 weeks. The mean peak serum drug concentration at Day 21 was 0.488 ng/mL.

TOXICOLOGY

Acute Toxicity: Acute dermal toxicity studies in rabbits with unformulated imiquimod under occlusion did not reveal any toxic effects at very high does levels - 5000 mg/kg. When administered orally, intraperitoneally, subcutaneously or intravenously, single does studies revealed that imiquimod produced central nervous system (CNS) stimulation andconvulsions at lethal doses. However, signs of CNS toxicity did not occur when animals were given lower repeat doses (100 mg/kg or lower).

Table 5

| SPECIES | ROUTE | $LD_{50}$ (MG/KG) |
|---|---|---|
| Mouse | oral | 403 |
| | intraperitoneal | 879 |
| Rat | oral | 1665 |
| | intraperitoneal | 763 |
| | subcutaneous | ≈20 |
| Rabbit | dermal | >5000 |
| Monkey | oral | >200 |
| | intravenous infusion | ≈8 |
| | intravenous bolus | >6 |

Irritation/Sensitization Studies: Skin irritation studies in rabbits showed that imiquimod was non-irritating when dosed unformulated at 500 mg or formulated up to 250 mg per site. Unformulated imiquimod produced mild or no eye irritation in rabbits when applied unformulated at 100 mg/eye or formulated up to 5 mg/eye. Formulated imiquimod was not irritating to rate or rabbit vaginal tract when applied every other day for 10 days at 10 and 50 mg/dose respectively. Dermal sensitization studies in guinea pigs showed that the imiquimod cream was not a dermal sensitizer. Comparison of the dermal reaction to imiquimod cream was not a dermal sensitizer. Comparison of the dermal reaction to imiquimod cream in animal species (rat, mouse, rabbit) with clinical study results, reveals that mouse and rabbit results aer comparable to humans. The more severe dermal irritation seen in the rate is not predictive of human response.

Long-Term Toxicity: Two repeat dose dermal toxicity studies in rats showed a compound related but non-dose related dermal irritation. A dose-related decrease in body weight of male rats was also observed. No systemic toxicity was found at doses up to 5 mg/kg three days per week for 4 weeks or at doses up to 2.5 mg/kg three days per week for 16 weeks.

The adverse effects observed for the high doses (10-30 mg/kg) in repeat dose oral tosicity studies in rats and monkeys could be related to exaggerated pharmacological effects of excessive cytokines induction and lymphoids stimulation: reduced body weight gains, anaemia, serum protein changes and death. High repeat daily doses of imiquimod did not produce necrosis in any organ; the compound is not cytotoxic. Recovery animals demonstrated that the adverse effects were readily reversible. An oral no-adverse-effect level of 3 mg/kg/day was determined in both rats and monkeys dosed daily for 6 months.

Carcinogenicity: Two-year bioassays in Wistar rats (up to 3 mg/kg orally per day) and CD-1 mice (up to 4.5 mg/kg applied topically 3 times per week) showed no evidenced of a carcinogenic effect in male and female rats and female mice. Liver tumours were increased in male mice exposed to the highest dose concentration, compared to the unexposed controls. However, the number of tumours was within the range seen historically for male CD-1 mice. It is generally accepted that an increase in liver tumours in male mice, in the absence of toher neoplastic responses in mice or rats, is not indicative of a carcinogenic risk for humans.

In a photocarcinogenicity study in hairless mice, animals received imiquimod cream 3 times per week at concentrationso f 0.03%, 0.1% and 0.3% and were irradiated with solar ultraviolet light for 5 days each week for 40 weeks and observed an additional 12 weeks. Vehicle cream enhanced UVR-induced skin tumour development. Imiquimod cream had no additional effect on tumour development beyond the vehicle effect (i.e., the addition of the active ingredient, imiquimod, to the vehicle cream did not result in an additional effect beyond the vehicle effet on tumour development).

Mutagenicity:
Imiquimod was without effect in a series of eight mutagenicity assays including Ames, mouse lymphoma, CHO chromosome aberration, human lymphocyte, chromosome aberration, SHE cell transformation, rate and hamster bone marrow cytogenetics, and mouse dominant lethal test.

Reproduction and Teratology: Teratology studies in rats and rabbits dosed 1-20 mg/kg orally and at 0.5-2.0 mg/kg intravenously, did not reveal any teratogenic effects. The high doses in both studies produced some adverse effets in the dams related to maternal toxicity. The maternal toxicity was reflected in ghe high dose pups: reduced pup weights and delayed ossification in the rate. A radiolabel intravenous study in pregnant rabbits dosed at 1 mg/kg between day 6 to 18 of gestation for a total of 13 doses, sowed radiolabel in the uteri, placenta, amniotic fluid and fetuses with no preferential concentration in the conceptus.

In a rat general reproduction study which utilized daily oral doses of 1.5-6.0 mg/kg, drug-related toxicity was observed at the high dose in the F0 generation with no adverse reproductive effects. Reverisble ossification defects were observed in pups at the high dose. No effects were observed in growth, development, behavior, learning/memory or reproduction of second generation. Daily oral administration of imiquimod to rats, at doses up to 8 times recommended human dose on a $mg/m^2$ basis throughout mating, gestation, parturition and lactation, demonstrated no impairment of reproduction.

REFERENCES

1. Arany I, Tyring S, Stanley MA, Tomai MA, Miller RL, Smith MH et al. Enhancement of the innate and cellular immune response in patients with genital warts treated with topical imiquimod cream 5%. Antiviral Res1999;43:55-63.

2. Bernstein DI, Harrison CJ. Effects of the Immunoodulating Agent R-837 on Acute and Latent Herpes Simplex, Virus Type 2 Infectietid. Antiallad Agents.and Cheittotlierapy1989; 33(9):1511-1515.

3. Bernstein DI, Miller RL, Harrison CJ. Effects of Therapy with an Immunomodulator (Imiquimod, R-837) Alone and with Acyclovir on Genital HSV-2 Infection in Guinea-Pigs When Begun After Lesion Development. Antiviral Res 1993; 20;45-55.

4. Dahl MV. Imiquimod; An immune response modifier. J. Am Acad Dermatol 2000;43(1):S1-5.

5. Edwards L. Imiquimod in clinical practice. J Am Acad Dermatol 2000;43(1):SI2-17.

6. Edwards L, Ferenczy A, Eron Baker D, Owens ML, Fox TL et al. Self-administered topical 5% imiquimod cream for external anogenital warts. Arch Dermatol 1998;134:25-30.

7. Gibson SJ, Lindh JM, Riter TR, et at. Plasmacytoid dendritic cells produce cytokines .and mature in response to the TLR7 agonists, imiquimod and resiquimod. Cell Immunol, 2002;218(1-2):74-.86.

8. Gollnick H, Barasso R, Jappe U, Ward K, Eul A, CareyYard M et al. Safety and efficacy of imiquimod 5% cream in the treatment of penile-genital warts in uncircumsised men-when applied three times weekly or once per day. Int J STD & AIDS 2001;12:22-28.

9. Harrison CS, Miller RL, Bernstein DI. Posttherapy Suppression of Genital Herpes Simplex Virus (HSV) Recurrence and Enhanecement of HSV-specific T-Cell Memory by Imiquimod in Guinea Pigs. Antimicro Agents and Chemo 1994; 38(9):2059-2064.

10. Hemini H, Kaisho T, Takeuchi O, Sato S, Sanjo H, Hoshino K, Horiuchi T, Tomizawa H, Takedi K, Akira S. Small anti-viral compounds activate immune cells *via* the TLR7 MyD88-dependent signaling pathway. Nat Immunol 2002; 3(2): 196-200.

11. Kende M, Lupton HW, Canonico PG. Treatment of Experimental Viral Infections with Immuno-modulators, Adv Biosci 1988,68:51-61.

12. Miller RL, Birmachu W, Gerster JF et al. Imiquimod Cytokine Induction and Antiviral Activity. Intl Antiviral News 1995; 3(7):111;113.

13. Miller RL. Gerster JF, Owens ML, Slade HB, Tomai MA. Imiquimod applied topically: a novel immune response modifier and new class of drug. Int J Immunopharm 1999;21:1-14.

14. Sauder DN. Immunomodulatory and pharmacologic properties of imiquimods. J Am Acad Dermatol 2000;43(1):S6-11.

15. Testerman TL,, Gerster JF, Imbertson LM,et al. Cytokine Induction by the Immunomodulators Imiquimod and S-27609. J Leuk Biol 1995; .58:365-372.

16. Tyring SK, Immune-response modifiers; A new paradigm in the treatment of human papillomavirus, Curr Ther Res 2000;60(9):584-596.

17. Tyring SK, Arany I, Stanley MA, Tomai MA, Miller RL, Smith MH et al. A randomized, controlled, molecular study of condylomata acuminata clearance during treatment with imiquimod. J Infect Dis 1998;178(August):551-555.

18. Weeks CE, Gibson SJ. Induction of Interferon and Other Cytokines by Imiquimod and its Hydroxylated Metabolite R-842. in Human Blood Cells *in Vitro* J Interferon Res 1994; 14:81-85.

PART III: CONSUMER INFORMATION

PRTRADENAME™
(IMIQUIMOD) CREAM, 3.75%

This leaglet is part III of a three-part "Product Monograph" published when TRADENAME™ was approved for sale in Canada and is designed specifically for Consumers. This leaflet is a summary and will not tell you everything about TRADENAME™. Contact your doctor or pharmacist if you have any questions about the drug.

ABOUT THIS MEDICATION

What the medication is used for:
TRADENAME is the brand name for imiquimod cream, 3.75%. It is used for the treatment of external gential and perianal warts/condyloma acuminate, whether present at the start of therapy or emerging during therapy, in patients 12 years or older.

What is does:
TRADENAME cream is an immune response modifier. TRADENAME cream is a medicine that works by stimulating your body's own immune response.

When it should not be used:
Do not use TRADENAME if you are allergic to imiquimod, or other medications that contain imiquimod (e.g. Aldara), or any of the other ingredients in TRADENAME.

What the medicinal ingredient is:
Imiquimod

What the important nonmedicinal ingredients are:
Isostearic acid, cetyl alcohol, stearyl alcohol, whie petrolatum, polysorbate 60m sorbitan monosterate, glycerin, xanthan gum, purified water, benzyl alcohol, methylparaben, and propylparaben.

What dosage forms it comes in:

TRADENAME cream contains 37.5 mg imiquimod per gram (3.75%) and is supplied in single-use packets which contain 250 mg of the cream. It is available as boxes of 28 packets.

WARNINGS AND PRECAUTIONS

- TRADENAME should not be used in pateients under 12 years of age
- Avoid exposure to of treated area(s) sunlight, sunlamp, or tanning bed during treatment with TRADENAME.
- TRADENAME may cause severe skin reactions.
- TRADENAME may also cause flu-like syumptoms before or during local skin reactions

BEFORE you use TRADENAME talk to your doctor or pharmacist if:

- You have or had other skin cancers or other growths on your body
- You are immunocompromised (have weak immune system)
- You have or have had any other treatment for your external genital/perianal warts, such as freezing or surgery
- You are pregnant or planning to become pregnant
- You are breastfeeding or planning to breastfeed

INTERACTIONS WITH THIS MEDICATION

Tell your doctor or pharmacist about all the medicines you take or have taken, including prescription and non-prescription medicines, vitamins and herbal supplements. It is not known if TRADENAME cream and other medicines can affect each other.

PROPER USE OF THIS MEDICATION

Use TRADENAME cream exactly as presecribed by your doctor. Do not use TRADENAME cream until your doctor has shown you the right way to use it.

Usual adult dose:

Apply TRADENAME cream to the external genital/perianal warts once a day just before bedtime.

TRADENAME Cream should be used for up to 8 weeks.

How to aply TRADENAME cream:

TRADENAME Cream should be applied just before your bedtime.

- Wash the area to be treated with mild soap and water. Allow the area to dry.
    - Uncircumcised males treating warts under their penis foreskin must pull their foreskin back and clean daily during the weeks of treatment
- Wash your hands
- Open a new packet(s) of TRADENAME Cream just before use.
- Apply a thin layer of TRADENAME Cream only to the affected area or areas.
- Do not get TRADENAME Cream in or around your eyes or mouth.
- Do not get TRADENAME in the anus when applying to perianal warts.
- Female patients treating genital warts must be careful when applying TRADENAME Cream around the vaginal opening. Female patients should take special care if applying the cream at the opening of the vagina because local skin reactions on the delicate moist surfaces can cause pain or swelling, and may cause problems passing urine. Do not put TRADENAME Cream in your vagina.

- Do not ocover the treated area(s) with an airtight bandage. Cotton gauze dressings can be used. Cotton underwear can be used after applying TRADENAME Cream to the genital or perianal area.
- Safely throw away the open packet of TRADENAME Cream so that children and pets cannot get it. The open packet should be thrown away even if all the TRADENAME Cream was not completely used.
- After applying TRADENAME Cream, wash your hands well with soap and water.
- Leave the cream on the affected area(s) for about 8 hours or as instructed by your doctor. Do not bathe or get the treated area(s) wet before the right time has passed. Do not leave TRADENAME Cream o your skin longer than prescribed.
- After about 8 hours, wash the treated area(s) with mild soap and water.
- If you get TRADENAME Cream in your mouth or in your eyes rinse well with water right away.

Avoid exposure of the treatet area(s) to sunlight, sunlamp or tanning-bed during the treatment with TRADENAME.

Overdose:

If you have used more TRADENAME Cream than you should, contact your doctor, or poison control center.

Missed Dose:

If you forgot to apply TRADENAME Cream, continue on your regular schedule and do not make up the missed dose(s).

SIDE EFFECTS AND WHAT TO DO ABOUT THEM

Side effects with TRADENAME Cream may include skin reactions at the treatment site such as:

- Redness
- Swelling
- A sore, blister, or ulcer
- Skin that becomes hard or thickened
- Skin peeling
- Scabbing and crusting
- Itching
- Burning
- Changes in skin color that do not always go away

During treatment and until the skin has healed, your skin in the treatment are is likely to appear noticeably different from the normal skin. Side effects at the site where TRADENAME Cream is applied are common. Sometimes the side effects go outside of the area where TRADENAME Cream was applied. Patients should be aware that new warts may develop during treatment, as TRADENAME Cream may not be a cure. You have a higher chance for severe skin reactions if you use too much TRADENAME Cream or use it the wrong way. Stop TRADENAME Cream right away and call you healthcare provider if you get any skin reactions that affect your daily activities, or that do not go away. Someimes, TRADENAME cream must be stopped for a while to allow your skin to heal. Talk to your healthcare provider if you have questions about your treatment or skin reactions.

Other side effects of TRADNAME Cream include pain, fever, muscle aches, and may also include headache, back pain, joint aches, tiredness, flu-like symptoms, nausea, and diarrhea.

If the reactions seem excessive, if either skin breaks down or sores develop during the first week of treatment, if flu-like symptoms develop or if you begin to not feel well at anytime, stop applying TRADENAME Cram and contact your healthcare provider.

These are not all the side effects of TRADENAME cream. For more information, ask your healthcare provider or pharmacist.

HOW TO STORE IT

Store TRADENAME Cream between 15-25° C. Do not freeze.

Safely throw away TRADENAME Cream that is out of date or that you do not need.

Keep TRADENAME Cream and all medicines out of the reach of children.

REPORTING SUSPECTING SIDE EFFECTS

To monitor drug safety, Health Canada through the Canada Vigilance Program collects information on serious and unexpected effects of drugs. If you suspect you have had a serous or unexpected reachion to this drug, you may notify Canada Vigilance:

You can report any suspected adverse reaction associated with the use of health products in the Canada Vigilance Program by one of the following 3 ways:

Report online at www.healthcanada.gc.ca/medeffect
Call toll-free at 1-866-234-2345
Complete a Canada Vigilance Reporting Form and:

- Fax toll-free to 1-866-678-6789, or
- Mail to: Canada Vigilance Program
  Health Canada
  Postal Locator 0701C
  Ottawa, ON K1AOK9

Postage paid labels, Canada Vigilance Reporting Form and the adverse reaction reporting guidelines are available on www.healthcanada.gc.ca/medeffect Note: Should you require information related to the management of side effects, contact your health professional. The Canada Vigilance Program does not provide medical advice.

MORE INFORMATION

This document plys the full product monograph, prepared for health professionals can be found at http://www.gracewaypharma.ca or by contacting the sponsor, Graceway Pharmaceuticals,, at 1-800-328-0255.

This leaflet was prepared by Graceway Pharmaceuticals, 252 Pall Mall St., Suite 302 London, Ontario, N6A 5P6.

Last revised: March 24, 2010

The complete disclosures of the patents, patent documents, and publications cited herein are incorporated by reference in their entireties as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method for treating genital or perianal warts in a subject 12 years old or older, the method comprising: applying an imiquimod pharmaceutical cream formulated with 3.75% by weight imiquimod to the warts, once per day, each day, for up to 8 consecutive weeks or until clearance is observed, whichever occurs earlier, to treat the warts.

2. The method of claim 1, wherein the imiquimod pharmaceutical cream further comprises a pharmaceutically acceptable vehicle.

3. The method of claim 2, wherein the pharmaceutically acceptable vehicle comprises a member selected from the group consisting of a fatty acid, an emollient, an emulsifier, a thickener, a preservative, a humectant, water, or a combination thereof.

4. The method of claim 3, wherein the fatty acid is selected from the group consisting of isostearic acid, linoleic acid, oleic acid, super purified oleic acid, and a combination thereof.

5. The method of claim 3, wherein the fatty acid is isostearic acid.

6. The method of claim 3, wherein the fatty acid is present in an amount of between about 5% to about 25% by weight.

7. The method of claim 3, wherein the emollient is selected from the group consisting of cetyl alcohol, stearyl alcohol, petrolatum, and a combination thereof.

8. The method of claim 3, wherein the emollient is present in an amount of between about 5% to about 10% by weight.

9. The method of claim 3, wherein the emulsifier is selected from the group consisting of polysorbate 60, sorbitan monostearate, and a combination thereof.

10. The method of claim 3, wherein the emulsifier is present in an amount of between about 2% to about 6% by weight.

11. The method of claim 3, wherein the preservative is selected from the group consisting of methylparaben, propylparaben, benzyl alcohol, and a combination thereof.

12. The method of claim 3, wherein the humectant is glycerin.

13. The method of claim 3, wherein the water is present in an amount of between about 45% to about 85% by weight.

14. The method of claim 2, wherein the pharmaceutically acceptable vehicle consists of isostearic acid, cetyl alcohol, stearyl alcohol, white petrolatum, polysorbate 60, sorbitan monostearate, glycerin, xanthan gum, water, benzyl alcohol, methylparaben, and propylparaben.

15. The method of claim 1, wherein for every 250 mg of the imiquimod pharmaceutical cream, the cream contains 9.375 mg of imiquimod.

16. The method of claim 1, wherein the imiquimod pharmaceutical cream is selected from the group of 3.75% imiquimod pharmaceutical creams listed in Example 29.

* * * * *